(12) United States Patent
Kamenecka et al.

(10) Patent No.: US 8,957,093 B2
(45) Date of Patent: *Feb. 17, 2015

(54) N-BIPHENYLMETHYLINDOLE MODULATORS OF PPARG

(75) Inventors: Theodore Mark Kamenecka, Palm Beach Gardens, FL (US); Patrick R. Griffin, Jupiter, FL (US); Marcel Koenig, Palm Beach Gardens, FL (US); Alice Astelan, Jupiter, FL (US); Anne-Laure Blayo, Jupiter, FL (US); Yuanjun He, Palm Beach Gardens, FL (US); Youseung Shin, Jupiter, FL (US)

(73) Assignee: The Scripps Research Institute, La Jolla, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/490,324

(22) Filed: Jun. 6, 2012

(65) Prior Publication Data

US 2012/0309757 A1    Dec. 6, 2012

Related U.S. Application Data

(60) Provisional application No. 61/493,883, filed on Jun. 6, 2011, provisional application No. 61/554,605, filed on Nov. 2, 2011.

(51) Int. Cl.
| | |
|---|---|
| A61K 31/404 | (2006.01) |
| C07D 209/42 | (2006.01) |
| C07D 401/10 | (2006.01) |
| C07D 401/12 | (2006.01) |
| C07D 403/10 | (2006.01) |
| C07D 403/12 | (2006.01) |
| C07D 407/12 | (2006.01) |
| C07D 409/12 | (2006.01) |
| C07D 413/10 | (2006.01) |
| C07D 413/12 | (2006.01) |
| C07D 417/12 | (2006.01) |
| C07D 471/04 | (2006.01) |
| C07D 493/04 | (2006.01) |

(52) U.S. Cl.
CPC ............ *C07D 209/42* (2013.01); *C07D 401/10* (2013.01); *C07D 401/12* (2013.01); *C07D 403/10* (2013.01); *C07D 403/12* (2013.01); *C07D 407/12* (2013.01); *C07D 409/12* (2013.01); *C07D 413/10* (2013.01); *C07D 413/12* (2013.01); *C07D 417/12* (2013.01); *C07D 471/04* (2013.01); *C07D 493/04* (2013.01)
USPC .......................... 514/339; 514/414; 514/419

(58) Field of Classification Search
USPC ......................... 514/339, 414, 419
See application file for complete search history.

(56) References Cited

U.S. PATENT DOCUMENTS

| | | |
|---|---|---|
| 5,541,229 A | 7/1996 | Narr et al. |
| 6,348,032 B1 | 2/2002 | Sperl et al. |
| 7,544,707 B2 | 6/2009 | Connor et al. |
| 2009/0062363 A1 | 3/2009 | Kaku et al. |
| 2009/0325956 A1 | 12/2009 | Taniguchi et al. |
| 2011/0028527 A1 | 2/2011 | Chiang et al. |
| 2012/0309769 A1 | 12/2012 | Kamenecka et al. |
| 2014/0249196 A1 | 9/2014 | Kamenecka et al. |

FOREIGN PATENT DOCUMENTS

| | | |
|---|---|---|
| EP | 0179619 A1 | 4/1986 |
| EP | 1445250 A1 | 8/2004 |
| EP | 1595866 A1 | 11/2005 |
| EP | 1988076 A1 | 11/2008 |
| JP | 08048671 A | 2/1996 |
| JP | 2005-162657 A | 6/2005 |
| WO | WO-0112187 A2 | 2/2001 |
| WO | WO-2004072025 A2 | 8/2004 |
| WO | WO-2006045478 A1 | 5/2006 |
| WO | WO-2009/083526 A1 | 7/2009 |
| WO | WO-2012/170554 A1 | 12/2012 |
| WO | WO-2012/170561 A1 | 12/2012 |
| WO | WO-2013/078233 A1 | 5/2013 |
| WO | WO-2013/078237 A1 | 5/2013 |
| WO | WO-2013/078240 A1 | 5/2013 |

OTHER PUBLICATIONS

Diabetes [online], retrieved on Mar. 15, 2009; retrieved from [URL; http://www.merck.com.mmpe/print/sec12/ch158/ch158b.html].*
Narr, et al. Document No. 117:48554, retrieved from CAPLUS, Aug. 8, 1992.*
Lamotte, et al. Document No. 152:429458, retrieved from CAPLUS, Feb. 10, 2010.*
Andersen, et al. Document No. 128:3688, retrieved from CAPLUS, Nov. 13, 1997.*

(Continued)

*Primary Examiner* — Shawquia Jackson
(74) *Attorney, Agent, or Firm* — Geoffrey K. Cooper; Thomas Fitting

(57) ABSTRACT

The invention provides molecular entities that bind with high affinity to PPARG (PPARγ), inhibit kinase-mediated, e.g., cdk5-mediated, phosphorylation of PPARG, but do not exert an agonistic effect on PPARG. Compounds of the invention can be used for treatment of conditions in patients wherein PPARG plays a role, such as diabetes, insulin resistance, impaired glucose tolerance, pre-diabetes, hyperglycemia, hyperinsulinemia, obesity, or inflammation. In methods of treatment of these conditions using a compound of the invention, the compound can avoid producing side effects of significant weight gain, edema, impairment of bone growth or formation, or cardiac hypertrophy, or any combination thereof, in the patient receiving the compound. Methods of preparation of the compounds, bioassay methods for evaluating compounds of the invention as non-agonistic PPARG binding compounds, and pharmaceutical compositions are also provided.

5 Claims, 14 Drawing Sheets

(56) References Cited

OTHER PUBLICATIONS

Is there a Diabetes Cure? [online]. retrieved from the internet on May 13, 2014. http://www.webmd.com/diabetesis-there-a-diabetes-cure?page=2.*

"U.S. Appl. No. 13/490,342, Non Final Office Action mailed Mar. 1, 2013", 24 pgs.

"U.S. Appl. No. 13/490,342, Response filed Feb. 13, 2013 to Restriction Requirement mailed Feb. 14, 2013", 41 pgs.

"International Application Serial No. PCT/US2012/066116, International Search Report mailed Feb. 12, 2013", 2 pgs.

"International Application Serial No. PCT/US2012/066118, Written Opinion mailed Feb. 12, 2013", 4 pgs.

"International Application Serial No. PCT/US2012/066123, International Search Report mailed Feb. 29, 2013", 3 pgs.

"International Application Serial No. PCT/US2012/066123, Written Opinion mailed Jan. 29, 2013", 6 pgs.

"International Application Serial No. PCT/US2012/066135, International Search Report mailed Feb. 8, 2013", 4 pgs.

"International Application Serial No. PCT/US2012/066135, Written Opinion mailed Feb. 8, 2013", 7 pgs.

Motani, Alykhan, et al., "INT131: A Selective Modulator of PPARgamma", *J. Mol. Biol.* 386, [Online. Retrieved from the Internet: <URL: http://www.intekrin.com/files/JMB386()1301_PPARg_T131-09.pdf>, (2009), 1301-1311.

"International Application Serial No. PCT/US2012/041129, International Search Report mailed Jul. 24, 2012", 4 pgs.

"International Application Serial No. PCT/US2012/041129, Written Opinion mailed Jul. 24, 2012", 9 pgs.

"International Application Serial No. PCT/US2012/041137, International Search Report mailed Jul. 30, 3012", 8 pgs.

"International Application Serial No. PCT/US2012/041137, Written Opinion mailed Jul. 30, 2012", 11 pgs.

Haggarty, S, "Dissecting cellular processes using small molecule: identification of colchicine-like. taxol-like and other small molecules that perturb mitosis.", Chemistry & Biology. vol. 7. No. 4, (Apr. 1, 2000), 275-286.

Hitoshi, Takami, et al., "Indole and benzimidazole derivatives as steroid 5[alpha]reductase inhibitors in the rat prostate.", Bioorganic & Medicinal Chemistry. vol. 6. No. 12., (Dec. 1, 1998), 2441-2448.

Hitoshi, Takami, et al., "Synthesis of Tricyclic Compounds as Steroid 5.ALPHA.-Reductase Inhibitors.", Chemical & Pharmaceutical Bulletin. vol. 48. No. 4., (Jan. 1, 2000), 552-555.

Jacobs, Robert T, et al., "Substituted 3-(phenylmethyl)-1H-indole-5-carboxamides and 1-(phenylmethyl)indole-6-carboxamides as potent. selective. orally active antagonists of the peptidoleukotrienes.", Journal of Medicinal Chemistry. American Chemical Society. US. vol. 36. No. 3., (Jan. 1, 1993), 394-409.

Jang, Hyun Choi, et al., "Antidiabetic actions of a non-agonist PPAR[gamma] ligand blocking Cdk5-mediated phosphorylation.", Nature, vol. 477, No. 7365, (Nov. 22, 2011), 477-481.

Jang Hyun, Choi, et al., "Antidiabetic actions of a non-agonist PPAR[gamma] ligand blocking Cdk5-mediated phosphorylation.", Nature val. 477, No. 7365, (Nov. 22, 2011), 477-481.

Kttcha, Daniel M, "The manganese(III) acetate oxidation of N-protected indolines.", Tetrahedron Letters. vol . 29. No. 18., (Jan. 1, 1988), 2151-2154.

Lamotte, Y., et al., "Synthesis and biological activities of novel indole derivatives as potent and selective PPAR<3> modulators", Bioorg Med Chem Lett., 20(4), (Feb. 15, 2010), 1399-1404.

Page, et al., "New 1.2.3.4-tetrahydropyrrolo[3.4-b]indole derivatives as selective CB2 receptor agonists.", Bioorganic & Medicinal Chemistry Letters. Ergamon. Elsevier Science. GB. vol. 17. No. 22., (Oct. 12, 2007), 6183-6187.

"U.S. Appl. No. 13/490,342, Restriction Requirement mailed Jan. 14, 2013", 14 pgs.

"U.S. Appl. No. 13/490,342, Response filed Jun. 26, 2013 to Non Final Office Action mailed Mar. 1, 2013", 45 pgs.

Bhattarai, Bharat Raj, et al., "Novel thiazolidinedione derivatives with anti-obesity effects: Dual action as PTP1B inhibitors and PPAR-? activators", Bioorganic and Medicinal Chemistry Letters, 20, 6758-6763, (Sep. 2010), 6758-6763.

Chen, Hong, et al., "Cevoglitazar, a Novel Peroxisome Proliferator-Activated Receptor-a/? Dual Agonist, Potently Reduces Food Intake and Body Weight in Obese Mice and Cynomolgus Monkeys", Endocrinology, 151(7), 3115-3124, (Jul. 2010), 3115-3124.

Foryst-Ludwig, Anna, et al., "PPARgamma activation attenuates T-lymphocytedependent inflammation of adipose tissue and development of insulin resistance in obese mice", Cardiovascular Diabetology 9:64, (2010), 9 pgs.

Lu, Min, et al., "Brain PPAR-? promotes obesity and is required for the insulin—sensitizing effect of thiazolidinediones", Nature Medicine, 17(5), 618-623, (May 1, 2011), 618-623.

Olefsky, Jerrold M., et al., "Macrophages, Inflammation, and Insulin Resistance", Ann. Rev. Physiol., 72:219-246, (Oct. 2009), 219-246.

"U.S. Appl. No. 13/490,342, Final Office Action mailed Sep. 26, 2013", 23 pgs.

"Chemical Abstract Registry No. 932514-67-5", indexed in the Registry File on STN CAS Online, (Apr. 26, 2007), 1 pg.

"International Application Serial No. PCT/US2012/041129, International Preliminary Report on Patentability mailed Dec. 27, 2014", 9 pgs.

"International Application Serial No. PCT/US2012/041137, International Preliminary Report on Patentability mailed Dec. 27, 2013", 11 pgs.

Ito, "A medium-term rat liver bioassay for rapid in vivo detection of carcinogenic potential of chemicals", Cancer Science, 94, (2003), 3-8.

"U.S. Appl. No. 13/490,342, Non Final Office Action mailed May 23, 2014", 32 pgs.

"U.S. Appl. No. 13/490,342, Response filed Aug. 25, 2014 to Non-Final Office Action mailed May 23, 2014", 34 pgs.

"U.S. Appl. No. 13/811,969, Non Final Office Action mailed Jun. 19, 2014", 33 pgs.

"U.S. Appl. No. 13/811,973, Restriction Requirement mailed Sep. 10, 2014", 8 pgs.

"Chemical abstract Registry No. 895115-61-4", indexed in the Registry File on STN CAS Online, (Jul. 23, 2006).

"International Application Serial No. PCT/US2012/066116, International Preliminary Report on Patentability mailed Jun. 5, 2014", 6 pgs.

"International Application Serial No. PCT/US2012/066123, International Preliminary Report on Patentability mailed Jun. 5, 2014", 6 pgs.

"International Application Serial No. PCT/US2012/066135, International Preliminary Report on Patentability mailed Jun. 5, 2014", 9 pgs.

Bruno, et al., "Expert Opinion Emerging Drugs", 10(4), (2005), 747-771.

Colagiuri, et al., "The Answer to Diabetes Prevention: Science, Surgery, Service Delivery, or Social Policy?", American Journal of Public Health, vol. 96, No. 9, (Sep. 2006), 1562-1569.

Curtis, et al., "The Journal of the American Board of Family Practice", vol. 18, (2005), 37-43.

Park, Kyong Soo, "Prevention of type 2 diabetes mellitus from the viewpoint of genetics", Diabetes Research and Clinical Practice 66S (2004), (2004), S33-S35.

Sime, et al., "Discovery of GSK1997132B a novel centrally penetrant benzimidazole PPARy partial agonist", Bioorganic & Medicinal Chemistry Letters (published online Jun. 29, 2011), 21 (18) (Jun. 29, 2011), 5568-5572.

Yanaka, et al., "An English translation of JP 08-048671", (1996).

* cited by examiner

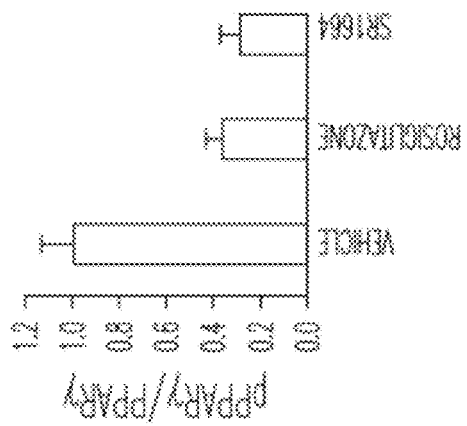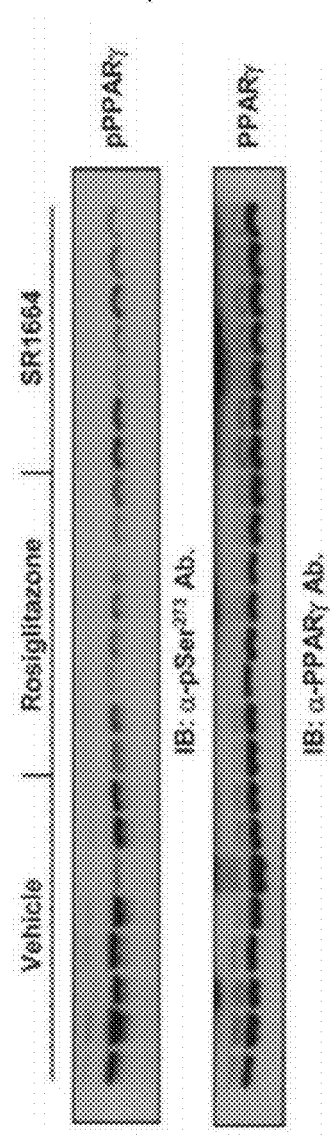
Fig. 4A

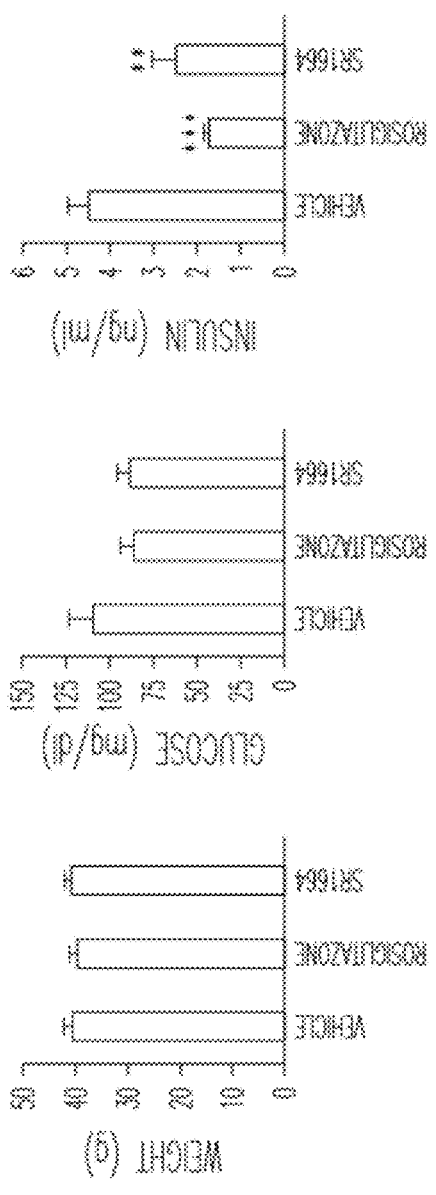
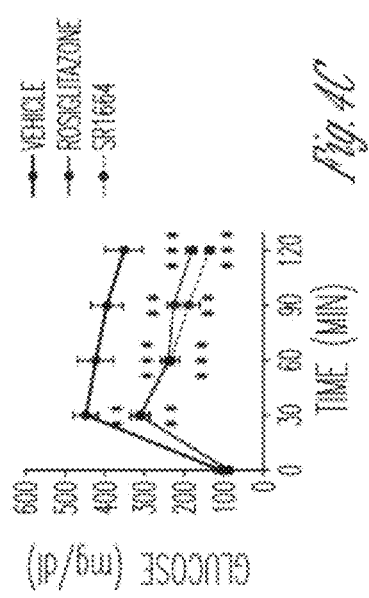
Fig. 4B
Fig. 4C

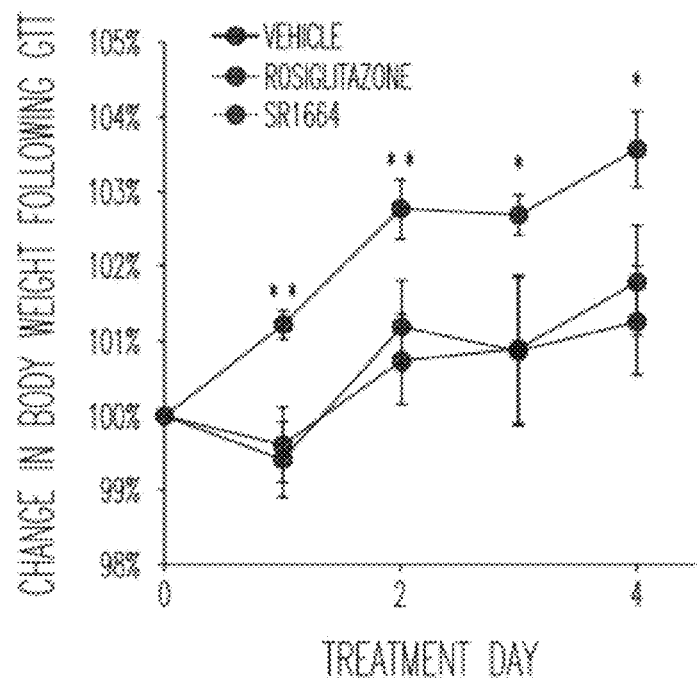
*Fig. 4D*
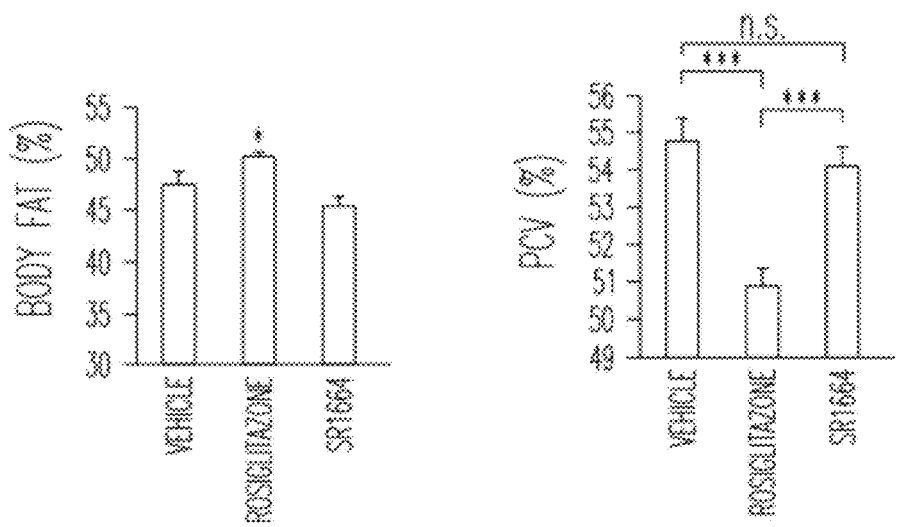
*Fig. 4E*  *Fig. 4F*

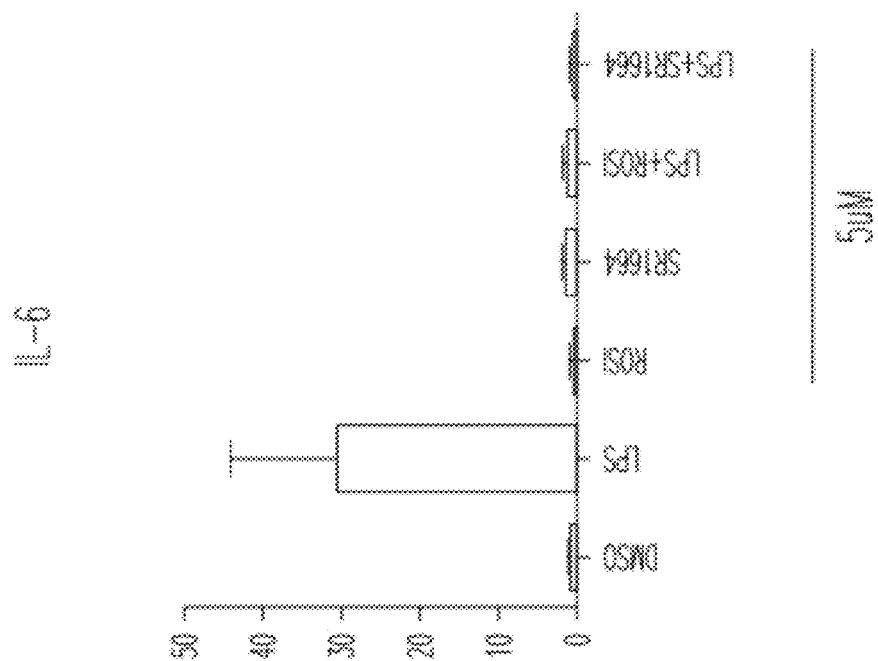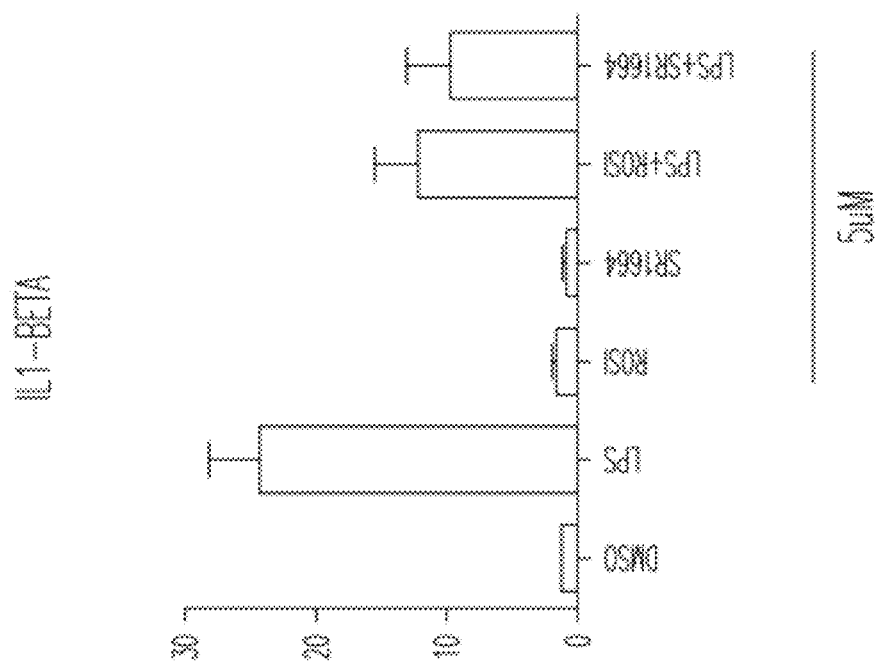
Fig. 5

US 8,957,093 B2

N-BIPHENYLMETHYLINDOLE MODULATORS OF PPARG

CROSS-REFERENCE TO RELATED APPLICATIONS

This application claims the priority of U.S. provisional application Ser. Nos. 61/493,883, filed Jun. 6, 2011, and 61/554,605, filed Nov. 2, 2011, which are incorporated herein by reference in their entireties.

BACKGROUND

The peroxisome proliferator active receptors (PPARs), members of the nuclear hormone receptor superfamily, comprise several subtypes such as PPARα, PPARβ, and PPARγ. The PPARγ subtype, also referred to as PPARG, is the target of the glitazone pharmaceutical agents used for treatment of type II diabetes. PPARG is also known as NR1C3 (the gene ID) and there exist PPARG1 and PPARG2, the two major isoforms of PPARG. The glitazones, such as pioglitazone and rosiglitazone, act as PPARG receptor agonists. However, other classes of pharmaceutical agents, such as Telmisartan, have been reported to act as partial agonists, binding in a different mode to PPARG and having different cofactor requirements. See Y. Lamotte, et al., *Bioorg. Med. Chem. Lett.* (2010), 20, 1399-1404.

SUMMARY

The present invention is directed to compounds that are non-activating (non-agonist) PPARG modulators, and to the use of these compounds in modulating the activity of PPARG, such as in treatment of conditions wherein non-activating modulation of PPARG is medically indicated, such as diabetes, insulin resistance, impaired glucose tolerance, pre-diabetes, hyperglycemia, hyperinsulinemia, obesity, or inflammation. Compounds of the invention can block kinase-mediated, such as cdk5-mediated, phosphorylation of PPARG, but are not agonists of the receptor itself. By avoiding agonism of the receptor, the compounds may exhibit no or reduced side effects associated with administration of full and partial agonists of PPARG, such as significant weight gain, edema, impairment of bone growth or formation, or cardiac hypertrophy, or any combination thereof. Compounds of the invention can bind both PPARG1 and PPARG2, the two major isoforms of PPARG.

In various embodiments, the invention provides a non-agonist PPARG modulatory compound of formula (I), or a pharmaceutically acceptable salt thereof:

(I)

wherein:
R is H or $(C_1-C_4)$alkyl;
$R^1$ and $R^2$ are independently H, $(C_1-C_6)$alkyl, $(C_3-C_9)$cycloalkyl, or $(C_1-C_6)$haloalkyl; or $R^1$ and $R^2$ together with the atoms to which they are bonded form a 5- to 9-membered ring, comprising 0-3 heteroatoms selected from the group consisting of O, NR, and $SO_q$ wherein q is 0, 1, or 2, and optionally mono- or pluri-substituted with independently selected $(C_1-C_6)$alkyl, $(C_2-C_6)$alkenyl, $(C_2-C_6)$alkynyl, $(C_6-C_{10})$aryl, $(C_3-C_9)$cycloalkyl, halo, $(C_1-C_6)$haloalkyl, nitro, cyano-$(C_0-C_6)$alkyl, $R'O_2C$—$(C_0-C_6)$alkyl, methylenedioxy, $R'O$—$(C_0-C_6)$alkyl, $(R')_2N$—$(C_0-C_6)$alkyl, $(R')_2NC(=O)$—$(C_0-C_6)$alkyl, $(C_1-C_6)$alkyl-$S(O)_q(C_0-C_6)$alkyl, aryl, aroyl, or $SO_2NR'_2$; $R^3$ is optionally mono- or multi-substituted $(C_1-C_6)$alkyl, $(C_1-C_6)$alkenyl, $(C_1-C_6)$alkynyl, aryl, arylalkyl, heteroaryl, heteroarylalkyl, cycloalkyl, heterocyclyl, cycloalkylalkyl, or heterocyclylalkyl; wherein if present each substituent on $R^3$ is independently selected from the group consisting of $(C_1-C_6)$alkyl, $(C_2-C_6)$alkenyl, $(C_2-C_6)$alkynyl, $(C_6-C_{10})$aryl, $(C_3-C_9)$cycloalkyl, 3-9 membered mono- and bicyclic heterocyclyl, 3-9 membered mono- and bicyclic heteroaryl, halo, haloalkyl, haloalkoxy, nitro, cyano, $CO_2R'$, methylenedioxy, $OR'$, $N(R')_2$, $C(O)N(R')_2$, $(C_1-C_4)$alkyl-$S(O)_q$, $SO_2NR'_2$, and $(C_1-C_6)$alkoxyl,
wherein R' is independently H, $(C_1-C_6)$ alkyl, $(C_1-C_6)$ haloalkyl, or $(C_3-C_9)$cycloalkyl, or wherein two R' bonded to an atom together with the atom form a 3-8 membered ring optionally further comprising a heteroatom selected from the group consisting of O, NR', and $S(O)_q$, and wherein alkyl, alkenyl, alkynyl, aryl, arylalkyl, or cycloalkyl is optionally mono- or independently multi-substituted with $(C_1-C_6)$alkyl, $(C_1-C_6)$haloalkyl, $(C_1-C_6)$alkoxy, $(C_1-C_6)$haloalkoxy, halo, $OR'$, $N(R')_2$, aryl, or aroyl; and wherein an alkyl or an alkyl group of a cycloalkylalkyl, heterocyclylalkyl, arylalkyl or heteroarylalkyl can be substituted with oxo;
each of $X^1$-$X^4$ is independently N or is C substituted with an independently selected $R^7$ or with Z, provided that no more than one of $X^1$-$X^4$ is N, and provided that there is one and only one Z group, present in the ring comprising $X^1$,
Z is a group of formula

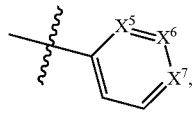

wherein a wavy line indicates a point of attachment, each $X^5$-$X^7$ is independently N or is C substituted with an independently selected H or $R^4$ provided that no more than one of $X^5$-$X^7$ is N;
each $R^4$ is independently halo, nitro, $(C_1-C_6)$fluoroalkyl, $R''$—$(C_1-C_6)$alkyl, $R''O_2C$—$(C_0-C_6)$alkyl, $NC$—$(C_0-C_6)$alkyl, $R''O$—$(C_0-C_6)$alkyl, $(R'')_2N$—$(C_0-C_6)$alkyl, $(R')_2NC(=O)$—$(C_0-C_6)$alkyl, C-bonded tetrazolyl, 3-hydroxypyrrolidin-1-carbonyl, 2-hydroxyethylaminocarbonyl, cyclohexylaminocarbonyl, 2-(N,N-dimethylaminocarbonyl)-2-hydroxyethylaminocarbonyl, N,N-dimethylaminoethylcarbonyl, N-methylaminocarbonyl, N-hydroxylaminocarbonyl, (1,3,4-oxadiazol-2(3H)-on)-yl, (1,2,4-oxadiazol-5(4H)-on)-3-yl, $(C_1-C_6)$alkyl-$S(O)_q(C_0-C_6)$alkyl, $R'S(O)_2NHC(O)$, $R'C(O)NHS(O)_2$, an unsubstituted or substituted aryl, an unsubstituted or substituted heteroaryl, $(C_1-C_6)$alkyl or $(C_3-C_9)$cycloalkyl-$(C_0-C_6)$alkyl, wherein any alkyl or cycloalkyl is optionally mono- or independently multi-substituted with R'', OR'', $N(R'')_2$, C-bonded tetrazolyl, ($C_1$-$C_6$)alkyl-S(O)$_q$($C_0$-$C_6$)alkyl, an unsubstituted or substituted aryl, or an unsubstituted or substituted heteroaryl; or R$^4$ is —(C(R")$_2$)$_m$CO$_2$R", —(C(R")$_2$)$_m$CON(R")$_2$, or —(C(R")$_2$)$_m$CN, —O(C(R")$_2$)$_m$CO$_2$R", —O(C(R")$_2$)$_m$CON(R")$_2$, or —O(C(R")$_2$)$_m$CN, wherein m is 1, 2, or 3;

R" is H, or ($C_1$-$C_6$) alkyl, or two R" together with an atom to which they are bonded form a ($C_3$-$C_9$)cycloalkyl;

q is 0, 1 or 2;

R$^5$ is H or ($C_1$-$C_4$)alkyl; R$^6$ is R$^7$; or R$^5$ and R$^6$ taken together form a —CH$_2$CH$_2$— group; and, R$^7$ is H, halo, CO$_2$R', CN, OR', N(R')$_2$, C(O)N(R')$_2$, ($C_1$-$C_4$)alkyl or ($C_1$-$C_4$)fluoroalkyl optionally substituted with OR' or N(R')$_2$, C-bonded tetrazolyl, or ($C_1$-$C_4$)alkyl-S(O)$_q$; or R$^7$ is —(C(R')$_2$)$_m$CO$_2$R' wherein m is 1, 2, or 3.

In various embodiments, the invention provides a pharmaceutical composition comprising a compound of the invention, and a pharmaceutically acceptable excipient.

In various embodiments, the invention provides a method of inhibiting a kinase-mediated, e.g., a cdk5-mediated, phosphorylation of PPARG in a mammal, comprising administering to the mammal an effective amount of a compound of the invention.

In various embodiments, the invention provides a method of treating a condition in a mammal, wherein binding of a ligand to PPARG or inhibition of kinase-mediated, such as cdk5-mediated, phosphorylation of PPARG, or both, is medically indicated, comprising administering to the mammal an effective amount of a compound of the invention at a frequency of dosing and for a duration of dosing effective to provide a beneficial effect to the mammal. For example, the condition can be diabetes, insulin resistance, impaired glucose tolerance, pre-diabetes, hyperglycemia, hyperinsulinemia, obesity, or inflammation. Side effects of significant weight gain, edema, impairment of bone growth or formation, or cardiac hypertrophy, or any combination thereof, can be avoided in the mammal receiving the compound.

In various embodiments, the invention provides a method of treatment of diabetes in a human, comprising administering to the human regularly over a duration of time an effective amount of a compound of the invention, optionally in conjunction with a second medicament effective for the treatment of the condition.

BRIEF DESCRIPTION OF THE FIGURES

FIG. 4 shows: (a) a graph showing reduction in PPARG phosphorylation at S273; (b) a graph showing fasting body weight or glucose levels (vehicle 110±13 mg/dL, rosiglitazone 88±13 mg/dL, and SR1664 90±12 mg/dL; mice receiving only the vehicle control remained hyperinsulinemic, but both rosiglitazone and SR1664 substantially reduced insulin levels; (c) a graph showing glucose tolerance tests were markedly improved with both rosiglitazone and SR1664, and the improvements in the areas under these glucose excursion curves were statistically indistinguishable, without changing body weight; (d) a graph showing increase in body weight from rosiglitazone treatment, an effect persisting for the duration of the experiment; and (e) and (f) graphs showing increase in body fat can also contribute to weight gain observed by MRI.

FIG. 5 is a bar graph showing inhibition of production of inflammatory cytokines by SR1664 (compound 73 herein) and rosiglitazone in lipopolysaccharide (LPS) stimulated RAW264.7 cells.

DETAILED DESCRIPTION

Overview

Figure 1A:
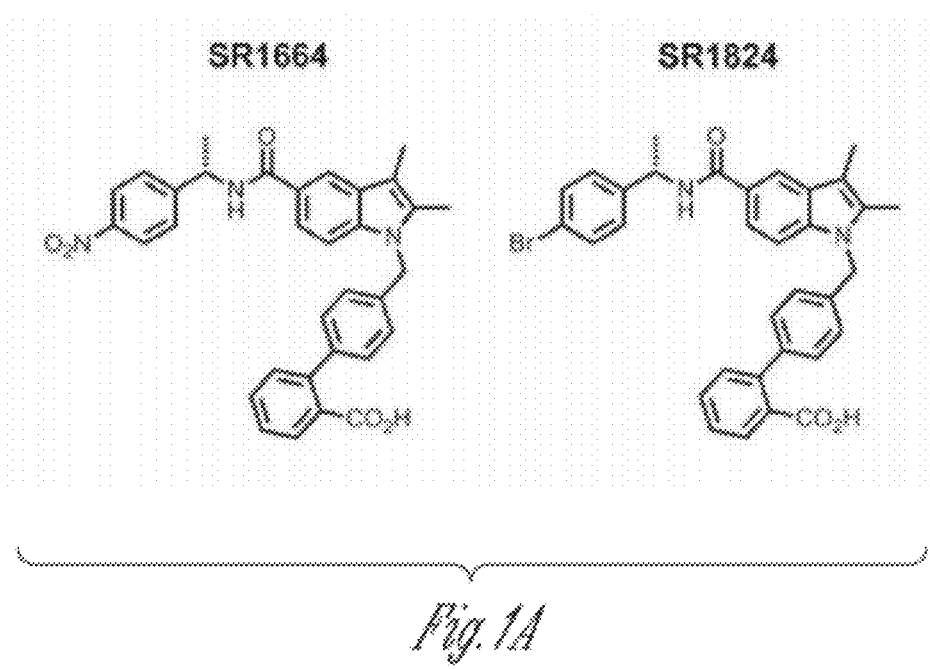
FIG. 1 shows: (a) compounds of the invention SR1664 (compound 73, below) and SR1824 (compound 1, below); (b) shows the results of a classical transcriptional activity assay on a tandem PPRE::Luc reporter; (c) gel electrophoresis Western blots showing rosiglitazone and SR1664 both effectively block the cdk5-mediated phosphorylation of PPARG in vitro with half-maximal effects between 20 and 200 nM; (d) gel electrophoresis Western blots showing no effect on the phosphorylation of a well characterized cdk5 substrate, the Rb protein; and (e) gel electrophoresis Western blots showing cdk5-mediated phosphorylation of PPARG in differentiated fat cells.

PPARG (also known as PPARγ) is a member of the nuclear receptor family of transcription factors. This protein is a dominant regulator of adipose cell differentiation and development. It is also the functioning receptor for the thiazolidinedione (TZD) class of anti-diabetic drugs, such as rosiglitazone and pioglitazone. These drugs were developed before their molecular modes of action were known, but later compounds were developed specifically as anti-diabetic drugs with high affinity and full agonism toward PPARG transcriptional activity. It has therefore been assumed that the therapeutic actions of these drugs result from their functional agonism on this receptor. From a clinical perspective, rosiglitazone (Avandia®) and pioglitazone (Actos®) are both highly effective oral medications for type 2 diabetes and are well tolerated by the majority of patients. Unfortunately, a substantial number of patients experience side effects from these drugs, including fluid retention, congestive heart failure and loss of bone mineral density. Since many diabetics have pre-existing cardiovascular disease or are at risk for heart problems, the fluid retention is particularly troubling. While some of the non-TZD full agonists also have good anti-diabetic activity, they also cause many of the same side effects, including fluid retention.

The therapeutic role of classical agonism of PPARG was made somewhat confusing by the development of several compounds that have less than full agonist properties (partial agonists) but retain substantial insulin-sensitizing and anti-diabetic actions in experimental models. Furthermore, we have recently shown that many anti-diabetic PPARG ligands of the TZD and other chemical classes have a second, distinct biochemical function: blocking the obesity-linked phosphorylation of PPARG by cyclin-dependent kinase 5 (cdk5) at serine 273. This is a direct action of the ligands and requires binding to the PPARG ligand binding domain (LBD) causing a conformational change that interferes with the ability of cdk5 to phosphorylate serine 273. Other kinase enzymes than ckd-5 can also mediate the phosphorylation of PPARG, and compounds of the invention can block the phosphorylation of PPARG without acting as PPARG agonists.

Rosiglitazone and MRL24 (a selective PPARG partial agonist) both modulate serine 273 phosphorylation at therapeutic doses in mice. Furthermore, a small clinical trial of newly diagnosed type 2 diabetics showed a remarkably close association in individual patients between the clinical effects of rosiglitazone and the blocking of this phosphorylation in PPARG. Thus, the contribution made by classical agonism to the therapeutic effects of these drugs or to their side effects can be deleterious.

The inventors herein have developed entirely new classes of compounds than can be effective anti-diabetic drugs that are optimized for the inhibition of cdk5-mediated phosphorylation of PPARG while being devoid of classical agonism. In this application we describe the development of a class of synthetic small molecules that bind tightly to PPARG and effectively inhibit phosphorylation at serine 273, yet are completely devoid of classical agonism. These compounds have unique binding modes in the ligand binding pocket of PPARG. An example possessing this type of bioactivity has been found to exhibits potent and dose-dependent anti-diabetic effects in obese mice. Importantly, this compound does not cause the fluid retention, weight gain, or impact mineralization in MC3T3 cells as is seen with rosiglitazone and other drugs that are full or partial agonists of PPARG.

Development of Novel Non-Agonistic PPARG Ligands

Figure 1B:
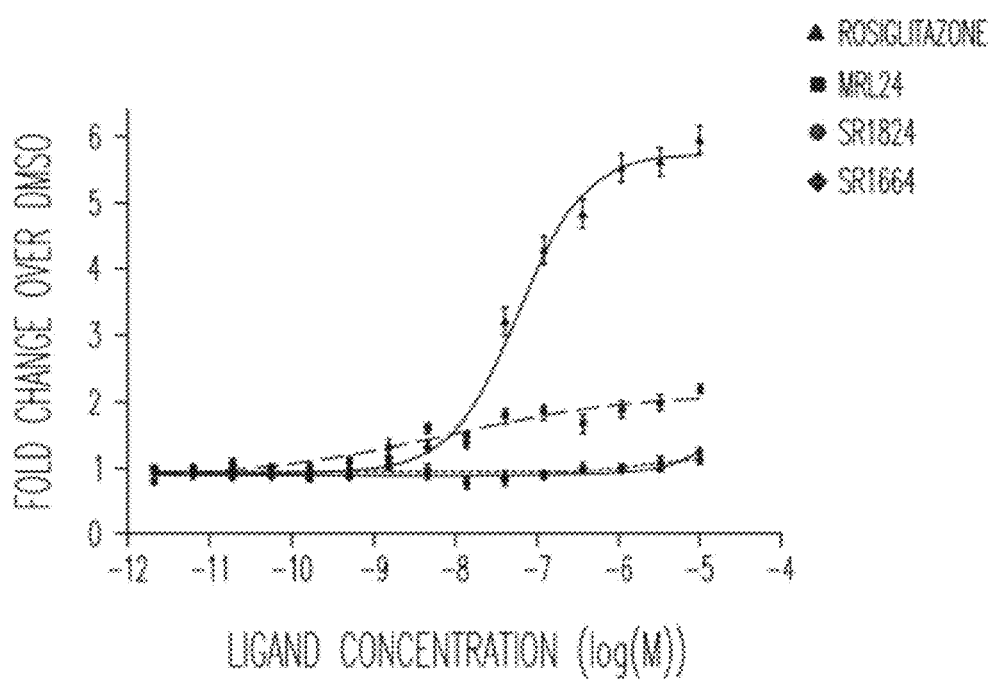
Figure 1C:
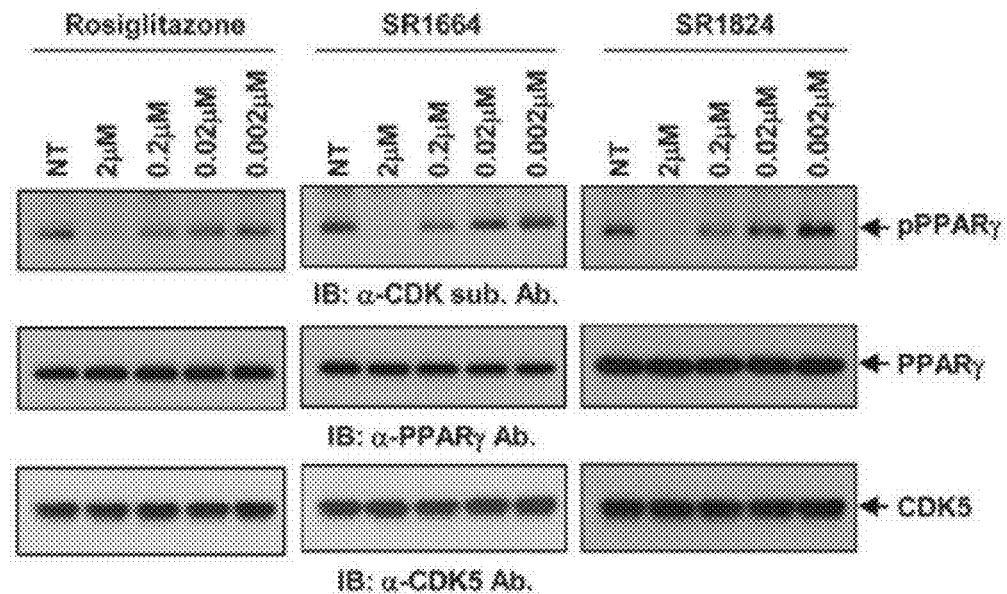
Figure 1D:
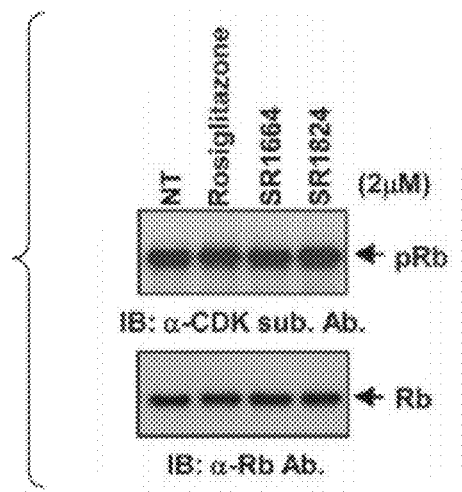
Figure 1B:
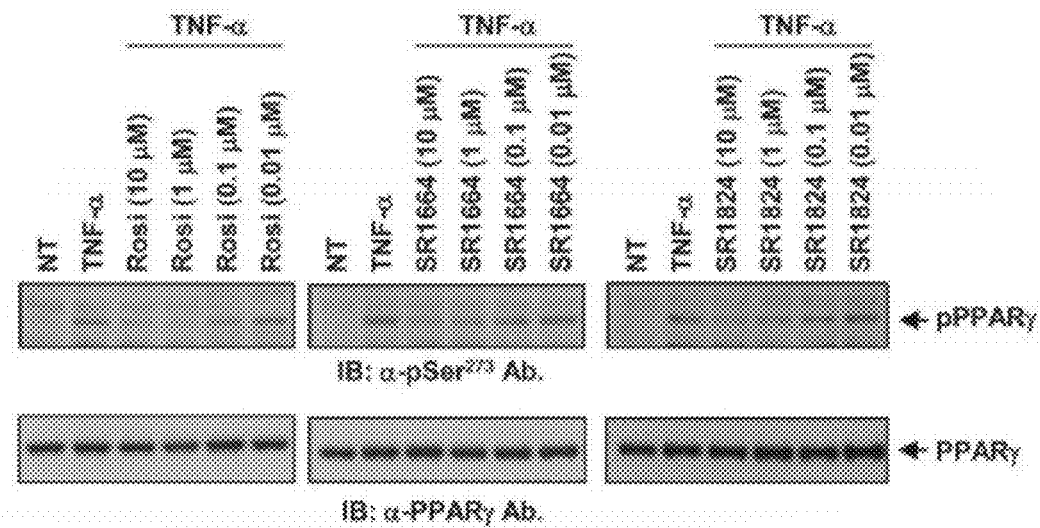

In order to develop a suitable ligand, we optimized compounds for (i) high binding affinity for PPARG, (ii) blocking the cdk5-mediated PPARG phosphorylation and (iii) lacking classical agonism. Classical agonism is defined here, as is standard in the nuclear receptor field, as an increased level of transcription through a tandem PPAR response element luciferase reporter (PPRE::Luc). Using a lanthascreen competitive binding assay, compound SR1664 (FIG. 1a) had an $IC_{50}$ of 80 nM, indicating potent PPARG binding in vitro. As shown in FIG. 1b, when compared to rosiglitazone or MRL24 (a partial agonist), in a classical transcriptional activity assay on a tandem PPRE::Luc reporter, SR1664 had essentially no transcriptional agonism at any concentration. Rosiglitazone and SR1664 both effectively blocked the cdk5-mediated phosphorylation of PPARG in vitro (FIG. 1c) with half-maximal effects between 20 and 200 nM. In contrast, they had no effect on the phosphorylation of a well characterized cdk5 substrate, the Rb protein (FIG. 1d). This suggested that these compounds do not disrupt the basic protein kinase function of cdk5. In addition, SR1664 was also effective at blocking cdk5-mediated phosphorylation of PPARG in differentiated fat cells (FIG. 1e), indicating that SR1664 is effective in penetrating into living cells.

Other compounds of formula (I) were also synthesized and tested. Another compound of the invention, SR1824 (FIG. 1a), was further characterized to demonstrate its ability to block cdk5-dependent phosphorylation of PPARG (FIG. 1b-e). These data demonstrate the existence of molecular entities that bind PPARG at nanomolar concentrations, potently block cdk5-dependent phosphorylation of PPARG in cells, while demonstrating little to no classical agonism.

SR1664, a specifically claimed compound of the invention, was thus identified as non-agonist inhibitor of cdk5-mediated PPARG phosphorylation. SR1664 also was found to possess adequate pharmacokinetic properties to move forward to biological and therapeutic assays. Adipogenesis was the first known biological function of PPARG (Tontonoz et al., 1994) and agonist ligands for PPARG have been shown to potently stimulate the differentiation of pre-adipose cell lines; this response has been widely used as a sensitive cellular test for PPARG agonism (Kliewer et al., 1995; Lehmann et al., 1995).

Figure 2A:
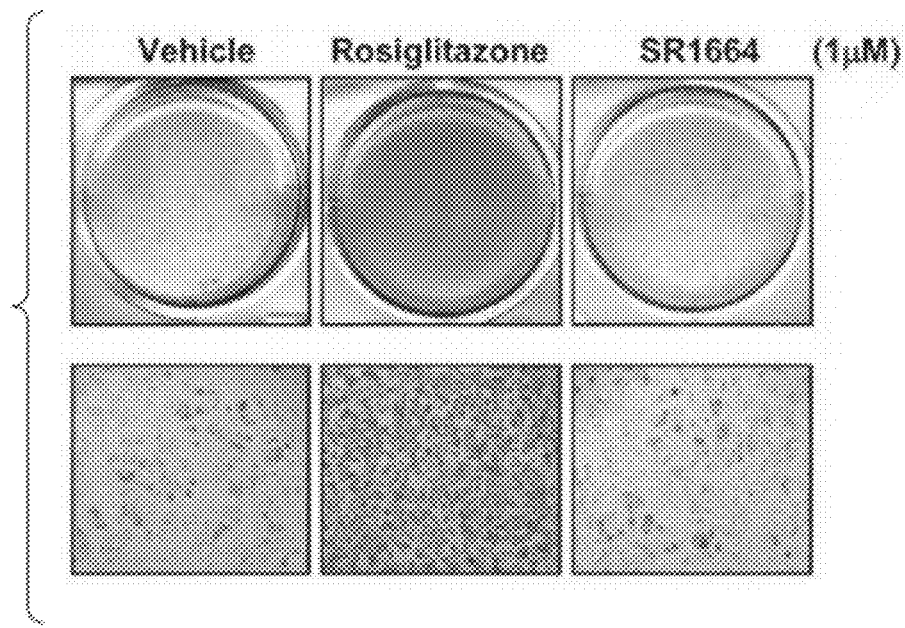
FIG. 2 shows: (a) photographs showing that rosiglitazone potently stimulated fat cell differentiation, as evidenced by Oil Red O staining of the cellular lipid; (b) graphs showing relative gene expression of aP2, C/EBPα and Glut4 in the presence of rosiglitazone and SR1664; and (c) mineralization (calcification) of mouse osteoblastic cells (MC3T3-E1 cells), as measured by Alizarin red S staining.
Figure 2B:
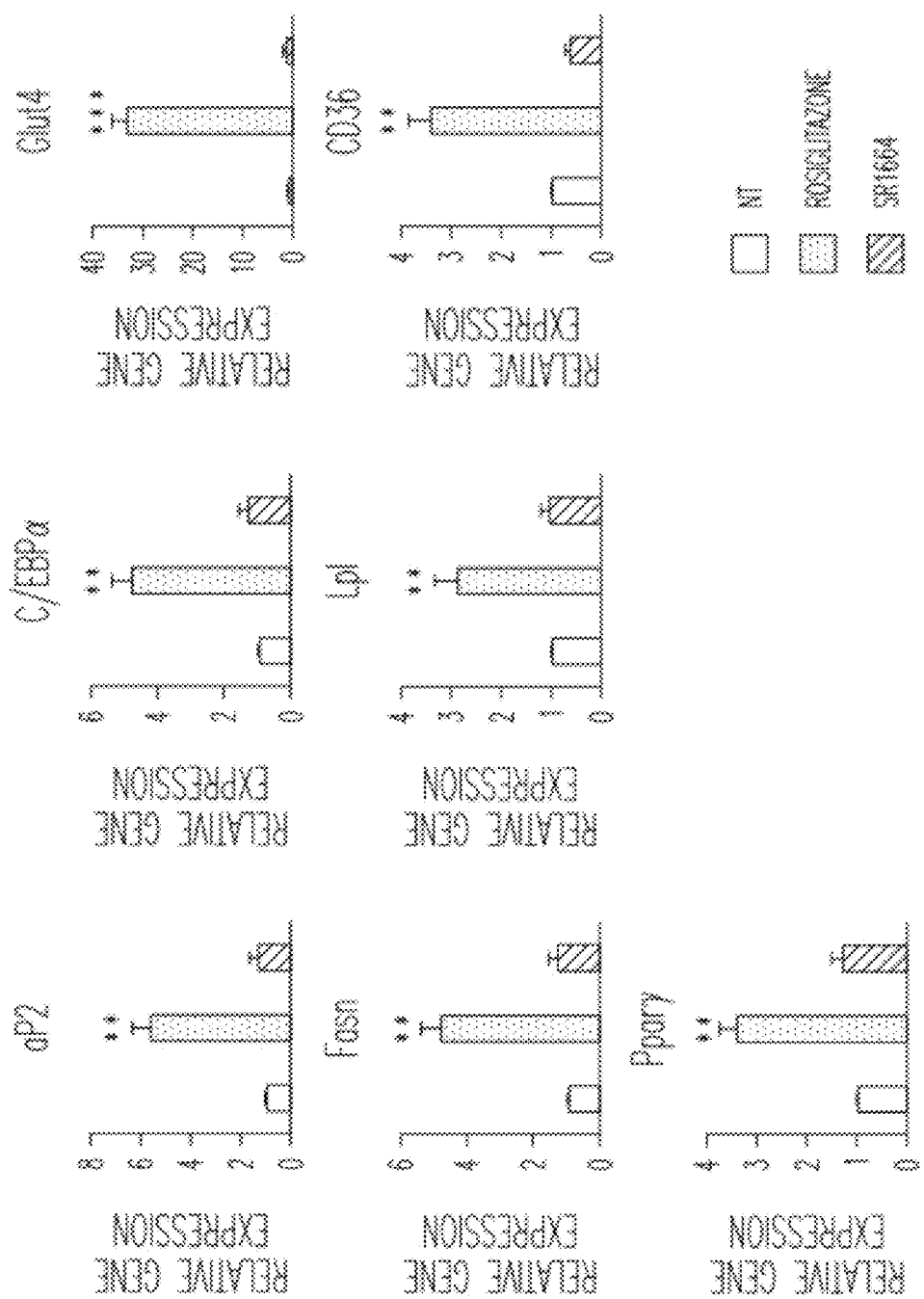

As shown in FIG. 2a, rosiglitazone potently stimulated fat cell differentiation, as evidenced by Oil Red O staining of the cellular lipid. In contrast, SR1664 did not stimulate increased lipid accumulation or changes in morphology characteristic of differentiating fat cells. The stimulation of fat cell gene expression was also apparent with rosiglitazone, as illustrated by an increased expression of aP2, C/EBPα and Glut4 (FIG. 2b). In contrast, SR1664 induced little or no change in the expression of these genes linked to adipogenesis.

Figure 2C:
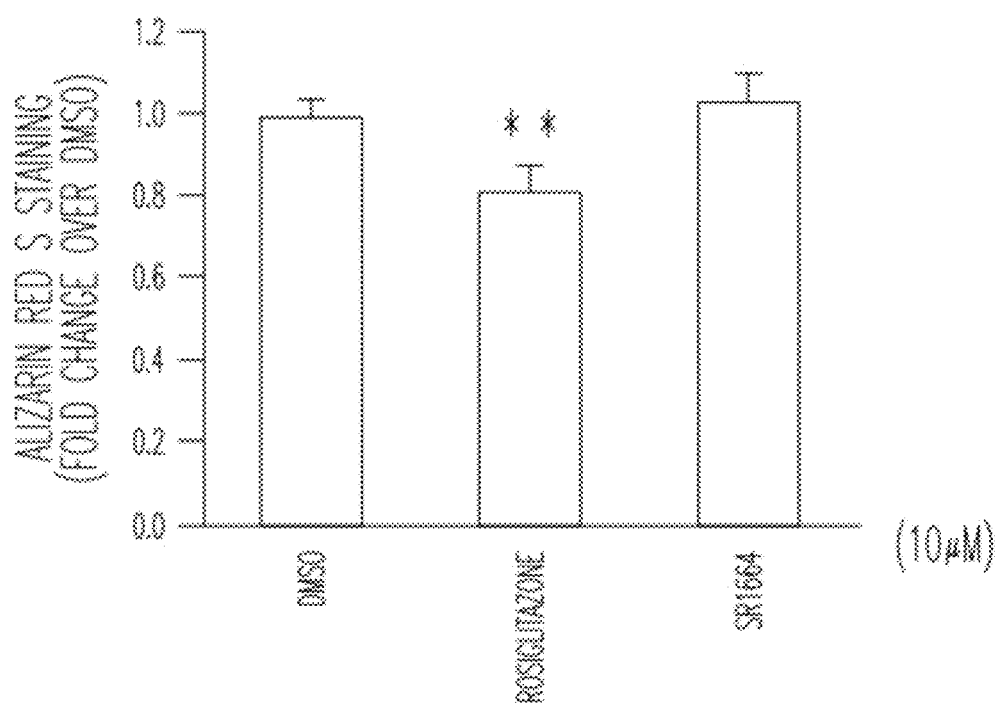
Figure 2D:
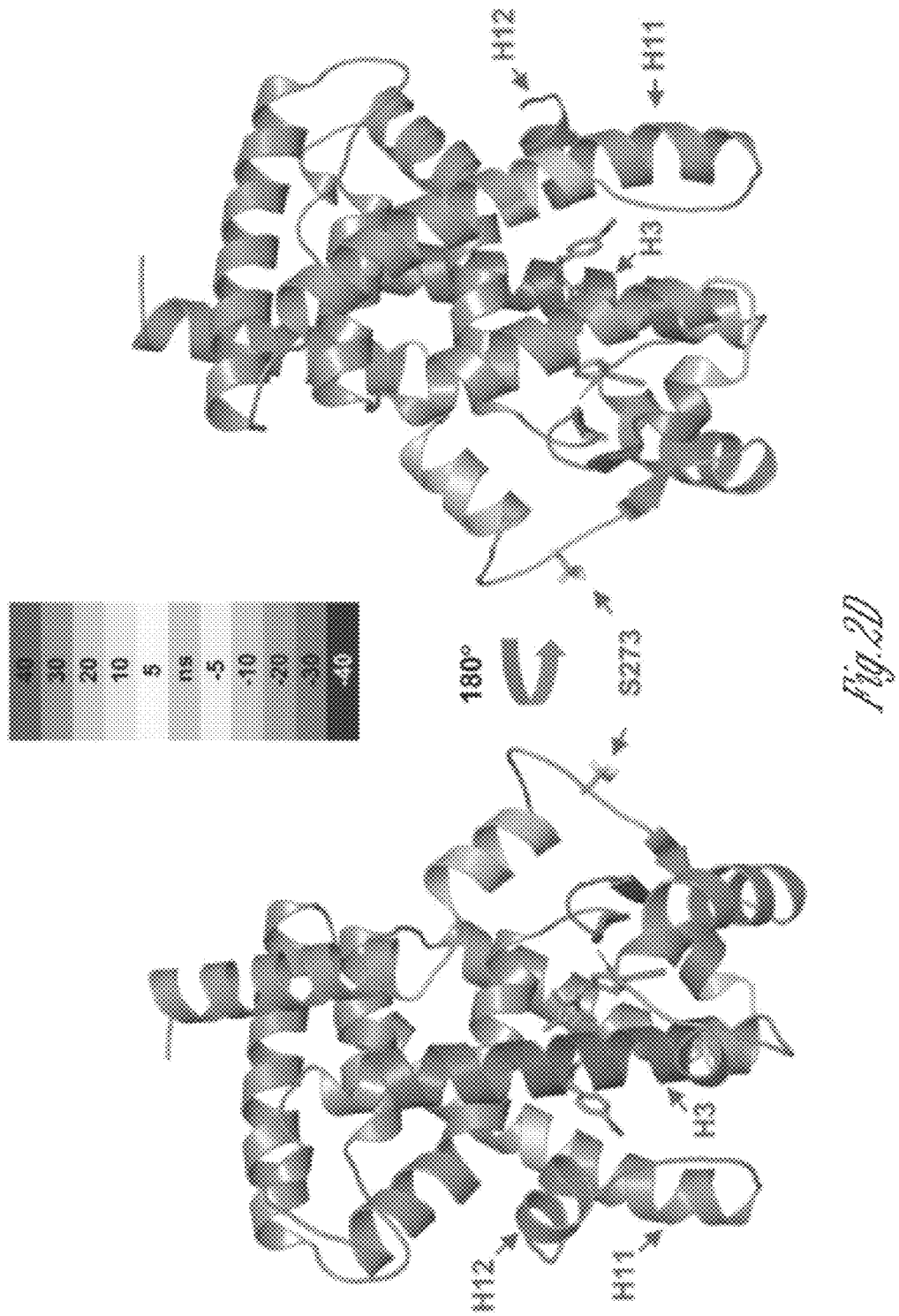

Another widely reported side effect of both rosiglitazone and pioglitazone is that they decrease bone formation and bone mineral density leading to an increase in fracture risk (Grey et al., 2007; Kahn et al., 2008). TZDs have also been shown to decrease bone mineralization in cultured osteoblasts (Lecka-Czemik, 1999). As shown in FIG. 2c, rosiglitazone treatment reduced the mineralization (calcification) of mouse osteoblastic cells (MC3T3-E1 cells), as measured by Alizarin red S staining. Moreover, the expression of genes involved in the differentiation of these cells was impaired (alkaline phosphatase, RANKL, type I collagen). Importantly, the treatment with SR1664 did not affect the extent of calcification or the expression of this osteoblast gene set in MC3T3-E1 cells.

Figures 3A, 3B:
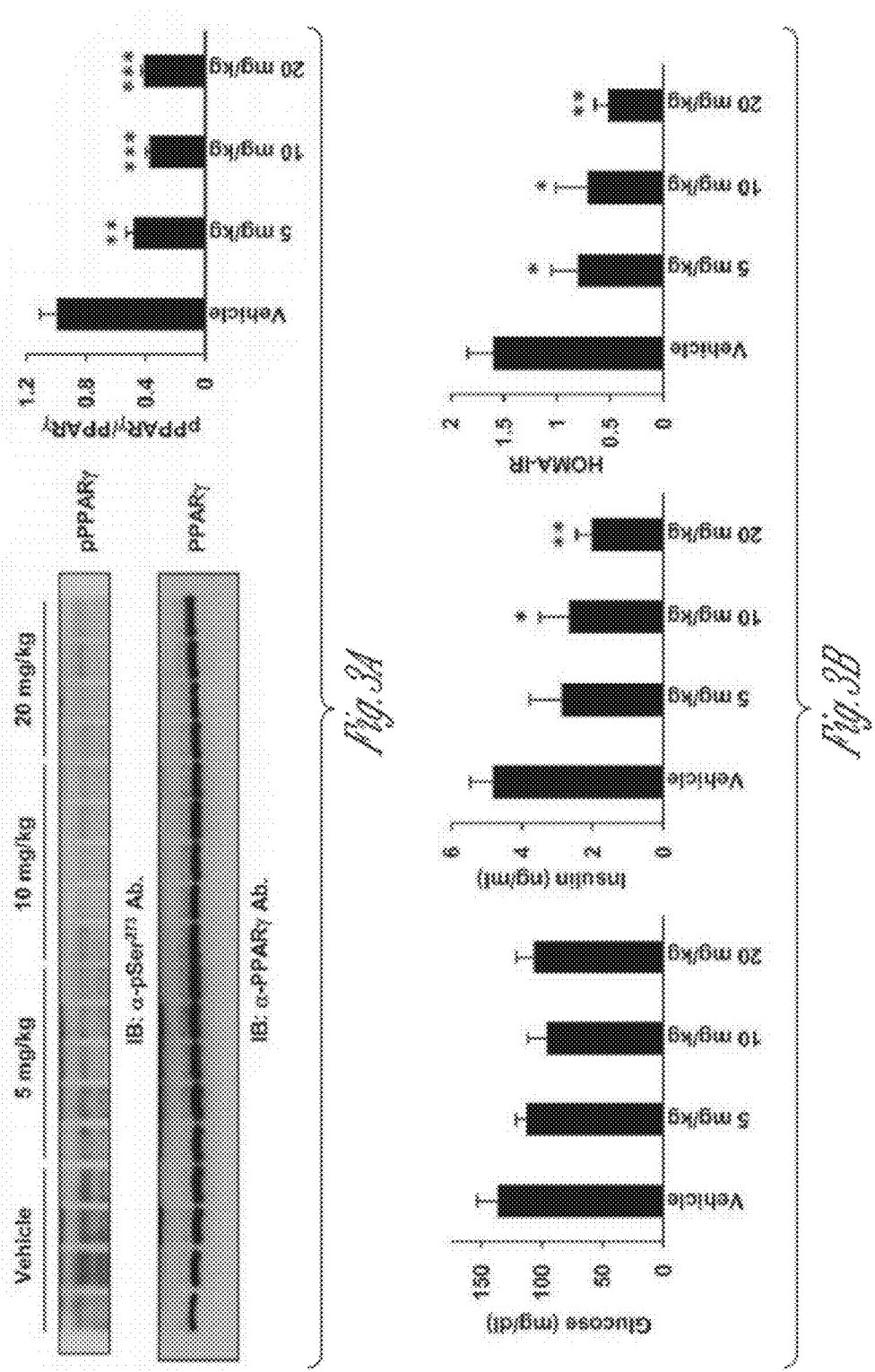
FIG. 3 shows: (a) gel electrophoresis Western blots showing the effect of SR1664, injected in mice twice daily for 5 days, causing a dose-dependent decrease in the cdk5-mediated phosphorylation of PPARG at serine 273 in adipose tissue; (b) a graph of insulin resistance, as computed by HOMA-IR, showed a clear and dose-dependent improvement with SR1664; (c) a graph showing the glucose infusion rate (GIR) needed to maintain euglycemia in the mice treated with SR1664 was significantly greater than in animals treated with the vehicle alone; (d) a graph showing changes in the expression of 11/17 (65%) of these genes, all in the direction predicted for the inhibition of the PPARG S273 phosphorylation; and (e) a graph showing changes in expression of 6/19 genes in this "agonist" gene set. Importantly, three of these changes were in the same direction as expected for an agonist, but three were changed in the opposite direction.

Anti-Diabetic Activity of a Non-Agonist that Blocks cdk5-Dependent Phosphorylation Wild-type mice fed a calorie dense diet high in sugar and fat become obese and insulin-resistant, with activation of cdk5 in their adipose tissues (Choi et al., 2010). FIG. 3a demonstrates that SR1664, injected twice daily for 5 days, caused a dose-dependent decrease in the cdk5-mediated phosphorylation of PPARG at serine 273 in adipose tissue. Moreover, SR1664 treatment also caused a trend toward lowered (and normalized) glucose levels, and a significant reduction in the fasting insulin levels. Insulin resistance, as computed by HOMA-IR, showed a clear and dose-dependent improvement with SR1664 (FIG. 3b). These changes occurred without significant differences in body weight compared to vehicle treated mice.

Figure 3C:
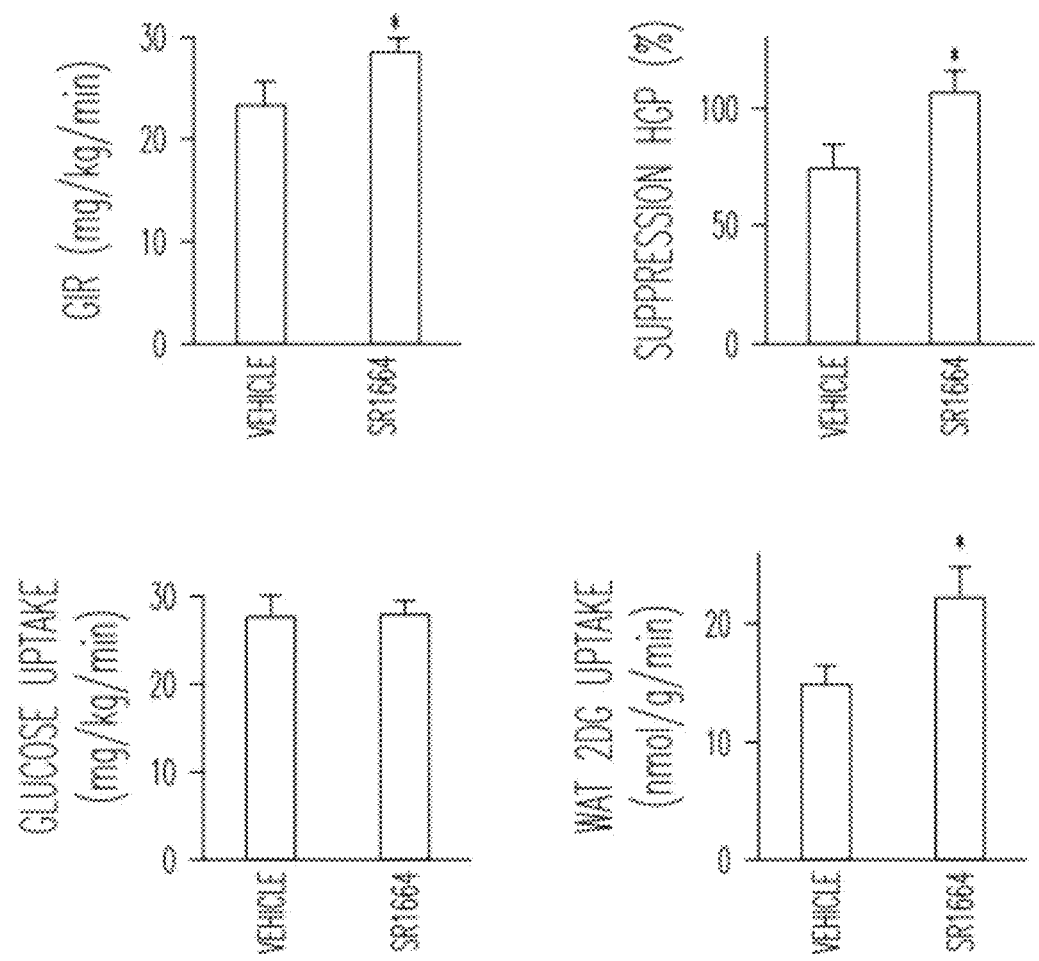

The most accurate method for measuring changes in insulin sensitivity is the hyperinsulinemic-euglycemic clamp (DeFronzo et al., 1979). In this method, animals are exposed to an elevated concentration of insulin while the amount of glucose infused is adjusted in real time to maintain fixed, or clamped glycemia. As shown in FIG. 3c, the glucose infusion rate (GIR) needed to maintain euglycemia in the mice treated with SR1664 was significantly greater than in animals treated with the vehicle alone. This indicates that SR1664 works as an insulin sensitizer. Suppression of endogenous hepatic glucose production (EGP), an important component of insulin action, was increased by SR1664. While whole body glucose utilization was not increased, glucose uptake in the adipose tissue, a marker of insulin sensitivity, was significantly enhanced. Similarly, the reduction in plasma FFA under basal and clamped conditions suggest improvements in adipose tissue insulin sensitivity. Thus, these data indicate that SR1664 improves insulin sensitivity.

Figure 3D:
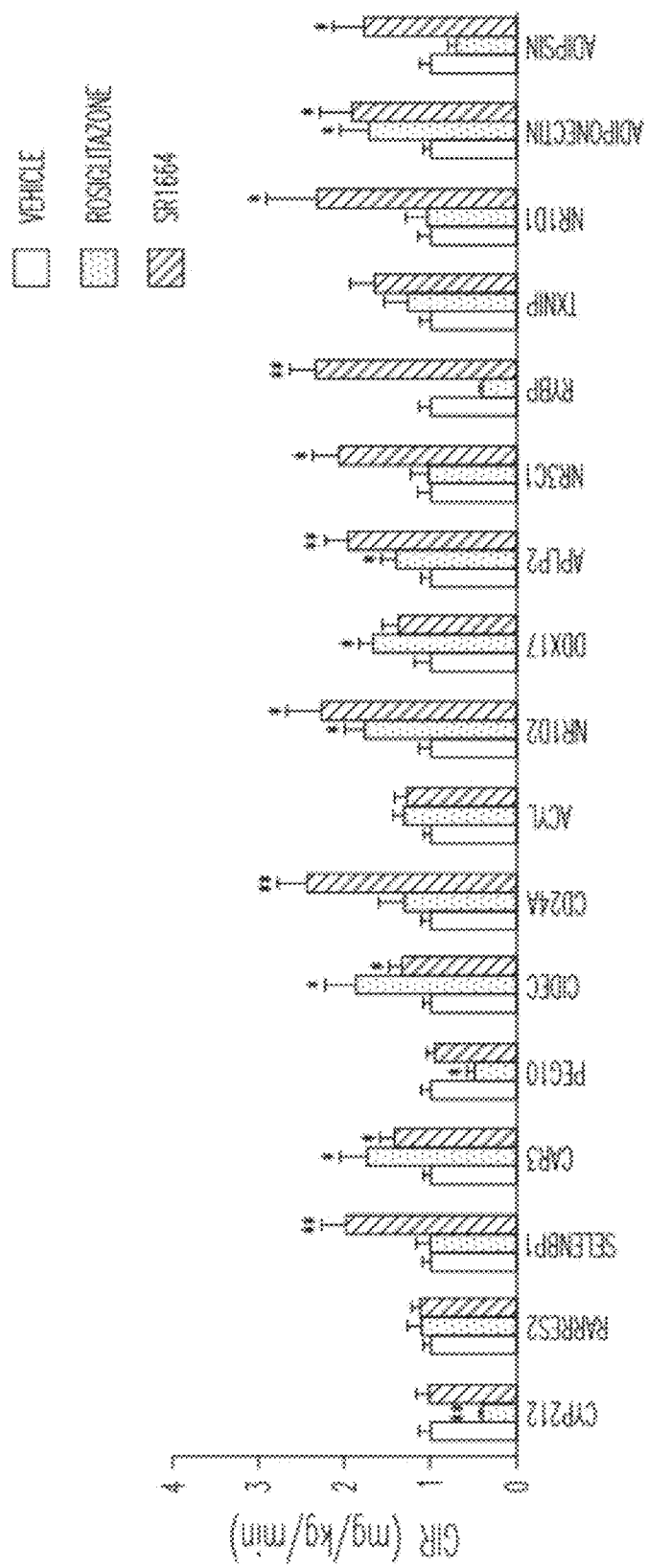
Figure 9B:
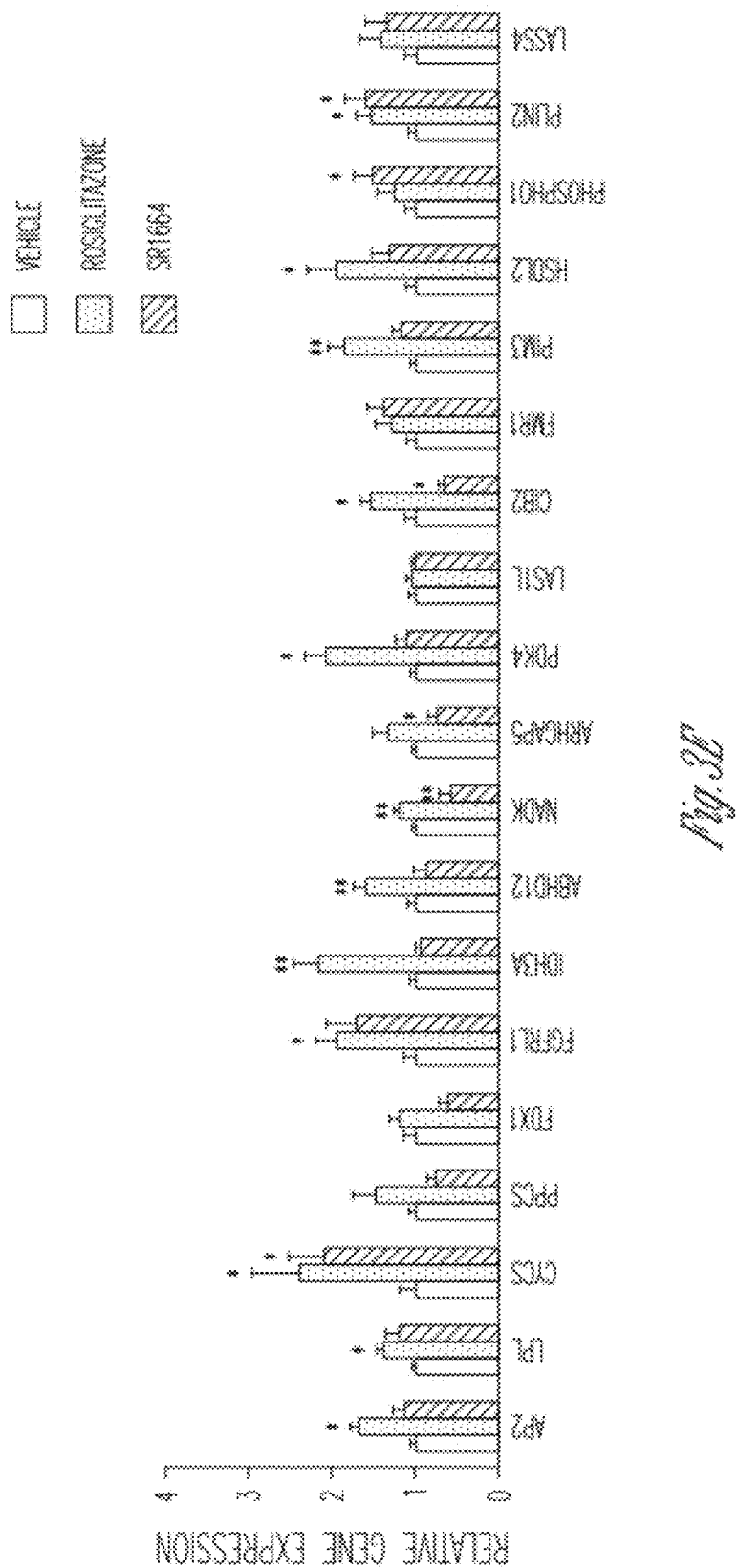

Using cells expressing the S273A mutant of PPARG, we previously defined a gene set in cultured adipose cells that was most sensitive to this phosphorylation (Choi et al, 2010). Inhibition of cdk5 with a chemical inhibitor or administration of a partial agonist caused significant changes in 9/17 (53%) members of this gene set (Choi et al, 2010). Treatment of mice with SR1664 caused changes in the expression of 11/17 (65%) of these genes, all in the direction predicted for the inhibition of the PPARG S273 phosphorylation (FIG. 3d). Adiponectin and adipsin, genes long recognized for being reduced in obesity (Hu et al, 1996; Yamauchi et al, 2001; Flier et al, 1987), are both induced by SR1664. We also defined a separate set of genes reflective of a full agonist (rosiglitazone) on cultured fat cells. SR1664 caused changes in expression of 6/19 genes in this "agonist" gene set; importantly, three of these changes were in the same direction as expected for an agonist, but three were changed in the opposite direction (FIG. 3e). Taken together, these data show that SR1664 has an insulin-sensitizing effect with preferential regulation of the gene set sensitive to the phosphorylation of PPARG by cdk5.

A more severe model of obesity is the leptin-deficient ob/ob mouse. These animals are very obese and insulin-resistant, with substantial compensatory hyperinsulinemia. We performed preliminary pharmacokinetic and pharmacodynamic experiments comparing rosiglitazone and SR1664, to determine dosing regimens. Comparable drug exposures were achieved with treatments of 40 mg/kg for SR1664 and 8 mg/kg for rosiglitazone, both injected twice daily. Functional analyses were performed at days 5 and 11 after the start of treatments. As shown in FIG. 4a, both drugs caused a similar reduction in PPARG phosphorylation at S273. After five days of treatment, there were no overt differences in fasting body weight or glucose levels (vehicle 110±13 mg/dL, rosiglitazone 88±13 mg/dL, and SR1664 90±12 mg/dL; FIG. 4b). Mice receiving only the vehicle control remained hyperinsulinemic, but both rosiglitazone and SR1664 substantially reduced these insulin levels (FIG. 4b). Glucose tolerance tests were markedly improved with both rosiglitazone and SR1664, and the improvements in the areas under these glucose excursion curves were statistically indistinguishable, without changing body weight (FIG. 4c).

Longer treatments with these drugs allowed an assessment of certain side effects. While there is no definitive proof, weight gain and fluid retention caused by TZD drugs like rosiglitazone are usually thought to be key factors in their increased cardiac risk (Kahn and McGraw, 2010). Rosiglitazone treated mice showed an increase in body weight, an effect persisting for the duration of the experiment (FIG. 4d). This increased mass is accounted for primarily by fluid retention, quantified by a characteristic decrease in hematocrit seen with hemodilution. However, an increase in body fat can also contribute to weight gain and this was observed by MRI (FIGS. 4e and 4f). Importantly, SR1664 treatment did not cause the weight gain seen with the rosiglitazone treatment. Furthermore, SR1664 treatment showed no decrease in the hematocrit or change in body adiposity. These results were confirmed by measurements showing a decreased concentration of hemoglobin in the mice treated with rosiglitazone but not those treated with SR1664. Taken together, these data indicate that SR1664, a non-agonist PPARG ligand, has antidiabetic actions in two murine models of insulin-resistance. Furthermore, this non-agonist does not stimulate two of the best documented side-effects of the PPARG agonist drugs in vivo. It has unexpectedly been discovered by the inventors that it is possible to create new ligands that have high affinity for PPARG, block the cdk5-mediated phosphorylation and lack classical agonism, and that these new molecular entities can be effective therapeutic agents for a variety of conditions such as type II diabetes.

That classical agonism is not required for strong anti-diabetic actions of a PPARG ligand is clear based on the effects of SR1664 in obese, insulin-resistant mice (FIGS. 3 and 4). In both diet induced obesity and genetically obese animals, SR1664 has clear-cut anti-diabetic actions. The ability to improve adipose tissue insulin sensitivity is similar to the effects shown for rosiglitazone (Mayerson et al., 2002). Using our best calculations to get approximately equal exposure to the two drugs in vivo, SR1664 has very robust anti-diabetic activity, roughly equivalent to rosiglitazone in the experiments shown in FIG. 4.

Side effects of PPARG ligands such as weight gain and fluid retention occur relatively rapidly in both humans and mice. As shown in FIG. 4, increased body weight, increased accretion of fat tissues and increased fluid retention all occur in mice within 11 days of treatment with rosiglitazone. The non-agonist SR1664 shows none of these side effects, even as it is effectively improving glucose homeostasis. Unlike rosiglitazone, SR1664 also does not affect bone cell mineralization in culture (FIG. 2c), though the precise relationship of this assay to bone loss in vivo under the TZD drugs must be considered speculative. However, taken together, these data argue rather strongly that many of the known side effects of the TZD drugs must occur as a consequence of classical agonism on target genes.

Our central hypothesis is that "classical agonism of PPARG correlates with the adverse side effects of TZDs (and likely partial agonists as well), and that the blockage of cdk5-mediated phosphorylation of PPARG correlates with insulin sensitization efficacy"

The compounds we identify as non-agonist PPARG mudulators are non-agonists that are potent blockers of cdk5-mediated phosphorylation of PPARG. Such a compound will have the following properties:
1. High affinity binding to PPARG
2. Minimal or no classical agonism
   a. Classical agonism is defined as AF-2 mediated coactivator interaction. Coactivator can be anyone of the p160 family or TRAP220 family members, as well as any coactivator shown to interact with PPARG
3. Compound is cell penetrant as determined by the cell based blockage of S273-P in differentiated preadipocytes or when a fixed concentration of compound added to cells alters the transcriptional activity of rosiglitazone on a tandem PPRE::Luc reporter. The compounds do not stimulate increased lipid accumulation or changes in morphology characteristic of differentiating fat cells.
4. Compounds may be antagonist of PPARG but not inverse agonists (they do not repress PPARG target genes).

In vivo such compounds do not increase the expression of a classified agonist gene set but do modulate the cdk5 gene set (Choi et al Nature. 2011 Sep. 4; 477(7365):477-81. doi: 10.1038/nature10383).

We currently believe a compound of the invention (i.e., a compound with the desirable properties recited above) is a compound that shows, at a concentration 10 times its IC50 in the lanthascreen assay, less than 5% transactivation relative to rosiglitazone in a receptor promoter reporter cotransfection assay with wild type human or mouse PPARG and a PPRE reporter. Specific protocols for the two assays, lanthascreen (IC50) and PPRE (EC50), and exemplary results are presented below.

FIG. 5 is a bar graph showing inhibition of production of inflammatory cytokines by SR1664 (compound 73 herein) and rosiglitazone in lipopolysaccharide (LPS) stimulated RAW264.7 cells. The results of this standard assay indicate that a compound of the invention possesses potent anti-inflammatory properties. Accordingly, it is believed that a compound of the invention can be used in the treatment of inflammation, with the potential of avoiding the undesired side-effects described herein that can result from agonism of PPARG.

Definitions

As used in the specification and the appended claims, the singular forms "a," "an" and "the" include plural referents unless the context clearly dictates otherwise.

The term "about" as used herein, when referring to a numerical value or range, allows for a degree of variability in the value or range, for example, within 10%, or within 5% of a stated value or of a stated limit of a range.

All percent compositions are given as weight-percentages, unless otherwise stated.

All average molecular weights of polymers are weight-average molecular weights, unless otherwise specified.

As used herein, "individual" (as in the subject of the treatment) or "patient" means both mammals and non-mammals. Mammals include, for example, humans; non-human primates, e.g., apes and monkeys; and non-primates, e.g., dogs, cats, cattle, horses, sheep, and goats. Non-mammals include, for example, fish and birds.

The term "disease" or "disorder" or "condition" are used interchangeably, and are used to refer to diseases or conditions wherein PPARG plays a role in the biochemical mechanisms involved in the disease or condition or symptom(s) thereof such that a therapeutically beneficial effect can be achieved by acting on PPARG. "Acting on" PPARG, or "modulating" PPARG, can include binding to PPARG and/or inhibiting the bioactivity of PPARG and/or allosterically regulating the bioactivity of PPARG in vivo.

In various embodiments, the compounds of the invention are not agonists of PPARG; i.e., binding of the compound to PPARG does not activate the receptor, as discussed in greater detail below. In various embodiments, compounds of the invention bring about inhibition of cdk5-mediated phosphorylation of PPARG while being devoid of classical agonism. When the term "modulator" is used herein, the term alludes to a compound of the invention, and it is understood that the terms "modulator" and "compound" or "compound of the invention" are synonymous when the context indicates that a compound of the present invention is being referred to.

The expression "effective amount", when used to describe therapy to an individual suffering from a disorder, refers to the amount of a compound of the invention that is effective to inhibit or otherwise act on PPARG in the individual's tissues wherein PPARG involved in the disorder is active, wherein such inhibition or other action occurs to an extent sufficient to produce a beneficial therapeutic effect.

"Substantially" as the term is used herein means completely or almost completely; for example, a composition that is "substantially free" of a component either has none of the component or contains such a trace amount that any relevant functional property of the composition is unaffected by the presence of the trace amount, or a compound is "substantially pure" is there are only negligible traces of impurities present.

"Treating" or "treatment" within the meaning herein refers to an alleviation of symptoms associated with a disorder or disease, or inhibition of further progression or worsening of those symptoms, or prevention or prophylaxis of the disease or disorder, or curing the disease or disorder. Similarly, as used herein, an "effective amount" or a "therapeutically effective amount" of a compound of the invention refers to an amount of the compound that alleviates, in whole or in part, symptoms associated with the disorder or condition, or halts or slows further progression or worsening of those symptoms, or prevents or provides prophylaxis for the disorder or condition. In particular, a "therapeutically effective amount" refers to an amount effective, at dosages and for periods of time necessary, to achieve the desired therapeutic result. A therapeutically effective amount is also one in which any toxic or detrimental effects of compounds of the invention are outweighed by the therapeutically beneficial effects.

Phrases such as "under conditions suitable to provide" or "under conditions sufficient to yield" or the like, in the context of methods of synthesis, as used herein refers to reaction conditions, such as time, temperature, solvent, reactant concentrations, and the like, that are within ordinary skill for an experimenter to vary, that provide a useful quantity or yield of a reaction product. It is not necessary that the desired reaction product be the only reaction product or that the starting materials be entirely consumed, provided the desired reaction product can be isolated or otherwise further used.

By "chemically feasible" is meant a bonding arrangement or a compound where the generally understood rules of organic structure are not violated; for example a structure within a definition of a claim that would contain in certain situations a pentavalent carbon atom that would not exist in nature would be understood to not be within the claim. The structures disclosed herein, in all of their embodiments are intended to include only "chemically feasible" structures, and any recited structures that are not chemically feasible, for example in a structure shown with variable atoms or groups, are not intended to be disclosed or claimed herein.

An "analog" of a chemical structure, as the term is used herein, refers to a chemical structure that preserves substantial similarity with the parent structure, although it may not be readily derived synthetically from the parent structure. A related chemical structure that is readily derived synthetically from a parent chemical structure is referred to as a "derivative."

When a substituent is specified to be an atom or atoms of specified identity, "or a bond", a configuration is referred to when the substituent is "a bond" that the groups that are immediately adjacent to the specified substituent are directly connected to each other in a chemically feasible bonding configuration.

All chiral, diastereomeric, racemic forms of a structure are intended, unless a particular stereochemistry or isomeric form is specifically indicated. Compounds used in the present invention can include enriched or resolved optical isomers at any or all asymmetric atoms as are apparent from the depictions, at any degree of enrichment. Both racemic and diastereomeric mixtures, as well as the individual optical isomers can be isolated or synthesized so as to be substantially free of their enantiomeric or diastereomeric partners, and these are all within the scope of the invention.

As used herein, the terms "stable compound" and "stable structure" are meant to indicate a compound that is sufficiently robust to survive isolation to a useful degree of purity from a reaction mixture, and formulation into an efficacious therapeutic agent. Only stable compounds are contemplated herein.

A "small molecule" refers to an organic compound, including an organometallic compound, of a molecular weight less than about 2 kDa, that is not a polynucleotide, a polypeptide, a polysaccharide, or a synthetic polymer composed of a plurality of repeating units.

As to any of the groups described herein, which contain one or more substituents, it is understood that such groups do not contain any substitution or substitution patterns which are sterically impractical and/or synthetically non-feasible. In addition, the compounds of this disclosed subject matter include all stereochemical isomers arising from the substitution of these compounds.

Selected substituents within the compounds described herein are present to a recursive degree. In this context, "recursive substituent" means that a substituent may recite another instance of itself. Because of the recursive nature of such substituents, theoretically, a large number may be present in any given claim. One of ordinary skill in the art of medicinal chemistry and organic chemistry understands that the total number of such substituents is reasonably limited by the desired properties of the compound intended. Such properties include, by of example and not limitation, physical properties such as molecular weight, solubility or log P, application properties such as activity against the intended target, and practical properties such as ease of synthesis. Recursive substituents are an intended aspect of the disclosed subject matter. One of ordinary skill in the art of medicinal and organic chemistry understands the versatility of such substituents. To the degree that recursive substituents are present in a claim of the disclosed subject matter, the total number should be determined as set forth above.

When a group, e.g., an "alkyl" group, is referred to without any limitation on the number of atoms in the group, it is understood that the claim is definite and limited with respect the size of the alkyl group, both by definition; i.e., the size (the number of carbon atoms) possessed by a group such as an alkyl group is a finite number, less than the total number of carbon atoms in the universe and bounded by the understanding of the person of ordinary skill as to the size of the group as being reasonable for a molecular entity; and by functionality, i.e., the size of the group such as the alkyl group is bounded by the functional properties the group bestows on a molecule containing the group such as solubility in aqueous or organic liquid media. Therefore, a claim reciting an "alkyl" or other chemical group or moiety is definite and bounded, as the number of atoms in the group cannot be infinite.

The inclusion of an isotopic form of one or more atoms in a molecule that is different from the naturally occurring isotopic distribution of the atom in nature is referred to as an "isotopically labeled form" of the molecule. All isotopic forms of atoms are included as options in the composition of any molecule, unless a specific isotopic form of an atom is indicated. For example, any hydrogen atom or set thereof in a molecule can be any of the isotopic forms of hydrogen, i.e., protium ($^1$H), deuterium ($^2$H), or tritium ($^3$H) in any combination. Similarly, any carbon atom or set thereof in a molecule can be any of the isotopic form of carbons, such as $^{11}$C, $^{12}$C, $^{13}$C, or $^{14}$C, or any nitrogen atom or set thereof in a molecule can be any of the isotopic forms of nitrogen, such as $^{13}$N, $^{14}$N, or $^{15}$N. A molecule can include any combination of isotopic forms in the component atoms making up the molecule, the isotopic form of every atom forming the molecule being independently selected. In a multi-molecular sample of a compound, not every individual molecule necessarily has the same isotopic composition. For example, a sample of a compound can include molecules containing various different isotopic compositions, such as in a tritium or $^{14}$C radiolabeled sample where only some fraction of the set of molecules making up the macroscopic sample contains a radioactive atom. It is also understood that many elements that are not artificially isotopically enriched themselves are mixtures of naturally occurring isotopic forms, such as $^{14}$N and $^{15}$N, $^{32}$S and $^{34}$S, and so forth. A molecule as recited herein is defined as including isotopic forms of all its constituent elements at each position in the molecule. As is well known in the art, isotopically labeled compounds can be prepared by the usual methods of chemical synthesis, except substituting an isotopically labeled precursor molecule. The isotopes, radiolabeled or stable, can be obtained by any method known in the art, such as generation by neutron absorption of a precursor nuclide in a nuclear reactor, by cyclotron reactions, or by isotopic separation such as by mass spectrometry. The isotopic forms are incorporated into precursors as required for use in any particular synthetic route. For example, $^{14}$C and $^3$H can be prepared using neutrons generated in a nuclear reactor. Following nuclear transformation, $^{14}$C and $^3$H are incorporated into precursor molecules, followed by further elaboration as needed.

The term "amino protecting group" or "N-protected" as used herein refers to those groups intended to protect an amino group against undesirable reactions during synthetic procedures and which can later be removed to reveal the amine. Commonly used amino protecting groups are disclosed in Protective Groups in Organic Synthesis, Greene, T. W.; Wuts, P. G. M., John Wiley & Sons, New York, N.Y., (3rd Edition, 1999). Amino protecting groups include acyl groups such as formyl, acetyl, propionyl, pivaloyl, t-butylacetyl, 2-chloroacetyl, 2-bromoacetyl, trifluoroacetyl, trichloroacetyl, o-nitrophenoxyacetyl, α-chlorobutyryl, benzoyl, 4-chlorobenzoyl, 4-bromobenzoyl, 4-nitrobenzoyl, and the like; sulfonyl groups such as benzenesulfonyl, p-toluenesulfonyl and the like; alkoxy- or aryloxy-carbonyl groups (which form urethanes with the protected amine) such as benzyloxycarbonyl (Cbz), p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxycarbonyl, t-butyloxycarbonyl (Boc), diisopropylmethoxycarbonyl, isopropyloxycarbonyl, ethoxycarbonyl, methoxycarbonyl, allyloxycarbonyl (Alloc), 2,2,2-trichloroethoxycarbonyl, 2-trimethylsilylethyloxycarbonyl (Teoc), phenoxycarbonyl, 4-nitrophenoxycarbonyl, fluorenyl-9-methoxycarbonyl (Fmoc), cyclopentyloxycarbonyl, adamantyloxycarbonyl, cyclohexyloxycarbonyl, phenylthiocarbonyl and the like; aralkyl groups such as benzyl, triphenylmethyl, benzyloxymethyl and the like; and silyl groups such as trimethylsilyl and the like. Amine protecting groups also include cyclic amino protecting groups such as phthaloyl and dithiosuccinimidyl, which incorporate the amino nitrogen into a heterocycle. Typically, amino protecting groups include formyl, acetyl, benzoyl, pivaloyl, t-butylacetyl, phenylsulfonyl, Alloc, Teoc, benzyl, Fmoc, Boc and Cbz. It is well within the skill of the ordinary artisan to select and use the appropriate amino protecting group for the synthetic task at hand.

The term "hydroxyl protecting group" or "O-protected" as used herein refers to those groups intended to protect an OH group against undesirable reactions during synthetic procedures and which can later be removed to reveal the amine. Commonly used hydroxyl protecting groups are disclosed in Protective Groups in Organic Synthesis, Greene, T. W.; Wuts, P. G. M., John Wiley & Sons, New York, N.Y., (3rd Edition, 1999). Hydroxyl protecting groups include acyl groups such as formyl, acetyl, propionyl, pivaloyl, t-butylacetyl, 2-chloroacetyl, 2-bromoacetyl, trifluoroacetyl, trichloroacetyl, o-nitrophenoxyacetyl, α-chlorobutyryl, benzoyl, 4-chlorobenzoyl, 4-bromobenzoyl, 4-nitrobenzoyl, and the like; sulfonyl groups such as benzenesulfonyl, p-toluenesulfonyl and the like; acyloxy groups (which form urethanes with the protected amine) such as benzyloxycarbonyl (Cbz), p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxycarbonyl, t-butyloxycarbonyl (Boc), diisopropylmethoxycarbonyl, isopropyloxycarbonyl, ethoxycarbonyl, methoxycarbonyl, allyloxycarbonyl (Alloc), 2,2,2-trichloroethoxycarbonyl, 2-trimethylsilylethyloxycarbonyl (Teoc), phenoxycarbonyl, 4-nitrophenoxycarbonyl, fluorenyl-9-methoxycarbonyl (Fmoc), cyclopentyloxycarbonyl, adamantyloxycarbonyl, cyclohexyloxycarbonyl, phenylthiocarbonyl and the like; aralkyl groups such as benzyl, triphenylmethyl, benzyloxymethyl and the like; and silyl groups such as trimethylsilyl and the like. It is well within the skill of the ordinary artisan to select and use the appropriate hydroxyl protecting group for the synthetic task at hand.

In general, "substituted" refers to an organic group as defined herein in which one or more bonds to a hydrogen atom contained therein are replaced by one or more bonds to a non-hydrogen atom such as, but not limited to, a halogen (i.e., F, Cl, Br, and I); an oxygen atom in groups such as hydroxyl groups, alkoxy groups, aryloxy groups, aralkyloxy groups, oxo(carbonyl) groups, carboxyl groups including carboxylic acids, carboxylates, and carboxylate esters; a sulfur atom in groups such as thiol groups, alkyl and aryl sulfide groups, sulfoxide groups, sulfone groups, sulfonyl groups, and sulfonamide groups; a nitrogen atom in groups such as amines, hydroxylamines, nitriles, nitro groups, N-oxides, hydrazides, azides, and enamines; and other heteroatoms in various other groups. Non-limiting examples of substituents J that can be bonded to a substituted carbon (or other) atom include F, Cl, Br, I, OR', OC(O)N(R')$_2$, CN, NO, NO$_2$, ONO$_2$, azido, CF$_3$, OCF$_3$, R', O (oxo), S (thiono), methylenedioxy, ethylenedioxy, N(R')$_2$, SR, SOR', SO$_2$R', SO$_2$N(R')$_2$, SO$_3$R', C(O)R', C(O)C(O)R', C(O)CH$_2$C(O)R', C(S)R', C(O)OR', OC(O)R', C(O)N(R')$_2$, OC(O)N(R')$_2$, C(S)N(R')$_2$, (CH$_2$)$_{0-2}$N(R')C(O)R', (CH$_2$)$_{0-2}$N(R')N(R')$_2$, N(R')N(R')C(O)R', N(R')N(R')C(O)OR', N(R')N(R')CON(R')$_2$, N(R')SO$_2$R', N(R')SO$_2$N(R')$_2$, N(R')C(O)OR', N(R')C(O)R', N(R')C(S)R', N(R')C(O)N(R')$_2$, N(R')C(S)N(R')$_2$, N(COR')COR', N(OR') R', C(=NH)N(R')$_2$, C(O)N(OR')R', or C(=NOR')R' wherein R' can be hydrogen or a carbon-based moiety, and wherein the carbon-based moiety can itself be further substituted; for example, wherein R' can be hydrogen, alkyl, acyl, cycloalkyl, aryl, aralkyl, heterocyclyl, heteroaryl, or heteroarylalkyl, wherein any alkyl, acyl, cycloalkyl, aryl, aralkyl, heterocyclyl, heteroaryl, or heteroarylalkyl or R' can be independently mono- or multi-substituted with J; or wherein two R' groups bonded to a nitrogen atom or to adjacent nitrogen atoms can together with the nitrogen atom or atoms form a heterocyclyl, which can be mono- or independently multi-substituted with J.

When a substituent is monovalent, such as, for example, F or Cl, it is bonded to the atom it is substituting by a single bond. When a substituent is more than monovalent, such as O, which is divalent, it can be bonded to the atom it is substituting by more than one bond, i.e., a divalent substituent is bonded by a double bond; for example, a C substituted with O forms a carbonyl group, C=O, which can also be written as "CO", "C(O)", or "C(=O)", wherein the C and the O are double bonded. When a carbon atom is substituted with a double-bonded oxygen (=O) group, the oxygen substituent is termed an "oxo" group. When a divalent substituent such as NR is double-bonded to a carbon atom, the resulting C(=NR) group is termed an "imino" group. When a divalent substituent such as S is double-bonded to a carbon atom, the results C(=S) group is termed a "thiocarbonyl" or "thiono" group.

Alternatively, a divalent substituent such as O or S can be connected by two single bonds to two different carbon atoms. For example, O, a divalent substituent, can be bonded to each of two adjacent carbon atoms to provide an epoxide group, or the O can form a bridging ether group, termed an "oxy" group, between adjacent or non-adjacent carbon atoms, for example bridging the 1,4-carbons of a cyclohexyl group to form a [2.2.1]-oxabicyclo system. Further, any substituent can be bonded to a carbon or other atom by a linker, such as (CH$_2$)$_n$ or (CR'$_2$)$_n$, wherein n is 1, 2, 3, or more, and each R' independently selected.

C(O) and S(O)$_2$ groups can also be bound to one or two heteroatoms, such as nitrogen or oxygen, rather than to a carbon atom. For example, when a C(O) group is bound to one carbon and one nitrogen atom, the resulting group is called an "amide" or "carboxamide." When a C(O) group is bound to two nitrogen atoms, the functional group is termed a "urea." When a C(O) is bonded to one oxygen and one nitrogen atom, the resulting group is termed a "carbamate" or "urethane." When a S(O)$_2$ group is bound to one carbon and one nitrogen atom, the resulting unit is termed a "sulfonamide." When a S(O)$_2$ group is bound to two nitrogen atoms, the resulting unit is termed a "sulfamate."

Substituted alkyl, alkenyl, alkynyl, cycloalkyl, and cycloalkenyl groups as well as other substituted groups also include groups in which one or more bonds to a hydrogen atom are replaced by one or more bonds, including double or triple bonds, to a carbon atom, or to a heteroatom such as, but not limited to, oxygen in carbonyl (oxo), carboxyl, ester, amide, imide, urethane, and urea groups; and nitrogen in imines, hydroxyimines, oximes, hydrazones, amidines, guanidines, and nitriles.

Substituted ring groups such as substituted cycloalkyl, aryl, heterocyclyl and heteroaryl groups also include rings and fused ring systems in which a bond to a hydrogen atom is replaced with a bond to a carbon atom. Therefore, substituted cycloalkyl, aryl, heterocyclyl and heteroaryl groups can also be substituted with alkyl, alkenyl, and alkynyl groups as defined herein.

By a "ring system" as the term is used herein is meant a moiety comprising one, two, three or more rings, which can be substituted with non-ring groups or with other ring systems, or both, which can be fully saturated, partially unsaturated, fully unsaturated, or aromatic, and when the ring system includes more than a single ring, the rings can be fused, bridging, or spirocyclic. By "spirocyclic" is meant the class of structures wherein two rings are fused at a single tetrahedral carbon atom, as is well known in the art.

As to any of the groups described herein, which contain one or more substituents, it is understood, of course, that such groups do not contain any substitution or substitution patterns which are sterically impractical and/or synthetically non-feasible. In addition, the compounds of this disclosed subject matter include all stereochemical isomers arising from the substitution of these compounds.

Alkyl groups include straight chain and branched alkyl groups and cycloalkyl groups having from 1 to about 20 carbon atoms, and typically from 1 to 12 carbons or, in some embodiments, from 1 to 8 carbon atoms. Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, t-butyl, neopentyl, isopentyl, and 2,2-dimethylpropyl groups. As used herein, the term "alkyl" encompasses n-alkyl, isoalkyl, and anteisoalkyl groups as well as other branched chain forms of alkyl. Representative substituted alkyl groups can be substituted one or more times with any of the groups listed above, for example, amino, hydroxy, cyano, carboxy, nitro, thio, alkoxy, and halogen groups.

Cycloalkyl groups are cyclic alkyl groups such as, but not limited to, cyclopropyl, cyclobutyl, cyclopentyl, cyclohexyl, cycloheptyl, and cyclooctyl groups. In some embodiments, the cycloalkyl group can have 3 to about 8-12 ring members, whereas in other embodiments the number of ring carbon atoms range from 3 to 4, 5, 6, or 7. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like. Cycloalkyl groups also include rings that are substituted with straight or branched chain alkyl groups as defined above. Representative substituted cycloalkyl groups can be mono-substituted or substituted more than once, such as, but not limited to, 2,2-, 2,3-, 2,4-2,5- or 2,6-disubstituted cyclohexyl groups or mono-, di- or tri-substituted norbornyl or cycloheptyl groups, which can be substituted with, for example, amino, hydroxy, cyano, carboxy, nitro, thio, alkoxy, and halogen groups. The term "cycloalkenyl" alone or in combination denotes a cyclic alkenyl group.

The terms "carbocyclic," "carbocyclyl," and "carbocycle" denote a ring structure wherein the atoms of the ring are carbon, such as a cycloalkyl group or an aryl group. In some embodiments, the carbocycle has 3 to 8 ring members, whereas in other embodiments the number of ring carbon atoms is 4, 5, 6, or 7. Unless specifically indicated to the contrary, the carbocyclic ring can be substituted with as many as N−1 substituents wherein N is the size of the carbocyclic ring with, for example, alkyl, alkenyl, alkynyl, amino, aryl, hydroxy, cyano, carboxy, heteroaryl, heterocyclyl, nitro, thio, alkoxy, and halogen groups, or other groups as are listed above. A carbocyclyl ring can be a cycloalkyl ring, a cycloalkenyl ring, or an aryl ring. A carbocyclyl can be monocyclic or polycyclic, and if polycyclic each ring can be independently be a cycloalkyl ring, a cycloalkenyl ring, or an aryl ring.

(Cycloalkyl)alkyl groups, also denoted cycloalkylalkyl, are alkyl groups as defined above in which a hydrogen or carbon bond of the alkyl group is replaced with a bond to a cycloalkyl group as defined above.

Alkenyl groups include straight and branched chain and cyclic alkyl groups as defined above, except that at least one double bond exists between two carbon atoms. Thus, alkenyl groups have from 2 to about 20 carbon atoms, and typically from 2 to 12 carbons or, in some embodiments, from 2 to 8 carbon atoms. Examples include, but are not limited to vinyl, —CH=CH(CH$_3$), —CH=C(CH$_3$)$_2$, —C(CH$_3$)=CH$_2$, —C(CH$_3$)=CH(CH$_3$), —C(CH$_2$CH$_3$)=CH$_2$, cyclohexenyl, cyclopentenyl, cyclohexadienyl, butadienyl, pentadienyl, and hexadienyl among others.

Cycloalkenyl groups include cycloalkyl groups having at least one double bond between 2 carbons. Thus for example, cycloalkenyl groups include but are not limited to cyclohexenyl, cyclopentenyl, and cyclohexadienyl groups. Cycloalkenyl groups can have from 3 to about 8-12 ring members, whereas in other embodiments the number of ring carbon atoms range from 3 to 5, 6, or 7. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like, provided they include at least one double bond within a ring. Cycloalkenyl groups also include rings that are substituted with straight or branched chain alkyl groups as defined above.

(Cycloalkenyl)alkyl groups are alkyl groups as defined above in which a hydrogen or carbon bond of the alkyl group is replaced with a bond to a cycloalkenyl group as defined above.

Alkynyl groups include straight and branched chain alkyl groups, except that at least one triple bond exists between two carbon atoms. Thus, alkynyl groups have from 2 to about 20 carbon atoms, and typically from 2 to 12 carbons or, in some embodiments, from 2 to 8 carbon atoms. Examples include, but are not limited to —C⊙CH, —C≡C(CH$_3$), —C≡C(CH$_2$CH$_3$), —CH$_2$C≡CH, —CH$_2$C≡C(CH$_3$), and —CH$_2$C≡C(CH$_2$CH$_3$) among others.

The term "heteroalkyl" by itself or in combination with another term means, unless otherwise stated, a stable straight or branched chain alkyl group consisting of the stated number of carbon atoms and one or two heteroatoms selected from the group consisting of O, N, and S, and wherein the nitrogen and sulfur atoms may be optionally oxidized and the nitrogen heteroatom may be optionally quaternized. The heteroatom(s) may be placed at any position of the heteroalkyl group, including between the rest of the heteroalkyl group and the fragment to which it is attached, as well as attached to the most distal carbon atom in the heteroalkyl group. Examples include: —O—CH$_2$—CH$_2$—CH$_3$, —CH$_2$—CH$_2$CH$_2$—OH, —CH$_2$—CH$_2$—NH—CH$_3$, —CH$_2$—S—CH$_2$—CH$_3$, —CH$_2$CH$_2$—S(=O)—CH$_3$, and —CH$_2$CH$_2$—O—CH$_2$CH$_2$—O—CH$_3$. Up to two heteroatoms may be consecutive, such as, for example, —CH$_2$—NH—OCH$_3$, or —CH$_2$—CH$_2$—S—S—CH$_3$.

A "cycloheteroalkyl" ring is a cycloalkyl ring containing at least one heteroatom. A cycloheteroalkyl ring can also be termed a "heterocyclyl," described below.

The term "heteroalkenyl" by itself or in combination with another term means, unless otherwise stated, a stable straight or branched chain monounsaturated or di-unsaturated hydrocarbon group consisting of the stated number of carbon atoms and one or two heteroatoms selected from the group consisting of O, N, and S, and wherein the nitrogen and sulfur atoms may optionally be oxidized and the nitrogen heteroatom may optionally be quaternized. Up to two heteroatoms may be placed consecutively. Examples include —CH=CH—O—CH$_3$, —CH=CH—CH$_2$—OH, —CH$_2$—CH=N—OCH$_3$, —CH=CH—N(CH$_3$)—CH$_3$, —CH$_2$—CH=CH—CH$_2$—SH, and —CH=CH—O—CH$_2$CH$_2$—O—CH$_3$.

Aryl groups are cyclic aromatic hydrocarbons that do not contain heteroatoms in the ring. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain about 6 to about 14 carbons in the ring portions of the groups. Aryl groups can be unsubstituted or substituted, as defined above. Representative substituted aryl groups can be monosubstituted or substituted more than once, such as, but not limited to, 2-, 3-, 4-, 5-, or 6-substituted phenyl or 2-8 substituted naphthyl groups, which can be substituted with carbon or non-carbon groups such as those listed above.

Aralkyl groups are alkyl groups as defined above in which a hydrogen or carbon bond of an alkyl group is replaced with a bond to an aryl group as defined above. Representative aralkyl groups include benzyl and phenylethyl groups and fused (cycloalkylaryl)alkyl groups such as 4-ethyl-indanyl. Aralkenyl group are alkenyl groups as defined above in which a hydrogen or carbon bond of an alkyl group is replaced with a bond to an aryl group as defined above.

Heterocyclyl groups or the term "heterocyclyl" includes aromatic and non-aromatic ring compounds containing 3 or more ring members, of which, one or more is a heteroatom such as, but not limited to, N, O, and S. Thus a heterocyclyl can be a cycloheteroalkyl, or a heteroaryl, or if polycyclic, any combination thereof.

In some embodiments, heterocyclyl groups include 3 to about 20 ring members, whereas other such groups have 3 to about 15 ring members. A heterocyclyl group designated as a $C_2$-heterocyclyl can be a 5-ring with two carbon atoms and three heteroatoms, a 6-ring with two carbon atoms and four heteroatoms and so forth. Likewise a $C_4$-heterocyclyl can be a 5-ring with one heteroatom, a 6-ring with two heteroatoms, and so forth. The number of carbon atoms plus the number of heteroatoms sums up to equal the total number of ring atoms. A heterocyclyl ring can also include one or more double bonds. A heteroaryl ring is an embodiment of a heterocyclyl group. The phrase "heterocyclyl group" includes fused ring species including those comprising fused aromatic and non-aromatic groups. For example, a dioxolanyl ring and a benzdioxolanyl ring system (methylenedioxyphenyl ring system) are both heterocyclyl groups within the meaning herein. The phrase also includes polycyclic ring systems containing a heteroatom such as, but not limited to, quinuclidyl. Heterocyclyl groups can be unsubstituted, or can be substituted as discussed above. Heterocyclyl groups include, but are not limited to, pyrrolidinyl, piperidinyl, piperazinyl, morpholinyl, pyrrolyl, pyrazolyl, triazolyl, tetrazolyl, oxazolyl, isoxazolyl, thiazolyl, pyridinyl, thiophenyl, benzothiophenyl, benzofuranyl, dihydrobenzofuranyl, indolyl, dihydroindolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, quinoxalinyl, and quinazolinyl groups. Representative substituted heterocyclyl groups can be monosubstituted or substituted more than once, such as, but not limited to, piperidinyl or quinolinyl groups, which are 2-, 3-, 4-, 5-, or 6-substituted, or disubstituted with groups such as those listed above.

Heteroaryl groups are aromatic ring compounds containing 5 or more ring members, of which, one or more is a heteroatom such as, but not limited to, N, O, and S; for instance, heteroaryl rings can have 5 to about 8-12 ring members. A heteroaryl group is a variety of a heterocyclyl group that possesses an aromatic electronic structure. A heteroaryl group designated as a $C_2$-heteroaryl can be a 5-ring with two carbon atoms and three heteroatoms, a 6-ring with two carbon atoms and four heteroatoms and so forth. Likewise a $C_4$-heteroaryl can be a 5-ring with one heteroatom, a 6-ring with two heteroatoms, and so forth. The number of carbon atoms plus the number of heteroatoms sums up to equal the total number of ring atoms. Heteroaryl groups include, but are not limited to, groups such as pyrrolyl, pyrazolyl, triazolyl, tetrazolyl, oxazolyl, isoxazolyl, thiazolyl, pyridinyl, thiophenyl, benzothiophenyl, benzofuranyl, indolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, quinoxalinyl, and quinazolinyl groups. Heteroaryl groups can be unsubstituted, or can be substituted with groups as is discussed above. Representative substituted heteroaryl groups can be substituted one or more times with groups such as those listed above.

Additional examples of aryl and heteroaryl groups include but are not limited to phenyl, biphenyl, indenyl, naphthyl (1-naphthyl, 2-naphthyl), N-hydroxytetrazolyl, N-hydroxytriazolyl, N-hydroxyimidazolyl, anthracenyl (1-anthracenyl, 2-anthracenyl, 3-anthracenyl), thiophenyl (2-thienyl, 3-thienyl), furyl (2-furyl, 3-furyl), indolyl, oxadiazolyl, isoxazolyl, quinazolinyl, fluorenyl, xanthenyl, isoindanyl, benzhydryl, acridinyl, thiazolyl, pyrrolyl (2-pyrrolyl), pyrazolyl (3-pyrazolyl), imidazolyl (1-imidazolyl, 2-imidazolyl, 4-imidazolyl, 5-imidazolyl), triazolyl (1,2,3-triazol-1-yl, 1,2,3-triazol-2-yl 1,2,3-triazol-4-yl, 1,2,4-triazol-3-yl), oxazolyl (2-oxazolyl, 4-oxazolyl, 5-oxazolyl), thiazolyl (2-thiazolyl, 4-thiazolyl, 5-thiazolyl), pyridyl (2-pyridyl, 3-pyridyl, 4-pyridyl), pyrimidinyl (2-pyrimidinyl, 4-pyrimidinyl, 5-pyrimidinyl, 6-pyrimidinyl), pyrazinyl, pyridazinyl (3-pyridazinyl, 4-pyridazinyl, 5-pyridazinyl), quinolyl (2-quinolyl, 3-quinolyl, 4-quinolyl, 5-quinolyl, 6-quinolyl, 7-quinolyl, 8-quinolyl), isoquinolyl (1-isoquinolyl, 3-isoquinolyl, 4-isoquinolyl, 5-isoquinolyl, 6-isoquinolyl, 7-isoquinolyl, 8-isoquinolyl), benzo[b]furanyl (2-benzo[b]furanyl, 3-benzo[b]furanyl, 4-benzo[b]furanyl, 5-benzo[b]furanyl, 6-benzo[b]furanyl, 7-benzo[b]furanyl), 2,3-dihydro-benzo[b]furanyl (2-(2,3-dihydro-benzo[b]furanyl), 3-(2,3-dihydro-benzo[b]furanyl), 4-(2,3-dihydro-benzo[b]furanyl), 5-(2,3-dihydro-benzo[b]furanyl), 6-(2,3-dihydro-benzo[b]furanyl), 7-(2,3-dihydro-benzo[b]furanyl), benzo[b]thiophenyl (2-benzo[b]thiophenyl, 3-benzo[b]thiophenyl, 4-benzo[b]thiophenyl, 5-benzo[b]thiophenyl, 6-benzo[b]thiophenyl, 7-benzo[b]thiophenyl), 2,3-dihydro-benzo[b]thiophenyl, (2-(2,3-dihydro-benzo[b]thiophenyl), 3-(2,3-dihydro-benzo[b]thiophenyl), 4-(2,3-dihydro-benzo[b]thiophenyl), 5-(2,3-dihydro-benzo[b]thiophenyl), 6-(2,3-dihydro-benzo[b]thiophenyl), 7-(2,3-dihydro-benzo[b]thiophenyl), indolyl (1-indolyl, 2-indolyl, 3-indolyl, 4-indolyl, 5-indolyl, 6-indolyl, 7-indolyl), indazole (1-indazolyl, 3-indazolyl, 4-indazolyl, 5-indazolyl, 6-indazolyl, 7-indazolyl), benzimidazolyl (1-benzimidazolyl, 2-benzimidazolyl, 4-benzimidazolyl, 5-benzimidazolyl, 6-benzimidazolyl, 7-benzimidazolyl, 8-benzimidazolyl), benzoxazolyl (1-benzoxazolyl, 2-benzoxazolyl), benzothiazolyl (1-benzothiazolyl, 2-benzothiazolyl, 4-benzothiazolyl, 5-benzothiazolyl, 6-benzothiazolyl, 7-benzothiazolyl), carbazolyl (1-carbazolyl, 2-carbazolyl, 3-carbazolyl, 4-carbazolyl), 5H-dibenz[b,f]azepine (5H-dibenz[b,f]azepin-1-yl, 5H-dibenz[b,f]azepine-2-yl, 5H-dibenz[b,f]azepine-3-yl, 5H-dibenz[b,f]azepine-4-yl, 5H-dibenz[b,f]azepine-5-yl), 10,11-dihydro-5H-dibenz[b,f]azepine (10,11-dihydro-5H-dibenz[b,f]azepine-1-yl, 10,11-dihydro-5H-dibenz[b,f]azepine-2-yl, 10,11-dihydro-5H-dibenz[b,f]azepine-3-yl, 10,11-dihydro-5H-dibenz[b,f]azepine-4-yl, 10,11-dihydro-5H-dibenz[b,f]azepine-5-yl), and the like.

Heterocyclylalkyl groups are alkyl groups as defined above in which a hydrogen or carbon bond of an alkyl group as defined above is replaced with a bond to a heterocyclyl group as defined above. Representative heterocyclyl alkyl groups include, but are not limited to, furan-2-yl methyl, furan-3-yl methyl, pyridine-3-yl methyl, tetrahydrofuran-2-yl ethyl, and indol-2-yl propyl.

Heteroarylalkyl groups are alkyl groups as defined above in which a hydrogen or carbon bond of an alkyl group is replaced with a bond to a heteroaryl group as defined above.

The term "alkoxy" refers to an oxygen atom connected to an alkyl group, including a cycloalkyl group, as are defined above. Examples of linear alkoxy groups include but are not limited to methoxy, ethoxy, propoxy, butoxy, pentyloxy, hexyloxy, and the like. Examples of branched alkoxy include but are not limited to isopropoxy, sec-butoxy, tert-butoxy, isopentyloxy, isohexyloxy, and the like. Examples of cyclic alkoxy include but are not limited to cyclopropyloxy, cyclobutyloxy, cyclopentyloxy, cyclohexyloxy, and the like. An alkoxy group can include one to about 12-20 carbon atoms bonded to the oxygen atom, and can further include double or triple bonds, and can also include heteroatoms. For example, an allyloxy group is an alkoxy group within the meaning herein. A methoxyethoxy group is also an alkoxy group within the meaning herein, as is a methylenedioxy group in a context where two adjacent atoms of a structures are substituted therewith.

The terms "halo" or "halogen" or "halide" by themselves or as part of another substituent mean, unless otherwise stated, a fluorine, chlorine, bromine, or iodine atom, preferably, fluorine, chlorine, or bromine.

A "haloalkyl" group includes mono-halo alkyl groups, poly-halo alkyl groups wherein all halo atoms can be the same or different, and per-halo alkyl groups, wherein all hydrogen atoms are replaced by halogen atoms, such as fluoro. Examples of haloalkyl include trifluoromethyl, 1,1-dichloroethyl, 1,2-dichloroethyl, 1,3-dibromo-3,3-difluoropropyl, perfluorobutyl, and the like.

A "haloalkoxy" group includes mono-halo alkoxy groups, poly-halo alkoxy groups wherein all halo atoms can be the same or different, and per-halo alkoxy groups, wherein all hydrogen atoms are replaced by halogen atoms, such as fluoro. Examples of haloalkoxy include trifluoromethoxy, 1,1-dichloroethoxy, 1,2-dichloroethoxy, 1,3-dibromo-3,3-difluoropropoxy, perfluorobutoxy, and the like.

The term "($C_x$-$C_y$)perfluoroalkyl," wherein x<y, means an alkyl group with a minimum of x carbon atoms and a maximum of y carbon atoms, wherein all hydrogen atoms are replaced by fluorine atoms. Preferred is —($C_1$-$C_6$)perfluoroalkyl, more preferred is —($C_1$-$C_3$)perfluoroalkyl, most preferred is —$CF_3$.

The term "($C_x$—$C_y$)perfluoroalkylene," wherein x<y, means an alkyl group with a minimum of x carbon atoms and a maximum of y carbon atoms, wherein all hydrogen atoms are replaced by fluorine atoms. Preferred is —($C_1$-$C_6$)perfluoroalkylene, more preferred is —($C_1$-$C_3$)perfluoroalkylene, most preferred is —$CF_2$—.

The terms "aryloxy" and "arylalkoxy" refer to, respectively, an aryl group bonded to an oxygen atom and an aralkyl group bonded to the oxygen atom at the alkyl moiety. Examples include but are not limited to phenoxy, naphthyloxy, and benzyloxy.

An "acyl" group as the term is used herein refers to a group containing a carbonyl moiety wherein the group is bonded via the carbonyl carbon atom. The carbonyl carbon atom is also bonded to another carbon atom, which can be part of an alkyl, aryl, aralkyl cycloalkyl, cycloalkylalkyl, heterocyclyl, heterocyclylalkyl, heteroaryl, heteroarylalkyl group or the like. In the special case wherein the carbonyl carbon atom is bonded to a hydrogen, the group is a "formyl" group, an acyl group as the term is defined herein. An acyl group can include 0 to about 12-additional carbon atoms bonded to the carbonyl group. An acyl group can include double or triple bonds within the meaning herein. An acryloyl group is an example of an acyl group. An acyl group can also include heteroatoms within the meaning here. A nicotinoyl group (pyridyl-3-carbonyl) group is an example of an acyl group within the meaning herein. Other examples include acetyl, benzoyl, phenylacetyl, pyridylacetyl, cinnamoyl, and acryloyl groups and the like. When the group containing the carbon atom that is bonded to the carbonyl carbon atom contains a halogen, the group is termed a "haloacyl" group. An example is a trifluoroacetyl group.

The term "amine" includes primary, secondary, and tertiary amines having, e.g., the formula N(group)$_3$ wherein each group can independently be H or non-H, such as alkyl, aryl, and the like. Amines include but are not limited to R—$NH_2$, for example, alkylamines, arylamines, alkylarylamines; $R_2NH$ wherein each R is independently selected, such as dialkylamines, diarylamines, aralkylamines, heterocyclylamines and the like; and $R_3N$ wherein each R is independently selected, such as trialkylamines, dialkylarylamines, alkyldiarylamines, triarylamines, and the like. The term "amine" also includes ammonium ions as used herein.

An "amino" group is a substituent of the form —$NH_2$, —NHR, —$NR_2$, —$NR_3^+$, wherein each R is independently selected, and protonated forms of each, except for —$NR_3^+$, which cannot be protonated. Accordingly, any compound substituted with an amino group can be viewed as an amine. An "amino group" within the meaning herein can be a primary, secondary, tertiary or quaternary amino group. An "alkylamino" group includes a monoalkylamino, dialkylamino, and trialkylamino group.

An "ammonium" ion includes the unsubstituted ammonium ion $NH_4^+$, but unless otherwise specified, it also includes any protonated or quaternarized forms of amines. Thus, trimethylammonium hydrochloride and tetramethylammonium chloride are both ammonium ions, and amines, within the meaning herein.

The term "amide" (or "amido") includes C- and N-amide groups, i.e., —C(O)$NR_2$, and —NRC(O)R groups, respectively. Amide groups therefore include but are not limited to primary carboxamide groups (—C(O)$NH_2$) and formamide groups (—NHC(O)H). A "carboxamido" group is a group of the formula C(O)$NR_2$, wherein R can be H, alkyl, aryl, etc.

The term "azido" refers to an $N_3$ group. An "azide" can be an organic azide or can be a salt of the azide ($N_3^-$) anion. The term "nitro" refers to an $NO_2$ group bonded to an organic moiety. The term "nitroso" refers to an NO group bonded to an organic moiety. The term nitrate refers to an $ONO_2$ group bonded to an organic moiety or to a salt of the nitrate ($NO_3^-$) anion.

The term "urethane" ("carbamoyl" or "carbamyl") includes N- and O-urethane groups, i.e., —NRC(O)OR and —OC(O)$NR_2$ groups, respectively.

The term "sulfonamide" (or "sulfonamido") includes S- and N-sulfonamide groups, i.e., —$SO_2NR_2$ and —$NRSO_2R$ groups, respectively. Sulfonamide groups therefore include but are not limited to sulfamoyl groups (—$SO_2NH_2$). An organosulfur structure represented by the formula —S(O)(NR)— is understood to refer to a sulfoximine, wherein both the oxygen and the nitrogen atoms are bonded to the sulfur atom, which is also bonded to two carbon atoms.

The term "amidine" or "amidino" includes groups of the formula —C(NR)$NR_2$. Typically, an amidino group is —C(NH)$NH_2$.

The term "guanidine" or "guanidino" includes groups of the formula —NRC(NR)NR$_2$. Typically, a guanidino group is —NHC(NH)NH$_2$.

A "salt" as is well known in the art includes an organic compound such as a carboxylic acid, a sulfonic acid, or an amine, in ionic form, in combination with a counterion. For example, acids in their anionic form can form salts with cations such as metal cations, for example sodium, potassium, and the like; with ammonium salts such as NH$_4^+$ or the cations of various amines, including tetraalkyl ammonium salts such as tetramethylammonium, or other cations such as trimethylsulfonium, and the like. A "pharmaceutically acceptable" or "pharmacologically acceptable" salt is a salt formed from an ion that has been approved for human consumption and is generally non-toxic, such as a chloride salt or a sodium salt. A "zwitterion" is an internal salt such as can be formed in a molecule that has at least two ionizable groups, one forming an anion and the other a cation, which serve to balance each other. For example, amino acids such as glycine can exist in a zwitterionic form. A "zwitterion" is a salt within the meaning herein. The compounds of the present invention may take the form of salts. The term "salts" embraces addition salts of free acids or free bases which are compounds of the invention. Salts can be "pharmaceutically-acceptable salts." The term "pharmaceutically-acceptable salt" refers to salts which possess toxicity profiles within a range that affords utility in pharmaceutical applications. Pharmaceutically unacceptable salts may nonetheless possess properties such as high crystallinity, which have utility in the practice of the present invention, such as for example utility in process of synthesis, purification or formulation of compounds of the invention.

Suitable pharmaceutically-acceptable acid addition salts may be prepared from an inorganic acid or from an organic acid. Examples of inorganic acids include hydrochloric, hydrobromic, hydriodic, nitric, carbonic, sulfuric, and phosphoric acids. Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid. Examples of pharmaceutically unacceptable acid addition salts include, for example, perchlorates and tetrafluoroborates.

Suitable pharmaceutically acceptable base addition salts of compounds of the invention include, for example, metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N'-dibenzylethylenediamine, chloroprocaine, choline, diethanolamine, ethylenediamine, meglumine (N-methylglucamine) and procaine. Examples of pharmaceutically unacceptable base addition salts include lithium salts and cyanate salts. Although pharmaceutically unacceptable salts are not generally useful as medicaments, such salts may be useful, for example as intermediates in the synthesis of Formula (I) compounds, for example in their purification by recrystallization. All of these salts may be prepared by conventional means from the corresponding compound according to Formula (I) by reacting, for example, the appropriate acid or base with the compound according to Formula (I). The term "pharmaceutically acceptable salts" refers to nontoxic inorganic or organic acid and/or base addition salts, see, for example, Lit et al., Salt Selection for Basic Drugs (1986), *Int J. Pharm.*, 33, 201-217, incorporated by reference herein.

A "hydrate" is a compound that exists in a composition with water molecules. The composition can include water in stoichiometric quantities, such as a monohydrate or a dihydrate, or can include water in random amounts. As the term is used herein a "hydrate" refers to a solid form, i.e., a compound in water solution, while it may be hydrated, is not a hydrate as the term is used herein.

A "solvate" is a similar composition except that a solvent other that water replaces the water. For example, methanol or ethanol can form an "alcoholate", which can again be stoichiometric or non-stoichiometric. As the term is used herein a "solvate" refers to a solid form, i.e., a compound in solution in a solvent, while it may be solvated, is not a solvate as the term is used herein.

A "prodrug" as is well known in the art is a substance that can be administered to a patient where the substance is converted in vivo by the action of biochemicals within the patients body, such as enzymes, to the active pharmaceutical ingredient. Examples of prodrugs include esters of carboxylic acid groups, which can be hydrolyzed by endogenous esterases as are found in the bloodstream of humans and other mammals. Conventional procedures for the selection and preparation of suitable prodrug derivatives are described, for example, in "Design of Prodrugs", ed. H. Bundgaard, Elsevier, 1985.

In addition, where features or aspects of the invention are described in terms of Markush groups, those skilled in the art will recognize that the invention is also thereby described in terms of any individual member or subgroup of members of the Markush group. For example, if X is described as selected from the group consisting of bromine, chlorine, and iodine, claims for X being bromine and claims for X being bromine and chlorine are fully described. Moreover, where features or aspects of the invention are described in terms of Markush groups, those skilled in the art will recognize that the invention is also thereby described in terms of any combination of individual members or subgroups of members of Markush groups. Thus, for example, if X is described as selected from the group consisting of bromine, chlorine, and iodine, and Y is described as selected from the group consisting of methyl, ethyl, and propyl, claims for X being bromine and Y being methyl are fully described.

If a value of a variable that is necessarily an integer, e.g., the number of carbon atoms in an alkyl group or the number of substituents on a ring, is described as a range, e.g., 0-4, what is meant is that the value can be any integer between 0 and 4 inclusive, i.e., 0, 1, 2, 3, or 4.

In various embodiments, the compound or set of compounds, such as are used in the inventive methods, can be any one of any of the combinations and/or sub-combinations of the above-listed embodiments.

In various embodiments, a compound as shown in any of the Examples, or among the exemplary compounds, is provided.

Provisos may apply to any of the disclosed categories or embodiments wherein any one or more of the other above disclosed embodiments or species may be excluded from such categories or embodiments.

The present invention further embraces isolated compounds of the invention. The expression "isolated compound" refers to a preparation of a compound of the invention, or a mixture of compounds the invention, wherein the isolated compound has been separated from the reagents used, and/or byproducts formed, in the synthesis of the compound or compounds. "Isolated" does not mean that the preparation is technically pure (homogeneous), but it is sufficiently pure to compound in a form in which it can be used therapeutically. Preferably an "isolated compound" refers to a preparation of a compound of the invention or a mixture of compounds of the invention, which contains the named compound or mixture of compounds of the invention in an amount of at least 10 percent by weight of the total weight. Preferably the preparation contains the named compound or mixture of compounds in an amount of at least 50 percent by weight of the total weight; more preferably at least 80 percent by weight of the total weight; and most preferably at least 90 percent, at least 95 percent or at least 98 percent by weight of the total weight of the preparation.

The compounds of the invention and intermediates may be isolated from their reaction mixtures and purified by standard techniques such as filtration, liquid-liquid extraction, solid phase extraction, distillation, recrystallization or chromatography, including flash column chromatography, or HPLC.

Isomerism and Tautomerism in Compounds of the Invention

Tautomerism

Within the present invention it is to be understood that a compound of the formula (I) or a salt thereof may exhibit the phenomenon of tautomerism whereby two chemical compounds that are capable of facile interconversion by exchanging a hydrogen atom between two atoms, to either of which it forms a covalent bond. Since the tautomeric compounds exist in mobile equilibrium with each other they may be regarded as different isomeric forms of the same compound. It is to be understood that the formulae drawings within this specification can represent only one of the possible tautomeric forms. However, it is also to be understood that the invention encompasses any tautomeric form, and is not to be limited merely to any one tautomeric form utilized within the formulae drawings. The formulae drawings within this specification can represent only one of the possible tautomeric forms and it is to be understood that the specification encompasses all possible tautomeric forms of the compounds drawn not just those forms which it has been convenient to show graphically herein. For example, tautomerism may be exhibited by a pyrazolyl group bonded as indicated by the wavy line. While both substituents would be termed a 4-pyrazolyl group, it is evident that a different nitrogen atom bears the hydrogen atom in each structure.

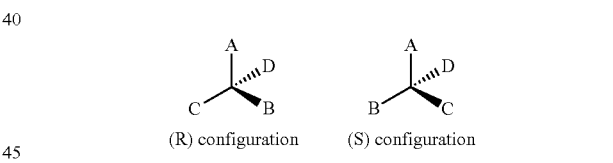

Such tautomerism can also occur with substituted pyrazoles such as 3-methyl, 5-methyl, or 3,5-dimethylpyrazoles, and the like. Another example of tautomerism is amido-imido (lactam-lactim when cyclic) tautomerism, such as is seen in heterocyclic compounds bearing a ring oxygen atom adjacent to a ring nitrogen atom. For example, the equilibrium:

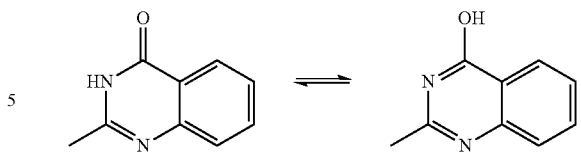

is an example of tautomerism. Accordingly, a structure depicted herein as one tautomer is intended to also include the other tautomer.

Optical Isomerism

It will be understood that when compounds of the present invention contain one or more chiral centers, the compounds may exist in, and may be isolated as pure enantiomeric or diastereomeric forms or as racemic mixtures. The present invention therefore includes any possible enantiomers, diastereomers, racemates or mixtures thereof of the compounds of the invention.

The isomers resulting from the presence of a chiral center comprise a pair of non-superimposable isomers that are called "enantiomers." Single enantiomers of a pure compound are optically active, i.e., they are capable of rotating the plane of plane polarized light. Single enantiomers are designated according to the Cahn-Ingold-Prelog system. The priority of substituents is ranked based on atomic weights, a higher atomic weight, as determined by the systematic procedure, having a higher priority ranking. Once the priority ranking of the four groups is determined, the molecule is oriented so that the lowest ranking group is pointed away from the viewer. Then, if the descending rank order of the other groups proceeds clockwise, the molecule is designated (R) and if the descending rank of the other groups proceeds counterclockwise, the molecule is designated (S). In the example in Scheme 14, the Cahn-Ingold-Prelog ranking is A>B>C>D. The lowest ranking atom, D is oriented away from the viewer.

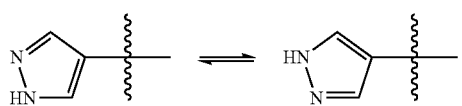

The present invention is meant to encompass diastereomers as well as their racemic and resolved, diastereomerically and enantiomerically pure forms and salts thereof. Diastereomeric pairs may be resolved by known separation techniques including normal and reverse phase chromatography, and crystallization.

"Isolated optical isomer" means a compound which has been substantially purified from the corresponding optical isomer(s) of the same formula. Preferably, the isolated isomer is at least about 80% pure, more preferably at least 90% pure, even more preferably at least 98% pure, most preferably at least about 99% pure, by weight.

Isolated optical isomers may be purified from racemic mixtures by well-known chiral separation techniques. According to one such method, a racemic mixture of a compound of the invention, or a chiral intermediate thereof, is separated into 99% wt. % pure optical isomers by HPLC using a suitable chiral column, such as a member of the series of DAICEL® CHIRALPAK® family of columns (Daicel Chemical Industries, Ltd., Tokyo, Japan). The column is operated according to the manufacturer's instructions.

Rotational Isomerism

It is understood that due to chemical properties (i.e., resonance lending some double bond character to the C—N bond) of restricted rotation about the amide bond linkage (as illustrated below) it is possible to observe separate rotamer species and even, under some circumstances, to isolate such species (see below). It is further understood that certain structural elements, including steric bulk or substituents on the amide nitrogen, may enhance the stability of a rotamer to the extent that a compound may be isolated as, and exist indefinitely, as a single stable rotamer. The present invention therefore includes any possible stable rotamers of formula (I) which are biologically active in the treatment of cancer or other proliferative disease states.

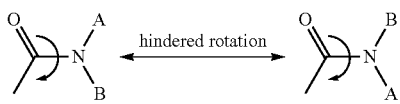

Regioisomerism

The preferred compounds of the present invention have a particular spatial arrangement of substituents on the aromatic rings, which is related to the structure activity relationship demonstrated by the compound class. Often such substitution arrangement is denoted by a numbering system; however, numbering systems are often not consistent between different ring systems. In six-membered aromatic systems, the spatial arrangements are specified by the common nomenclature "para" for 1,4-substitution, "meta" for 1,3-substitution and "ortho" for 1,2-substitution as shown below.

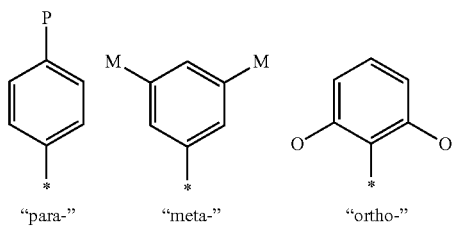

In various embodiments, the compound or set of compounds, such as are among the inventive compounds or are used in the inventive methods, can be any one of any of the combinations and/or sub-combinations of the above-listed embodiments.

Compounds of the Invention

In various embodiments, the invention provides a non-agonist PPARG modulatory compound of formula (I), or a pharmaceutically acceptable salt thereof:

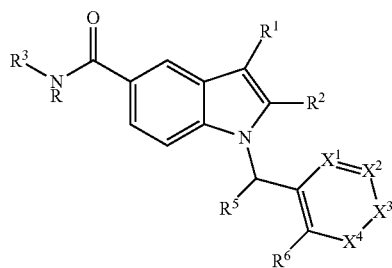

wherein:

R is H or $(C_1-C_4)$alkyl;

$R^1$ and $R^2$ are independently H, $(C_1-C_6)$alkyl, $(C_3-C_9)$cycloalkyl, or $(C_1-C_6)$haloalkyl; or $R^1$ and $R^2$ together with the atoms to which they are bonded form a 5- to 9-membered ring, comprising 0-3 heteroatoms selected from the group consisting of O, NR, and $SO_q$ wherein q is 0, 1, or 2, and optionally mono- or pluri-substituted with independently selected $(C_1-C_6)$alkyl, $(C_2-C_6)$alkenyl, $(C_2-C_6)$alkynyl, $(C_6-C_{10})$aryl, $(C_3-C_9)$cycloalkyl, halo, $(C_1-C_6)$haloalkyl, nitro, cyano-$(C_0-C_6)$alkyl, $R'O_2C$—$(C_0-C_6)$alkyl, methylenedioxy, $R'O$—$(C_0-C_6)$alkyl, $(R')_2N$—$(C_0-C_6)$alkyl, $(R')_2NC(=O)$—$(C_0-C_6)$alkyl, $(C_1-C_6)$alkyl-$S(O)_q(C_0-C_6)$alkyl, aryl, aroyl, or $SO_2NR'_2$; $R^3$ is optionally mono- or multi-substituted $(C_1-C_6)$alkyl, $(C_1-C_6)$alkenyl, $(C_1-C_6)$alkynyl, aryl, arylalkyl, heteroaryl, heteroarylalkyl, cycloalkyl, heterocyclyl, cycloalkylalkyl, or heterocyclylalkyl; wherein if present each substituent on $R^3$ is independently selected from the group consisting of $(C_1-C_6)$alkyl, $(C_2-C_6)$alkenyl, $(C_2-C_6)$alkynyl, $(C_6-C_{10})$aryl, $(C_3-C_9)$cycloalkyl, 3-9 membered mono- and bicyclic heterocyclyl, 3-9 membered mono- and bicyclic heteroaryl, halo, haloalkyl, haloalkoxy, nitro, cyano, $CO_2R'$, methylenedioxy, $OR'$, $N(R')_2$, $C(O)N(R')_2$, $(C_1-C_4)$alkyl-$S(O)_q$, $SO_2NR'_2$, and $(C_1-C_6)$alkoxyl, wherein R' is independently H, $(C_1-C_6)$ alkyl, $(C_1-C_6)$ haloalkyl, or $(C_3-C_9)$cycloalkyl, or wherein two R' bonded to an atom together with the atom form a 3-8 membered ring optionally further comprising a heteroatom selected from the group consisting of O, NR', and $S(O)_q$, and wherein alkyl, alkenyl, alkynyl, aryl, arylalkyl, or cycloalkyl is optionally mono- or independently multi-substituted with $(C_1-C_6)$alkyl, $(C_1-C_6)$haloalkyl, $(C_1-C_6)$alkoxy, $(C_1-C_6)$haloalkoxy, halo, $OR'$, $N(R')_2$, aryl, or aroyl; and wherein an alkyl or an alkyl group of a cycloalkylalkyl, heterocyclylalkyl, arylalkyl or heteroarylalkyl can be substituted with oxo;

each of $X^1$-$X^4$ is independently N or is C substituted with an independently selected $R^7$ or with Z, provided that no more than one of $X^1$-$X^4$ is N, and provided that there is one and only one Z group, present in the ring comprising $X^1$, Z is a group of formula

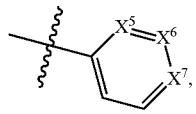

wherein a wavy line indicates a point of attachment, each $X^5$-$X^7$ is independently N or is C substituted with an independently selected H or $R^4$; provided that no more than one of $X^5$-$X^7$ is N;

each $R^4$ is independently halo, nitro, $(C_1-C_6)$fluoroalkyl, $R''$—$(C_1-C_6)$alkyl, $R''O_2C$—$(C_0-C_6)$alkyl, $NC$—$(C_0-C_6)$ alkyl, $R''O$—$(C_0-C_6)$alkyl, $(R'')_2N$—$(C_0-C_6)$alkyl, $(R')_2NC(=O)$—$(C_0-C_6)$alkyl, C-bonded tetrazolyl, 3-hydroxypyrrolidin-1-carbonyl, 2-hydroxyethylaminocarbonyl, cyclohexylaminocarbonyl, 2-(N,N-dimethylaminocarbonyl)-2-hydroxyethylaminocarbonyl, N,N-dimethylaminoethylcarbonyl, N-methylaminocarbonyl, N-hydroxylaminocarbonyl, (1,3,4-oxadiazol-2(3H)-on)-yl, (1,2,4-oxadiazol-5(4H)-on)-3-yl, $(C_1-C_6)$alkyl-$S(O)_q(C_0-C_6)$alkyl, $R'S(O)_2NHC(O)$, $R'C(O)NHS(O)_2$, an unsubstituted or substituted aryl, an unsubstituted or substituted heteroaryl, $(C_1-C_6)$alkyl or $(C_3-C_9)$cycloalkyl-$(C_0-C_6)$alkyl, wherein any alkyl or cycloalkyl is optionally mono- or independently multi-substituted with $R''$, $OR''$, $N(R'')_2$, C-bonded tetrazolyl, ($C_1$-$C_6$)alkyl-S(O)$_q$($C_0$-$C_6$)alkyl, an unsubstituted or substituted aryl, or an unsubstituted or substituted heteroaryl; or $R^4$ is —(C(R")$_2$)$_m$CO$_2$R", —(C(R")$_2$)$_m$CON(R")$_2$, or —(C(R")$_2$)$_m$CN, —O(C(R")$_2$)$_m$CO$_2$R", —O(C(R")$_2$)$_m$CON(R")$_2$, or —O(C(R")$_2$)$_m$CN, wherein m is 1, 2, or 3;

R" is H, or ($C_1$-$C_6$) alkyl, or two R" together with an atom to which they are bonded form a ($C_3$-$C_9$)cycloalkyl;

q is 0, 1 or 2;

$R^5$ is H or ($C_1$-$C_4$)alkyl; $R^6$ is $R^7$; or $R^5$ and $R^6$ taken together form a —CH$_2$CH$_2$— group; and, $R^7$ is H, halo, CO$_2$R', CN, OR', N(R')$_2$, C(O)N(R')$_2$, ($C_1$-$C_4$)alkyl or ($C_1$-$C_4$)fluoroalkyl optionally substituted with OR' or N(R')$_2$, C-bonded tetrazolyl, or ($C_1$-$C_4$)alkyl-S(O)$_q$; or $R^7$ is —(C(R')$_2$)$_m$CO$_2$R' wherein m is 1, 2, or 3.

For example, in various embodiments, $R^1$ and $R^2$ are each independently H or methyl. More specifically, both $R^1$ and $R^2$ can be H, or both $R^1$ and $R^2$ can both be methyl.

In various embodiments, $R^3$ can be a variety of unsubstituted or substituted ($C_1$-$C_6$)alkyl, ($C_1$-$C_6$)alkenyl, ($C_1$-$C_6$)alkynyl, aryl, arylalkyl, heteroaryl, heteroarylalkyl, cycloalkyl, heterocyclyl, cycloalkylalkyl, or heterocyclylalkyl groups, as disclosed and claimed herein. For example, $R^3$ is unsubstituted or substituted arylalkyl, such as an unsubstituted or substituted benzyl or α-phenethyl, or $R^3$ can be an unsubstituted or substituted cycloalkyl or heterocyclylalkyl, or heteroarylalkyl.

More specifically, $R^3$ can be an unsubstituted or substituted group selected from any one of:

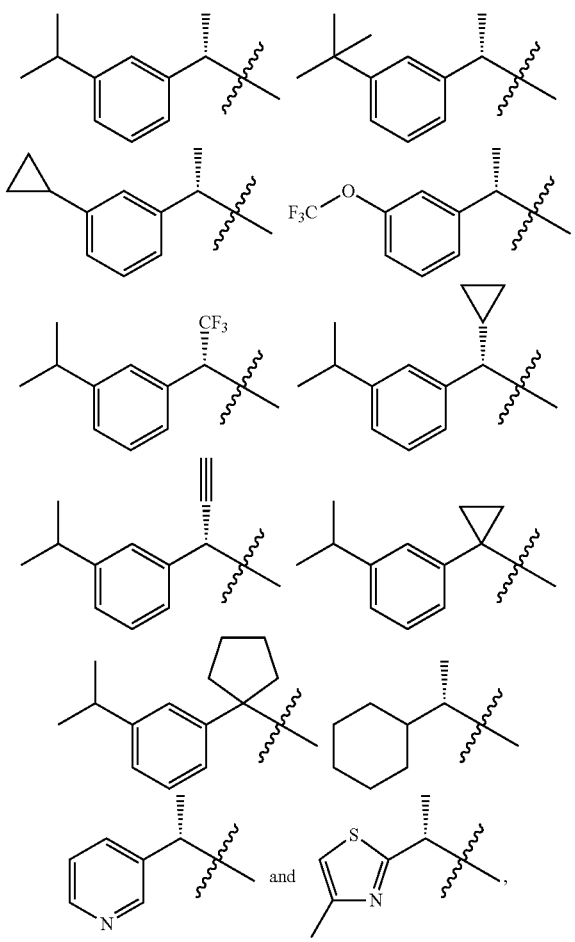

wherein a wavy line indicates a point of attachment. The $R^3$ group can be unsubstituted, or can be substituted with one or more independently selected ($C_1$-$C_6$)alkyl, ($C_2$-$C_6$)alkenyl, ($C_2$-$C_6$)alkynyl, ($C_6$-$C_{10}$)aryl, ($C_3$-$C_9$)cycloalkyl, 3-9 membered mono- or bicyclic heterocyclyl, 3-9 membered mono- or bicyclic heteroaryl, halo, haloalkyl, haloalkoxy, nitro, cyano, CO$_2$R', methylenedioxy, OR', N(R')$_2$, ($C_1$-$C_4$)alkyl-S(O)$_q$, SO$_2$NR'$_2$, or ($C_1$-$C_6$)alkoxyl groups wherein R' is as defined herein.

In various embodiments, groups $X^5$, $X^6$, and $X^7$ can all represent carbon, such that group Z is an unsubstituted or substituted phenyl group. Alternatively, one of $X^5$, $X^6$, and $X^7$ can be a nitrogen atom, such that group Z is an unsubstituted or substituted pyridinyl ring.

The Z ring can be substituted with an $R^4$ group. In various embodiments, $R^4$ is disposed on $X^5$, such that the $R^4$ is para to the point of attachment of Z to the ring comprising $X^3$. For example, $R^4$ can be CO$_2$H, CN, 3-hydroxypyrrolidin-1-carbonyl, 2-hydroxyethylaminocarbonyl, cyclohexylaminocarbonyl, 2-(N,N-dimethylaminocarbonyl)-2-hydroxyethylaminocarbonyl, N,N-dimethylaminoethylcarbonyl, N-methylaminocarbonyl, N-hydroxylaminocarbonyl, or C-bonded tetrazolyl, or can be CH$_2$CO$_2$H, C(CH$_3$)$_2$CO$_2$H, or a cyclopropylcarboxylic acid group.

In various embodiments, the compound is any of those shown in Table 1, below. A compound shown in Table 1 listed as a "prophetic example" is a compound believed by the inventors herein to be a compound of the invention, but which has not yet been specifically synthesized. Such compounds can be prepared by synthetic methods disclosed herein in combination with the knowledge of a person of ordinary skill in the art of organic synthesis, including the use of appropriately selected precursors, intermediates, reagents, and reaction conditions and mechanisms.

More specifically, the compound is

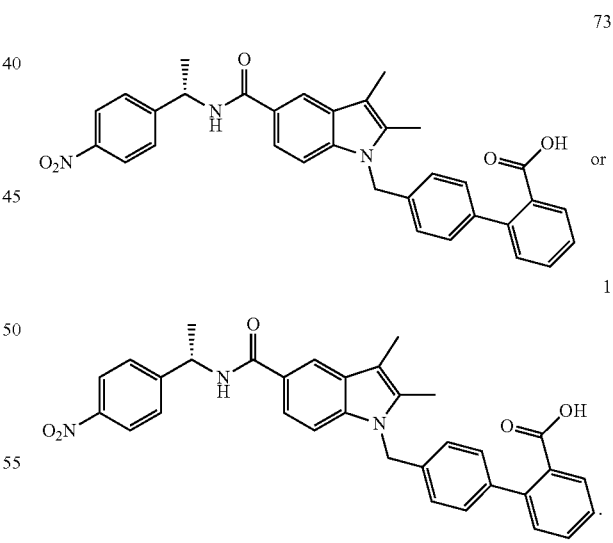

In various embodiments, the invention provides a pharmaceutical composition comprising a compound of the invention and a pharmaceutically acceptable excipient.

Another aspect of an embodiment of the invention provides compositions of the compounds of the invention, alone or in combination with another medicament. As set forth herein, compounds of the invention include stereoisomers, tautomers, solvates, prodrugs, pharmaceutically acceptable salts and mixtures thereof. Compositions containing a compound of the invention can be prepared by conventional techniques, e.g., as described in Remington: *The Science and Practice of Pharmacy*, 19th Ed., 1995, or later versions thereof, incorporated by reference herein. The compositions can appear in conventional forms, for example capsules, tablets, aerosols, solutions, suspensions or topical applications.

Typical compositions include a compound of the invention and a pharmaceutically acceptable excipient which can be a carrier or a diluent. For example, the active compound will usually be mixed with a carrier, or diluted by a carrier, or enclosed within a carrier which can be in the form of an ampoule, capsule, sachet, paper, or other container. When the active compound is mixed with a carrier, or when the carrier serves as a diluent, it can be solid, semi-solid, or liquid material that acts as a vehicle, excipient, or medium for the active compound. The active compound can be adsorbed on a granular solid carrier, for example contained in a sachet. Some examples of suitable carriers are water, salt solutions, alcohols, polyethylene glycols, polyhydroxyethoxylated castor oil, peanut oil, olive oil, gelatin, lactose, terra alba, sucrose, dextrin, magnesium carbonate, sugar, cyclodextrin, amylose, magnesium stearate, talc, gelatin, agar, pectin, acacia, stearic acid or lower alkyl ethers of cellulose, silicic acid, fatty acids, fatty acid amines, fatty acid monoglycerides and diglycerides, pentaerythritol fatty acid esters, polyoxyethylene, hydroxymethylcellulose and polyvinylpyrrolidone. Similarly, the carrier or diluent can include any sustained release material known in the art, such as glyceryl monostearate or glyceryl distearate, alone or mixed with a wax.

The formulations can be mixed with auxiliary agents which do not deleteriously react with the active compounds. Such additives can include wetting agents, emulsifying and suspending agents, salt for influencing osmotic pressure, buffers and/or coloring substances preserving agents, sweetening agents or flavoring agents. The compositions can also be sterilized if desired.

The route of administration can be any route which effectively transports the active compound of the invention to the appropriate or desired site of action, such as oral, nasal, pulmonary, buccal, subdermal, intradermal, transdermal or parenteral, e.g., rectal, depot, subcutaneous, intravenous, intraurethral, intramuscular, intranasal, ophthalmic solution or an ointment, the oral route being preferred.

If a solid carrier is used for oral administration, the preparation can be tableted, placed in a hard gelatin capsule in powder or pellet form or it can be in the form of a troche or lozenge. If a liquid carrier is used, the preparation can be in the form of a syrup, emulsion, soft gelatin capsule or sterile injectable liquid such as an aqueous or non-aqueous liquid suspension or solution.

Injectable dosage forms generally include aqueous suspensions or oil suspensions which can be prepared using a suitable dispersant or wetting agent and a suspending agent Injectable forms can be in solution phase or in the form of a suspension, which is prepared with a solvent or diluent. Acceptable solvents or vehicles include sterilized water, Ringer's solution, or an isotonic aqueous saline solution. Alternatively, sterile oils can be employed as solvents or suspending agents. Preferably, the oil or fatty acid is non-volatile, including natural or synthetic oils, fatty acids, mono-, di- or tri-glycerides.

For injection, the formulation can also be a powder suitable for reconstitution with an appropriate solution as described above. Examples of these include, but are not limited to, freeze dried, rotary dried or spray dried powders, amorphous powders, granules, precipitates, or particulates. For injection, the formulations can optionally contain stabilizers, pH modifiers, surfactants, bioavailability modifiers and combinations of these. The compounds can be formulated for parenteral administration by injection such as by bolus injection or continuous infusion. A unit dosage form for injection can be in ampoules or in multi-dose containers.

The formulations of the invention can be designed to provide quick, sustained, or delayed release of the active ingredient after administration to the patient by employing procedures well known in the art. Thus, the formulations can also be formulated for controlled release or for slow release.

Compositions contemplated by the present invention can include, for example, micelles or liposomes, or some other encapsulated form, or can be administered in an extended release form to provide a prolonged storage and/or delivery effect. Therefore, the formulations can be compressed into pellets or cylinders and implanted intramuscularly or subcutaneously as depot injections. Such implants can employ known inert materials such as silicones and biodegradable polymers, e.g., polylactide-polyglycolide. Examples of other biodegradable polymers include poly(orthoesters) and poly (anhydrides).

For nasal administration, the preparation can contain a compound of the invention, dissolved or suspended in a liquid carrier, preferably an aqueous carrier, for aerosol application. The carrier can contain additives such as solubilizing agents, e.g., propylene glycol, surfactants, absorption enhancers such as lecithin (phosphatidylcholine) or cyclodextrin, or preservatives such as parabens.

For parenteral application, particularly suitable are injectable solutions or suspensions, preferably aqueous solutions with the active compound dissolved in polyhydroxylated castor oil.

Tablets, dragees, or capsules having talc and/or a carbohydrate carrier or binder or the like are particularly suitable for oral application. Preferable carriers for tablets, dragees, or capsules include lactose, corn starch, and/or potato starch. A syrup or elixir can be used in cases where a sweetened vehicle can be employed.

A typical tablet that can be prepared by conventional tabletting techniques can contain:

| Core: | |
|---|---|
| Active compound (as free compound or salt thereof) | 250 mg |
| Colloidal silicon dioxide (Aerosil ®) | 1.5 mg |
| Cellulose, microcryst. (Avicel ®) | 70 mg |
| Modified cellulose gum (Ac-Di-Sol ®) | 7.5 mg |
| Magnesium stearate | Ad. |
| Coating: | |
| HPMC approx. | 9 mg |
| *Mywacett 9-40 T approx. | 0.9 mg |

*Acylated monoglyceride used as plasticizer for film coating.

A typical capsule for oral administration contains compounds of the invention (250 mg), lactose (75 mg) and magnesium stearate (15 mg). The mixture is passed through a 60 mesh sieve and packed into a No. 1 gelatin capsule. A typical injectable preparation is produced by aseptically placing 250 mg of compounds of the invention into a vial, aseptically freeze-drying and sealing. For use, the contents of the vial are mixed with 2 mL of sterile physiological saline, to produce an injectable preparation.

The compounds of the invention can be administered to a mammal, especially a human in need of such treatment, prevention, elimination, alleviation or amelioration of a condition. Such mammals include also animals, both domestic animals, e.g., household pets, farm animals, and non-domestic animals such as wildlife.

The compounds of the invention are effective over a wide dosage range. For example, in the treatment of adult humans, dosages from about 0.05 to about 5000 mg, preferably from about 1 to about 2000 mg, and more preferably between about 2 and about 2000 mg per day can be used. A typical dosage is about 10 mg to about 1000 mg per day. In choosing a regimen for patients it can frequently be necessary to begin with a higher dosage and when the condition is under control to reduce the dosage. The exact dosage will depend upon the activity of the compound, mode of administration, on the therapy desired, form in which administered, the subject to be treated and the body weight of the subject to be treated, and the preference and experience of the physician or veterinarian in charge.

Generally, the compounds of the invention are dispensed in unit dosage form including from about 0.05 mg to about 1000 mg of active ingredient together with a pharmaceutically acceptable carrier per unit dosage.

Usually, dosage forms suitable for oral, nasal, pulmonal or transdermal administration include from about 125 μg to about 1250 mg, preferably from about 250 μg to about 500 mg, and more preferably from about 2.5 mg to about 250 mg, of the compounds admixed with a pharmaceutically acceptable carrier or diluent.

Dosage forms can be administered daily, or more than once a day, such as twice or thrice daily. Alternatively dosage forms can be administered less frequently than daily, such as every other day, or weekly, if found to be advisable by a prescribing physician.

Methods of the Invention

In various embodiments, the invention provides methods of inhibiting kinase-mediated, such as cdk5-mediated, phosphorylation of PPARG in a mammal, comprising administering to the mammal an effective amount of a compound of the invention. The effective amount of the compound for inhibiting, e.g., cdk5-mediated phosphorylation of PPARG can avoid producing an agonistic effect on PPARG. By avoiding agonism of PPARG, various side effects can be avoided, including such as significant weight gain, edema, impairment of bone growth or formation, or cardiac hypertrophy, or any combination thereof.

In various embodiments, the invention provides a method of treating a condition in a mammal, wherein binding of a ligand to PPARG or inhibition of, e.g., cdk5-mediated phosphorylation of PPARG, or both, is medically indicated, comprising administering to the mammal an effective amount of a compound of the invention at a frequency of dosing and for a duration of dosing effective to provide a beneficial effect to the mammal. The mammal under treatment can be a human. In various embodiments, the effective amount, frequency of dosing, and duration of dosing of the compound for binding of a ligand to PPARG or inhibition of cdk5-mediated phosphorylation of PPARG, or both, do not produce an agonistic effect on PPARG. For example, administration of a compound of the invention can be used for treatment of diabetes, insulin resistance, impaired glucose tolerance, pre-diabetes, hyperglycemia, hyperinsulinemia, obesity, or inflammation. Due to the avoidance of agonism of PPARG, an effective amount, frequency of dosing, and duration of dosing of the compound does not significantly produce side effects of weight gain, edema, or cardiac hypertrophy in the mammal receiving the compound.

Specifically, the invention provides a method of treatment of diabetes in a human, comprising administering to the human regularly over a duration of time an effective amount of a compound of the invention, optionally in conjunction with a second medicament effective for the treatment of diabetes. More specifically the compound can be

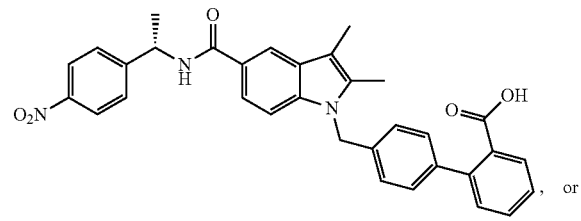

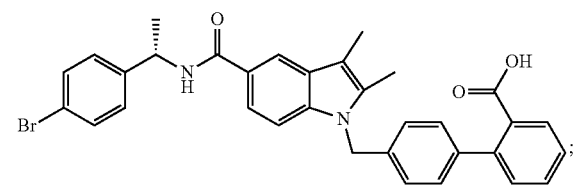

or a pharmaceutically acceptable salt thereof. When the compound of the invention is used in combination with a second medicament comprising an effective antidiabetes agent, the second agent can be any suitable drug approved for diabetes treatment, such as biguanides such as metformin and the like, sulfonylureas such as gliburide and the like, or thiazolidinediones such as rosiglitazone and the like.

Documents Cited

Bruning, J. B., Chalmers, M. J., Prasad, S., Busby, S. A., Kamenecka, T. M., He, Y., Nettles, K. W., and Griffin, P. R. (2007). Partial agonists activate PPARgamma using a helix 12 independent mechanism. *Structure* 15, 1258-1271.

Chawla, A., Schwarz, E. J., Dimaculangan, D. D., and Lazar, M. A. (1994). Peroxisome proliferator-activated receptor (PPAR) gamma: adipose-predominant expression and induction early in adipocyte differentiation. *Endocrinology* 135, 798-800.

Choi, J. H., Banks, A. S., Estall, J. L., Kajimura, S., Bostrom, P., Laznik, D., Ruas, J. L., Chalmers, M. J., Kamenecka, T. M., Bluher, M., et al. (2010). Anti-diabetic drugs inhibit obesity-linked phosphorylation of PPARgamma by Cdk5. *Nature* 466, 451-456.

DeFronzo, R. A., Tobin, J. D., and Andres, R. (1979). Glucose clamp technique: a method for quantifying insulin secretion and resistance. *Am J Physiol* 237, E214-223.

Grey, A., Bolland, M., Gamble, G., Wattie, D., Home, A., Davidson, J., and Reid, I. R. (2007). The peroxisome proliferator-activated receptor-gamma agonist rosiglitazone decreases bone formation and bone mineral density in healthy postmenopausal women: a randomized, controlled trial. *J Clin Endocrinol Metab* 92, 1305-1310.

Kahn, B. B., and McGraw, T. E. (2010). Rosiglitazone, PPARgamma, and type 2 diabetes. *The New England journal of medicine* 363, 2667-2669.

Kahn, S. E., Zinman, B., Lachin, J. M., Haffner, S. M., Herman, W. H., Holman, R. R., Kravitz, B. G., Yu, D., Heise, M. A., Aftring, R. P., et al. (2008). Rosiglitazone-Associated Fractures in Type 2 Diabetes. *Diabetes care* 31, 845-851.

Kliewer, S. A., Lenhard, J. M., Willson, T. M., Patel, I., Morris, D. C., and Lehmann, J. M. (1995). A prostaglandin J2 metabolite binds peroxisome proliferator-activated receptor [gamma] and promotes adipocyte differentiation. *Cell* 83, 813-819.

Lamotte, Y., Martres, P., Faucher, N., Laroze, A., Grillot, D., Ancellin, N., Saintillan, Y., Beneton, V., and Gampe, R. T., Jr. (2010). Synthesis and biological activities of novel indole derivatives as potent and selective PPARgamma modulators. *Bioorg Med Chem Lett* 20, 1399-1404.

Lehmann, J. M., Moore, L. B., Smith-Oliver, T. A., Wilkison, W. O., Willson, T. M., and Kliewer, S. A. (1995). An antidiabetic thiazolidinedione is a high affinity ligand for peroxisome proliferator-activated receptor gamma (PPAR gamma). *The Journal of biological chemistry* 270, 12953-12956.

Mayerson, A. B., Hundal, R. S., Dufour, S., Lebon, V., Befroy, D., Cline, G. W., Enocksson, S., Inzucchi, S. E., Shulman, G. I., and Petersen, K. F. (2002). The Effects of Rosiglitazone on Insulin Sensitivity, Lipolysis, and Hepatic and Skeletal Muscle Triglyceride Content in Patients With Type 2 Diabetes. *Diabetes* 51, 797-802.

Nolte, R. T., Wisely, G. B., Westin, S., Cobb, J. E., Lambert, M. H., Kurokawa, R., Rosenfeld, M. G., Willson, T. M., Glass, C. K., and Milbum, M. V. (1998). Ligand binding and co-activator assembly of the peroxisome proliferator-activated receptor-gamma. *Nature* 395, 137-143.

Tontonoz, P., Hu, E., and Spiegelman, B. M. (1994). Stimulation of adipogenesis in fibroblasts by PPAR gamma 2, a lipid-activated transcription factor. *Cell* 79, 1147-1156.

EXAMPLES

TABLE 1

| # | Structure | Substituents |
|---|---|---|
| 1 | 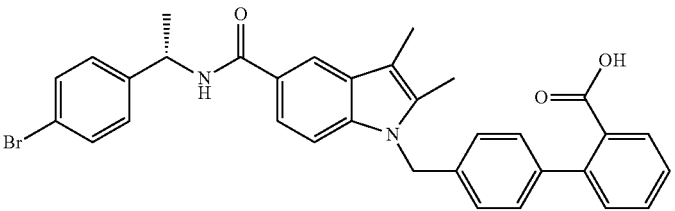 [SMILES: Cc1c(C)n(Cc2ccc(-c3ccccc3C(=O)O)cc2)c2ccc(C(=O)N[C@@H](C)c3ccc(Br)cc3)cc12] | R1 = methyl<br>R2 = methyl<br>R3 = 4-bromophenyl-1-ethyl<br>R4 = CO$_2$H<br>R5 = H<br>R6 = H<br>R7 = H |
| 2 | 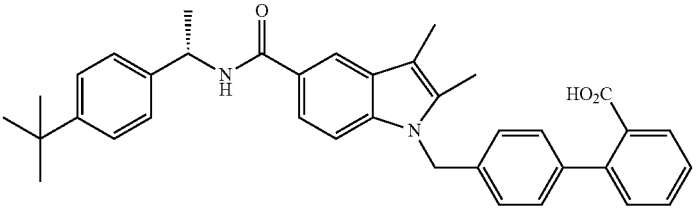 [SMILES: Cc1c(C)n(Cc2ccc(-c3ccccc3C(=O)O)cc2)c2ccc(C(=O)N[C@@H](C)c3ccc(C(C)(C)C)cc3)cc12] | R1 = methyl<br>R2 = methyl<br>R3 = 4-t-butylphenyl-1-ethyl<br>R4 = CO$_2$H<br>R5 = H<br>R6 = H<br>R7 = H |
| 3 | 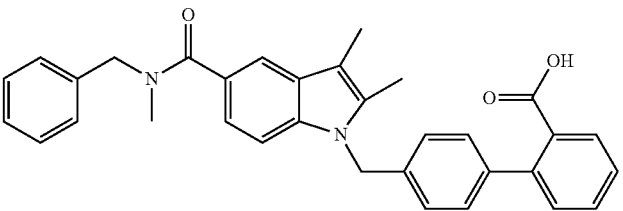 [SMILES: Cc1c(C)n(Cc2ccc(-c3ccccc3C(=O)O)cc2)c2ccc(C(=O)N(C)Cc3ccccc3)cc12] | R = methyl<br>R1 = methyl<br>R2 = methyl<br>R3 = benzyl<br>R4 = CO$_2$H<br>R5 = H<br>R6 = H<br>R7 = H |
| 4 | 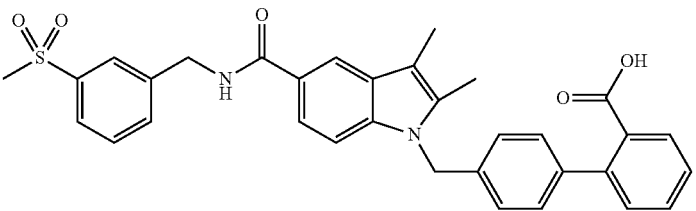 [SMILES: Cc1c(C)n(Cc2ccc(-c3ccccc3C(=O)O)cc2)c2ccc(C(=O)NCc3cccc(S(C)(=O)=O)c3)cc12] | R1 = methyl<br>R2 = methyl<br>R3 = 3-methanesulfonylbenzyl<br>R4 = CO$_2$H<br>R5 = H<br>R6 = H<br>R7 = H |
| 5 | 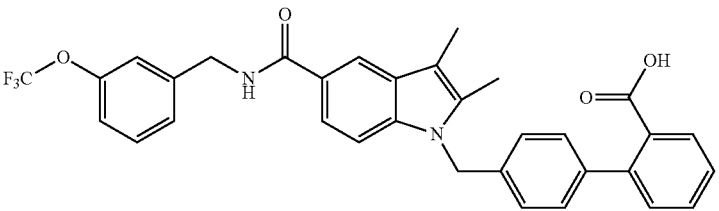 [SMILES: Cc1c(C)n(Cc2ccc(-c3ccccc3C(=O)O)cc2)c2ccc(C(=O)NCc3cccc(OC(F)(F)F)c3)cc12] | R1 = methyl<br>R2 = methyl<br>R3 = 3-trifluoromethoxybenzyl<br>R4 = CO$_2$H<br>R5 = H<br>R6 = H<br>R7 = H |

TABLE 1-continued

Specific Compounds of the Invention

| # | Structure | Substituents |
|---|-----------|--------------|
| 6 | 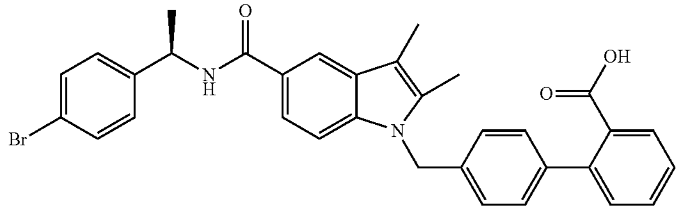 [SMILES: Cc1c(C)n(Cc2ccc(-c3ccccc3C(=O)O)cc2)c2ccc(C(=O)N[C@H](C)c3ccc(Br)cc3)cc12] | R1 = methyl<br>R2 = methyl<br>R3 = 4-bromophenyl-1-ethyl<br>R4 = CO$_2$H<br>R5 = H<br>R6 = H<br>R7 = H |
| 7 | 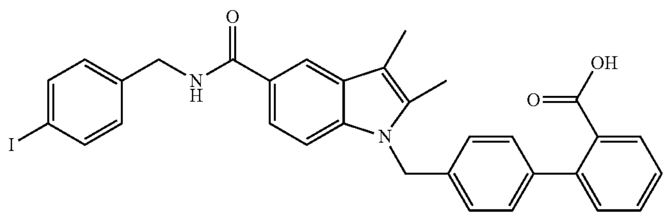 [SMILES: Cc1c(C)n(Cc2ccc(-c3ccccc3C(=O)O)cc2)c2ccc(C(=O)NCc3ccc(I)cc3)cc12] | R1 = methyl<br>R2 = methyl<br>R3 = 4-iodobenzyl<br>R4 = CO$_2$H<br>R5 = H<br>R6 = H<br>R7 = H |
| 8 | 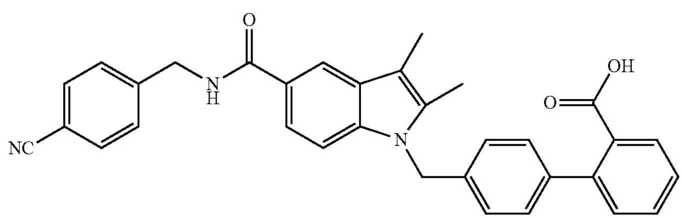 [SMILES: Cc1c(C)n(Cc2ccc(-c3ccccc3C(=O)O)cc2)c2ccc(C(=O)NCc3ccc(C#N)cc3)cc12] | R1 = methyl<br>R2 = methyl<br>R3 = 4-cyanobenzyl<br>R4 = CO$_2$H<br>R5 = H<br>R6 = H<br>R7 = H |
| 9 | 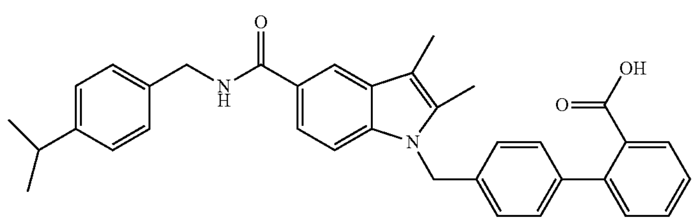 [SMILES: Cc1c(C)n(Cc2ccc(-c3ccccc3C(=O)O)cc2)c2ccc(C(=O)NCc3ccc(C(C)C)cc3)cc12] | R1 = methyl<br>R2 = methyl<br>R3 = 4-isopropylbenzyl<br>R4 = CO$_2$H<br>R5 = H<br>R6 = H<br>R7 = H |
| 10 | 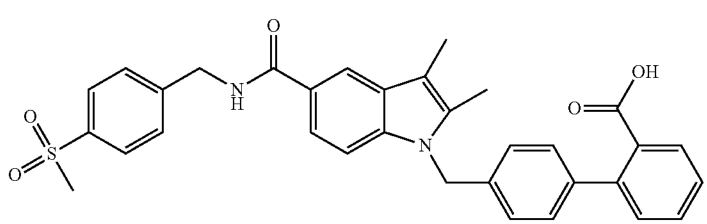 [SMILES: Cc1c(C)n(Cc2ccc(-c3ccccc3C(=O)O)cc2)c2ccc(C(=O)NCc3ccc(S(C)(=O)=O)cc3)cc12] | R1 = methyl<br>R2 = methyl<br>R3 = 4-methanesulfonylbenzyl<br>R4 = CO$_2$H<br>R5 = H<br>R6 = H<br>R7 = H |
| 11 | 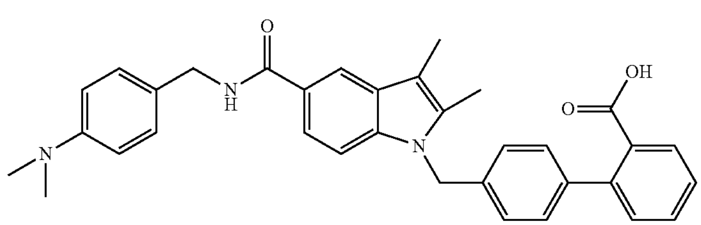 [SMILES: Cc1c(C)n(Cc2ccc(-c3ccccc3C(=O)O)cc2)c2ccc(C(=O)NCc3ccc(N(C)C)cc3)cc12] | R1 = methyl<br>R2 = methyl<br>R3 = 4-dimethylaminobenzyl<br>R4 = CO$_2$H<br>R5 = H<br>R6 = H<br>R7 = H |
| 12 | 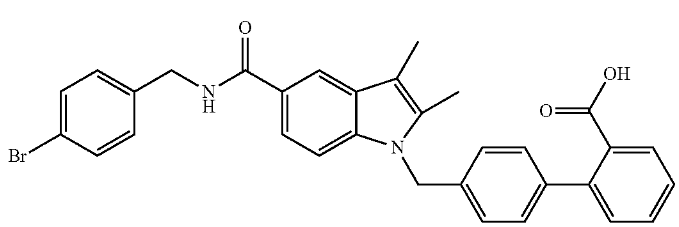 | R1 = methyl<br>R2 = methyl<br>R3 = 4-bromobenzyl<br>R4 = CO$_2$H<br>R5 = H<br>R6 = H<br>R7 = H |

TABLE 1-continued

Specific Compounds of the Invention

| # | Structure | Substituents |
|---|---|---|
| 13 | 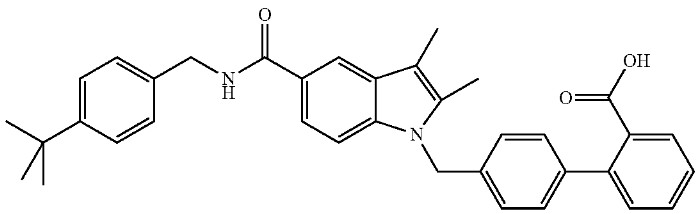 [SMILES: Cc1c(C)n(Cc2ccc(-c3ccccc3C(=O)O)cc2)c2ccc(C(=O)NCc3ccc(C(C)(C)C)cc3)cc12] | R1 = methyl<br>R2 = methyl<br>R3 = 4-tertbutylbenzyl<br>R4 = CO$_2$H<br>R5 = H<br>R6 = H<br>R7 = H |
| 14 | 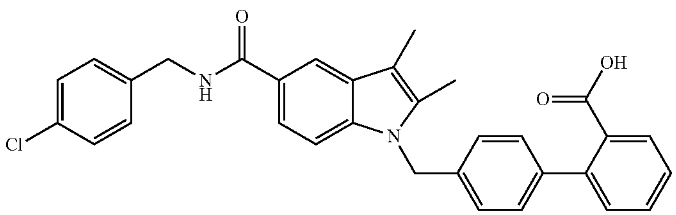 [SMILES: Cc1c(C)n(Cc2ccc(-c3ccccc3C(=O)O)cc2)c2ccc(C(=O)NCc3ccc(Cl)cc3)cc12] | R1 = methyl<br>R2 = methyl<br>R3 = 4-chlorobenzyl<br>R4 = CO$_2$H<br>R5 = H<br>R6 = H<br>R7 = H |
| 15 | 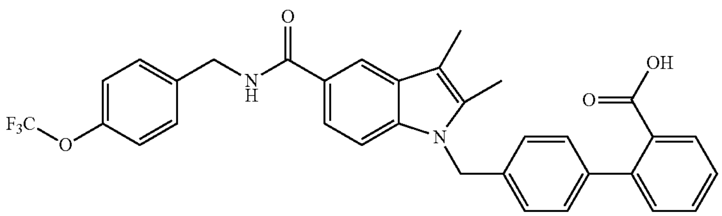 [SMILES: Cc1c(C)n(Cc2ccc(-c3ccccc3C(=O)O)cc2)c2ccc(C(=O)NCc3ccc(OC(F)(F)F)cc3)cc12] | R1 = methyl<br>R2 = methyl<br>R3 = 4-trifluoromethoxybenzyl<br>R4 = CO$_2$H<br>R5 = H<br>R6 = H<br>R7 = H |
| 16 | 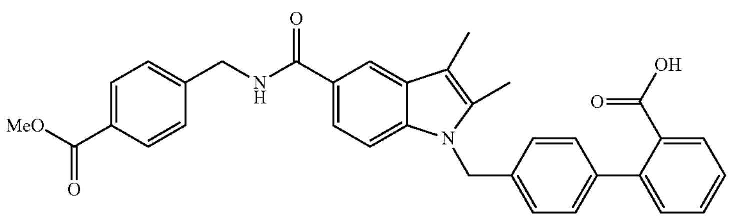 [SMILES: COC(=O)c1ccc(CNC(=O)c2ccc3c(c2)c(C)c(C)n3Cc2ccc(-c3ccccc3C(=O)O)cc2)cc1] | R1 = methyl<br>R2 = methyl<br>R3 = 4-methoxycarbonylbenzyl<br>R4 = CO$_2$H<br>R5 = H<br>R6 = H<br>R7 = H |
| 17 | 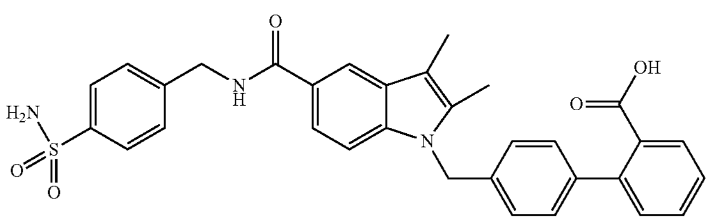 [SMILES: Cc1c(C)n(Cc2ccc(-c3ccccc3C(=O)O)cc2)c2ccc(C(=O)NCc3ccc(S(N)(=O)=O)cc3)cc12] | R1 = methyl<br>R2 = methyl<br>R3 = 4-aminosulfonylbenzyl<br>R4 = CO$_2$H<br>R5 = H<br>R6 = H<br>R7 = H |
| 18 | 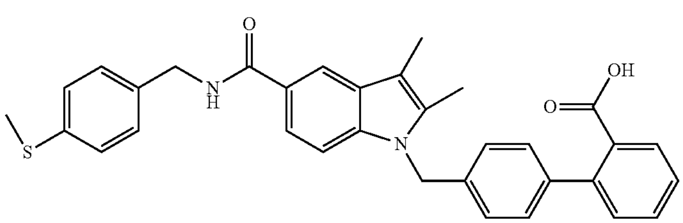 [SMILES: CSc1ccc(CNC(=O)c2ccc3c(c2)c(C)c(C)n3Cc2ccc(-c3ccccc3C(=O)O)cc2)cc1] | R1 = methyl<br>R2 = methyl<br>R3 = 4-methylthiobenzyl<br>R4 = CO$_2$H<br>R5 = H<br>R6 = H<br>R7 = H |
| 19 | 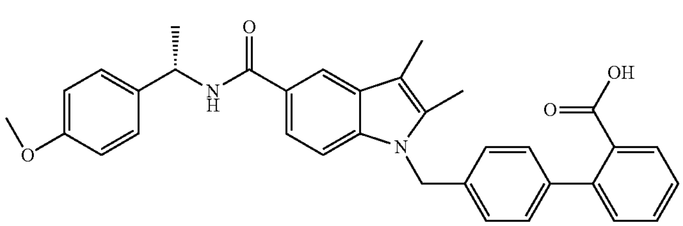 | R1 = methyl<br>R2 = methyl<br>R3 = 4-methoxyphenyl-1-ethyl<br>R4 = CO$_2$H<br>R5 = H<br>R6 = H<br>R7 = H |

TABLE 1-continued

Specific Compounds of the Invention

| # | Structure | Substituents |
|---|---|---|
| 20 | 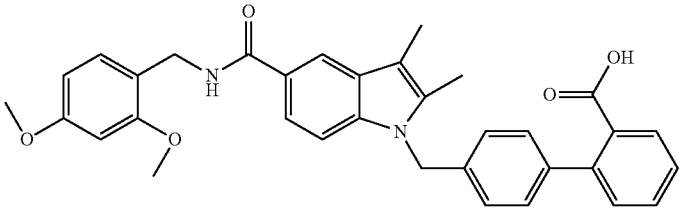 [SMILES: COc1ccc(CNC(=O)c2ccc3c(c2)c(C)c(C)n3Cc2ccc(-c3ccccc3C(=O)O)cc2)c(OC)c1] | R1 = methyl<br>R2 = methyl<br>R3 = 2,4-dimethoxybenzyl<br>R4 = CO₂H<br>R5 = H<br>R6 = H<br>R7 = H |
| 21 | 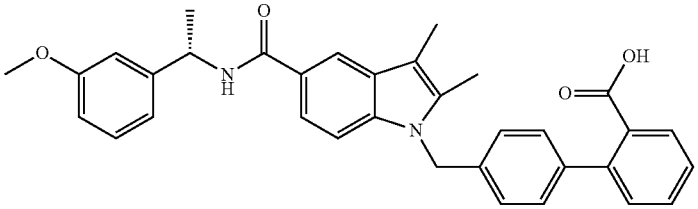 [SMILES: COc1cccc([C@H](C)NC(=O)c2ccc3c(c2)c(C)c(C)n3Cc2ccc(-c3ccccc3C(=O)O)cc2)c1] | R1 = methyl<br>R2 = methyl<br>R3 = 3-methoxyphenyl-1-ethyl<br>R4 = CO₂H<br>R5 = H<br>R6 = H<br>R7 = H |
| 22 | 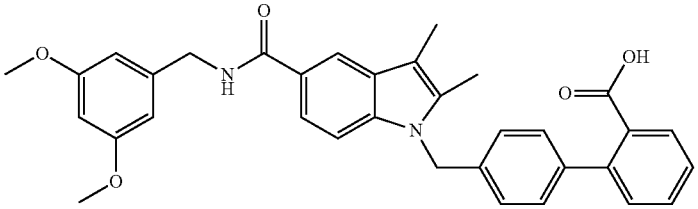 [SMILES: COc1cc(CNC(=O)c2ccc3c(c2)c(C)c(C)n3Cc2ccc(-c3ccccc3C(=O)O)cc2)cc(OC)c1] | R1 = methyl<br>R2 = methyl<br>R3 = 3,5-dimethoxybenzyl<br>R4 = CO₂H<br>R5 = H<br>R6 = H<br>R7 = H |
| 23 | 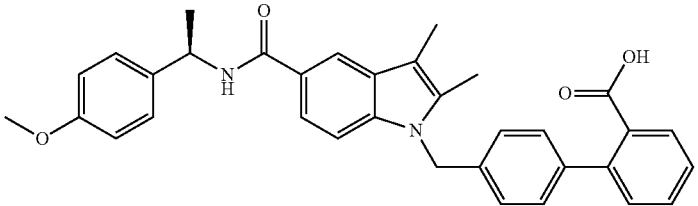 [SMILES: COc1ccc([C@@H](C)NC(=O)c2ccc3c(c2)c(C)c(C)n3Cc2ccc(-c3ccccc3C(=O)O)cc2)cc1] | R1 = methyl<br>R2 = methyl<br>R3 = 4-methoxyphenyl-1-ethyl<br>R4 = CO₂H<br>R5 = H<br>R6 = H<br>R7 = H |
| 24 | 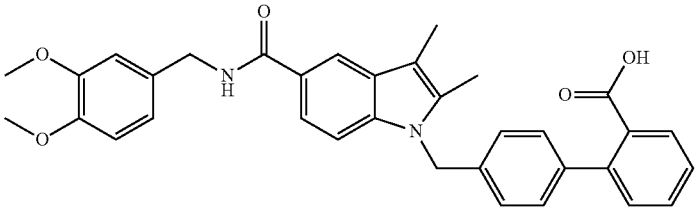 [SMILES: COc1ccc(CNC(=O)c2ccc3c(c2)c(C)c(C)n3Cc2ccc(-c3ccccc3C(=O)O)cc2)cc1OC] | R1 = methyl<br>R2 = methyl<br>R3 = 3,4-dimethoxybenzyl<br>R4 = CO₂H<br>R5 = H<br>R6 = H<br>R7 = H |
| 25 | 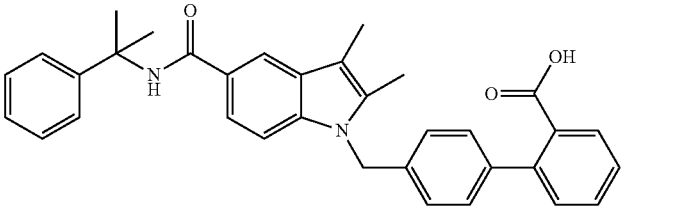 [SMILES: Cc1c(C)n(Cc2ccc(-c3ccccc3C(=O)O)cc2)c2ccc(C(=O)NC(C)(C)c3ccccc3)cc12] | R1 = methyl<br>R2 = methyl<br>R3 = 2-phenylpropan-2-yl<br>R4 = CO₂H<br>R5 = H<br>R6 = H<br>R7 = H |
| 26 | 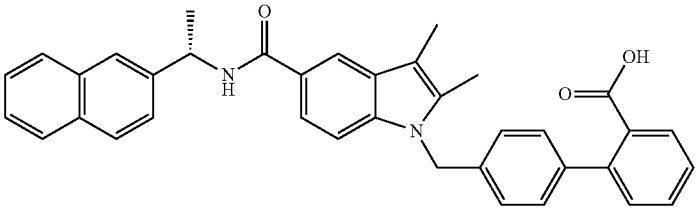 [SMILES: Cc1c(C)n(Cc2ccc(-c3ccccc3C(=O)O)cc2)c2ccc(C(=O)N[C@@H](C)c3ccc4ccccc4c3)cc12] | R1 = methyl<br>R2 = methyl<br>R3 = 1-(naphth-2-yl)-ethyl<br>R4 = CO₂H<br>R5 = H<br>R6 = H<br>R7 = H |

TABLE 1-continued

Specific Compounds of the Invention

| # | Structure | Substituents |
|---|-----------|--------------|
| 27 | 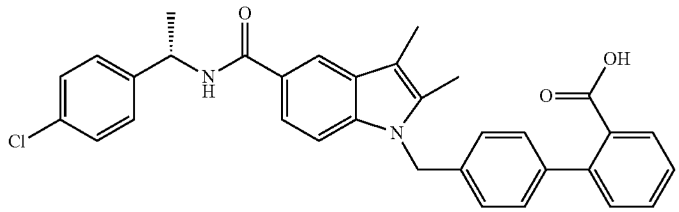 [SMILES: Cc1c(C)n(Cc2ccc(-c3ccccc3C(=O)O)cc2)c2ccc(C(=O)N[C@@H](C)c3ccc(Cl)cc3)cc12] | R1 = methyl<br>R2 = methyl<br>R3 = 4-chlorophenyl-1-ethyl<br>R4 = CO$_2$H<br>R5 = H<br>R6 = H<br>R7 = H |
| 30 | 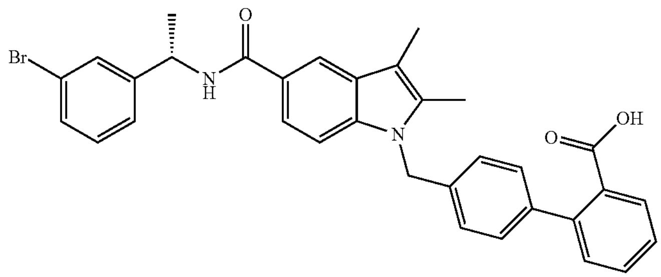 | R1 = methyl<br>R2 = methyl<br>R3 = 3-bromophenyl-1-ethyl<br>R4 = CO$_2$H<br>R5 = H<br>R6 = H<br>R7 = H |
| 31 | 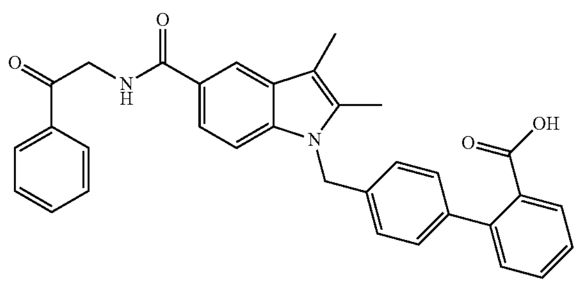 [SMILES: Cc1c(C)n(Cc2ccc(-c3ccccc3C(=O)O)cc2)c2ccc(C(=O)NCC(=O)c3ccccc3)cc12] | R1 = methyl<br>R2 = methyl<br>R3 = 2-oxo-2-phenylethyl<br>R4 = CO$_2$H<br>R5 = H<br>R6 = H<br>R7 = H |
| 34 | 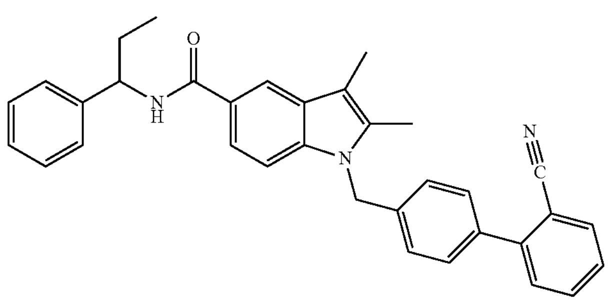 [SMILES: CCC(NC(=O)c1ccc2c(c1)c(C)c(C)n2Cc1ccc(-c2ccccc2C#N)cc1)c1ccccc1] | R1 = methyl<br>R2 = methyl<br>R3 = phenyl-(propyl-1-yl)<br>R4 = CN<br>R5 = H<br>R6 = H<br>R7 = H |
| 35 | 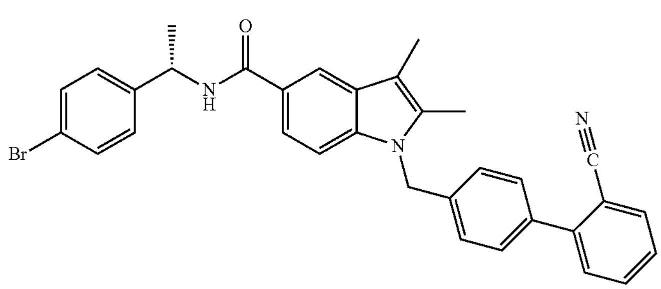 | R1 = methyl<br>R2 = methyl<br>R3 = 4-bromophenyl-1-ethyl<br>R4 = CN<br>R5 = H<br>R6 = H<br>R7 = H |

TABLE 1-continued

Specific Compounds of the Invention

| # | Structure | Substituents |
|---|---|---|
| 36 | 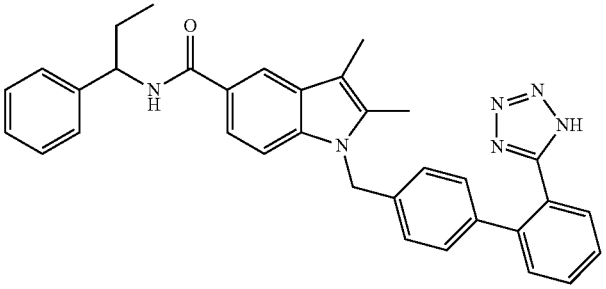 [SMILES: CCC(NC(=O)c1ccc2c(c1)c(C)c(C)n2Cc1ccc(-c2ccccc2-c2nnn[nH]2)cc1)c1ccccc1] | R1 = methyl<br>R2 = methyl<br>R3 = phenyl-(propyl-1-yl)<br>R4 = 1H-tetrazol-5-yl<br>R5 = H<br>R6 = H<br>R7 = H |
| 37 | 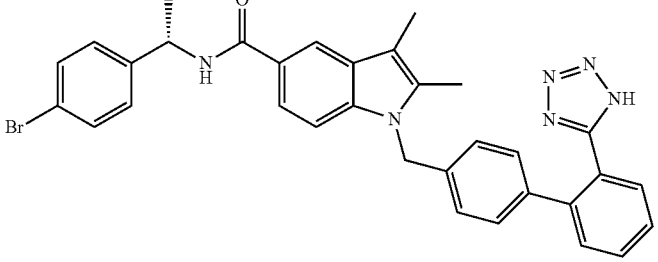 | R1 = methyl<br>R2 = methyl<br>R3 = 4-bromophenyl-1-ethyl<br>R4 = 1H-tetrazol-5-yl<br>R5 = H<br>R6 = H<br>R7 = H |
| 38 | 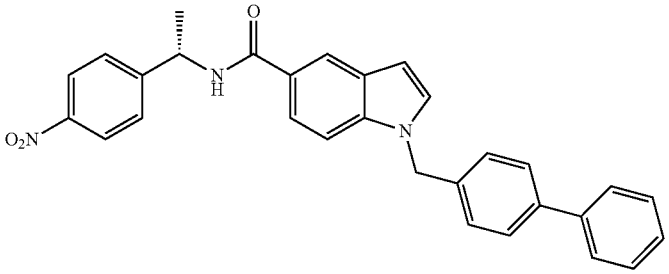 [SMILES: C[C@H](NC(=O)c1ccc2c(ccn2Cc2ccc(-c3ccccc3)cc2)c1)c1ccc([N+](=O)[O-])cc1] | R1 = H<br>R2 = H<br>R3 = 4-nitrophenyl-1-ethyl<br>R4 = H<br>R5 = H<br>R6 = H<br>R7 = H |
| 39 | 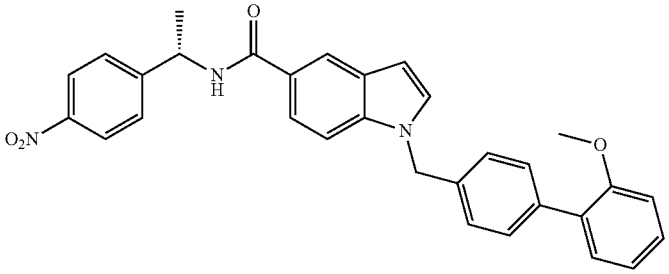 | R1 = H<br>R2 = H<br>R3 = 4-nitrophenyl-1-ethyl<br>R4 = OCH$_3$<br>R5 = H<br>R6 = H<br>R7 = H |
| 40 | 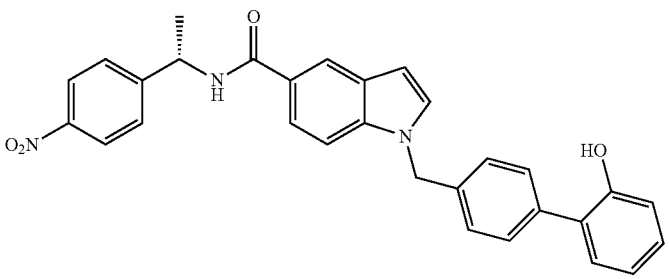 | R1 = H<br>R2 = H<br>R3 = 4-nitrophenyl-1-ethyl<br>R4 = OH<br>R5 = H<br>R6 = H<br>R7 = H |

TABLE 1-continued

Specific Compounds of the Invention

| # | Structure | Substituents |
|---|---|---|
| 41 | 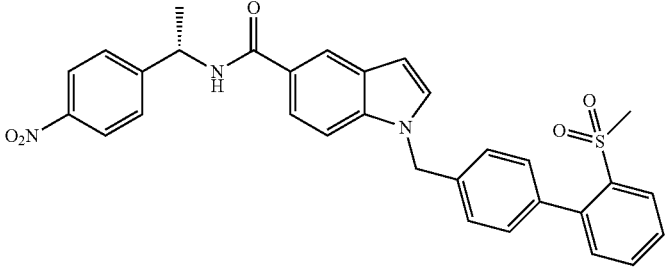 [SMILES: C[C@H](NC(=O)c1ccc2c(ccn2Cc2ccc(-c3ccccc3S(C)(=O)=O)cc2)c1)c1ccc([N+](=O)[O-])cc1] | R1 = H<br>R2 = H<br>R3 = 4-nitrophenyl-1-ethyl<br>R4 = methanesulfonyl<br>R5 = H<br>R6 = H<br>R7 = H |
| 42 | 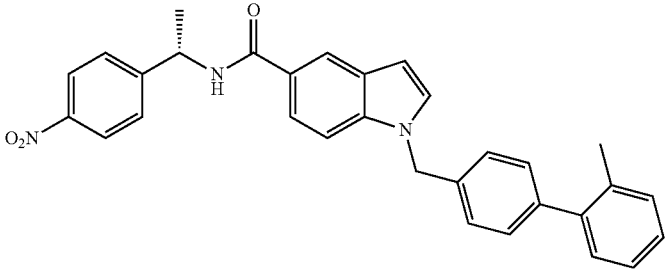 [SMILES: Cc1ccccc1-c1ccc(Cn2ccc3cc(C(=O)N[C@@H](C)c4ccc([N+](=O)[O-])cc4)ccc32)cc1] | R1 = H<br>R2 = H<br>R3 = 4-nitrophenyl-1-ethyl<br>R4 = methyl<br>R5 = H<br>R6 = H<br>R7 = H |
| 43 | 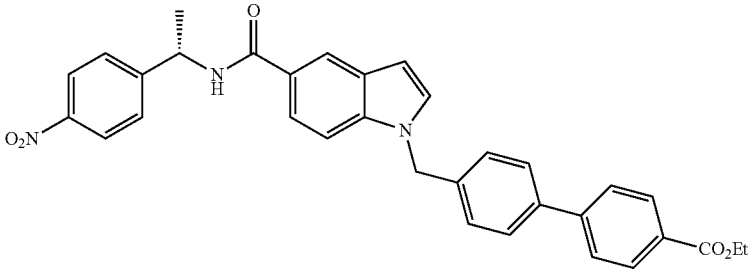 [SMILES: CCOC(=O)c1ccc(-c2ccc(Cn3ccc4cc(C(=O)N[C@@H](C)c5ccc([N+](=O)[O-])cc5)ccc43)cc2)cc1] | R1 = H<br>R2 = H<br>R3 = 4-nitrophenyl-1-ethyl<br>R4 = CO$_2$Et<br>R5 = H<br>R6 = H<br>R7 = H |
| 44 | 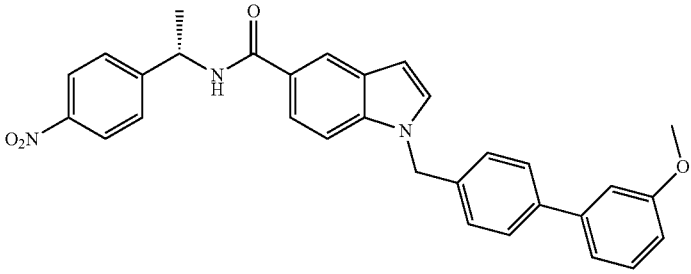 [SMILES: COc1cccc(-c2ccc(Cn3ccc4cc(C(=O)N[C@@H](C)c5ccc([N+](=O)[O-])cc5)ccc43)cc2)c1] | R1 = H<br>R2 = H<br>R3 = 4-nitrophenyl-1-ethyl<br>R4 = OCH$_3$<br>R5 = H<br>R6 = H<br>R7 = H |
| 45 | 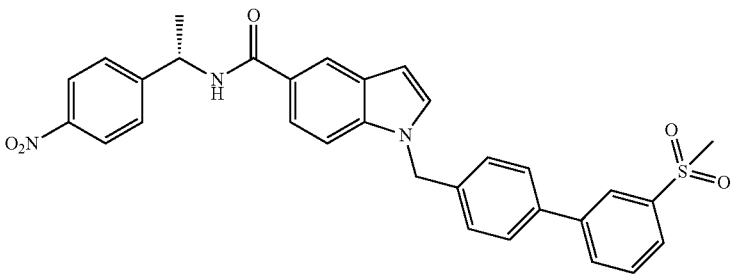 [SMILES: C[C@H](NC(=O)c1ccc2c(ccn2Cc2ccc(-c3cccc(S(C)(=O)=O)c3)cc2)c1)c1ccc([N+](=O)[O-])cc1] | R1 = H<br>R2 = H<br>R3 = 4-nitrophenyl-1-ethyl<br>R4 = methanesulfonyl<br>R5 = H<br>R6 = H<br>R7 = H |

TABLE 1-continued

Specific Compounds of the Invention

| # | Structure | Substituents |
|---|---|---|
| 46 | 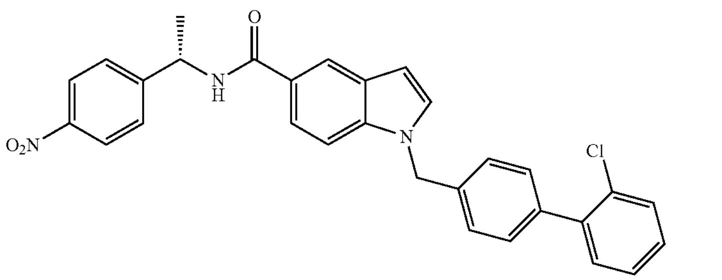 [SMILES: C[C@H](NC(=O)c1ccc2c(ccn2Cc2ccc(-c3ccccc3Cl)cc2)c1)c1ccc([N+](=O)[O-])cc1] | R1 = H<br>R2 = H<br>R3 = 4-nitrophenyl-1-ethyl<br>R4 = Cl<br>R5 = H<br>R6 = H<br>R7 = H |
| 47 | 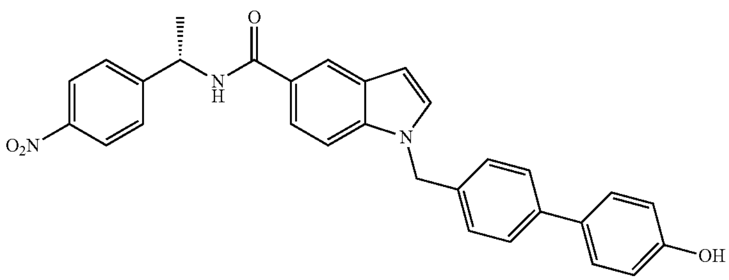 [SMILES: C[C@H](NC(=O)c1ccc2c(ccn2Cc2ccc(-c3ccc(O)cc3)cc2)c1)c1ccc([N+](=O)[O-])cc1] | R1 = H<br>R2 = H<br>R3 = 4-nitrophenyl-1-ethyl<br>R4 = OH<br>R5 = H<br>R6 = H<br>R7 = H |
| 48 | 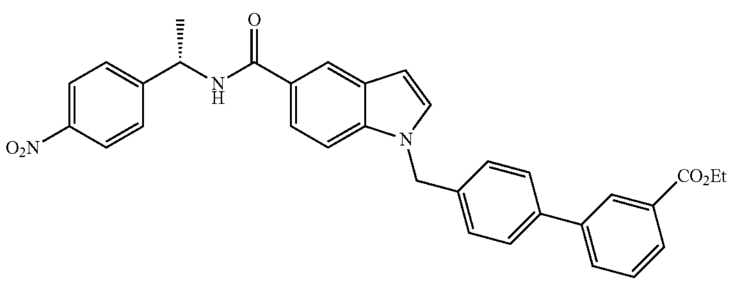 [SMILES: CCOC(=O)c1cccc(-c2ccc(Cn3ccc4cc(C(=O)N[C@@H](C)c5ccc([N+](=O)[O-])cc5)ccc43)cc2)c1] | R1 = H<br>R2 = H<br>R3 = 4-nitrophenyl-1-ethyl<br>R4 = $CO_2Et$<br>R5 = H<br>R6 = H<br>R7 = H |
| 49 | 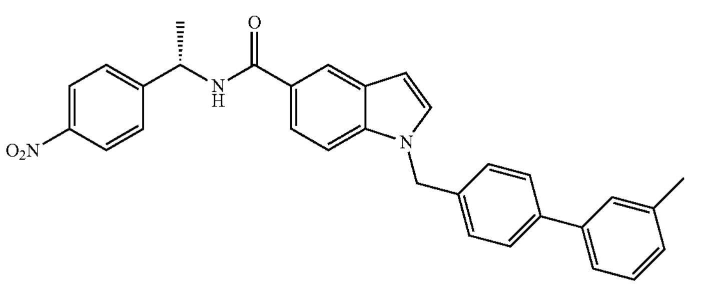 [SMILES: Cc1cccc(-c2ccc(Cn3ccc4cc(C(=O)N[C@@H](C)c5ccc([N+](=O)[O-])cc5)ccc43)cc2)c1] | R1 = H<br>R2 = H<br>R3 = 4-nitrophenyl-1-ethyl<br>R4 = methyl<br>R5 = H<br>R6 = H<br>R7 = H |
| 50 | 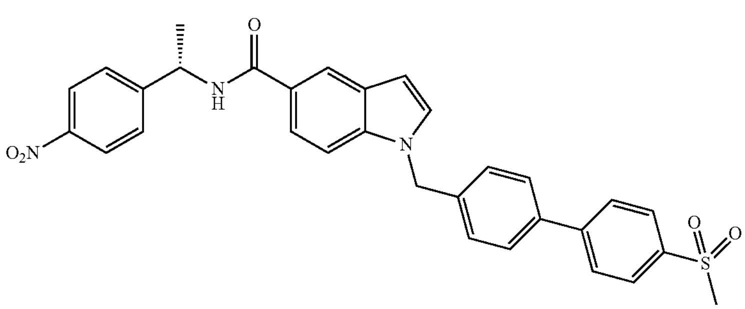 [SMILES: C[C@H](NC(=O)c1ccc2c(ccn2Cc2ccc(-c3ccc(S(C)(=O)=O)cc3)cc2)c1)c1ccc([N+](=O)[O-])cc1] | R1 = H<br>R2 = H<br>R3 = 4-nitrophenyl-1-ethyl<br>R4 = methanesulfonyl<br>R5 = H<br>R6 = H<br>R7 = H |

TABLE 1-continued

Specific Compounds of the Invention

| # | Structure | Substituents |
|---|---|---|
| 51 | 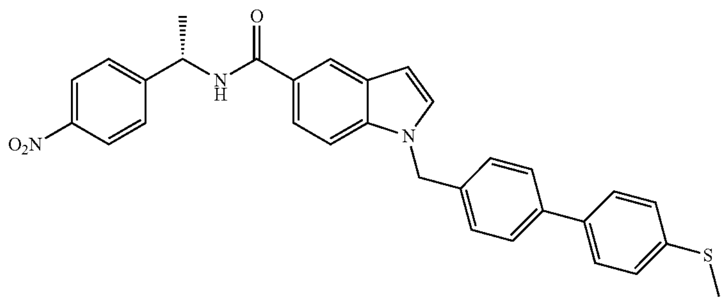 [SMILES: CSc1ccc(-c2ccc(Cn3ccc4cc(C(=O)N[C@@H](C)c5ccc([N+](=O)[O-])cc5)ccc43)cc2)cc1] | R1 = H<br>R2 = H<br>R3 = 4-nitrophenyl-1-ethyl<br>R4 = SCH₃<br>R5 = H<br>R6 = H<br>R7 = H |
| 52 | 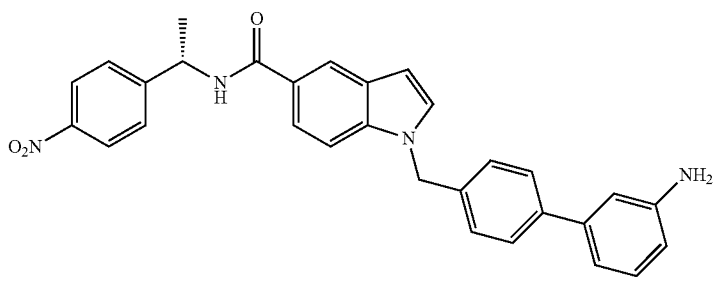 [SMILES: C[C@H](NC(=O)c1ccc2c(ccn2Cc2ccc(-c3cccc(N)c3)cc2)c1)c1ccc([N+](=O)[O-])cc1] | R1 = H<br>R2 = H<br>R3 = 4-nitrophenyl-1-ethyl<br>R4 = NH₂<br>R5 = H<br>R6 = H<br>R7 = H |
| 53 | 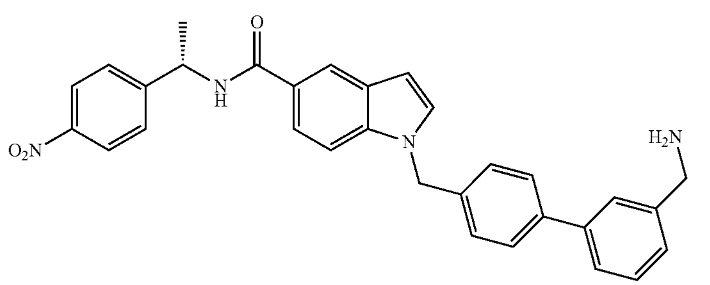 [SMILES: C[C@H](NC(=O)c1ccc2c(ccn2Cc2ccc(-c3cccc(CN)c3)cc2)c1)c1ccc([N+](=O)[O-])cc1] | R1 = H<br>R2 = H<br>R3 = 4-nitrophenyl-1-ethyl<br>R4 = CH₂NH₂<br>R5 = H<br>R6 = H<br>R7 = H |
| 54 | 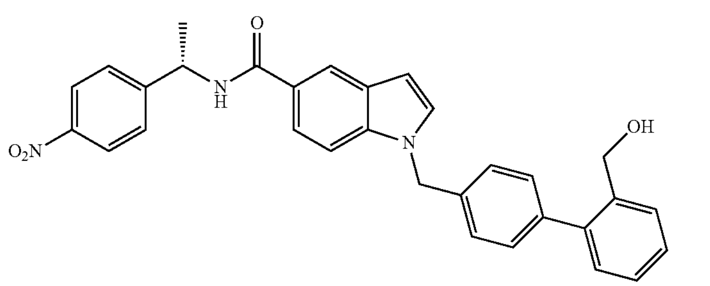 [SMILES: C[C@H](NC(=O)c1ccc2c(ccn2Cc2ccc(-c3ccccc3CO)cc2)c1)c1ccc([N+](=O)[O-])cc1] | R1 = H<br>R2 = H<br>R3 = 4-nitrophenyl-1-ethyl<br>R4 = CH2OH<br>R5 = H<br>R6 = H<br>R7 = H |
| 55 | 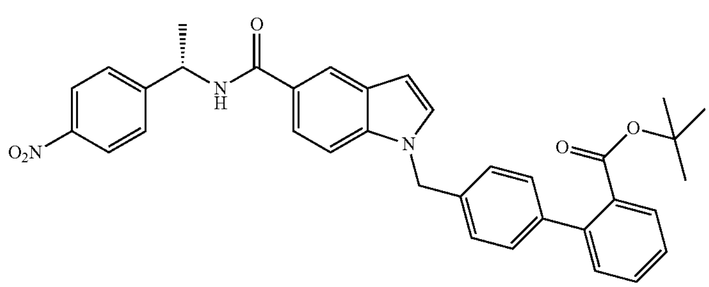 [SMILES: C[C@H](NC(=O)c1ccc2c(ccn2Cc2ccc(-c3ccccc3C(=O)OC(C)(C)C)cc2)c1)c1ccc([N+](=O)[O-])cc1] | R1 = H<br>R2 = H<br>R3 = 4-nitrophenyl-1-ethyl<br>R4 = tert-butoxycarbonyl<br>R5 = H<br>R6 = H<br>R7 = H |

TABLE 1-continued

Specific Compounds of the Invention

| # | Structure | Substituents |
|---|---|---|
| 56 | 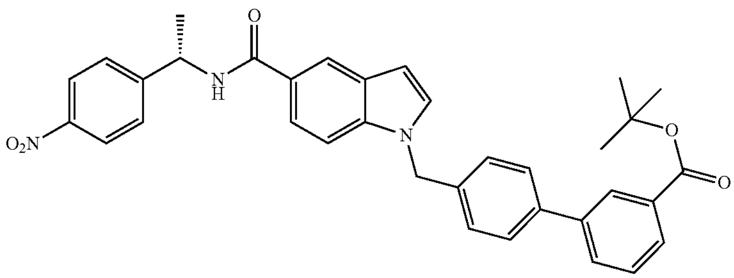 [SMILES: C[C@H](NC(=O)c1ccc2c(ccn2Cc2ccc(-c3cccc(C(=O)OC(C)(C)C)c3)cc2)c1)c1ccc([N+](=O)[O-])cc1] | R1 = H<br>R2 = H<br>R3 = 4-nitrophenyl-1-ethyl<br>R4 = tert-butoxycarbonyl<br>R5 = H<br>R6 = H<br>R7 = H |
| 57 | 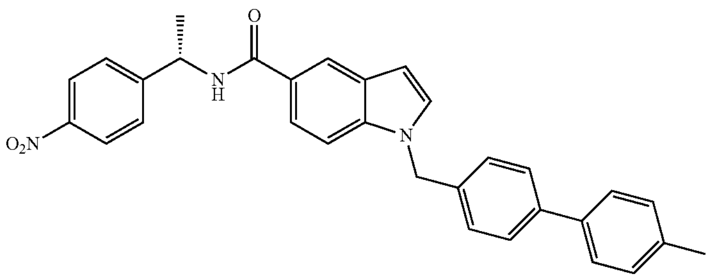 [SMILES: Cc1ccc(-c2ccc(Cn3ccc4cc(C(=O)N[C@@H](C)c5ccc([N+](=O)[O-])cc5)ccc43)cc2)cc1] | R1 = H<br>R2 = H<br>R3 = 4-nitrophenyl-1-ethyl<br>R4 = methyl<br>R5 = H<br>R6 = H<br>R7 = H |
| 58 | 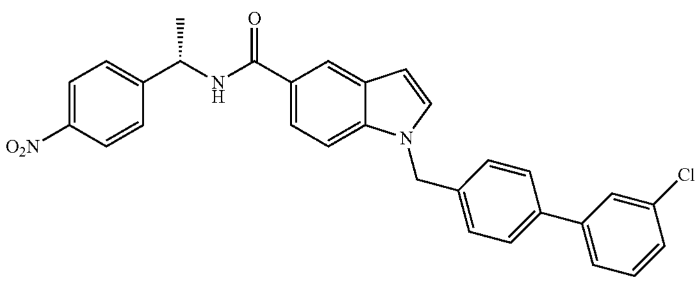 [SMILES: C[C@H](NC(=O)c1ccc2c(ccn2Cc2ccc(-c3cccc(Cl)c3)cc2)c1)c1ccc([N+](=O)[O-])cc1] | R1 = H<br>R2 = H<br>R3 = 4-nitrophenyl-1-ethyl<br>R4 = Cl<br>R5 = H<br>R6 = H<br>R7 = H |
| 59 | 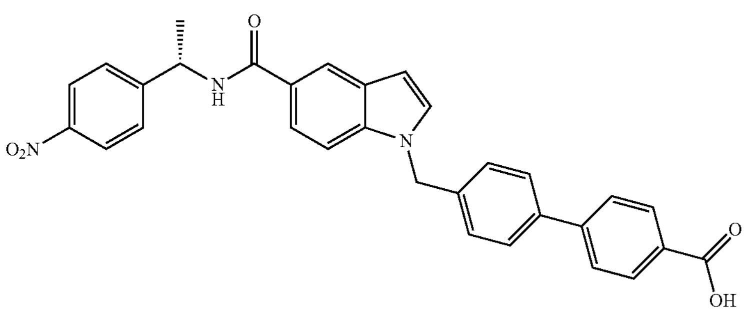 [SMILES: C[C@H](NC(=O)c1ccc2c(ccn2Cc2ccc(-c3ccc(C(=O)O)cc3)cc2)c1)c1ccc([N+](=O)[O-])cc1] | R1 = H<br>R2 = H<br>R3 = 4-nitrophenyl-1-ethyl<br>R4 = $CO_2H$<br>R5 = H<br>R6 = H<br>R7 = H |
| 60 | 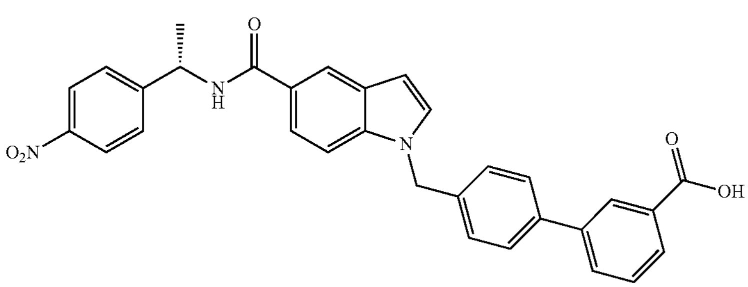 [SMILES: C[C@H](NC(=O)c1ccc2c(ccn2Cc2ccc(-c3cccc(C(=O)O)c3)cc2)c1)c1ccc([N+](=O)[O-])cc1] | R1 = H<br>R2 = H<br>R3 = 4-nitrophenyl-1-ethyl<br>R4 = $CO_2H$<br>R5 = H<br>R6 = H<br>R7 = H |

US 8,957,093 B2

TABLE 1-continued

Specific Compounds of the Invention

| # | Structure | Substituents |
|---|-----------|--------------|
| 61 | 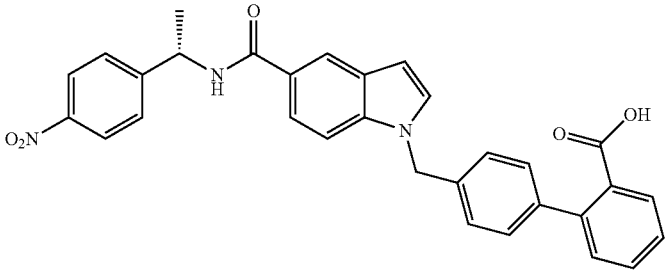 [SMILES: C[C@H](NC(=O)c1ccc2c(ccn2Cc2ccc(-c3ccccc3C(=O)O)cc2)c1)c1ccc([N+](=O)[O-])cc1] | R1 = H<br>R2 = H<br>R3 = 4-nitrophenyl-1-ethyl<br>R4 = CO$_2$H<br>R5 = H<br>R6 = H<br>R7 = H |
| 62 | 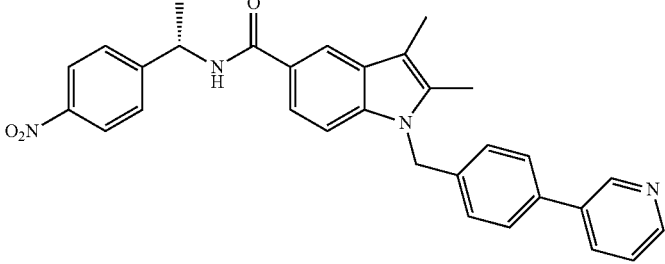 | R1 = methyl<br>R2 = methyl<br>R3 = 4-nitrophenyl-1-ethyl<br>R4 = H<br>R5 = H<br>R6 = H<br>R7 = H<br>X6 = N |
| 63 | 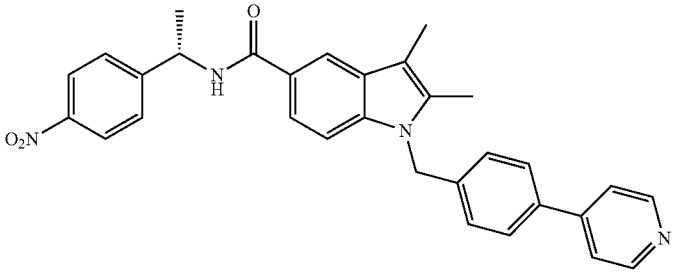 [SMILES: Cc1c(C)n(Cc2ccc(-c3ccncc3)cc2)c2ccc(C(=O)N[C@@H](C)c3ccc([N+](=O)[O-])cc3)cc12] | R1 = methyl<br>R2 = methyl<br>R3 = 4-nitrophenyl-1-ethyl<br>R4 = H<br>R5 = H<br>R6 = H<br>R7 = H<br>X7 = N |
| 64 | 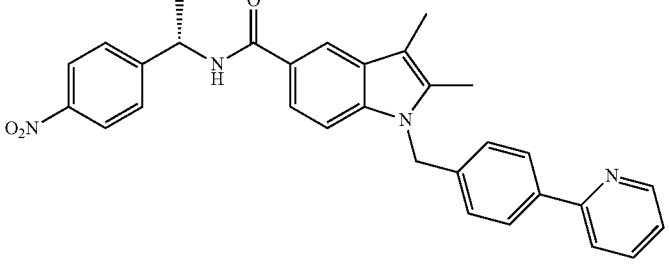 | R1 = methyl<br>R2 = methyl<br>R3 = 4-nitrophenyl-1-ethyl<br>R4 = H<br>R5 = H<br>R6 = H<br>R7 = H<br>X5 = N |
| 65 | 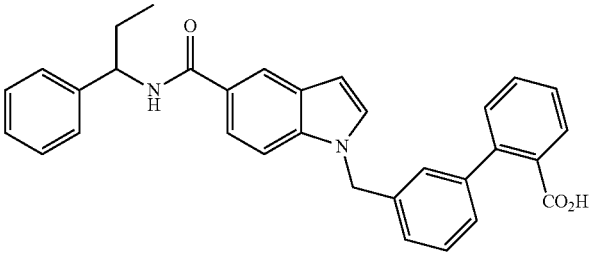 [SMILES: CCC(NC(=O)c1ccc2c(ccn2Cc2cccc(-c3ccccc3C(=O)O)c2)c1)c1ccccc1] | R1 = H<br>R2 = H<br>R3 = phenyl-(propyl-1-yl)<br>R4 = 2-carboxylic acid<br>R5 = H<br>R6 = H<br>R7 = H |

TABLE 1-continued

Specific Compounds of the Invention

| # | Structure | Substituents |
|---|---|---|
| 66 | 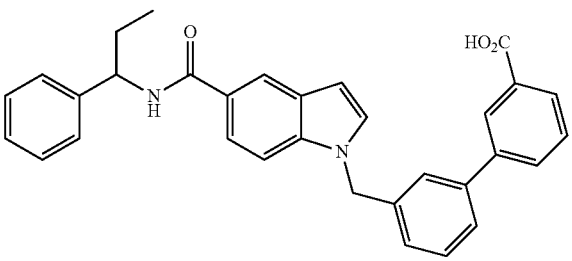 [SMILES: CCC(NC(=O)c1ccc2c(ccn2Cc2cccc(-c3cccc(C(=O)O)c3)c2)c1)c1ccccc1] | R1 = H<br>R2 = H<br>R3 = phenyl-(propyl-1-yl)<br>R4 = 3-carboxylic acid<br>R5 = H<br>R6 = H<br>R7 = H |
| 67 | 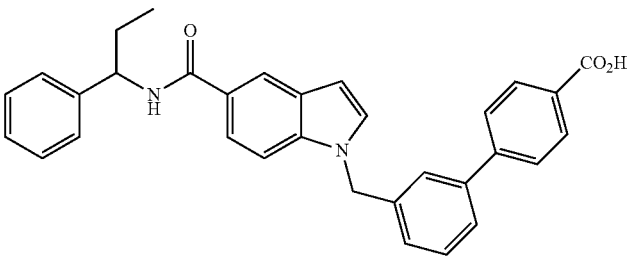 [SMILES: CCC(NC(=O)c1ccc2c(ccn2Cc2cccc(-c3ccc(C(=O)O)cc3)c2)c1)c1ccccc1] | R1 = H<br>R2 = H<br>R3 = phenyl-(propyl-1-yl)<br>R4 = 4-carboxylic acid<br>R5 = H<br>R6 = H<br>R7 = H |
| 68 | 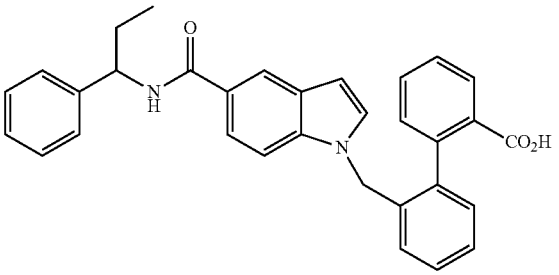 [SMILES: CCC(NC(=O)c1ccc2c(ccn2Cc2ccccc2-c2ccccc2C(=O)O)c1)c1ccccc1] | R1 = H<br>R2 = H<br>R3 = phenyl-(propyl-1-yl)<br>R4 = 2-carboxylic acid<br>R5 = H<br>R6 = H<br>R7 = H |
| 69 | 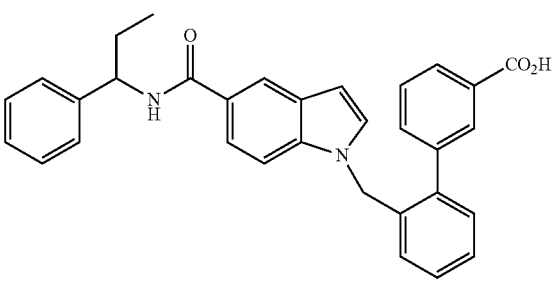 [SMILES: CCC(NC(=O)c1ccc2c(ccn2Cc2ccccc2-c2cccc(C(=O)O)c2)c1)c1ccccc1] | R1 = H<br>R2 = H<br>R3 = phenyl-(propyl-1-yl)<br>R4 = 3-carboxylic acid<br>R5 = H<br>R6 = H<br>R7 = H |
| 70 | 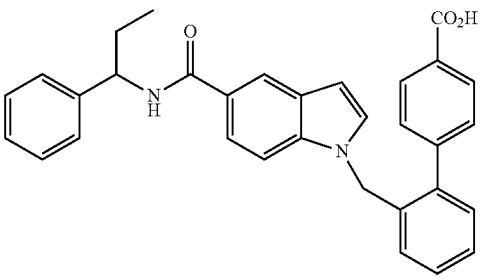 [SMILES: CCC(NC(=O)c1ccc2c(ccn2Cc2ccccc2-c2ccc(C(=O)O)cc2)c1)c1ccccc1] | R1 = H<br>R2 = H<br>R3 = phenyl-(propyl-1-yl)<br>R4 = 4-carboxylic acid<br>R5 = H<br>R6 = H<br>R7 = H<br>X1-X7 = C |

TABLE 1-continued

Specific Compounds of the Invention

| # | Structure | Substituents |
|---|---|---|
| 72 | 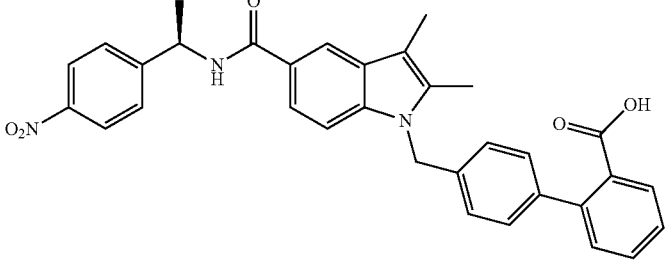 | R1 = methyl<br>R2 = methyl<br>R3 = 4-nitrophenyl-1-ethyl<br>R4 = $CO_2H$<br>R5 = H<br>R6 = H<br>R7 = H |
| 73 | 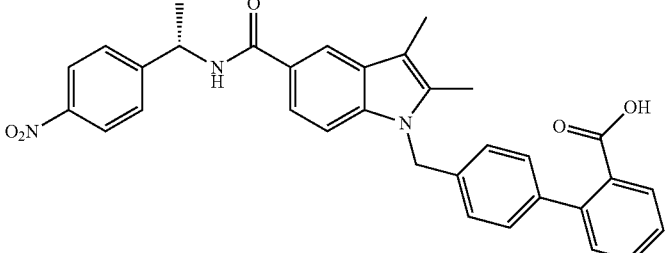 | R1 = methyl<br>R2 = methyl<br>R3 = 4-nitrophenyl-1-ethyl<br>R4 = $CO_2H$<br>R5 = H<br>R6 = H<br>R7 = H |
| 74 | 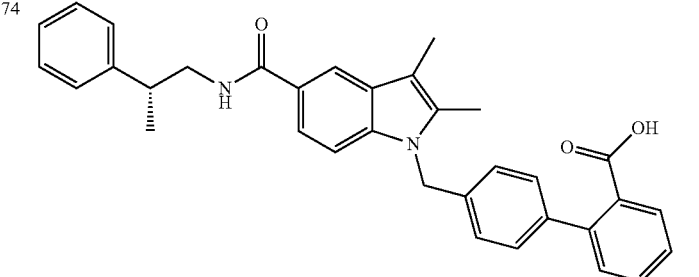 | R1 = methyl<br>R2 = methyl<br>R3 = 2-phenylpropan-1-yl<br>R4 = $CO_2H$<br>R5 = H<br>R6 = H<br>R7 = H |
| 75 | 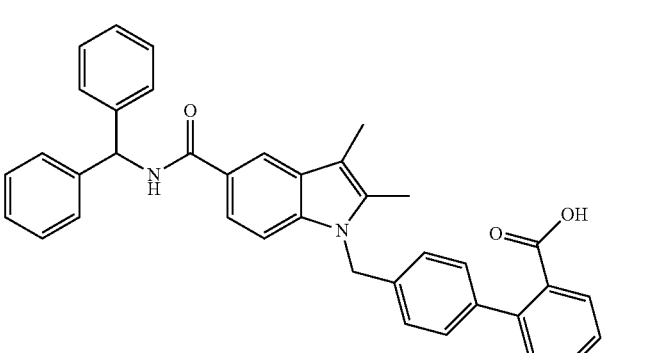 | R1 = methyl<br>R2 = methyl<br>R3 = diphenyl-1-methyl<br>R4 = $CO_2H$<br>R5 = H<br>R6 = H<br>R7 = H |
| 76 | 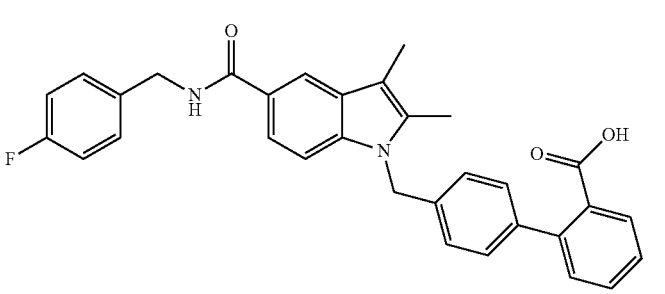 [SMILES: Cc1c(C)n(Cc2ccc(-c3ccccc3C(=O)O)cc2)c2ccc(C(=O)NCc3ccc(F)cc3)cc12] | R1 = methyl<br>R2 = methyl<br>R3 = 4-fluorobenzyl<br>R4 = $CO_2H$<br>R5 = H<br>R6 = H<br>R7 = H |

TABLE 1-continued

Specific Compounds of the Invention

| # | Structure | Substituents |
|---|---|---|
| 77 | 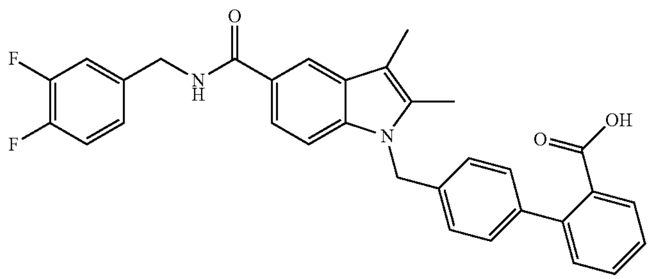 [SMILES: Cc1c(C)n(Cc2ccc(-c3ccccc3C(=O)O)cc2)c2ccc(C(=O)NCc3ccc(F)c(F)c3)cc12] | R1 = methyl<br>R2 = methyl<br>R3 = 3,4-difluorobenzyl<br>R4 = CO$_2$H<br>R5 = H<br>R6 = H<br>R7 = H |
| 78 | 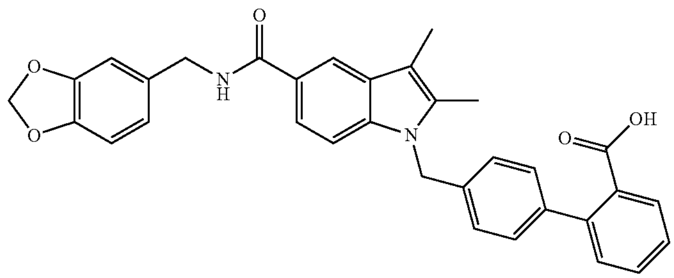 [SMILES: Cc1c(C)n(Cc2ccc(-c3ccccc3C(=O)O)cc2)c2ccc(C(=O)NCc3ccc4c(c3)OCO4)cc12] | R1 = methyl<br>R2 = methyl<br>R3 = Benzo[1,3]dioxole-5ylmethyl<br>R4 = CO$_2$H<br>R5 = H<br>R6 = H<br>R7 = H |
| 79 | 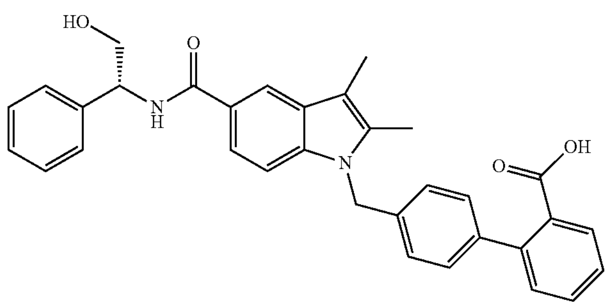 [SMILES: Cc1c(C)n(Cc2ccc(-c3ccccc3C(=O)O)cc2)c2ccc(C(=O)N[C@@H](CO)c3ccccc3)cc12] | R1 = methyl<br>R2 = methyl<br>R3 = 2-hydroxy-1-phenyl-ethyl<br>R4 = CO$_2$H<br>R5 = H<br>R6 = H<br>R7 = H |
| 80 | 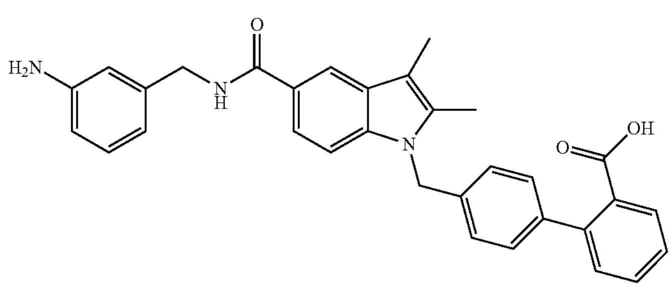 | R1 = methyl<br>R2 = methyl<br>R3 = 3-amino-benzyl<br>R4 = CO$_2$H<br>R5 = H<br>R6 = H<br>R7 = H |
| 81 | 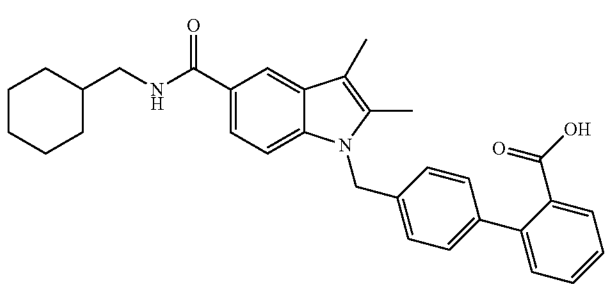 [SMILES: Cc1c(C)n(Cc2ccc(-c3ccccc3C(=O)O)cc2)c2ccc(C(=O)NCC3CCCCC3)cc12] | R1 = methyl<br>R2 = methyl<br>R3 = Cyclohexyl-1-methyl<br>R4 = CO$_2$H<br>R5 = H<br>R6 = H<br>R7 = H |

TABLE 1-continued

Specific Compounds of the Invention

| # | Structure | Substituents |
|---|---|---|
| 82 | 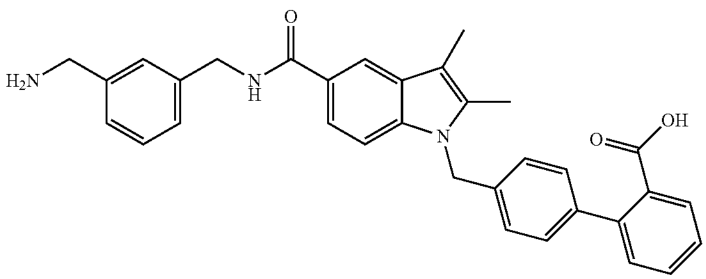 [SMILES: Cc1c(C)n(Cc2ccc(-c3ccccc3C(=O)O)cc2)c2ccc(C(=O)NCc3cccc(CN)c3)cc12] | R1 = methyl<br>R2 = methyl<br>R3 = 3-aminomethyl-benzyl<br>R4 = $CO_2H$<br>R5 = H<br>R6 = H<br>R7 = H |
| 83 | 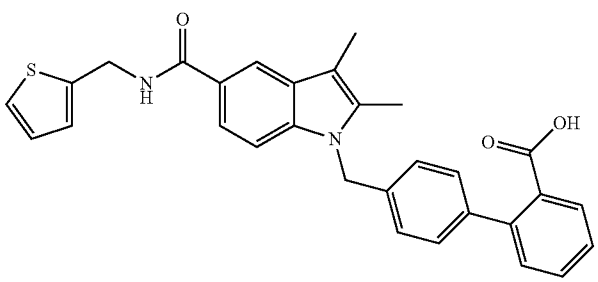 [SMILES: Cc1c(C)n(Cc2ccc(-c3ccccc3C(=O)O)cc2)c2ccc(C(=O)NCc3cccs3)cc12] | R1 = methyl<br>R2 = methyl<br>R3 = thiophen-2ylmethyl<br>R4 = $CO_2H$<br>R5 = H<br>R6 = H<br>R7 = H |
| 84 | 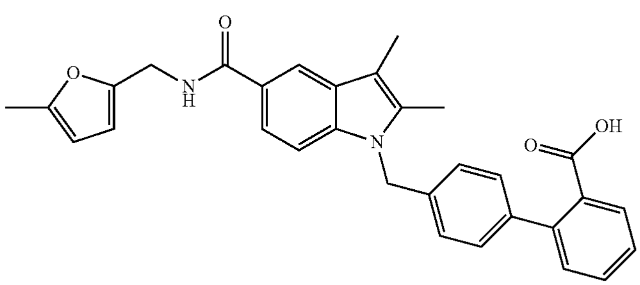 [SMILES: Cc1ccc(CNC(=O)c2ccc3c(c2)c(C)c(C)n3Cc2ccc(-c3ccccc3C(=O)O)cc2)o1] | R1 = methyl<br>R2 = methyl<br>R3 = 5-methyl-furan-2yl-methyl<br>R4 = $CO_2H$<br>R5 = H<br>R6 = H<br>R7 = H |
| 85 | 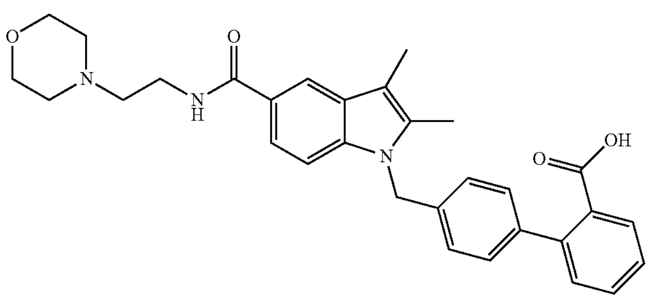 [SMILES: Cc1c(C)n(Cc2ccc(-c3ccccc3C(=O)O)cc2)c2ccc(C(=O)NCCN3CCOCC3)cc12] | R1 = methyl<br>R2 = methyl<br>R3 = 2-morpholine-4-yl-ethyl<br>R4 = $CO_2H$<br>R5 = H<br>R6 = H<br>R7 = H |
| 86 | 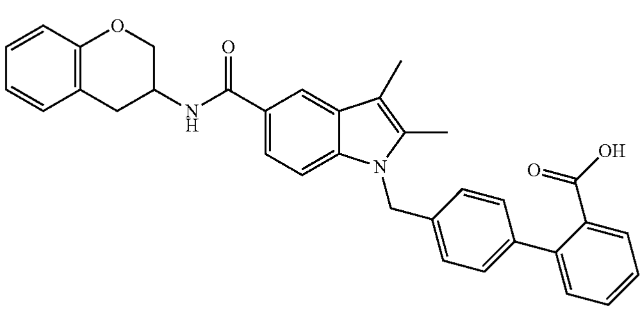 | R1 = methyl<br>R2 = methyl<br>R3 = (chroman-3yl)<br>R4 = $CO_2H$<br>R5 = H<br>R6 = H<br>R7 = H |

TABLE 1-continued

Specific Compounds of the Invention

| # | Structure | Substituents |
|---|---|---|
| 87 | 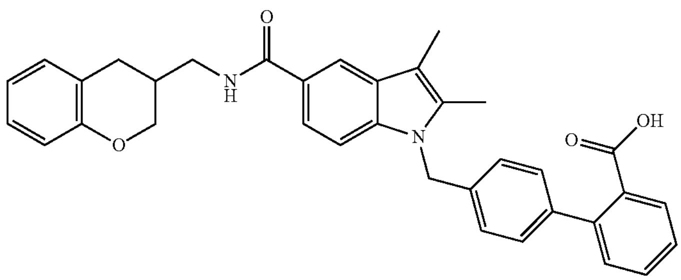 | R1 = methyl<br>R2 = methyl<br>R3 = chroman-3ylmethyl<br>R4 = CO$_2$H<br>R5 = H<br>R6 = H<br>R7 = H |
| 88 | 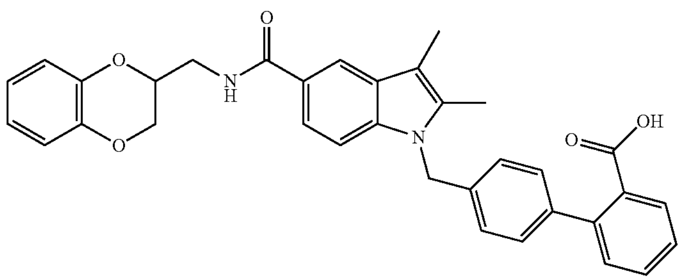 [SMILES: Cc1c(C)n(Cc2ccc(-c3ccccc3C(=O)O)cc2)c2ccc(C(=O)NCC3COc4ccccc4O3)cc12] | R1 = methyl<br>R2 = methyl<br>R3 = 2,3-dihydro-benzo[1,4]dioxin-2-ylmethyl<br>R4 = CO$_2$H<br>R5 = H<br>R6 = H<br>R7 = H |
| 89 | 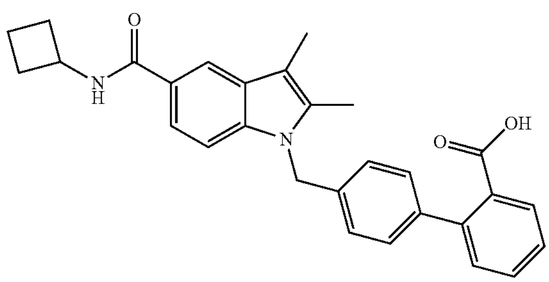 [SMILES: Cc1c(C)n(Cc2ccc(-c3ccccc3C(=O)O)cc2)c2ccc(C(=O)NC3CCC3)cc12] | R1 = methyl<br>R2 = methyl<br>R3 = cyclobutyl<br>R4 = CO$_2$H<br>R5 = H<br>R6 = H<br>R7 = H |
| 90 | 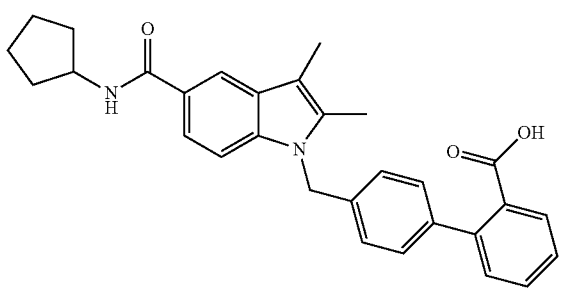 [SMILES: Cc1c(C)n(Cc2ccc(-c3ccccc3C(=O)O)cc2)c2ccc(C(=O)NC3CCCC3)cc12] | R1 = methyl<br>R2 = methyl<br>R3 = cyclopentyl<br>R4 = CO$_2$H<br>R5 = H<br>R6 = H<br>R7 = H |
| 91 | 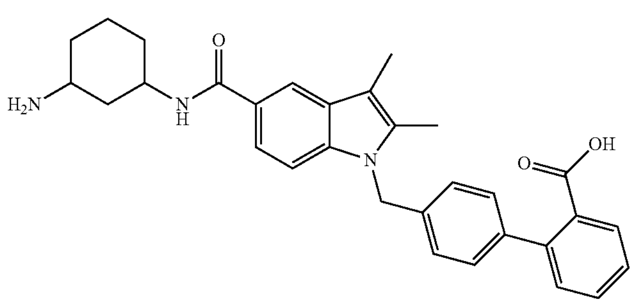 [SMILES: Cc1c(C)n(Cc2ccc(-c3ccccc3C(=O)O)cc2)c2ccc(C(=O)NC3CCCC(N)C3)cc12] | R1 = methyl<br>R2 = methyl<br>R3 = 3-amino cyclohexyl<br>R4 = CO$_2$H<br>R5 = H<br>R6 = H<br>R7 = H |

TABLE 1-continued

Specific Compounds of the Invention

| # | Structure | Substituents |
|---|---|---|
| 92 | 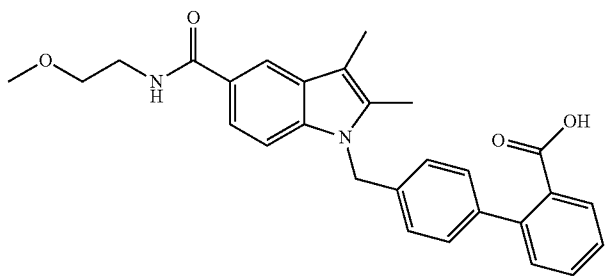 [SMILES: COCCNC(=O)c1ccc2c(c1)c(C)c(C)n2Cc1ccc(-c2ccccc2C(=O)O)cc1] | R1 = methyl<br>R2 = methyl<br>R3 = methoxyethyl<br>R4 = CO₂H<br>R5 = H<br>R6 = H<br>R7 = H |
| 93 | 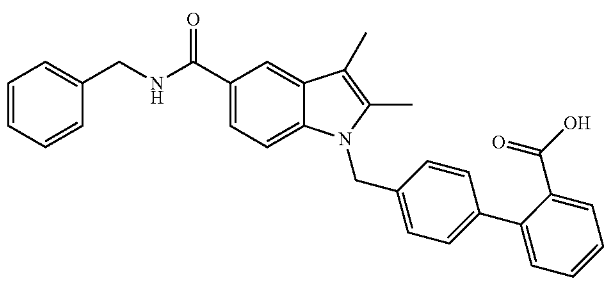 [SMILES: Cc1c(C)n(Cc2ccc(-c3ccccc3C(=O)O)cc2)c2ccc(C(=O)NCc3ccccc3)cc12] | R1 = methyl<br>R2 = methyl<br>R3 = benzyl<br>R4 = CO₂H<br>R5 = H<br>R6 = H<br>R7 = H |
| 94 | 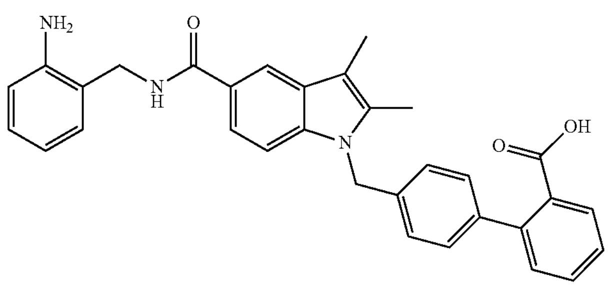 [SMILES: Cc1c(C)n(Cc2ccc(-c3ccccc3C(=O)O)cc2)c2ccc(C(=O)NCc3ccccc3N)cc12] | R1 = methyl<br>R2 = methyl<br>R3 = 2-aminobenzyl<br>R4 = CO₂H<br>R5 = H<br>R6 = H<br>R7 = H |
| 95 | 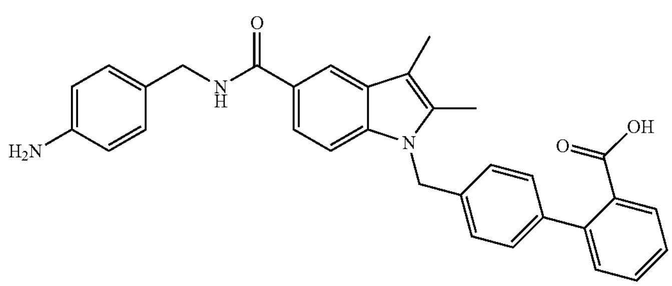 | R1 = methyl<br>R2 = methyl<br>R3 = p-aminobenzyl<br>R4 = CO₂H<br>R5 = H<br>R6 = H<br>R7 = H |
| 96 | 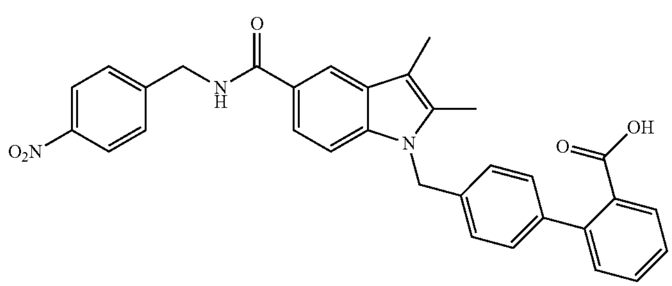 [SMILES: Cc1c(C)n(Cc2ccc(-c3ccccc3C(=O)O)cc2)c2ccc(C(=O)NCc3ccc([N+](=O)[O-])cc3)cc12] | R1 = methyl<br>R2 = methyl<br>R3 = p-nitrobenzyl<br>R4 = CO₂H<br>R5 = H<br>R6 = H<br>R7 = H |

TABLE 1-continued

Specific Compounds of the Invention

| # | Structure | Substituents |
|---|-----------|--------------|
| 97 | 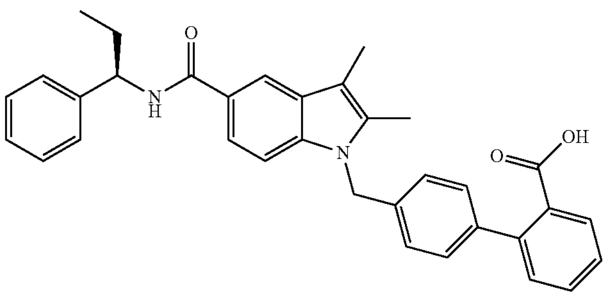 [SMILES: CC[C@@H](NC(=O)c1ccc2c(c1)c(C)c(C)n2Cc1ccc(-c2ccccc2C(=O)O)cc1)c1ccccc1] | R1 = methyl<br>R2 = methyl<br>R3 = phenylpropyl<br>R4 = CO$_2$H<br>R5 = H<br>R6 = H<br>R7 = H |
| 98 | 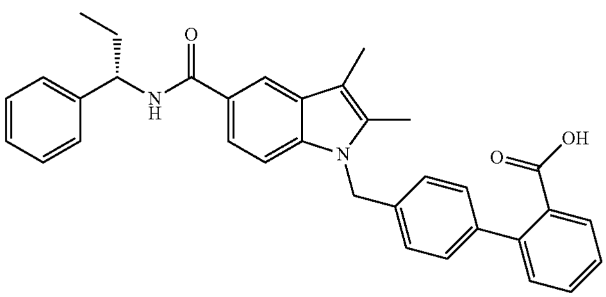 [SMILES: CC[C@H](NC(=O)c1ccc2c(c1)c(C)c(C)n2Cc1ccc(-c2ccccc2C(=O)O)cc1)c1ccccc1] | R1 = methyl<br>R2 = methyl<br>R3 = phenylpropyl<br>R4 = CO$_2$H<br>R5 = H<br>R6 = H<br>R7 = H |
| 99 | 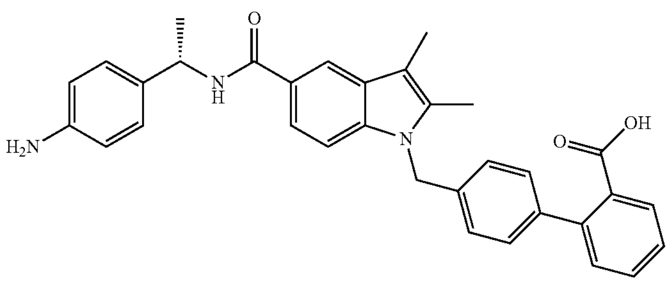 | R1 = methyl<br>R2 = methyl<br>R3 = p-amino-phenyl-ethyl<br>R4 = CO$_2$H<br>R5 = H<br>R6 = H<br>R7 = H |
| 100 | 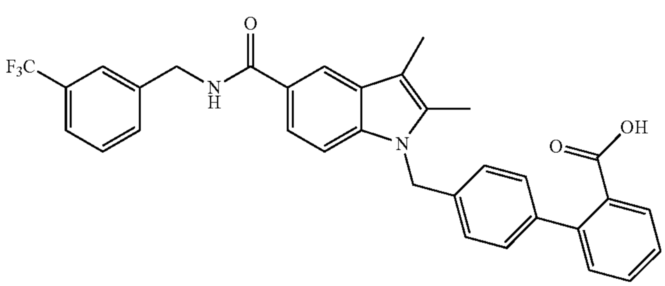 [SMILES: Cc1c(C)n(Cc2ccc(-c3ccccc3C(=O)O)cc2)c2ccc(C(=O)NCc3cccc(C(F)(F)F)c3)cc12] | R1 = methyl<br>R2 = methyl<br>R3 = 3-trifluoromethylbenzyl<br>R4 = CO$_2$H<br>R5 = H<br>R6 = H<br>R7 = H |
| 101 | 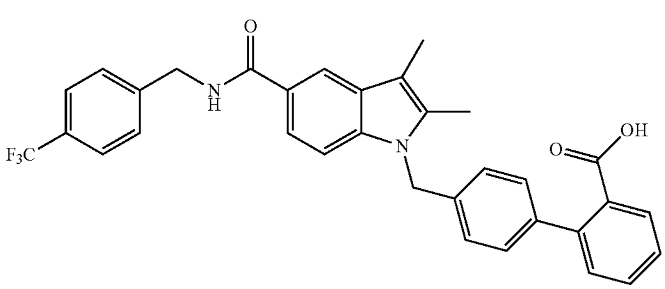 [SMILES: Cc1c(C)n(Cc2ccc(-c3ccccc3C(=O)O)cc2)c2ccc(C(=O)NCc3ccc(C(F)(F)F)cc3)cc12] | R1 = methyl<br>R2 = methyl<br>R3 = 4-trifluoromethylbenzyl<br>R4 = CO$_2$H<br>R5 = H<br>R6 = H<br>R7 = H |

TABLE 1-continued

Specific Compounds of the Invention

| # | Structure | Substituents |
|---|---|---|
| 102 | 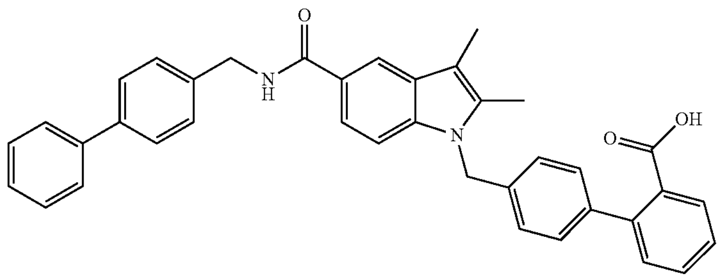 [SMILES: Cc1c(C)n(Cc2ccc(-c3ccccc3C(=O)O)cc2)c2ccc(C(=O)NCc3ccc(-c4ccccc4)cc3)cc12] | R1 = methyl<br>R2 = methyl<br>R3 = biphenyl-4ylmethyl<br>R4 = CO$_2$H<br>R5 = H<br>R6 = H<br>R7 = H |
| 103 | 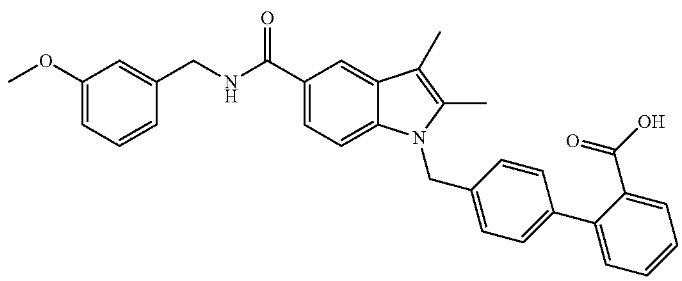 [SMILES: COc1cccc(CNC(=O)c2ccc3c(c2)c(C)c(C)n3Cc2ccc(-c3ccccc3C(=O)O)cc2)c1] | R1 = methyl<br>R2 = methyl<br>R3 = 3-methoxybenzyl<br>R4 = CO$_2$H<br>R5 = H<br>R6 = H<br>R7 = H |
| 104 | 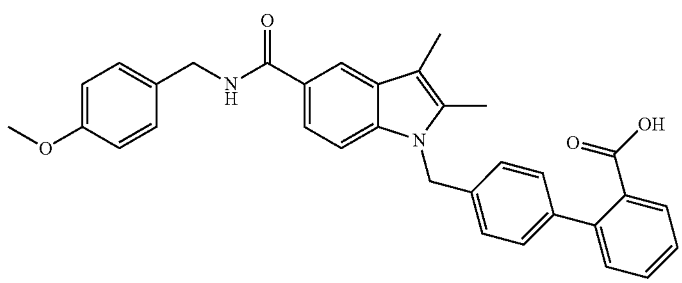 [SMILES: COc1ccc(CNC(=O)c2ccc3c(c2)c(C)c(C)n3Cc2ccc(-c3ccccc3C(=O)O)cc2)cc1] | R1 = methyl<br>R2 = methyl<br>R3 = 4-methoxybenzyl<br>R4 = CO$_2$H<br>R5 = H<br>R6 = H<br>R7 = H |
| 105 | 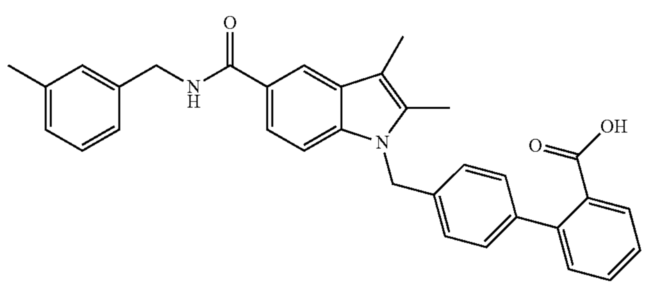 [SMILES: Cc1cccc(CNC(=O)c2ccc3c(c2)c(C)c(C)n3Cc2ccc(-c3ccccc3C(=O)O)cc2)c1] | R1 = methyl<br>R2 = methyl<br>R3 = 3-methylbenzyl<br>R4 = CO$_2$H<br>R5 = H<br>R6 = H<br>R7 = H |
| 106 | 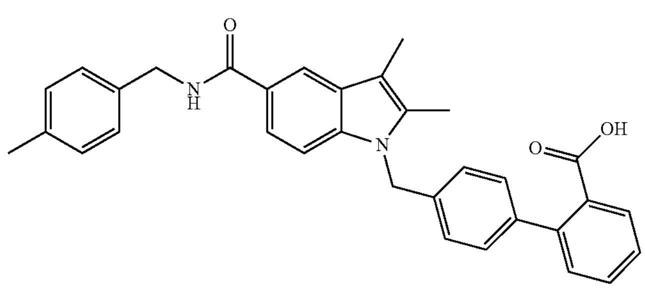 [SMILES: Cc1ccc(CNC(=O)c2ccc3c(c2)c(C)c(C)n3Cc2ccc(-c3ccccc3C(=O)O)cc2)cc1] | R1 = methyl<br>R2 = methyl<br>R3 = 4-methylbenzyl<br>R4 = C$_o$2H<br>R5 = H<br>R6 = H<br>R7 = H |

TABLE 1-continued

Specific Compounds of the Invention

| # | Structure | Substituents |
|---|---|---|
| 107 | 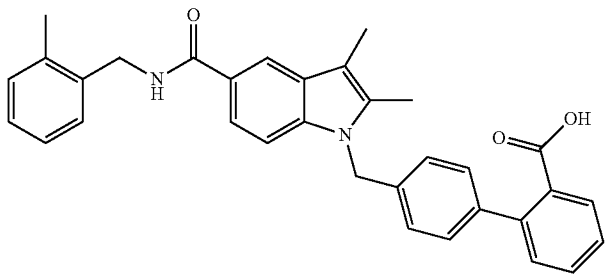 [SMILES: Cc1ccccc1CNC(=O)c1ccc2c(c1)c(C)c(C)n2Cc1ccc(-c2ccccc2C(=O)O)cc1] | R1 = methyl<br>R2 = methyl<br>R3 = 2-methylbenzyl<br>R4 = CO$_2$H<br>R5 = H<br>R6 = H<br>R7 = H |
| 108 | 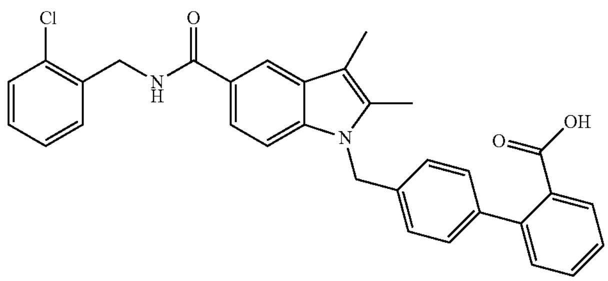 [SMILES: Cc1c(C)n(Cc2ccc(-c3ccccc3C(=O)O)cc2)c2ccc(C(=O)NCc3ccccc3Cl)cc12] | R1 = methyl<br>R2 = methyl<br>R3 = 2-chlorobenzyl<br>R4 = CO$_2$H<br>R5 = H<br>R6 = H<br>R7 = H |
| 109 | 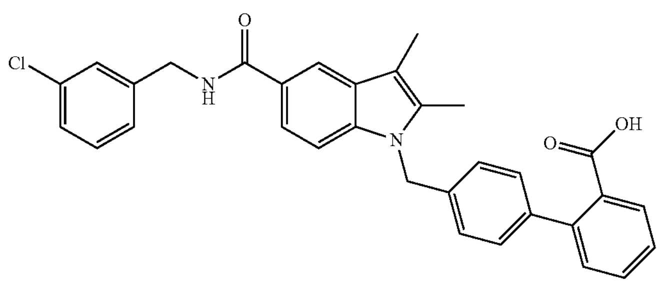 [SMILES: Cc1c(C)n(Cc2ccc(-c3ccccc3C(=O)O)cc2)c2ccc(C(=O)NCc3cccc(Cl)c3)cc12] | R1 = methyl<br>R2 = methyl<br>R3 = 3-chlorobenzyl<br>R4 = CO$_2$H<br>R5 = H<br>R6 = H<br>R7 = H |
| 110 | 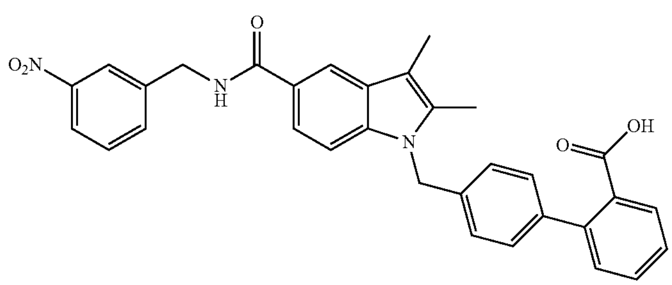 [SMILES: Cc1c(C)n(Cc2ccc(-c3ccccc3C(=O)O)cc2)c2ccc(C(=O)NCc3cccc([N+](=O)[O-])c3)cc12] | R1 = methyl<br>R2 = methyl<br>R3 = 3-nitrobenzyl<br>R4 = CO$_2$H<br>R5 = H<br>R6 = H<br>R7 = H |
| 111 | 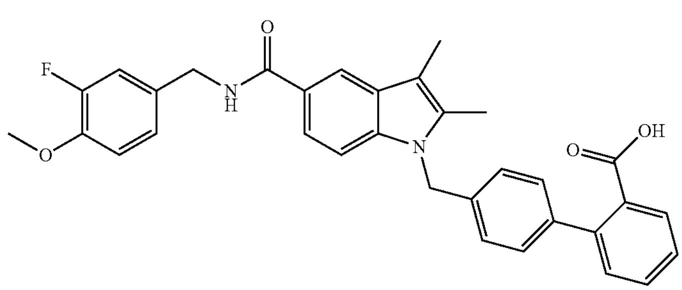 [SMILES: COc1ccc(CNC(=O)c2ccc3c(c2)c(C)c(C)n3Cc2ccc(-c3ccccc3C(=O)O)cc2)cc1F] | R1 = methyl<br>R2 = methyl<br>R3 = 3-fluoro-4-methoxybenzyl<br>R4 = CO$_2$H<br>R5 = H<br>R6 = H<br>R7 = H |

TABLE 1-continued

Specific Compounds of the Invention

| # | Structure | Substituents |
|---|---|---|
| 112 | 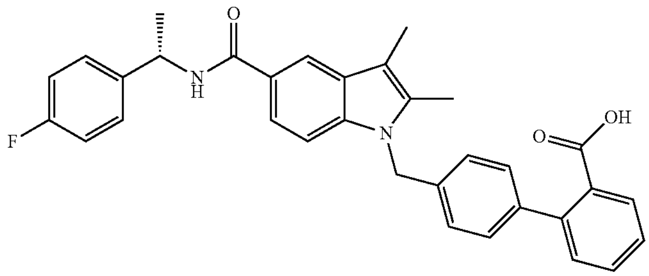 [SMILES: Cc1c(C)n(Cc2ccc(-c3ccccc3C(=O)O)cc2)c2ccc(C(=O)N[C@@H](C)c3ccc(F)cc3)cc12] | R1 = methyl<br>R2 = methyl<br>R3 = 4-fluorophenyl-1-ethyl<br>R4 = CO$_2$H<br>R5 = H<br>R6 = H<br>R7 = H |
| 113 | 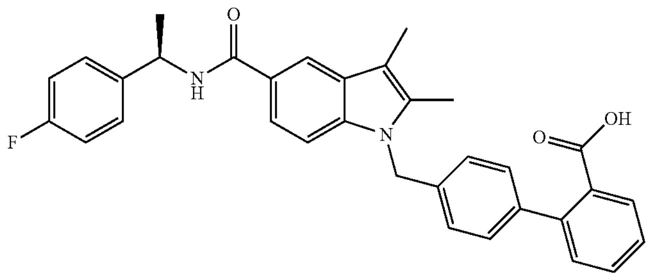 [SMILES: Cc1c(C)n(Cc2ccc(-c3ccccc3C(=O)O)cc2)c2ccc(C(=O)N[C@H](C)c3ccc(F)cc3)cc12] | R1 = methyl<br>R2 = methyl<br>R3 = 4-fluorophenyl-1-ethyl<br>R4 = CO$_2$H<br>R5 = H<br>R6 = H<br>R7 = H |
| 114 | 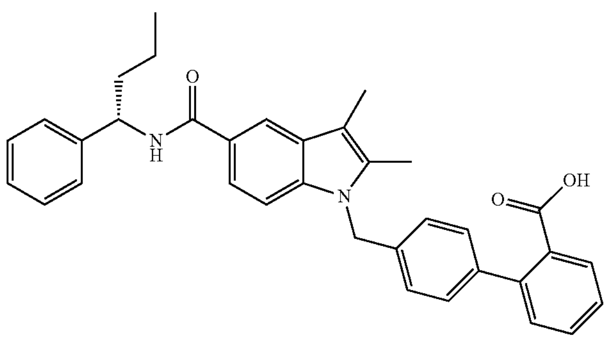 [SMILES: CCC[C@H](NC(=O)c1ccc2c(c1)c(C)c(C)n2Cc1ccc(-c2ccccc2C(=O)O)cc1)c1ccccc1] | R1 = methyl<br>R2 = methyl<br>R3 = phenyl-1-butyl<br>R4 = CO$_2$H<br>R5 = H<br>R6 = H<br>R7 = H |
| 115 | 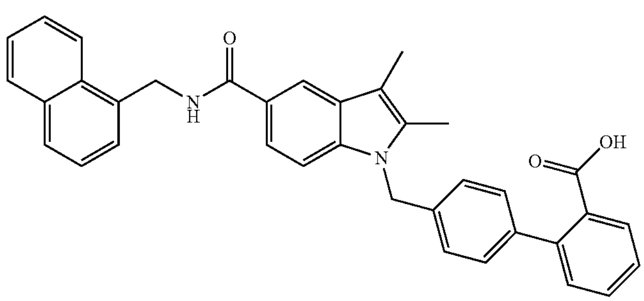 [SMILES: Cc1c(C)n(Cc2ccc(-c3ccccc3C(=O)O)cc2)c2ccc(C(=O)NCc3cccc4ccccc34)cc12] | R1 = methyl<br>R2 = methyl<br>R3 = 1-(naphth-2yl)-1-methyl<br>R4 = CO$_2$H<br>R5 = H<br>R6 = H<br>R7 = H |
| 116 | 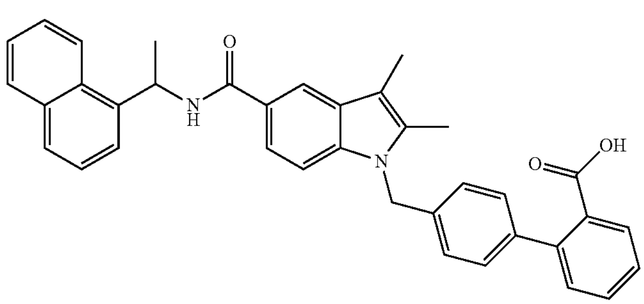 [SMILES: Cc1c(C)n(Cc2ccc(-c3ccccc3C(=O)O)cc2)c2ccc(C(=O)NC(C)c3cccc4ccccc34)cc12] | R1 = methyl<br>R2 = methyl<br>R3 = 1-(naphth-2yl)-1-ethyl<br>R4 = CO$_2$H<br>R5 = H<br>R6 = H<br>R7 = H |

TABLE 1-continued

Specific Compounds of the Invention

| # | Structure | Substituents |
|---|-----------|--------------|
| 117 | 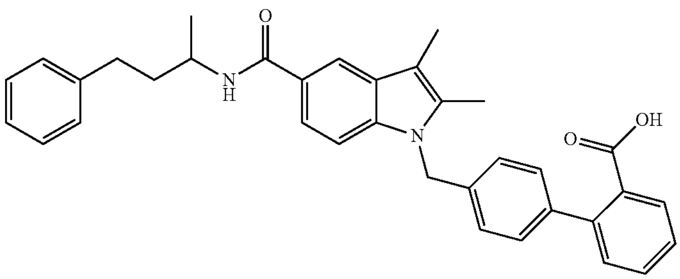 [SMILES: Cc1c(C)n(Cc2ccc(-c3ccccc3C(=O)O)cc2)c2ccc(C(=O)NC(C)CCc3ccccc3)cc12] | R1 = methyl<br>R2 = methyl<br>R3 = phenylpropyl-1-methyl<br>R4 = CO$_2$H<br>R5 = H<br>R6 = H<br>R7 = H |
| 118 | 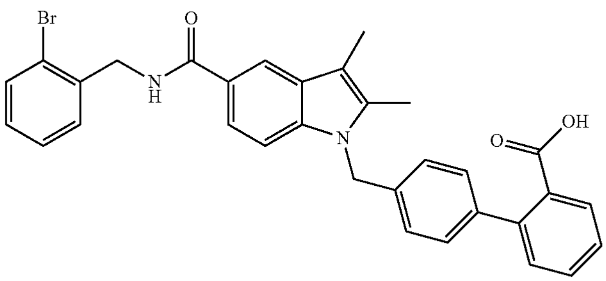 [SMILES: Cc1c(C)n(Cc2ccc(-c3ccccc3C(=O)O)cc2)c2ccc(C(=O)NCc3ccccc3Br)cc12] | R1 = methyl<br>R2 = methyl<br>R3 = 2-bromobenzyl<br>R4 = CO$_2$H<br>R5 = H<br>R6 = H<br>R7 = H |
| 119 | 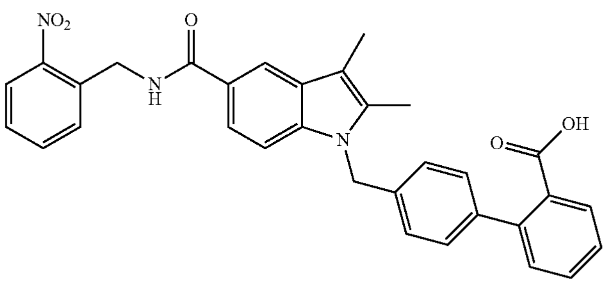 | R1 = methyl<br>R2 = methyl<br>R3 = 2-nitrobenzyl<br>R4 = CO$_2$H<br>R5 = H<br>R6 = H<br>R7 = H |
| 120 | 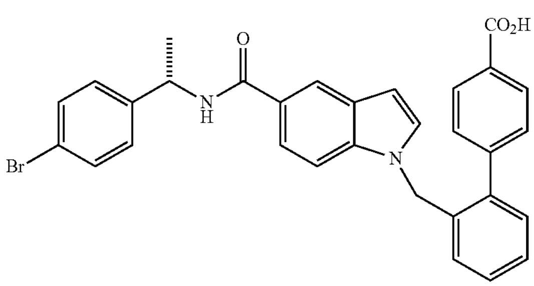 [SMILES: C[C@H](NC(=O)c1ccc2c(ccn2Cc2ccccc2-c2ccc(C(=O)O)cc2)c1)c1ccc(Br)cc1] | R1 = H<br>R2 = H<br>R3 = 4-bromophenyl-1-ethyl<br>R4 = 4-carboxylic acid<br>R5 = H<br>R6 = H<br>R7 = H |
| 121 | 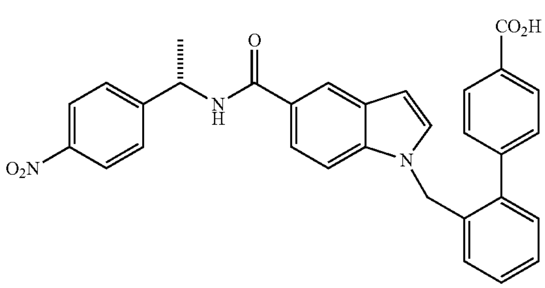 [SMILES: C[C@H](NC(=O)c1ccc2c(ccn2Cc2ccccc2-c2ccc(C(=O)O)cc2)c1)c1ccc([N+](=O)[O-])cc1] | R1 = H<br>R2 = H<br>R3 = 4-nitrophenyl-1-ethyl<br>R4 = 4-carboxylic acid<br>R5 = H<br>R6 = H<br>R7 = H |

TABLE 1-continued

Specific Compounds of the Invention

| # | Structure | Substituents |
|---|---|---|
| 122 | 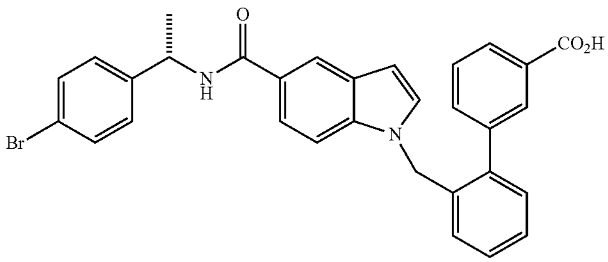 [SMILES: C[C@H](NC(=O)c1ccc2c(ccn2Cc2ccccc2-c2cccc(C(=O)O)c2)c1)c1ccc(Br)cc1] | R1 = H<br>R2 = H<br>R3 = 4-bromophenyl-1-ethyl<br>R4 = 3-carboxylic acid<br>R5 = H<br>R6 = H<br>R7 = H |
| 123 | 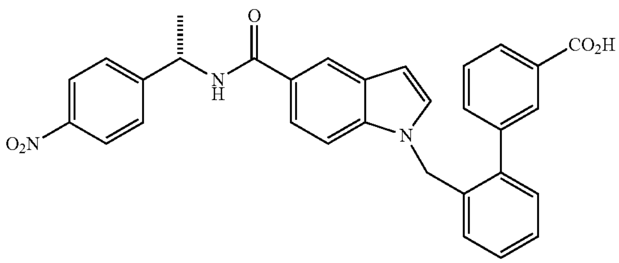 [SMILES: C[C@H](NC(=O)c1ccc2c(ccn2Cc2ccccc2-c2cccc(C(=O)O)c2)c1)c1ccc([N+](=O)[O-])cc1] | R1 = H<br>R2 = H<br>R3 = 4-nitrophenyl-1-ethyl<br>R4 = 3-carboxylic acid<br>R5 = H<br>R6 = H<br>R7 = H |
| 124 | 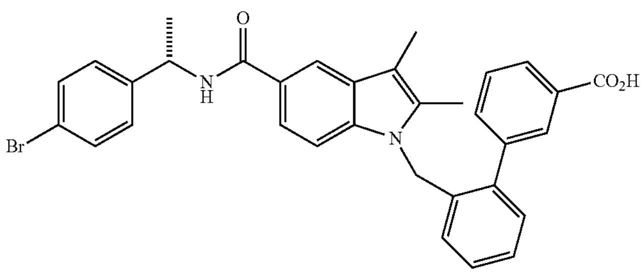 [SMILES: Cc1c(C)n(Cc2ccccc2-c2cccc(C(=O)O)c2)c2ccc(C(=O)N[C@@H](C)c3ccc(Br)cc3)cc12] | R1 = Me<br>R2 = Me<br>R3 = 4-bromophenyl-1-ethyl<br>R4 = 3-carboxylic acid<br>R5 = H<br>R6 = H<br>R7 = H |
| 125 | 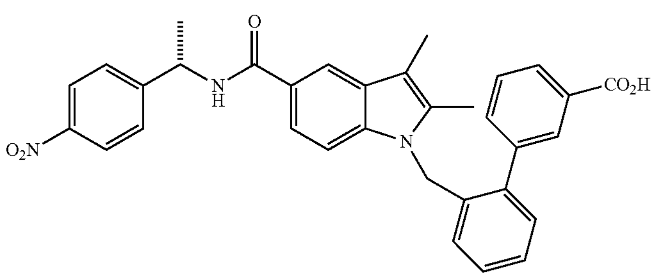 [SMILES: Cc1c(C)n(Cc2ccccc2-c2cccc(C(=O)O)c2)c2ccc(C(=O)N[C@@H](C)c3ccc([N+](=O)[O-])cc3)cc12] | R1 = Me<br>R2 = Me<br>R3 = 4-nitrophenyl-1-ethyl<br>R4 = 3-carboxylic acid<br>R5 = H<br>R6 = H<br>R7 = H |
| 126 | 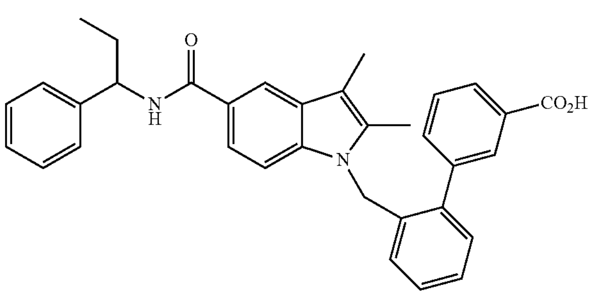 [SMILES: CCC(NC(=O)c1ccc2c(c1)c(C)c(C)n2Cc1ccccc1-c1cccc(C(=O)O)c1)c1ccccc1] | R1 = Me<br>R2 = Me<br>R3 = phenyl-(propyl-1-yl)<br>R4 = 3-carboxylic acid<br>R5 = H<br>R6 = H<br>R7 = H |

TABLE 1-continued

Specific Compounds of the Invention

| # | Structure | Substituents |
|---|---|---|
| 127 | 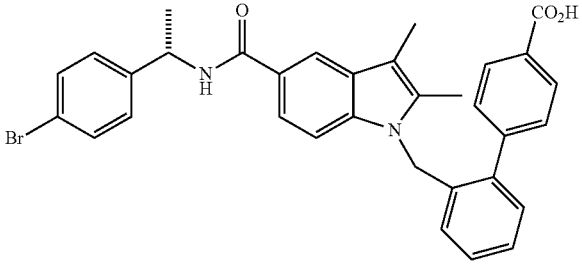 [SMILES: Cc1c(C)n(Cc2ccccc2-c2ccc(C(=O)O)cc2)c2ccc(C(=O)N[C@@H](C)c3ccc(Br)cc3)cc12] | R1 = Me<br>R2 = Me<br>R3 = 4-bromophenyl-1-ethyl<br>R4 = 4-carboxylic acid<br>R5 = H<br>R6 = H<br>R7 = H |
| 128 | 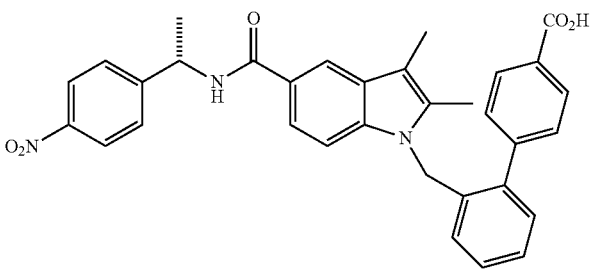 [SMILES: Cc1c(C)n(Cc2ccccc2-c2ccc(C(=O)O)cc2)c2ccc(C(=O)N[C@@H](C)c3ccc([N+](=O)[O-])cc3)cc12] | R1 = Me<br>R2 = Me<br>R3 = 4-nitrophenyl-1-ethyl<br>R4 = 4-carboxylic acid<br>R5 = H<br>R6 = H<br>R7 = H |
| 129 | 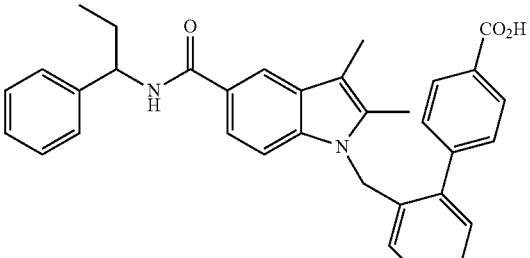 | R1 = Me<br>R2 = Me<br>R3 = phenyl-(propyl-1-yl)<br>R4 = 4-carboxylic acid<br>R5 = H<br>R6 = H<br>R7 = H |
| 130 | 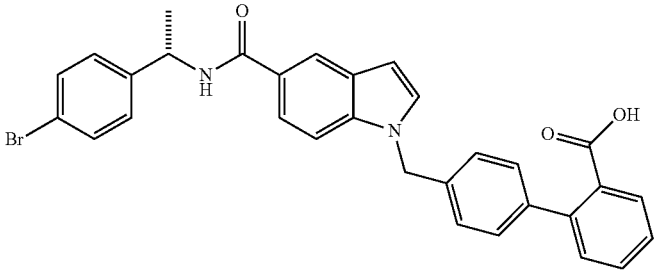 [SMILES: C[C@H](NC(=O)c1ccc2c(ccn2Cc2ccc(-c3ccccc3C(=O)O)cc2)c1)c1ccc(Br)cc1] | R1 = H<br>R2 = H<br>R3 = 4-bromophenyl-1-ethyl<br>R4 = $CO_2H$<br>R5 = H<br>R6 = H<br>R7 = H |
| 131 | 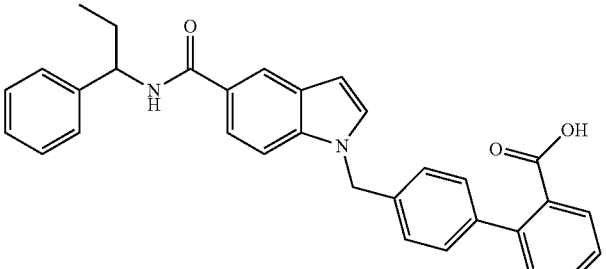 | R1 = H<br>R2 = H<br>R3 = phenyl-(propyl-1-yl)<br>R4 = $CO_2H$<br>R5 = H<br>R6 = H<br>R7 = H |

TABLE 1-continued

Specific Compounds of the Invention

| # | Structure | Substituents |
|---|---|---|
| 132 | 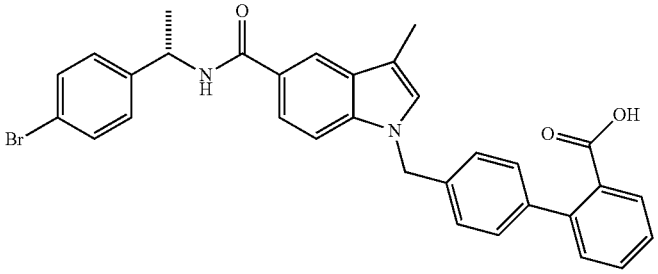 [SMILES: Cc1cn(Cc2ccc(-c3ccccc3C(=O)O)cc2)c2ccc(C(=O)N[C@@H](C)c3ccc(Br)cc3)cc12] | R1 = Me<br>R2 = H<br>R3 = 4-bromophenyl-1-ethyl<br>R4 = CO$_2$H<br>R5 = H<br>R6 = H<br>R7 = H |
| 133 | 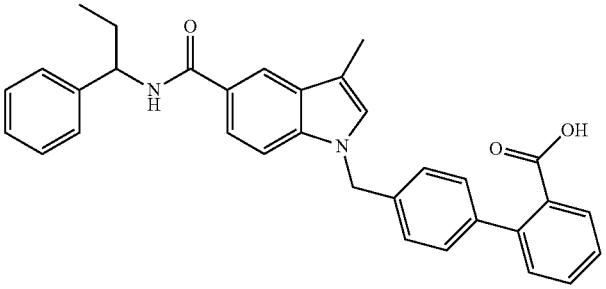 [SMILES: CCC(NC(=O)c1ccc2c(c1)c(C)cn2Cc1ccc(-c2ccccc2C(=O)O)cc1)c1ccccc1] | R1 = Me<br>R2 = H<br>R3 = phenyl-(propyl-1-yl)<br>R4 = CO$_2$H<br>R5 = H<br>R6 = H<br>R7 = H |
| 134 | 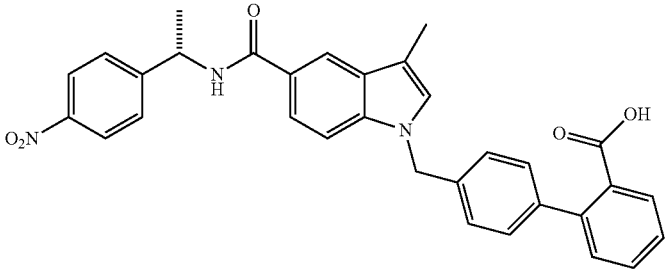 [SMILES: Cc1cn(Cc2ccc(-c3ccccc3C(=O)O)cc2)c2ccc(C(=O)N[C@@H](C)c3ccc([N+](=O)[O-])cc3)cc12] | R1 = Me<br>R2 = H<br>R3 = 4-nitrophenyl-1-ethyl<br>R4 = CO$_2$H<br>R5 = H<br>R6 = H<br>R7 = H |
| 135 | 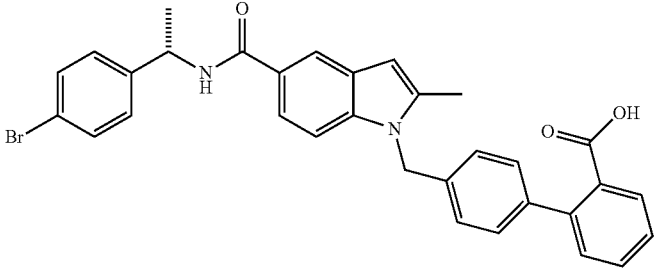 | R1 = H<br>R2 = Me<br>R3 = 4-bromophenyl-1-ethyl<br>R4 = CO$_2$H<br>R5 = H<br>R6 = H<br>R7 = H |
| 136 | 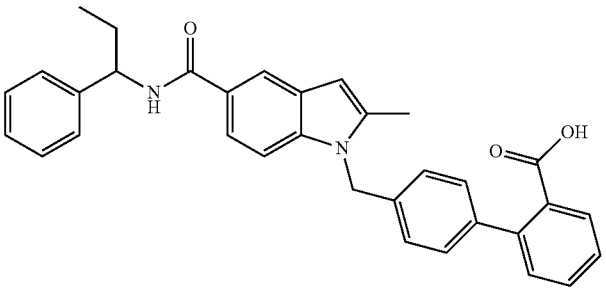 [SMILES: CCC(NC(=O)c1ccc2c(c1)cc(C)n2Cc1ccc(-c2ccccc2C(=O)O)cc1)c1ccccc1] | R1 = H<br>R2 = Me<br>R3 = phenyl-(propyl-1-yl)<br>R4 = CO$_2$H<br>R5 = H<br>R6 = H<br>R7 = H |

TABLE 1-continued

Specific Compounds of the Invention

| # | Structure | Substituents |
|---|---|---|
| 137 | 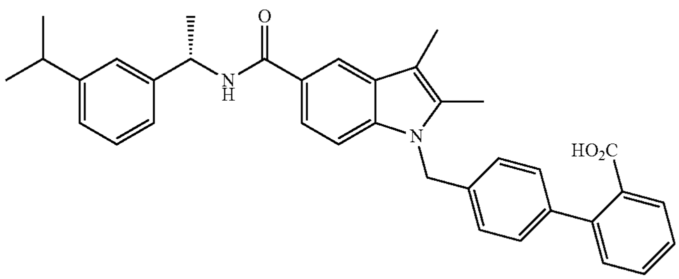 [SMILES: Cc1c(C)n(Cc2ccc(-c3ccccc3C(=O)O)cc2)c2ccc(C(=O)N[C@@H](C)c3cccc(C(C)C)c3)cc12] | R1 = Me<br>R2 = Me<br>R3 = 3-isopropylphenyl-1-ethyl<br>R4 = CO$_2$H<br>R5 = H<br>R6 = H<br>R7 = H |
| 138 | 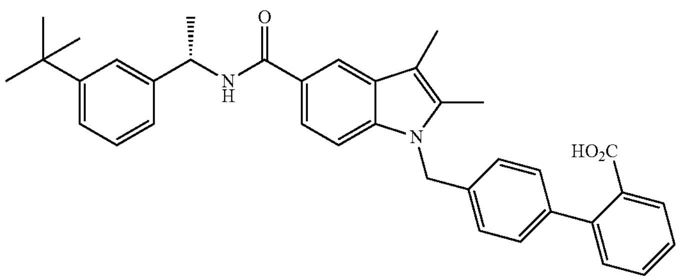 [SMILES: Cc1c(C)n(Cc2ccc(-c3ccccc3C(=O)O)cc2)c2ccc(C(=O)N[C@@H](C)c3cccc(C(C)(C)C)c3)cc12] | R1 = Me<br>R2 = Me<br>R3 = 3-t-butylphenyl-1-ethyl<br>R4 = CO$_2$H<br>R5 = H<br>R6 = H<br>R7 = H |
| 139 | 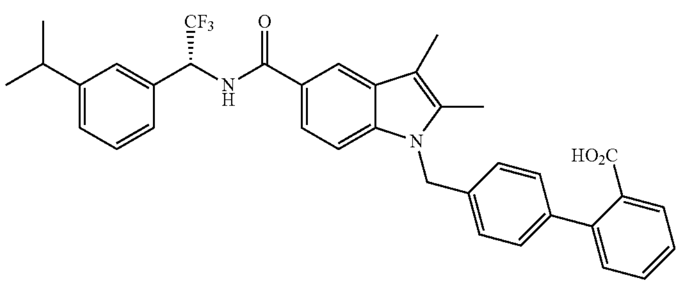 | R1 = Me<br>R2 = Me<br>R3 = 3-isopropylphenyl-1-(2,2,2-trifluoroethyl)<br>R4 = CO$_2$H<br>R5 = H<br>R6 = H<br>R7 = H |
| 140 | 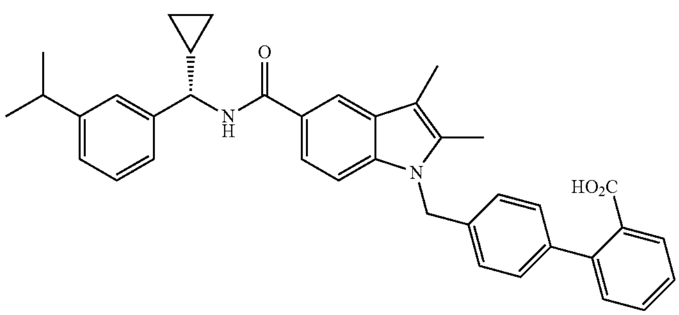 [SMILES: Cc1c(C)n(Cc2ccc(-c3ccccc3C(=O)O)cc2)c2ccc(C(=O)N[C@H](c3cccc(C(C)C)c3)C3CC3)cc12] | R1 = Me<br>R2 = Me<br>R3 = 3-isopropylphenyl-1-(cyclopropylmethyl)<br>R4 = CO$_2$H<br>R5 = H<br>R6 = H<br>R7 = H |
| 141 | 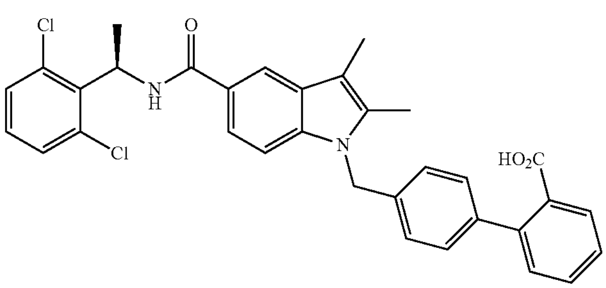 [SMILES: Cc1c(C)n(Cc2ccc(-c3ccccc3C(=O)O)cc2)c2ccc(C(=O)N[C@H](C)c3c(Cl)cccc3Cl)cc12] | R1 = Me<br>R2 = Me<br>R3 = 2,6-dichlorophenyl-1-ethyl<br>R4 = CO$_2$H<br>R5 = H<br>R6 = H<br>R7 = H |

TABLE 1-continued

Specific Compounds of the Invention

| # | Structure | Substituents |
|---|---|---|
| 142 | 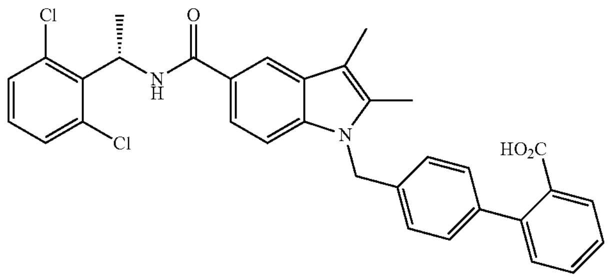 [SMILES: Cc1c(C)n(Cc2ccc(-c3ccccc3C(=O)O)cc2)c2ccc(C(=O)N[C@@H](C)c3c(Cl)cccc3Cl)cc12] | R1 = Me<br>R2 = Me<br>R3 = 2,6-dichlorophenyl-1-ethyl<br>R4 = CO$_2$H<br>R5 = H<br>R6 = H<br>R7 = H |
| 143 | 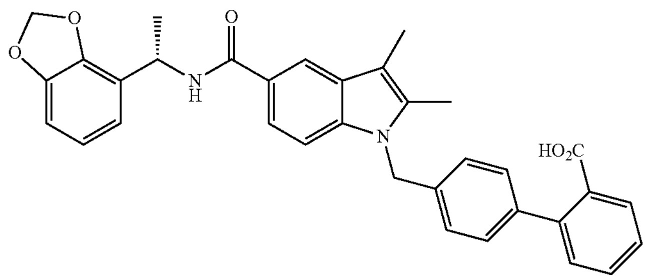 [SMILES: Cc1c(C)n(Cc2ccc(-c3ccccc3C(=O)O)cc2)c2ccc(C(=O)N[C@@H](C)c3cccc4c3OCO4)cc12] | R1 = Me<br>R2 = Me<br>R3 = 2,3-methylenedioxy-phenyl-1-ethyl<br>R4 = CO$_2$H<br>R5 = H<br>R6 = H<br>R7 = H |
| 144 | 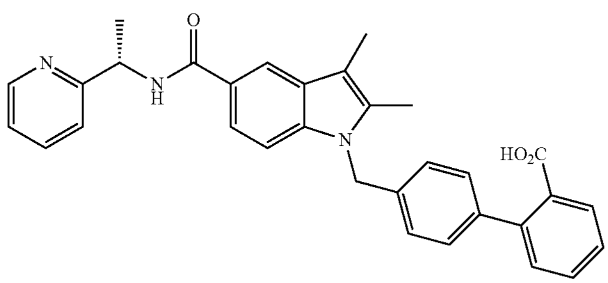 [SMILES: Cc1c(C)n(Cc2ccc(-c3ccccc3C(=O)O)cc2)c2ccc(C(=O)N[C@@H](C)c3ccccn3)cc12] | R1 = Me<br>R2 = Me<br>R3 = 2-pyridyl-1-ethyl<br>R4 = CO$_2$H<br>R5 = H<br>R6 = H<br>R7 = H |
| 145 | 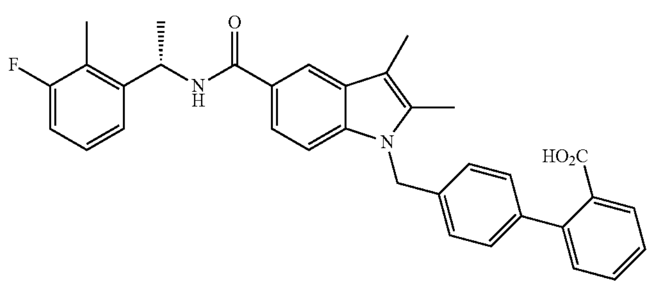 | R1 = Me<br>R2 = Me<br>R3 = 2-methyl-3-fluorophenyl-1-ethyl<br>R4 = CO$_2$H<br>R5 = H<br>R6 = H<br>R7 = H |
| 146 | 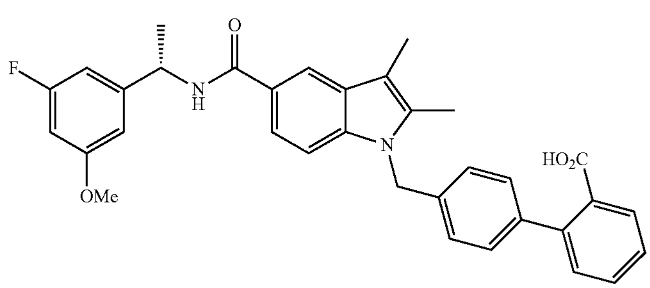 [SMILES: COc1cc(F)cc([C@H](C)NC(=O)c2ccc3c(c2)c(C)c(C)n3Cc2ccc(-c3ccccc3C(=O)O)cc2)c1] | R1 = Me<br>R2 = Me<br>R3 = 3-fluoro-5-methoxyphenyl-1-ethyl<br>R4 = CO$_2$H<br>R5 = H<br>R6 = H<br>R7 = H |

TABLE 1-continued

Specific Compounds of the Invention

| # | Structure | Substituents |
|---|-----------|--------------|
| 147 | 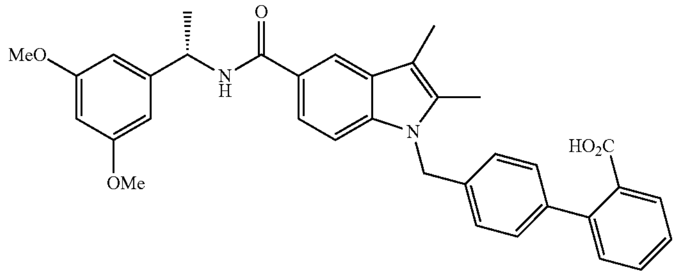 [SMILES: COc1cc(OC)cc([C@H](C)NC(=O)c2ccc3c(c2)c(C)c(C)n3Cc2ccc(-c3ccccc3C(=O)O)cc2)c1] | R1 = Me<br>R2 = Me<br>R3 = 3,5-dimethoxyphenyl-1-ethyl<br>R4 = CO$_2$H<br>R5 = H<br>R6 = H<br>R7 = H |
| 148 | 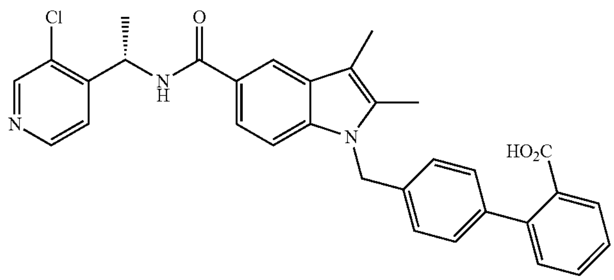 [SMILES: Cc1c(C)n(Cc2ccc(-c3ccccc3C(=O)O)cc2)c2ccc(C(=O)N[C@@H](C)c3ccncc3Cl)cc12] | R1 = Me<br>R2 = Me<br>R3 = 2-chloropyrid-4-yll-1-ethyl<br>R4 = CO$_2$H<br>R5 = H<br>R6 = H<br>R7 = H |
| 149 | 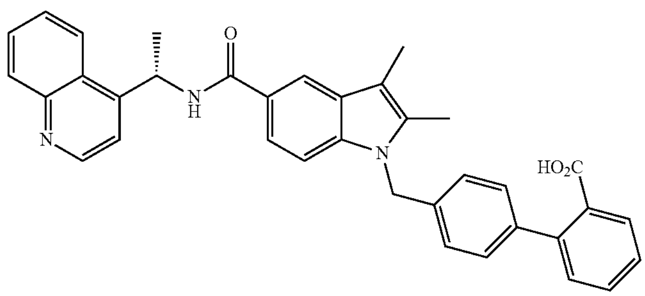 [SMILES: Cc1c(C)n(Cc2ccc(-c3ccccc3C(=O)O)cc2)c2ccc(C(=O)N[C@@H](C)c3ccnc4ccccc34)cc12] | R1 = Me<br>R2 = Me<br>R3 = 4-quinolyl-1-ethyl<br>R4 = CO$_2$H<br>R5 = H<br>R6 = H<br>R7 = H |
| 150 | 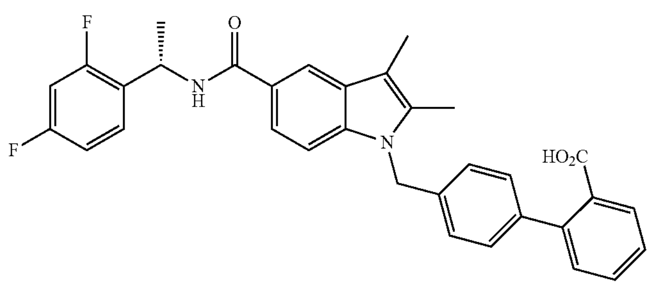 [SMILES: Cc1c(C)n(Cc2ccc(-c3ccccc3C(=O)O)cc2)c2ccc(C(=O)N[C@@H](C)c3ccc(F)cc3F)cc12] | R1 = Me<br>R2 = Me<br>R3 = 2,4-difluorophenyl-1-ethyl<br>R4 = CO$_2$H<br>R5 = H<br>R6 = H<br>R7 = H |
| 151 | 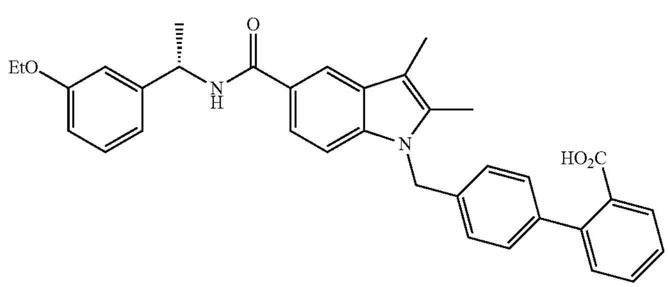 [SMILES: CCOc1cccc([C@H](C)NC(=O)c2ccc3c(c2)c(C)c(C)n3Cc2ccc(-c3ccccc3C(=O)O)cc2)c1] | R1 = Me<br>R2 = Me<br>R3 = 3-ethoxyphenyl-1-ethyl<br>R4 = CO$_2$H<br>R5 = H<br>R6 = H<br>R7 = H |

TABLE 1-continued

Specific Compounds of the Invention

| # | Structure | Substituents |
|---|---|---|
| 152 | 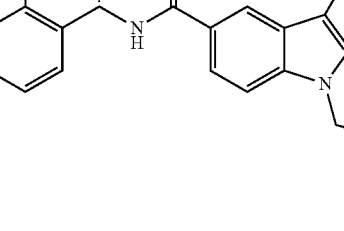 | R1 = Me<br>R2 = Me<br>R3 = naphth-1-yl-1-ethyl<br>R4 = CO$_2$H<br>R5 = H<br>R6 = H<br>R7 = H |
| 153 | 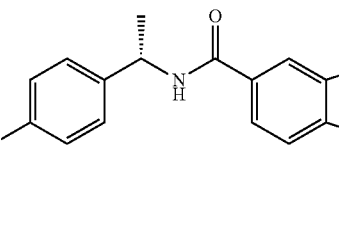 | R1 = Me<br>R2 = Me<br>R3 = 4-trifluoromethoxy-phenyl-1-ethyl<br>R4 = CO$_2$H<br>R5 = H<br>R6 = H<br>R7 = H |
| 154 | 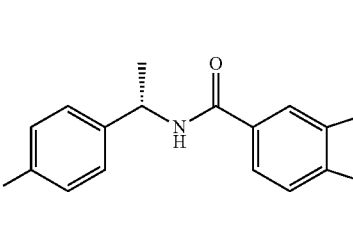 | R1 = Me<br>R2 = Me<br>R3 = 4-trifluoromethyl-phenyl-1-ethyl<br>R4 = CO$_2$H<br>R5 = H<br>R6 = H<br>R7 = H |
| 155 | 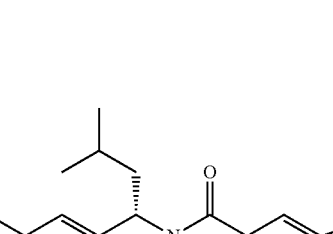 | R1 = Me<br>R2 = Me<br>R3 = 3-isopropylphenyl-1-isopentyl<br>R4 = CO$_2$H<br>R5 = H<br>R6 = H<br>R7 = H |
| 156 | 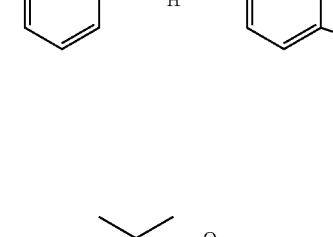 | R1 = Me<br>R2 = Me<br>R3 = 3-isopropylphenyl-1-isobutyl<br>R4 = CO$_2$H<br>R5 = H<br>R6 = H<br>R7 = H |

TABLE 1-continued

Specific Compounds of the Invention

| # | Structure | Substituents |
|---|---|---|
| 157 | 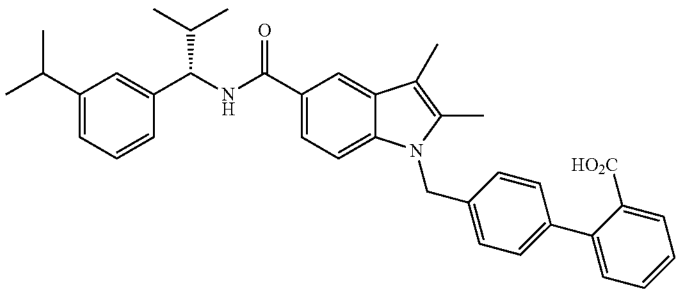 [SMILES: Cc1c(C)n(Cc2ccc(-c3ccccc3C(=O)O)cc2)c2ccc(C(=O)N[C@H](c3cccc(C(C)C)c3)C(C)C)cc12] | R1 = Me<br>R2 = Me<br>R3 = 3-isopropylphenyl-1-isobutyl<br>R4 = CO$_2$H<br>R5 = H<br>R6 = H<br>R7 = H |
| 158 | 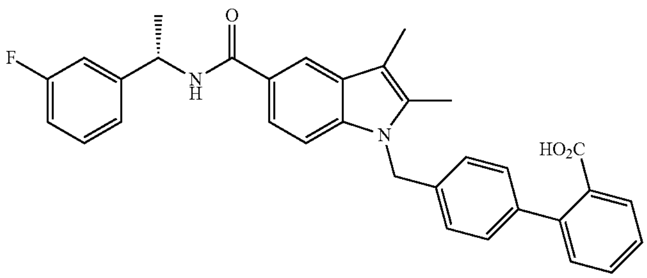 [SMILES: Cc1c(C)n(Cc2ccc(-c3ccccc3C(=O)O)cc2)c2ccc(C(=O)N[C@@H](C)c3cccc(F)c3)cc12] | R1 = Me<br>R2 = Me<br>R3 = 3-fluorophenyl-1-ethyl<br>R4 = CO$_2$H<br>R5 = H<br>R6 = H<br>R7 = H |
| 159 | 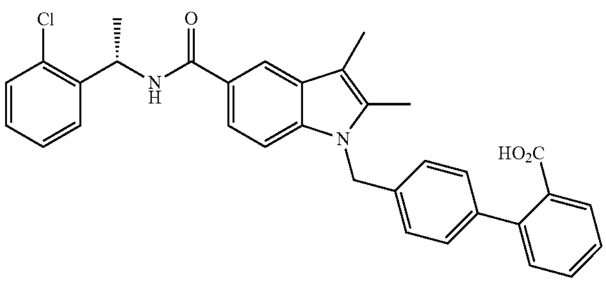 | R1 = Me<br>R2 = Me<br>R3 = 2-chlorophenyl-1-ethyl<br>R4 = CO$_2$H<br>R5 = H<br>R6 = H<br>R7 = H |
| 160 | 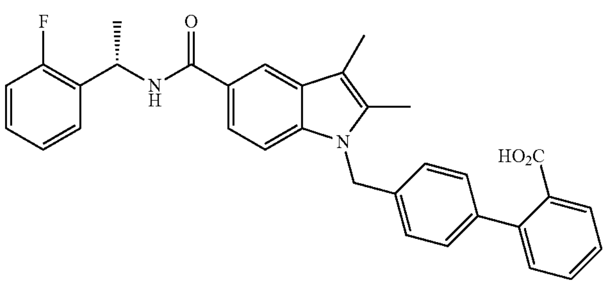 [SMILES: Cc1c(C)n(Cc2ccc(-c3ccccc3C(=O)O)cc2)c2ccc(C(=O)N[C@@H](C)c3ccccc3Cl)cc12] | R1 = Me<br>R2 = Me<br>R3 = 2-fluorophenyl-1-ethyl<br>R4 = CO$_2$H<br>R5 = H<br>R6 = H<br>R7 = H |
| 161 | 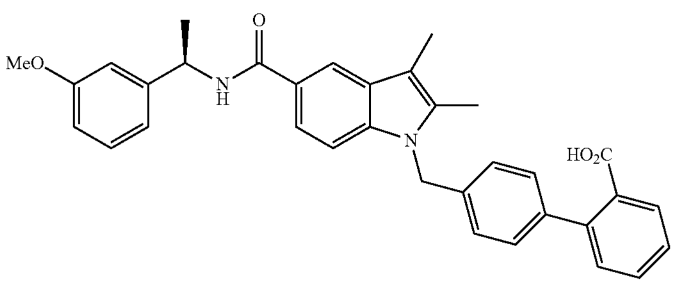 [SMILES: COc1cccc([C@@H](C)NC(=O)c2ccc3c(c2)c(C)c(C)n3Cc2ccc(-c3ccccc3C(=O)O)cc2)c1] | R1 = Me<br>R2 = Me<br>R3 = 3-methoxyphenyl-1-ethyl<br>R4 = CO$_2$H<br>R5 = H<br>R6 = H<br>R7 = H |

TABLE 1-continued

Specific Compounds of the Invention

| # | Structure | Substituents |
|---|---|---|
| 162 | 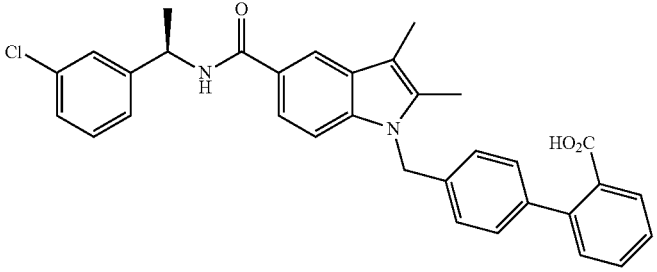 [SMILES: Cc1c(C)n(Cc2ccc(-c3ccccc3C(=O)O)cc2)c2ccc(C(=O)N[C@H](C)c3cccc(Cl)c3)cc12] | R1 = Me<br>R2 = Me<br>R3 = 3-chlorophenyl-1-ethyl<br>R4 = CO₂H<br>R5 = H<br>R6 = H<br>R7 = H |
| 163 | 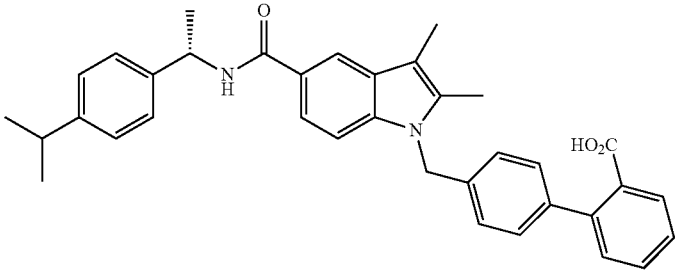 [SMILES: Cc1c(C)n(Cc2ccc(-c3ccccc3C(=O)O)cc2)c2ccc(C(=O)N[C@@H](C)c3ccc(C(C)C)cc3)cc12] | R1 = Me<br>R2 = Me<br>R3 = 4-isopropylphenyl-1-ethyl<br>R4 = CO₂H<br>R5 = H<br>R6 = H<br>R7 = H |
| 164 | 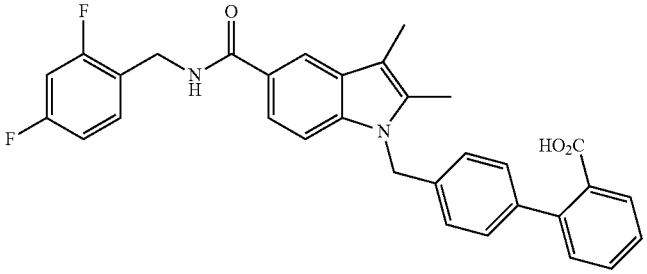 [SMILES: Cc1c(C)n(Cc2ccc(-c3ccccc3C(=O)O)cc2)c2ccc(C(=O)NCc3ccc(F)cc3F)cc12] | R1 = Me<br>R2 = Me<br>R3 = 2,4-difluorophenyl-1-ethyl<br>R4 = CO₂H<br>R5 = H<br>R6 = H<br>R7 = H |
| 165 | 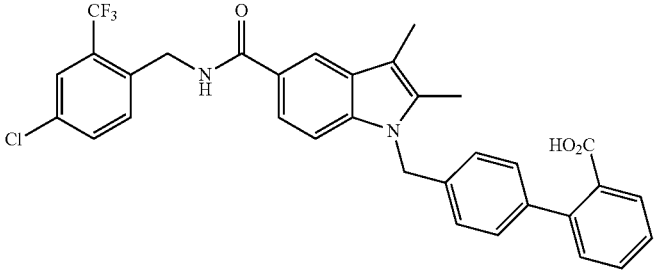 | R1 = Me<br>R2 = Me<br>R3 = 2-trifluoromethyl-4-chlorophenyl-1-ethyl<br>R4 = CO₂H<br>R5 = H<br>R6 = H<br>R7 = H |
| 166 | 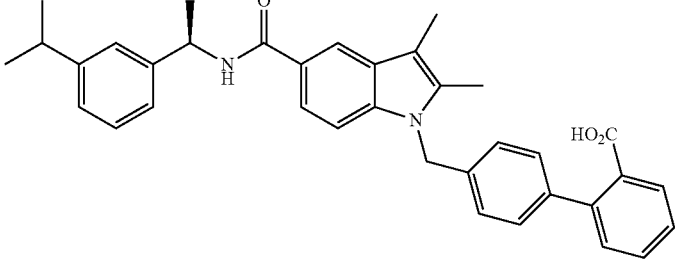 | R1 = Me<br>R2 = Me<br>R3 = 3-isopropylphenyl-1-ethyl<br>R4 = CO₂H<br>R5 = H<br>R6 = H<br>R7 = H |

TABLE 1-continued

Specific Compounds of the Invention

| # | Structure | Substituents |
|---|---|---|
| 167 | 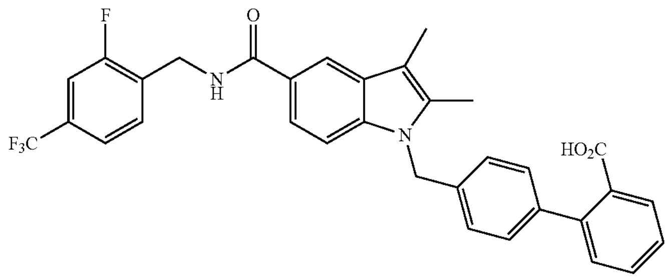 [SMILES: Cc1c(C)n(Cc2ccc(-c3ccccc3C(=O)O)cc2)c2ccc(C(=O)NCc3ccc(C(F)(F)F)cc3F)cc12] | R1 = Me<br>R2 = Me<br>R3 = 2-fluoro-4-trifluoromethylphenyl-methyl<br>R4 = CO$_2$H<br>R5 = H<br>R6 = H<br>R7 = H |
| 168 | 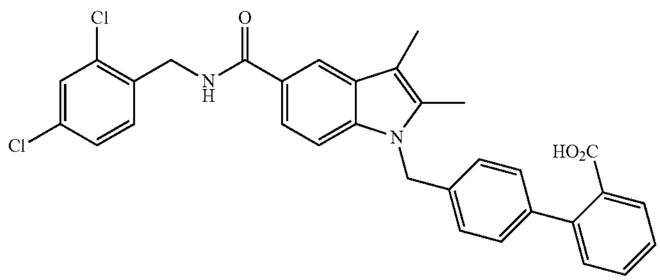 [SMILES: Cc1c(C)n(Cc2ccc(-c3ccccc3C(=O)O)cc2)c2ccc(C(=O)NCc3ccc(Cl)cc3Cl)cc12] | R1 = Me<br>R2 = Me<br>R3 = 2,4-dichlorophenyl-methyl<br>R4 = CO$_2$H<br>R5 = H<br>R6 = H<br>R7 = H |
| 169 | 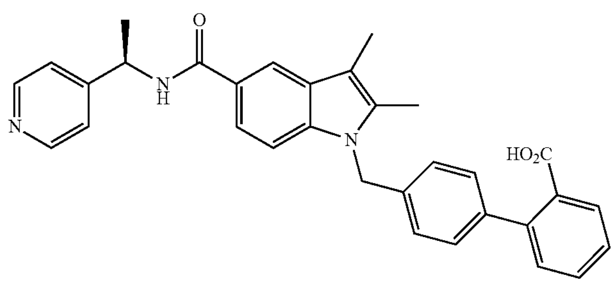 [SMILES: Cc1c(C)n(Cc2ccc(-c3ccccc3C(=O)O)cc2)c2ccc(C(=O)N[C@H](C)c3ccncc3)cc12] | R1 = Me<br>R2 = Me<br>R3 = pyrid-4-yl-1-ethyl<br>R4 = CO$_2$H<br>R5 = H<br>R6 = H<br>R7 = H |
| 170 | 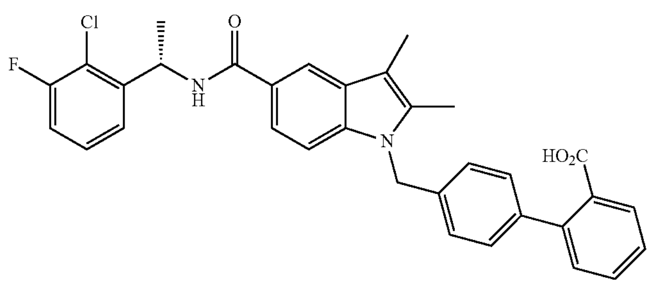 [SMILES: Cc1c(C)n(Cc2ccc(-c3ccccc3C(=O)O)cc2)c2ccc(C(=O)N[C@@H](C)c3cccc(F)c3Cl)cc12] | R1 = Me<br>R2 = Me<br>R3 = 2-chloro-3-fluorophenyl-1-ethyl<br>R4 = CO$_2$H<br>R5 = H<br>R6 = H<br>R7 = H |
| 171 | 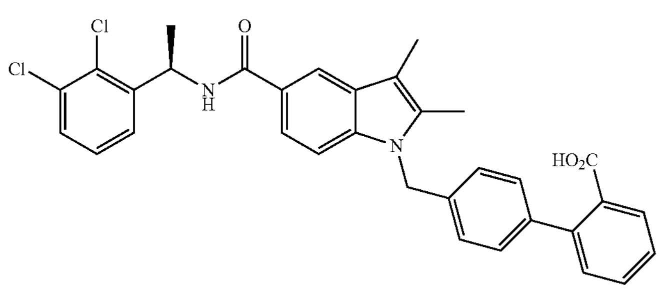 [SMILES: Cc1c(C)n(Cc2ccc(-c3ccccc3C(=O)O)cc2)c2ccc(C(=O)N[C@H](C)c3cccc(Cl)c3Cl)cc12] | R1 = Me<br>R2 = Me<br>R3 = 2,3-dichlorophenyl-1-ethyl<br>R4 = CO$_2$H<br>R5 = H<br>R6 = H<br>R7 = H |

TABLE 1-continued

Specific Compounds of the Invention

| # | Structure | Substituents |
|---|-----------|--------------|
| 172 | 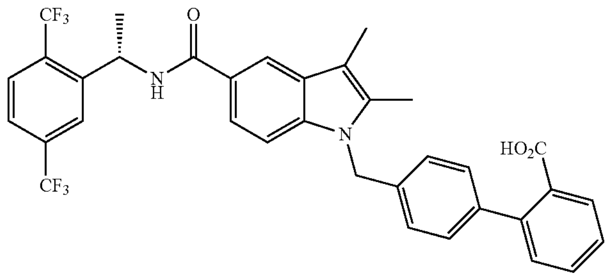 [SMILES: Cc1c(C)n(Cc2ccc(-c3ccccc3C(=O)O)cc2)c2ccc(C(=O)N[C@@H](C)c3cc(C(F)(F)F)ccc3C(F)(F)F)cc12] | R1 = Me<br>R2 = Me<br>R3 = 2,5-bis(trifluoromethyl)-phenyl-1-ethyl<br>R4 = CO$_2$H<br>R5 = H<br>R6 = H<br>R7 = H |
| 173 | 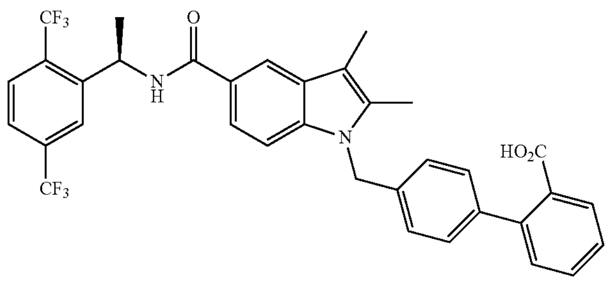 | R1 = Me<br>R2 = Me<br>R3 = 2,5-bis(trifluoromethyl)-phenyl-1-ethyl<br>R4 = CO$_2$H<br>R5 = H<br>R6 = H<br>R7 = H |
| 174 | 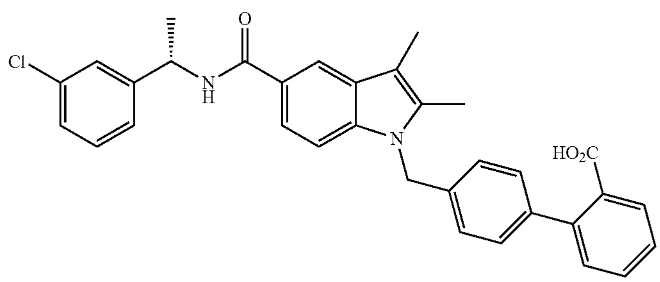 [SMILES: Cc1c(C)n(Cc2ccc(-c3ccccc3C(=O)O)cc2)c2ccc(C(=O)N[C@@H](C)c3cccc(Cl)c3)cc12] | R1 = Me<br>R2 = Me<br>R3 = 3-chlorophenyl-1-ethyl<br>R4 = CO$_2$H<br>R5 = H<br>R6 = H<br>R7 = H |
| 175 | 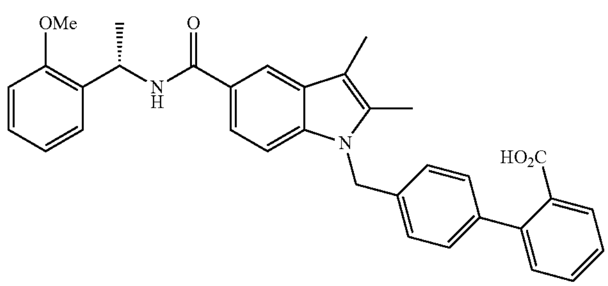 [SMILES: COc1ccccc1[C@H](C)NC(=O)c1ccc2c(c1)c(C)c(C)n2Cc1ccc(-c2ccccc2C(=O)O)cc1] | R1 = Me<br>R2 = Me<br>R3 = 2-methoxyphenyl-1-ethyl<br>R4 = CO$_2$H<br>R5 = H<br>R6 = H<br>R7 = H |
| 176 | 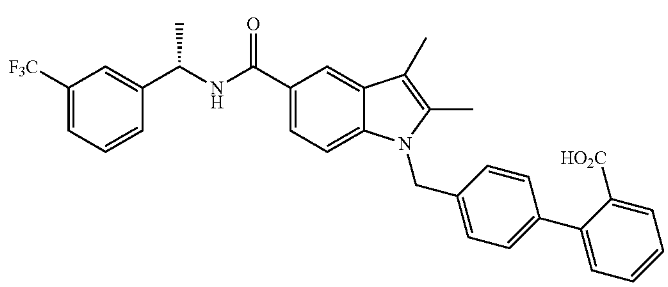 [SMILES: Cc1c(C)n(Cc2ccc(-c3ccccc3C(=O)O)cc2)c2ccc(C(=O)N[C@@H](C)c3cccc(C(F)(F)F)c3)cc12] | R1 = Me<br>R2 = Me<br>R3 = 3-trifluromethyl-phenyl-1-ethyl<br>R4 = CO$_2$H<br>R5 = H<br>R6 = H<br>R7 = H |

TABLE 1-continued

Specific Compounds of the Invention

| # | Structure | Substituents |
|---|-----------|--------------|
| 177 | 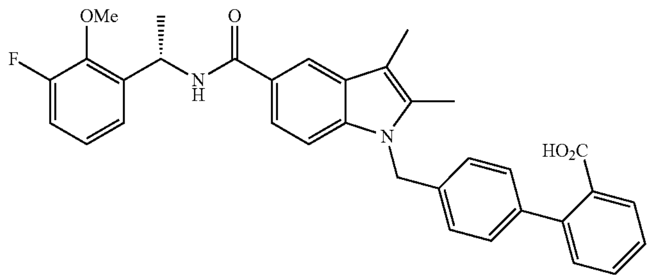 [SMILES: COc1c(F)cccc1[C@H](C)NC(=O)c1ccc2c(c1)c(C)c(C)n2Cc1ccc(-c2ccccc2C(=O)O)cc1] | R1 = Me<br>R2 = Me<br>R3 = 2-methoxy-3-fluoro-phenyl-1-ethyl<br>R4 = CO₂H<br>R5 = H<br>R6 = H<br>R7 = H |
| 178 | 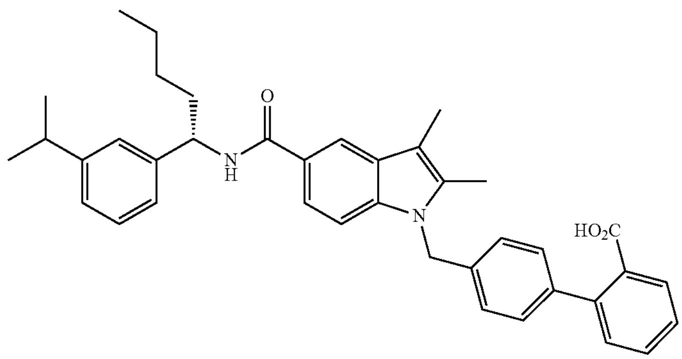 [SMILES: CCCC[C@H](NC(=O)c1ccc2c(c1)c(C)c(C)n2Cc1ccc(-c2ccccc2C(=O)O)cc1)c1cccc(C(C)C)c1] | R1 = Me<br>R2 = Me<br>R3 = 3-isopropylphenyl-1-pentyl<br>R4 = CO₂H<br>R5 = H<br>R6 = H<br>R7 = H |
| 179 | 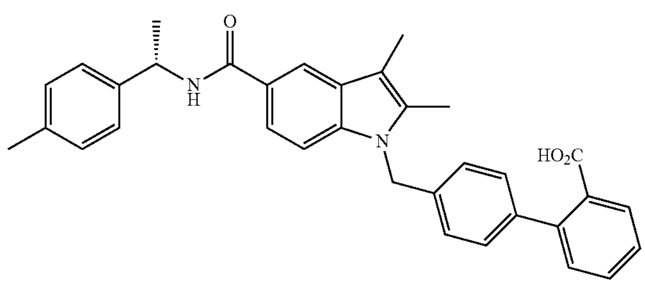 [SMILES: Cc1ccc([C@H](C)NC(=O)c2ccc3c(c2)c(C)c(C)n3Cc2ccc(-c3ccccc3C(=O)O)cc2)cc1] | R1 = Me<br>R2 = Me<br>R3 = 4-methylphenyl-1-ethyl<br>R4 = CO₂H<br>R5 = H<br>R6 = H<br>R7 = H |
| 180 | 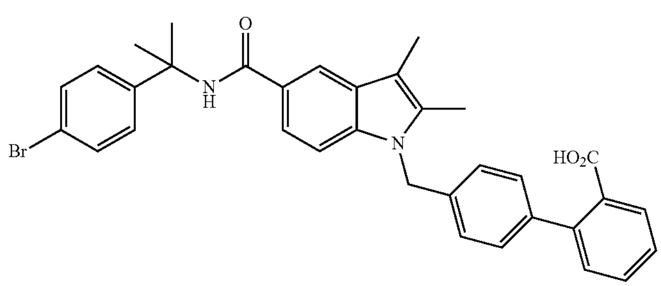 [SMILES: Cc1c(C)n(Cc2ccc(-c3ccccc3C(=O)O)cc2)c2ccc(C(=O)NC(C)(C)c3ccc(Br)cc3)cc12] | R1 = Me<br>R2 = Me<br>R3 = 4-bromophenyl-2-isopropyl<br>R4 = CO₂H<br>R5 = H<br>R6 = H<br>R7 = H |
| 181 | 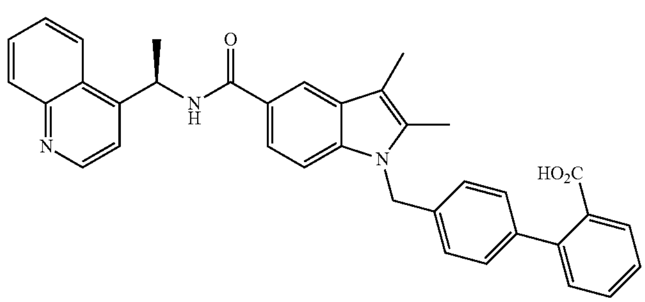 [SMILES: Cc1c(C)n(Cc2ccc(-c3ccccc3C(=O)O)cc2)c2ccc(C(=O)N[C@H](C)c3ccnc4ccccc34)cc12] | R1 = Me<br>R2 = Me<br>R3 = 4-quinolyl-1-ethyl<br>R4 = CO₂H<br>R5 = H<br>R6 = H<br>R7 = H |

TABLE 1-continued

Specific Compounds of the Invention

| # | Structure | Substituents |
|---|---|---|
| 182 | 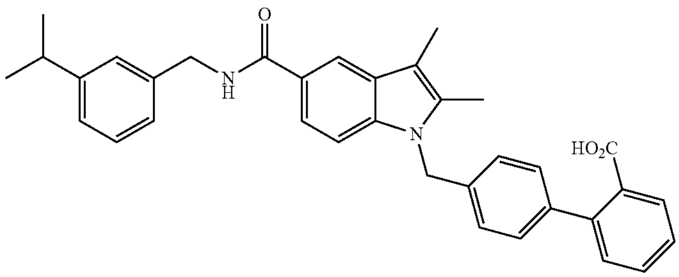 [SMILES: Cc1c(C)n(Cc2ccc(-c3ccccc3C(=O)O)cc2)c2ccc(C(=O)NCc3cccc(C(C)C)c3)cc12] | R1 = Me<br>R2 = Me<br>R3 = 3-isopropylphenyl-methyl<br>R4 = CO$_2$H<br>R5 = H<br>R6 = H<br>R7 = H |
| 183 | 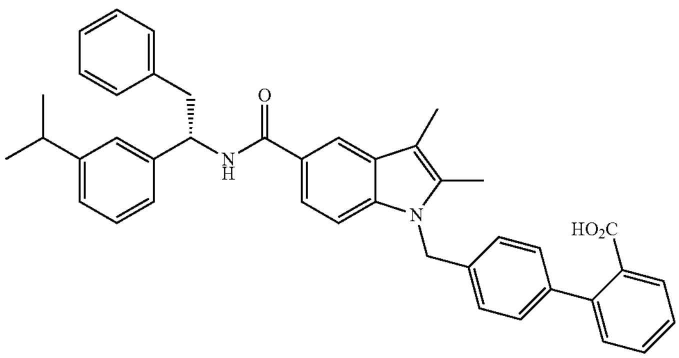 [SMILES: Cc1c(C)n(Cc2ccc(-c3ccccc3C(=O)O)cc2)c2ccc(C(=O)N[C@@H](Cc3ccccc3)c3cccc(C(C)C)c3)cc12] | R1 = Me<br>R2 = Me<br>R3 = 3-isopropylphenyl-2-phenethyl<br>R4 = CO$_2$H<br>R5 = H<br>R6 = H<br>R7 = H |
| 184 | 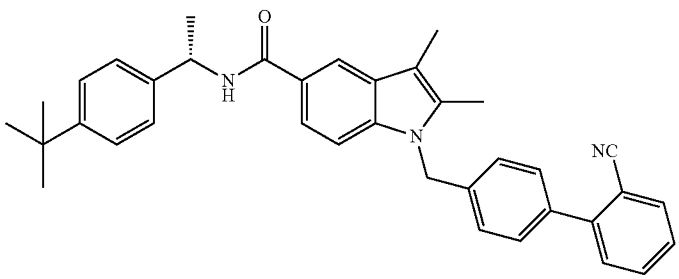 [SMILES: Cc1c(C)n(Cc2ccc(-c3ccccc3C#N)cc2)c2ccc(C(=O)N[C@@H](C)c3ccc(C(C)(C)C)cc3)cc12] | R1 = Me<br>R2 = Me<br>R3 = 4-t-butylphenyl-1-ethyl<br>R4 = CN<br>R5 = H<br>R6 = H<br>R7 = H |
| 185 | 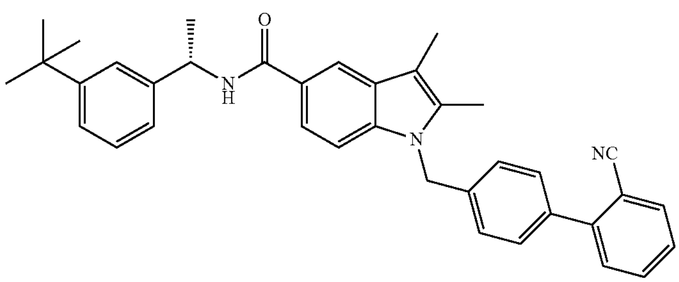 [SMILES: Cc1c(C)n(Cc2ccc(-c3ccccc3C#N)cc2)c2ccc(C(=O)N[C@@H](C)c3cccc(C(C)(C)C)c3)cc12] | R1 = Me<br>R2 = Me<br>R3 = 3-t-butylphenyl-1-ethyl<br>R4 = CN<br>R5 = H<br>R6 = H<br>R7 = H |
| 186 | 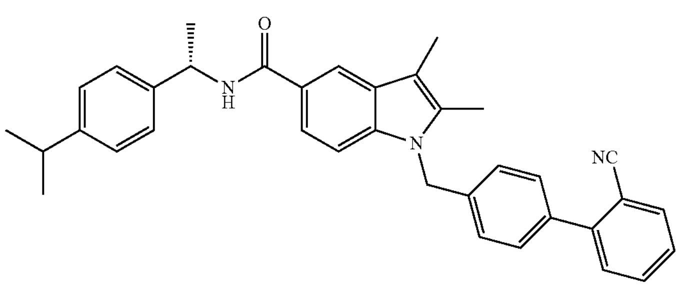 [SMILES: Cc1c(C)n(Cc2ccc(-c3ccccc3C#N)cc2)c2ccc(C(=O)N[C@@H](C)c3ccc(C(C)C)cc3)cc12] | R1 = Me<br>R2 = Me<br>R3 = 4-isopropyllphenyl-1-ethyl<br>R4 = CN<br>R5 = H<br>R6 = H<br>R7 = H |

TABLE 1-continued

Specific Compounds of the Invention

| # | Structure | Substituents |
|---|---|---|
| 187 | 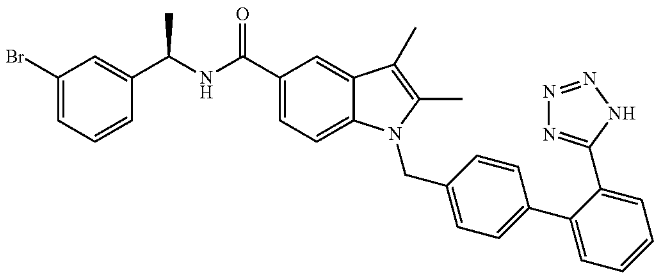 [SMILES: Cc1c(C)n(Cc2ccc(-c3ccccc3-c3nnn[nH]3)cc2)c2ccc(C(=O)N[C@H](C)c3cccc(Br)c3)cc12] | R1 = Me<br>R2 = Me<br>R3 = 3-bromophenyl-1-ethyl<br>R4 = C-bonded tetrazole<br>R5 = H<br>R6 = H<br>R7 = H |
| 188 | 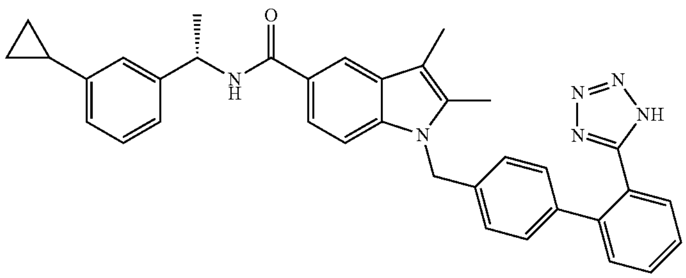 [SMILES: Cc1c(C)n(Cc2ccc(-c3ccccc3-c3nnn[nH]3)cc2)c2ccc(C(=O)N[C@@H](C)c3cccc(C4CC4)c3)cc12] | R1 = Me<br>R2 = Me<br>R3 = 3-cyclopropyl-phenyl-1-ethyl<br>R4 = C-bonded tetrazole<br>R5 = H<br>R6 = H<br>R7 = H |
| 189 | 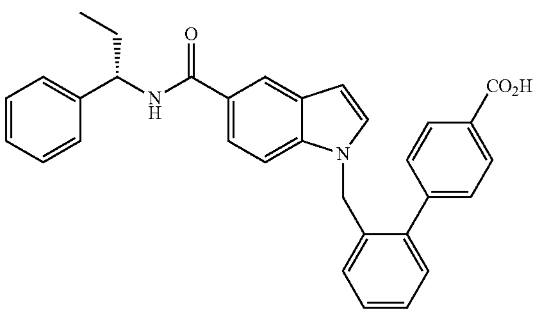 [SMILES: CC[C@H](NC(=O)c1ccc2c(ccn2Cc2ccccc2-c2ccc(C(=O)O)cc2)c1)c1ccccc1] | R1 = H<br>R2 = H<br>R3 = phenyl-1-propyl<br>R4 = CO$_2$H<br>R5 = H<br>R6 = H<br>R7 = H |
| 190 | 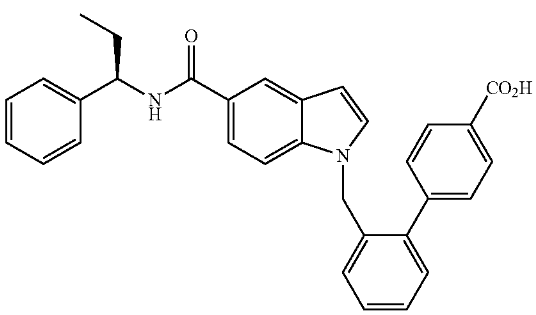 [SMILES: CC[C@@H](NC(=O)c1ccc2c(ccn2Cc2ccccc2-c2ccc(C(=O)O)cc2)c1)c1ccccc1] | R1 = H<br>R2 = H<br>R3 = phenyl-1-propyl<br>R4 = CO$_2$H<br>R5 = H<br>R6 = H<br>R7 = H |
| 191 | 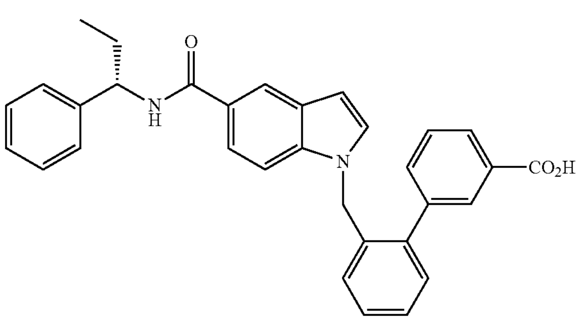 [SMILES: CC[C@H](NC(=O)c1ccc2c(ccn2Cc2ccccc2-c2cccc(C(=O)O)c2)c1)c1ccccc1] | R1 = H<br>R2 = H<br>R3 = phenyl-1-propyl<br>R4 = CO$_2$H<br>R5 = H<br>R6 = H<br>R7 = H |

TABLE 1-continued

Specific Compounds of the Invention

| # | Structure | Substituents |
|---|---|---|
| 192 | 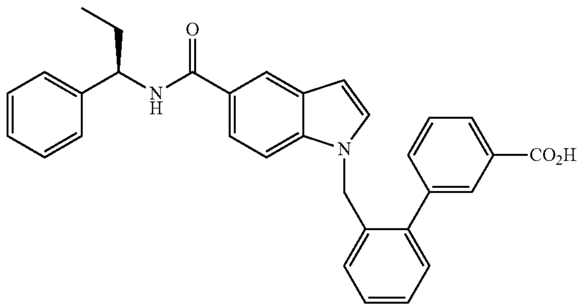 [SMILES: CC[C@@H](NC(=O)c1ccc2c(ccn2Cc2ccccc2-c2cccc(C(=O)O)c2)c1)c1ccccc1] | R1 = H<br>R2 = H<br>R3 = phenyl-1-propyl<br>R4 = $CO_2H$<br>R5 = H<br>R6 = H<br>R7 = H |
| 193 | 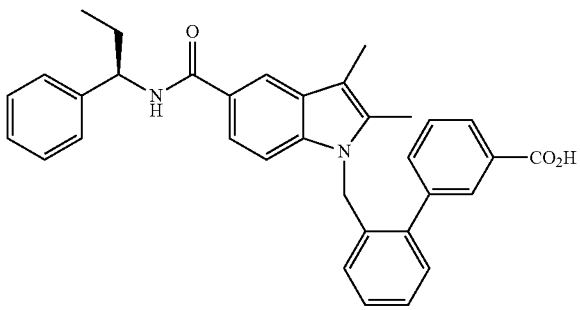 [SMILES: CC[C@@H](NC(=O)c1ccc2c(c1)c(C)c(C)n2Cc1ccccc1-c1cccc(C(=O)O)c1)c1ccccc1] | R1 = Me<br>R2 = Me<br>R3 = phenyl-1-propyl<br>R4 = $CO_2H$<br>R5 = H<br>R6 = H<br>R7 = H |
| 194 | 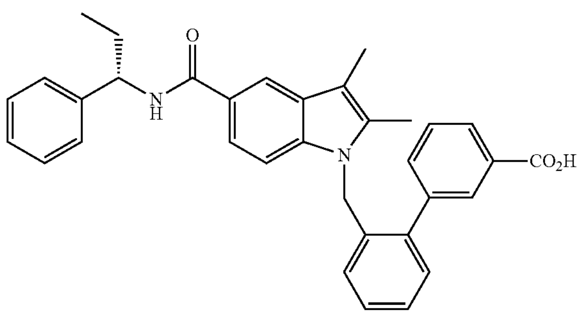 [SMILES: CC[C@H](NC(=O)c1ccc2c(c1)c(C)c(C)n2Cc1ccccc1-c1cccc(C(=O)O)c1)c1ccccc1] | R1 = Me<br>R2 = Me<br>R3 = phenyl-1-propyl<br>R4 = $CO_2H$<br>R5 = H<br>R6 = H<br>R7 = H |
| 195 | 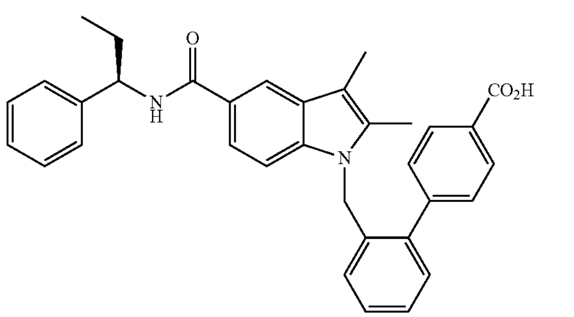 [SMILES: CC[C@@H](NC(=O)c1ccc2c(c1)c(C)c(C)n2Cc1ccccc1-c1ccc(C(=O)O)cc1)c1ccccc1] | R1 = Me<br>R2 = Me<br>R3 = phenyl-1-propyl<br>R4 = $CO_2H$<br>R5 = H<br>R6 = H<br>R7 = H |
| 196 | 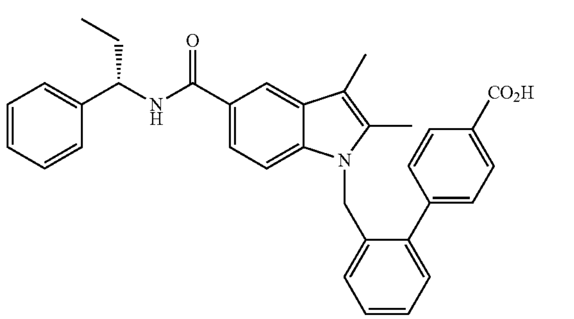 [SMILES: CC[C@H](NC(=O)c1ccc2c(c1)c(C)c(C)n2Cc1ccccc1-c1ccc(C(=O)O)cc1)c1ccccc1] | R1 = Me<br>R2 = Me<br>R3 = phenyl-1-propyl<br>R4 = $CO_2H$<br>R5 = H<br>R6 = H<br>R7 = H |

TABLE 1-continued

Specific Compounds of the Invention

| # | Structure | Substituents |
|---|---|---|
| 197 | 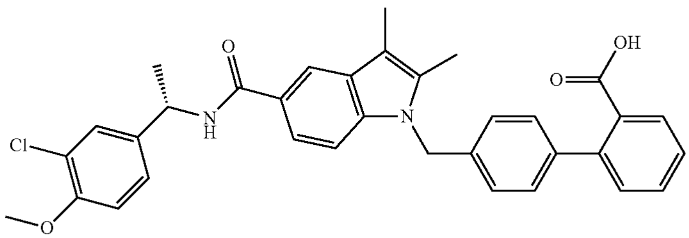 [SMILES: COc1ccc([C@H](C)NC(=O)c2ccc3c(c2)c(C)c(C)n3Cc2ccc(-c3ccccc3C(=O)O)cc2)cc1Cl] | R1 = Me<br>R2 = Me<br>R3 = 3-chloro-4-methoxy-phenyl-1-ethyl<br>R4 = CO$_2$H<br>R5 = H<br>R6 = H<br>R7 = H |
| 198 | 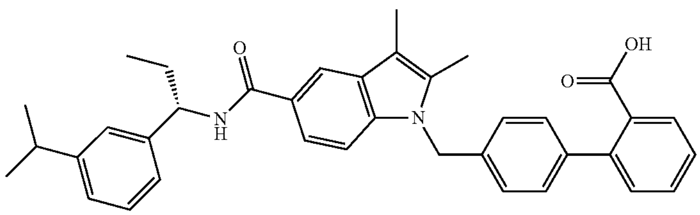 [SMILES: CC[C@H](NC(=O)c1ccc2c(c1)c(C)c(C)n2Cc1ccc(-c2ccccc2C(=O)O)cc1)c1cccc(C(C)C)c1] | R1 = Me<br>R2 = Me<br>R3 = 3-isopropylphenyl-1-ethyl<br>R4 = CO$_2$H<br>R5 = H<br>R6 = H<br>R7 = H |
| 199 | 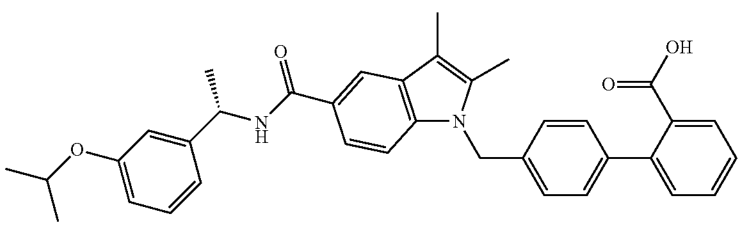 [SMILES: Cc1c(C)n(Cc2ccc(-c3ccccc3C(=O)O)cc2)c2ccc(C(=O)N[C@@H](C)c3cccc(OC(C)C)c3)cc12] | R1 = Me<br>R2 = Me<br>R3 = 3-isopropoxy-phenyl-1-ethyl<br>R4 = CO$_2$H<br>R5 = H<br>R6 = H<br>R7 = H |
| 200 | 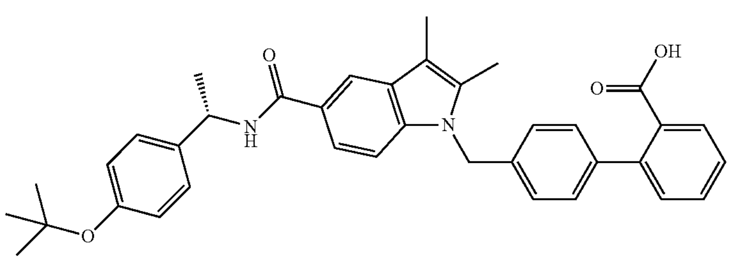 [SMILES: Cc1c(C)n(Cc2ccc(-c3ccccc3C(=O)O)cc2)c2ccc(C(=O)N[C@@H](C)c3ccc(OC(C)(C)C)cc3)cc12] | R1 = Me<br>R2 = Me<br>R3 = 4-t-butoxyphenyl-1-ethyl<br>R4 = CO$_2$H<br>R5 = H<br>R6 = H<br>R7 = H |
| 201 | 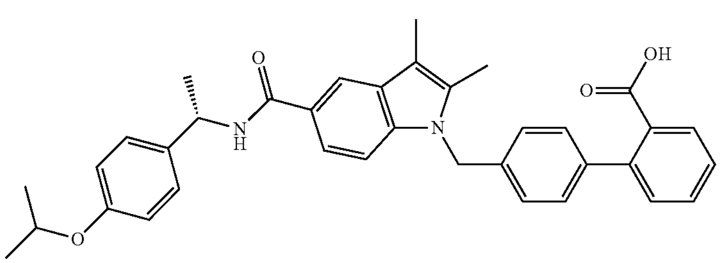 [SMILES: Cc1c(C)n(Cc2ccc(-c3ccccc3C(=O)O)cc2)c2ccc(C(=O)N[C@@H](C)c3ccc(OC(C)C)cc3)cc12] | R1 = Me<br>R2 = Me<br>R3 = 4-isopropoxy-phenyl-1-ethyl<br>R4 = CO$_2$H<br>R5 = H<br>R6 = H<br>R7 = H |

TABLE 1-continued

Specific Compounds of the Invention

| # | Structure | Substituents |
|---|---|---|
| 202 | 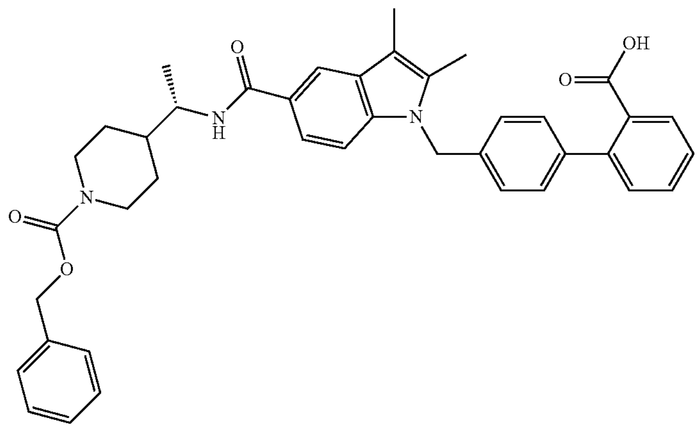 | R1 = Me<br>R2 = Me<br>R3 = N-benzyloxycarbonyl-piperdin-4-yl-1-ethyl<br>R4 = CO$_2$H<br>R5 = H<br>R6 = H<br>R7 = H |
| 203 | 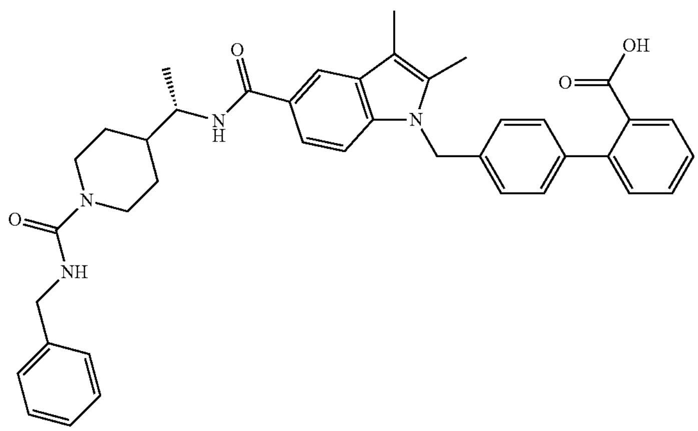 [SMILES: Cc1c(C)n(Cc2ccc(-c3ccccc3C(=O)O)cc2)c2ccc(C(=O)N[C@@H](C)C3CCN(C(=O)OCc4ccccc4)CC3)cc12] | R1 = Me<br>R2 = Me<br>R3 = N-benzylamino-carbonyl-piperdin-4-yl-1-ethyl<br>R4 = CO$_2$H<br>R5 = H<br>R6 = H<br>R7 = H |
| 204 | 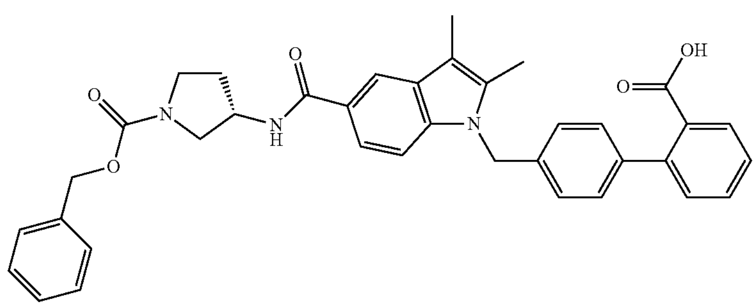 [SMILES: Cc1c(C)n(Cc2ccc(-c3ccccc3C(=O)O)cc2)c2ccc(C(=O)N[C@H]3CCN(C(=O)OCc4ccccc4)C3)cc12] | R1 = Me<br>R2 = Me<br>R3 = N-benzyloxycarbonyl-pyrrolidin-3-yl-1-ethyl<br>R4 = CO$_2$H<br>R5 = H<br>R6 = H<br>R7 = H |
| 205 | 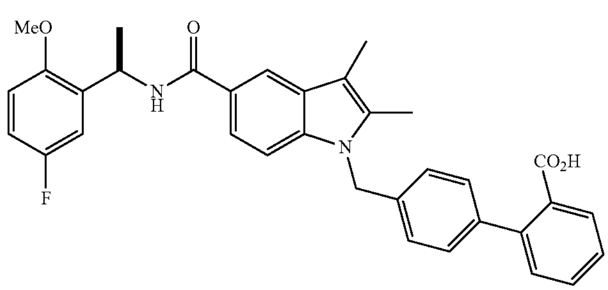 [SMILES: COc1ccc(F)cc1[C@@H](C)NC(=O)c1ccc2c(c1)c(C)c(C)n2Cc1ccc(-c2ccccc2C(=O)O)cc1] | R1 = Me<br>R2 = Me<br>R3 = 2-methoxy-5-fluorophenyl-1-ethyl<br>R4 = CO$_2$H<br>R5 = H<br>R6 = H<br>R7 = H |

TABLE 1-continued

Specific Compounds of the Invention

| # | Structure | Substituents |
|---|---|---|
| 206 | 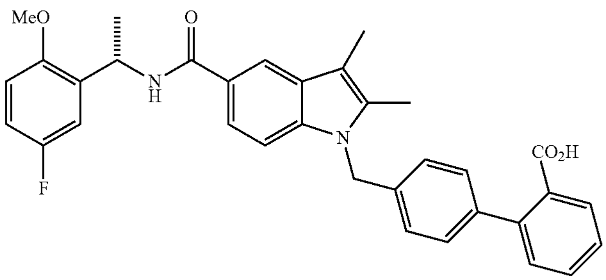 [SMILES: COc1ccc(F)cc1[C@H](C)NC(=O)c1ccc2c(c1)c(C)c(C)n2Cc1ccc(-c2ccccc2C(=O)O)cc1] | R1 = Me<br>R2 = Me<br>R3 = 2-methoxy-5-fluorophenyl-1-ethyl<br>R4 = CO$_2$H<br>R5 = H<br>R6 = H<br>R7 = H |
| 207 | 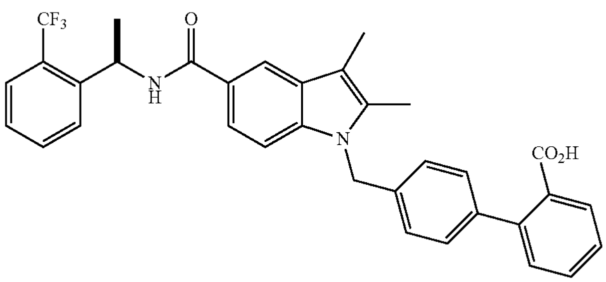 [SMILES: Cc1c(C)n(Cc2ccc(-c3ccccc3C(=O)O)cc2)c2ccc(C(=O)N[C@H](C)c3ccccc3C(F)(F)F)cc12] | R1 = Me<br>R2 = Me<br>R3 = 2-trifluoromethyl-phenyl-1-ethyl<br>R4 = CO$_2$H<br>R5 = H<br>R6 = H<br>R7 = H |
| 208 | 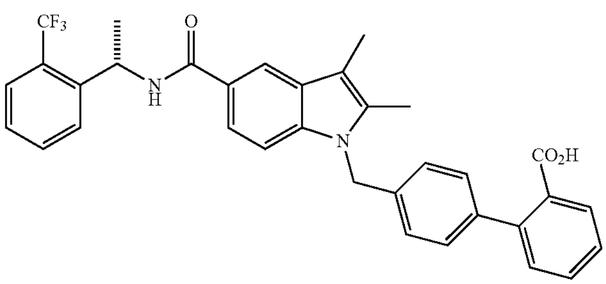 [SMILES: Cc1c(C)n(Cc2ccc(-c3ccccc3C(=O)O)cc2)c2ccc(C(=O)N[C@@H](C)c3ccccc3C(F)(F)F)cc12] | R1 = Me<br>R2 = Me<br>R3 = 2-trifluoromethyl-phenyl-1-ethyl<br>R4 = CO$_2$H<br>R5 = H<br>R6 = H<br>R7 = H |
| 209 | 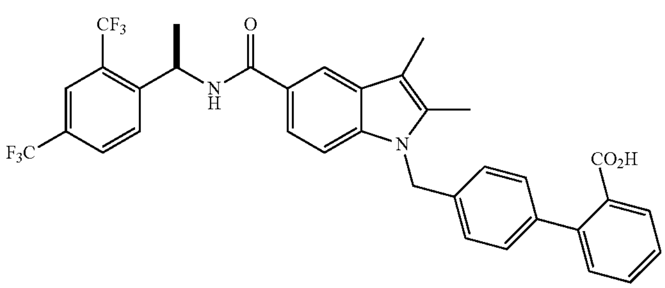 [SMILES: Cc1c(C)n(Cc2ccc(-c3ccccc3C(=O)O)cc2)c2ccc(C(=O)N[C@H](C)c3ccc(C(F)(F)F)cc3C(F)(F)F)cc12] | R1 = Me<br>R2 = Me<br>R3 = 2,4-bis(trifluoromethyl)-phenyl-1-ethyl<br>R4 = CO$_2$H<br>R5 = H<br>R6 = H<br>R7 = H |
| 210 | 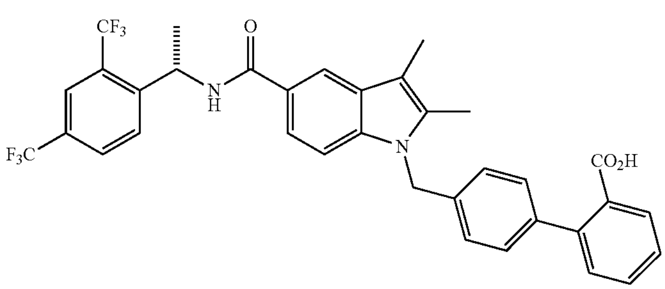 [SMILES: Cc1c(C)n(Cc2ccc(-c3ccccc3C(=O)O)cc2)c2ccc(C(=O)N[C@@H](C)c3ccc(C(F)(F)F)cc3C(F)(F)F)cc12] | R1 = Me<br>R2 = Me<br>R3 = 2,4-bis(trifluoromethyl)-phenyl-1-ethyl<br>R4 = CO$_2$H<br>R5 = H<br>R6 = H<br>R7 = H |

TABLE 1-continued

Specific Compounds of the Invention

| # | Structure | Substituents |
|---|-----------|--------------|
| 211 | 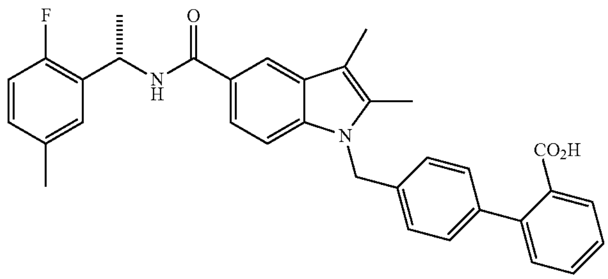 [SMILES: Cc1ccc(F)c([C@H](C)NC(=O)c2ccc3c(c2)c(C)c(C)n3Cc2ccc(-c3ccccc3C(=O)O)cc2)c1] | R1 = Me<br>R2 = Me<br>R3 = 2-fluoro-5-methylphenyl-1-ethyl<br>R4 = CO$_2$H<br>R5 = H<br>R6 = H<br>R7 = H |
| 212 | 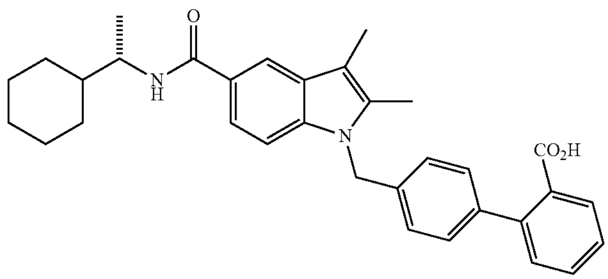 [SMILES: Cc1c(C)n(Cc2ccc(-c3ccccc3C(=O)O)cc2)c2ccc(C(=O)N[C@@H](C)C3CCCCC3)cc12] | R1 = Me<br>R2 = Me<br>R3 = cyclohexyl-1-ethyl<br>R4 = CO$_2$H<br>R5 = H<br>R6 = H<br>R7 = H |
| 213 | 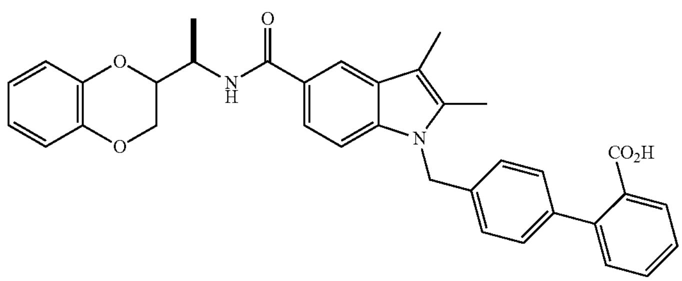 | R1 = Me<br>R2 = Me<br>R3 = benzo-1-4-dioxan-2-yl-1-ethyl<br>R4 = CO$_2$H<br>R5 = H<br>R6 = H<br>R7 = H |
| 214 | 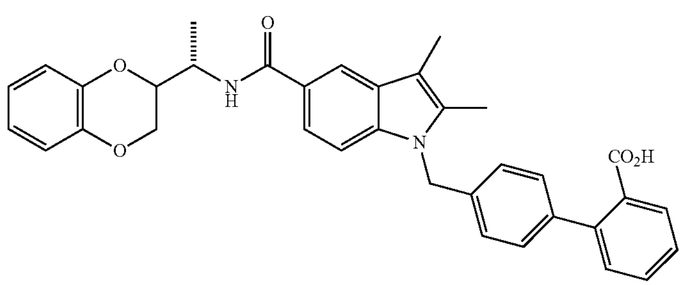 [SMILES: Cc1c(C)n(Cc2ccc(-c3ccccc3C(=O)O)cc2)c2ccc(C(=O)N[C@@H](C)C3COc4ccccc4O3)cc12] | R1 = Me<br>R2 = Me<br>R3 = 2,3-dihydrobenzo-1,4-dioxan-2-yl-1-ethyl<br>R4 = CO$_2$H<br>R5 = H<br>R6 = H<br>R7 = H |
| 215 | 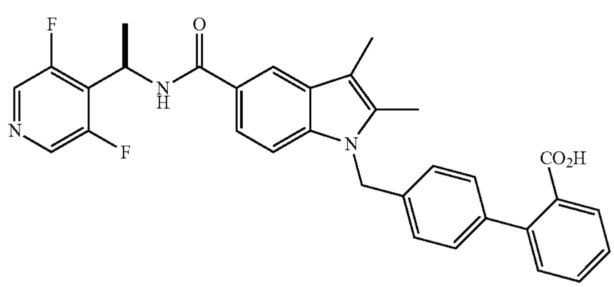 [SMILES: Cc1c(C)n(Cc2ccc(-c3ccccc3C(=O)O)cc2)c2ccc(C(=O)N[C@H](C)c3c(F)cncc3F)cc12] | R1 = Me<br>R2 = Me<br>R3 = 3,5-difluoropyrid-4-yl-1-ethyl<br>R4 = CO$_2$H<br>R5 = H<br>R6 = H<br>R7 = H |

TABLE 1-continued

Specific Compounds of the Invention

| # | Structure | Substituents |
|---|---|---|
| 216 | 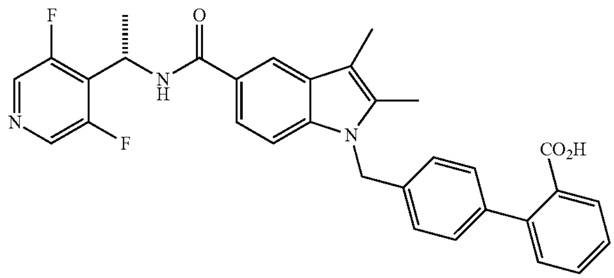 [SMILES: Cc1c(C)n(Cc2ccc(-c3ccccc3C(=O)O)cc2)c2ccc(C(=O)N[C@@H](C)c3c(F)cncc3F)cc12] | R1 = Me<br>R2 = Me<br>R3 = 3,5-difluoropyrid-4-yl-1-ethyl<br>R4 = CO$_2$H<br>R5 = H<br>R6 = H<br>R7 = H |
| 217 | 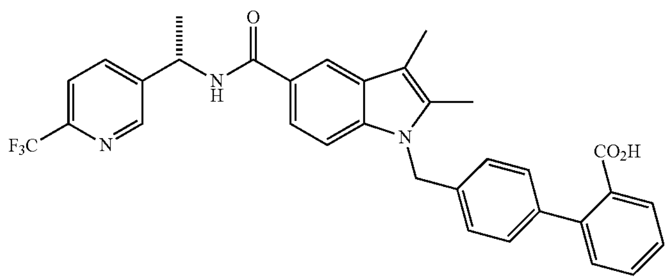 [SMILES: Cc1c(C)n(Cc2ccc(-c3ccccc3C(=O)O)cc2)c2ccc(C(=O)N[C@@H](C)c3ccc(C(F)(F)F)nc3)cc12] | R1 = Me<br>R2 = Me<br>R3 = 2-trifluoromethylpyrid-5-yl-1-ethyl<br>R4 = CO$_2$H<br>R5 = H<br>R6 = H<br>R7 = H |
| 218 | 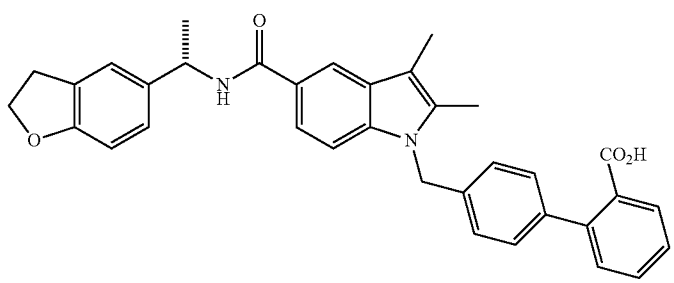 [SMILES: Cc1c(C)n(Cc2ccc(-c3ccccc3C(=O)O)cc2)c2ccc(C(=O)N[C@@H](C)c3ccc4c(c3)CCO4)cc12] | R1 = Me<br>R2 = Me<br>R3 = 2,3-dihydrobenzofur-5-yl-1-ethyl<br>R4 = CO$_2$H<br>R5 = H<br>R6 = H<br>R7 = H |
| 219 | 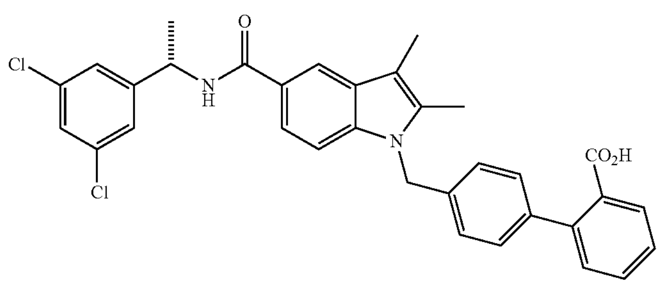 [SMILES: Cc1c(C)n(Cc2ccc(-c3ccccc3C(=O)O)cc2)c2ccc(C(=O)N[C@@H](C)c3cc(Cl)cc(Cl)c3)cc12] | R1 = Me<br>R2 = Me<br>R3 = 3,5-dichlorophenyl-1-ethyl<br>R4 = CO$_2$H<br>R5 = H<br>R6 = H<br>R7 = H |
| 220 | 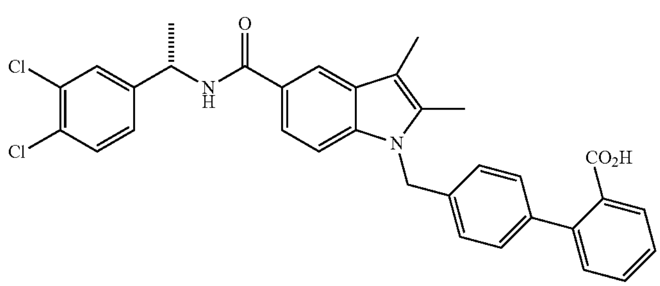 [SMILES: Cc1c(C)n(Cc2ccc(-c3ccccc3C(=O)O)cc2)c2ccc(C(=O)N[C@@H](C)c3ccc(Cl)c(Cl)c3)cc12] | R1 = Me<br>R2 = Me<br>R3 = 3,4-dichlorophenyl-1-ethyl<br>R4 = CO$_2$H<br>R5 = H<br>R6 = H<br>R7 = H |

TABLE 1-continued

Specific Compounds of the Invention

| # | Structure | Substituents |
|---|---|---|
| 221 | 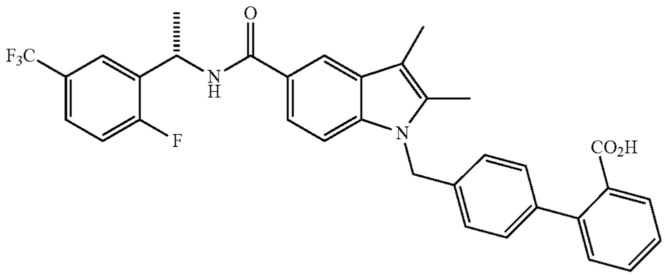 [SMILES: Cc1c(C)n(Cc2ccc(-c3ccccc3C(=O)O)cc2)c2ccc(C(=O)N[C@@H](C)c3cc(C(F)(F)F)ccc3F)cc12] | R1 = Me<br>R2 = Me<br>R3 = 2-fluoro-5-trifluoromethylphenyl-1-ethyl<br>R4 = CO$_2$H<br>R5 = H<br>R6 = H<br>R7 = H |
| 222 | 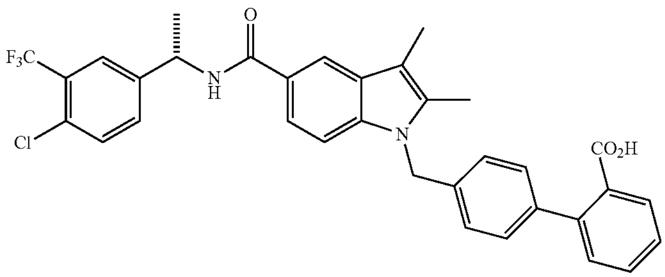 [SMILES: Cc1c(C)n(Cc2ccc(-c3ccccc3C(=O)O)cc2)c2ccc(C(=O)N[C@@H](C)c3ccc(Cl)c(C(F)(F)F)c3)cc12] | R1 = Me<br>R2 = Me<br>R3 = 4-chloro-3-trifluoromethylphenyl-1-ethyl<br>R4 = CO$_2$H<br>R5 = H<br>R6 = H<br>R7 = H |
| 223 | 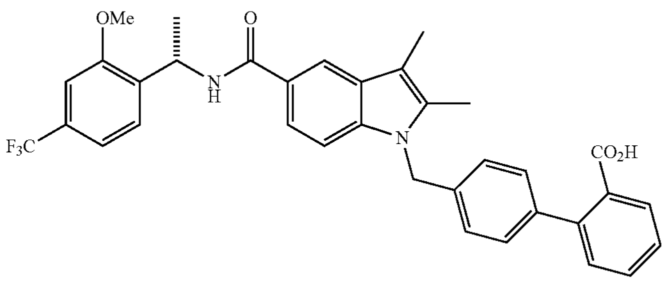 [SMILES: COc1cc(C(F)(F)F)ccc1[C@H](C)NC(=O)c1ccc2c(c1)c(C)c(C)n2Cc1ccc(-c2ccccc2C(=O)O)cc1] | R1 = Me<br>R2 = Me<br>R3 = 2-methoxy-4-trifluoromethylphenyl-1-ethyl<br>R4 = CO$_2$H<br>R5 = H<br>R6 = H<br>R7 = H |
| 224 | 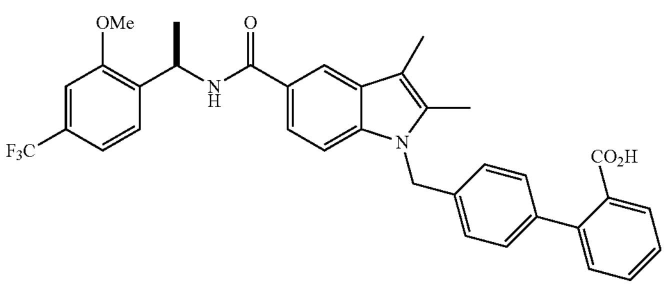 | R1 = Me<br>R2 = Me<br>R3 = 2-methoxy-4-trifluoromethylphenyl-1-ethyl<br>R4 = CO$_2$H<br>R5 = H<br>R6 = H<br>R7 = H |
| 225 | 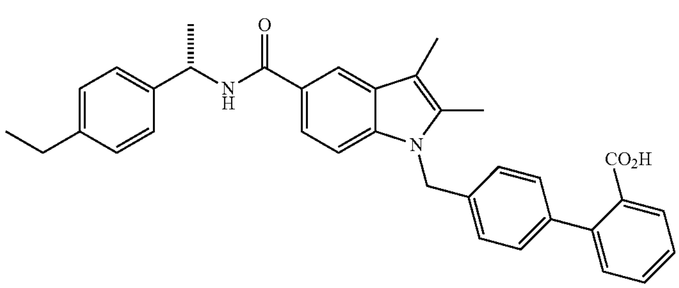 [SMILES: CCc1ccc([C@H](C)NC(=O)c2ccc3c(c2)c(C)c(C)n3Cc2ccc(-c3ccccc3C(=O)O)cc2)cc1] | R1 = Me<br>R2 = Me<br>R3 = 4-ethylphenyl-1-ethyl<br>R4 = CO$_2$H<br>R5 = H<br>R6 = H<br>R7 = H |

TABLE 1-continued

Specific Compounds of the Invention

| # | Structure | Substituents |
|---|-----------|--------------|
| 226 | 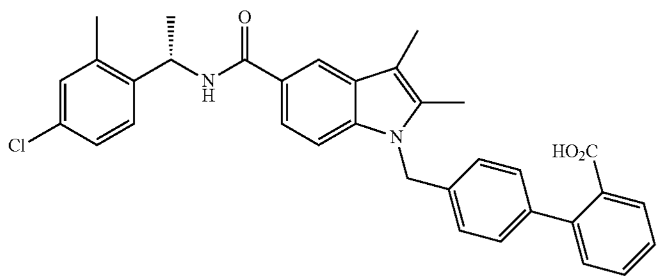 [SMILES: Cc1cc(Cl)ccc1[C@H](C)NC(=O)c1ccc2c(c1)c(C)c(C)n2Cc1ccc(-c2ccccc2C(=O)O)cc1] | R1 = Me<br>R2 = Me<br>R3 = 2-methyl-4-chlorophenyl-1-ethyl<br>R4 = CO$_2$H<br>R5 = H<br>R6 = H<br>R7 = H |
| 227 | 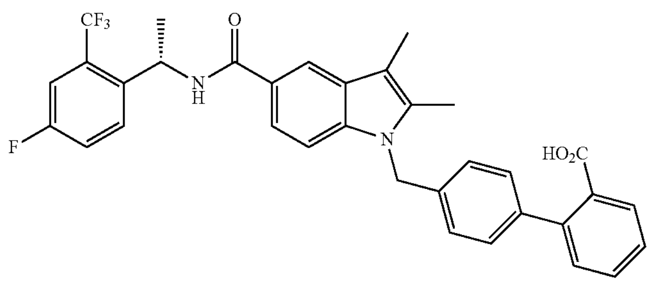 [SMILES: Cc1c(C)n(Cc2ccc(-c3ccccc3C(=O)O)cc2)c2ccc(C(=O)N[C@@H](C)c3ccc(F)cc3C(F)(F)F)cc12] | R1 = Me<br>R2 = Me<br>R3 = 2-trifluoromethyl-4-fluorophenyl-1-ethyl<br>R4 = CO$_2$H<br>R5 = H<br>R6 = H<br>R7 = H |
| 228 | 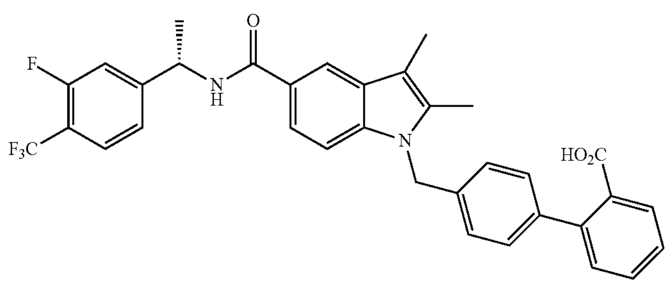 [SMILES: Cc1c(C)n(Cc2ccc(-c3ccccc3C(=O)O)cc2)c2ccc(C(=O)N[C@@H](C)c3ccc(C(F)(F)F)c(F)c3)cc12] | R1 = Me<br>R2 = Me<br>R3 = 3-fluoro-4-trifluoromethylphenyl-1-ethyl<br>R4 = CO$_2$H<br>R5 = H<br>R6 = H<br>R7 = H |
| 229 | 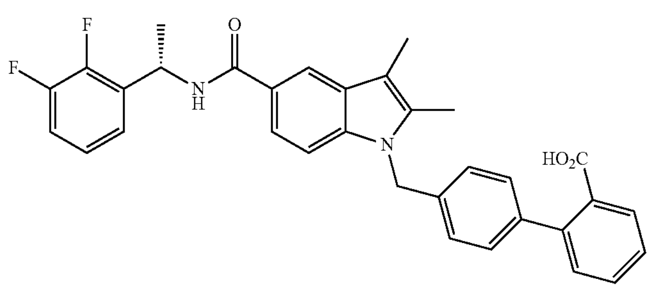 | R1 = Me<br>R2 = Me<br>R3 = 2,3-difluorophenyl-1-ethyl<br>R4 = CO$_2$H<br>R5 = H<br>R6 = H<br>R7 = H |
| 230 | 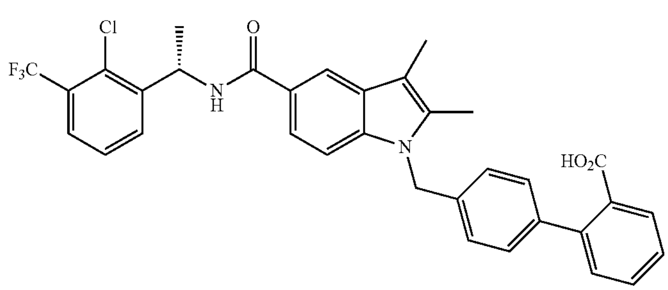 [SMILES: Cc1c(C)n(Cc2ccc(-c3ccccc3C(=O)O)cc2)c2ccc(C(=O)N[C@@H](C)c3cccc(C(F)(F)F)c3Cl)cc12] | R1 = Me<br>R2 = Me<br>R3 = 2-chloro-3-trifluoromethylphenyl-1-ethyl<br>R4 = CO$_2$H<br>R5 = H<br>R6 = H<br>R7 = H |

TABLE 1-continued

Specific Compounds of the Invention

| # | Structure | Substituents |
|---|---|---|
| 231 | 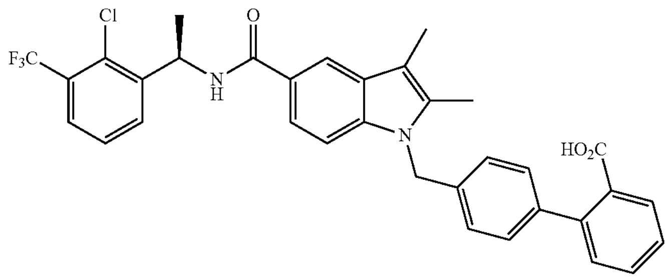 [SMILES: Cc1c(C)n(Cc2ccc(-c3ccccc3C(=O)O)cc2)c2ccc(C(=O)N[C@H](C)c3cccc(C(F)(F)F)c3Cl)cc12] | R1 = Me<br>R2 = Me<br>R3 = 2-chloro-3-trifluoromethylphenyl-1-ethyl<br>R4 = CO₂H<br>R5 = H<br>R6 = H<br>R7 = H |
| 232 | 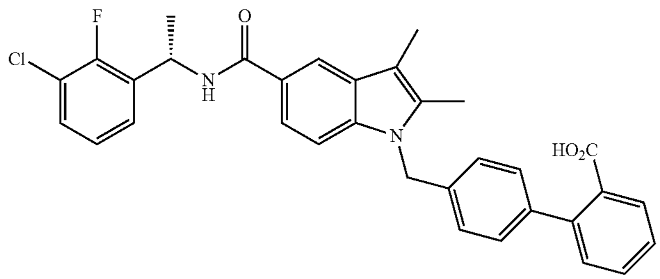 [SMILES: Cc1c(C)n(Cc2ccc(-c3ccccc3C(=O)O)cc2)c2ccc(C(=O)N[C@@H](C)c3cccc(Cl)c3F)cc12] | R1 = Me<br>R2 = Me<br>R3 = 2-fluoro-3-chlorophenyl-1-ethyl<br>R4 = CO₂H<br>R5 = H<br>R6 = H<br>R7 = H |
| 233 | 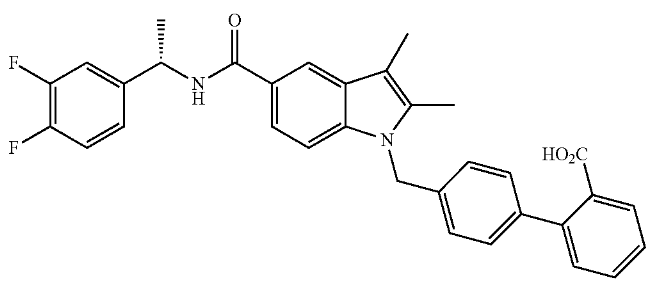 [SMILES: Cc1c(C)n(Cc2ccc(-c3ccccc3C(=O)O)cc2)c2ccc(C(=O)N[C@@H](C)c3ccc(F)c(F)c3)cc12] | R1 = Me<br>R2 = Me<br>R3 = 3,4-difluorophenyl-1-ethyl<br>R4 = CO₂H<br>R5 = H<br>R6 = H<br>R7 = H |
| 234 | 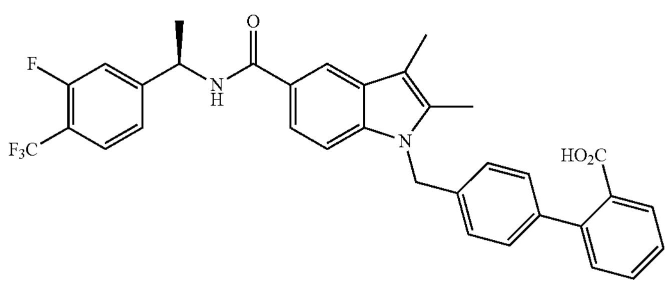 [SMILES: Cc1c(C)n(Cc2ccc(-c3ccccc3C(=O)O)cc2)c2ccc(C(=O)N[C@H](C)c3ccc(C(F)(F)F)c(F)c3)cc12] | R1 = Me<br>R2 = Me<br>R3 = 3-fluoro-4-trifluoromethylphenyl-1-ethyl<br>R4 = CO₂H<br>R5 = H<br>R6 = H<br>R7 = H |
| 235 | 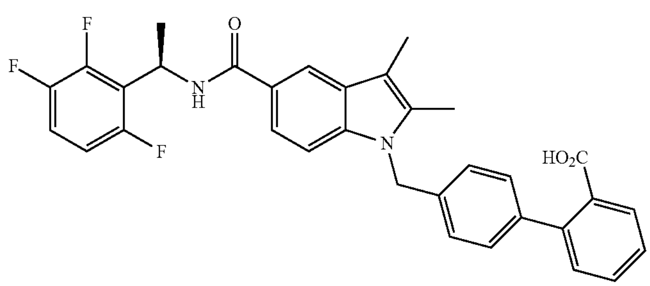 [SMILES: Cc1c(C)n(Cc2ccc(-c3ccccc3C(=O)O)cc2)c2ccc(C(=O)N[C@H](C)c3c(F)ccc(F)c3F)cc12] | R1 = Me<br>R2 = Me<br>R3 = 2,3,6-trifluorophenyl-1-ethyl<br>R4 = CO₂H<br>R5 = H<br>R6 = H<br>R7 = H |

TABLE 1-continued

Specific Compounds of the Invention

| # | Structure | Substituents |
|---|---|---|
| 236 | 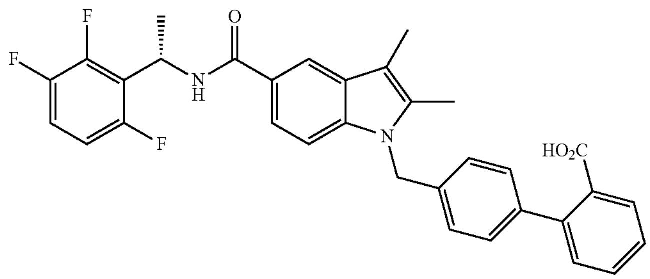 [SMILES: Cc1c(C)n(Cc2ccc(-c3ccccc3C(=O)O)cc2)c2ccc(C(=O)N[C@@H](C)c3c(F)ccc(F)c3F)cc12] | R1 = Me<br>R2 = Me<br>R3 = 2,3,6-trifluorophenyl-1-ethyl<br>R4 = CO$_2$H<br>R5 = H<br>R6 = H<br>R7 = H |
| 237 | 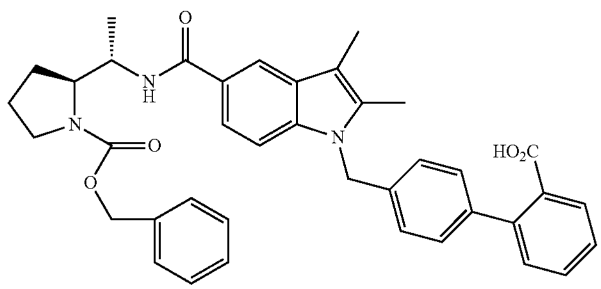 [SMILES: Cc1c(C)n(Cc2ccc(-c3ccccc3C(=O)O)cc2)c2ccc(C(=O)N[C@@H](C)[C@@H]3CCCN3C(=O)OCc3ccccc3)cc12] | R1 = Me<br>R2 = Me<br>R3 = N-benzyloxycarbonyl-pyrrolidin-2-yl-1-ethyl<br>R4 = CO$_2$H<br>R5 = H<br>R6 = H<br>R7 = H |
| 238 | 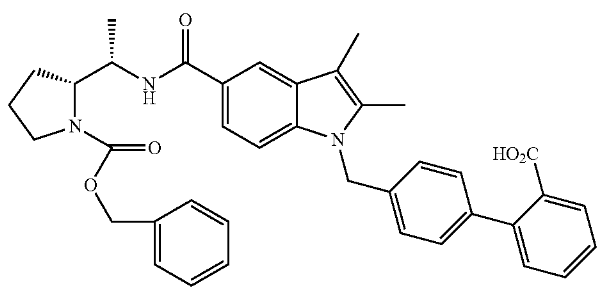 [SMILES: Cc1c(C)n(Cc2ccc(-c3ccccc3C(=O)O)cc2)c2ccc(C(=O)N[C@@H](C)[C@H]3CCCN3C(=O)OCc3ccccc3)cc12] | R1 = Me<br>R2 = Me<br>R3 = N-benzyloxycarbonyl-pyrrolidin-2-yl-1-ethyl<br>R4 = CO$_2$H<br>R5 = H<br>R6 = H<br>R7 = H |
| 239 | 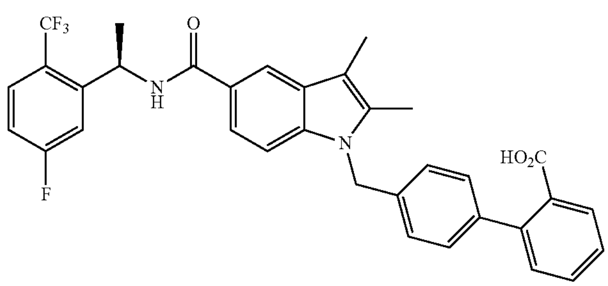 [SMILES: Cc1c(C)n(Cc2ccc(-c3ccccc3C(=O)O)cc2)c2ccc(C(=O)N[C@H](C)c3cc(F)ccc3C(F)(F)F)cc12] | R1 = Me<br>R2 = Me<br>R3 = 2-trifluoromethyl-5-fluorophenyl-1-ethyl<br>R4 = CO$_2$H<br>R5 = H<br>R6 = H<br>R7 = H |
| 240 | 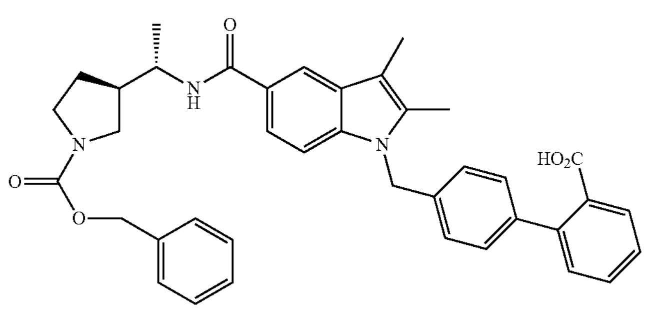 [SMILES: Cc1c(C)n(Cc2ccc(-c3ccccc3C(=O)O)cc2)c2ccc(C(=O)N[C@@H](C)[C@@H]3CCN(C(=O)OCc4ccccc4)C3)cc12] | R1 = Me<br>R2 = Me<br>R3 = N-benzyloxycarbonyl-pyrrolidin-3-yl-1-ethyl<br>R4 = CO$_2$H<br>R5 = H<br>R6 = H<br>R7 = H |

TABLE 1-continued

Specific Compounds of the Invention

| # | Structure | Substituents |
|---|---|---|
| 241 | 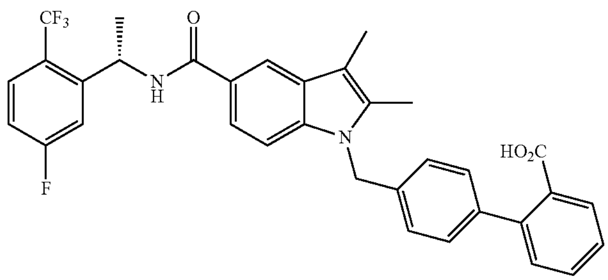 [SMILES: Cc1c(C)n(Cc2ccc(-c3ccccc3C(=O)O)cc2)c2ccc(C(=O)N[C@@H](C)c3cc(F)ccc3C(F)(F)F)cc12] | R1 = Me<br>R2 = Me<br>R3 = 2-trifluoromethyl-5-fluorophenyl-1-ethyl<br>R4 = CO$_2$H<br>R5 = H<br>R6 = H<br>R7 = H |
| 242 | 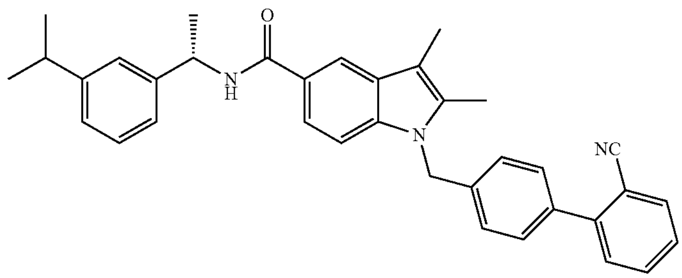 [SMILES: Cc1c(C)n(Cc2ccc(-c3ccccc3C#N)cc2)c2ccc(C(=O)N[C@@H](C)c3cccc(C(C)C)c3)cc12] | R1 = Me<br>R2 = Me<br>R3 = 3-isopropylphenyl-1-ethyl<br>R4 = CN<br>R5 = H<br>R6 = H<br>R7 = H |
| 243 | 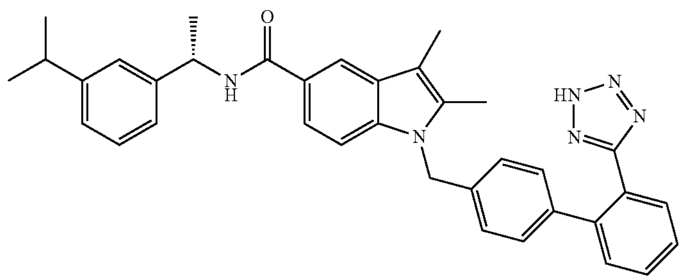 [SMILES: Cc1c(C)n(Cc2ccc(-c3ccccc3-c3nn[nH]n3)cc2)c2ccc(C(=O)N[C@@H](C)c3cccc(C(C)C)c3)cc12] | R1 = Me<br>R2 = Me<br>R3 = 3-isopropylphenyl-1-ethyl<br>R4 = C-substituted tetrazole<br>R5 = H<br>R6 = H<br>R7 = H |
| 244 | 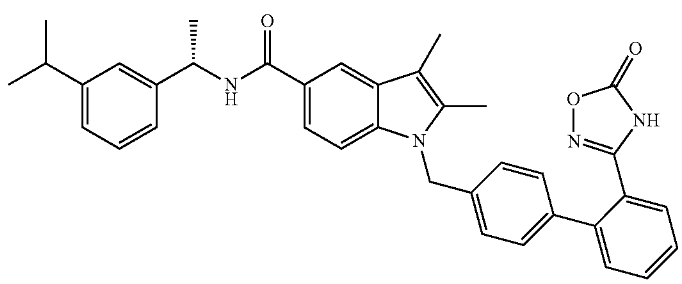 [SMILES: Cc1c(C)n(Cc2ccc(-c3ccccc3-c3noc(=O)[nH]3)cc2)c2ccc(C(=O)N[C@@H](C)c3cccc(C(C)C)c3)cc12] | R1 = Me<br>R2 = Me<br>R3 = 3-isopropylphenyl-1-ethyl<br>R4 = C-substituted oxadiazolone<br>R5 = H<br>R6 = H<br>R7 = H |
| 245 | 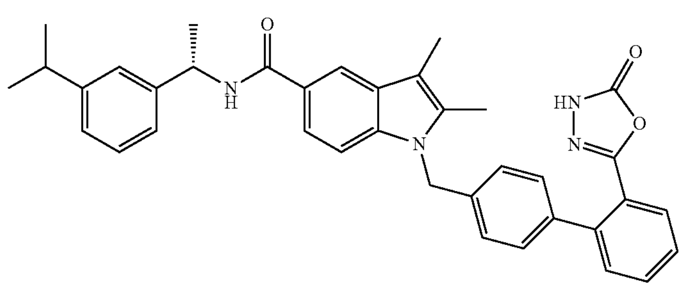 [SMILES: Cc1c(C)n(Cc2ccc(-c3ccccc3-c3n[nH]c(=O)o3)cc2)c2ccc(C(=O)N[C@@H](C)c3cccc(C(C)C)c3)cc12] | R1 = Me<br>R2 = Me<br>R3 = 3-isopropylphenyl-1-ethyl<br>R4 = C-substituted oxadiazolone<br>R5 = H<br>R6 = H<br>R7 = H |

TABLE 1-continued

Specific Compounds of the Invention

| # | Structure | Substituents |
|---|---|---|
| 246 | 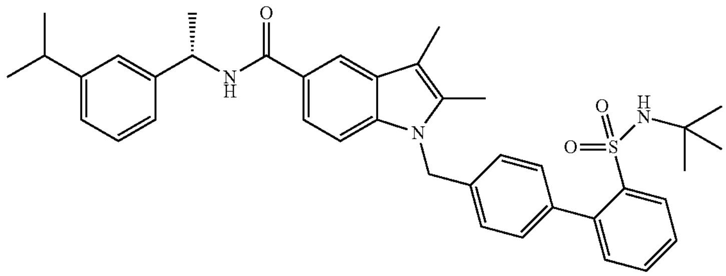 [SMILES: Cc1c(C)n(Cc2ccc(-c3ccccc3S(=O)(=O)NC(C)(C)C)cc2)c2ccc(C(=O)N[C@@H](C)c3cccc(C(C)C)c3)cc12] | R1 = Me<br>R2 = Me<br>R3 = 3-isopropylphenyl-1-ethyl<br>R4 = t-butylaminosulfonyl<br>R5 = H<br>R6 = H<br>R7 = H |
| 247 | 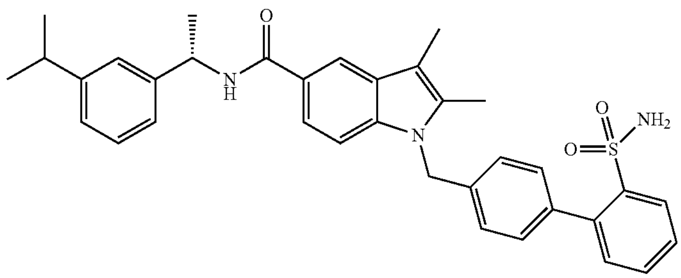 [SMILES: Cc1c(C)n(Cc2ccc(-c3ccccc3S(N)(=O)=O)cc2)c2ccc(C(=O)N[C@@H](C)c3cccc(C(C)C)c3)cc12] | R1 = Me<br>R2 = Me<br>R3 = 3-isopropylphenyl-1-ethyl<br>R4 = aminosulfonyl<br>R5 = H<br>R6 = H<br>R7 = H |
| 248 | 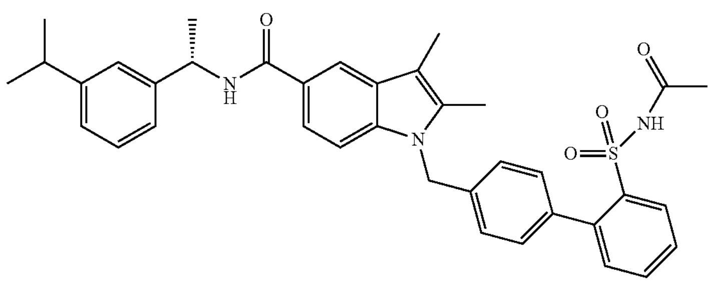 [SMILES: CC(=O)NS(=O)(=O)c1ccccc1-c1ccc(Cn2c(C)c(C)c3cc(C(=O)N[C@@H](C)c4cccc(C(C)C)c4)ccc32)cc1] | R1 = Me<br>R2 = Me<br>R3 = 3-isopropylphenyl-1-ethyl<br>R4 = acetamidosulfonyl<br>R5 = H<br>R6 = H<br>R7 = H |
| 249 | 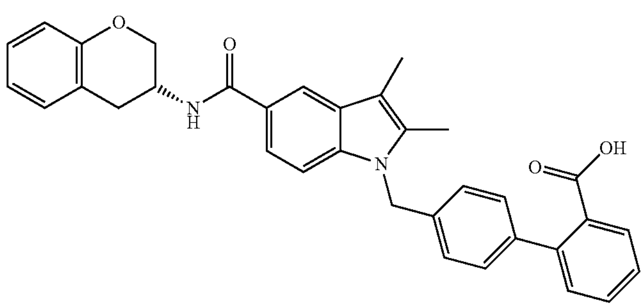 | R1 = Me<br>R2 = Me<br>R3 = 2,3-dihydrobenzo-1,4-pyran-3-yl<br>R4 = $CO_2H$<br>R5 = H<br>R6 = H<br>R7 = H |
| 250 | 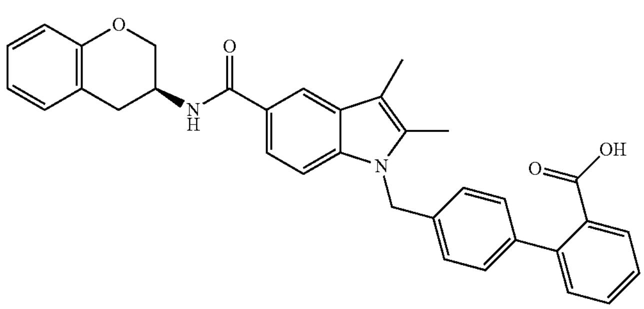 [SMILES: Cc1c(C)n(Cc2ccc(-c3ccccc3C(=O)O)cc2)c2ccc(C(=O)N[C@@H]3COc4ccccc4C3)cc12] | R1 = Me<br>R2 = Me<br>R3 = 2,3-dihydrobenzo-1,4-pyran-3-yl<br>R4 = $CO_2H$<br>R5 = H<br>R6 = H<br>R7 = H |

TABLE 1-continued

Specific Compounds of the Invention

| # | Structure | Substituents |
|---|---|---|
| 251 | 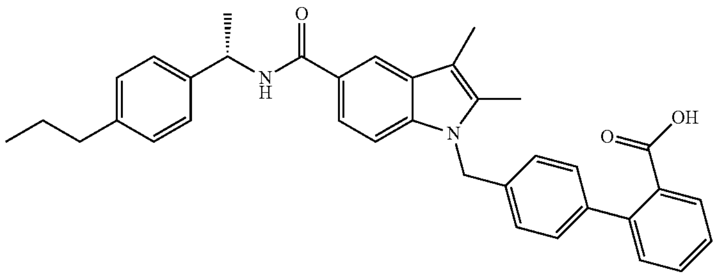 [SMILES: CCCc1ccc([C@H](C)NC(=O)c2ccc3c(c2)c(C)c(C)n3Cc2ccc(-c3ccccc3C(=O)O)cc2)cc1] | R1 = Me<br>R2 = Me<br>R3 = 4-propylphenyl-1-ethyl<br>R4 = CO$_2$H<br>R5 = H<br>R6 = H<br>R7 = H |
| 252 | 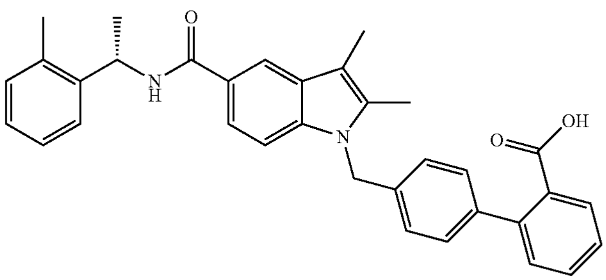 [SMILES: Cc1ccccc1[C@H](C)NC(=O)c1ccc2c(c1)c(C)c(C)n2Cc1ccc(-c2ccccc2C(=O)O)cc1] | R1 = Me<br>R2 = Me<br>R3 = 2-methylphenyl-1-ethyl<br>R4 = CO$_2$H<br>R5 = H<br>R6 = H<br>R7 = H |
| 253 | 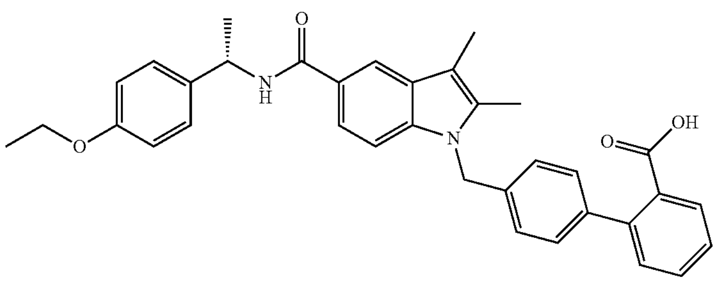 [SMILES: CCOc1ccc([C@H](C)NC(=O)c2ccc3c(c2)c(C)c(C)n3Cc2ccc(-c3ccccc3C(=O)O)cc2)cc1] | R1 = Me<br>R2 = Me<br>R3 = 4-ethoxyphenyl-1-ethyl<br>R4 = CO$_2$H<br>R5 = H<br>R6 = H<br>R7 = H |
| 254 | 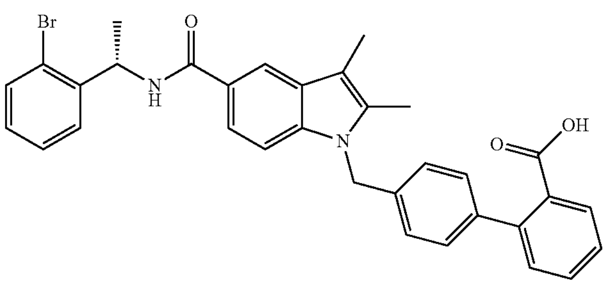 [SMILES: Cc1c(C)n(Cc2ccc(-c3ccccc3C(=O)O)cc2)c2ccc(C(=O)N[C@@H](C)c3ccccc3Br)cc12] | R1 = Me<br>R2 = Me<br>R3 = 2-bromophenyl-1-ethyl<br>R4 = CO$_2$H<br>R5 = H<br>R6 = H<br>R7 = H |
| 255 | 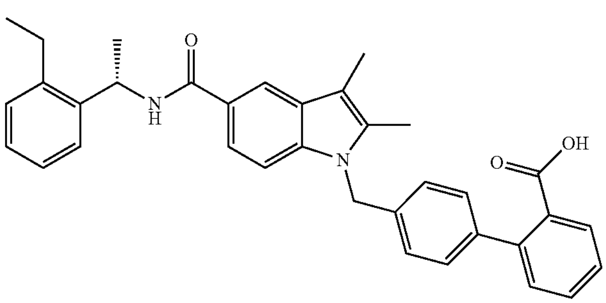 [SMILES: CCc1ccccc1[C@H](C)NC(=O)c1ccc2c(c1)c(C)c(C)n2Cc1ccc(-c2ccccc2C(=O)O)cc1] | R1 = Me<br>R2 = Me<br>R3 = 2-ethylphenyl-1-ethyl<br>R4 = CO$_2$H<br>R5 = H<br>R6 = H<br>R7 = H |

TABLE 1-continued

Specific Compounds of the Invention

| # | Structure | Substituents |
|---|---|---|
| 256 | 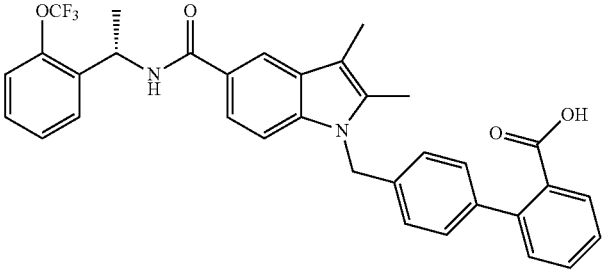 [SMILES: Cc1c(C)n(Cc2ccc(-c3ccccc3C(=O)O)cc2)c2ccc(C(=O)N[C@@H](C)c3ccccc3OC(F)(F)F)cc12] | R1 = Me<br>R2 = Me<br>R3 = 2-trifluoromethoxy-phenyl-1-ethyl<br>R4 = CO$_2$H<br>R5 = H<br>R6 = H<br>R7 = H |
| 257 | 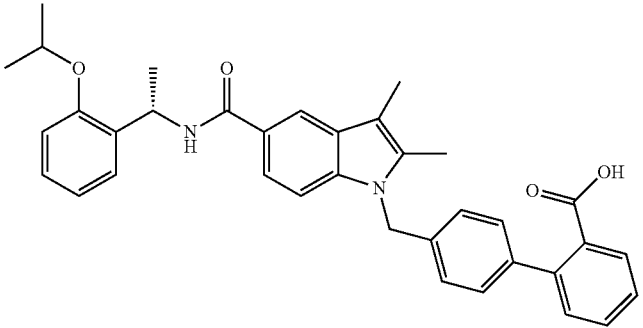 [SMILES: Cc1c(C)n(Cc2ccc(-c3ccccc3C(=O)O)cc2)c2ccc(C(=O)N[C@@H](C)c3ccccc3OC(C)C)cc12] | R1 = Me<br>R2 = Me<br>R3 = 2-isopropoxy-phenyl-1-ethyl<br>R4 = CO$_2$H<br>R5 = H<br>R6 = H<br>R7 = H |
| 258 | 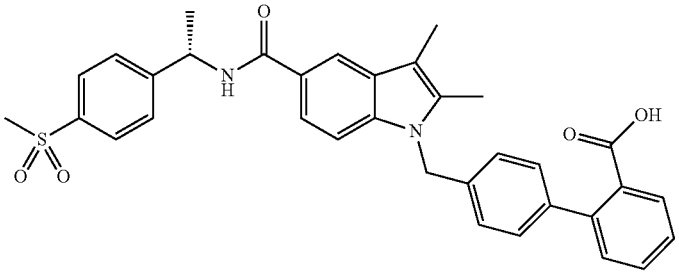 [SMILES: Cc1c(C)n(Cc2ccc(-c3ccccc3C(=O)O)cc2)c2ccc(C(=O)N[C@@H](C)c3ccc(S(C)(=O)=O)cc3)cc12] | R1 = Me<br>R2 = Me<br>R3 = 4-methansulfonyl-phenyl-1-ethyl<br>R4 = CO$_2$H<br>R5 = H<br>R6 = H<br>R7 = H |
| 259 | 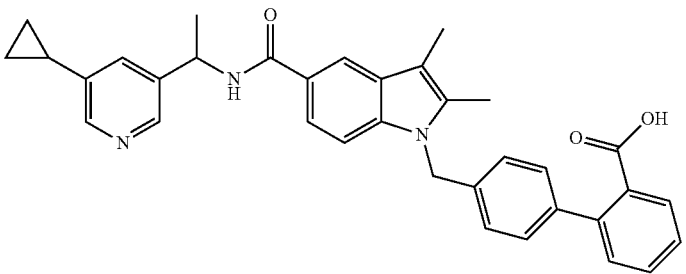 | R1 = Me<br>R2 = Me<br>R3 = 3-cyclopropylpyridin-5-yl-1-ethyl<br>R4 = CO$_2$H<br>R5 = H<br>R6 = H<br>R7 = H |
| 260 | 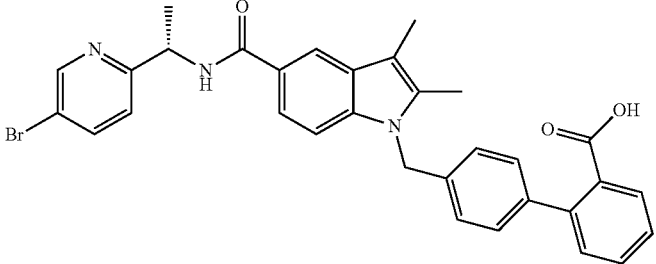 | R1 = Me<br>R2 = Me<br>R3 = 5-bromopyridin-2-yl-1-ethyl<br>R4 = CO$_2$H<br>R5 = H<br>R6 = H<br>R7 = H |

TABLE 1-continued

Specific Compounds of the Invention

| # | Structure | Substituents |
|---|-----------|--------------|
| 261 | 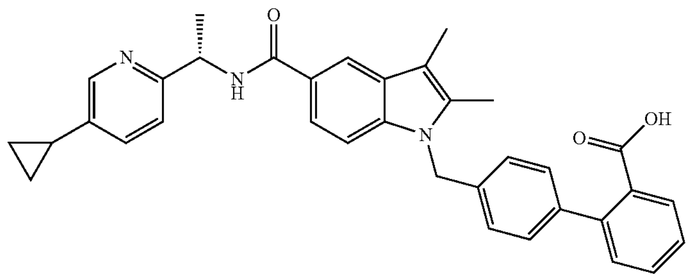 [SMILES: Cc1c(C)n(Cc2ccc(-c3ccccc3C(=O)O)cc2)c2ccc(C(=O)N[C@@H](C)c3ccc(C4CC4)cn3)cc12] | R1 = Me<br>R2 = Me<br>R3 = 5-cyclopropylpyridin-2-yl-1-ethyl<br>R4 = CO₂H<br>R5 = H<br>R6 = H<br>R7 = H |
| 262 | 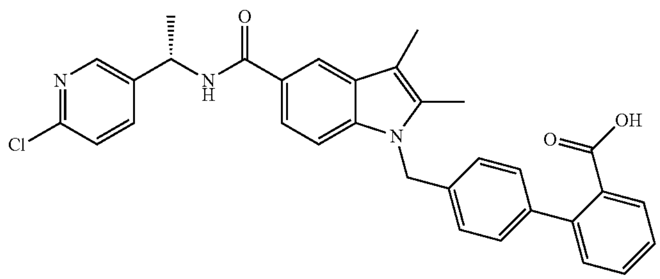 [SMILES: Cc1c(C)n(Cc2ccc(-c3ccccc3C(=O)O)cc2)c2ccc(C(=O)N[C@@H](C)c3ccc(Cl)nc3)cc12] | R1 = Me<br>R2 = Me<br>R3 = 2-chloropyridin-5-yl-1-ethyl<br>R4 = CO₂H<br>R5 = H<br>R6 = H<br>R7 = H |
| 263 | 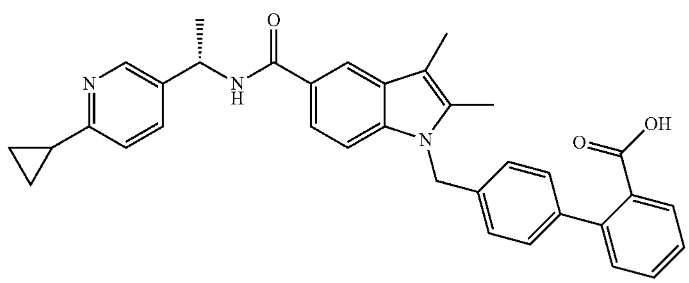 [SMILES: Cc1c(C)n(Cc2ccc(-c3ccccc3C(=O)O)cc2)c2ccc(C(=O)N[C@@H](C)c3ccc(C4CC4)nc3)cc12] | R1 = Me<br>R2 = Me<br>R3 = 2-cyclopropylpyridin-5-yl-1-ethyl<br>R4 = CO₂H<br>R5 = H<br>R6 = H<br>R7 = H |
| 264 | 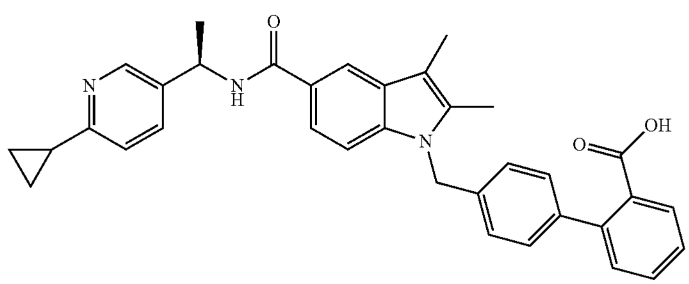 [SMILES: Cc1c(C)n(Cc2ccc(-c3ccccc3C(=O)O)cc2)c2ccc(C(=O)N[C@H](C)c3ccc(C4CC4)nc3)cc12] | R1 = Me<br>R2 = Me<br>R3 = 2-cyclopropylpyridin-5-yl-1-ethyl<br>R4 = CO₂H<br>R5 = H<br>R6 = H<br>R7 = H |
| 265 | 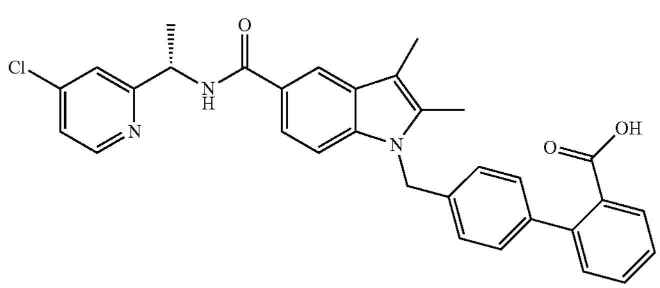 | R1 = Me<br>R2 = Me<br>R3 = 4-chloropyridin-2-yl-1-ethyl<br>R4 = CO₂H<br>R5 = H<br>R6 = H<br>R7 = H |

TABLE 1-continued

Specific Compounds of the Invention

| # | Structure | Substituents |
|---|---|---|
| 266 | 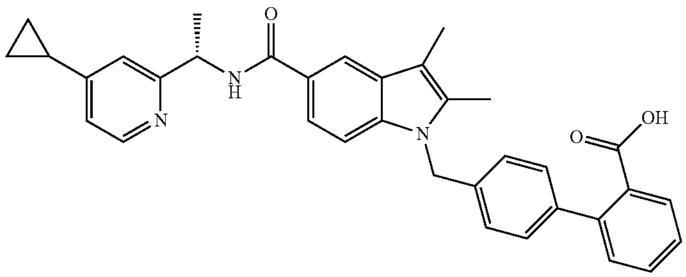 | R1 = Me<br>R2 = Me<br>R3 = 4-cyclopropylpyridin-2-yl-1-ethyl<br>R4 = CO₂H<br>R5 = H<br>R6 = H<br>R7 = H |
| 267 | 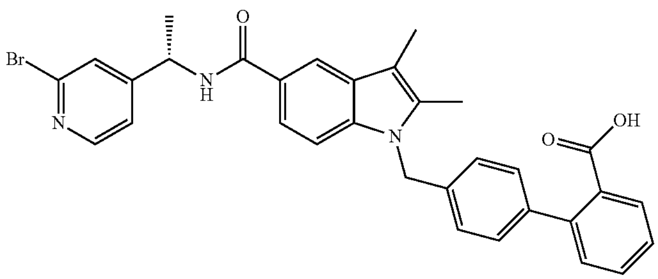 [SMILES: Cc1c(C)n(Cc2ccc(-c3ccccc3C(=O)O)cc2)c2ccc(C(=O)N[C@@H](C)c3ccnc(Br)c3)cc12] | R1 = Me<br>R2 = Me<br>R3 = 2-bromopyridin-4-yl-1-ethyl<br>R4 = CO₂H<br>R5 = H<br>R6 = H<br>R7 = H |
| 268 | 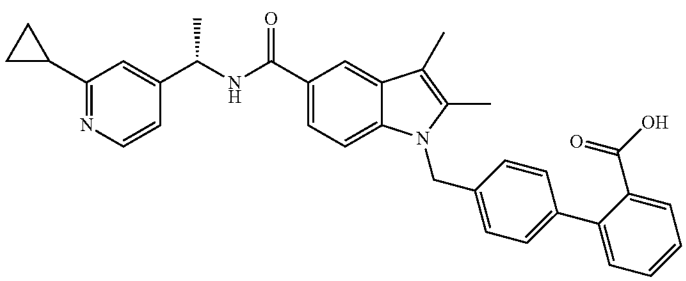 [SMILES: Cc1c(C)n(Cc2ccc(-c3ccccc3C(=O)O)cc2)c2ccc(C(=O)N[C@@H](C)c3ccnc(C4CC4)c3)cc12] | R1 = Me<br>R2 = Me<br>R3 = 2-cyclopropylpyridin-4-yl-1-ethyl<br>R4 = CO₂H<br>R5 = H<br>R6 = H<br>R7 = H |
| 269 | 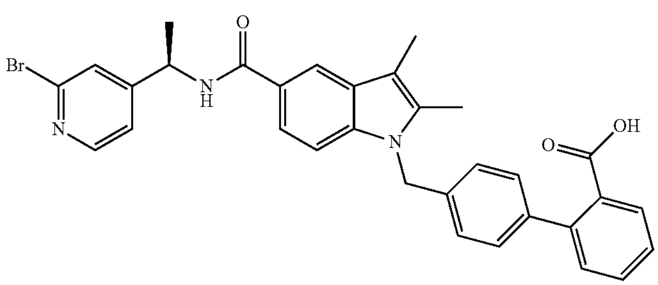 [SMILES: Cc1c(C)n(Cc2ccc(-c3ccccc3C(=O)O)cc2)c2ccc(C(=O)N[C@H](C)c3ccnc(Br)c3)cc12] | R1 = Me<br>R2 = Me<br>R3 = 2-bromopyridin-4-yl-1-ethyl<br>R4 = CO₂H<br>R5 = H<br>R6 = H<br>R7 = H |
| 270 | 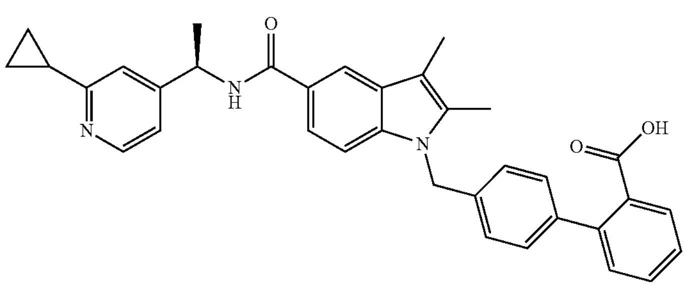 [SMILES: Cc1c(C)n(Cc2ccc(-c3ccccc3C(=O)O)cc2)c2ccc(C(=O)N[C@H](C)c3ccnc(C4CC4)c3)cc12] | R1 = Me<br>R2 = Me<br>R3 = 2-cyclopropylpyridin-4-yl-1-ethyl<br>R4 = CO₂H<br>R5 = H<br>R6 = H<br>R7 = H |

TABLE 1-continued

Specific Compounds of the Invention

| # | Structure | Substituents |
|---|---|---|
| 271 | 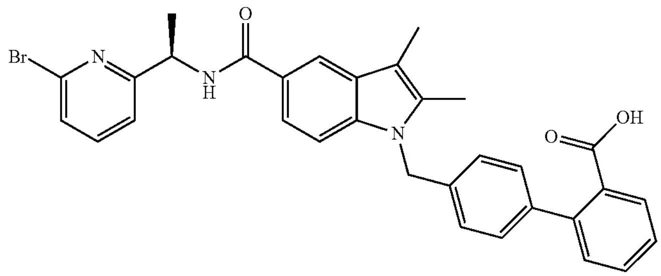 [SMILES: Cc1c(C)n(Cc2ccc(-c3ccccc3C(=O)O)cc2)c2ccc(C(=O)N[C@H](C)c3cccc(Br)n3)cc12] | R1 = Me<br>R2 = Me<br>R3 = 2-bromopyridin-6-yl-1-ethyl<br>R4 = CO$_2$H<br>R5 = H<br>R6 = H<br>R7 = H |
| 272 | 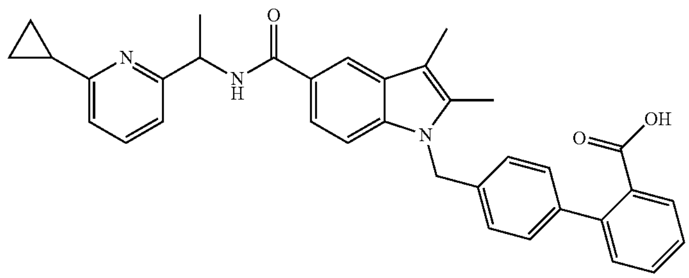 | R1 = Me<br>R2 = Me<br>R3 = 2-cyclopropylpyridin-6-yl-1-ethyl<br>R4 = CO$_2$H<br>R5 = H<br>R6 = H<br>R7 = H |
| 273 | 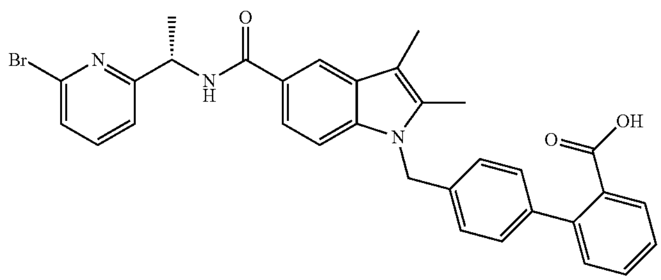 [SMILES: Cc1c(C)n(Cc2ccc(-c3ccccc3C(=O)O)cc2)c2ccc(C(=O)N[C@@H](C)c3cccc(Br)n3)cc12] | R1 = Me<br>R2 = Me<br>R3 = 2-bromopyridin-6-yl-1-ethyl<br>R4 = CO$_2$H<br>R5 = H<br>R6 = H<br>R7 = H |
| 274 | 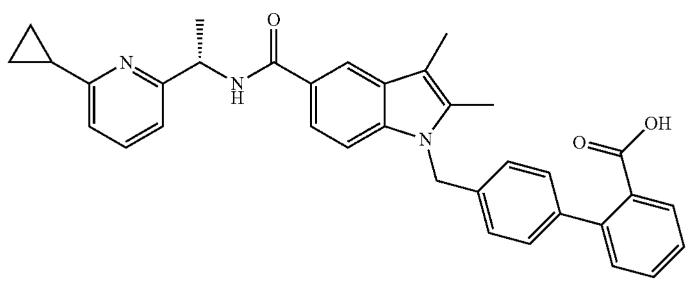 [SMILES: Cc1c(C)n(Cc2ccc(-c3ccccc3C(=O)O)cc2)c2ccc(C(=O)N[C@@H](C)c3cccc(C4CC4)n3)cc12] | R1 = Me<br>R2 = Me<br>R3 = 2-cyclopropylpyridin-6-yl-1-ethyl<br>R4 = CO$_2$H<br>R5 = H<br>R6 = H<br>R7 = H |
| 275 | 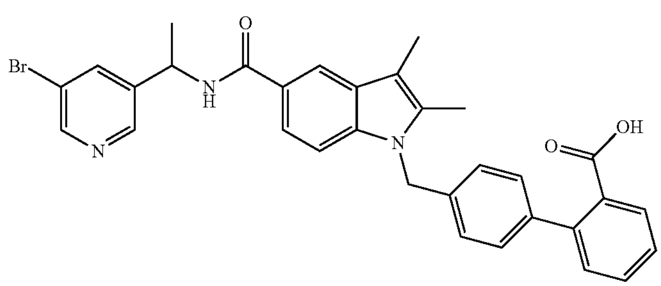 [SMILES: Cc1c(C)n(Cc2ccc(-c3ccccc3C(=O)O)cc2)c2ccc(C(=O)NC(C)c3cncc(Br)c3)cc12] | R1 = Me<br>R2 = Me<br>R3 = 3-bromopyridin-5-yl-1-ethyl<br>R4 = CO$_2$H<br>R5 = H<br>R6 = H<br>R7 = H |

TABLE 1-continued

Specific Compounds of the Invention

| # | Structure | Substituents |
|---|---|---|
| 276 | 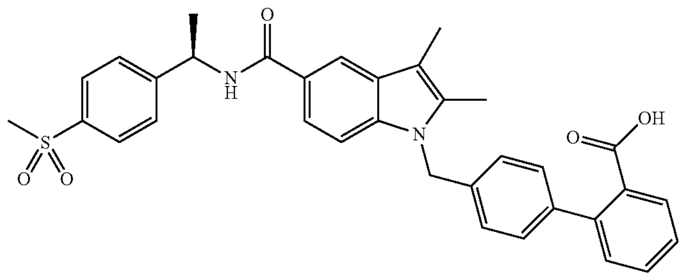 [SMILES: Cc1c(C)n(Cc2ccc(-c3ccccc3C(=O)O)cc2)c2ccc(C(=O)N[C@H](C)c3ccc(S(C)(=O)=O)cc3)cc12] | R1 = Me<br>R2 = Me<br>R3 = 4-methansulfonyl-phenyl-1-ethyl<br>R4 = CO$_2$H<br>R5 = H<br>R6 = H<br>R7 = H |
| 277 | 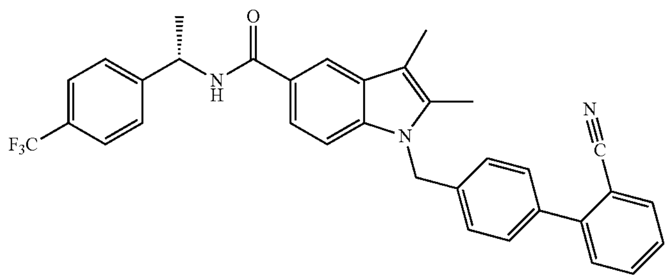 [SMILES: Cc1c(C)n(Cc2ccc(-c3ccccc3C#N)cc2)c2ccc(C(=O)N[C@@H](C)c3ccc(C(F)(F)F)cc3)cc12] | R1 = Me<br>R2 = Me<br>R3 = 4-trifluoromethyl-phenyl-1-ethyl<br>R4 = CN<br>R5 = H<br>R6 = H<br>R7 = H |
| 278 | 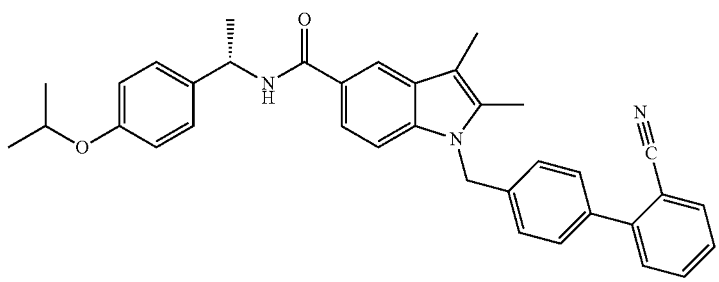 [SMILES: Cc1c(C)n(Cc2ccc(-c3ccccc3C#N)cc2)c2ccc(C(=O)N[C@@H](C)c3ccc(OC(C)C)cc3)cc12] | R1 = Me<br>R2 = Me<br>R3 = 4-isopropoxyphenyl-1-ethyl<br>R4 = CN<br>R5 = H<br>R6 = H<br>R7 = H |
| 279 | 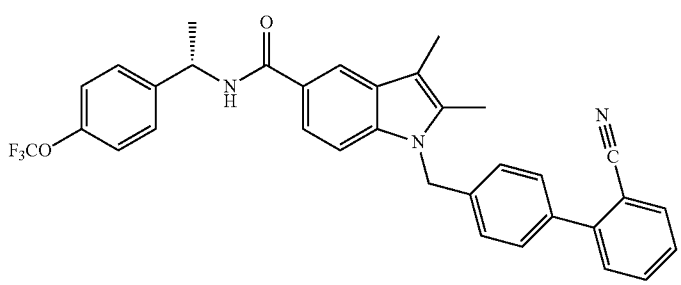 [SMILES: Cc1c(C)n(Cc2ccc(-c3ccccc3C#N)cc2)c2ccc(C(=O)N[C@@H](C)c3ccc(OC(F)(F)F)cc3)cc12] | R1 = Me<br>R2 = Me<br>R3 = 4-trifluoromethoxy-phenyl-1-ethyl<br>R4 = CN<br>R5 = H<br>R6 = H<br>R7 = H |
| 280 | 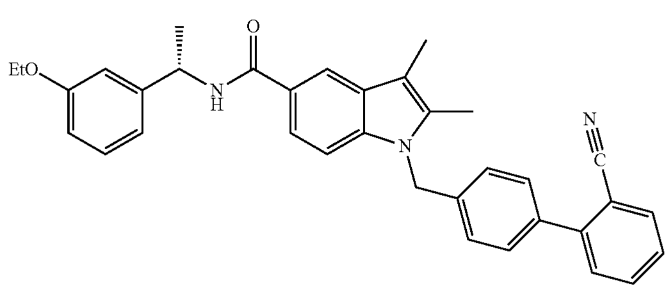 | R1 = Me<br>R2 = Me<br>R3 = 3-ethoxyphenyl-1-ethyl<br>R4 = CN<br>R5 = H<br>R6 = H<br>R7 = H |

TABLE 1-continued

Specific Compounds of the Invention

| # | Structure | Substituents |
|---|-----------|--------------|
| 281 | 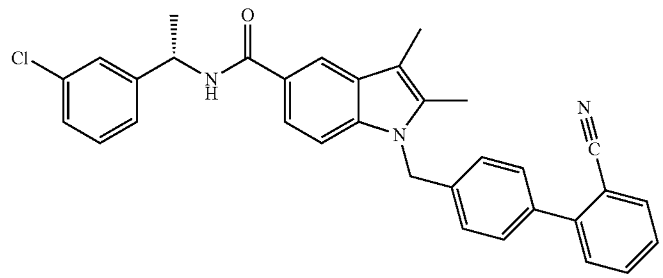 [SMILES: Cc1c(C)n(Cc2ccc(-c3ccccc3C#N)cc2)c2ccc(C(=O)N[C@@H](C)c3cccc(Cl)c3)cc12] | R1 = Me<br>R2 = Me<br>R3 = 3-chlorophenyl-1-ethyl<br>R4 = CN<br>R5 = H<br>R6 = H<br>R7 = H |
| 282 | 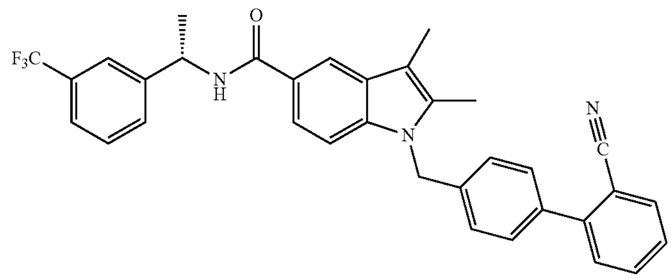 [SMILES: Cc1c(C)n(Cc2ccc(-c3ccccc3C#N)cc2)c2ccc(C(=O)N[C@@H](C)c3cccc(C(F)(F)F)c3)cc12] | R1 = Me<br>R2 = Me<br>R3 = 3-trifluoromethyl-phenyl-1-ethyl<br>R4 = CN<br>R5 = H<br>R6 = H<br>R7 = H |
| 283 | 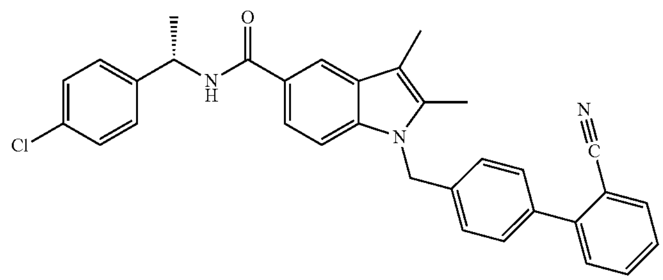 [SMILES: Cc1c(C)n(Cc2ccc(-c3ccccc3C#N)cc2)c2ccc(C(=O)N[C@@H](C)c3ccc(Cl)cc3)cc12] | R1 = Me<br>R2 = Me<br>R3 = 4-chlorophenyl-1-ethyl<br>R4 = CN<br>R5 = H<br>R6 = H<br>R7 = H |
| 284 | 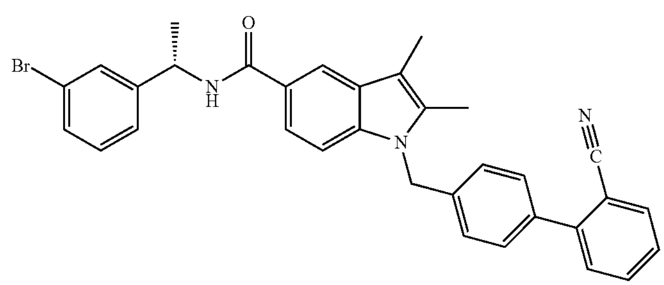 | R1 = Me<br>R2 = Me<br>R3 = 3-bromophenyl-1-ethyl<br>R4 = CN<br>R5 = H<br>R6 = H<br>R7 = H |
| 285 | 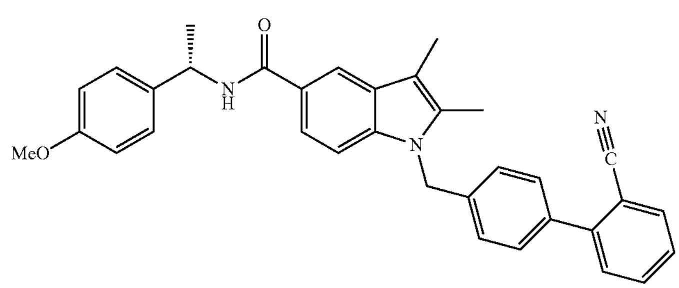 [SMILES: COc1ccc([C@H](C)NC(=O)c2ccc3c(c2)c(C)c(C)n3Cc2ccc(-c3ccccc3C#N)cc2)cc1] | R1 = Me<br>R2 = Me<br>R3 = 4-methoxyphenyl-1-ethyl<br>R4 = CN<br>R5 = H<br>R6 = H<br>R7 = H |

TABLE 1-continued

Specific Compounds of the Invention

| # | Structure | Substituents |
|---|---|---|
| 286 | 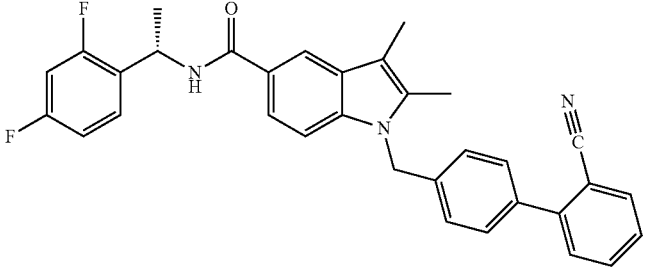 [SMILES: Cc1c(C)n(Cc2ccc(-c3ccccc3C#N)cc2)c2ccc(C(=O)N[C@@H](C)c3ccc(F)cc3F)cc12] | R1 = Me<br>R2 = Me<br>R3 = 2,4-difluorophenyl-1-ethyl<br>R4 = CN<br>R5 = H<br>R6 = H<br>R7 = H |
| 287 | 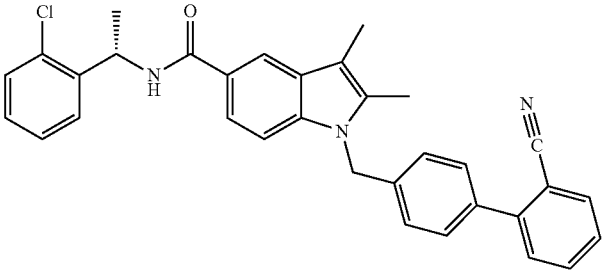 [SMILES: Cc1c(C)n(Cc2ccc(-c3ccccc3C#N)cc2)c2ccc(C(=O)N[C@@H](C)c3ccccc3Cl)cc12] | R1 = Me<br>R2 = Me<br>R3 = 2-chlorophenyl-1-ethyl<br>R4 = CN<br>R5 = H<br>R6 = H<br>R7 = H |
| 288 | 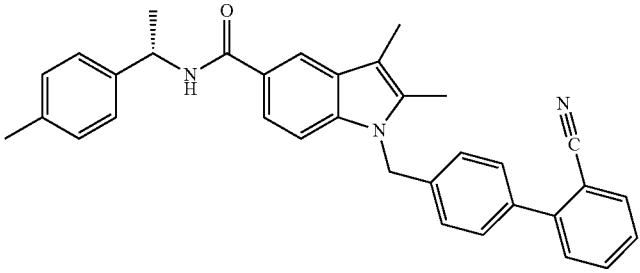 [SMILES: Cc1ccc([C@H](C)NC(=O)c2ccc3c(c2)c(C)c(C)n3Cc2ccc(-c3ccccc3C#N)cc2)cc1] | R1 = Me<br>R2 = Me<br>R3 = 4-methylphenyl-1-ethyl<br>R4 = CN<br>R5 = H<br>R6 = H<br>R7 = H |
| 289 | 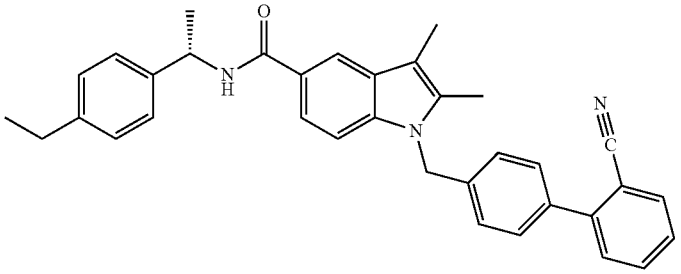 [SMILES: CCc1ccc([C@H](C)NC(=O)c2ccc3c(c2)c(C)c(C)n3Cc2ccc(-c3ccccc3C#N)cc2)cc1] | R1 = Me<br>R2 = Me<br>R3 = 4-ethylphenyl-1-ethyl<br>R4 = CN<br>R5 = H<br>R6 = H<br>R7 = H |
| 290 | 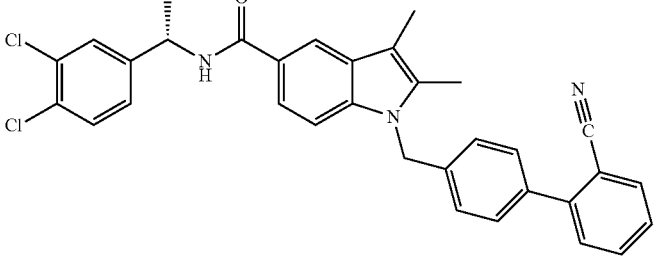 | R1 = Me<br>R2 = Me<br>R3 = 3,4-dichlorophenyl-1-ethyl<br>R4 = CN<br>R5 = H<br>R6 = H<br>R7 = H |

TABLE 1-continued

Specific Compounds of the Invention

| # | Structure | Substituents |
|---|---|---|
| 291 | 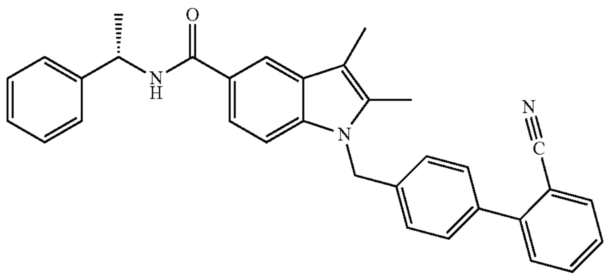 [SMILES: Cc1c(C)n(Cc2ccc(-c3ccccc3C#N)cc2)c2ccc(C(=O)N[C@@H](C)c3ccccc3)cc12] | R1 = Me<br>R2 = Me<br>R3 = phenyl-1-ethyl<br>R4 = CN<br>R5 = H<br>R6 = H<br>R7 = H |
| 292 | 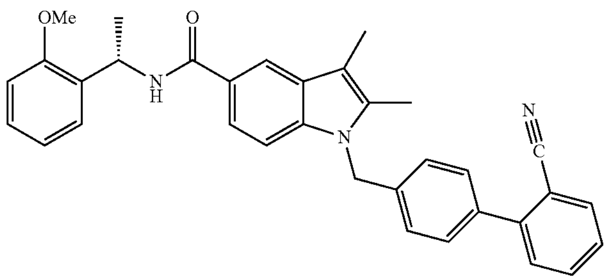 | R1 = Me<br>R2 = Me<br>R3 = 2-methoxyphenyl-1-ethyl<br>R4 = CN<br>R5 = H<br>R6 = H<br>R7 = H |
| 293 | 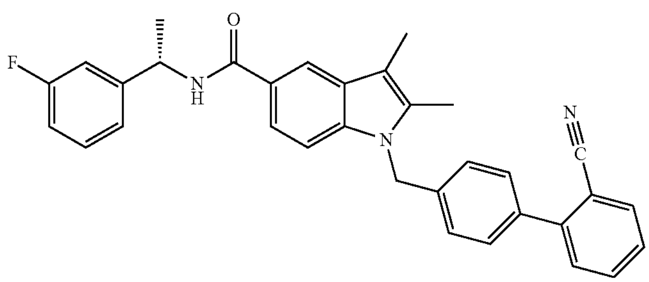 [SMILES: Cc1c(C)n(Cc2ccc(-c3ccccc3C#N)cc2)c2ccc(C(=O)N[C@@H](C)c3cccc(F)c3)cc12] | R1 = Me<br>R2 = Me<br>R3 = 3-fluorophenyl-1-ethyl<br>R4 = CN<br>R5 = H<br>R6 = H<br>R7 = H |
| 294 | 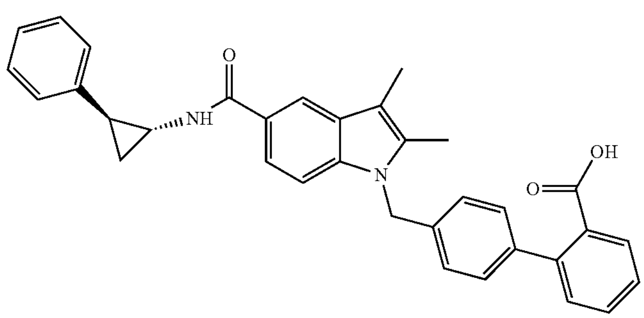 [SMILES: Cc1c(C)n(Cc2ccc(-c3ccccc3C(=O)O)cc2)c2ccc(C(=O)N[C@@H]3C[C@H]3c3ccccc3)cc12] | R1 = Me<br>R2 = Me<br>R3 = 2-phenylcyclopropyl<br>R4 = CO$_2$H<br>R5 = H<br>R6 = H<br>R7 = H |
| 295 | 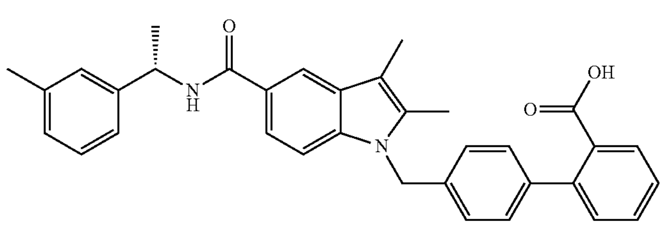 [SMILES: Cc1cccc([C@H](C)NC(=O)c2ccc3c(c2)c(C)c(C)n3Cc2ccc(-c3ccccc3C(=O)O)cc2)c1] | R1 = Me<br>R2 = Me<br>R3 = 3-methylphenyl-1-ethyl<br>R4 = CO$_2$H<br>R5 = H<br>R6 = H<br>R7 = H |

TABLE 1-continued

Specific Compounds of the Invention

| # | Structure | Substituents |
|---|-----------|--------------|
| 296 | 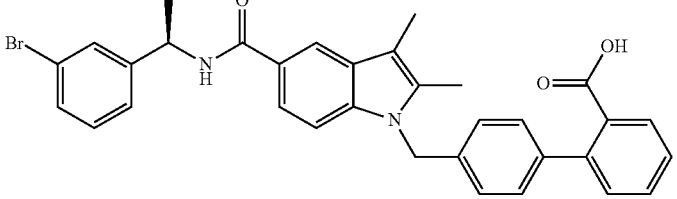 | R1 = Me<br>R2 = Me<br>R3 = 3-bromophenyl-1-ethyl<br>R4 = CO$_2$H<br>R5 = H<br>R6 = H<br>R7 = H |
| 297 | 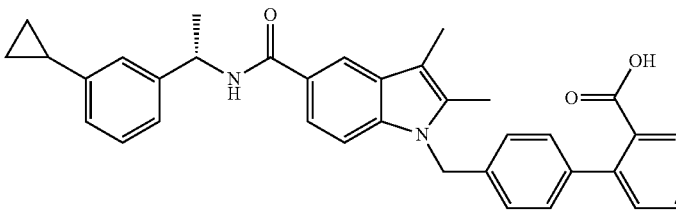 | R1 = Me<br>R2 = Me<br>R3 = 3-cyclopropylphenyl-1-ethyl<br>R4 = CO$_2$H<br>R5 = H<br>R6 = H<br>R7 = H |
| 298 | 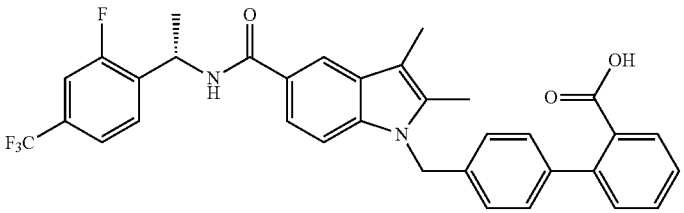 [SMILES: Cc1c(C)n(Cc2ccc(-c3ccccc3C(=O)O)cc2)c2ccc(C(=O)N[C@@H](C)c3ccc(C(F)(F)F)cc3F)cc12] | R1 = Me<br>R2 = Me<br>R3 = 2-fluoro-4-trifluoromethylphenyl-1-ethyl<br>R4 = CO$_2$H<br>R5 = H<br>R6 = H<br>R7 = H |
| 299 | 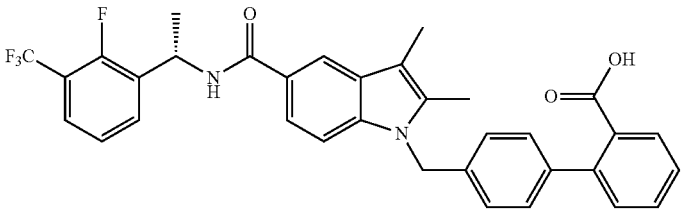 [SMILES: Cc1c(C)n(Cc2ccc(-c3ccccc3C(=O)O)cc2)c2ccc(C(=O)N[C@@H](C)c3cccc(C(F)(F)F)c3F)cc12] | R1 = Me<br>R2 = Me<br>R3 = 2-fluoro-3-trifluoromethylphenyl-1-ethyl<br>R4 = CO$_2$H<br>R5 = H<br>R6 = H<br>R7 = H |
| 300 | 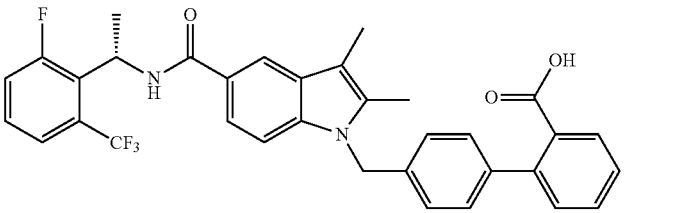 [SMILES: Cc1c(C)n(Cc2ccc(-c3ccccc3C(=O)O)cc2)c2ccc(C(=O)N[C@@H](C)c3c(F)cccc3C(F)(F)F)cc12] | R1 = Me<br>R2 = Me<br>R3 = 2-fluoro-6-trifluoromethylphenyl-1-ethyl<br>R4 = CO$_2$H<br>R5 = H<br>R6 = H<br>R7 = H |
| 301 | 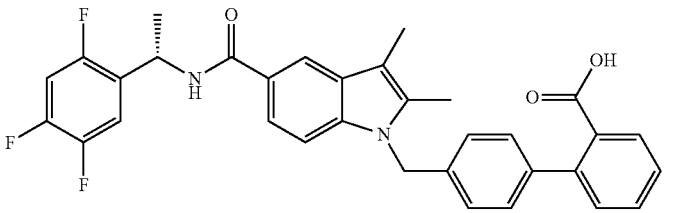 [SMILES: Cc1c(C)n(Cc2ccc(-c3ccccc3C(=O)O)cc2)c2ccc(C(=O)N[C@@H](C)c3cc(F)c(F)cc3F)cc12] | R1 = Me<br>R2 = Me<br>R3 = 2,4,5-trifluorophenyl-1-ethyl<br>R4 = CO$_2$H<br>R5 = H<br>R6 = H<br>R7 = H |
| 302 | 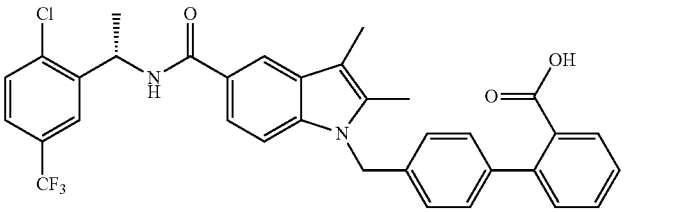 [SMILES: Cc1c(C)n(Cc2ccc(-c3ccccc3C(=O)O)cc2)c2ccc(C(=O)N[C@@H](C)c3cc(C(F)(F)F)ccc3Cl)cc12] | R1 = Me<br>R2 = Me<br>R3 = 2-chloro-5-trifluoromethylphenyl-1-ethyl<br>R4 = CO$_2$H<br>R5 = H<br>R6 = H<br>R7 = H |

TABLE 1-continued

Specific Compounds of the Invention

| # | Structure | Substituents |
|---|---|---|
| 303 | 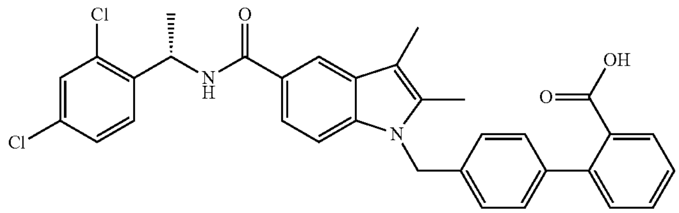 [SMILES: Cc1c(C)n(Cc2ccc(-c3ccccc3C(=O)O)cc2)c2ccc(C(=O)N[C@@H](C)c3ccc(Cl)cc3Cl)cc12] | R1 = Me<br>R2 = Me<br>R3 = 2,4-dichlorophenyl-1-ethyl<br>R4 = CO$_2$H<br>R5 = H<br>R6 = H<br>R7 = H |
| 304 | 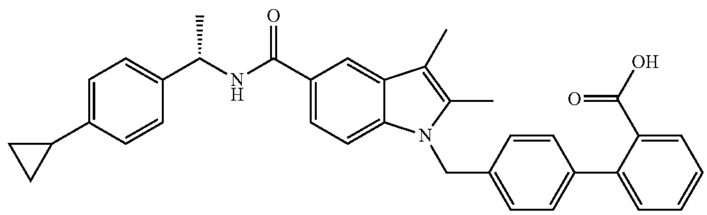 [SMILES: Cc1c(C)n(Cc2ccc(-c3ccccc3C(=O)O)cc2)c2ccc(C(=O)N[C@@H](C)c3ccc(C4CC4)cc3)cc12] | R1 = Me<br>R2 = Me<br>R3 = 4-cyclopropylphenyl-1-ethyl<br>R4 = CO$_2$H<br>R5 = H<br>R6 = H<br>R7 = H |
| 305 | 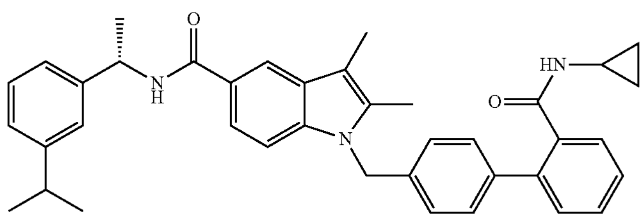 [SMILES: Cc1c(C)n(Cc2ccc(-c3ccccc3C(=O)NC3CC3)cc2)c2ccc(C(=O)N[C@@H](C)c3cccc(C(C)C)c3)cc12] | R1 = Me<br>R2 = Me<br>R3 = 3-isopropylphenyl-1-ethyl<br>R4 = cyclopropylcarbamoyl<br>R5 = H<br>R6 = H<br>R7 = H |
| 306 | 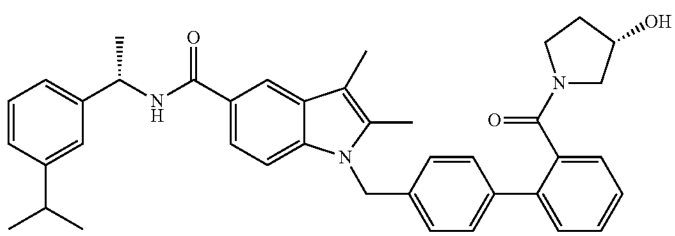 [SMILES: Cc1c(C)n(Cc2ccc(-c3ccccc3C(=O)N3CC[C@H](O)C3)cc2)c2ccc(C(=O)N[C@@H](C)c3cccc(C(C)C)c3)cc12] | R1 = Me<br>R2 = Me<br>R3 = 3-isopropylphenyl-1-ethyl<br>R4 = 3-hydroxypyrrolidin-1-carbonyl<br>R5 = H<br>R6 = H<br>R7 = H |
| 307 | 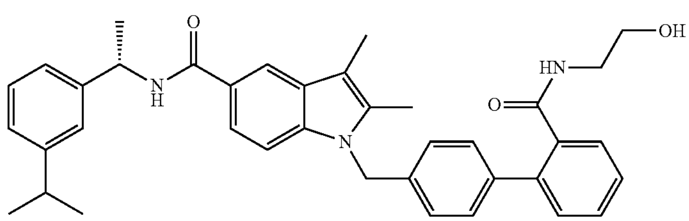 [SMILES: Cc1c(C)n(Cc2ccc(-c3ccccc3C(=O)NCCO)cc2)c2ccc(C(=O)N[C@@H](C)c3cccc(C(C)C)c3)cc12] | R1 = Me<br>R2 = Me<br>R3 = 3-isopropylphenyl-1-ethyl<br>R4 = 2-hydroxyethylamino-carbonyl<br>R5 = H<br>R6 = H<br>R7 = H |
| 308 | 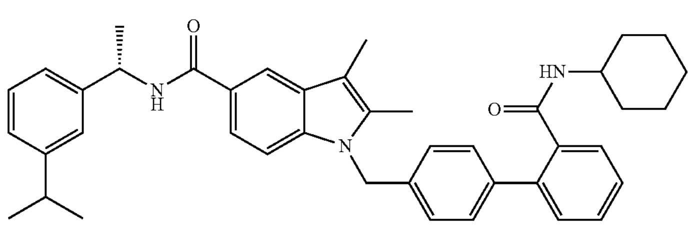 [SMILES: Cc1c(C)n(Cc2ccc(-c3ccccc3C(=O)NC3CCCCC3)cc2)c2ccc(C(=O)N[C@@H](C)c3cccc(C(C)C)c3)cc12] | R1 = Me<br>R2 = Me<br>R3 = 3-isopropylphenyl-1-ethyl<br>R4 = cyclohexylamino-carbonyl<br>R5 = H<br>R6 = H<br>R7 = H |

TABLE 1-continued

Specific Compounds of the Invention

| # | Structure | Substituents |
|---|-----------|--------------|
| 309 | 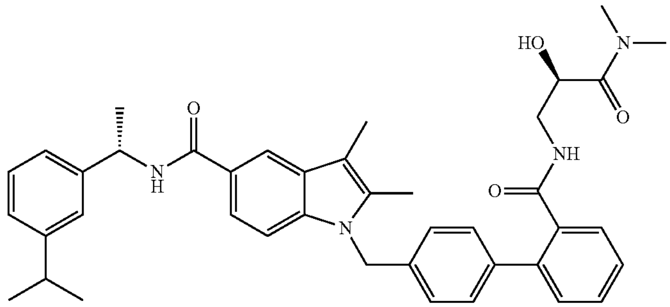 [SMILES: Cc1c(C)n(Cc2ccc(-c3ccccc3C(=O)NC[C@@H](O)C(=O)N(C)C)cc2)c2ccc(C(=O)N[C@@H](C)c3cccc(C(C)C)c3)cc12] | R1 = Me<br>R2 = Me<br>R3 = 3-isopropylphenyl-1-ethyl<br>R4 = 2-(N,N-dimethylaminocarbonyl)-2-hydroxyethylaminocarbonyl<br>R5 = H<br>R6 = H<br>R7 = H |
| 310 | 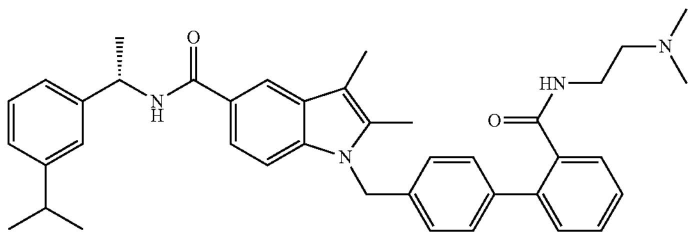 [SMILES: Cc1c(C)n(Cc2ccc(-c3ccccc3C(=O)NCCN(C)C)cc2)c2ccc(C(=O)N[C@@H](C)c3cccc(C(C)C)c3)cc12] | R1 = Me<br>R2 = Me<br>R3 = 3-isopropylphenyl-1-ethyl<br>R4 = N,N-dimethylaminoethylcarbonyl<br>R5 = H<br>R6 = H<br>R7 = H |
| 311 | 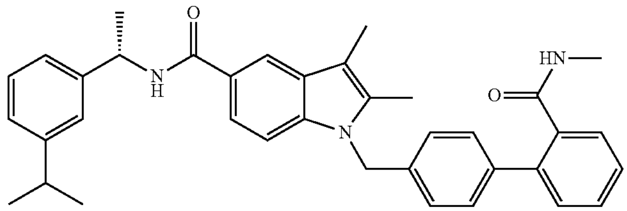 | R1 = Me<br>R2 = Me<br>R3 = 3-isopropylphenyl-1-ethyl<br>R4 = N-methylaminocarbonyl<br>R5 = H<br>R6 = H<br>R7 = H |
| 312 | 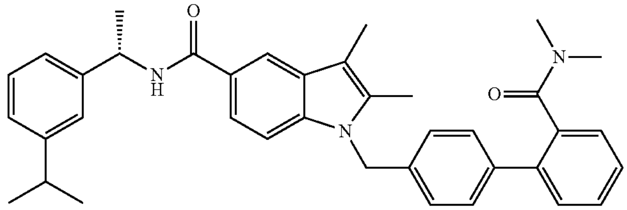 [SMILES: CNC(=O)c1ccccc1-c1ccc(Cn2c(C)c(C)c3cc(C(=O)N[C@@H](C)c4cccc(C(C)C)c4)ccc32)cc1] | R1 = Me<br>R2 = Me<br>R3 = 3-isopropylphenyl-1-ethyl<br>R4 = N,N-dimethylaminocarbonyl<br>R5 = H<br>R6 = H<br>R7 = H |
| 313 | 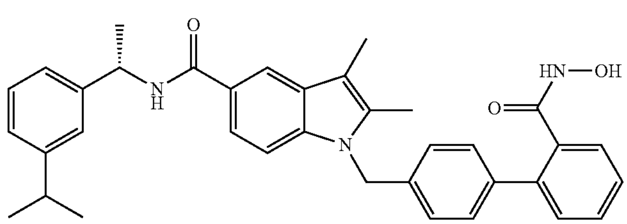 [SMILES: Cc1c(C)n(Cc2ccc(-c3ccccc3C(=O)NO)cc2)c2ccc(C(=O)N[C@@H](C)c3cccc(C(C)C)c3)cc12] | R1 = Me<br>R2 = Me<br>R3 = 3-isopropylphenyl-1-ethyl<br>R4 = N-hydroxylaminocarbonyl<br>R5 = H<br>R6 = H<br>R7 = H |
| 314 | 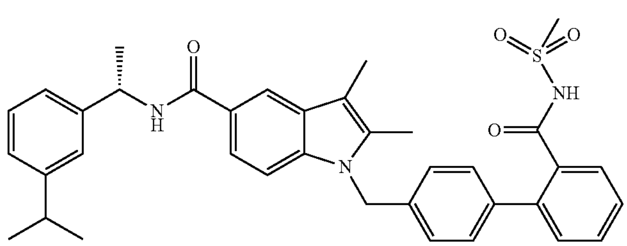 [SMILES: Cc1c(C)n(Cc2ccc(-c3ccccc3C(=O)NS(C)(=O)=O)cc2)c2ccc(C(=O)N[C@@H](C)c3cccc(C(C)C)c3)cc12] | R1 = Me<br>R2 = Me<br>R3 = 3-isopropylphenyl-1-ethyl<br>R4 = methansulfonamidocarbonyl<br>R5 = H<br>R6 = H<br>R7 = H |

TABLE 1-continued

Specific Compounds of the Invention

| # | Structure | Substituents |
|---|---|---|
| 315 | 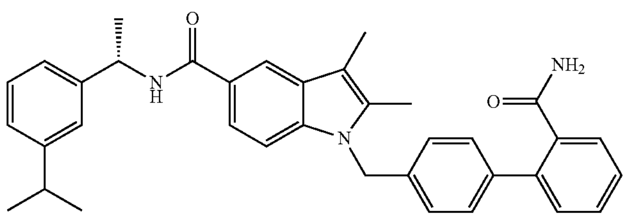 [SMILES: Cc1c(C)n(Cc2ccc(-c3ccccc3C(N)=O)cc2)c2ccc(C(=O)N[C@@H](C)c3cccc(C(C)C)c3)cc12] | R1 = Me<br>R2 = Me<br>R3 = 3-isopropylphenyl-1-ethyl<br>R4 = carboxamido<br>R5 = H<br>R6 = H<br>R7 = H |
| P | | R1 = H<br>R2 = Me<br>R3 = 4-nitrophenyl-1-ethyl<br>R4 = CO$_2$H<br>R5 = H<br>R6 = H<br>R7 = H |
| P | | R1 = Me<br>R2 = Me<br>R3 = 3-trifluoromethoxy-phenyl-1-ethyl<br>R4 = CO$_2$H<br>R5 = H<br>R6 = H<br>R7 = H |
| P | | R1 = Me<br>R2 = Me<br>R3 = 3-isopropylphenyl-3-propynyl<br>R4 = CO$_2$H<br>R5 = H<br>R6 = H<br>R7 = H |
| P | | R1 = Me<br>R2 = Me<br>R3 = 3-isopropylphenyl-1-cyclopropyl<br>R4 = CO$_2$H<br>R5 = H<br>R6 = H<br>R7 = H |

TABLE 1-continued

Specific Compounds of the Invention

| # | Structure | Substituents |
|---|-----------|--------------|
| P | | R1 = Me<br>R2 = Me<br>R3 = 3-isopropylphenyl-1-cyclopentyl<br>R4 = CO$_2$H<br>R5 = H<br>R6 = H<br>R7 = H |
| P | | R1 = Me<br>R2 = Me<br>R3 = 2-cyanophenyl-1-ethyl<br>R4 = CO$_2$H<br>R5 = H<br>R6 = H<br>R7 = H |
| P | | R1 = Me<br>R2 = Me<br>R3 = 2-cyanophenyl-1-ethyl<br>R4 = CO$_2$H<br>R5 = H<br>R6 = H<br>R7 = H |
| P | | R1 = Me<br>R2 = Me<br>R3 = 2-methyl-4-chlorophenyl-1-ethyl<br>R4 = CO$_2$H<br>R5 = H<br>R6 = H<br>R7 = H |
| P | | R1 = Me<br>R2 = Me<br>R3 = 2-trifluoromethyl-4-fluorophenyl-1-ethyl<br>R4 = CO$_2$H<br>R5 = H<br>R6 = H<br>R7 = H |

TABLE 1-continued

Specific Compounds of the Invention

| # | Structure | Substituents |
|---|---|---|
| P | | R1 = Me<br>R2 = Me<br>R3 = 2-chloro-4-fluoro-1-ethyl<br>R4 = CO$_2$H<br>R5 = H<br>R6 = H<br>R7 = H |
| P | | R1 = Me<br>R2 = Me<br>R3 = 2-chloro-4-fluoro-1-ethyl<br>R4 = CO$_2$H<br>R5 = H<br>R6 = H<br>R7 = H |
| P | | R1 = Me<br>R2 = Me<br>R3 = pyridin-3-yl-1-ethyl<br>R4 = CO$_2$H<br>R5 = H<br>R6 = H<br>R7 = H |
| P | | R1 = Me<br>R2 = Me<br>R3 = 2-chloro-3-methoxy-phenyl-1 ethyl<br>R4 = CO$_2$H<br>R5 = H<br>R6 = H<br>R7 = H |
| P | | R1 = Me<br>R2 = Me<br>R3 = 5-isopropylpyridin-2-yl-1-ethyl<br>R4 = CO$_2$H<br>R5 = H<br>R6 = H<br>R7 = H |

TABLE 1-continued

Specific Compounds of the Invention

| # | Structure | Substituents |
|---|-----------|--------------|
| P | | R1 = Me<br>R2 = Me<br>R3 = 5-trifluoromethyl-pyridin-2-yl-1-ethyl<br>R4 = CO₂H<br>R5 = H<br>R6 = H<br>R7 = H |
| P | | R1 = Me<br>R2 = Me<br>R3 = 4-trifluoromethyllpyridin-2-yl-1-ethyl<br>R4 = CO₂H<br>R5 = H<br>R6 = H<br>R7 = H |
| P | | R1 = Me<br>R2 = Me<br>R3 = 5-trifluoromethyllpyridin-3-yl-1-ethyl<br>R4 = CO₂H<br>R5 = H<br>R6 = H<br>R7 = H |
| P | | R1 = Me<br>R2 = Me<br>R3 = 2-fluoro-3-methoxy-phenyl-1-ethyl<br>R4 = CO₂H<br>R5 = H<br>R6 = H<br>R7 = H |
| P | | R1 = Me<br>R2 = Me<br>R3 = 5-isopropylpyridin-3-yl-1-ethyl<br>R4 = CO₂H<br>R5 = H<br>R6 = H<br>R7 = H |

TABLE 1-continued

Specific Compounds of the Invention

| # | Structure | Substituents |
|---|-----------|--------------|
| P | | R1 = Me<br>R2 = Me<br>R3 = 2-methoxypyridin-5-yl-1-ethyl<br>R4 = CO$_2$H<br>R5 = H<br>R6 = H<br>R7 = H |
| P | | R1 = Me<br>R2 = Me<br>R3 = 2-fluoro-6-trifluoromethyl-phenyl-1-ethyl<br>R4 = CO$_2$H<br>R5 = H<br>R6 = H<br>R7 = H |
| P | | R1 = Me<br>R2 = Me<br>R3 = 2-chloro-5-trifluoromethyl-phenyl-1-ethyl<br>R4 = CO$_2$H<br>R5 = H<br>R6 = H<br>R7 = H |
| P | | R1 = Me<br>R2 = Me<br>R3 = 3-cyclopropoxy-phenyl-1-ethyl<br>R4 = CO$_2$H<br>R5 = H<br>R6 = H<br>R7 = H |
| P | | R1 = Me<br>R2 = Me<br>R3 = 2,4-dichlorophenyl-1-ethyl<br>R4 = CO$_2$H<br>R5 = H<br>R6 = H<br>R7 = H |

TABLE 1-continued

Specific Compounds of the Invention

| # | Structure | Substituents |
|---|-----------|--------------|
| P | | R1 = Me<br>R2 = Me<br>R3 = 2-fluoro-4-trifluoromethylphenyl-1-ethyl<br>R4 = CO$_2$H<br>R5 = H<br>R6 = H<br>R7 = H |
| P | | R1 = Me<br>R2 = Me<br>R3 = 3-isopropylphenyl-1-cyclopropylmethyl<br>R4 = CO$_2$H<br>R5 = H<br>R6 = H<br>R7 = H |
| P | | R1 = Me<br>R2 = Me<br>R3 = 3-isopropylphenyl-1-propyn-3-yl<br>R4 = CO$_2$H<br>R5 = H<br>R6 = H<br>R7 = H |
| P | | R1 = Me<br>R2 = Me<br>R3 = 3-isopropylphenyl-2,2-dimethyl-1-propyl<br>R4 = CO$_2$H<br>R5 = H<br>R6 = H<br>R7 = H |
| P | | R1 = Me<br>R2 = Me<br>R3 = 3-isopropylphenyl-2,2-dimethyl-1-propyl<br>R4 = CO$_2$H<br>R5 = H<br>R6 = H<br>R7 = H |

TABLE 1-continued

Specific Compounds of the Invention

| # | Structure | Substituents |
|---|---|---|
| P | 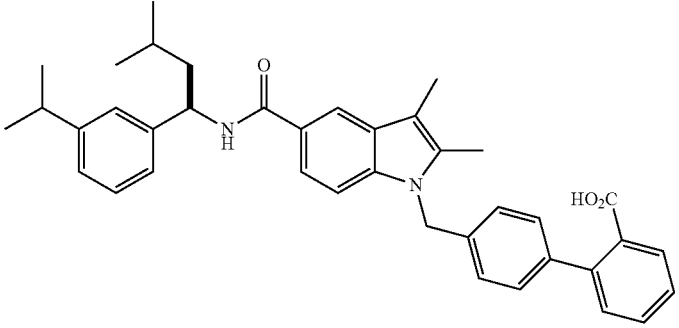 | R1 = Me<br>R2 = Me<br>R3 = 3-isopropylphenyl-3-methyl-1-butyl<br>R4 = CO$_2$H<br>R5 = H<br>R6 = H<br>R7 = H |
| P | 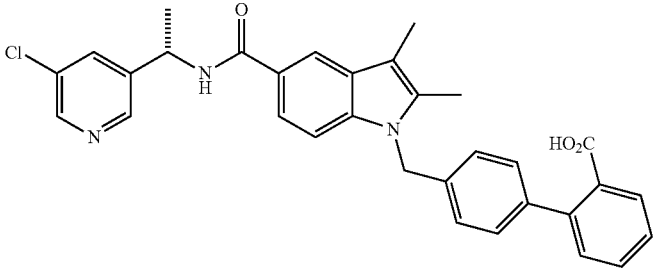 [SMILES: Cc1c(C)n(Cc2ccc(-c3ccccc3C(=O)O)cc2)c2ccc(C(=O)N[C@@H](C)c3cncc(Cl)c3)cc12] | R1 = Me<br>R2 = Me<br>R3 = 5-chloropyridin-3-yl-1-ethyl<br>R4 = CO$_2$H<br>R5 = H<br>R6 = H<br>R7 = H |
| P | 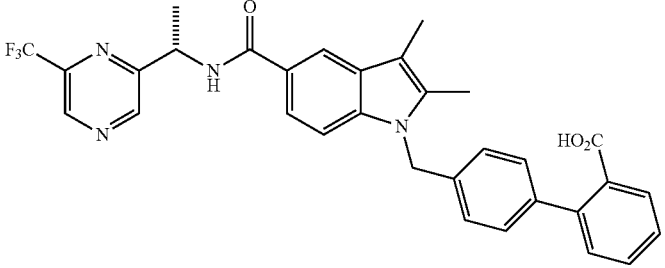 [SMILES: Cc1c(C)n(Cc2ccc(-c3ccccc3C(=O)O)cc2)c2ccc(C(=O)N[C@@H](C)c3cncc(C(F)(F)F)n3)cc12] | R1 = Me<br>R2 = Me<br>R3 = 6-trifluoromethyllpyrazin-2-yl-1-ethyl<br>R4 = CO$_2$H<br>R5 = H<br>R6 = H<br>R7 = H |
| P | 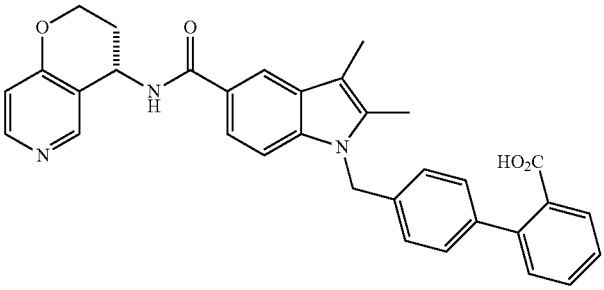 [SMILES: Cc1c(C)n(Cc2ccc(-c3ccccc3C(=O)O)cc2)c2ccc(C(=O)N[C@H]3CCOc4ccncc43)cc12] | R1 = Me<br>R2 = Me<br>R3 = 3,4-dihydro-2H-pyrano[3,2-c]pyridin-4-yl<br>R4 = CO$_2$H<br>R5 = H<br>R6 = H<br>R7 = H |
| P | 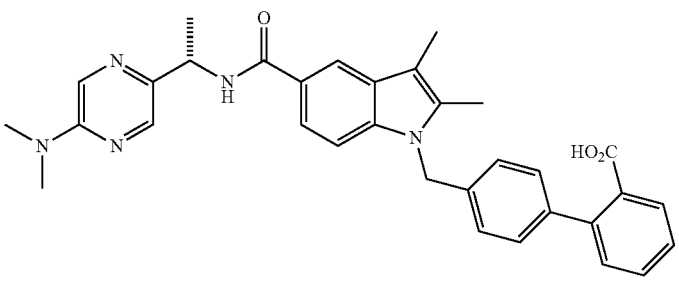 [SMILES: Cc1c(C)n(Cc2ccc(-c3ccccc3C(=O)O)cc2)c2ccc(C(=O)N[C@@H](C)c3cnc(N(C)C)cn3)cc12] | R1 = Me<br>R2 = Me<br>R3 = 5-N,N-dimethylamino-pyrazin-2-yl-1-ethyl<br>R4 = CO$_2$H<br>R5 = H<br>R6 = H<br>R7 = H |

TABLE 1-continued

Specific Compounds of the Invention

| # | Structure | Substituents |
|---|---|---|
| P | | R1 = Me<br>R2 = Me<br>R3 = 6-cyclopropyl-pyrazin-2-yl-1-ethyl<br>R4 = CO$_2$H<br>R5 = H<br>R6 = H<br>R7 = H |
| P | | R1 = Me<br>R2 = Me<br>R3 = 5-isopropoxy-pyrazin-2-yl-1-ethyl<br>R4 = CO$_2$H<br>R5 = H<br>R6 = H<br>R7 = H |
| P | | R1 = Me<br>R2 = Me<br>R3 = 1-methyl-1,2,3,4-tetrahydro-1,6-naphthyridin-4-yl<br>R4 = CO$_2$H<br>R5 = H<br>R6 = H<br>R7 = H |
| P | | R1 = Me<br>R2 = Me<br>R3 = 1,2,3,4-tetrahydro-1,8-naphthyridin-6-yl-1-ethyl<br>R4 = CO$_2$H<br>R5 = H<br>R6 = H<br>R7 = H |
| P | | R1 = Me<br>R2 = Me<br>R3 = 2,3-dihydro-1H-pyrrolo[2,3-b]pyridin-5-yl-1-ethyl<br>R4 = CO$_2$H<br>R5 = H<br>R6 = H<br>R7 = H |

TABLE 1-continued

Specific Compounds of the Invention

| # | Structure | Substituents |
|---|---|---|
| P | | R1 = Me<br>R2 = Me<br>R3 = N-isopropylpyrazol-4-yl-1-ethyl<br>R4 = CO₂H<br>R5 = H<br>R6 = H<br>R7 = H |
| P | | R1 = Me<br>R2 = Me<br>R3 = 1-cyclopropyl-[1H]-triazol-3-yl-1-ethyl<br>R4 = CO₂H<br>R5 = H<br>R6 = H<br>R7 = H |
| P | | R1 = Me<br>R2 = Me<br>R3 = 1-isopropyl-[1H]-triazol-3-yl-1-ethyl<br>R4 = CO₂H<br>R5 = H<br>R6 = H<br>R7 = H |
| P | | R1 = Me<br>R2 = Me<br>R3 = 2-cyclopropyl-thiazol-4-yl-1-ethyl<br>R4 = CO₂H<br>R5 = H<br>R6 = H<br>R7 = H |
| P | | R1 = Me<br>R2 = Me<br>R3 = N-t-butylpyrrolidin-3-yl-1-ethyl<br>R4 = CO₂H<br>R5 = H<br>R6 = H<br>R7 = H |

TABLE 1-continued

Specific Compounds of the Invention

| # | Structure | Substituents |
|---|-----------|--------------|
| P | 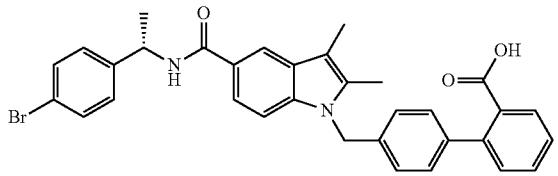 | R1 = Me<br>R2 = Me<br>R3 = N-cyclopropylpiperidin-3-yl-1-ethyl<br>R4 = CO₂H<br>R5 = H<br>R6 = H<br>R7 = H |

Note:
Ph = phenyl, CO = carbonyl, Bn = benzyl; $X^1$-$X^7$ = C, R = H, unless otherwise indicated.
"P" = prophetic example Synthetic Methods The following abbreviations are used throughout this document.

BOP  Benzotriazol-1-yl-oxy-tris-(dimethylamino)phosphonium hexafluorophosphate
CDI  Carbonyl diimidazole
DBU  Diazabicycloundecane
DCM  Dichloromethane
DIPEA, $^iPr_2$ EtN  N,N-Diisopropylethylamine
DMAP  4-(N,N-dimethylamino)pyridine
DMF  N,N-Dimethylformamide
DMSO  Dimethylsulfoxide
EDAC  1-Ethyl-3-(3-dimethylaminopropyl)carbodiimide hydrochloride
eq  Equivalents
$Et_2O$  Diethyl ether
EtOAc  Ethyl acetate
h  Hours
HATU  O-(7-Azabenzotriazole-1-yl)-N,N,N'N'-tetramethyluronium hexafluorophosphate
HCl  Hydrochloric acid
HOAT  Hydroxyazabenztriazole
HOBT  Hydroxybenzotriazole
LiHDMS  Lithium hexamethyldisilazide
LiOH  Lithium hydroxide
mg  Milligrams
min  Minutes
mL  Milliliters
μL  Microliters
mmole  Millimoles
MS  Mass spectroscopy
MeOH  Methanol
$NaBH_3$ CN  Sodium cyanoborohydride
NaH  Sodium hydride
$NaIO_4$  Sodium periodate
NMM  N-Methylmorpholine
rb  Round-bottom
RT, rt  Room temperature
sat.  Saturated
TEA  Triethylamine
TFA  Trifluoroacetic acid
THF  Tetrahydrofuran

EXAMPLES

Example 1

(S)-4'-((5-(1-(4-Bromophenyl)ethylcarbamoyl)-2,3-dimethyl-1H-indol-1-yl)methyl)biphenyl-2-carboxylic acid

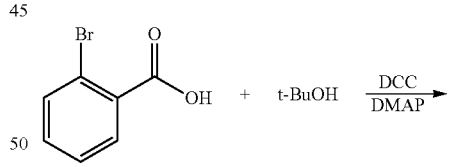

Step 1: tert-Butyl 2-bromobenzoate

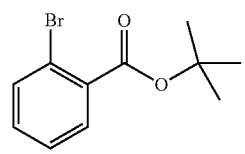

To a solution of 2-bromobenzoic acid (8.08 g, 40.2 mmol), DMAP (0.492 g, 8.0 mmol) and t-BuOH (9.3 mL, 80.4 mmol) in dry DCM (300 mL) under argon, was added DCC (9.96 g, 48.2 mmol). The reaction mixture was stirred at room temperature for 20 h. The resulting mixture was filtered and the filtrate was evaporated in vacuo. The crude mixture was dissolved in AcOEt (300 mL) and washed with saturated aqueous $NaHCO_3$ (261), brine and then dried over $Na_2SO_4$. After filtration, solvent was evaporated. The crude product was purified by flash chromatography on silica gel (AcOEt/hexane 0→30%) to obtain the title compound.

Step 2: tert-Butyl 4'-methylbiphenyl-2-carboxylate

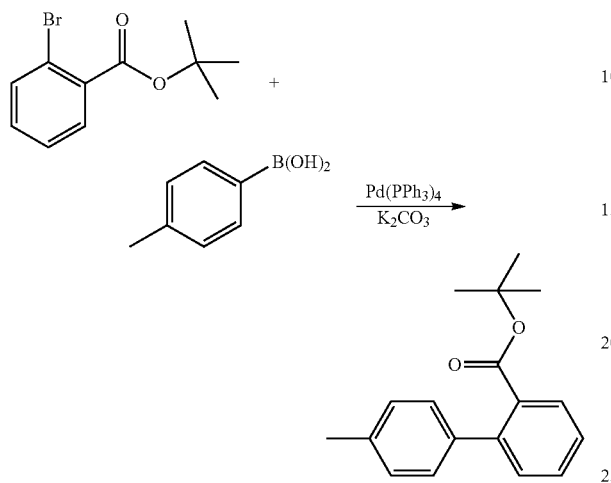

To a 350 mL high-pressure vial was added tert-butyl 2-bromobenzoate (5.142 g, 20.0 mmol), p-tolylboronic acid (4.08 g, 30.0 mmol), Pd(PPh$_3$)$_4$ (3.47 g, 3.0 mmol), potassium carbonate (8.29 g, 60.0 mmol) and dioxane with water (4:1, 200 mL). The mixture was degassed for 5 min and sealed. The mixture was heated at 100° C. for 40 min wherein analytical HPLC analysis indicated the completion of the reaction. The mixture was filtered through Celite and MeOH was used to wash the Celite pad. The solvent was removed and the crude was purified by flash chromatography (AcOEt/Hexane 0→30%) to obtain the title compound.

Step 3: tert-butyl 4'-(bromomethyl)biphenyl-2-carboxylate

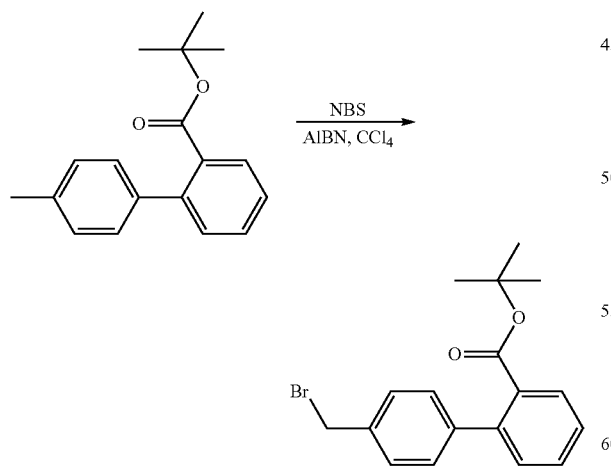

To a 500 mL round-bottom flask was added tert-butyl 4'-methylbiphenyl-2-carboxylate (7.04 g, 26.23 mmol), NBS (5.14 g, 28.85 mmol), AIBN (0.43 g, 2.62 mmol) and CCl$_4$ (200 mL). The reaction mixture was refluxed for 2 h at 100° C. The completion of the reaction was monitored by analytical HPLC. The reaction mixture was allowed to cool to room temperature and filtered. The filtrate was concentrated to obtain the crude product which was purified by flash chromatography (AcOEt/Hexane 0→30%) to obtain the title compound.

Step 4: tert-Butyl 1-(4-(ethoxycarbonyl)phenyl)hydrazinecarboxylate

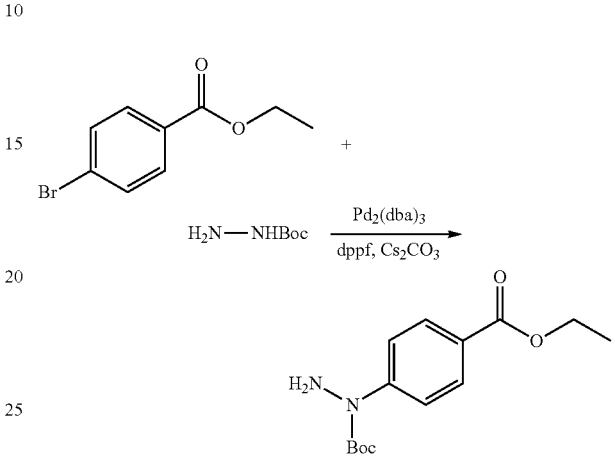

To a 350 mL high-pressure vial was added ethyl 4-bromobenzoate (12.92 g, 56.4 mmol), t-butyl carbazate (14.91 g, 112.8 mmol), Pd$_2$(dba)$_3$ (0.516 g, 0.56 mmol), dppf (0.938 g, 1.69 mmol), Cs$_2$CO$_3$ (18.4 g, 56.4 mmol), and dry toluene (113 mL). The reaction mixture was degassed for 5 min, sealed and heated to 100° C. for 16 h. The completion of the reaction was monitored by analytical HPLC. The reaction mixture was allowed to cool to room temperature, diluted with DCM, filtered and the filtrate was concentrated. The crude was then purified by flash chromatography (AcOEt/Hexane (0→30%) to afford the desired product. ESI-MS (m/z): 265 [M+H—NH$_3$]$^+$, 225 [M+H-tBu]$^+$, 181 [M+H-Boc]$^+$. $^1$H NMR (400 MHz, DMSO-d$_6$): δ (ppm) 1.31 (t, J=7.1 Hz, 3H, CH$_3$ ethyl), 1.50 (s, 9H, CH$_3$ Boc), 4.28 (q, J=7.1 Hz, 2H, CH$_2$ ethyl), 5.14 (s, 2H, NH$_2$), 7.70 (dt, J=8.8, 2.2 Hz, 2H, H$_2$ and H$_6$ phenyl), 7.87 (dt, J=8.8, 2.2 Hz, 2H, H$_3$ and H$_5$ phenyl).

Step 5: Ethyl 2,3-dimethyl-1H-indole-5-carboxylate

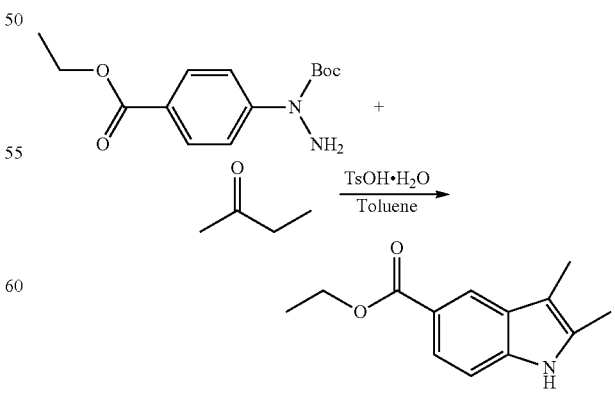

A mixture of tert-butyl 1-(4-(ethoxycarbonyl)phenyl)hydrazinecarboxylate (5.27 g, 18.8 mmol), butan-2-one (2.53 mL, 28.2 mmol), and TsOH monohydrate (21.5 g, 112.8 mmol) in toluene (300 mL) was heated at 80° C. for 2 h. The reaction mixture was allowed to cool to room temperature and filtered. The filtrate was concentrated and then purified by flash chromatography (AcOEt/Hexane 5%) to obtain the title compound. ESI-MS (m/z): 218 [M+H]+.

$^1$H NMR (400 MHz, DMSO-d$_6$): δ (ppm) 1.33 (t, J=7.2 Hz, 3H, CH$_3$ ethyl), 2.18 (s, 3H, CH$_3$), 2.32 (s, 3H, CH$_3$), 4.29 (q, J=7.2 Hz, 2H, CH$_2$ ethyl), 7.28 (dd, J=8.4, 0.4 Hz, 1H, H$_7$ indole), 7.64 (dd, J=8.4, 1.6 Hz, 1H, H$_6$ indole), 8.05 (m, 1H, H$_4$ indole).

Step 6: Ethyl 1-((2'-(tert-butoxycarbonyl)biphenyl-4-yl)methyl)-2,3-dimethyl-1H-indole-5-carboxylate

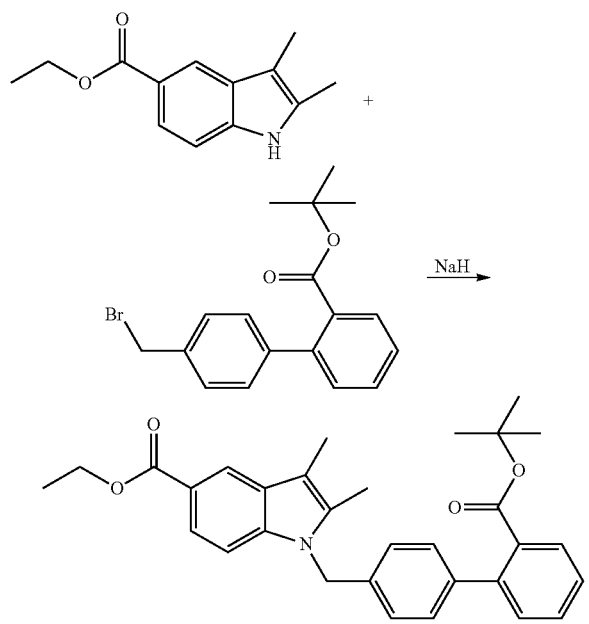

To a mixture of ethyl 2,3-dimethyl-1H-indole-5-carboxylate (1.493 g, 6.87 mmol) in dry DMF (10 mL) at 0° C. under argon was added NaH (0.3 g, 60% dispersion in mineral oil, 7.56 mmol) in portions. The reaction mixture was stirred at rt for 30 min and then re-cooled to 0° C. Tert-butyl 4'-(bromomethyl)biphenyl-2-carboxylate (2.62 g, 7.56 mmol) in DMF (2 mL) was slowly added. The reaction mixture was stirred at rt for another 1 h. The completion of the reaction was monitored by anal. HPLC. The reaction was quenched with MeOH, and then the solvent was removed in vacuo. The crude was dissolved in AcOEt, washed with saturated aqueous NaHCO$_3$, brine and dried over Na$_2$SO$_4$ and filtered. The filtrate was evaporated in vacuo to obtain the crude which was purified by flash chromatography (AcOEt/Hex 10→100%) to obtain the title compound. ESI-MS (m/z): 484 [M+H]+.

Step 7: 1-((2'-(tert-Butoxycarbonyl)biphenyl-4-yl)methyl)-2,3-dimethyl-1H-indole-5-carboxylic acid

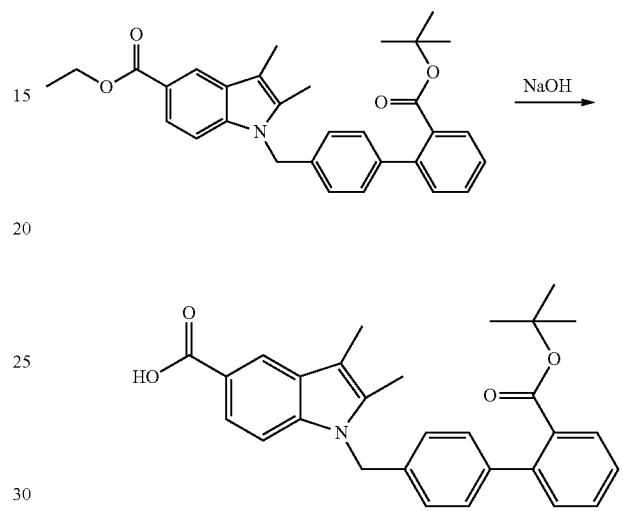

A mixture of ethyl 1-((2'-(tert-butoxycarbonyl)biphenyl-4-yl)methyl)-2,3-dimethyl-1H-indole-5-carboxylate (3.72 g, 7.69 mmol) and NaOH (7.7 mL, 2 N, 15.4 mmol) in EtOH (30 mL) was refluxed at 100° C. for 2 h. The completion of the reaction was monitored by anal. HPLC. The reaction mixture was cooled to rt, then acidified to pH~4 with 2 N HCl solution. The mixture was evaporated in vacuo to obtain the crude, which was precipitated from water and filtered to obtain the title compound. ESI-MS (m/z): 456 [M+H]+.

$^1$H NMR (400 MHz, DMSO-d$_6$): δ (ppm) 1.13 (s, 9H, CH$_3$ tBu), 2.26 (s, 3H, CH$_3$ indole), 2.33 (s, 3H, CH$_3$ indole), 5.49 (s, 2H, CH$_2$-biphenyl), 7.01 (d, J=8 Hz, 2H, H$_7$ and H$_9$ biphenyl), 7.19 (d, J=8 Hz, 2H, H$_6$ and H$_{10}$ biphenyl), 7.30 (d, J=7.6 Hz, 1H, H$_7$ indole), 7.40-7.47 (m, 2H, H$_2$ and H$_4$ biphenyl), 7.53 (dt, J=1.2, 7.6 Hz, 1H, H$_3$ biphenyl), 7.63-7.69 (m, 2H H$_6$ indole and H$_5$ biphenyl), 8.13 (d, J=1.2 Hz, 1H, H$_4$ indole).

Step 8: (S)-tert-Butyl 4'-((5-(1-(4-bromophenyl)ethylcarbamoyl)-2,3-dimethyl-1H-indol-1-yl)methyl)biphenyl-2-carboxylate

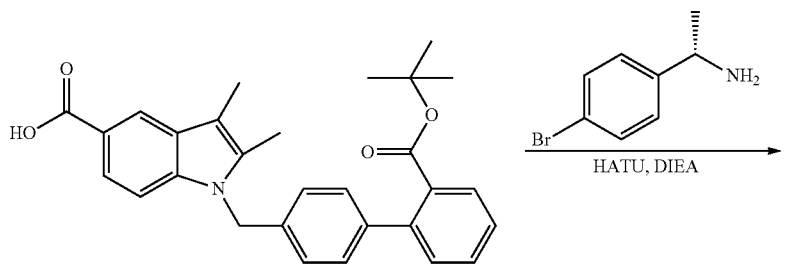

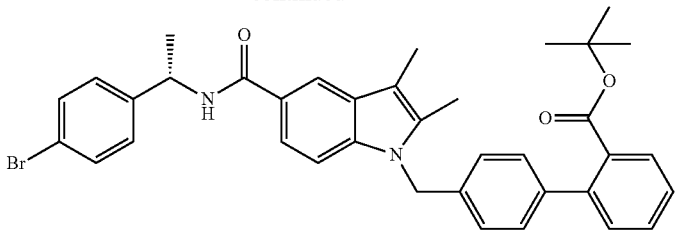

To a mixture of 1-((2'-(tert-butoxycarbonyl)biphenyl-4-yl)methyl)-2,3-dimethyl-1H-indole-5-carboxylic acid (46 mg, 0.1 mmol) in DMF (1 mL) was added DIEA (26 mg, 0.2 mmol) and HATU (46 mg, 0.12 mmol). The mixture was stirred for 5 min, and then (S)-1-(4-bromophenyl)ethanamine (20 mg, 0.13 mmol) was added. The reaction mixture was stirred at rt for 30 min. The completion of the reaction was monitored by anal. HPLC. The solvent was removed in vacuo to obtain the crude which was purified by flash chromatography (AcOEt/Hex 10→100%) to obtain the title compound. ESI-MS (m/z): 637/639 [M+H]$^+$.

Step 9: (S)-4'-((5-(1-(4-Bromophenyl)ethylcarbamoyl)-2,3-dimethyl-1H-indol-1-yl)methyl)biphenyl-2-carboxylic acid

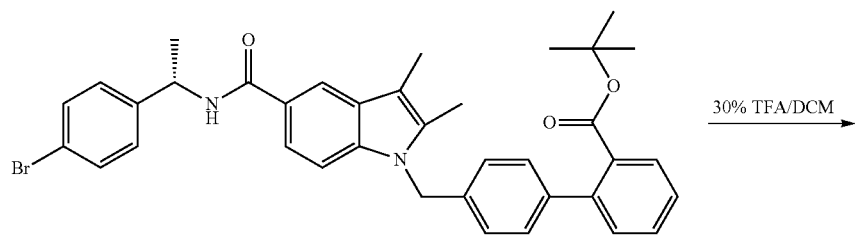

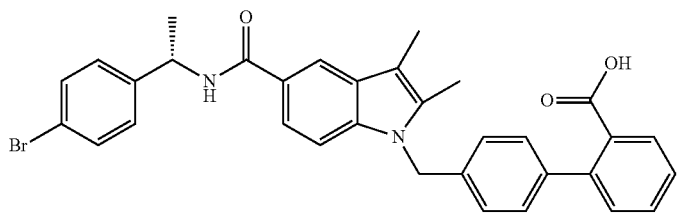

A mixture of (S)-tert-butyl 4'-((5-(1-(4-bromophenyl)ethylcarbamoyl)-2,3-dimethyl-1H-indol-1-yl)methyl)biphenyl-2-carboxylate (20 mg, 0.03 mmol) in TFA/DCM (1 mL, 30%) was stirred at rt for 2 h. The completion of the reaction was monitored by anal. HPLC. The solvent was removed to obtain the crude which was purified by reverse phase prep-HPLC (MeOH/Acetonitrile/water) to obtain the title compound. ESI-MS (m/z): 581/583 [M+H]$^+$.

$^1$H NMR (400 MHz, DMSO-d$_6$): δ (ppm) 1.48 (d, J=6.8 Hz, 3H, CH$_3$ (4-bromophenyl)ethylcarbamoyl), 2.28 (s, 3H, CH$_3$ indole), 2.32 (s, 3H, CH$_3$ indole), 5.17 (quintuplet, J=7.6 Hz, 1H, CH (4-bromophenyl)ethylcarbamoyl), 5.47 (s, 2H, CH$_2$-biphenyl), 6.99 (d, J=8 Hz, 2H, H$_7$ and H$_9$ biphenyl), 7.24 (d, J=8 Hz, 2H, H$_6$ and H$_{10}$ biphenyl), 7.31 (d, J=7.6 Hz, 1H, H$_7$ indole), 7.36-7.55 (m, 7H, H$_2$, H$_3$ and H$_4$ biphenyl, H$_6$ indole and H 4-bromophenyl), 8.10 (d, J=1.6 Hz, 1H, H₄ indole), 8.65 (d, J=8 Hz, 1H, NH amide).

Example 2

(S)-4'-((5-((1-(4-(tert-butyl)phenyl)ethyl)carbamoyl)-2,3-dimethyl-1H-indol-1-yl)methyl)-[1,1'-biphenyl]-2-carboxylic acid

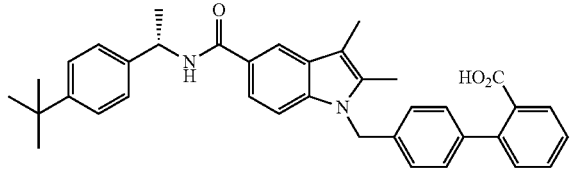 [SMILES: Cc1c(C)n(Cc2ccc(-c3ccccc3C(=O)O)cc2)c2ccc(C(=O)N[C@@H](C)c3ccc(C(C)(C)C)cc3)cc12]

Step 1: (R)—N—((S)-1-(4-(tert-butyl)phenyl)ethyl)-2-methylpropane-2-sulfinamide

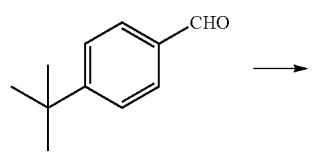

To a solution of 4-t-butylbenzaldehyde (753 µL) in THF (8 mL) was added (R)-2-methylpropane-2-sulfinamide (500 mg) followed by Ti(OiPr)₄ (2.5 mL). The resulting solution was allowed to stir at room temperature for 18 h, and then quenched with saturated aqueous NH₄Cl and diluted with EtOAc. The mixture was filtered through a pad of celite, and washed with EtOAc. The layers were separated, and the organic phase was washed with brine (2×), dried (MgSO₄) and concentrated to give the imine as a light yellow oil (1.20 g) which was used without further purification.

To a solution of the crude imine in CH₂Cl₂ (10 mL) at −50° C. was added MeMgBr (2.7 mL, 3.0 M in Et2O). The reaction was maintained at −50° C. for 6 h, and then allowed to warm to room temperature overnight. After 16 h, the reaction was quenched with brine and diluted with EtOAc and the layers were separated. The organic layer was washed with brine (2×), dried (MgSO₄) and concentrated. The crude residue was purified by chromatography on silica gel (EtOAc/hex) to afford the title compound as a colorless solid (1.01 g). ESI-MS (m/z): 282 [MH]⁺

Step 2: (S)-1-(4-(tert-butyl)phenyl)ethanaminium chloride

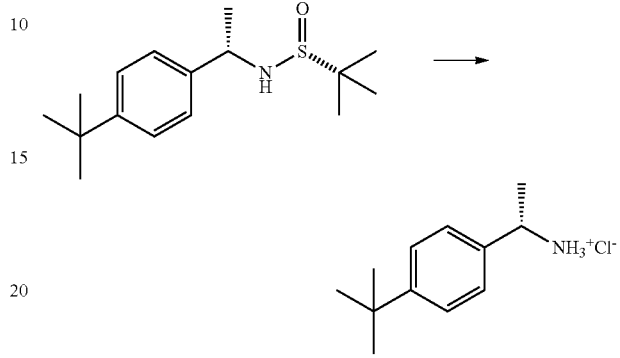

To a solution of (R)—N—((S)-1-(4-(tert-butyl)phenyl) ethyl)-2-methylpropane-2-sulfinamide (977 mg) in MeOH (1.75 mL) was added conc. HCl (1.75 mL). The reaction was aged at room temperature monitoring disappearance of starting material by analytical reverse-phase HPLC. When the starting material was consumed, the reaction was concentrated in vacuo. The crude residue was resuspended in MeOH (1 mL) and crashed out of solution by the addition of Et₂O. Filtration afforded the title compound as a colorless solid (559 mg). ESI-MS (m/z): 161 [M+H—NH₃]⁺, 338 [2M+H—NH₃]⁺

Step 3: (S)-tert-butyl 4'-((5-((1-(4-(tert-butyl)phenyl) ethyl)carbamoyl)-2,3-dimethyl-1H-indol-1-yl)methyl)-[1,1'-biphenyl]-2-carboxylate

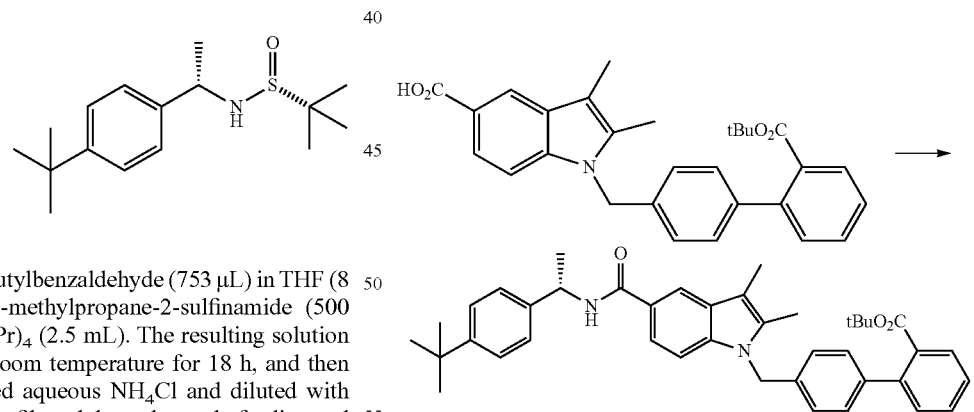

To a mixture of 1-((2'-(tert-butoxycarbonyl)biphenyl-4-yl) methyl)-2,3-dimethyl-1H-indole-5-carboxylic acid (100 mg) in DMF (2 mL) was added DIEA (116 µL) and HATU (88 mg). The mixture was stirred for 5 min, and then (S)-1-(4-(tert-butyl)phenyl)ethanaminium chloride (49 mg) was added. The reaction mixture was stirred at rt for 30 min. The completion of the reaction was monitored by anal. HPLC. The solvent was removed in vacuo to obtain the crude which was purified by flash chromatography (AcOEt/Hex 10→100%) to obtain the title compound (120 mg). ESI-MS (m/z): 559 [M+H-tBu]⁺, 615 [M+H]⁺, 637 [M+Na]⁺

Step 4: (S)-4'-((5-(1-(4-Bromophenyl)ethylcarbamoyl)-2,3-dimethyl-1H-indol-1-yl)methyl)biphenyl-2-carboxylic acid

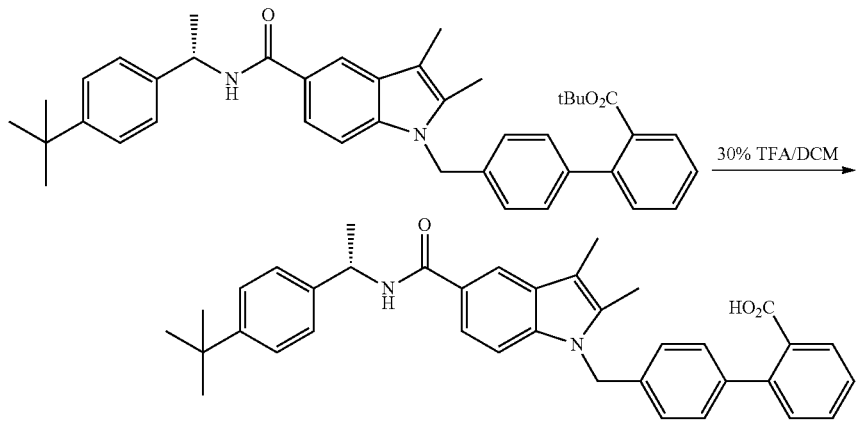

A mixture of (S)-tert-butyl 4'-((5-(((1-(4-(tert-butyl)phenyl)ethyl)carbamoyl)-2,3-dimethyl-1H-indol-1-yl)methyl)-[1,1'-biphenyl]-2-carboxylate (120 mg) in TFA/DCM (1 mL, 30%) was stirred at rt for 2 h. The completion of the reaction was monitored by anal. HPLC. The solvent was removed to obtain the crude which was purified by reverse phase prep-HPLC (MeOH/Acetonitrile/water) to obtain the title compound (70 mg). ESI-MS (m/z): 559 [M+H]$^+$ $^1$H NMR (400 MHz, DMSO-d$_6$): δ (ppm) 1.26 (s, 9H), 1.49 (d, J=7.2 Hz, 3H), 2.28 (s, 3H), 2.32 (s, 3H), 5.19 (quintuplet, 1H), 5.47 (s, 2H), 6.99 (d, J=8.0 Hz, 2H), 7.24 (d, J=8.0 Hz, 2H), 7.29-7.39 (m, 5H), 7.39-7.49 (m, 2H), 7.53 (t, J=7.2 Hz, 1H), 7.65 (d, J=8.4 Hz, 1H), 7.69 (d, J=7.6 Hz, 1H), 8.1 (s, 1H,), 8.58 (d, J=8.0 Hz, 1H).

Example 3

4'-((5-(Benzyl(methyl)carbamoyl)-2,3-dimethyl-1H-indol-1-yl)methyl)biphenyl-2-carboxylic acid

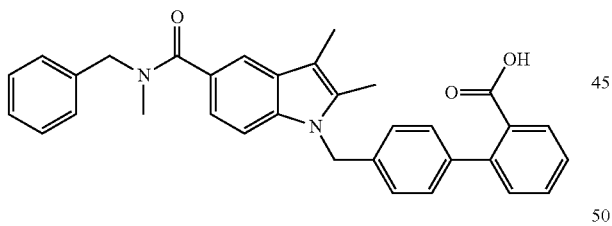

Step 1: tert-Butyl 4'-((5-(benzyl(methyl)carbamoyl)-2,3-dimethyl-1H-indol-1-yl)methyl)biphenyl-2-carboxylate

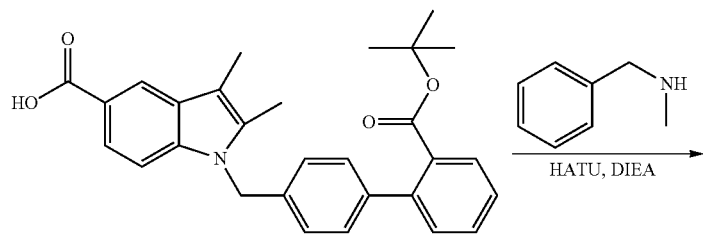

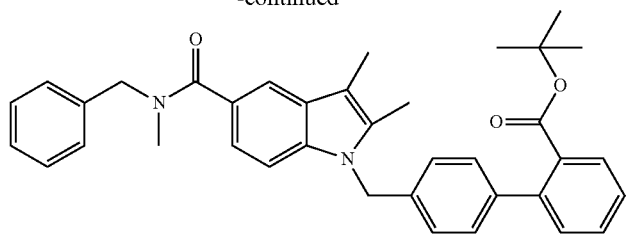

The title compound was prepared following the same general protocol as described in Step 8, Example 1, using N-methyl-1-phenylmethanamine instead of (S)-1-(4-bromophenyl)ethanamine. ESI-MS (m/z): 559 [M+H]⁺.

Step 2: 4'-((5-(Benzyl(methyl)carbamoyl)-2,3-dimethyl-1H-indol-1-yl)methyl)biphenyl-2-carboxylic acid

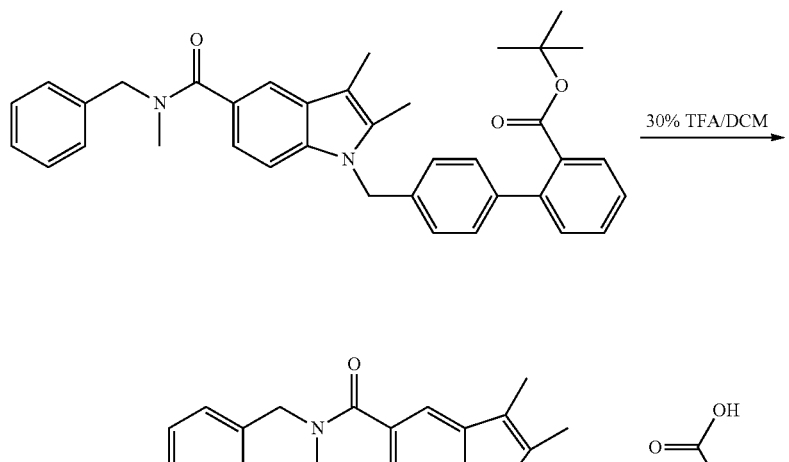

The title compound was prepared following the same general protocol as described in Step 9, Example 1. ESI-MS (m/z): 503 [M+H]⁺.

Example 4

4'-((2,3-Dimethyl-5-(3-(methylsulfonyl)benzylcarbamoyl)-1H-indol-1-yl)methyl)biphenyl-2-carboxylic acid

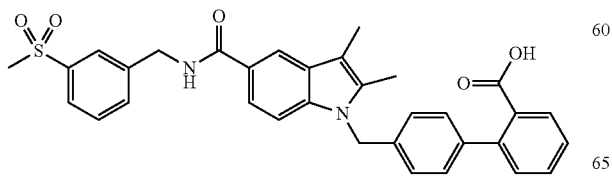

Step 1: tert-Butyl 4'-((2,3-dimethyl-5-(3-(methylsulfonyl)benzylcarbamoyl)-1H-indol-1-yl)methyl)biphenyl-2-carboxylate

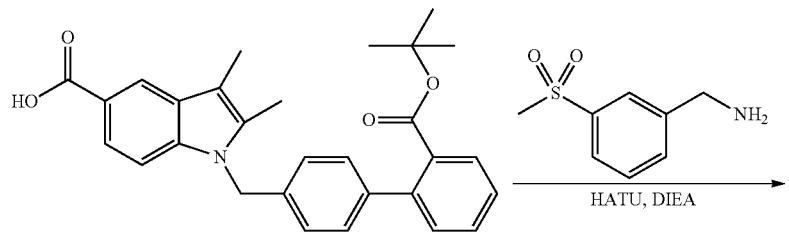

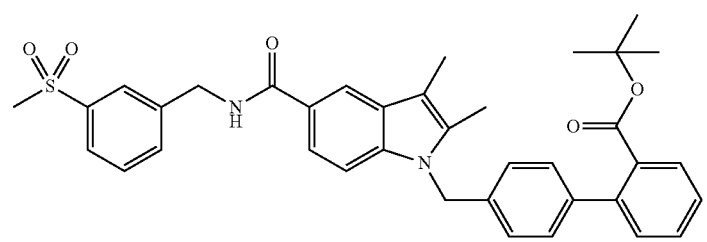

The title compound was prepared following the same general protocol as described in Step 8, Example 1, using (3-(methylsulfonyl)phenyl)methanamine instead of (S)-1-(4-bromophenyl)ethanamine. ESI-MS (m/z): 567 [M+H]$^+$-tert-butyl.

Step 2: 4'-((2,3-Dimethyl-5-(3-(methylsulfonyl)benzylcarbamoyl)-1H-indol-1-yl)methyl)biphenyl-2-carboxylic acid

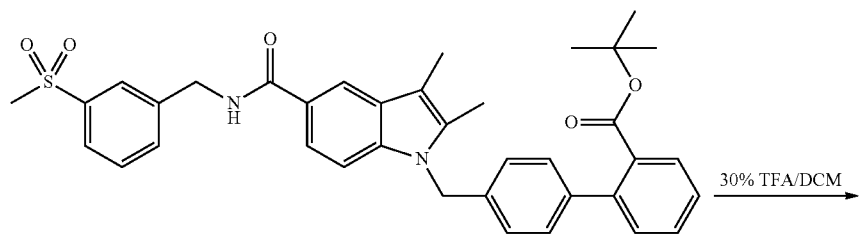

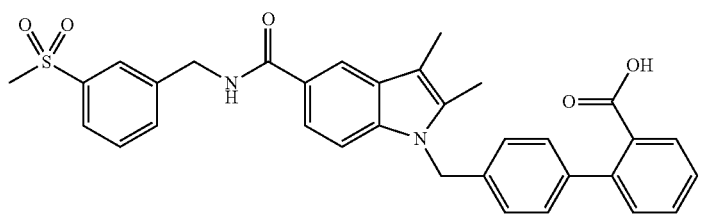

The title compound was prepared following the same general protocol as described in Step 9, Example 1. ESI-MS (m/z): 567 [M+H]⁺.

Example 5

4'-((2,3-Dimethyl-5-(3-(trifluoromethoxy)benzylcarbamoyl)-1H-indol-1-yl)methyl)biphenyl-2-carboxylic acid

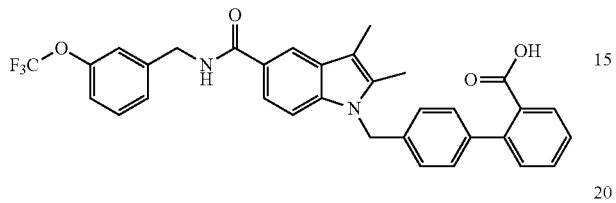

Step 1: tert-Butyl 4'-((2,3-dimethyl-5-(3-(trifluoromethoxy)benzylcarbamoyl)-1H-indol-1-yl)methyl)biphenyl-2-carboxylate

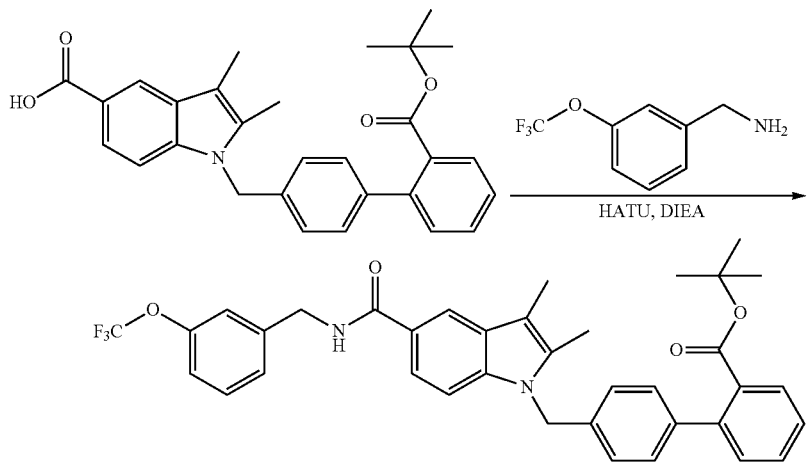

The title compound was prepared following the same general protocol as described in Step 8, Example 1, using (3-(trifluoromethoxy)phenyl)methanamine instead of (S)-1-(4-bromophenyl)ethanamine. ESI-MS (m/z): 629 [M+H]⁺.

Step 2: 4'-((2,3-Dimethyl-5-(3-(trifluoromethoxy)benzylcarbamoyl)-1H-indol-1-yl)methyl)biphenyl-2-carboxylic acid

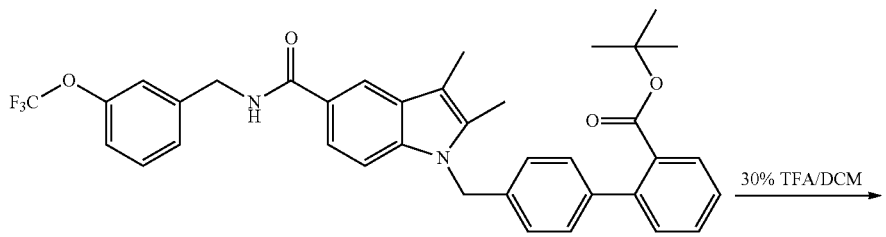

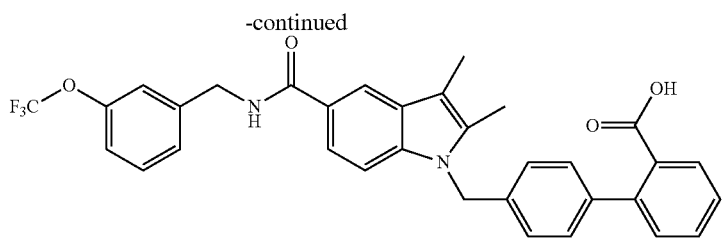

The title compound was prepared following the same general protocol as described in Step 9, Example 1. ESI-MS (m/z): 573 [M+H]⁺.

Example 6

(R)-4'-((5-(1-(4-Bromophenyl)ethylcarbamoyl)-2,3-dimethyl-1H-indol-1-yl)methyl)biphenyl-2-carboxylic acid

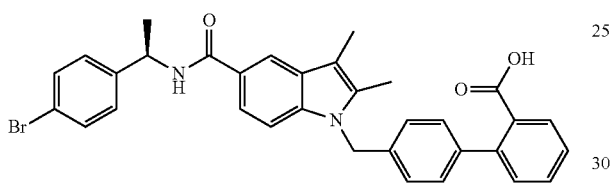

Step 1: (R)-tert-Butyl 4'-((5-(1-(4-bromophenyl)ethylcarbamoyl)-2,3-dimethyl-1H-indol-1-yl)methyl)biphenyl-2-carboxylate

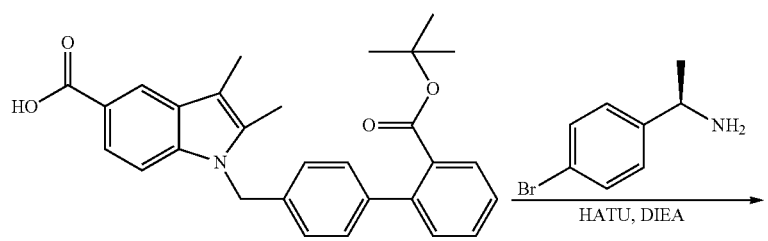

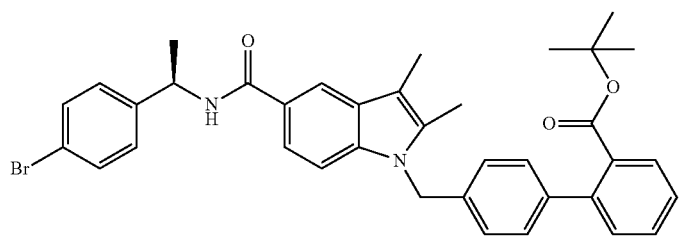

The title compound was prepared following the same general protocol as described in Step 8, Example 1, using (R)-1-(4-bromophenyl)ethanamine instead of (S)-1-(4-bromophenyl)ethanamine. ESI-MS (m/z): 637/639 [M+H]⁺.

Step 2: (R)-4'-((5-(1-(4-Bromophenyl)ethylcarbamoyl)-2,3-dimethyl-H-indol-1-yl)methyl)biphenyl-2-carboxylic acid

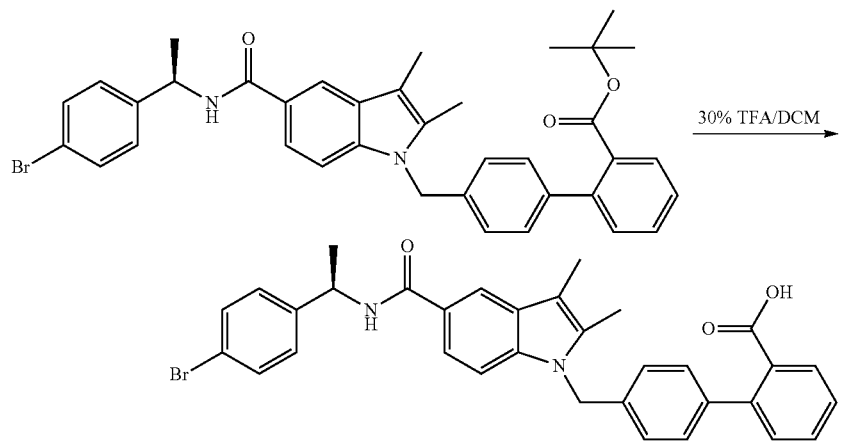

The title compound was prepared following the same general protocol as described in Step 9, Example 1. ESI-MS (m/z): 581/583 $[M+H]^+$.

Example 7

4'-((5-(4-Iodobenzylcarbamoyl)-2,3-dimethyl-1H-indol-1-yl)methyl)biphenyl-2-carboxylic acid

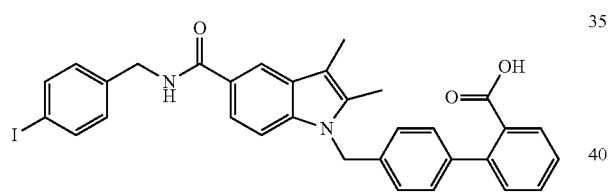

Step 1: tert-Butyl 4'-((5-(4-iodobenzylcarbamoyl)-2,3-dimethyl-1H-indol-1-yl)methyl)biphenyl-2-carboxylate

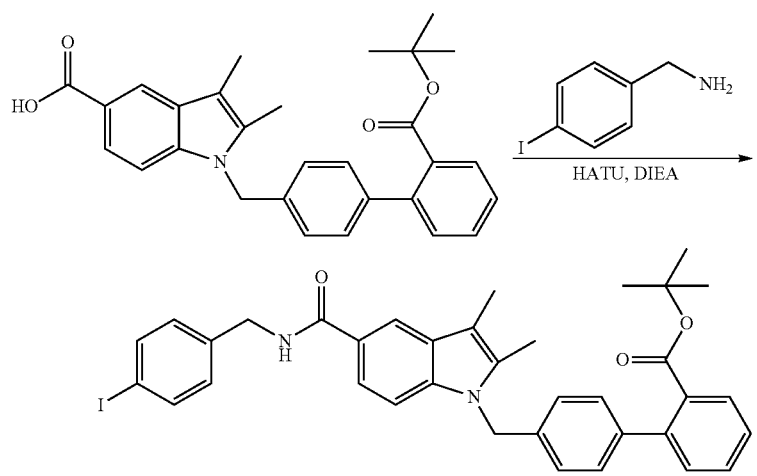

The title compound was prepared following the same general protocol as described in Step 8, Example 1, using (4-iodophenyl)methanamine instead of (S)-1-(4-bromophenyl)ethanamine. ESI-MS (m/z): 671 [M+H]$^+$.

Step 2: 4'-((5-(4-Iodobenzylcarbamoyl)-2,3-dimethyl-1H-indol-1-yl)methyl)biphenyl-2-carboxylic acid

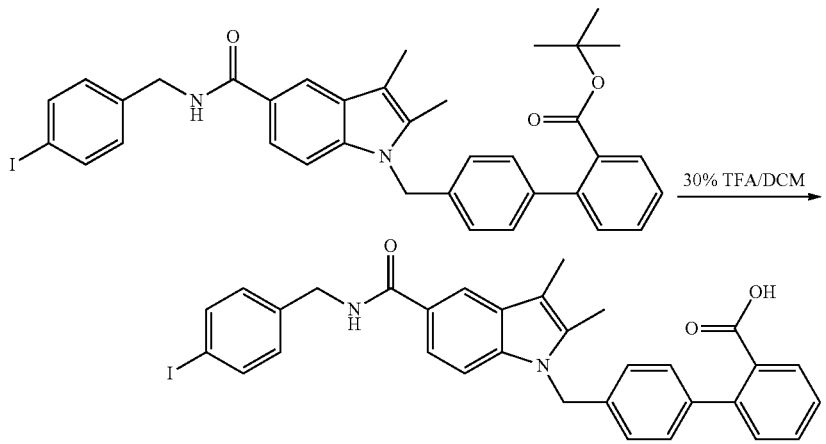

The title compound was prepared following the same general protocol as described in Step 9, Example 1. ESI-MS (m/z): 615 [M+H]$^+$.

Example 8

4'-((5-(4-Cyanobenzylcarbamoyl)-2,3-dimethyl-1H-indol-1-yl)methyl)biphenyl-2-carboxylic acid

Step 1: tert-Butyl 4'-((5-(4-cyanobenzylcarbamoyl)-2,3-dimethyl-1H-indol-1-yl)methyl)biphenyl-2-carboxylate

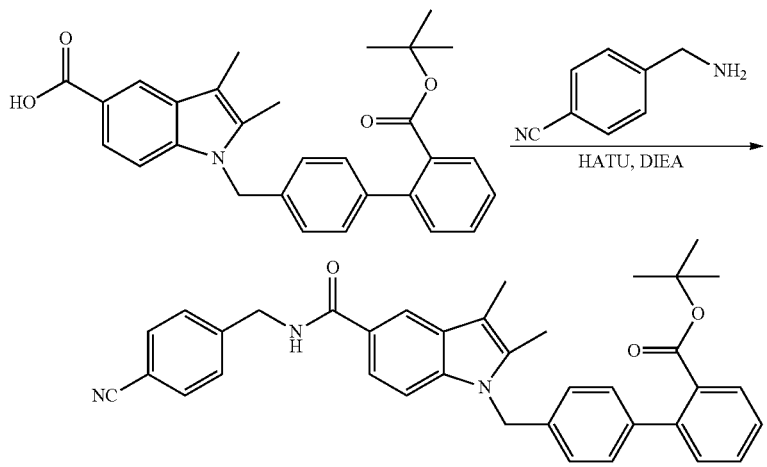

The title compound was prepared following the same general protocol as described in Step 8, Example 1, using 4-(aminomethyl)benzonitrile instead of (S)-1-(4-bromophenyl)ethanamine. ESI-MS (m/z): 514 [M+H]$^+$-tert-butyl.

Step 2: 4'-((5-(4-Cyanobenzylcarbamoyl)-2,3-dimethyl-1H-indol-1-yl)methyl)biphenyl-2-carboxylic acid

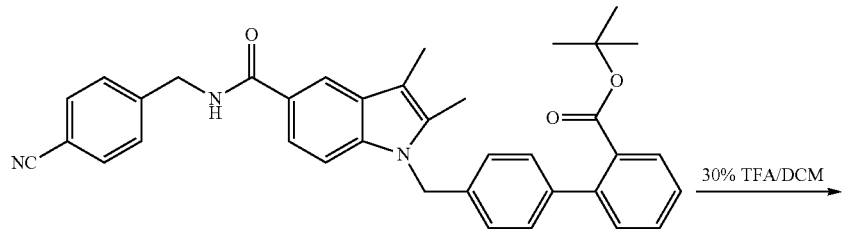

The title compound was prepared following the same general protocol as described in Step 9, Example 1. ESI-MS (m/z): 514 [M+H]$^+$.

Example 9

4'-((5-(4-Isopropylbenzylcarbamoyl)-2,3-dimethyl-1H-indol-1-yl)methyl)biphenyl-2-carboxylic acid

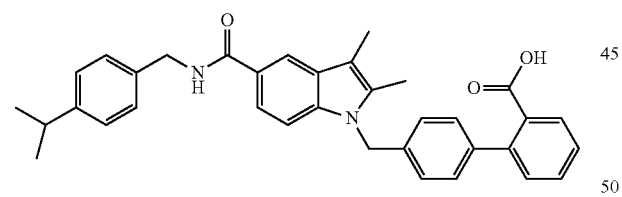

Step 1: tert-Butyl 4'-((5-(4-isopropylbenzylcarbamoyl)-2,3-dimethyl-1H-indol-1-yl)methyl)biphenyl-2-carboxylate

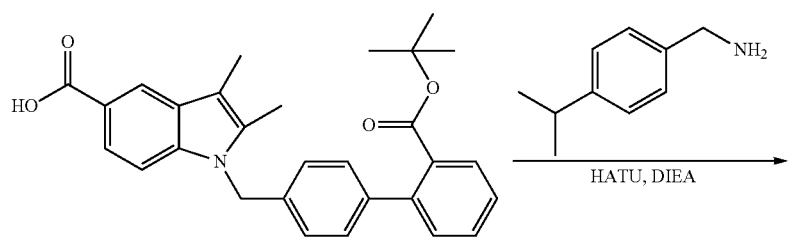

-continued

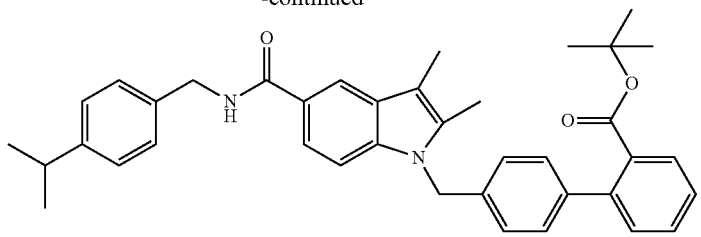

The title compound was prepared following the same general protocol as described in Step 8, Example 1, using (4-isopropylphenyl)methanamine instead of (S)-1-(4-bromophenyl)ethanamine. ESI-MS (m/z): 587 [M+H]$^+$.

Step 2: 4'-((5-(4-Isopropylbenzylcarbamoyl)-2,3-dimethyl-1H-indol-1-yl)methyl)biphenyl-2-carboxylic acid

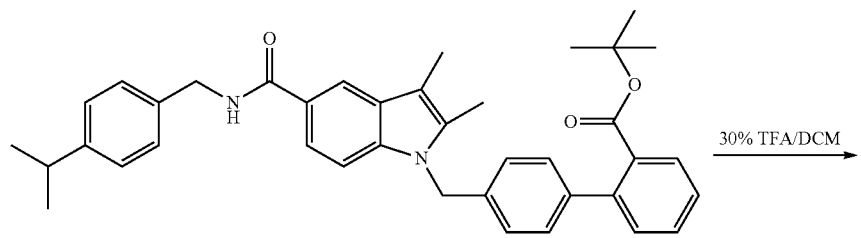

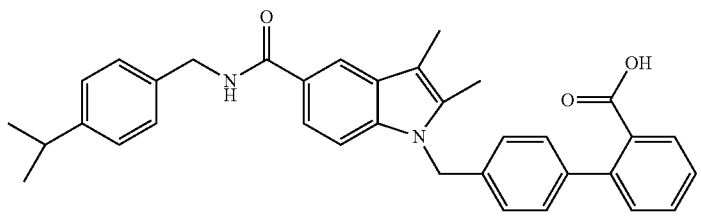

The title compound was prepared following the same general protocol as described in Step 9, Example 1. ESI-MS (m/z): 531 [M+H]$^+$.

Example 10

4'-((2,3-Dimethyl-5-(4-(methylsulfonyl)benzylcarbamoyl)-1H-indol-1-yl)methyl)biphenyl-2-carboxylic acid

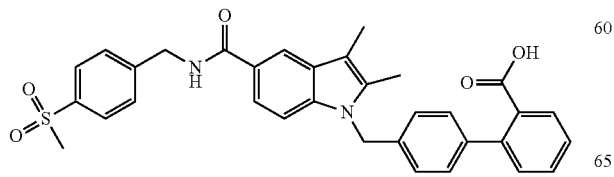

Step 1: tert-Butyl 4'-((2,3-dimethyl-5-(4-(methylsulfonyl)benzylcarbamoyl)-1H-indol-1-yl)methyl)biphenyl-2-carboxylate

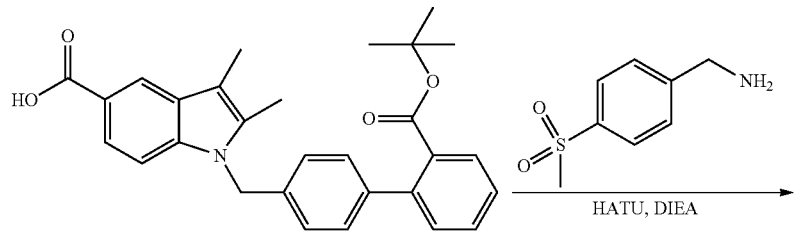

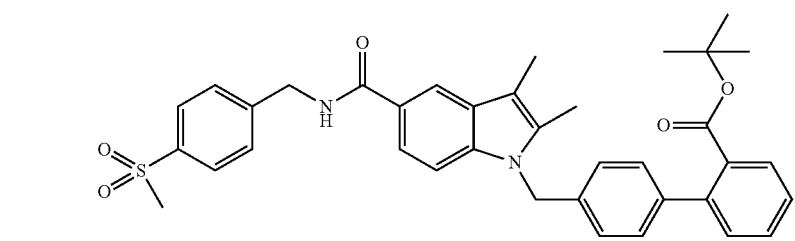

The title compound was prepared following the same general protocol as described in Step 8, Example 1, using (4-(methylsulfonyl)phenyl)methanamine instead of (S)-1-(4-bromophenyl)ethanamine. ESI-MS (m/z): 567 [M+H]$^+$-tert-butyl.

Step 2: 4'-((2,3-Dimethyl-5-(4-(methylsulfonyl)benzylcarbamoyl)-1H-indol-1-yl)methyl)biphenyl-2-carboxylic acid

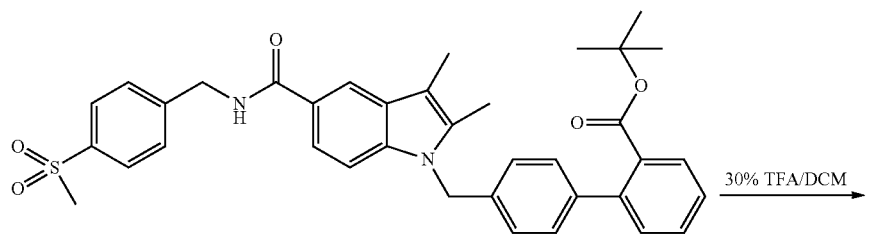

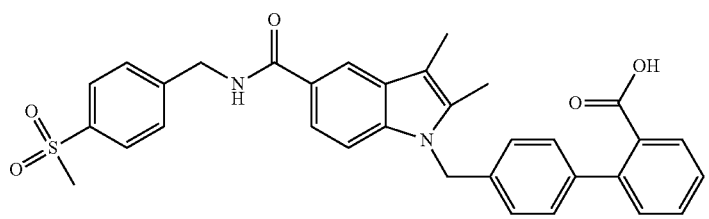 [SMILES: Cc1c(C)n(Cc2ccc(-c3ccccc3C(=O)O)cc2)c2ccc(C(=O)NCc3ccc(S(C)(=O)=O)cc3)cc12]

The title compound was prepared following the same general protocol as described in Step 9, Example 1. ESI-MS (m/z): 567 [M+H]$^+$.

Example 11

4'-((5-(4-(Dimethylamino)benzylcarbamoyl)-2,3-dimethyl-1H-indol-1-yl)methyl)biphenyl-2-carboxylic acid

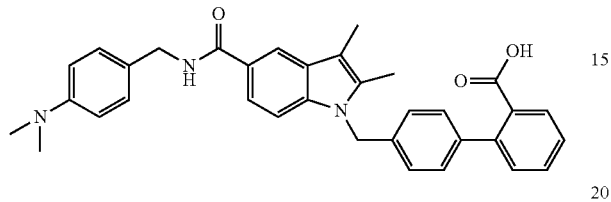

Step 1: tert-Butyl 4'-((5-(4-(dimethylamino)benzylcarbamoyl)-2,3-dimethyl-1H-indol-1-yl)methyl)biphenyl-2-carboxylate

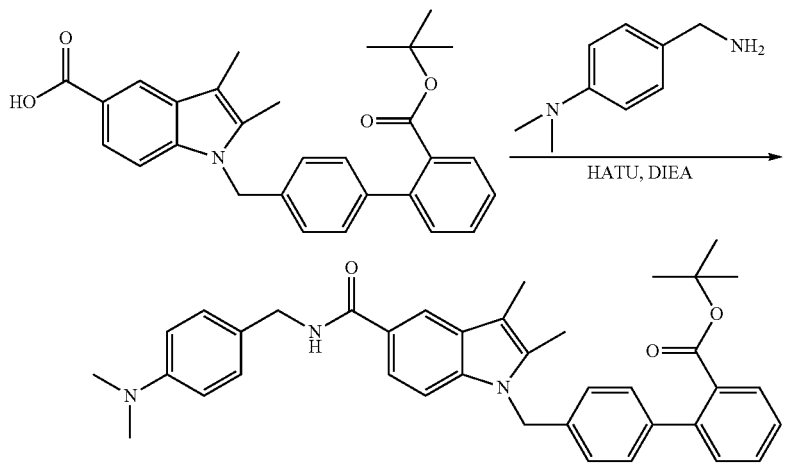

The title compound was prepared following the same general protocol as described in Step 8, Example 1, using 4-(aminomethyl)-N,N-dimethylaniline instead of (S)-1-(4-bromophenyl)ethanamine. ESI-MS (m/z): 588 [M+H]$^+$.

Step 2: 4'-((5-(4-(Dimethylamino)benzylcarbamoyl)-2,3-dimethyl-1H-indol-1-yl)methyl)biphenyl-2-carboxylic acid

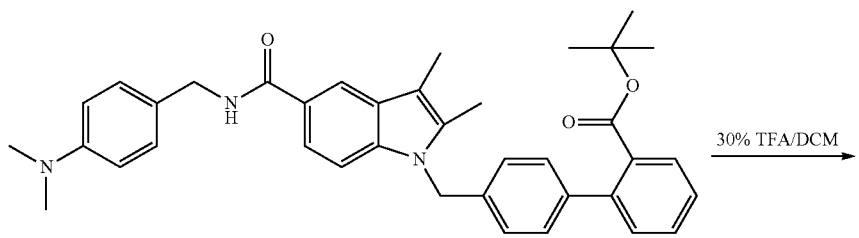

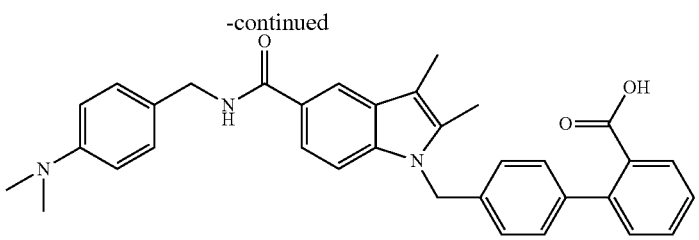

The title compound was prepared following the same general protocol as described in Step 9, Example 1. ESI-MS (m/z): 532 [M+H]⁺.

Example 12

4'-((5-(4-Bromobenzylcarbamoyl)-2,3-dimethyl-1H-indol-1-yl)methyl)biphenyl-2-carboxylic acid

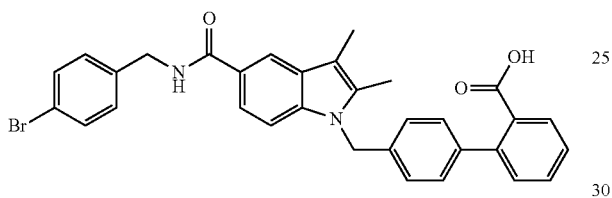

Step 1: tert-Butyl 4'-((5-(4-bromobenzylcarbamoyl)-2,3-dimethyl-1H-indol-1-yl)methyl)biphenyl-2-carboxylate

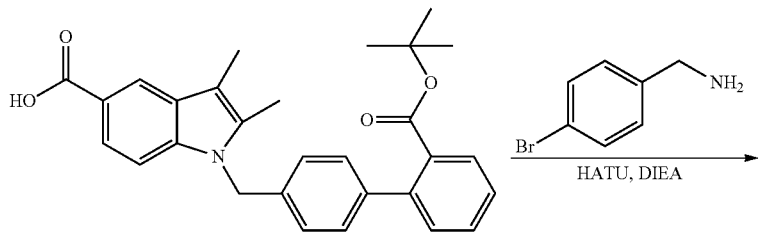

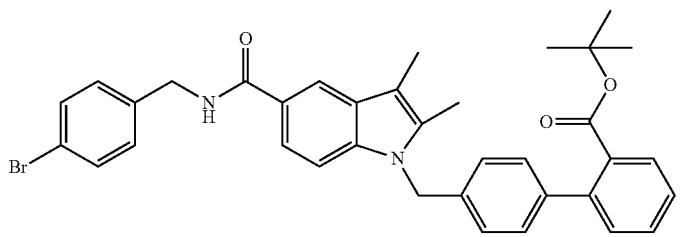

The title compound was prepared following the same general protocol as described in Step 8, Example 1, using (4-bromophenyl)methanamine instead of(S)-1-(4-bromophenyl)ethanamine. ESI-MS (m/z): 567/569, [M+H]⁺-tert-butyl.

Step 2: 4'-((5-(4-Bromobenzylcarbamoyl)-2,3-dimethyl-1H-indol-1-yl)methyl)biphenyl-2-carboxylic acid

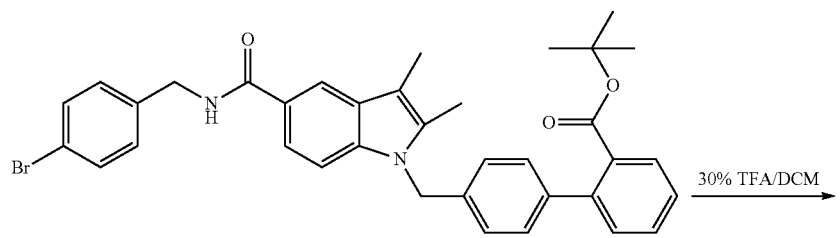

30% TFA/DCM

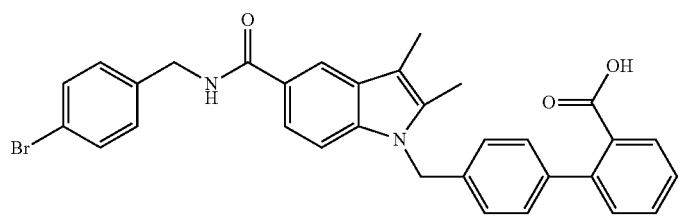

The title compound was prepared following the same general protocol as described in Step 9, Example 1. ESI-MS (m/z): 567/569 [M+H]$^+$.

Example 13

4'-((5-(4-tert-Butylbenzylcarbamoyl)-2,3-dimethyl-1H-indol-1-yl)methyl)biphenyl-2-carboxylic acid

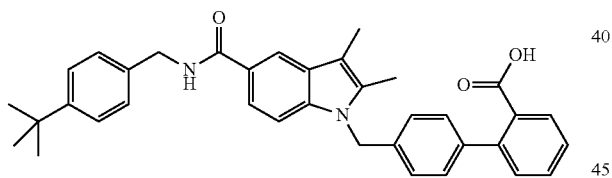

Step 1: tert-Butyl 4'-((5-(4-tert-butylbenzylcarbamoyl)-2,3-dimethyl-1H-indol-1-yl)methyl)biphenyl-2-carboxylate

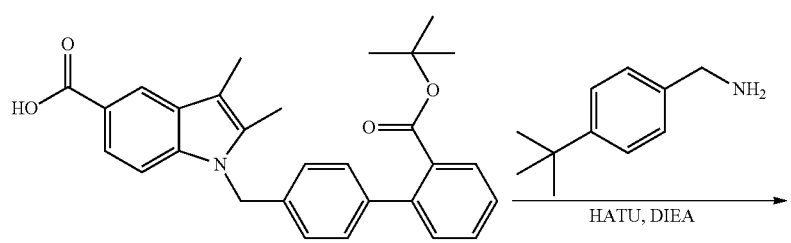

HATU, DIEA

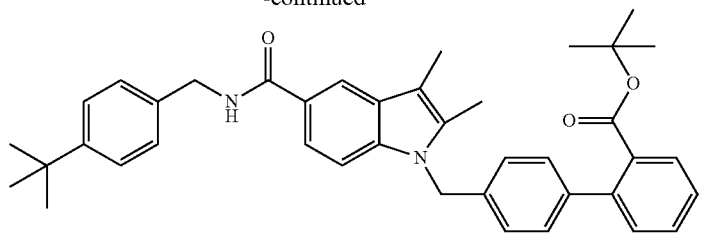

The title compound was prepared following the same general protocol as described in Step 8, Example 1, using (4-tert-butylphenyl)methanamine instead of (S)-1-(4-bromophenyl)ethanamine. ESI-MS (m/z): 601 [M+H]$^+$.

Step 2: 4'-((5-(4-tert-Butylbenzylcarbamoyl)-2,3-dimethyl-1H-indol-1-yl)methyl)biphenyl-2-carboxylic acid

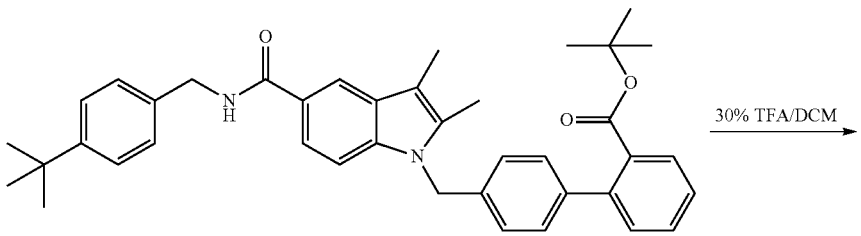

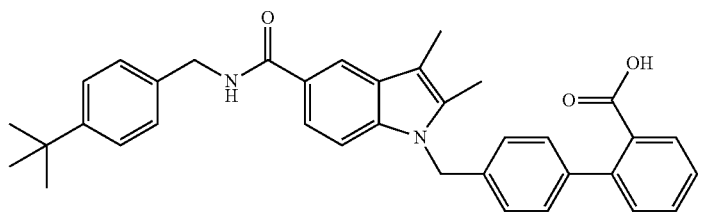

The title compound was prepared following the same general protocol as described in Step 9, Example 1. ESI-MS (m/z): 545 [M+H]$^+$.

Example 14

4'-((5-(4-Chlorobenzylcarbamoyl)-2,3-dimethyl-1H-indol-1-yl)methyl)biphenyl-2-carboxylic acid

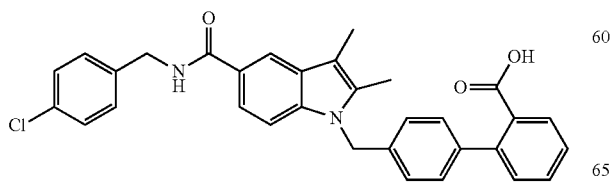

Step 1: tert-Butyl 4'-((5-(4-chlorobenzylcarbamoyl)-2,3-dimethyl-1H-indol-1-yl)methyl)biphenyl-2-carboxylate

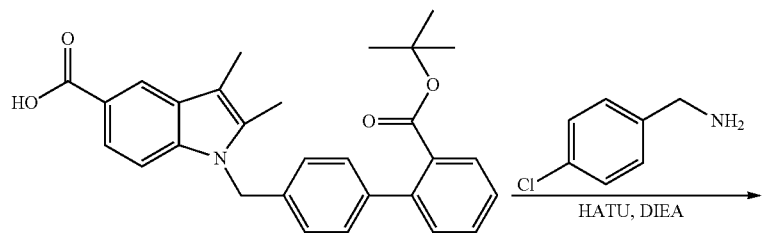

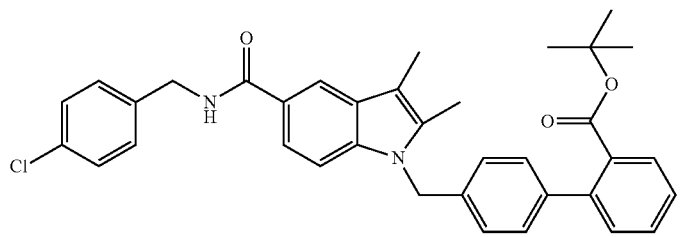

The title compound was prepared following the same general protocol as described in Step 8, Example 1, using (4-chlorophenyl)methanamine instead of (S)-1-(4-bromophenyl)ethanamine. ESI-MS (m/z): 523 [M+H]⁺-tert-butyl.

Step 2: 4'-((5-(4-Chlorobenzylcarbamoyl)-2,3-dimethyl-1H-indol-1-yl)methyl)biphenyl-2-carboxylic acid

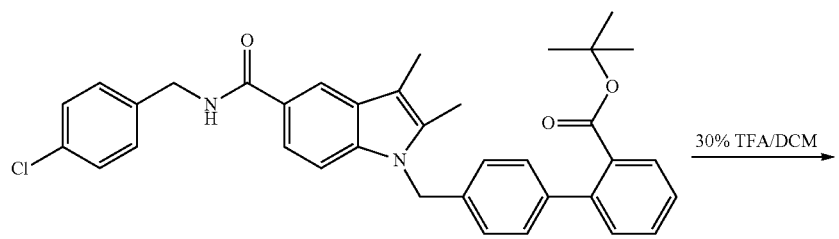

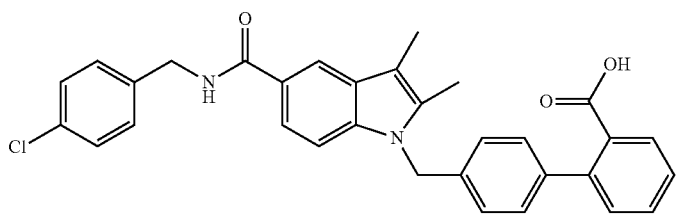

The title compound was prepared following the same general protocol as described in Step 9, Example 1. ESI-MS (m/z): 523 [M+H]$^+$.

Example 15

4'-((2,3-Dimethyl-5-(4-(trifluoromethoxy)benzylcarbamoyl)-1H-indol-1-yl)methyl)biphenyl-2-carboxylic acid

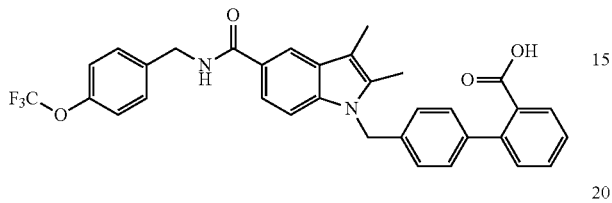

Step 1: tert-Butyl 4'-((2,3-dimethyl-5-(4-(trifluoromethoxy)benzylcarbamoyl)-1H-indol-1-yl)methyl)biphenyl-2-carboxylate

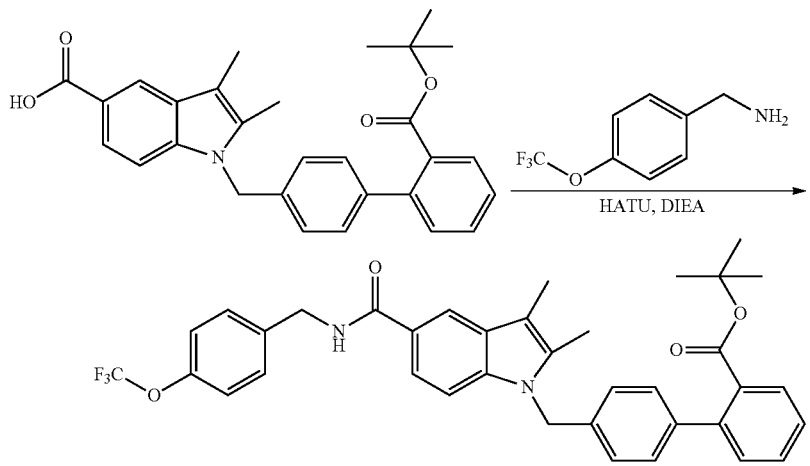

The title compound was prepared following the same general protocol as described in Step 8, Example 1, using (4-(trifluoromethoxy)phenyl)methanamine instead of (S)-1-(4-bromophenyl)ethanamine. ESI-MS (m/z): 573 [M+H]$^+$-tert-butyl.

Step 2: 4'-((2,3-Dimethyl-5-(4-(trifluoromethoxy)benzylcarbamoyl)-1H-indol-1-yl)methyl)biphenyl-2-carboxylic acid

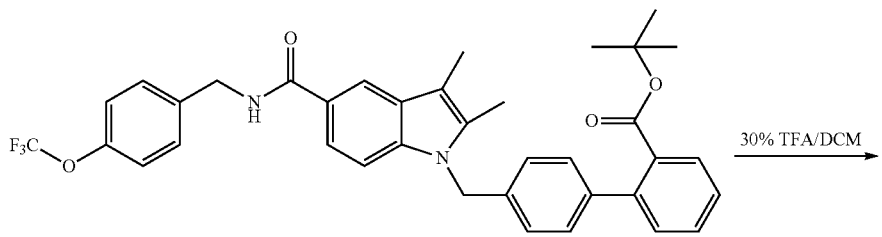

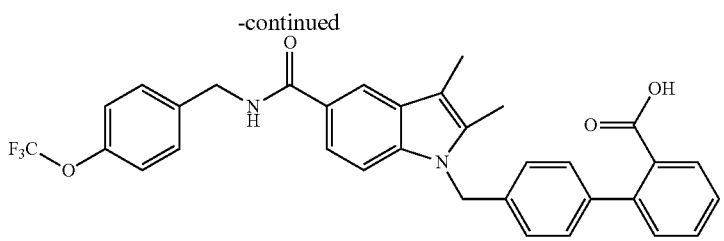

The title compound was prepared following the same general protocol as described in Step 9, Example 1. ESI-MS (m/z): 573 [M+H]⁺.

Example 16

4'-((5-(4-(Methoxycarbonyl)benzylcarbamoyl)-2,3-dimethyl-1H-indol-1-yl)methyl)biphenyl-2-carboxylic acid

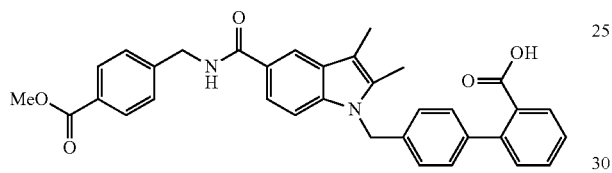

Step 1: tert-Butyl 4'-((5-(4-(methoxycarbonyl)benzylcarbamoyl)-2,3-dimethyl-H-indol-1-yl)methyl)biphenyl-2-carboxylate

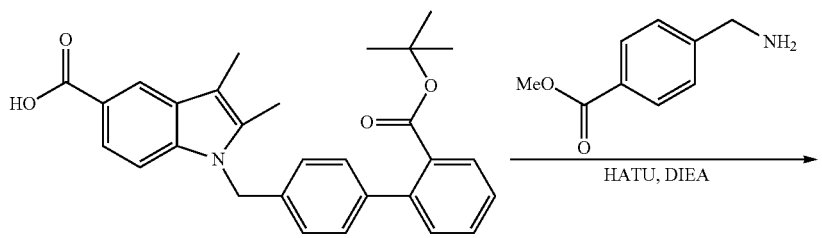

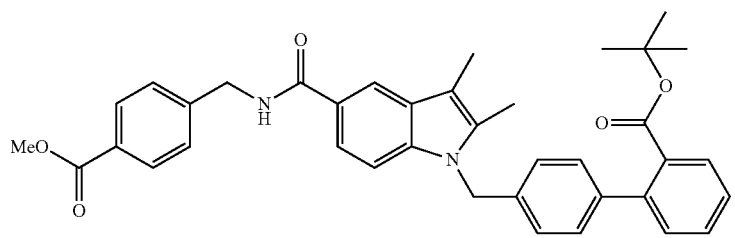

The title compound was prepared following the same general protocol as described in Step 8, Example 1, using methyl 4-(aminomethyl)benzoate instead of (S)-1-(4-bromophenyl)ethanamine. ESI-MS (m/z): 547 [M+H]⁺-tert-butyl.

Step 2: 4'-((5-(4-(Methoxycarbonyl)benzylcarbamoyl)-2,3-dimethyl-1H-indol-1-yl)methyl)biphenyl-2-carboxylic acid

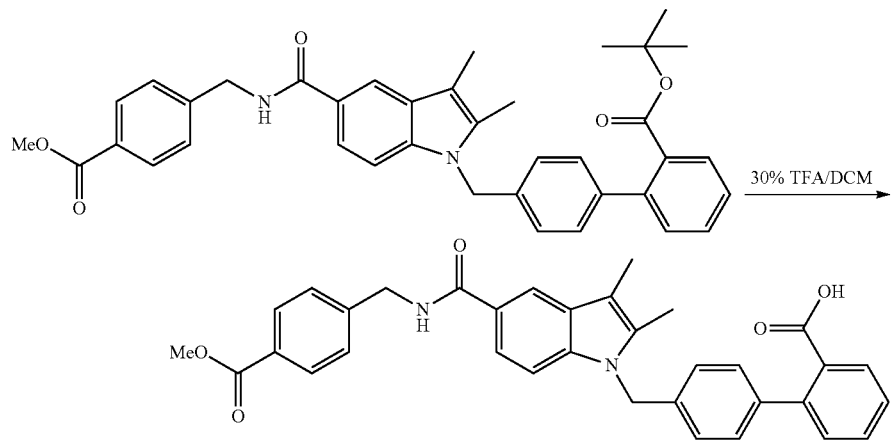

The title compound was prepared following the same general protocol as described in Step 9, Example 1. ESI-MS (m/z): 547 [M+H]$^+$.

Example 17

4'-((2,3-Dimethyl-5-(4-sulfamoylbenzylcarbamoyl)-1H-indol-1-yl)methyl)biphenyl-2-carboxylic acid

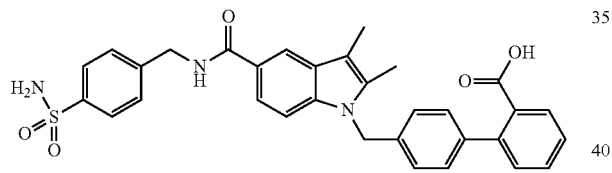

Step 1: tert-Butyl 4'-((2,3-dimethyl-5-(4-sulfamoylbenzylcarbamoyl)-1H-indol-1-yl)methyl)biphenyl-2-carboxylate

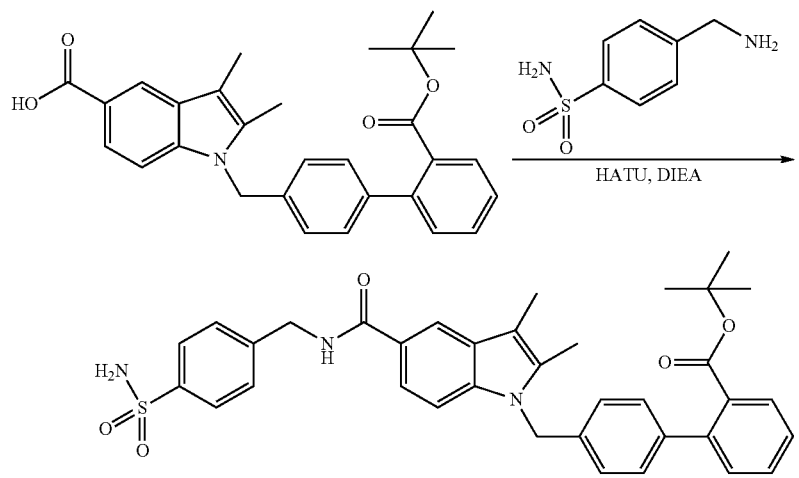

The title compound was prepared following the same general protocol as described in Step 8, Example 1, using 4-(aminomethyl)benzenesulfonamide instead of (S)-1-(4-bromophenyl)ethanamine. ESI-MS (m/z): 568 [M+H]$^+$-tert-butyl.

Step 2: 4'-((2,3-Dimethyl-5-(4-sulfamoylbenzylcarbamoyl)-1H-indol-1-yl)methyl)biphenyl-2-carboxylic acid

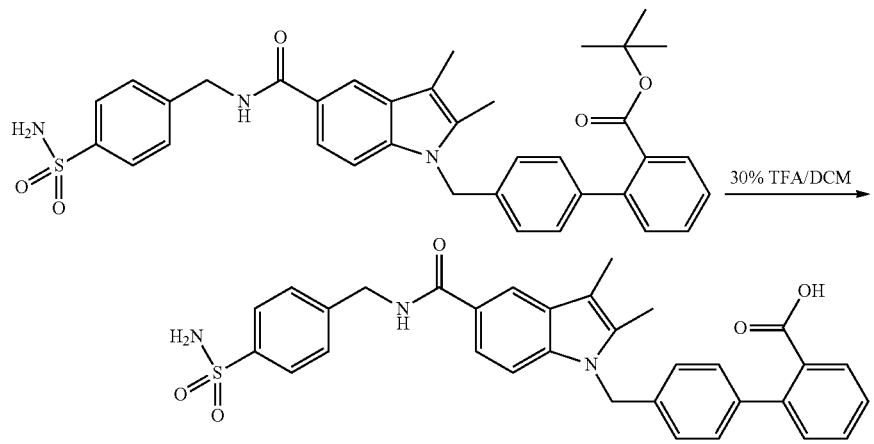

The title compound was prepared following the same general protocol as described in Step 9, Example 1. ESI-MS (m/z): 568 [M+H]$^+$.

Example 18

4'-((2,3-Dimethyl-5-(4-(methylthio)benzylcarbamoyl)-1H-indol-1-yl)methyl)biphenyl-2-carboxylic acid

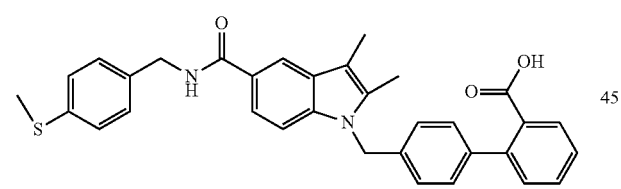

Step 1: tert-Butyl 4'-((2,3-dimethyl-5-(4-(methylthio)benzylcarbamoyl)-1H-indol-1-yl)methyl)biphenyl-2-carboxylate

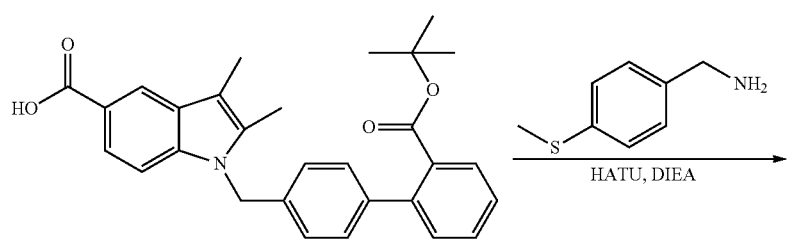

-continued

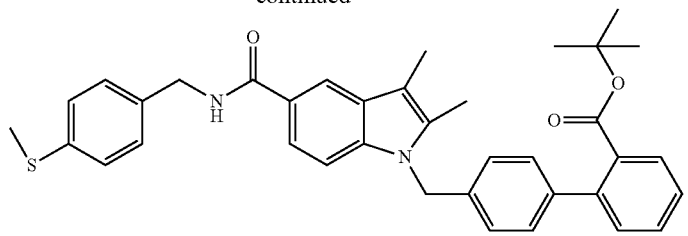

The title compound was prepared following the same general protocol as described in Step 8, Example 1, using (4-(methylthio)phenyl)methanamine instead of (S)-1-(4-bromophenyl)ethanamine. ESI-MS (m/z): 591 [M+H]$^+$.

Step 2: 4'-((2,3-Dimethyl-5-(4-(methylthio)benzylcarbamoyl)-1H-indol-1-yl)methyl)biphenyl-2-carboxylic acid

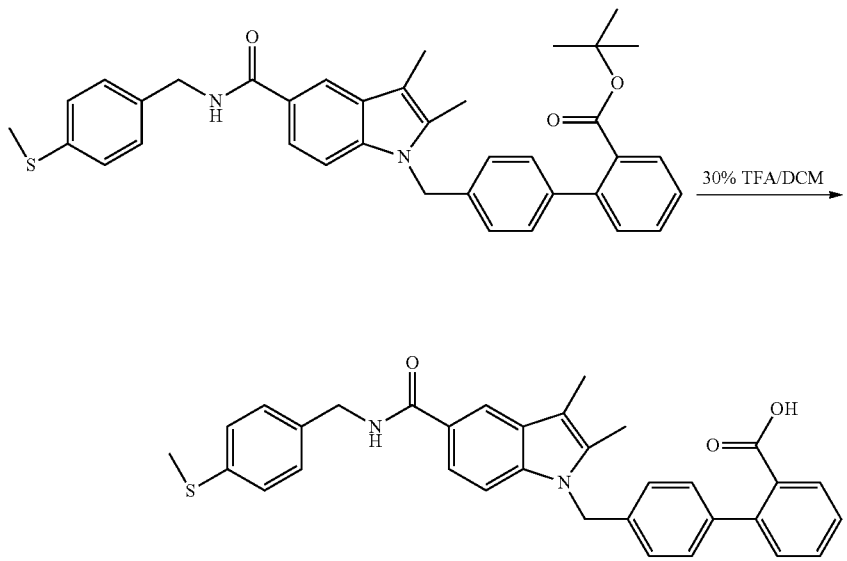

The title compound was prepared following the same general protocol as described in Step 9, Example 1. ESI-MS (m/z): 535 [M+H]$^+$.

Example 19

(S)-4'-((5-(1-(4-Methoxyphenyl)ethylcarbamoyl)-2,3-dimethyl-1H-indol-1-yl)methyl)biphenyl-2-carboxylic acid

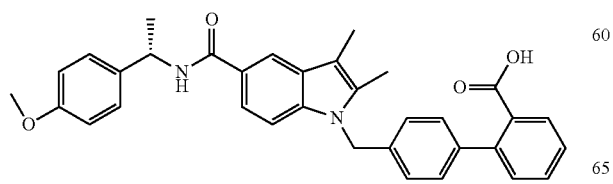

Step 1: (S)-tert-Butyl 4'-((5-(1-(4-methoxyphenyl)ethylcarbamoyl)-2,3-dimethyl-1H-indol-1-yl)methyl)biphenyl-2-carboxylate

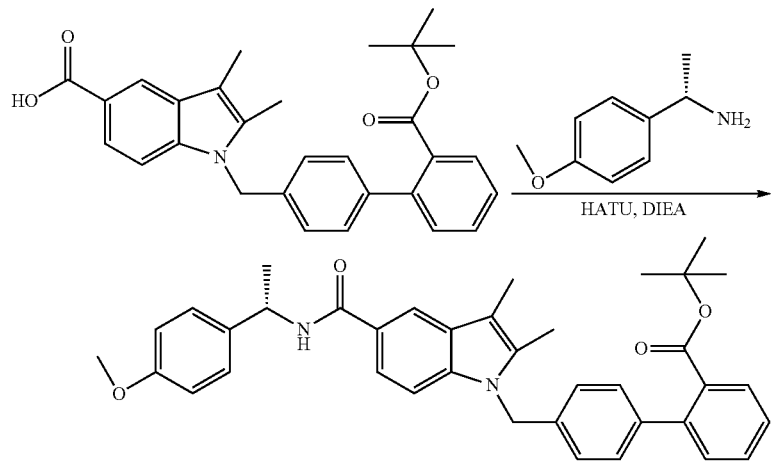

The title compound was prepared following the same general protocol as described in Step 8, Example 1, using (S)-1-(4-methoxyphenyl)ethanamine instead of (S)-1-(4-bromophenyl)ethanamine. ESI-MS (m/z): 589 [M+H]$^+$.

Step 2: (S)-4'-((5-(1-(4-Methoxyphenyl)ethylcarbamoyl)-2,3-dimethyl-1H-indol-1-yl)methyl)biphenyl-2-carboxylic acid

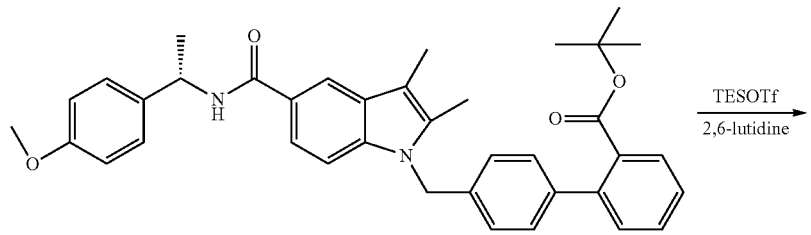

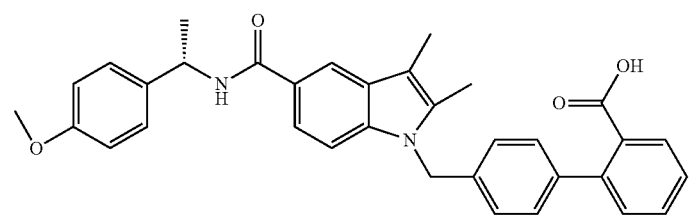

To a mixture of (S)-tert-butyl 4'-((5-(1-(4-methoxyphenyl)ethylcarbamoyl)-2,3-dimethyl-1H-indol-1-yl)methyl)biphenyl-2-carboxylate (58.9 mg, 0.1 mmol) and 2,6-lutidine (0.13 mL, 1.15 mmol) in DCM (1 mL) at 0° C. was added TESOTf (0.17 mL, 0.75 mmol). The reaction mixture was stirred at rt for 2 h. The completion of the reaction was monitored by anal. HPLC. The mixture was evaporated in vacuo to obtain the crude which was purified by prep. HPLC (MeOH/Acetonitrile/water) to obtain the title compound. ESI-MS (m/z): 533 [M+H]$^+$.

Example 20

4'-((5-(2,4-Dimethoxybenzylcarbamoyl)-2,3-dimethyl-1H-indol-1-yl)methyl)biphenyl-2-carboxylic acid

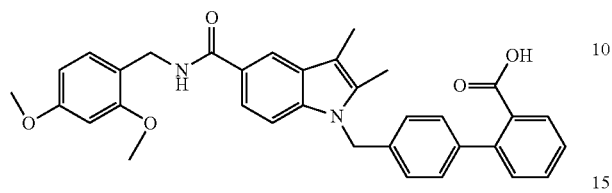

Step 1: tert-Butyl 4'-((5-(2,4-dimethoxybenzylcarbamoyl)-2,3-dimethyl-1H-indol-1-yl)methyl)biphenyl-2-carboxylate

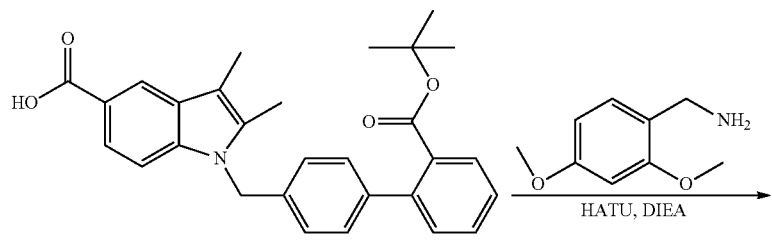

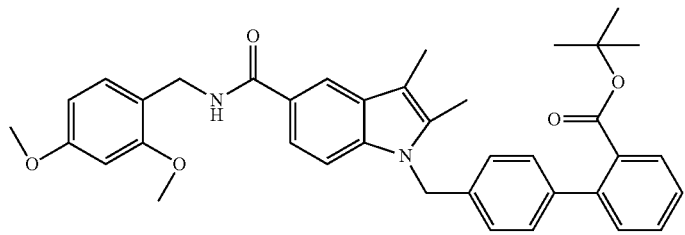

The title compound was prepared following the same general protocol as described in Step 8, Example 1, using (2,4-dimethoxyphenyl)methanamine instead of (S)-1-(4-bromophenyl)ethanamine. ESI-MS (m/z): 605 [M+H]$^+$.

Step 2: 4'-((5-(2,4-Dimethoxybenzylcarbamoyl)-2,3-dimethyl-1H-indol-1-yl)methyl)biphenyl-2-carboxylic acid

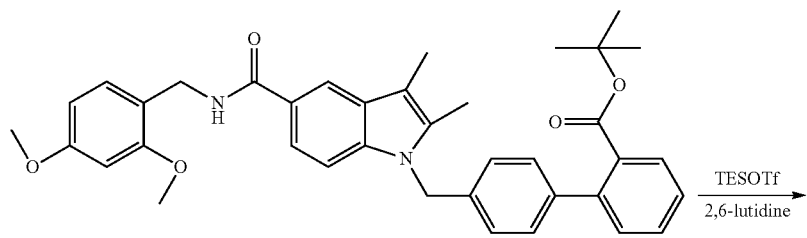

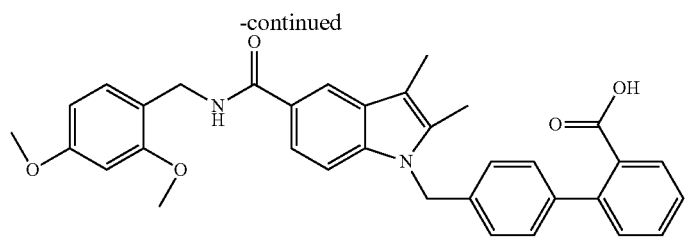

The title compound was prepared following the same general protocol as described in Step 2, Example 19. ESI-MS (m/z): 549 [M+H]⁺.

Example 21

(S)-4'-((5-(1-(3-Methoxyphenyl)ethylcarbamoyl)-2,3-dimethyl-1H-indol-1-yl)methyl)biphenyl-2-carboxylic acid

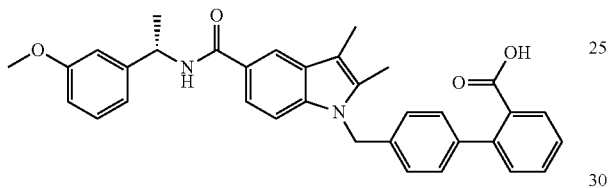

Step 1: (S)-tert-Butyl 4'-((5-(1-(3-methoxyphenyl)ethylcarbamoyl)-2,3-dimethyl-1H-indol-1-yl)methyl)biphenyl-2-carboxylate

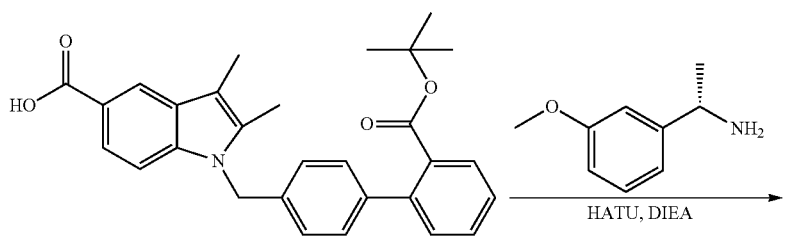

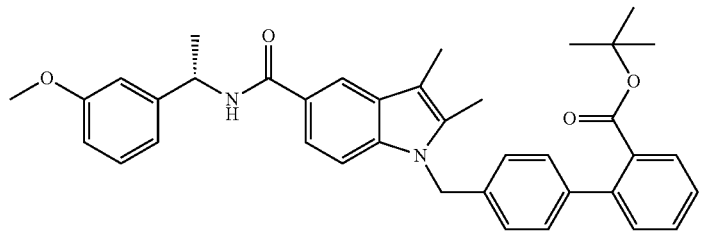

The title compound was prepared following the same general protocol as described in Step 8, Example 1, using (S)-1-(3-methoxyphenyl)ethanamine instead of (S)-1-(4-bromophenyl)ethanamine. ESI-MS (m/z): 589 [M+H]⁺.

Step 2: (S)-4'-((5-(1-(3-Methoxyphenyl)ethylcarbamoyl)-2,3-dimethyl-1H-indol-1-yl)methyl)biphenyl-2-carboxylic acid

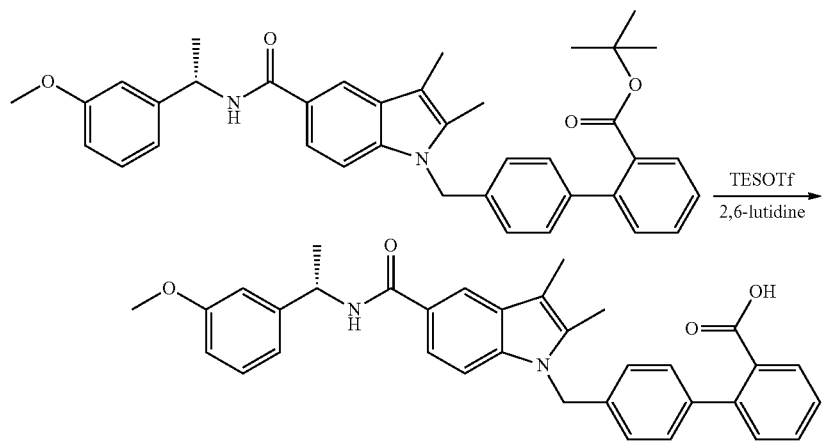

The title compound was prepared following the same general protocol as described in Step 2, Example 19. ESI-MS (m/z): 533 [M+H]$^+$.

Example 22

4'-((5-(3,5-Dimethoxybenzylcarbamoyl)-2,3-dimethyl-1H-indol-1-yl)methyl)biphenyl-2-carboxylic acid

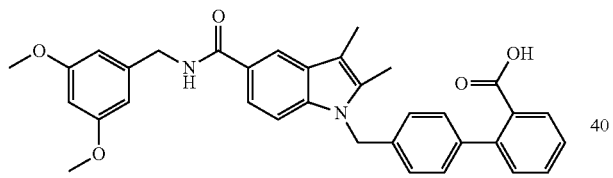

Step 1: tert-Butyl 4'-((5-(3,5-dimethoxybenzylcarbamoyl)-2,3-dimethyl-1H-indol-1-yl)methyl)biphenyl-2-carboxylate

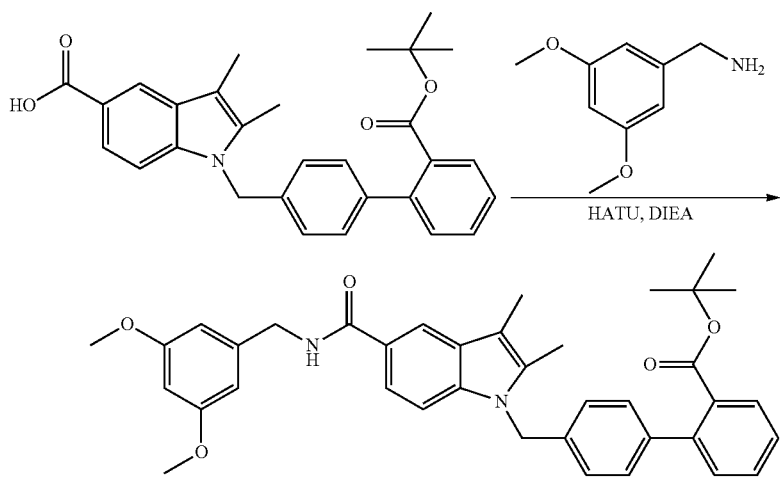

The title compound was prepared following the same general protocol as described in Step 8, Example 1, using (3,5-dimethoxyphenyl)methanamine instead of (S)-1-(4-bromophenyl)ethanamine. ESI-MS (m/z): 605 [M+H]$^+$.

Step 2: 4'-((5-(3,5-Dimethoxybenzylcarbamoyl)-2,3-dimethyl-1H-indol-1-yl)methyl)biphenyl-2-carboxylic acid

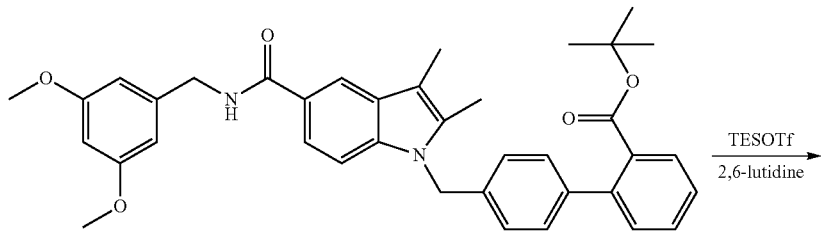

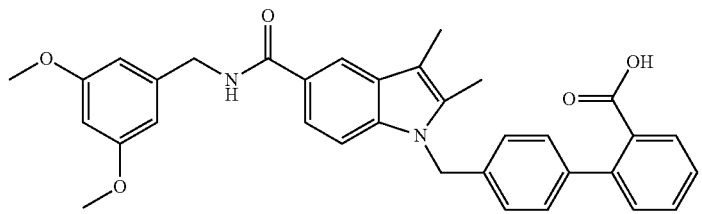

The title compound was prepared following the same general protocol as described in Step 2, Example 19. ESI-MS (m/z): 549 [M+H]$^+$.

Example 23

(R)-4'-((5-(1-(4-Methoxyphenyl)ethylcarbamoyl)-2,3-dimethyl-1H-indol-1-yl)methyl)biphenyl-2-carboxylic acid

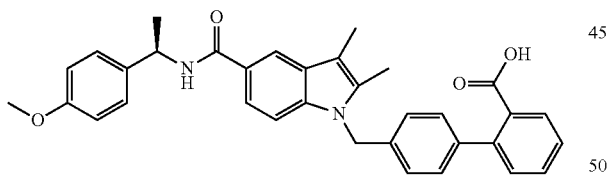

Step 1: (R)-tert-Butyl 4'-((5-(1-(4-methoxyphenyl)ethylcarbamoyl)-2,3-dimethyl-1H-indol-1-yl)methyl)biphenyl-2-carboxylate

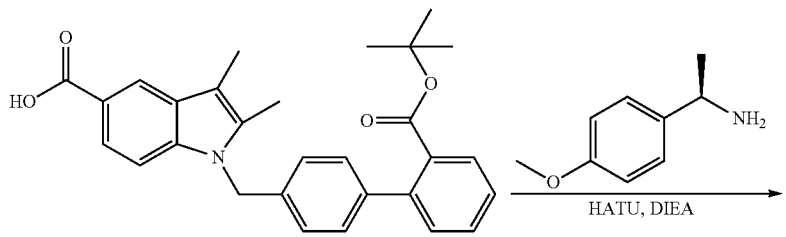

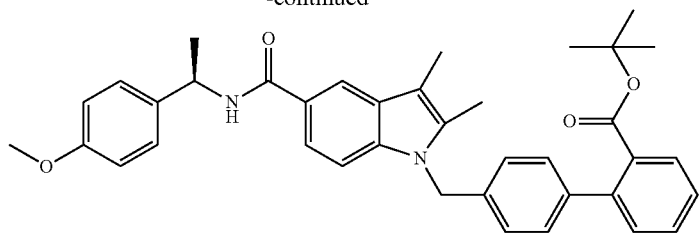

The title compound was prepared following the same general protocol as described in Step 8, Example 1, using (R)-1-(4-methoxyphenyl)ethanamine instead of (S)-1-(4-bromophenyl)ethanamine. ESI-MS (m/z): 589 [M+H]$^+$.

Step 2: (R)-4'-((5-(1-(4-Methoxyphenyl)ethylcarbamoyl)-2,3-dimethyl-1H-indol-1-yl)methyl)biphenyl-2-carboxylic acid

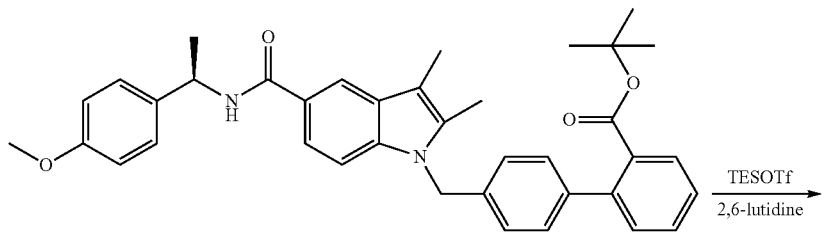

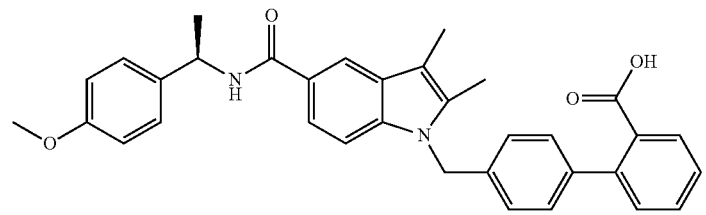 [SMILES: COc1ccc([C@@H](C)NC(=O)c2ccc3c(c2)c(C)c(C)n3Cc2ccc(-c3ccccc3C(=O)O)cc2)cc1]

The title compound was prepared following the same general protocol as described in Step 2, Example 19. ESI-MS (m/z): 533 [M+H]$^+$.

Example 24

4'-((5-(3,4-Dimethoxybenzylcarbamoyl)-2,3-dimethyl-1H-indol-1-yl)methyl)biphenyl-2-carboxylic acid

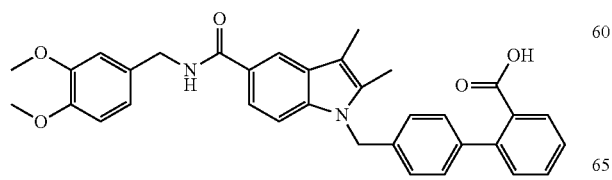

Step 1: tert-Butyl 4'-((5-(3,4-dimethoxybenzylcarbamoyl)-2,3-dimethyl-1H-indol-1-yl)methyl)biphenyl-2-carboxylate

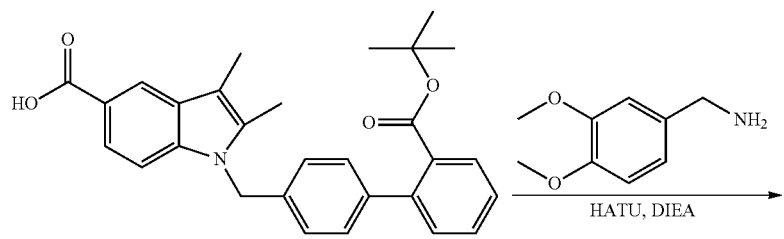

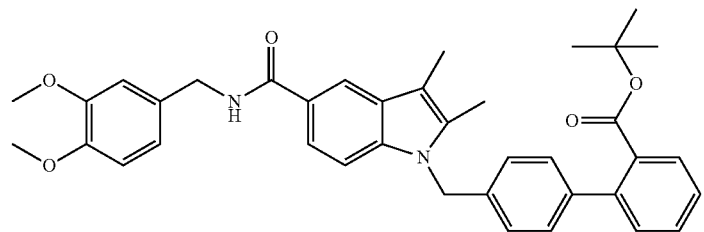

The title compound was prepared following the same general protocol as described in Step 8, Example 1, using (3,4-dimethoxyphenyl)methanamine instead of (S)-1-(4-bromophenyl)ethanamine. ESI-MS (m/z): 605 [M+H]$^+$.

Step 2: 4'-((5-(3,4-Dimethoxybenzylcarbamoyl)-2,3-dimethyl-1H-indol-1-yl)methyl)biphenyl-2-carboxylic acid

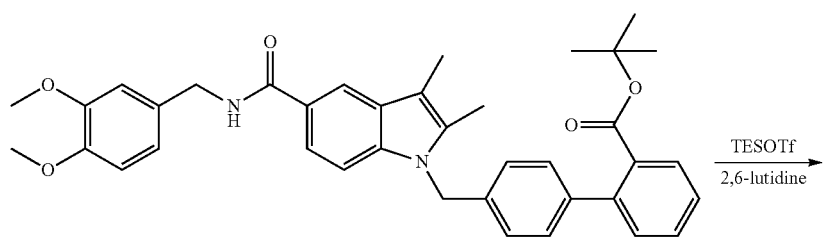

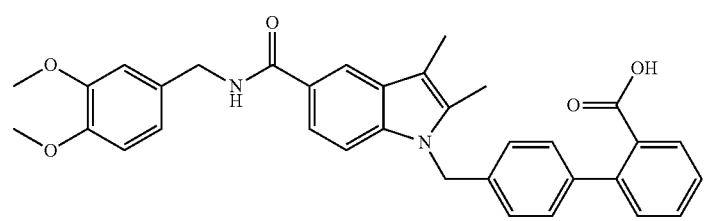

The title compound was prepared following the same general protocol as described in Step 2, Example 19. ESI-MS (m/z): 549 [M+H]⁺.

Example 25

4'-((2,3-Dimethyl-5-((2-phenylpropan-2-yl)carbamoyl)-1H-indol-1-yl)methyl)-[1,1'-biphenyl]-2-carboxylic acid

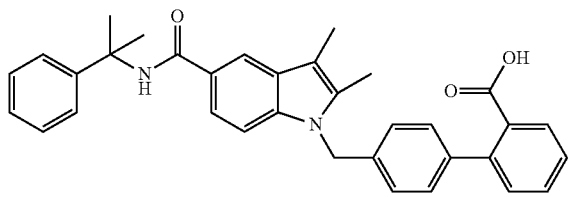

Step 1: tert-Butyl 4'-((2,3-dimethyl-5-((2-phenylpropan-2-yl)carbamoyl)-1H-indol-1-yl)methyl)-[1,1'-biphenyl]-2-carboxylate

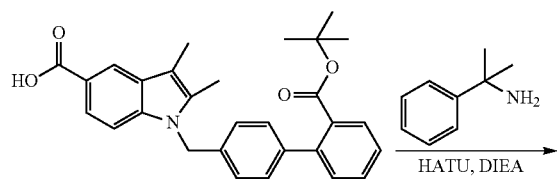

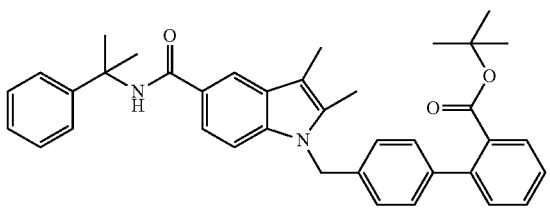

The title compound was prepared following the same general protocol as described in Step 8, Example 1, using 2-phenylpropan-2-amine instead of (S)-1-(4-bromophenyl)ethanamine. ESI-MS (m/z): 573 [M+H]⁺.

Step 2: 4'-((2,3-Dimethyl-5-((2-phenylpropan-2-yl)carbamoyl)-1H-indol-1-yl)methyl)-[1,1'-biphenyl]-2-carboxylic acid

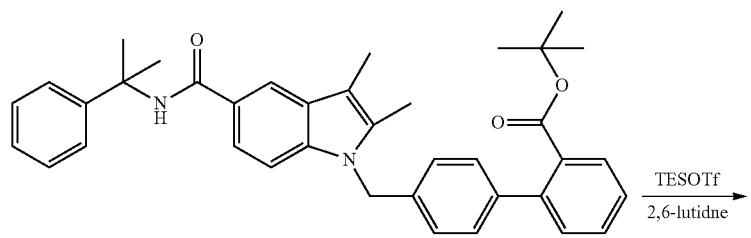

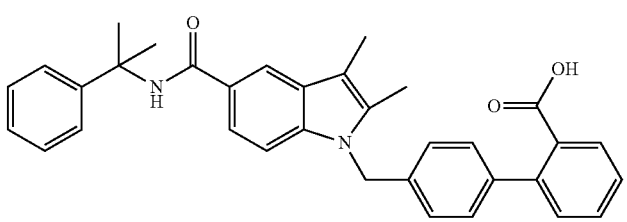 [SMILES: Cc1c(C)n(Cc2ccc(-c3ccccc3C(=O)O)cc2)c2ccc(C(=O)NC(C)(C)c3ccccc3)cc12]

The title compound was prepared following the same general protocol as described in Step 2, Example 19. ESI-MS (m/z): 517 [M+H]⁺.

Example 26

(S)-4'-((2,3-Dimethyl-5-((1-(naphthalen-2-yl)ethyl)carbamoyl)-1H-indol-1-yl)methyl)-[1,1'-biphenyl]-2-carboxylic acid

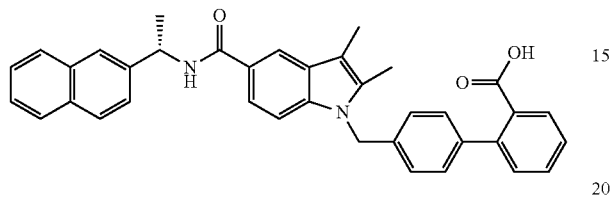

Step 1: (S)-tert-Butyl 4'-((2,3-dimethyl-5-((1-(naphthalen-2-yl)ethyl)carbamoyl)-1H-indol-1-yl)methyl)-[1,1'-biphenyl]-2-carboxylate

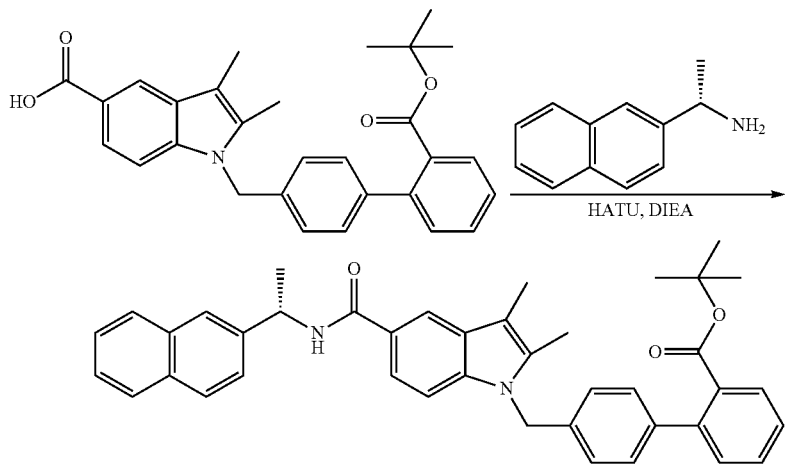

The title compound was prepared following the same general protocol as described in Step 8, Example 1, using (S)-1-(naphthalen-2-yl)ethanamine instead of (S)-1-(4-bromophenyl)ethanamine. ESI-MS (m/z): 609 [M+H]⁺

Step 2: (S)-4'-((2,3-Dimethyl-5-((1-(naphthalen-2-yl)ethyl)carbamoyl)-1H-indol-1-yl)methyl)-[1,1'-biphenyl]-2-carboxylic acid

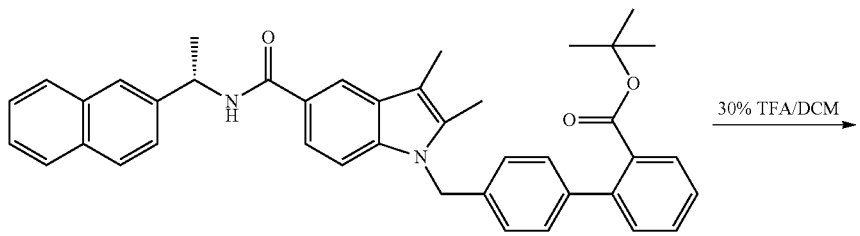

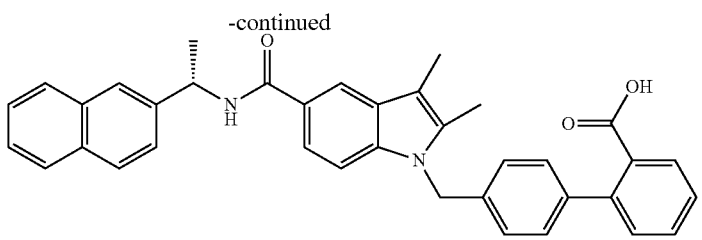

The title compound was prepared following the same general protocol as described in Step 9, Example 1. ESI-MS (m/z): 553 [M+H]⁺.

Example 27

(S)-4'-((5-((1-(4-Chlorophenyl)ethyl)carbamoyl)-2,3-dimethyl-1H-indol-1-yl)methyl)-[1,1'-biphenyl]-2-carboxylic acid

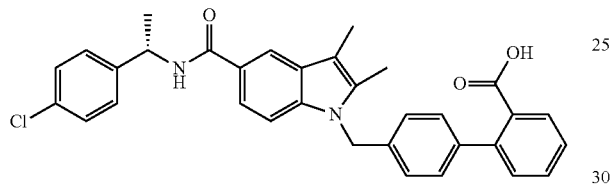

Step 1: (S)-tert-Butyl 4'-((5-((1-(4-chlorophenyl)ethyl)carbamoyl)-2,3-dimethyl-1H-indol-1-yl)methyl)-[1,1'-biphenyl]-2-carboxylate

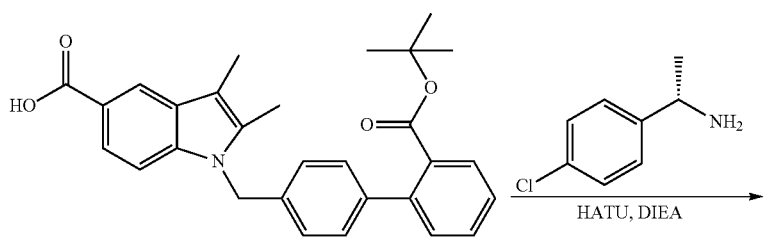

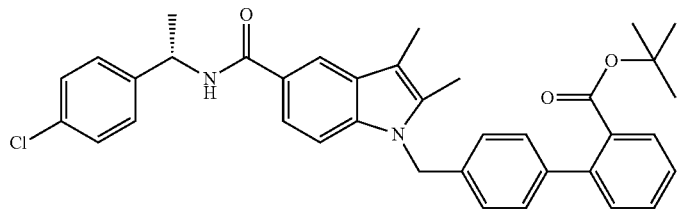

The title compound was prepared following the same general protocol as described in Step 8, Example 1, using (S)-1-(4-chlorophenyl)ethanamine instead of (S)-1-(4-bromophenyl)ethanamine. ESI-MS (m/z): 537 [M+H]⁺-tert-butyl Step 2: (S)-4'-((5-((1-(4-Chlorophenyl)ethyl)carbamoyl)-2,3-dimethyl-1H-indol-1-yl)methyl)-[1,1'-biphenyl]-2-carboxylic acid

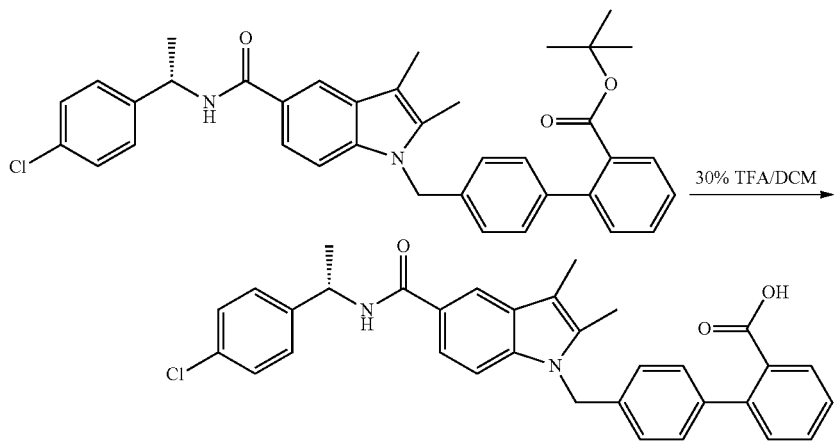

The title compound was prepared following the same general protocol as described in Step 9, Example 1. ESI-MS (m/z): 537 [M+H]$^+$.

Example 30

(S)-4'-((5-((1-(3-Bromophenyl)ethyl)carbamoyl)-2,3-dimethyl-1H-indol-1-yl)methyl)-[1,1'-biphenyl]-2-carboxylic acid

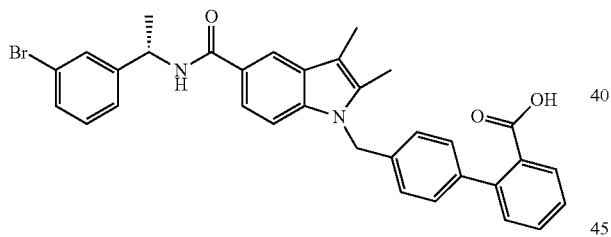

Step 1: (S)-tert-Butyl 4'-((5-((1-(3-bromophenyl)ethyl)carbamoyl)-2,3-dimethyl-1H-indol-1-yl)methyl)-[1,1'-biphenyl]-2-carboxylate

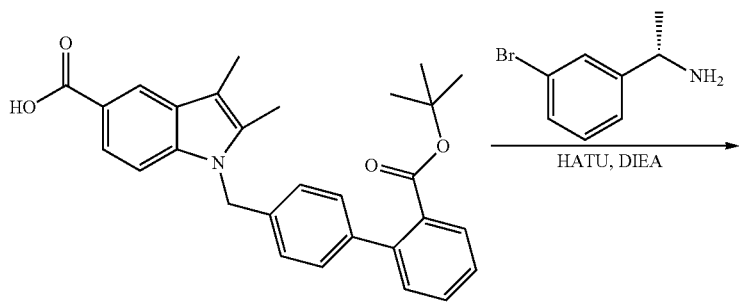

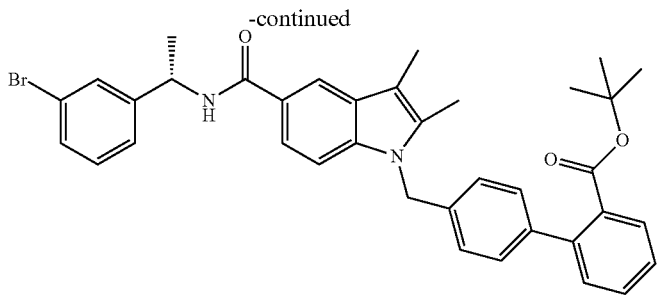
The title compound was prepared following the same general protocol as described in Step 8, Example 1, using (S)-1-(3-bromophenyl)ethanamine was used instead of (S)-1-(4-bromophenyl)ethanamine. ESI-MS (m/z): 659/661 [M+H]$^+$.
Step 2: (S)-4'-((5-(((1-(3-Bromophenyl)ethyl)carbamoyl)-2,3-dimethyl-1H-indol-1-yl)methyl)-[1,1'-biphenyl]-2-carboxylic acid
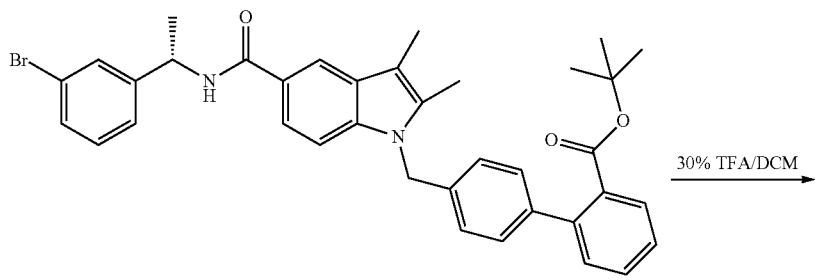
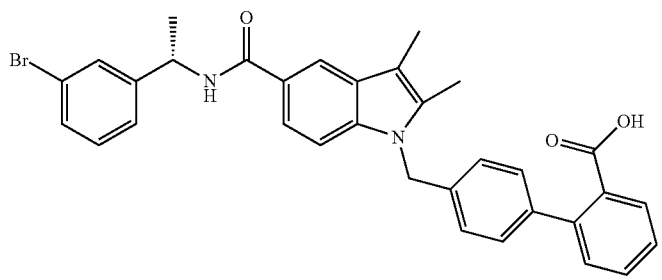

The title compound was prepared following the same general protocol as described in Step 9, Example 1. ESI-MS (m/z): 581/583 [M+H]+.

Example 31

4'-((2,3-Dimethyl-5-((2-oxo-2-phenylethyl)carbamoyl)-1H-indol-1-yl)methyl)-[1,1'-biphenyl]-2-carboxylic acid

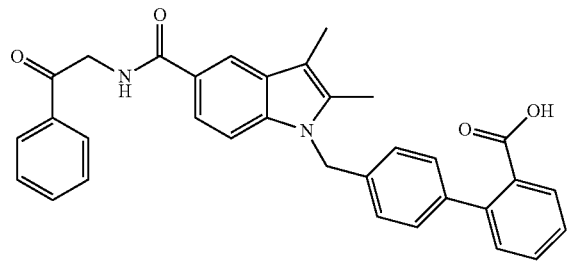 [SMILES: Cc1c(C)n(Cc2ccc(-c3ccccc3C(=O)O)cc2)c2ccc(C(=O)NCC(=O)c3ccccc3)cc12]

Step 1: tert-Butyl 4'-((2,3-dimethyl-5-((2-oxo-2-phenylethyl)carbamoyl)-1H-indol-1-yl)methyl)-[1,1'-biphenyl]-2-carboxylate

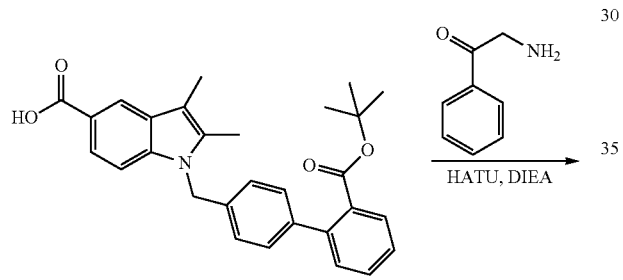

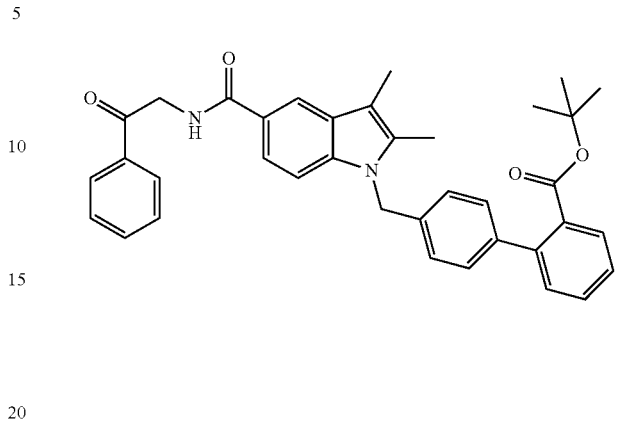

The title compound was prepared following the same general protocol as described in Step 8, Example 1, using 2-amino-1-phenylethanone instead of (S)-1-(4-bromophenyl)ethanamine. ESI-MS (m/z): 573 [M+H]+.

Step 2: 4'-((2,3-Dimethyl-5-((2-oxo-2-phenylethyl)carbamoyl)-1H-indol-1-yl)methyl)-[1,1'-biphenyl]-2-carboxylic acid

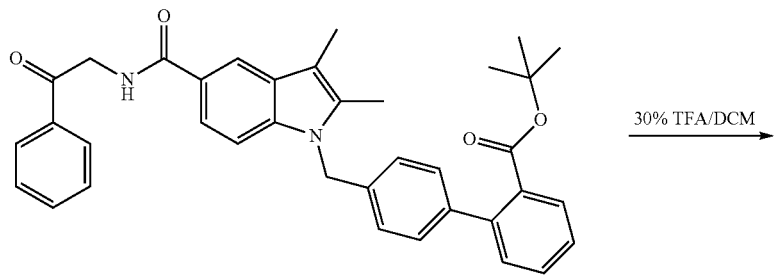

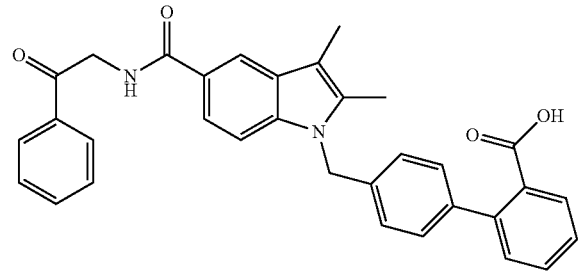

The title compound was prepared following the same general protocol as described in Step 9, Example 1. ESI-MS (m/z): 517 [M+H]+.

Example 34

1-((2'-Cyano-[1,1'-biphenyl]-4-yl)methyl)-2,3-dimethyl-N-(1-phenylpropyl)-1H-indole-5-carboxamide

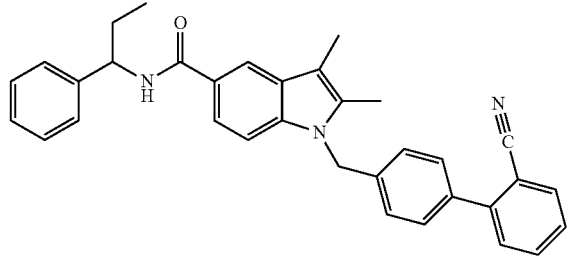 [SMILES: CCC(NC(=O)c1ccc2c(c1)c(C)c(C)n2Cc1ccc(-c2ccccc2C#N)cc1)c1ccccc1]

Step 1: 4'-Methyl-[1,1'-biphenyl]-2-carbonitrile

The title compound was prepared following the same protocol as described in Step 2, Example 1, using 2-bromobenzonitrile instead of the tert-butyl 2-bromobenzoate. $^1$H NMR (400 MHz, DMSO-$d_6$): δ (ppm) 2.38 (s, 3H, CH$_3$), 7.34 (d, J=8 Hz, 2H, H$_7$ and H$_8$ biphenyl), 7.47 (d, J=8 Hz, 2H, H$_5$ and H$_6$ biphenyl), 7.55 (dt, J=1.2, 7.6 Hz, 1H, H$_4$ biphenyl), 7.59 (m, 1H, H$_2$ biphenyl), 7.77 (dt, J=1.2, 7.6 Hz, 1H, H$_3$ biphenyl), 7.93 (m, 1H, H$_5$ biphenyl).

Step 2: 4'-(Bromomethyl)-[1,1'-biphenyl]-2-carbonitrile

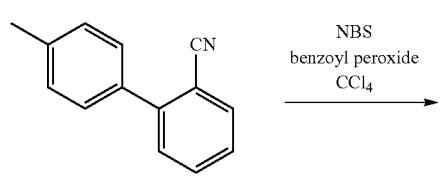

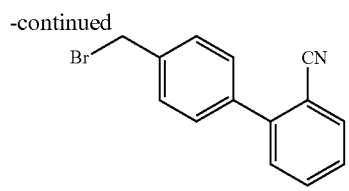

The title compound was prepared following the same protocol as described in Step 3, Example 1, using 4'-methyl-[1,1'-biphenyl]-2-carbonitrile instead of the tert-butyl 4'-methylbiphenyl-2-carboxylate and benzoyl peroxide instead of AIBN. $^1$H NMR (400 MHz, DMSO-$d_6$): δ (ppm) 4.79 (s, 2H, CH$_2$), 7.55-7.68 (m, 6H, H$_2$, H$_4$, H$_5$, H$_6$, H$_7$ and H$_8$ biphenyl), 7.77 (t, J=7.2 Hz, 1H, H$_3$ biphenyl), 7.93 (d, J=7.2 Hz, 1H, H$_5$ biphenyl).

Step 3: Ethyl 1-((2'-cyano-1,1'-biphenyl-4-yl))-2,3-dimethyl-1H-indole-5-carboxylate

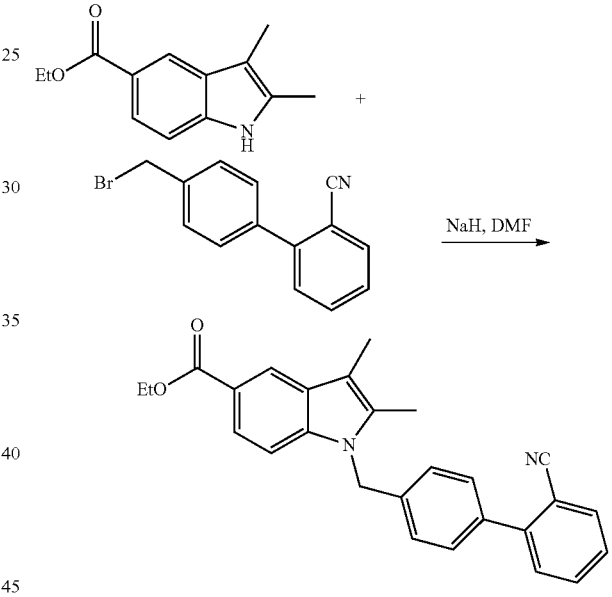

The title compound was prepared following the same protocol as described in Step 6, Example 1, using 4'-(Bromomethyl)-[1,1'-biphenyl]-2-carbonitrile instead of the tert-butyl 4'-(bromomethyl)biphenyl-2-carboxylate. ESI-MS (m/z): 409 [M+H]+.

Step 4: 1-((2'-Cyano-[1,1'-biphenyl]-4-yl)-2,3-dimethyl-1H-indole-5-carboxylic acid

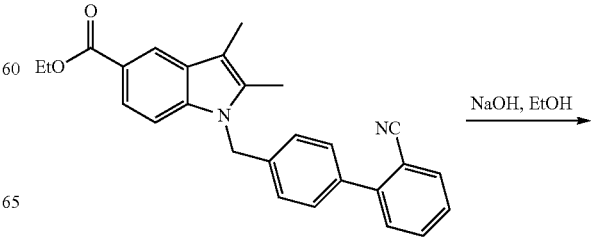

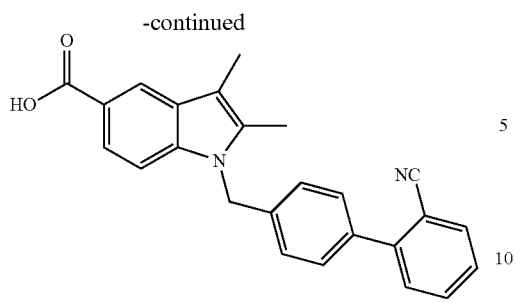

The title compound was prepared following the same protocol as described in Step 7, Example 1, using ethyl 1-((2'-cyano-[1,1'-biphenyl]-4-yl)methyl)-2,3-dimethyl-1H-indole-5-carboxylate instead of the ethyl 1-((2'-(tert-butoxycarbonyl)biphenyl-4-yl)methyl)-2,3-dimethyl-1H-indole-5-carboxylate. ESI-MS (m/z): 381 [M+H]⁺.

Step 5: 1-((2'-Cyano-[1,1'-biphenyl]-4-yl)methyl)-2,3-dimethyl-N-(1-phenylpropyl)-1H-indole-5-carboxamide

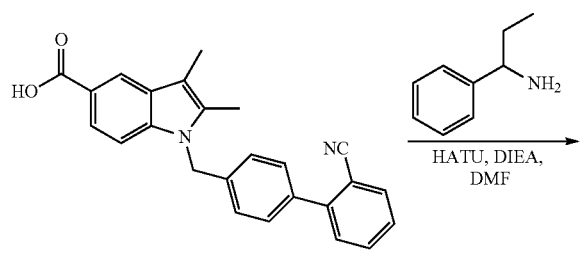

The title compound was prepared following the same protocol as described in Step 8, Example 1, using 1-((2'-cyano-[1,1'-biphenyl]-4-yl)methyl)-2,3-dimethyl-1H-indole-5-carboxylic acid instead of the 1-((2'-(tert-butoxycarbonyl)biphenyl-4-yl)methyl)-2,3-dimethyl-1H-indole-5-carboxylic acid, and 1-phenylpropan-1-amine instead of the (S)-1-(4-bromophenyl)ethanamine. ESI-MS (m/z): 498 [M+H]⁺.

Example 35

(S)—N-(1-(4-Bromophenyl)ethyl)-1-((2'-cyano-[1,1'-biphenyl]-4-yl)methyl)-2,3-dimethyl-1H-indole-5-carboxamide

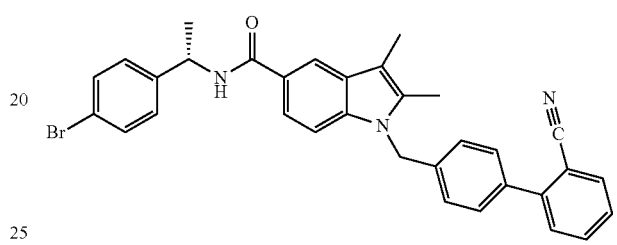

The title compound was prepared following the same protocol as described in Step 5, Example 34, using (S)-1-(4-bromophenyl)ethanamine instead of the 1-phenylpropan-1-amine. ESI-MS (m/z): 562/564 [M+H]⁺.

Example 36

1-((2'-(1H-Tetrazol-5-yl)-[1,1'-biphenyl]-4-yl)methyl)-2,3-dimethyl-N-(1-phenylpropyl)-1H-indole-5-carboxamide

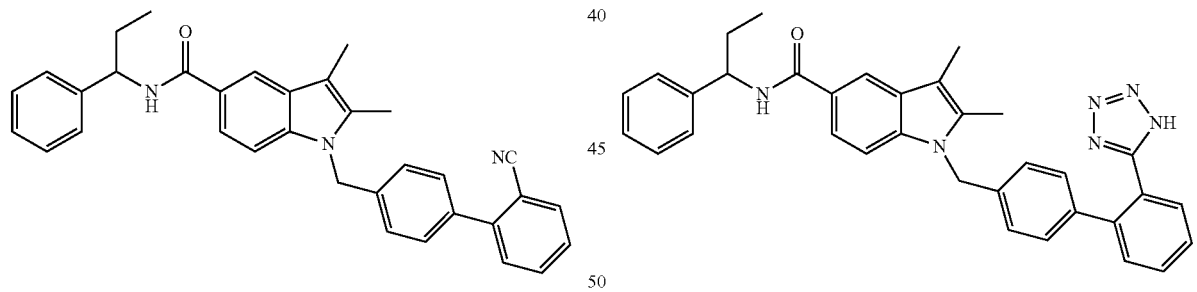

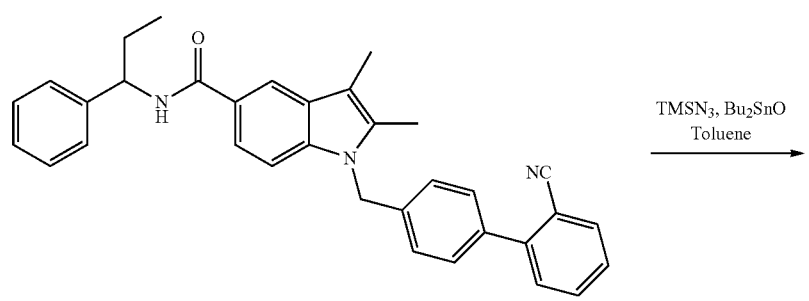

-continued

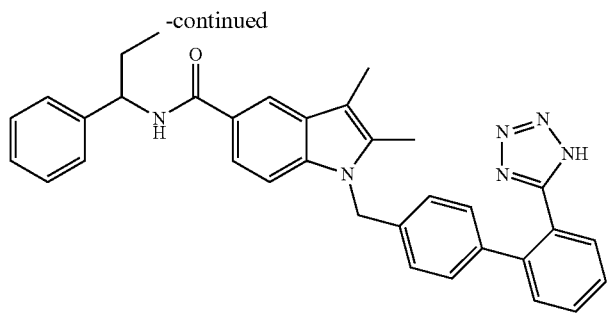

To a solution of 1-((2'-cyano-[1,1'-biphenyl]-4-yl)methyl)-2,3-dimethyl-N-(1-phenylpropyl)-1H-indole-5-carboxamide (27 mg, 0.05 mmol, 1 equiv) in toluene (0.6 mL) in a high-pressure vial were added TMSN₃ (14 µL, 0.05 mmol, 2 equiv) and Bu₂SnO (2 mg, 0.005 mmol, 0.1 equiv). The vial was sealed and the reaction mixture was heated at reflux for 2 h. After concentration, the residue was purified by preparative HPLC to afford a beige powder. ESI-MS (m/z): 541 [M+H]⁺.

Example 37

(S)-1-((2'-(1H-tetrazol-5-yl)-[1,1'-biphenyl]-4-yl)methyl)-N-(1-(4-bromophenyl)ethyl)-2,3-dimethyl-1H-indole-5-carboxamide

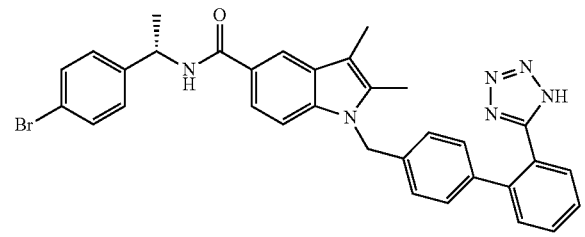 [SMILES: Cc1c(C)n(Cc2ccc(-c3ccccc3-c3nnn[nH]3)cc2)c2ccc(C(=O)N[C@@H](C)c3ccc(Br)cc3)cc12]

The title compound was prepared following the same protocol as described in Example 36, using (S)—N-(1-(4-bromophenyl)ethyl)-1-((2'-cyano-[1,1'-biphenyl]-4-yl)methyl)-2,3-dimethyl-1H-indole-5-carboxamide instead of the 1-((2'-cyano-[1,1'-biphenyl]-4-yl)methyl)-2,3-dimethyl-N-(1-phenylpropyl)-1H-indole-5-carboxamide. ESI-MS (m/z): 605/607 [M+H]⁺.

Example 38

(S)-1-([1,1'-Biphenyl]-4-ylmethyl)-N-(1-(4-nitrophenyl)ethyl)-1H-indole-5-carboxamide

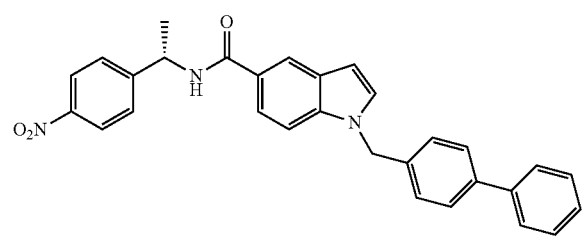 [SMILES: C[C@H](NC(=O)c1ccc2c(ccn2Cc2ccc(-c3ccccc3)cc2)c1)c1ccc([N+](=O)[O-])cc1]

Step 1: Methyl 1H-indole-5-carboxylate

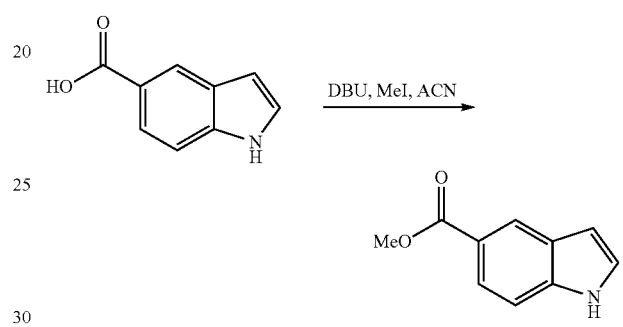

To a solution of 1H-indole-5-carboxylic acid (1 g, 6.2 mmol, 1.0 equiv) in acetonitrile (40 mL) were added 1,8-Diazabicyclo[5.4.0]undec-7-ene (1.1 mL, 7.4 mmol, 1.2 equiv) and iodomethane (2.3 mL, 37.2 mmol, 6 equiv). The solution was stirred under reflux overnight. The reaction mixture was concentrated in vacuo. The residue was dissolved in AcOEt, washed with a 0.5 N HCl aqueous solution, a saturated NaHCO₃ solution and brine, dried over MgSO4 and concentrated in vacuo. The obtained oil was used in the next step without further purification.

Step 2: Methyl 1-(4-bromobenzyl)-1H-indole-5-carboxylate

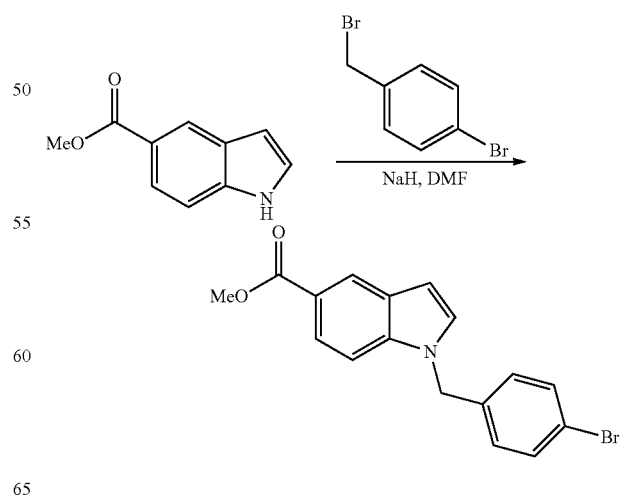

To a solution of methyl 1H-indole-5-carboxylate (1.09 g, 6.2 mmol, 1 equiv) and 1-(bromomethyl)-4-bromobenzene (1.70 g, 6.82 mmol, 1.1 equiv) in anhydrous DMF (30 mL) under argon atmosphere was added sodium hydride (500 mg, 12.4 mmol, 2 equiv) in small portions. The mixture was stirred 2 h at room temperature. The reaction mixture was then neutralized by addition of methanol and concentrated in vacuo. The residue was dissolved in AcOEt, washed with brine and dried over MgSO$_4$. The crude was purified by flash chromatography (Hexane/AcOEt 7.5/2.5) to afford the title compound as a white powder (1.09 g, 3.2 mmol, 52%). ESI-MS (m/z): 344/346 [M+H]$^+$.

Step 3: 1-(4-Bromobenzyl)-1H-indole-5-carboxylic acid

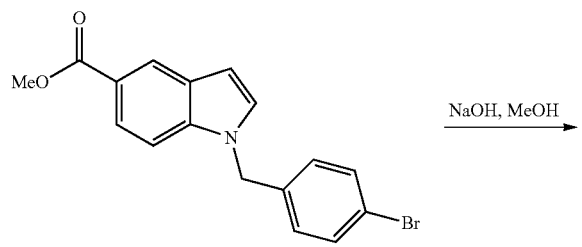

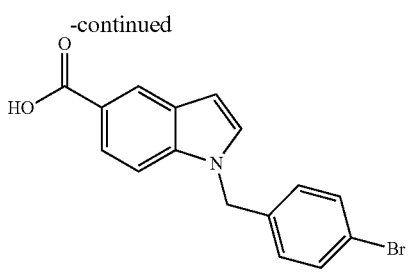

To a solution of methyl 1-(4-bromobenzyl)-1H-indole-5-carboxylate (1.09 g, 3.2 mmol, 1 equiv) in methanol (30 mL) was added a 5 N NaOH solution (6.3 mL, 32 mmol, 10 equiv). The reaction mixture was stirred 2 h at 40° C. The mixture was then acidified and extracted with DCM. After concentration in vacuo, the title compound was precipitated in Et$_2$O to afford a white powder (1.03 g, 3.1 mmol, 99%). ESI-MS (m/z): 330/332 [M+H]$^+$.

Step 4: (S)-1-(4-Bromobenzyl)-N-(1-(4-nitrophenyl)ethyl)-1H-indole-5-carboxamide

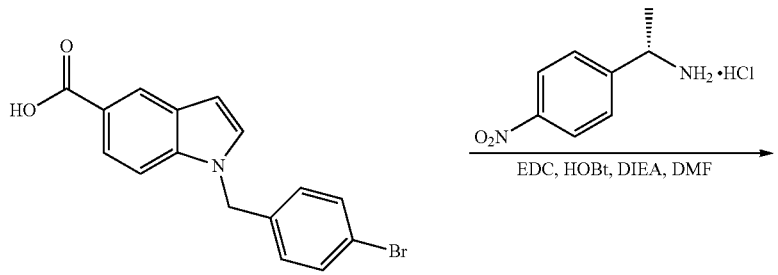

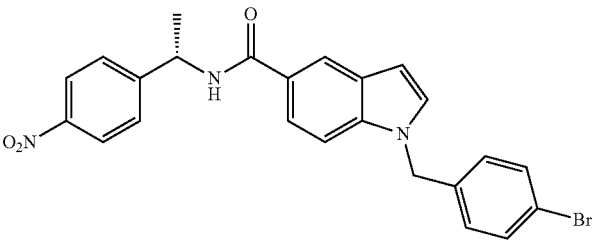

To a solution of 1-(4-bromobenzyl)-1H-indole-5-carboxylic acid (1.03 g, 3.1 mmol, 1 equiv) in DMF (30 mL) were added the (S)-1-(4-nitrophenyl)ethanamine hydrochloride (695 mg, 3.4 mmol, 1.1 equiv), DIEA (600 μL, 3.4 mmol, 1.1 equiv), HOBt (525 mg, 3.4 mmol, 1.1 equiv) and EDC (658 mg, 3.4 mmol, 1.1 equiv). After stirring 4 h at room temperature, the mixture was diluted with AcOEt and washed with a 0.5 N HCl aqueous solution, a saturated NaHCO$_3$ solution and brine, dried over MgSO$_4$ and concentrated in vacuo. The crude was purified by flash chromatography (Hexane/AcOEt 1/1) to afford a yellow powder (1.3 g, 2.7 mmol, 87%). ESI-MS (m/z): 478/480 [M+H]$^+$.

Step 5: (S)-1-([1,1'-Biphenyl]-4-ylmethyl)-N-(1-(4-nitrophenyl)ethyl)-1H-indole-5-carboxamide

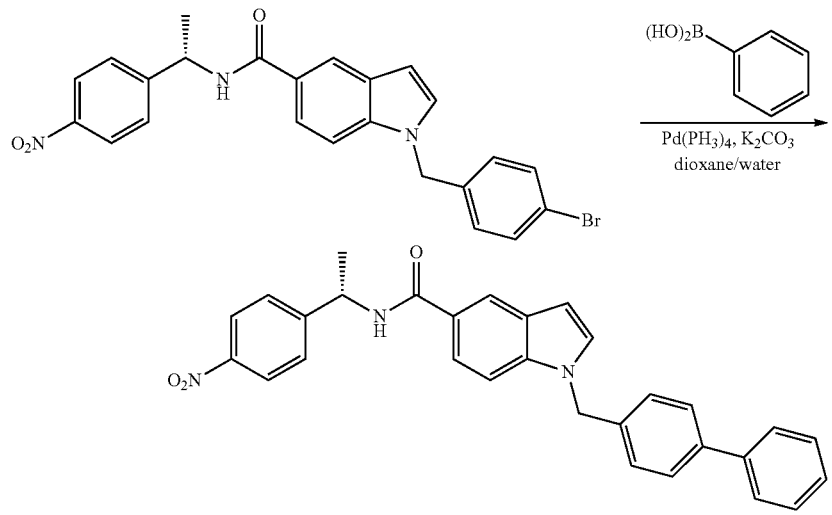

A high-pressure vial was filled with the (S)-1-(4-bromobenzyl)-N-(1-(4-nitrophenyl)ethyl)-1H-indole-5-carboxamide (50 mg, 0.1 mmol, 1 equiv), the phenylboronic acid (19 mg, 0.15 mmol, 1.5 equiv), K$_2$CO$_3$ (29 mg, 0.2 mmol, 2 equiv), Pd(PPh$_3$)$_4$ (12 mg, 0.01 mmol, 0.1 equiv), dioxane (1.5 mL) and water (0.3 mL). The mixture was degassed for 5 min under argon atmosphere and the vial was sealed. The reaction mixture was heated at 100° C. for 30 min under microwaves. The solution was then concentrated in vacuo, filtered and purified by preparative HPLC to afford a beige powder (50 mg, 0.1 mmol, 100%). ESI-MS (m/z): 476 [M+H]$^+$.

Example 39

(S)-1-((2'-Methoxy-[1,1'-biphenyl]-4-yl)methyl)-N-(1-(4-nitrophenyl)ethyl)-1H-indole-5-carboxamide

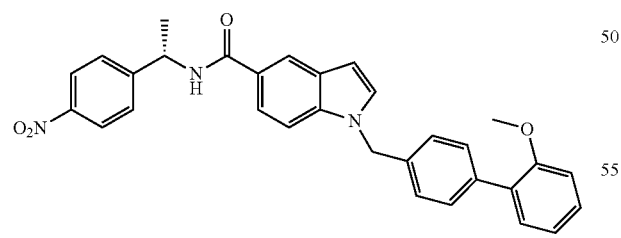

The title compound was prepared following the same general protocol as described in Step 5, Example 38, using (2-methoxyphenyl)boronic acid instead of the phenylboronic acid. A yellow powder was obtained (32 mg, 0.06 mmol, 61%).
ESI-MS (m/z): 506 [M+H]$^+$.

Example 40

(S)-1-((2'-Hydroxy-[1,1'-biphenyl]-4-yl)methyl)-N-(1-(4-nitrophenyl)ethyl)-1H-indole-5-carboxamide

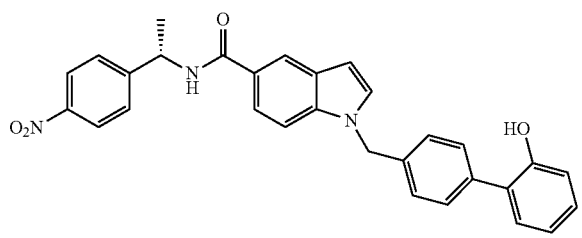 [SMILES: C[C@H](NC(=O)c1ccc2c(ccn2Cc2ccc(-c3ccccc3O)cc2)c1)c1ccc([N+](=O)[O-])cc1]

The title compound was prepared following the same general protocol as described in Step 5, Example 38, using (2-hydroxyphenyl)boronic acid instead of the phenylboronic acid. A yellow powder was obtained (39 mg, 0.08 mmol, 76%).
ESI-MS (m/z): 492 [M+H]$^+$.

Example 41

(S)-1-((2'-(Methylsulfonyl)-[1,1'-biphenyl]-4-yl)methyl)-N-(1-(4-nitrophenyl)ethyl)-1H-indole-5-carboxamide

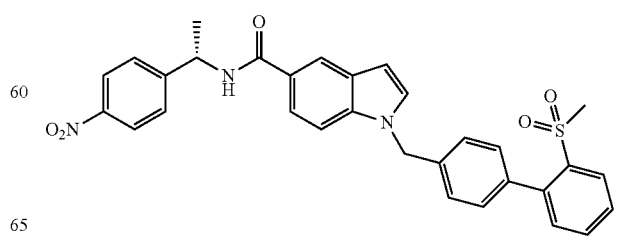

The title compound was prepared following the same general protocol as described in Step 5, Example 38, using (2-(methylsulfonyl)phenyl)boronic acid instead of the phenylboronic acid. A beige powder was obtained (46 mg, 0.08 mmol, 80%). ESI-MS (m/z): 554 [M+H]$^+$.

Example 42

(S)-1-((2'-Methyl-[1,1'-biphenyl]-4-yl)methyl)-N-(1-(4-nitrophenyl)ethyl)-1H-indole-5-carboxamide

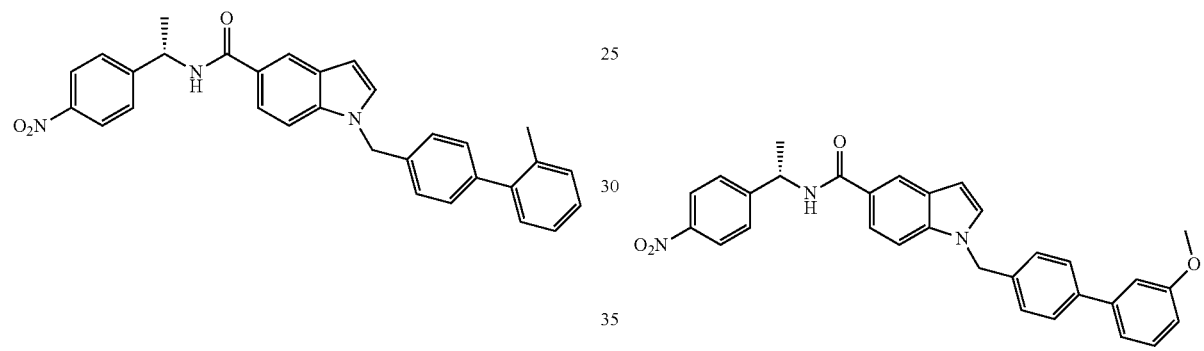

The title compound was prepared following the same general protocol as described in Step 5, Example 38, using o-tolylboronic acid instead of the phenylboronic acid. A yellow powder was obtained (35 mg, 0.07 mmol, 69%). ESI-MS (m/z): 490 [M+H]$^+$.

Example 43

(S)-Ethyl 4'-((5-((1-(4-nitrophenyl)ethyl)carbamoyl)-1H-indol-1-yl)methyl)-[1,1'-biphenyl]-4-carboxylate

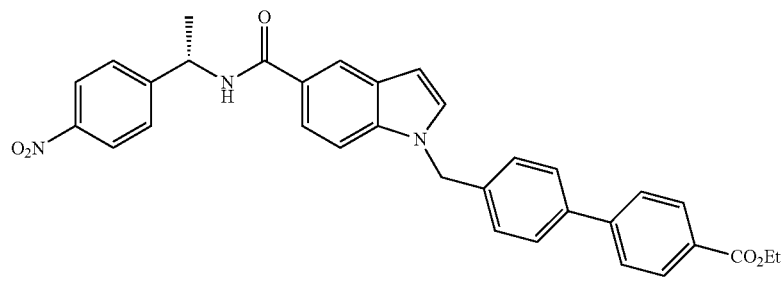 [SMILES: CCOC(=O)c1ccc(-c2ccc(Cn3ccc4cc(C(=O)N[C@@H](C)c5ccc([N+](=O)[O-])cc5)ccc43)cc2)cc1]

The title compound was prepared following the same general protocol as described in Step 5, Example 38, using (4-(ethoxycarbonyl)phenyl)boronic acid instead of the phenylboronic acid. A yellow powder was obtained (41 mg, 0.07 mmol, 72%). ESI-MS (m/z): 548 [M+H]$^+$.

Example 44

(S)-1-((3'-Methoxy-[1,1'-biphenyl]-4-yl)methyl)-N-(1-(4-nitrophenyl)ethyl)-1H-indole-5-carboxamide The title compound was prepared following the same general protocol as described in Step 5, Example 38, using (3-methoxyphenyl)boronic acid instead of the phenylboronic acid. A yellow powder was obtained (44 mg, 0.09 mmol, 84%).

ESI-MS (m/z): 506 [M+H]$^+$.

Example 45

(S)-1-((3'-(Methylsulfonyl)-[1,1'-biphenyl]-4-yl)methyl)-N-(1-(4-nitrophenyl)ethyl)-1H-indole-5-carboxamide

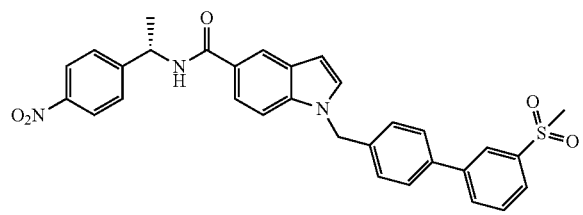 [SMILES: C[C@H](NC(=O)c1ccc2c(ccn2Cc2ccc(-c3cccc(S(C)(=O)=O)c3)cc2)c1)c1ccc([N+](=O)[O-])cc1]

The title compound was prepared following the same general protocol as described in Step 5, Example 38, using (3-(methylsulfonyl)phenyl)boronic acid instead of the phenylboronic acid. A yellow powder was obtained (49 mg, 0.09 mmol, 85%). ESI-MS (m/z): 554 [M+H]$^+$.

Example 46

(S)-1-((2'-Chloro-[1,1'-biphenyl]-4-yl)methyl)-N-(1-(4-nitrophenyl)ethyl)-1H-indole-5-carboxamide

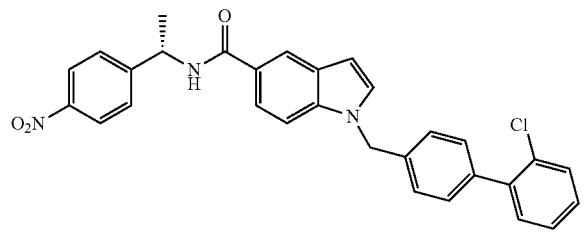 [SMILES: C[C@H](NC(=O)c1ccc2c(ccn2Cc2ccc(-c3ccccc3Cl)cc2)c1)c1ccc([N+](=O)[O-])cc1]

The title compound was prepared following the same general protocol as described in Step 5, Example 38, using (2-chlorophenyl)boronic acid instead of the phenylboronic acid. A beige powder was obtained (39 mg, 0.08 mmol, 74%). ESI-MS (m/z): 510 [M+H]$^+$.

Example 47

(S)-1-((4'-Hydroxy-[1,1'-biphenyl]-4-yl)methyl)-N-(1-(4-nitrophenyl)ethyl)-1H-indole-5-carboxamide

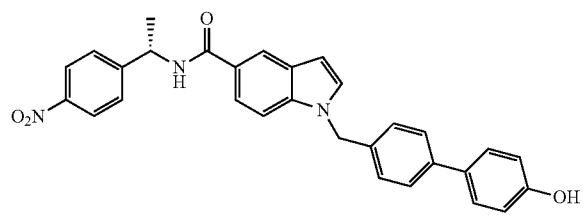 [SMILES: C[C@H](NC(=O)c1ccc2c(ccn2Cc2ccc(-c3ccc(O)cc3)cc2)c1)c1ccc([N+](=O)[O-])cc1]

The title compound was prepared following the same general protocol as described in Step 5, Example 38, using (4-hydroxyphenyl)boronic acid instead of the phenylboronic acid. A yellow powder was obtained (37 mg, 0.08 mmol, 72%) ESI-MS (m/z): 492 [M+H]$^+$..

Example 48

(S)-Ethyl 4'-((5-((1-(4-nitrophenyl)ethyl)carbamoyl)-1H-indol-1-yl)methyl)-[1,1'-biphenyl]-3-carboxylate

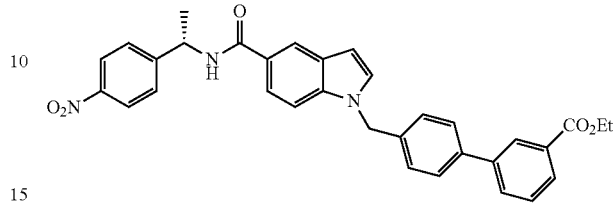

The title compound was prepared following the same general protocol as described in Step 5, Example 38, using (3-(ethoxycarbonyl)phenyl)boronic acid instead of the phenylboronic acid. A yellow powder was obtained (48 mg, 0.09 mmol, 84%). ESI-MS (m/z): 548 [M+H]$^+$.

Example 49

(S)-1-((3'-Methyl-[1,1'-biphenyl]-4-yl)methyl)-N-(1-(4-nitrophenyl)ethyl)-1H-indole-5-carboxamide

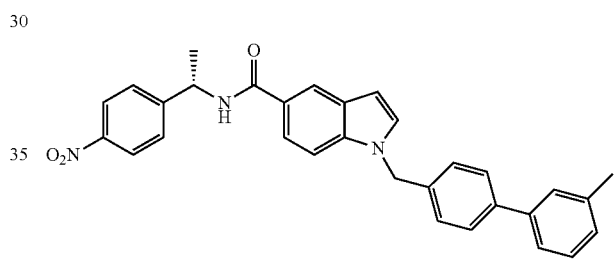

The title compound was prepared following the same general protocol as described in Step 5, Example 38, using m-tolylboronic acid instead of the phenylboronic acid. A yellow powder was obtained (38 mg, 0.08 mmol, 75%). ESI-MS (m/z): 490 [M+H]$^+$.

Example 50

(S)-1-((4'-(Methylsulfonyl)-[1,1'-biphenyl]-4-yl)methyl)-N-(1-(4-nitrophenyl)ethyl)-1H-indole-5-carboxamide

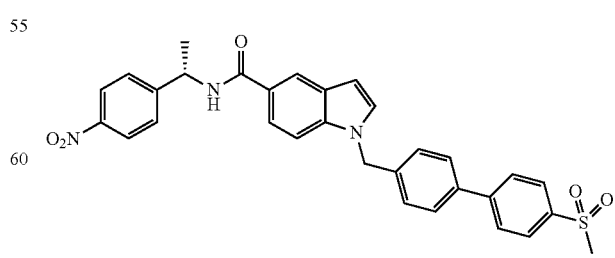

The title compound was prepared following the same general protocol as described in Step 5, Example 38, using (4-

(methylsulfonyl)phenyl)boronic acid instead of the phenylboronic acid. A beige powder was obtained (46 mg, 0.08 mmol, 80%). ESI-MS (m/z): 554 [M+H]+.

Example 51

(S)-1-((4'-(Methylthio)-[1,1'-biphenyl]-4-yl)methyl)-N-(1-(4-nitrophenyl)ethyl)-1H-indole-5-carboxamide

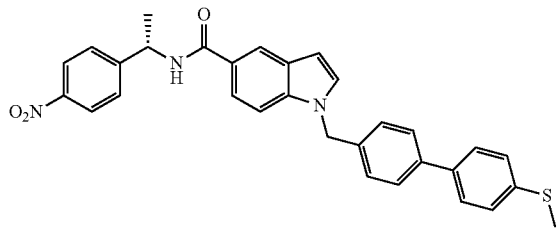 [SMILES: CSc1ccc(-c2ccc(Cn3ccc4cc(C(=O)N[C@@H](C)c5ccc([N+](=O)[O-])cc5)ccc43)cc2)cc1]

The title compound was prepared following the same general protocol as described in Step 5, Example 38, using (4-(methylthio)phenyl)boronic acid instead of the phenylboronic acid. A yellow powder was obtained (29 mg, 0.06 mmol, 53%). ESI-MS (m/z): 522 [M+H]+.

Example 52

(S)-1-((3'-Amino-[1,1'-biphenyl]-4-yl)methyl)-N-(1-(4-nitrophenyl)ethyl)-1H-indole-5-carboxamide

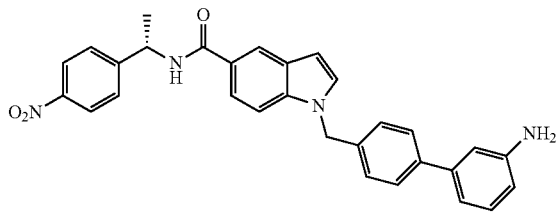 [SMILES: C[C@H](NC(=O)c1ccc2c(ccn2Cc2ccc(-c3cccc(N)c3)cc2)c1)c1ccc([N+](=O)[O-])cc1]

The title compound was prepared following the same general protocol as described in Step 5, Example 38, using (3-aminophenyl)boronic acid instead of the phenylboronic acid. A beige powder was obtained (40 mg, 0.08 mmol, 78%). ESI-MS (m/z): 491 [M+H]+.

Example 53

(S)-1-((3'-(Aminomethyl)-[1,1'-biphenyl]-4-yl)methyl)-N-(1-(4-nitrophenyl)ethyl)-1H-indole-5-carboxamide

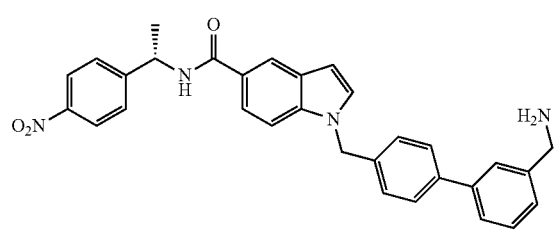 [SMILES: C[C@H](NC(=O)c1ccc2c(ccn2Cc2ccc(-c3cccc(CN)c3)cc2)c1)c1ccc([N+](=O)[O-])cc1]

The title compound was prepared following the same general protocol as described in Step 5, Example 38, using (3-(aminomethyl)phenyl)boronic acid instead of the phenylboronic acid. A beige powder was obtained (47 mg, 0.09 mmol, 90%). ESI-MS (m/z): 505 [M+H]+.

Example 54

(S)-1-((2'-(Hydroxymethyl)-[1,1'-biphenyl]-4-yl)methyl)-N-(1-(4-nitrophenyl)ethyl)-1H-indole-5-carboxamide

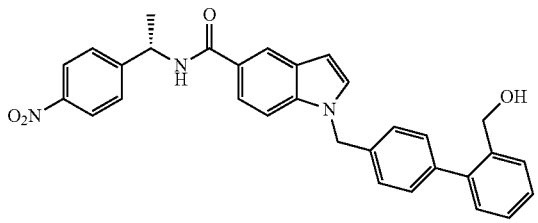 [SMILES: C[C@H](NC(=O)c1ccc2c(ccn2Cc2ccc(-c3ccccc3CO)cc2)c1)c1ccc([N+](=O)[O-])cc1]

The title compound was prepared following the same general protocol as described in Step 5, Example 38, using (2-(hydroxymethyl)phenyl)boronic acid instead of the phenylboronic acid. A beige powder was obtained (17 mg, 0.03 mmol, 32%). ESI-MS (m/z): 506 [M+H]+.

Example 55

(S)-tert-Butyl 4'-((5-((1-(4-nitrophenyl)ethyl)carbamoyl)-1H-indol-1-yl)methyl)-[1,1'-biphenyl]-2-carboxylate

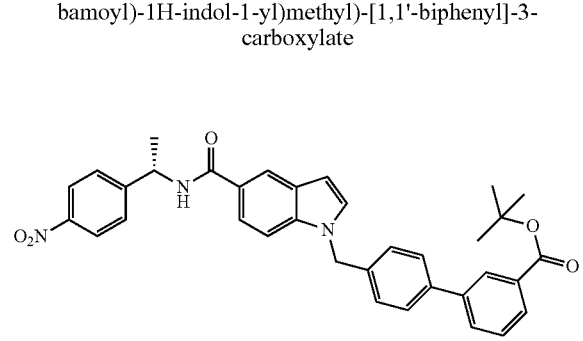

The title compound was prepared following the same general protocol as described in Step 5, Example 38, using (2-(tert-butoxycarbonyl)phenyl)boronic acid instead of the phenylboronic acid. A yellow powder was obtained (47 mg, 0.08 mmol, 79%). ESI-MS (m/z): 576 [M+H]+.

Example 56

(S)-tert-Butyl 4'-((5-((1-(4-nitrophenyl)ethyl)carbamoyl)-1H-indol-1-yl)methyl)-[1,1'-biphenyl]-3-carboxylate The title compound was prepared following the same general protocol as described in Step 5, Example 38, using (3-(tert-butoxycarbonyl)phenyl)boronic acid instead of the phenylboronic acid. A yellow powder was obtained (43 mg, 0.07 mmol, 72%). ESI-MS (m/z): 576 [M+H]+.

Example 57

(S)-1-((4'-Methyl-[1,1'-biphenyl]-4-yl)methyl)-N-(1-(4-nitrophenyl)ethyl)-1H-indole-5-carboxamide

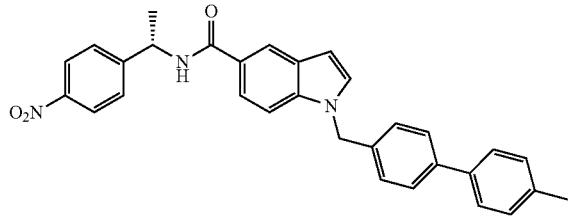 [SMILES: Cc1ccc(-c2ccc(Cn3ccc4cc(C(=O)N[C@@H](C)c5ccc([N+](=O)[O-])cc5)ccc43)cc2)cc1]

The title compound was prepared following the same general protocol as described in Step 5, Example 38, using p-tolylboronic acid instead of the phenylboronic acid. A beige powder was obtained (13 mg, 0.03 mmol, 26%). ESI-MS (m/z): 490 [M+H]+.

Example 58

(S)-1-((3'-Chloro-[1,1'-biphenyl]-4-yl)methyl)-N-(1-(4-nitrophenyl)ethyl)-1H-indole-5-carboxamide

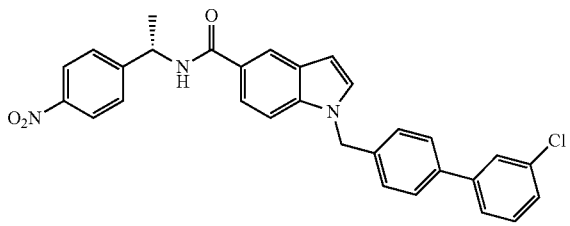 [SMILES: C[C@H](NC(=O)c1ccc2c(ccn2Cc2ccc(-c3cccc(Cl)c3)cc2)c1)c1ccc([N+](=O)[O-])cc1]

The title compound was prepared following the same general protocol as described in Step 5, Example 38, using (3-chlorophenyl)boronic acid instead of the phenylboronic acid. A beige powder was obtained (18 mg, 0.04 mmol, 34%). ESI-MS (m/z): 510 [M+H]+.

Example 59

(S)-4'-((5-((1-(4-Nitrophenyl)ethyl)carbamoyl)-1H-indol-1-yl)methyl)-[1,1'-biphenyl]-4-carboxylic acid

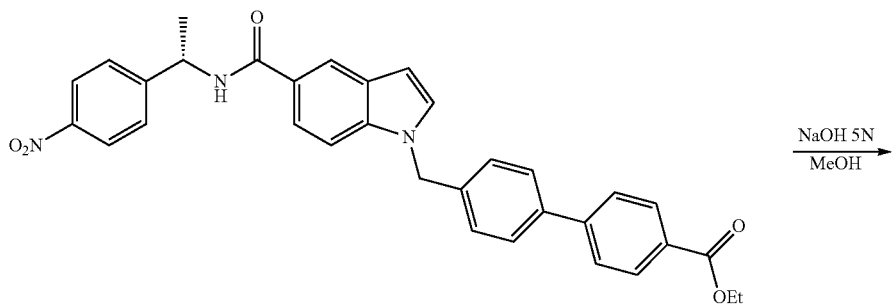

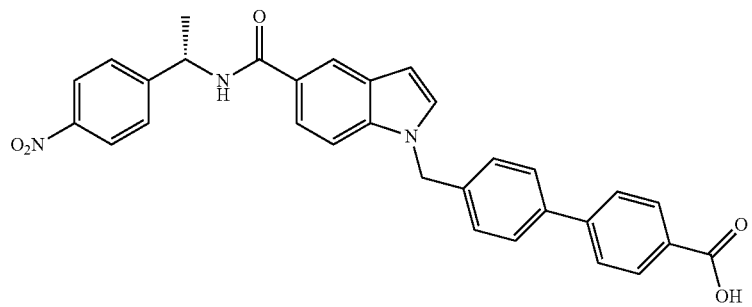

To a solution of (S)-ethyl 4'-((5-((1-(4-nitrophenyl)ethyl) carbamoyl)-1H-indol-1-yl)methyl)-[1,1'-biphenyl]-4-carboxylate (23 mg, 0.04 mmol, 1 equiv) in MeOH (1 mL) was added 100 L of a 5 N NaOH solution. The mixture is stirred at room temperature overnight and then hydrolyzed by addition of a 1 N HCl solution. After concentration, the crude is purified by preparative HPLC to afford a beige powder (9 mg, 0.02 mmol, 43%). ESI-MS (m/z): 520 [M+H]$^+$.

Example 60

(S)-4'-((5-((1-(4-Nitrophenyl)ethyl)carbamoyl)-1H-indol-1-yl)methyl)-[1,1'-biphenyl]-3-carboxylic acid

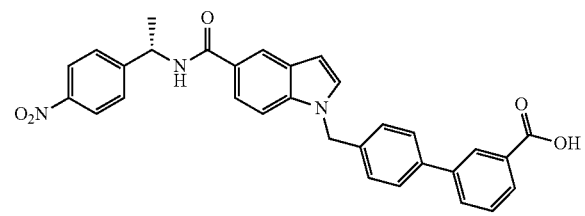 [SMILES: C[C@H](NC(=O)c1ccc2c(ccn2Cc2ccc(-c3cccc(C(=O)O)c3)cc2)c1)c1ccc([N+](=O)[O-])cc1]

The title compound was prepared following the same general protocol as described in Example 59, using (S)-ethyl 4'-((5-((1-(4-nitrophenyl)ethyl)carbamoyl)-1H-indol-1-yl)methyl)-[1,1'-biphenyl]-3-carboxylate instead of the (S)-ethyl 4'-((5-((1-(4-nitrophenyl)ethyl)carbamoyl)-1H-indol-1-yl)methyl)-[1,1'-biphenyl]-4-carboxylate. A beige powder was obtained (18 mg, 0.04 mmol, 34%). ESI-MS (m/z): 520 [M+H]$^+$.

Example 61

(S)-4'-((5-((1-(4-Nitrophenyl)ethyl)carbamoyl)-1H-indol-1-yl)methyl)-[1,1'-biphenyl]-2-carboxylic acid

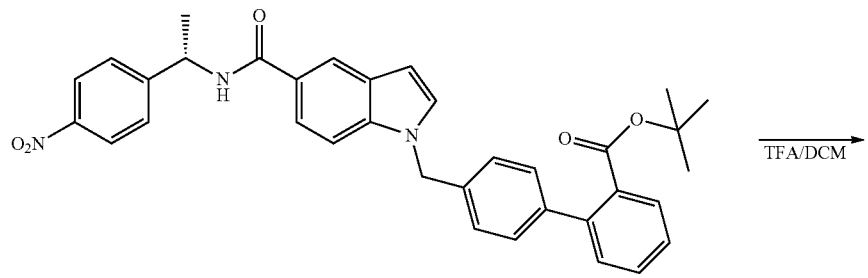

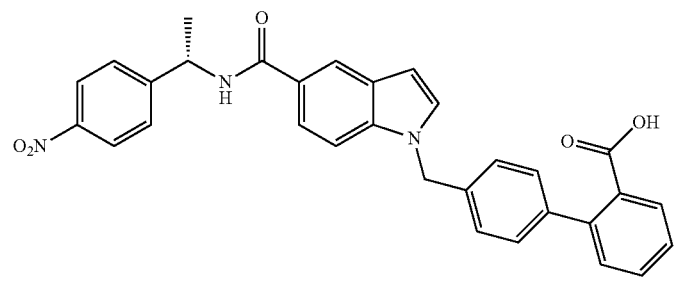

A solution of (S)-tert-butyl 4'-((5-((1-(4-nitrophenyl) ethyl)carbamoyl)-1H-indol-1-yl)methyl)-[1,1'-biphenyl]-2-carboxylate (23 mg, 0.04 mmol, 1 equiv) in DCM/TFA 1/1 was stirred for 30 min at room temperature. The reaction mixture was neutralized by addition of DIEA, concentrated and purified by preparative HPLC to afford a beige powder (9 mg, 0.02 mmol, 43%). ESI-MS (m/z): 520 [M+H]$^+$.

Example 62

(S)-2,3-Dimethyl-N-(1-(4-nitrophenyl)ethyl)-1-(4-(pyridin-3-yl)benzyl)-1H-indole-5-carboxamide

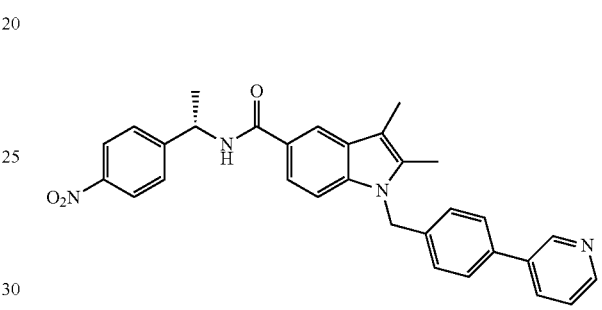

The title compound was prepared following the same general protocol as described in Step 5, Example 38, using pyridin-3-ylboronic acid instead of the phenylboronic acid. A beige powder was obtained (34 mg, 0.07 mmol, 69%). ESI-MS (m/z): 477 [M+H]+.

Example 63

(S)-2,3-Dimethyl-N-(1-(4-nitrophenyl)ethyl)-1-(4-(pyridin-4-yl)benzyl)-1H-indole-5-carboxamide

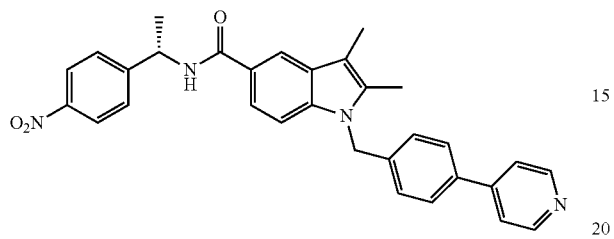

The title compound was prepared following the same general protocol as described in Step 5, Example 38, using pyridin-4-ylboronic acid instead of the phenylboronic acid. A beige powder was obtained (37 mg, 0.08 mmol, 75%). ESI-MS (m/z): 477 [M+H]+

Example 64

(S)-2,3-Dimethyl-N-(1-(4-nitrophenyl)ethyl)-1-(4-(pyridin-2-yl)benzyl)-1H-indole-5-carboxamide

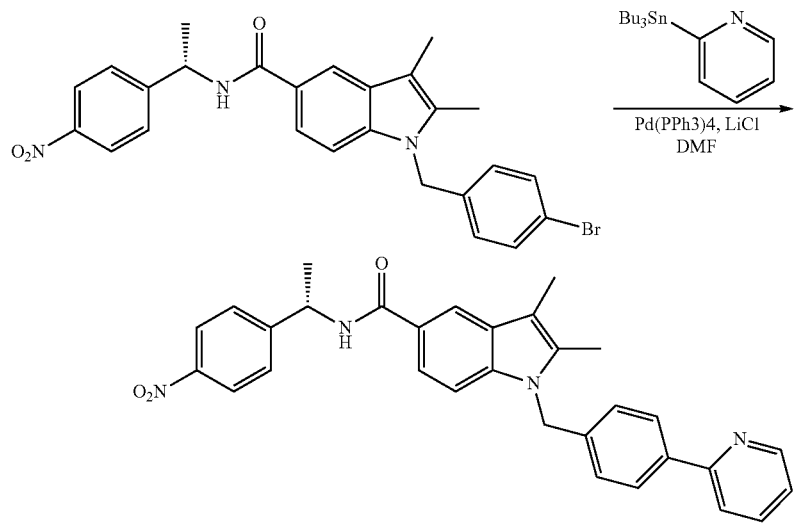

A high-pressure vial was filled with the (S)-1-(4-bromobenzyl)-N-(1-(4-nitrophenyl)ethyl)-1H-indole-5-carboxamide (37 mg, 0.08 mmol, 1 equiv), 2-(tributylstannyl)pyridine (28 μL, 0.09 mmol, 1.1 equiv), LiCl (10 mg, 0.24 mmol, 3 equiv), Pd(PPh3)4 (9 mg, 0.008 mmol, 0.1 equiv), and anhydrous DMF (1 mL). The mixture was degassed for 5 min under argon atmosphere and the vial was sealed. The reaction mixture was heated at 120° C. for 1 h under microwaves. The solution was then concentrated in vacuo, filtered and purified by preparative HPLC to afford a beige powder (18 mg, 0.4 mmol, 50%). ESI-MS (m/z): 477 [M+H]+.

Example 65

3'-((5-((1-phenylpropyl)carbamoyl)-1H-indol-1-yl)methyl)-[1,1'-biphenyl]-2-carboxylic acid

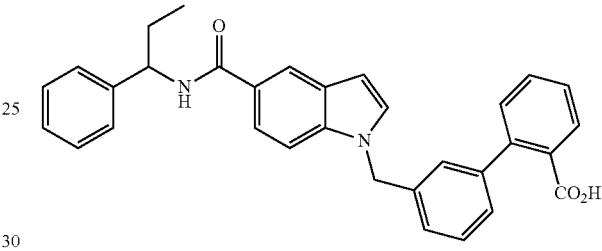

Step 1: 1-(3-Bromobenzyl)-2,3-dimethyl-1H-indole-5-carboxylic acid

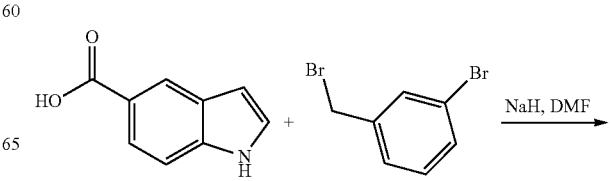

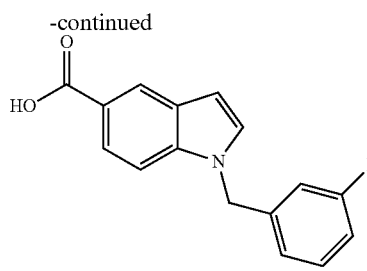

The title compound is prepared following the same protocol as described in Step 2, Example 38, using 1H-indole-5-carboxylic acid instead of the methyl 1H-indole-5-carboxylate, and 1-bromo-3-(bromomethyl)benzene instead of the 1-bromo-4-(bromomethyl)benzene. ESI-MS (m/z): 331 [M+H]$^+$.

Step 2: 1-(3-Bromobenzyl)-N-(1-phenylpropyl)-1H-indole-5-carboxamide

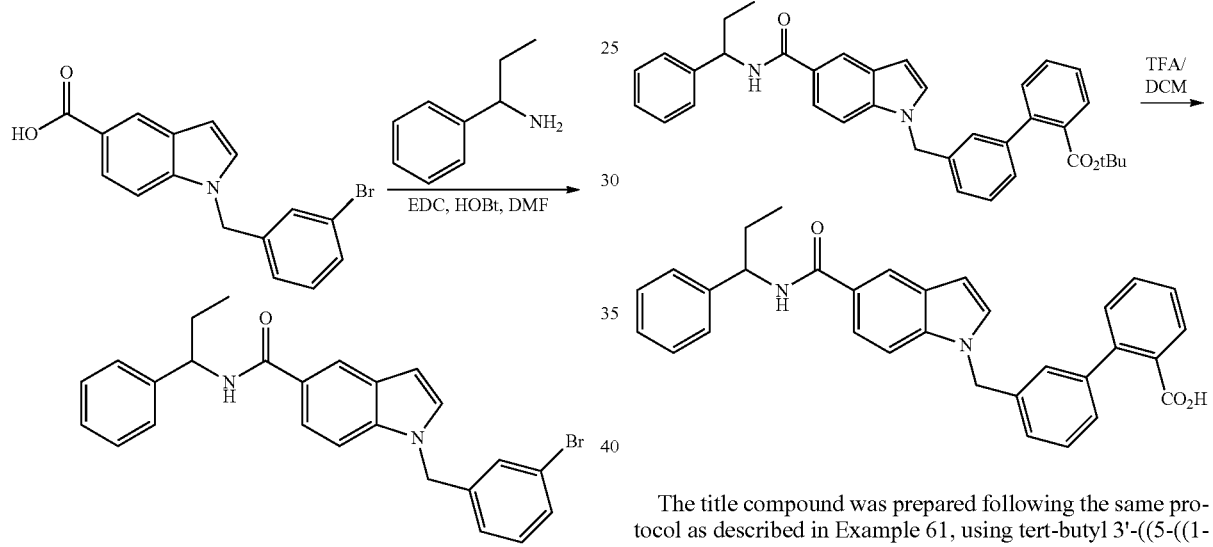

The title compound was prepared following the same protocol as described in Step 4, Example 38, using 1-phenylpropan-1-amine instead of the (S)-1-(4-nitrophenyl)ethanamine hydrochloride, and 1-(2-Bromobenzyl)-2,3-dimethyl-1H-indole-5-carboxylic acid instead of the 1-(4-bromobenzyl)-1H-indole-5-carboxylic acid. ESI-MS (m/z): 447/449 [M+H]$^+$.

Step 3: tert-Butyl 3'-((5-(((1-phenylpropyl)carbamoyl)-1H-indol-1-yl)methyl)-[1,1'-biphenyl]-2-carboxylate

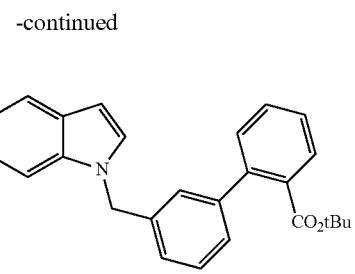

The title compound was prepared following the same protocol as described in Example 55, using 1-(3-Bromobenzyl)-N-(1-phenylpropyl)-1H-indole-5-carboxamide instead of the (S)-1-(4-bromobenzyl)-N-(1-(4-nitrophenyl)ethyl)-1H-indole-5-carboxamide.

Step 4: 3'-((5-((1-Phenylpropyl)carbamoyl)-1H-indol-1-yl)methyl)-[1,1'-biphenyl]-2-carboxylic acid The title compound was prepared following the same protocol as described in Example 61, using tert-butyl 3'-((5-((1-phenylpropyl)carbamoyl)-1H-indol-1-yl)methyl)-[1,1'-biphenyl]-2-carboxylate instead of the (S)-tert-butyl 4'-((5-((1-(4-nitrophenyl)ethyl)carbamoyl)-1H-indol-1-yl)methyl)-[1,1'-biphenyl]-2-carboxylate.
ESI-MS (m/z): 489 [M+H]$^+$.

Example 66

3'-((5-((1-Phenylpropyl)carbamoyl)-1H-indol-1-yl)methyl)-[1,1'-biphenyl]-3-carboxylic acid

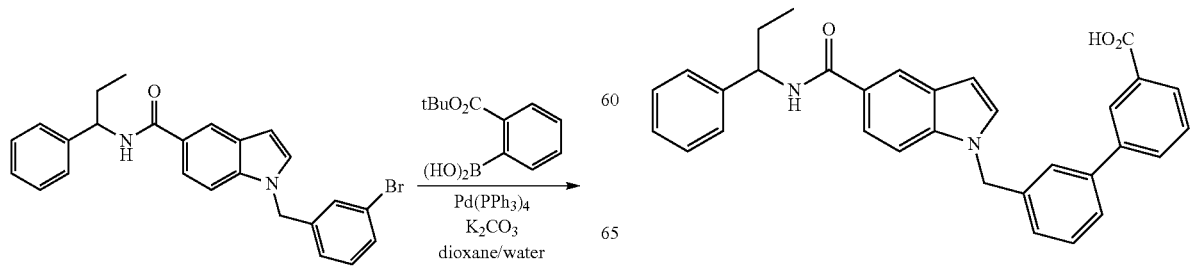

Step 1: tert-Butyl 3'-((5-((1-phenylpropyl)carbamoyl)-1H-indol-1-yl)methyl)-[1,1'-biphenyl]-3-carboxylate

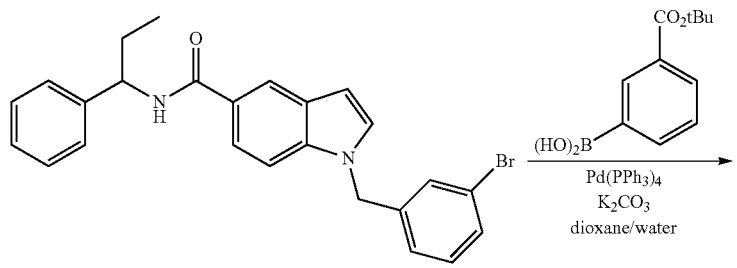

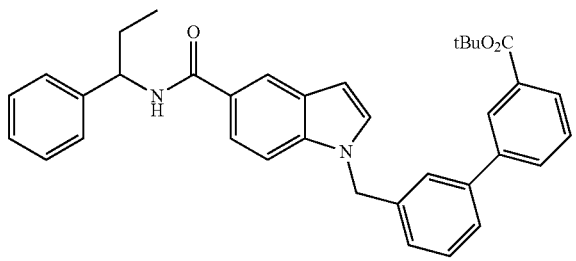 [SMILES: CCC(NC(=O)c1ccc2c(ccn2Cc2cccc(-c3cccc(C(=O)O)c3)c2)c1)c1ccccc1]

The title compound was prepared following the same protocol as described in Example 56, using 1-(3-Bromobenzyl)-N-(1-phenylpropyl)-1H-indole-5-carboxamide instead of the (S)-1-(4-bromobenzyl)-N-(1-(4-nitrophenyl)ethyl)-1H-indole-5-carboxamide.

Step 2: 3'-((5-((1-Phenylpropyl)carbamoyl)-1H-indol-1-yl)methyl)-[1,1'-biphenyl]-3-carboxylic acid

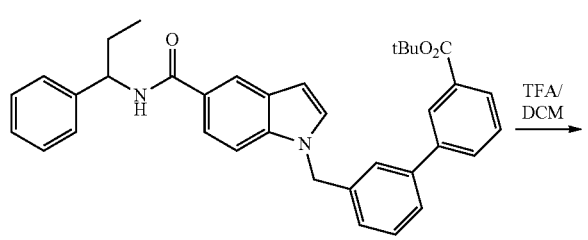

The title compound was prepared following the same protocol as described in Example 60, using tert-butyl 3'-((5-((1-phenylpropyl)carbamoyl)-1H-indol-1-yl)methyl)-[1,1'-biphenyl]-3-carboxylate instead of the (S)-tert-butyl 4'-((5-((1-(4-nitrophenyl)ethyl)carbamoyl)-1H-indol-1-yl)methyl)-[1,1'-biphenyl]-3-carboxylate.

ESI-MS (m/z): 489 [M+H]$^+$.

Example 67

3'-((5-((1-Phenylpropyl)carbamoyl)-1H-indol-1-yl)methyl)-[1,1'-biphenyl]-4-carboxylic acid

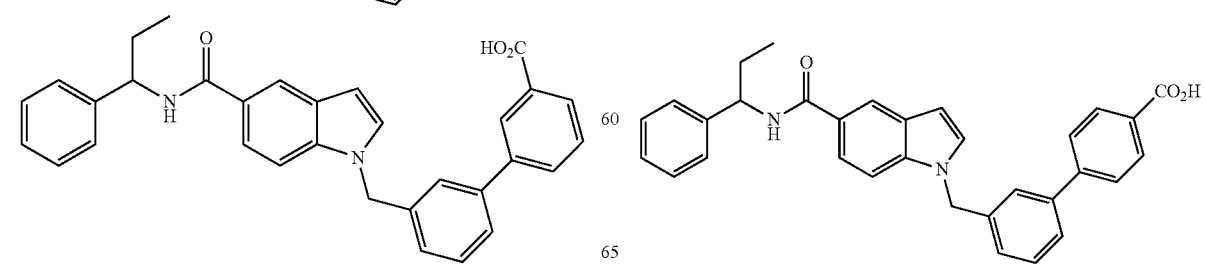

Step 1: Ethyl 3'-((5-((1-phenylpropyl)carbamoyl)-1H-indol-1-yl)methyl)-[1,1'-biphenyl]-4-carboxylate

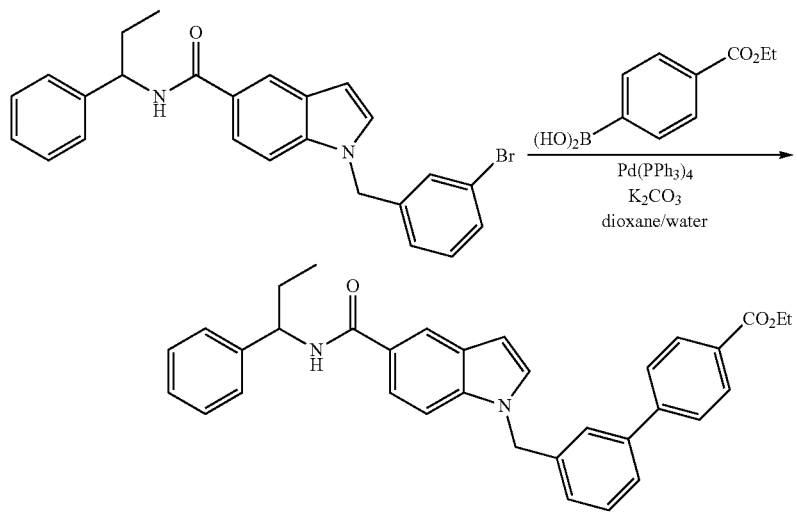

The title compound was prepared following the same protocol as described in Example 43, using 1-(3-Bromobenzyl)-N-(1-phenylpropyl)-1H-indole-5-carboxamide instead of the (S)-1-(4-bromobenzyl)-N-(1-(4-nitrophenyl)ethyl)-1H-indole-5-carboxamide.

Step 2: 3'-((5-((1-Phenylpropyl)carbamoyl)-1H-indol-1-yl)methyl)-[1,1'-biphenyl]-4-carboxylic acid

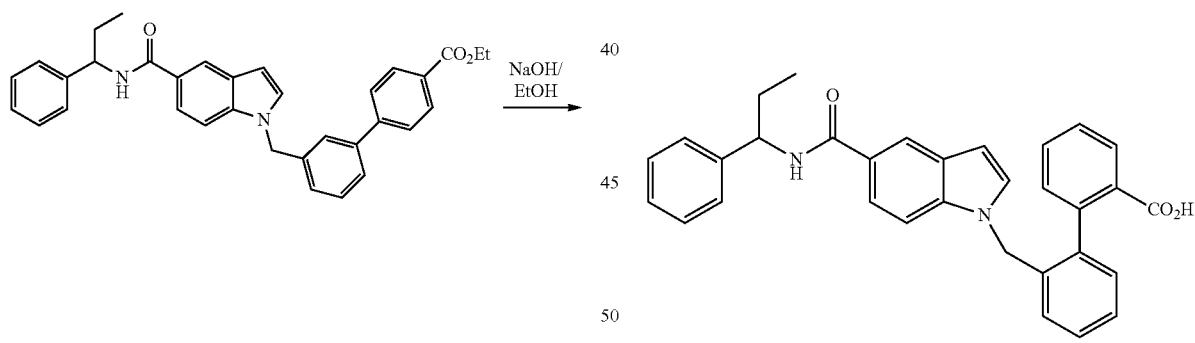

The title compound was prepared following the same protocol as described in Example 59, using ethyl 3'-((5-((1-phenylpropyl)carbamoyl)-1H-indol-1-yl)methyl)-[1,1'-biphenyl]-4-carboxylate instead of the (S)-ethyl 4'-((5-((1-(4-nitrophenyl)ethyl)carbamoyl)-1H-indol-1-yl)methyl)-[1,1'-biphenyl]-4-carboxylate.

ESI-MS (m/z): 489 [M+H]$^+$.

Example 68

2'-((5-((1-phenylpropyl)carbamoyl)-1H-indol-1-yl)methyl)-[1,1'-biphenyl]-2-carboxylic acid Step 1: 1-(2-Bromobenzyl)-2,3-dimethyl-1H-indole-5-carboxylic acid

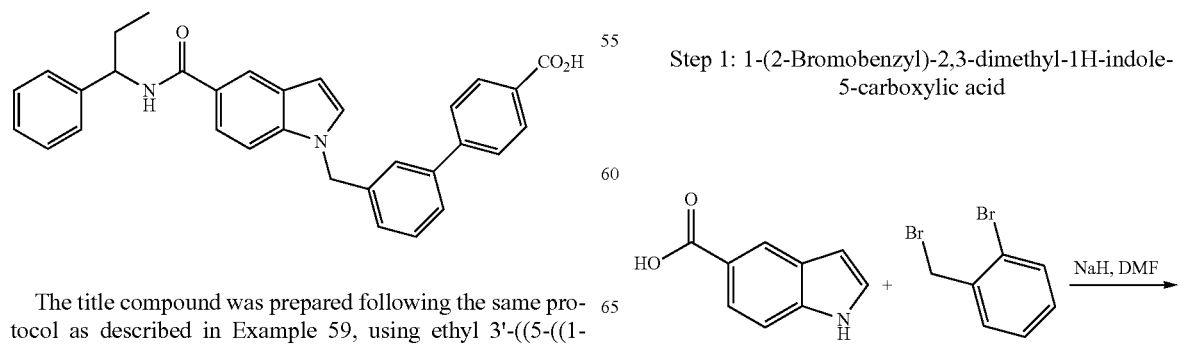

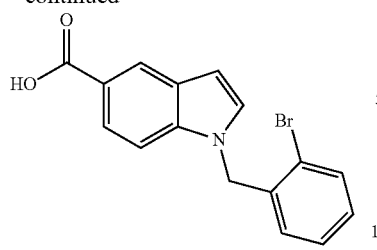

The title compound was prepared following the same protocol as described in Step 2, Example 38, using 1H-indole-5-carboxylic acid instead of the methyl 1H-indole-5-carboxylate, and 1-bromo-2-(bromomethyl)benzene instead of the 1-bromo-4-(bromomethyl)benzene.

ESI-MS (m/z): 331 [M+H]⁺

Step 2: 1-(2-Bromobenzyl)-N-(1-phenylpropyl)-1H-indole-5-carboxamide

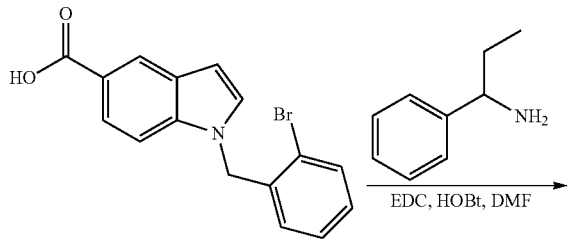

The title compound was prepared following the same protocol as described in Step 4, Example 38, using 1-phenylpropan-1-amine instead of the (S)-1-(4-nitrophenyl)ethanamine hydrochloride, and 1-(2-Bromobenzyl)-2,3-dimethyl-1H-indole-5-carboxylic acid instead of the 1-(4-bromobenzyl)-1H-indole-5-carboxylic acid. ESI-MS (m/z): 447/449 [M+H]⁺.

Step 3: tert-Butyl 2'-((5-((1-phenylpropyl)carbamoyl)-1H-indol-1-yl)methyl)-[1,1'-biphenyl]-2-carboxylate

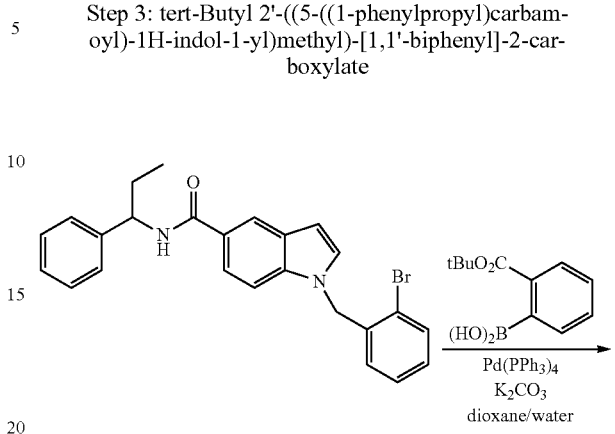

The title compound was prepared following the same protocol as described in Example 55, using 1-(2-Bromobenzyl)-N-(1-phenylpropyl)-1H-indole-5-carboxamide instead of the (S)-1-(4-bromobenzyl)-N-(1-(4-nitrophenyl)ethyl)-1H-indole-5-carboxamide.

Step 4: 2'-((5-((1-Phenylpropyl)carbamoyl)-1H-indol-1-yl)methyl)-[1,1'-biphenyl]-2-carboxylic acid

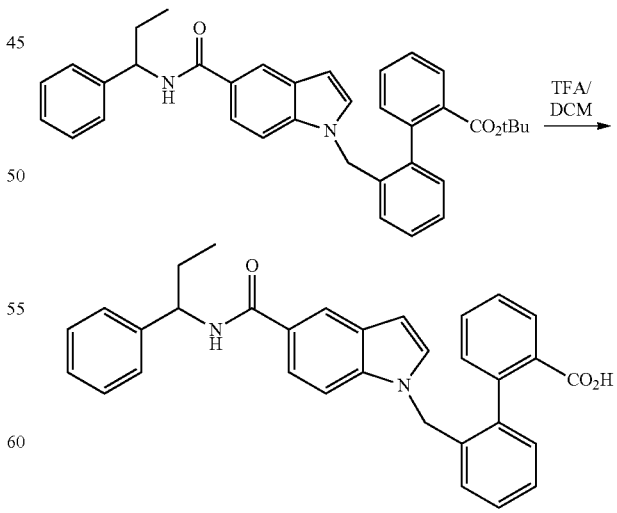

The title compound was prepared following the same protocol as described in Example 61, using tert-butyl 2'-((5-((1-phenylpropyl)carbamoyl)-1H-indol-1-yl)methyl)-[1,1'-biphenyl]-2-carboxylate instead of the (S)-tert-butyl 4'-((5-((1-(4-nitrophenyl)ethyl)carbamoyl)-1H-indol-1-yl)methyl)-[1,1'-biphenyl]-2-carboxylate.

ESI-MS (m/z): 489 [M+H]$^+$.

Example 69

2'-((5-((1-Phenylpropyl)carbamoyl)-1H-indol-1-yl)methyl)-[1,1'-biphenyl]-3-carboxylic acid

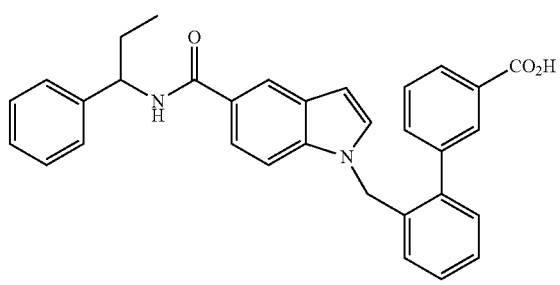 [SMILES: CCC(NC(=O)c1ccc2c(ccn2Cc2ccccc2-c2cccc(C(=O)O)c2)c1)c1ccccc1]

Step 1: tert-Butyl 2'-((5-((1-phenylpropyl)carbamoyl)-1H-indol-1-yl)methyl)-[1,1'-biphenyl]-3-carboxylate

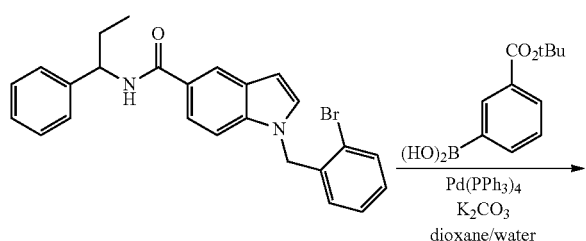

The title compound was prepared following the same protocol as described in Example 56, using 1-(2-Bromobenzyl)-N-(1-phenylpropyl)-1H-indole-5-carboxamide instead of the (S)-1-(4-bromobenzyl)-N-(1-(4-nitrophenyl)ethyl)-1H-indole-5-carboxamide.

Step 2: 2'-((5-((1-Phenylpropyl)carbamoyl)-1H-indol-1-yl)methyl)-[1,1'-biphenyl]-3-carboxylic acid

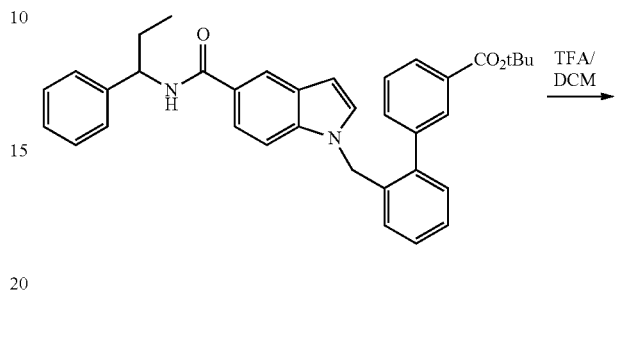

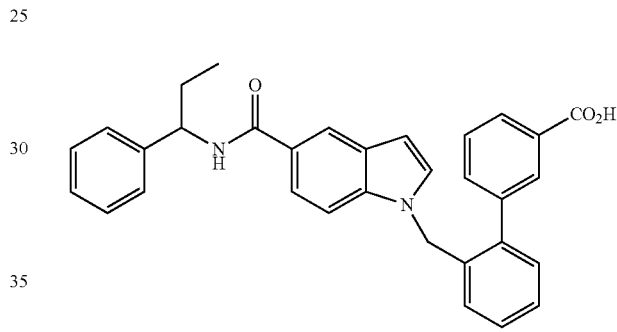

The title compound was prepared following the same protocol as described in Example 60, using tert-butyl 2'-((5-((1-phenylpropyl)carbamoyl)-1H-indol-1-yl)methyl)-[1,1'-biphenyl]-3-carboxylate instead of the (S)-tert-butyl 4'-((5-((1-(4-nitrophenyl)ethyl)carbamoyl)-1H-indol-1-yl)methyl)-[1,1'-biphenyl]-3-carboxylate.

ESI-MS (m/z): 489 [M+H]$^+$.

Example 70

2'-((5-((1-Phenylpropyl)carbamoyl)-1H-indol-1-yl)methyl)-[1,1'-biphenyl]-4-carboxylic acid

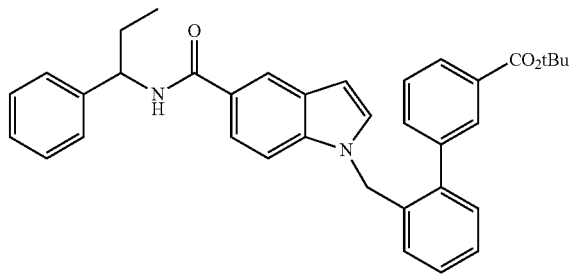

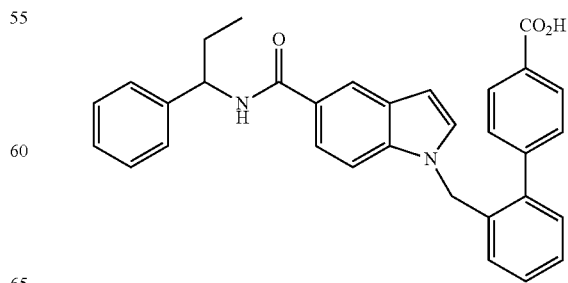

Step 1: Ethyl 2'-((5-((1-phenylpropyl)carbamoyl)-1H-indol-1-yl)methyl)-[1,1'-biphenyl]-4-carboxylate

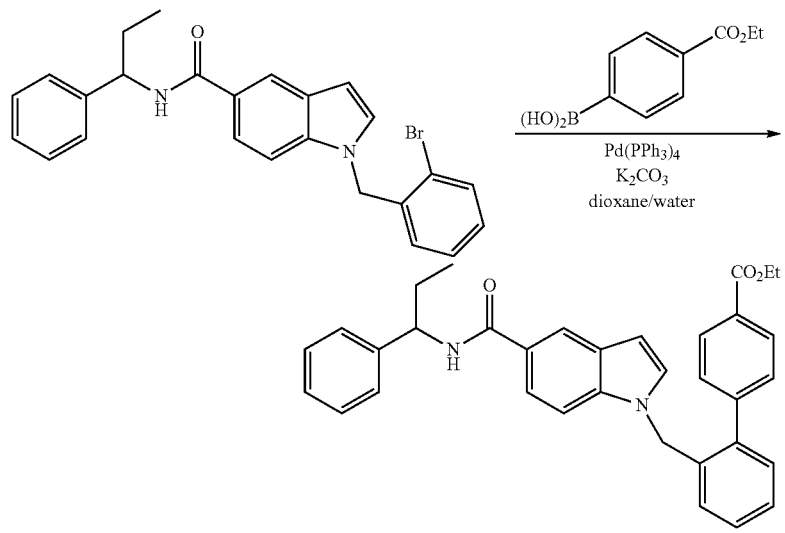

The title compound was prepared following the same protocol as described in Example 43, using 1-(2-Bromobenzyl)-N-(1-phenylpropyl)-1H-indole-5-carboxamide instead of the (S)-1-(4-bromobenzyl)-N-(1-(4-nitrophenyl)ethyl)-1H-indole-5-carboxamide.

Step 2: 2'-((5-((1-Phenylpropyl)carbamoyl)-1H-indol-1-yl)methyl)-[1,1'-biphenyl]-4-carboxylic acid

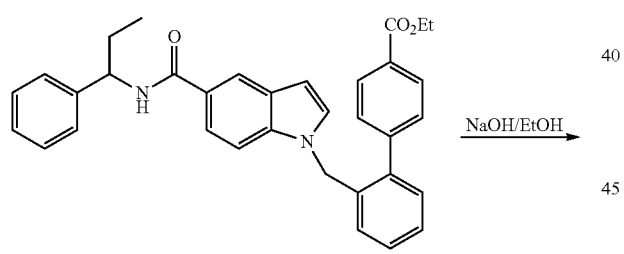

The title compound was prepared following the same protocol as described in Example 59, using ethyl 2'-((5-((1-phenylpropyl)carbamoyl)-1H-indol-1-yl)methyl)-[1,1'-biphenyl]-4-carboxylate instead of the (S)-ethyl 4'-((5-((1-(4-nitrophenyl)ethyl)carbamoyl)-1H-indol-1-yl)methyl)-[1,1'-biphenyl]-4-carboxylate.

ESI-MS (m/z): 489 [M+H]$^+$

Example 72

(R)-4'-((2,3-dimethyl-5-(1-(4-nitrophenyl)ethylcarbamoyl)-1H-indol-1-yl)methyl)biphenyl-2-carboxylic acid

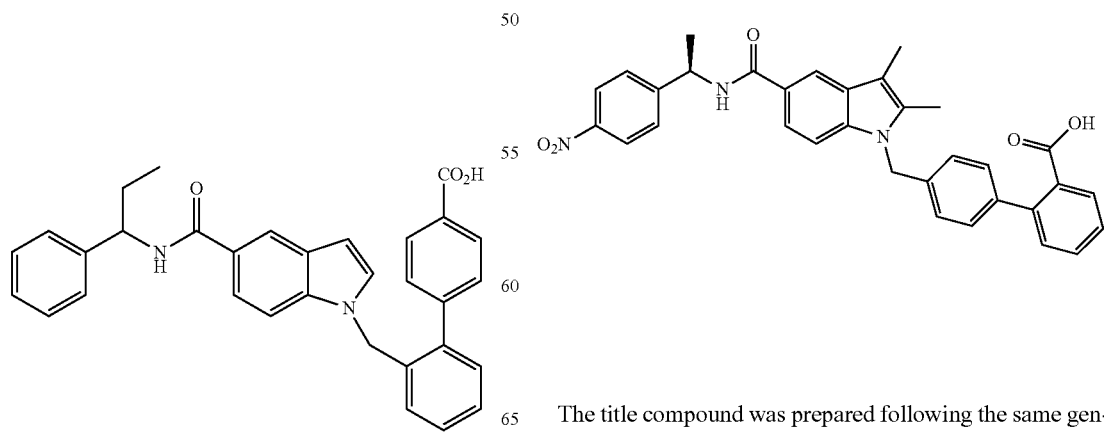

The title compound was prepared following the same general protocol as described in Steps 8-9, Example 1, using (R)-α-methyl-4-nitrobenzylamine and 1-((2'-(tert-butoxycarbonyl)biphenyl-4-yl)methyl)-2,3-dimethyl-1H-indole-5-carboxylic acid. LC-MS 548 (M+H).

Example 73

(S)-4'-((2,3-dimethyl-5-(1-(4-nitrophenyl)ethylcarbamoyl)-1H-indol-1-yl)methyl)biphenyl-2-carboxylic acid

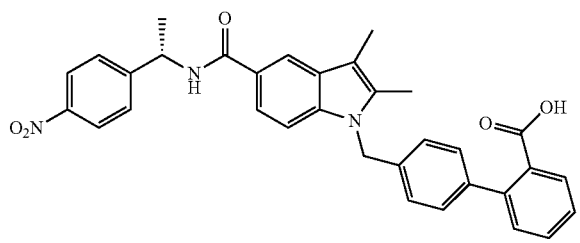

The title compound was prepared following the same general protocol as described in Steps 8-9, Example 1, using (S)-α-methyl-4-nitrobenzylamine and 1-((2'-(tert-butoxycarbonyl)biphenyl-4-yl)methyl)-2,3-dimethyl-1H-indole-5-carboxylic acid. LC-MS 548 (M+H).

Example 74

(R)-4'-((2,3-dimethyl-5-(2-phenylpropylcarbamoyl)-1H-indol-1-yl)methyl)biphenyl-2-carboxylic acid

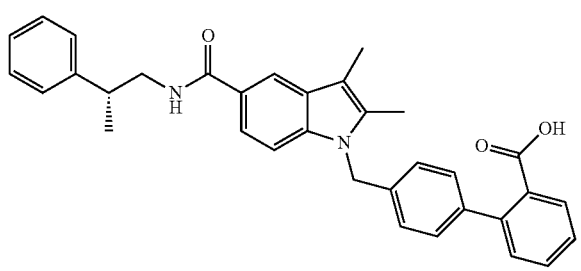 [SMILES: Cc1c(C)n(Cc2ccc(-c3ccccc3C(=O)O)cc2)c2ccc(C(=O)NC[C@H](C)c3ccccc3)cc12]

The title compound was prepared following the same general protocol as described in Steps 8-9, Example 1, using (R)-2-phenylpropan-1-amine and 1-((2'-(tert-butoxycarbonyl)biphenyl-4-yl)methyl)-2,3-dimethyl-1H-indole-5-carboxylic acid. LC-MS 517 (M+H).

Example 75

4'-((5-(benzhydrylcarbamoyl)-2,3-dimethyl-1H-indol-1-yl)methyl)biphenyl-2-carboxylic acid

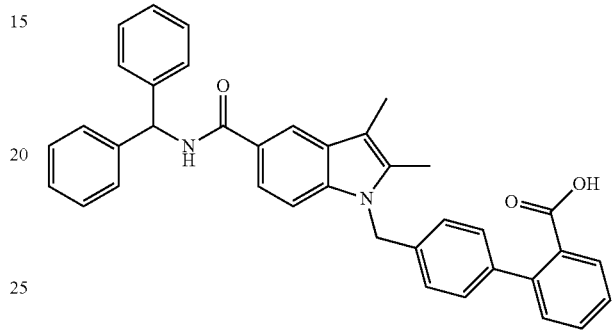

The title compound was prepared following the same general protocol as described in Steps 8-9, Example 1, using diphenylmethanamine and 1-((2'-(tert-butoxycarbonyl)biphenyl-4-yl)methyl)-2,3-dimethyl-1H-indole-5-carboxylic acid.
LC-MS 515 (M+H).

Example 76

4'-((5-(4-fluorobenzylcarbamoyl)-2,3-dimethyl-1H-indol-1-yl)methyl)biphenyl-2-carboxylic acid

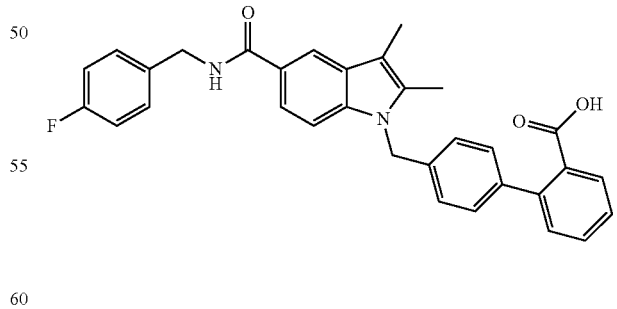

The title compound was prepared following the same general protocol as described in Steps 8-9, Example 1, using 4-fluorobenzylamine and 1-((2'-(tert-butoxycarbonyl)biphenyl-4-yl)methyl)-2,3-dimethyl-1H-indole-5-carboxylic acid.
LC-MS 507 (M+H).

Example 77

4'-((5-(3,4-difluorobenzylcarbamoyl)-2,3-dimethyl-1H-indol-1-yl)methyl)biphenyl-2-carboxylic acid

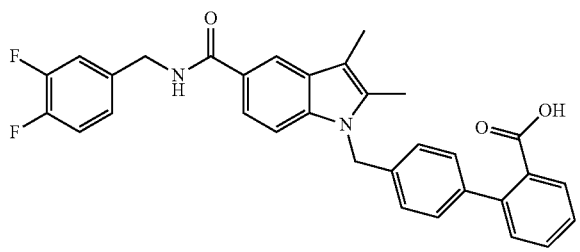

The title compound was prepared following the same general protocol as described in Steps 8-9, Example 1, using 3,4-fluorobenzylamine and 1-((2'-(tert-butoxycarbonyl)biphenyl-4-yl)methyl)-2,3-dimethyl-1H-indole-5-carboxylic acid.

LC-MS 524 (M+H).

Example 78

4'-((5-(benzo[d][1,3]dioxol-5-ylmethylcarbamoyl)-2,3-dimethyl-1H-indol-1-yl)methyl)biphenyl-2-carboxylic acid

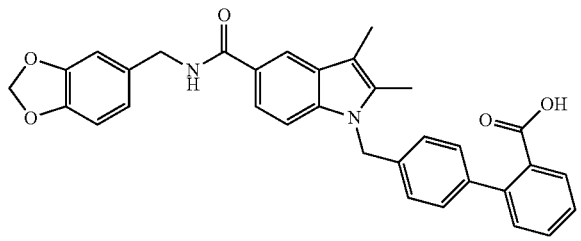 [SMILES: Cc1c(C)n(Cc2ccc(-c3ccccc3C(=O)O)cc2)c2ccc(C(=O)NCc3ccc4c(c3)OCO4)cc12]

The title compound was prepared following the same general protocol as described in Steps 8-9, Example 1, using benzo[d][1,3]dioxol-5-ylmethanamine and 1-((2'-(tert-butoxycarbonyl)biphenyl-4-yl)methyl)-2,3-dimethyl-1H-indole-5-carboxylic acid. LC-MS 533 (M+H).

Example 79

(R)-4'-((5-(2-hydroxy-1-phenylethylcarbamoyl)-2,3-dimethyl-1H-indol-1-yl)methyl)biphenyl-2-carboxylic acid

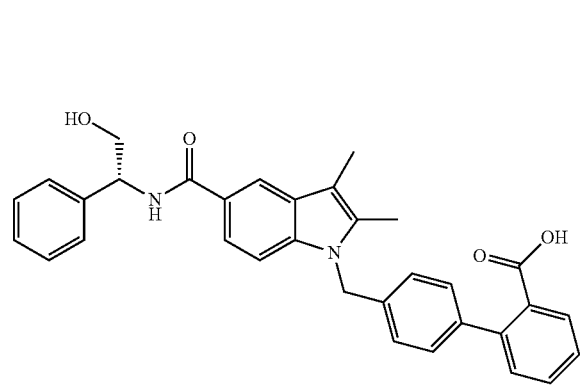 [SMILES: Cc1c(C)n(Cc2ccc(-c3ccccc3C(=O)O)cc2)c2ccc(C(=O)N[C@@H](CO)c3ccccc3)cc12]

The title compound was prepared following the same general protocol as described in Steps 8-9, Example 1, using (R)-2-amino-2-phenylethanol and 1-((2'-(tert-butoxycarbonyl)biphenyl-4-yl)methyl)-2,3-dimethyl-1H-indole-5-carboxylic acid. LC-MS 519 (M+H).

Example 80

4'-((5-(3-aminobenzylcarbamoyl)-2,3-dimethyl-1H-indol-1-yl)methyl)biphenyl-2-carboxylic acid

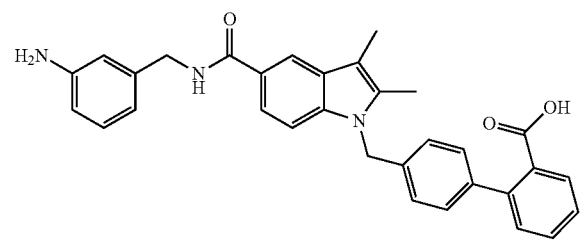 [SMILES: Cc1c(C)n(Cc2ccc(-c3ccccc3C(=O)O)cc2)c2ccc(C(=O)NCc3cccc(N)c3)cc12]

The title compound was prepared following the same general protocol as described in Steps 8-9, Example 1, using 3-aminobenzylamine and 1-((2'-(tert-butoxycarbonyl)biphenyl-4-yl)methyl)-2,3-dimethyl-1H-indole-5-carboxylic acid.

LC-MS 504 (M+H).

Example 81

4'-((5-(cyclohexylmethylcarbamoyl)-2,3-dimethyl-1H-indol-1-yl)methyl)biphenyl-2-carboxylic acid

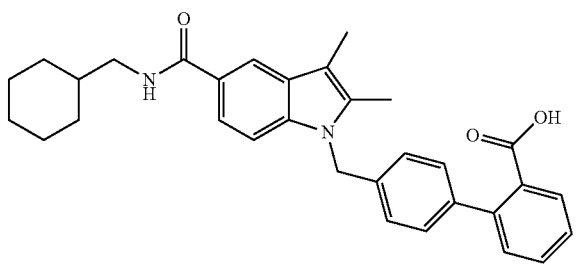 [SMILES: Cc1c(C)n(Cc2ccc(-c3ccccc3C(=O)O)cc2)c2ccc(C(=O)NCC3CCCCC3)cc12]

The title compound was prepared following the same general protocol as described in Steps 8-9, Example 1, using cyclohexylmethylamine and 1-((2'-(tert-butoxycarbonyl)biphenyl-4-yl)methyl)-2,3-dimethyl-1H-indole-5-carboxylic acid.

LC-MS 495 (M+H).

Example 82

4'-((5-(3-(aminomethyl)benzylcarbamoyl)-2,3-dimethyl-1H-indol-1-yl)methyl)biphenyl-2-carboxylic acid

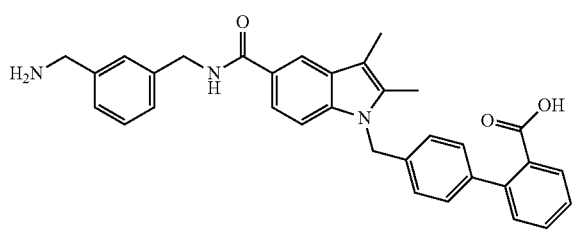 [SMILES: Cc1c(C)n(Cc2ccc(-c3ccccc3C(=O)O)cc2)c2ccc(C(=O)NCc3cccc(CN)c3)cc12]

The title compound was prepared following the same general protocol as described in Steps 8-9, Example 1, using tert-butyl 3-(aminomethyl)benzylcarbamate and 1-((2'-(tert-butoxycarbonyl)biphenyl-4-yl)methyl)-2,3-dimethyl-1H-indole-5-carboxylic acid. LC-MS 518 (M+H).

Example 83

4'-((2,3-dimethyl-5-(thiophen-2-ylmethylcarbamoyl)-1H-indol-1-yl)methyl)biphenyl-2-carboxylic acid

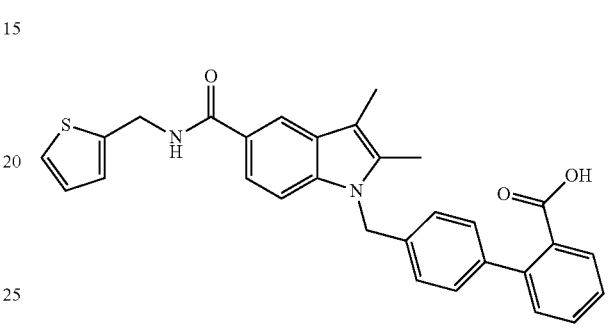

The title compound was prepared following the same general protocol as described in Steps 8-9, Example 1, using 2-thiophenemethylamine and 1-((2'-(tert-butoxycarbonyl)biphenyl-4-yl)methyl)-2,3-dimethyl-1H-indole-5-carboxylic acid.

LC-MS 495 (M+H).

Example 84

4'-((2,3-dimethyl-5-((5-methylfuran-2-yl)methylcarbamoyl)-1H-indol-1-yl)methyl)biphenyl-2-carboxylic acid

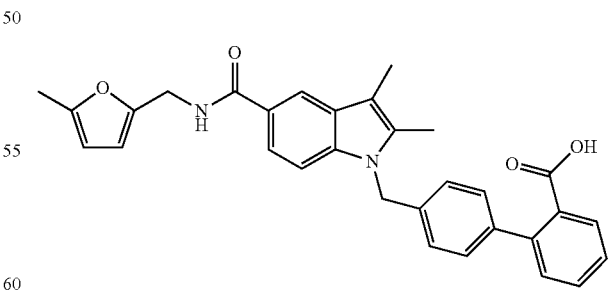

The title compound was prepared following the same general protocol as described in Steps 8-9, Example 1, using 5-methyl-2-furanylmethylamine and 1-((2'-(tert-butoxycarbonyl)biphenyl-4-yl)methyl)-2,3-dimethyl-1H-indole-5-carboxylic acid. LC-MS 493 (M+H).

Example 85

4'-((2,3-dimethyl-5-(2-morpholinoethylcarbamoyl)-1H-indol-1-yl)methyl)biphenyl-2-carboxylic acid

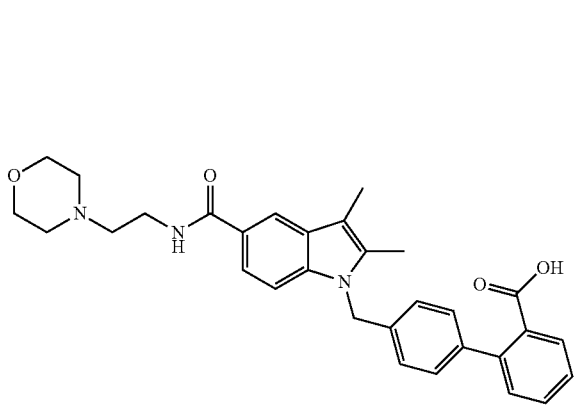 [SMILES: Cc1c(C)n(Cc2ccc(-c3ccccc3C(=O)O)cc2)c2ccc(C(=O)NCCN3CCOCC3)cc12]

The title compound was prepared following the same general protocol as described in Steps 8-9, Example 1, using 2-morphormethylamine and 1-((2'-(tert-butoxycarbonyl)biphenyl-4-yl)methyl)-2,3-dimethyl-1H-indole-5-carboxylic acid.

LC-MS 512 (M+H).

Example 86

4'-((5-(chroman-3-ylcarbamoyl)-2,3-dimethyl-1H-indol-1-yl)methyl)biphenyl-2-carboxylic acid

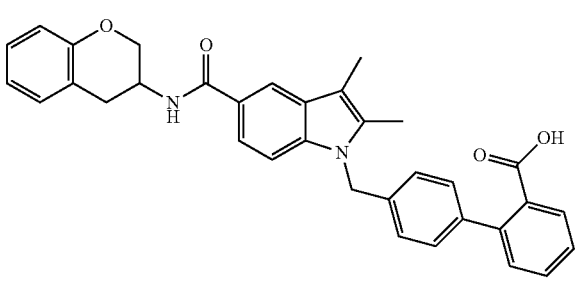 [SMILES: Cc1c(C)n(Cc2ccc(-c3ccccc3C(=O)O)cc2)c2ccc(C(=O)NC3COc4ccccc4C3)cc12]

The title compound was prepared following the same general protocol as described in Steps 8-9, Example 1, using chroman-3-amine and 1-((2'-(tert-butoxycarbonyl)biphenyl-4-yl)methyl)-2,3-dimethyl-1H-indole-5-carboxylic acid.

LC-MS 531 (M+H).

Example 87

4'-((5-(chroman-3-ylmethylcarbamoyl)-2,3-dimethyl-1H-indol-1-yl)methyl)biphenyl-2-carboxylic acid

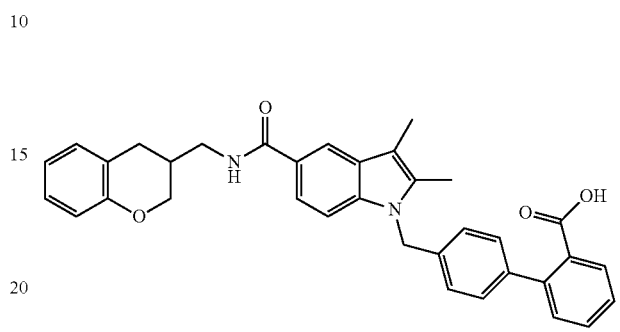

The title compound was prepared following the same general protocol as described in Steps 8-9, Example 1, using chroman-3-ylmethanamine and 1-((2'-(tert-butoxycarbonyl)biphenyl-4-yl)methyl)-2,3-dimethyl-1H-indole-5-carboxylic acid. LC-MS 545 (M+H).

Example 88

4'-((5-((2,3-dihydrobenzo[b][1,4]dioxin-2-yl)methylcarbamoyl)-2,3-dimethyl-1H-indol-1-yl)methyl)biphenyl-2-carboxylic acid

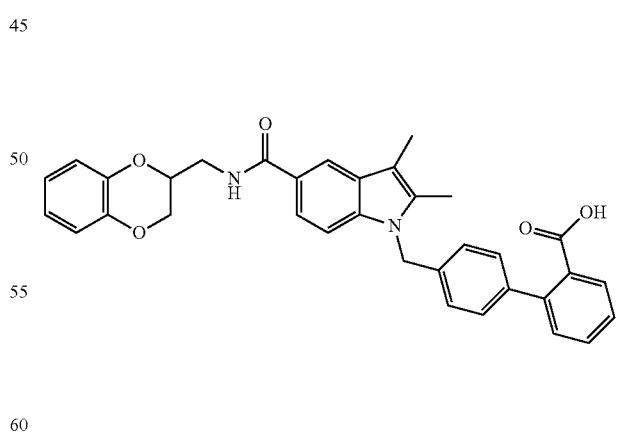

The title compound was prepared following the same general protocol as described in Steps 8-9, Example 1, using (2,3-dihydrobenzo[b][1,4]dioxin-2-yl)methanamine and 1-((2'-(tert-butoxycarbonyl)biphenyl-4-yl)methyl)-2,3-dimethyl-1H-indole-5-carboxylic acid. LC-MS 547 (M+H).

Example 89

4'-((5-(cyclobutylcarbamoyl)-2,3-dimethyl-1H-indol-1-yl)methyl)biphenyl-2-carboxylic acid

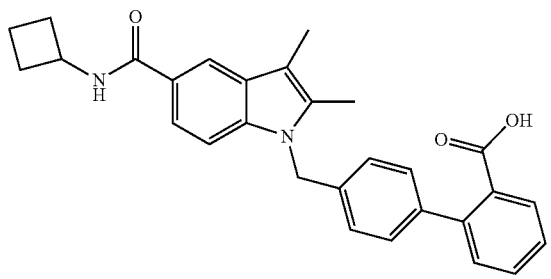 [SMILES: Cc1c(C)n(Cc2ccc(-c3ccccc3C(=O)O)cc2)c2ccc(C(=O)NC3CCC3)cc12]

The title compound was prepared following the same general protocol as described in Steps 8-9, Example 1, using cyclobutylamine and 1-((2'-(tert-butoxycarbonyl)biphenyl-4-yl)methyl)-2,3-dimethyl-1H-indole-5-carboxylic acid.
LC-MS 453 (M+H).

Example 90

4'-((5-(cyclopentylcarbamoyl)-2,3-dimethyl-1H-indol-1-yl)methyl)biphenyl-2-carboxylic acid

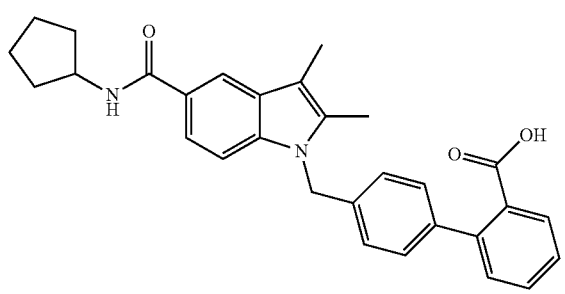 [SMILES: Cc1c(C)n(Cc2ccc(-c3ccccc3C(=O)O)cc2)c2ccc(C(=O)NC3CCCC3)cc12]

The title compound was prepared following the same general protocol as described in Steps 8-9, Example 1, using cyclopentylamine and 1-((2'-(tert-butoxycarbonyl)biphenyl-4-yl)methyl)-2,3-dimethyl-1H-indole-5-carboxylic acid.
LC-MS 467 (M+H).

Example 91

4'-((5-(3-aminocyclohexylcarbamoyl)-2,3-dimethyl-1H-indol-1-yl)methyl)biphenyl-2-carboxylic acid

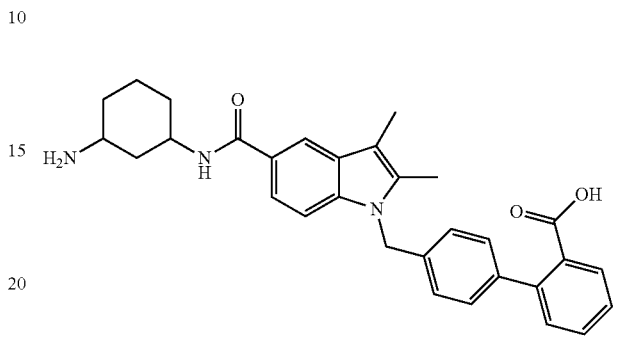

The title compound was prepared following the same general protocol as described in Steps 8-9, Example 1, using tert-butyl 3-aminocyclohexylcarbamate and 1-((2'-(tert-butoxycarbonyl)biphenyl-4-yl)methyl)-2,3-dimethyl-1H-indole-5-carboxylic acid. LC-MS 496 (M+H).

Example 92

4'-((5-(2-methoxyethylcarbamoyl)-2,3-dimethyl-1H-indol-1-yl)methyl)biphenyl-2-carboxylic acid

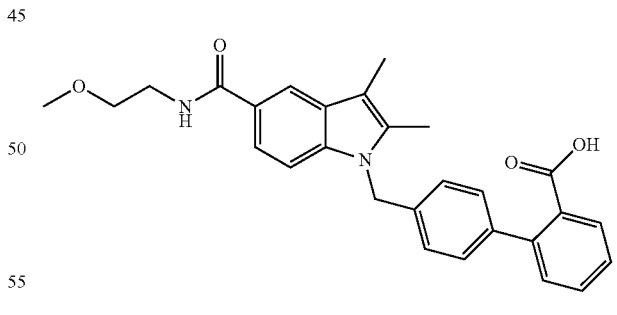

The title compound was prepared following the same general protocol as described in Steps 8-9, Example 1, using 2-methoxyethyleneamine and 1-((2'-(tert-butoxycarbonyl)biphenyl-4-yl)methyl)-2,3-dimethyl-1H-indole-5-carboxylic acid.
LC-MS 457 (M+H).

Example 93

4'-((5-(benzylcarbamoyl)-2,3-dimethyl-1H-indol-1-yl)methyl)biphenyl-2-carboxylic acid

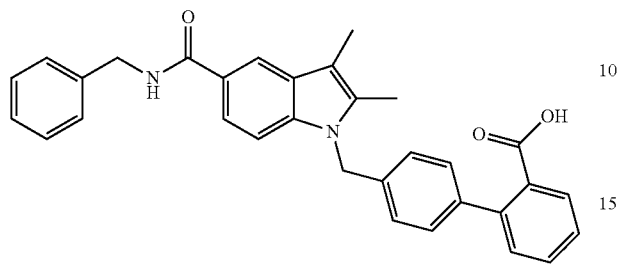

The title compound was prepared following the same general protocol as described in Steps 8-9, Example 1, using benzylamine and 1-((2'-(tert-butoxycarbonyl)biphenyl-4-yl)methyl)-2,3-dimethyl-1H-indole-5-carboxylic acid.
LC-MS 489 (M+H).

Example 94

4'-((5-(2-aminobenzylcarbamoyl)-2,3-dimethyl-1H-indol-1-yl)methyl)biphenyl-2-carboxylic acid

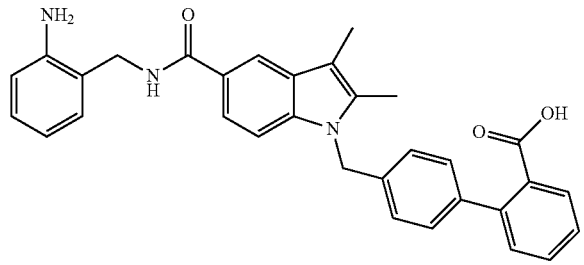

The title compound was prepared following the same general protocol as described in Steps 8-9, Example 1, using 2-aminobenzylamine and 1-((2'-(tert-butoxycarbonyl)biphenyl-4-yl)methyl)-2,3-dimethyl-1H-indole-5-carboxylic acid.
LC-MS 504 (M+H).

Example 95

4'-((5-(4-aminobenzylcarbamoyl)-2,3-dimethyl-1H-indol-1-yl)methyl)biphenyl-2-carboxylic acid

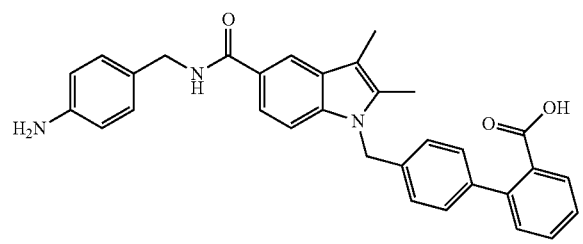 [SMILES: Cc1c(C)n(Cc2ccc(-c3ccccc3C(=O)O)cc2)c2ccc(C(=O)NCc3ccc([N+](=O)[O-])cc3)cc12]

The title compound was prepared following the same general protocol as described in Steps 8-9, Example 1, using 4-aminobenzylamine and 1-((2'-(tert-butoxycarbonyl)biphenyl-4-yl)methyl)-2,3-dimethyl-1H-indole-5-carboxylic acid.
LC-MS 504 (M+H).

Example 96

4'-((2,3-dimethyl-5-(4-nitrobenzylcarbamoyl)-1H-indol-1-yl)methyl)biphenyl-2-carboxylic acid

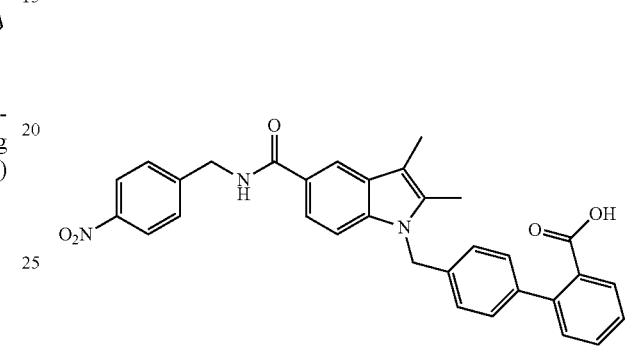

The title compound was prepared following the same general protocol as described in Steps 8-9, Example 1, using 4-nitrobenzylamine and 1-((2'-(tert-butoxycarbonyl)biphenyl-4-yl)methyl)-2,3-dimethyl-1H-indole-5-carboxylic acid.
LC-MS 534 (M+H).

Example 97

(R)-4'-((2,3-dimethyl-5-(1-phenylpropylcarbamoyl)-1H-indol-1-yl)methyl)biphenyl-2-carboxylic acid

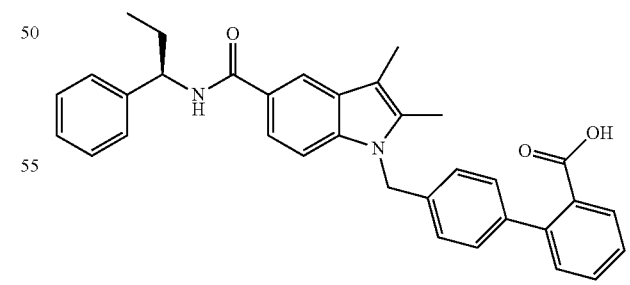

The title compound was prepared following the same general protocol as described in Steps 8-9, Example 1, using (R)-α-ethylbenzylamine and 1-((2'-(tert-butoxycarbonyl)biphenyl-4-yl)methyl)-2,3-dimethyl-1H-indole-5-carboxylic acid.
LC-MS 517 (M+H).

Example 98

(S)-4'-((2,3-dimethyl-5-(1-phenylpropylcarbamoyl)-1H-indol-1-yl)methyl)biphenyl-2-carboxylic acid

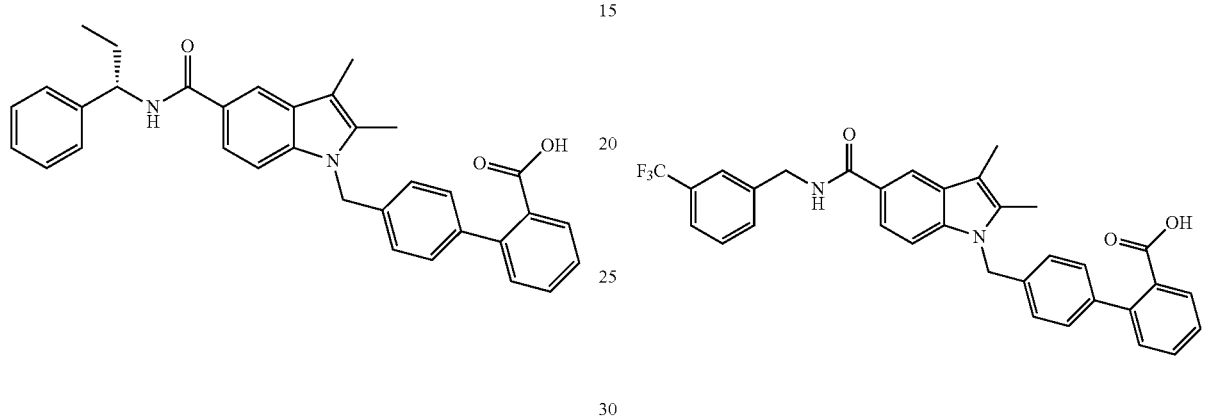

The title compound was prepared following the same general protocol as described in Steps 8-9, Example 1, using (S)-α-ethylbenzylamine and 1-((2'-(tert-butoxycarbonyl)biphenyl-4-yl)methyl)-2,3-dimethyl-1H-indole-5-carboxylic acid.

LC-MS 517 (M+H).

Example 99

(S)-4'-((5-(1-(4-aminophenyl)ethylcarbamoyl)-2,3-dimethyl-1H-indol-1-yl)methyl)biphenyl-2-carboxylic acid The title compound was prepared following the same general protocol as described in Steps 8-9, Example 1, using 4-amino-(S)-α-methylbenzylamine and 1-((2'-(tert-butoxycarbonyl)biphenyl-4-yl)methyl)-2,3-dimethyl-1H-indole-5-carboxylic acid. LC-MS 518 (M+H).

Example 100

4'-((2,3-dimethyl-5-(3-(trifluoromethyl)benzylcarbamoyl)-1H-indol-1-yl)methyl)biphenyl-2-carboxylic acid

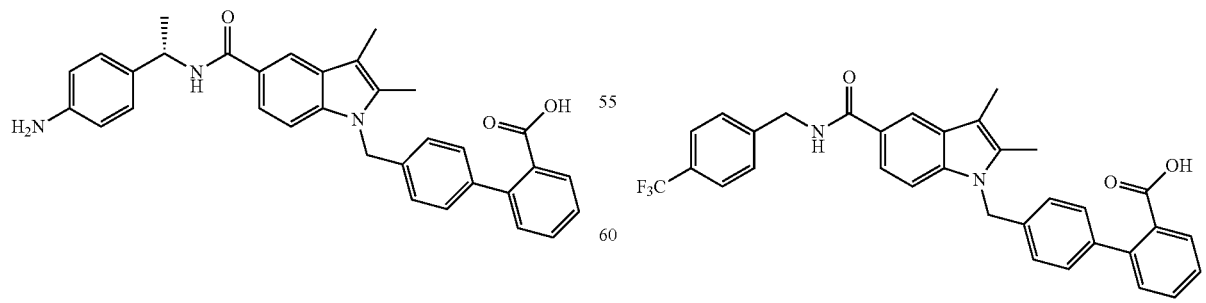

The title compound was prepared following the same general protocol as described in Steps 8-9, Example 1, using 3-trifluoromethylbenzylamine and 1-((2'-(tert-butoxycarbonyl)biphenyl-4-yl)methyl)-2,3-dimethyl-1H-indole-5-carboxylic acid. LC-MS 557 (M+H).

Example 101

4'-((2,3-dimethyl-5-(4-(trifluoromethyl)benzylcarbamoyl)-1H-indol-1-yl)methyl)biphenyl-2-carboxylic acid The title compound was prepared following the same general protocol as described in Steps 8-9, Example 1, using 4-trifluoromethylbenzylamine and 1-((2'-(tert-butoxycarbonyl)biphenyl-4-yl)methyl)-2,3-dimethyl-1H-indole-5-carboxylic acid. LC-MS 557 (M+H).

Example 102

4'-((5-(biphenyl-4-ylmethylcarbamoyl)-2,3-dimethyl-1H-indol-1-yl)methyl)biphenyl-2-carboxylic acid

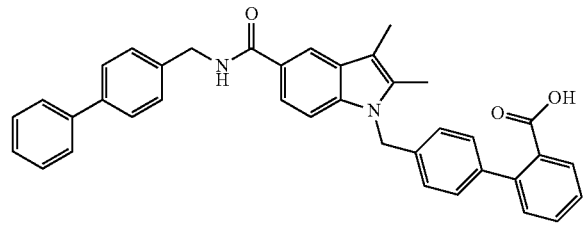 [SMILES: Cc1c(C)n(Cc2ccc(-c3ccccc3C(=O)O)cc2)c2ccc(C(=O)NCc3ccc(-c4ccccc4)cc3)cc12]

The title compound was prepared following the same general protocol as described in Steps 8-9, Example 1, using 4-phenylbenzylamine and 1-((2'-(tert-butoxycarbonyl)biphenyl-4-yl)methyl)-2,3-dimethyl-1H-indole-5-carboxylic acid.

LC-MS 565 (M+H).

Example 103

4'-((5-(3-methoxybenzylcarbamoyl)-2,3-dimethyl-1H-indol-1-yl)methyl)biphenyl-2-carboxylic acid

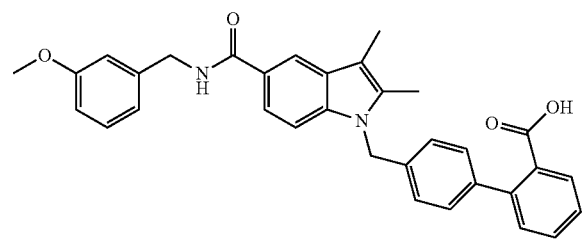 [SMILES: COc1cccc(CNC(=O)c2ccc3c(c2)c(C)c(C)n3Cc2ccc(-c3ccccc3C(=O)O)cc2)c1]

The title compound was prepared following the same general protocol as described in Steps 8-9, Example 1, using 3-methoxylbenzylamine and 1-((2'-(tert-butoxycarbonyl)biphenyl-4-yl)methyl)-2,3-dimethyl-1H-indole-5-carboxylic acid.

LC-MS 519 (M+H).

Example 104

4'-((5-(4-methoxybenzylcarbamoyl)-2,3-dimethyl-1H-indol-1-yl)methyl)biphenyl-2-carboxylic acid

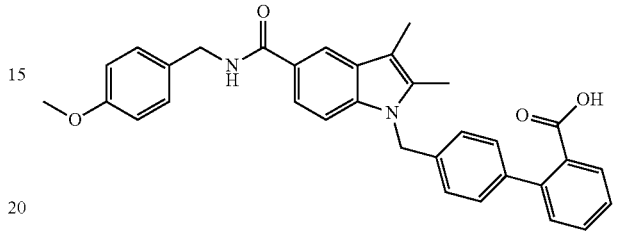

The title compound was prepared following the same general protocol as described in Steps 8-9, Example 1, using 4-methoxylbenzylamine and 1-((2'-(tert-butoxycarbonyl)biphenyl-4-yl)methyl)-2,3-dimethyl-1H-indole-5-carboxylic acid.

LC-MS 519 (M+H).

Example 105

4'-((2,3-dimethyl-5-(3-methylbenzylcarbamoyl)-1H-indol-1-yl)methyl)biphenyl-2-carboxylic acid The title compound was prepared following the same general protocol as described in Steps 8-9, Example 1, using 3-methylbenzylamine and 1-((2'-(tert-butoxycarbonyl)biphenyl-4-yl)methyl)-2,3-dimethyl-1H-indole-5-carboxylic acid.

LC-MS 503 (M+H).

Example 106

4'-((2,3-dimethyl-5-(4-methylbenzylcarbamoyl)-1H-indol-1-yl)methyl)biphenyl-2-carboxylic acid

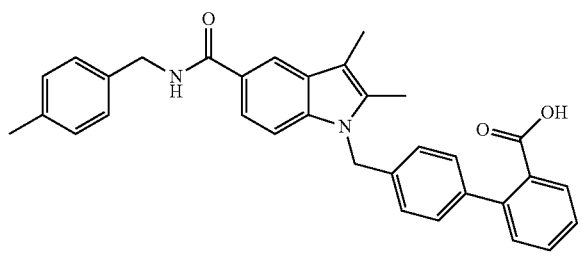 [SMILES: Cc1ccc(CNC(=O)c2ccc3c(c2)c(C)c(C)n3Cc2ccc(-c3ccccc3C(=O)O)cc2)cc1]

The title compound was prepared following the same general protocol as described in Steps 8-9, Example 1, using 4-methylbenzylamine and 1-((2'-(tert-butoxycarbonyl)biphenyl-4-yl)methyl)-2,3-dimethyl-1H-indole-5-carboxylic acid.
LC-MS 503 (M+H).

Example 107

4'-((2,3-dimethyl-5-(2-methylbenzylcarbamoyl)-1H-indol-1-yl)methyl)biphenyl-2-carboxylic acid

The title compound was prepared following the same general protocol as described in Steps 8-9, Example 1, using 2-methylbenzylamine and 1-((2'-(tert-butoxycarbonyl)biphenyl-4-yl)methyl)-2,3-dimethyl-1H-indole-5-carboxylic acid.
LC-MS 503 (M+H).

Example 108

4'-((5-(2-chlorobenzylcarbamoyl)-2,3-dimethyl-1H-indol-1-yl)methyl)biphenyl-2-carboxylic acid

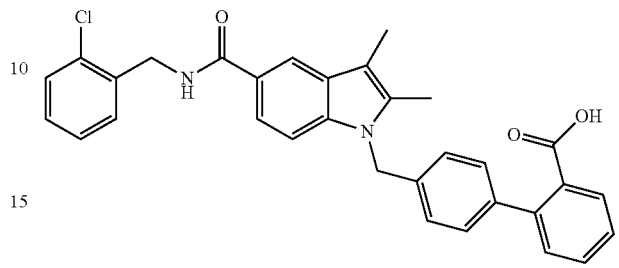

The title compound was prepared following the same general protocol as described in Steps 8-9, Example 1, using 2-chlorobenzylamine and 1-((2'-(tert-butoxycarbonyl)biphenyl-4-yl)methyl)-2,3-dimethyl-1H-indole-5-carboxylic acid.
LC-MS 523 (M+H).

Example 109

4'-((5-(3-chlorobenzylcarbamoyl)-2,3-dimethyl-1H-indol-1-yl)methyl)biphenyl-2-carboxylic acid

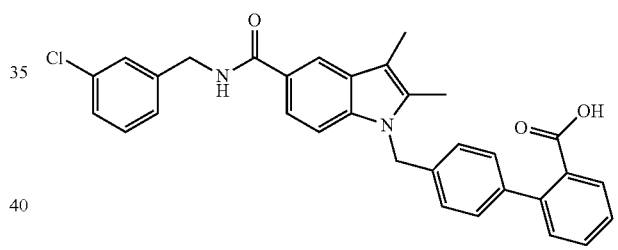

The title compound was prepared following the same general protocol as described in Steps 8-9, Example 1, using 3-chlorobenzylamine and 1-((2'-(tert-butoxycarbonyl)biphenyl-4-yl)methyl)-2,3-dimethyl-1H-indole-5-carboxylic acid.
LC-MS 523 (M+H).

Example 110

4'-((2,3-dimethyl-5-(3-nitrobenzylcarbamoyl)-1H-indol-1-yl)methyl)biphenyl-2-carboxylic acid

The title compound was prepared following the same general protocol as described in Steps 8-9, Example 1, using 3-nitrobenzylamine and 1-((2'-(tert-butoxycarbonyl)biphenyl-4-yl)methyl)-2,3-dimethyl-1H-indole-5-carboxylic acid. LC-MS 534 (M+H).

Example 111

4'-((5-(3-fluoro-4-methoxybenzylcarbamoyl)-2,3-dimethyl-1H-indol-1-yl)methyl)biphenyl-2-carboxylic acid

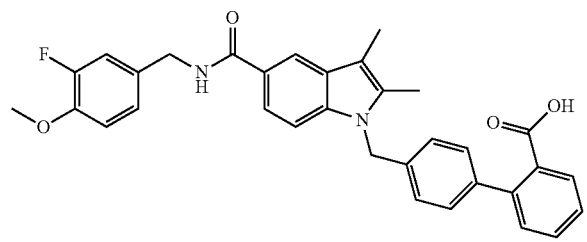 [SMILES: COc1ccc(CNC(=O)c2ccc3c(c2)c(C)c(C)n3Cc2ccc(-c3ccccc3C(=O)O)cc2)cc1F]

The title compound was prepared following the same general protocol as described in Steps 8-9, Example 1, using 3-fluoro-4-methoxybenzylamine and 1-((2'-(tert-butoxycarbonyl)biphenyl-4-yl)methyl)-2,3-dimethyl-1H-indole-5-carboxylic acid. LC-MS 537 (M+H).

Example 112

(S)-4'-((5-(1-(4-fluorophenyl)ethylcarbamoyl)-2,3-dimethyl-1H-indol-1-yl)methyl)biphenyl-2-carboxylic acid

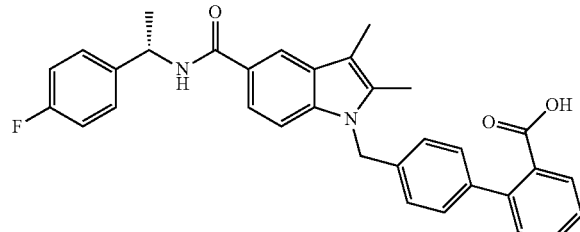

The title compound was prepared following the same general protocol as described in Steps 8-9, Example 1, using 4-fluoro-α-(S)-methylbenzylamine and 1-((2'-(tert-butoxycarbonyl)biphenyl-4-yl)methyl)-2,3-dimethyl-1H-indole-5-carboxylic acid. LC-MS 521 (M+H).

Example 113

(R)-4'-((5-(1-(4-fluorophenyl)ethylcarbamoyl)-2,3-dimethyl-1H-indol-1-yl)methyl)biphenyl-2-carboxylic acid

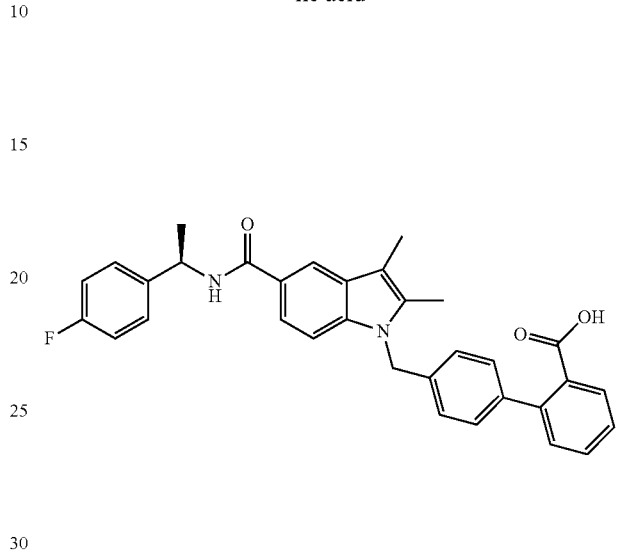

The title compound was prepared following the same general protocol as described in Steps 8-9, Example 1, using 4-fluoro-α-(R)-methylbenzylamine and 1-((2'-(tert-butoxycarbonyl)biphenyl-4-yl)methyl)-2,3-dimethyl-1H-indole-5-carboxylic acid. LC-MS 521 (M+H).

Example 114

(S)-4'-((2,3-dimethyl-5-(1-phenylbutylcarbamoyl)-1H-indol-1-yl)methyl)biphenyl-2-carboxylic acid

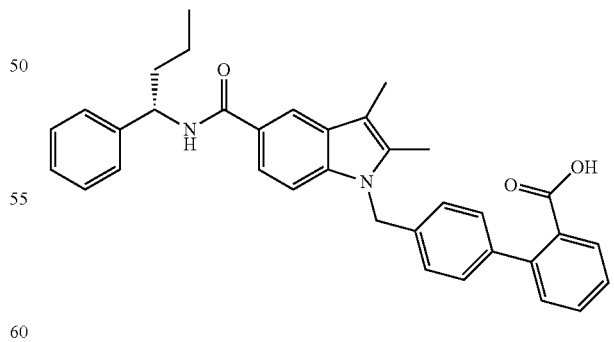

The title compound was prepared following the same general protocol as described in Steps 8-9, Example 1, using α-(S)-ethylbenzylamine and 1-((2'-(tert-butoxycarbonyl)biphenyl-4-yl)methyl)-2,3-dimethyl-1H-indole-5-carboxylic acid.
LC-MS 531 (M+H).

Example 115

4'-((2,3-dimethyl-5-(naphthalen-1-ylmethylcarbamoyl)-1H-indol-1-yl)methyl)biphenyl-2-carboxylic acid

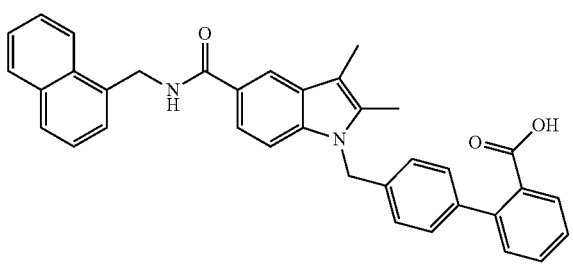

The title compound was prepared following the same general protocol as described in Steps 8-9, Example 1, using 1-naphthylmethylamine and 1-((2'-(tert-butoxycarbonyl)biphenyl-4-yl)methyl)-2,3-dimethyl-1H-indole-5-carboxylic acid.

LC-MS 539 (M+H).

Example 116

4'-((2,3-dimethyl-5-(1-(naphthalen-1-yl)ethylcarbamoyl)-1H-indol-1-yl)methyl)biphenyl-2-carboxylic acid

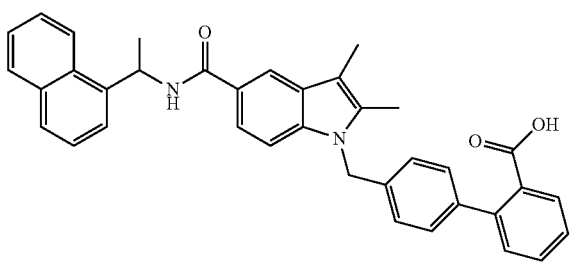 [SMILES: Cc1c(C)n(Cc2ccc(-c3ccccc3C(=O)O)cc2)c2ccc(C(=O)NC(C)c3cccc4ccccc34)cc12]

The title compound was prepared following the same general protocol as described in Steps 8-9, Example 1, using 1-(naphthalen-1-yl)ethanamine and 1-((2'-(tert-butoxycarbonyl)biphenyl-4-yl)methyl)-2,3-dimethyl-1H-indole-5-carboxylic acid. LC-MS 553 (M+H).

Example 117

4'-((2,3-dimethyl-5-(4-phenylbutan-2-ylcarbamoyl)-1H-indol-1-yl)methyl)biphenyl-2-carboxylic acid

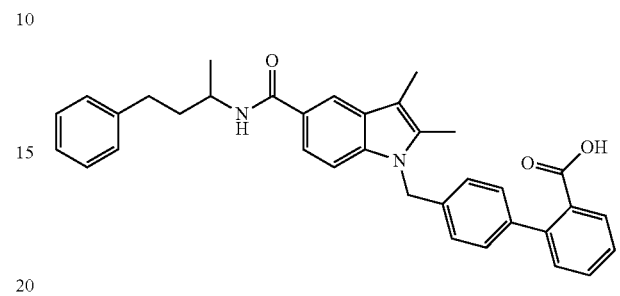

The title compound was prepared following the same general protocol as described in Steps 8-9, Example 1, using 4-phenylbutan-2-amine and 1-((2'-(tert-butoxycarbonyl)biphenyl-4-yl)methyl)-2,3-dimethyl-1H-indole-5-carboxylic acid.

LC-MS 531 (M+H).

Example 118

4'-((5-((2-Bromobenzyl)carbamoyl)-2,3-dimethyl-1H-indol-1-yl)methyl)-[1,1'-biphenyl]-2-carboxylic acid (SR-3-2223)

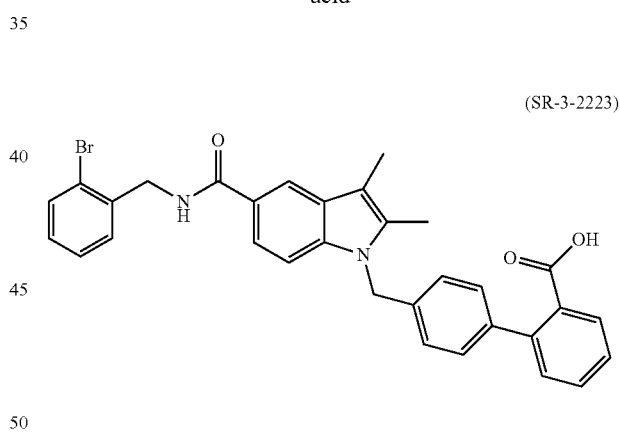

Step 1: tert-Butyl 4'-((5-((2-bromobenzyl)carbamoyl)-2,3-dimethyl-1H-indol-1-yl)methyl)-[1,1'-biphenyl]-2-carboxylate

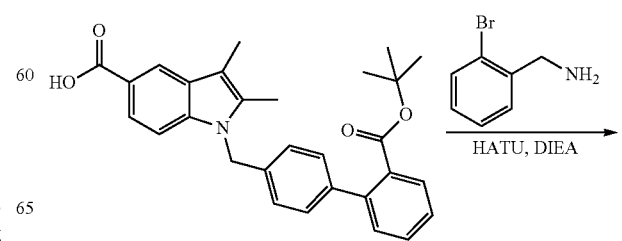

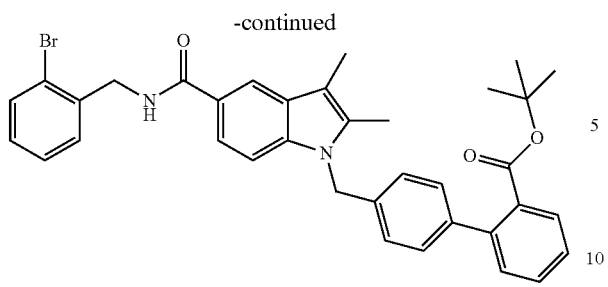

The title compound was prepared following the same general protocol as described in Step 8, Example 1, the (2-bromophenyl)methanamine was used instead of the (S)-1-(4-bromophenyl)ethanamine.

ESI-MS (m/z): 623/625 [M+H]$^+$.

Step 2: 4'-((5-((2-Bromobenzyl)carbamoyl)-2,3-dimethyl-1H-indol-1-yl)methyl)-[1,1'-biphenyl]-2-carboxylic acid

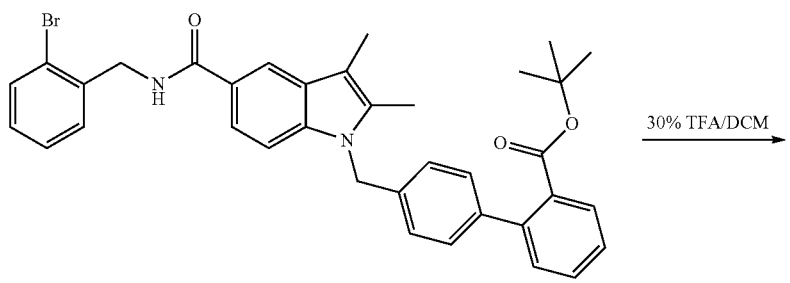

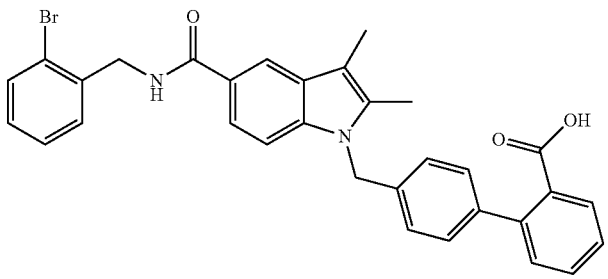

The title compound was prepared following the same general protocol as described in Step 9, Example 1.
ESI-MS (m/z): 567/569 [M+H]$^+$.

Example 119

4'-((5-((2-Nitrobenzyl)carbamoyl)-2,3-dimethyl-1H-indol-1-yl)methyl)-[1,1'-biphenyl]-2-carboxylic acid (SR-3-2224)

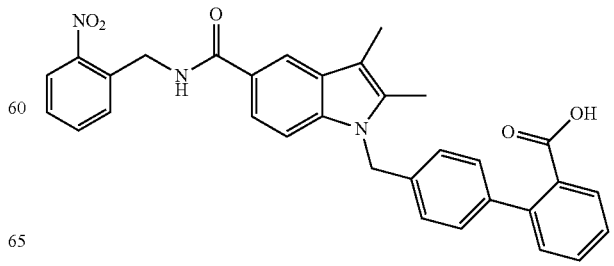

305

Step 1: tert-Butyl 4'-((5-((2-nitrobenzyl)carbamoyl)-2,3-dimethyl-1H-indol-1-yl)methyl)-[1,1'-biphenyl]-2-carboxylate

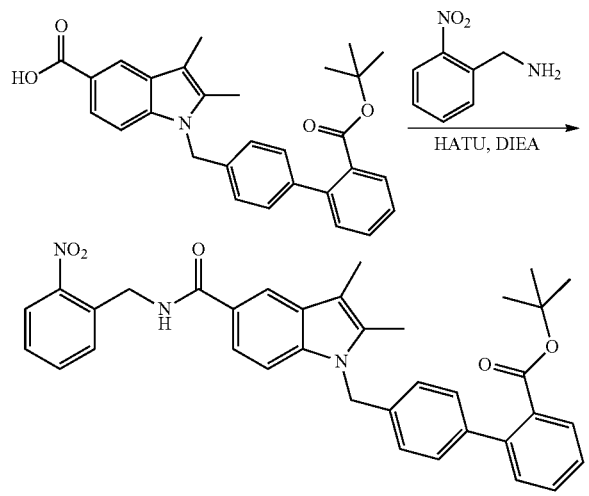

The title compound was prepared following the same general protocol as described in Step 8, Example 1, the (2-nitrophenyl)methanamine was used instead of the (S)-1-(4-bromophenyl)ethanamine.

ESI-MS (m/z): 590 [M+H]$^+$.

Step 2: 4'-((5-((2-Nitrobenzyl)carbamoyl)-2,3-dimethyl-1H-indol-1-yl)methyl)-[1,1'-biphenyl]-2-carboxylic acid

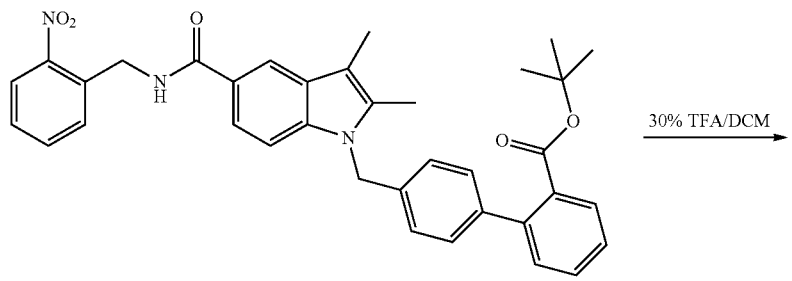

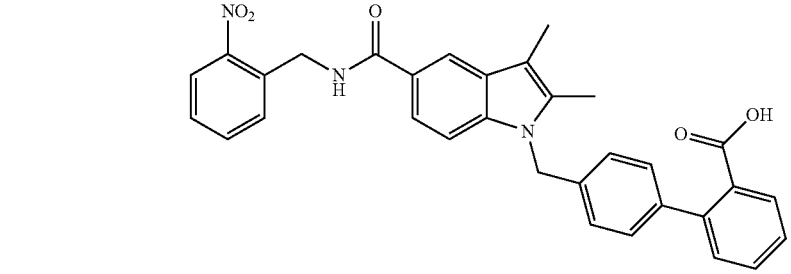

306

The title compound was prepared following the same general protocol as described in Step 9, Example 1.

ESI-MS (m/z): 534 [M+H]$^+$.

Example 120

(S)-2'-((5-((1-(4-Bromophenyl)ethyl)carbamoyl)-1H-indol-1-yl)methyl)-[1,1'-biphenyl]-4-carboxylic acid

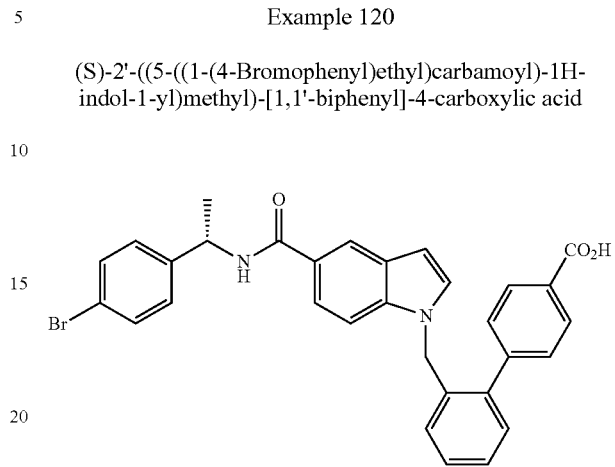

Step 1: 1-(3-Bromobenzyl)-2,3-dimethyl-1H-indole-5-carboxylic acid

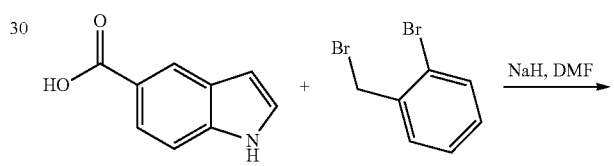

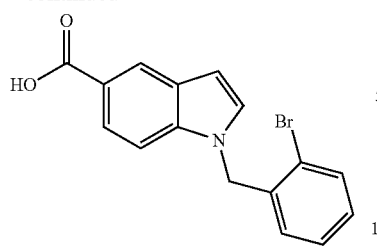

The title compound was prepared following the same protocol as described in Step 2, Example 38, using 1H-indole-5-carboxylic acid instead of the methyl 1H-indole-5-carboxylate, and 1-bromo-2-(bromomethyl)benzene instead of the 1-bromo-4-(bromomethyl)benzene. ESI-MS (m/z): 330/332 [M+H]$^+$.

Step 2: 1-((4'-(Ethoxycarbonyl)-[1,1'-biphenyl]-2-yl)methyl)-1H-indole-5-carboxylic acid

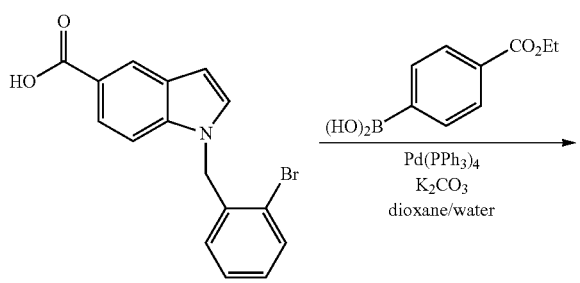

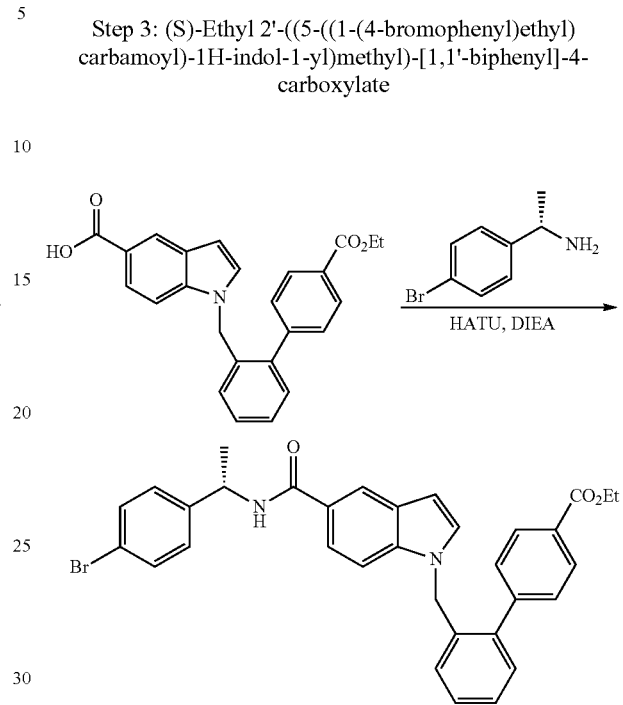

carboxamide and the (4-(ethoxycarbonyl)phenyl)boronic acid instead of the phenylboronic acid. ESI-MS (m/z): 400 [M+H]$^+$.

Step 3: (S)-Ethyl 2'-((5-((1-(4-bromophenyl)ethyl)carbamoyl)-1H-indol-1-yl)methyl)-[1,1'-biphenyl]-4-carboxylate The title compound was prepared following the same protocol as described in Step 8, Example 1, using the 1-((4'-(ethoxycarbonyl)-[1,1'-biphenyl]-2-yl)methyl)-1H-indole-5-carboxylic acid instead of the 1-((2'-(tert-Butoxycarbonyl)biphenyl-4-yl)methyl)-2,3-dimethyl-1H-indole-5-carboxylic acid.

Step 4: (S)-2'-((5-((1-(4-Bromophenyl)ethyl)carbamoyl)-1H-indol-1-yl)methyl)-[1,1'-biphenyl]-4-carboxylic acid

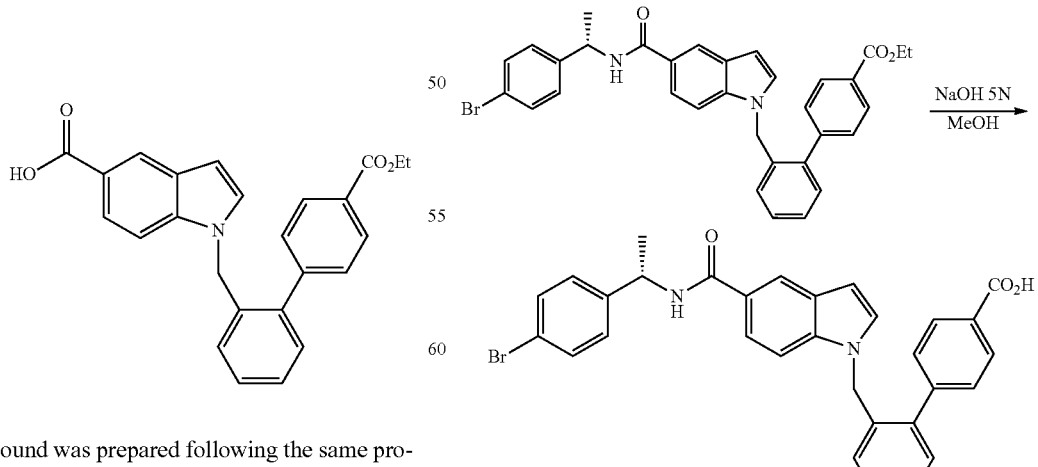

The title compound was prepared following the same protocol as described in Step 5, Example 38, using 1-(2-bromobenzyl)-1H-indole-5-carboxylic acid instead of the (S)-1-(4-bromobenzyl)-N-(1-(4-nitrophenyl)ethyl)-1H-indole-5-

309

The title compound was prepared following the same protocol as described in Example 59, using (S)-ethyl 2'-((5-((1-(4-bromophenyl)ethyl)carbamoyl)-1H-indol-1-yl)methyl)-[1,1'-biphenyl]-4-carboxylate instead of the (S)-ethyl 4'-((5-((1-(4-nitrophenyl)ethyl)carbamoyl)-1H-indol-1-yl)methyl)-[1,1'-biphenyl]-4-carboxylate. ESI-MS (m/z): 553/555 [M+H]+.

Example 121

(S)-2'-((5-((1-(4-Nitrophenyl)ethyl)carbamoyl)-1H-indol-1-yl)methyl)-[1,1'-biphenyl]-4-carboxylic acid

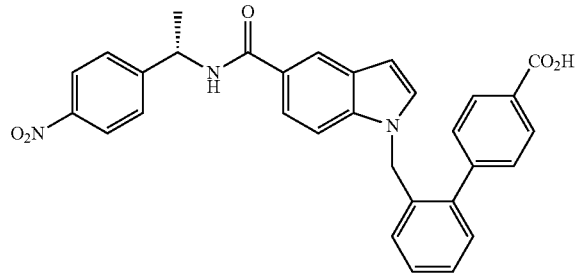

310

Step 1: (S)-Ethyl 2'-((5-((1-(4-nitrophenyl)ethyl)carbamoyl)-1H-indol-1-yl)methyl)-[1,1'-biphenyl]-4-carboxylate

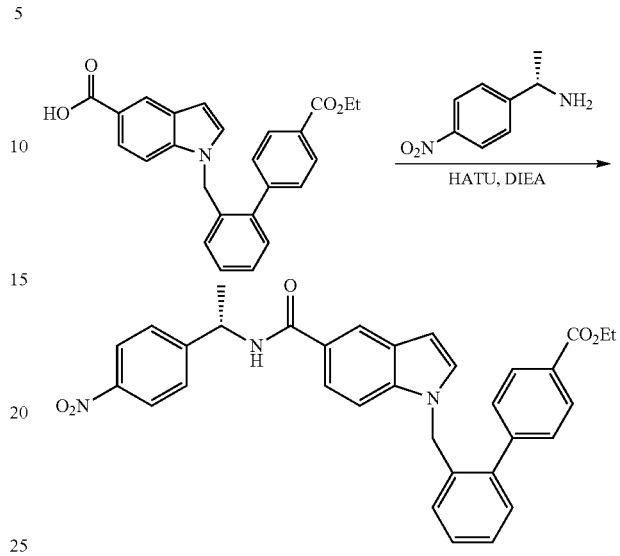

The title compound was prepared following the same protocol as described in Step 8, Example 1, using the 1-((4'-(ethoxycarbonyl)-[1,1'-biphenyl]-2-yl)methyl)-1H-indole-5-carboxylic acid instead of the 1-((2'-(tert-Butoxycarbonyl)biphenyl-4-yl)methyl)-2,3-dimethyl-1H-indole-5-carboxylic acid and the (S)-1-(4-nitrophenyl)ethanamine instead of the (S)-1-(4-bromophenyl)ethanamine.

Step 2: (S)-2'-((5-((1-(4-Nitrophenyl)ethyl)carbamoyl)-1H-indol-1-yl)methyl)-[1,1'-biphenyl]-4-carboxylic acid

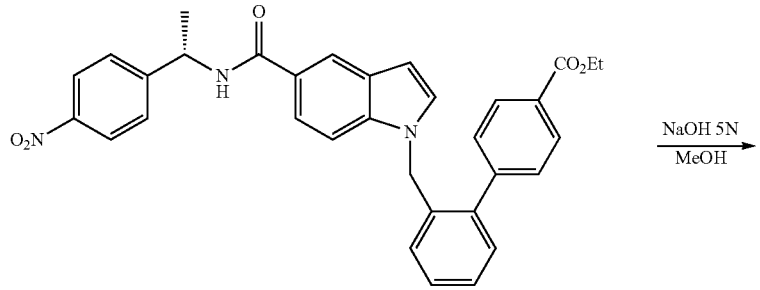

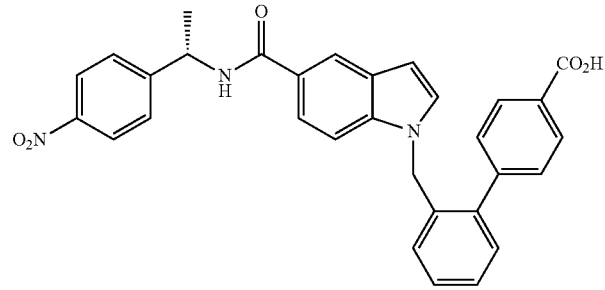 [SMILES: C[C@H](NC(=O)c1ccc2c(ccn2Cc2ccccc2-c2ccc(C(=O)O)cc2)c1)c1ccc([N+](=O)[O-])cc1]

311

The title compound was prepared following the same protocol as described in Example 59, using (S)-ethyl 2'-((5-((1-(4-nitrophenyl)ethyl)carbamoyl)-1H-indol-1-yl)methyl)-[1,1'-biphenyl]-4-carboxylate instead of the (S)-ethyl 4'-((5-((1-(4-nitrophenyl)ethyl)carbamoyl)-1H-indol-1-yl)methyl)-[1,1'-biphenyl]-4-carboxylate.

ESI-MS (m/z): 520 [M+H]⁺.

Example 122

(S)-2'-((5-((1-(4-Bromophenyl)ethyl)carbamoyl)-1H-indol-1-yl)methyl)-[1,1'-biphenyl]-3-carboxylic acid

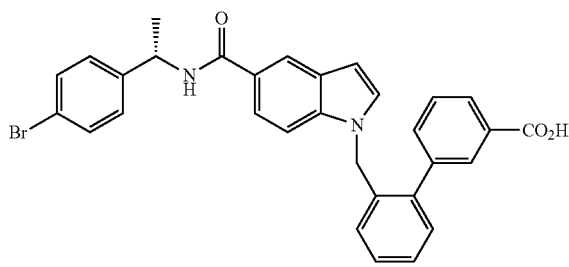 [SMILES: C[C@H](NC(=O)c1ccc2c(ccn2Cc2ccccc2-c2cccc(C(=O)O)c2)c1)c1ccc(Br)cc1]

312

Step 1: 1-((3'-(Ethoxycarbonyl)-[1,1'-biphenyl]-2-yl)methyl)-1H-indole-5-carboxylic acid

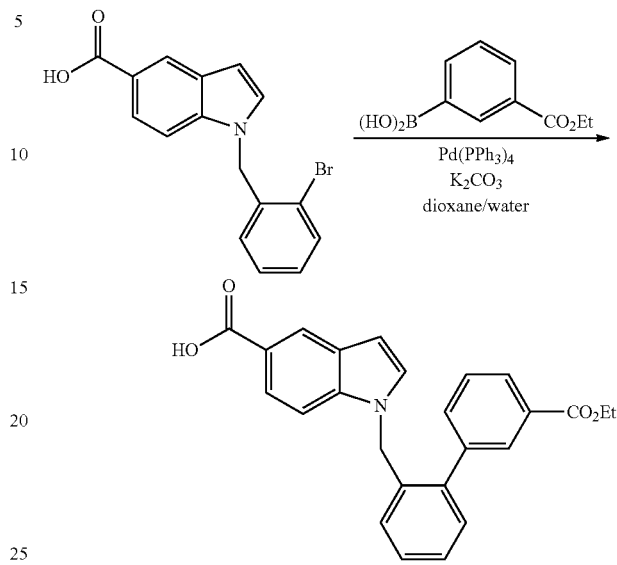

The title compound was prepared following the same protocol as described in Step 5, Example 38, using 1-(2-bromobenzyl)-1H-indole-5-carboxylic acid instead of the (S)-1-(4-bromobenzyl)-N-(1-(4-nitrophenyl)ethyl)-1H-indole-5-carboxamide and the (3-(ethoxycarbonyl)phenyl)boronic acid instead of the phenylboronic acid. ESI-MS (m/z): 400 [M+H]⁺.

Step 2: (S)-Ethyl 2'-((5-((1-(4-bromophenyl)ethyl)carbamoyl)-1H-indol-1-yl)methyl)-[1,1'-biphenyl]-3-carboxylate

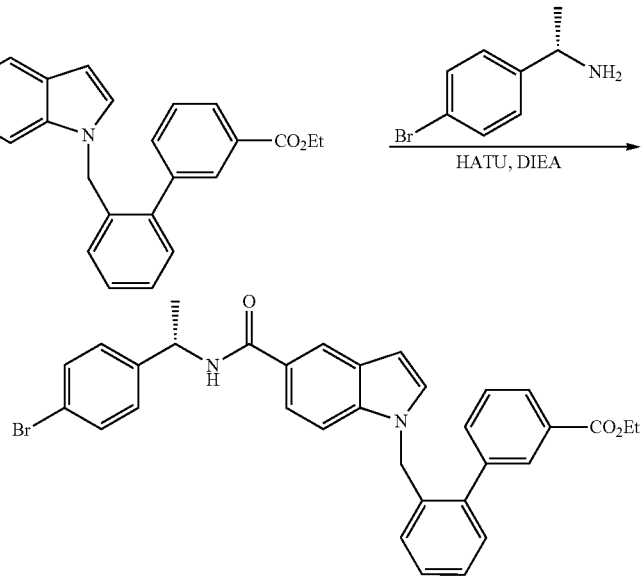

The title compound was prepared following the same protocol as described in Step 8, Example 1, using the 1-((3'-(ethoxycarbonyl)-[1,1'-biphenyl]-2-yl)methyl)-1H-indole-5-carboxylic acid instead of the 1-((2'-(tert-Butoxycarbonyl)biphenyl-4-yl)methyl)-2,3-dimethyl-1H-indole-5-carboxylic acid.

Step 3: (S)-2'-((5-((1-(4-Bromophenyl)ethyl)carbamoyl)-1H-indol-1-yl)methyl)-[1,1'-biphenyl]-3-carboxylic acid

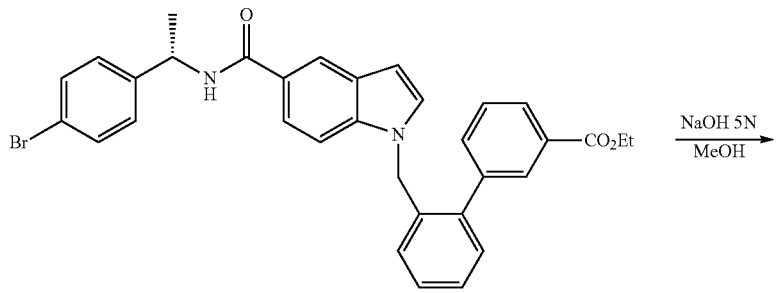

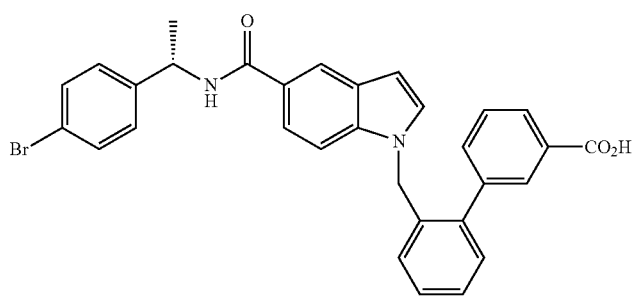

The title compound was prepared following the same protocol as described in Example 59, using (S)-ethyl 2'-((5-((1-(4-bromophenyl)ethyl)carbamoyl)-1H-indol-1-yl)methyl)-[1,1'-biphenyl]-3-carboxylate instead of the (S)-ethyl 4'-((5-((1-(4-nitrophenyl)ethyl)carbamoyl)-1H-indol-1-yl)methyl)-[1,1'-biphenyl]-4-carboxylate. ESI-MS (m/z): 553/555 [M+H]$^+$.

Example 123

(S)-2'-((5-((1-(4-Nitrophenyl)ethyl)carbamoyl)-1H-indol-1-yl)methyl)-[1,1'-biphenyl]-3-carboxylic acid

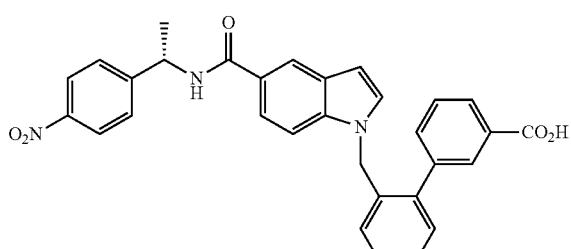

Step 1: (S)-Ethyl 2'-((5-((1-(4-nitrophenyl)ethyl)carbamoyl)-1H-indol-1-yl)methyl)-[1,1'-biphenyl]-3-carboxylate

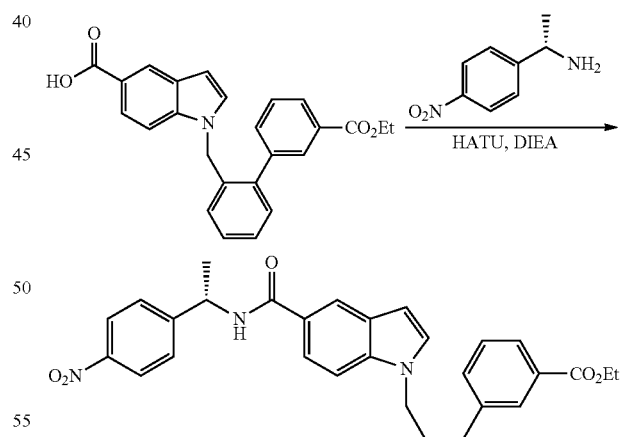

The title compound was prepared following the same protocol as described in Step 8, Example 1, using the 1-((3'-(ethoxycarbonyl)-[1,1'-biphenyl]-2-yl)methyl)-1H-indole-5-carboxylic acid instead of the 1-((2'-(tert-Butoxycarbonyl)biphenyl-4-yl)methyl)-2,3-dimethyl-1H-indole-5-carboxylic acid and the (S)-1-(4-nitrophenyl)ethanamine instead of the (S)-1-(4-bromophenyl)ethanamine.

Step 2: (S)-2'-((5-((1-(4-Nitrophenyl)ethyl)carbamoyl)-1H-indol-1-yl)methyl)-[1,1'-biphenyl]-3-carboxylic acid

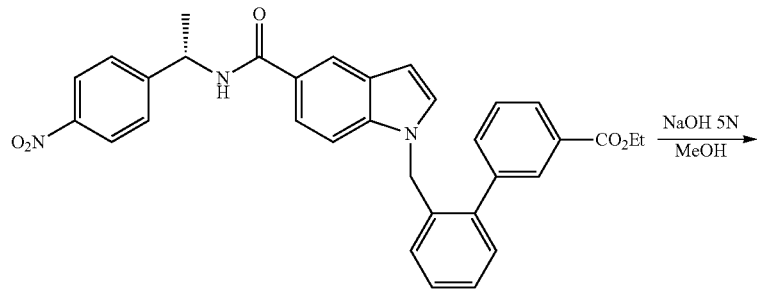

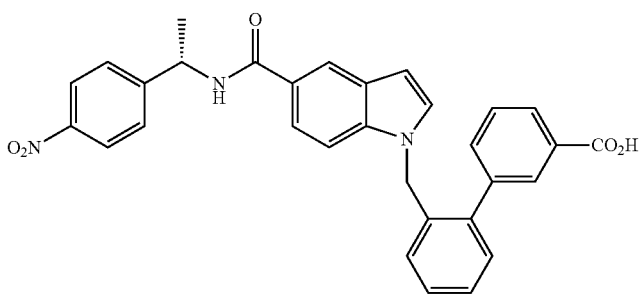

The title compound was prepared following the same protocol as described in Example 59, using (S)-ethyl 2'-((5-((1-(4-nitrophenyl)ethyl)carbamoyl)-1H-indol-1-yl)methyl)-[1,1'-biphenyl]-3-carboxylate instead of the (S)-ethyl 4'-((5-((1-(4-nitrophenyl)ethyl)carbamoyl)-1H-indol-1-yl)methyl)-[1,1'-biphenyl]-4-carboxylate.

ESI-MS (m/z): 520 [M+H]$^+$.

Example 124

(S)-2'-((5-((1-(4-Bromophenyl)ethyl)carbamoyl)-2,3-dimethyl-1H-indol-1-yl)methyl)-[1,1'-biphenyl]-3-carboxylic acid

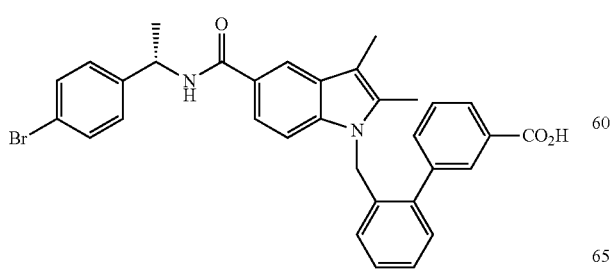

Step 1: Ethyl 1-(2-bromobenzyl)-2,3-dimethyl-1H-indole-5-carboxylate

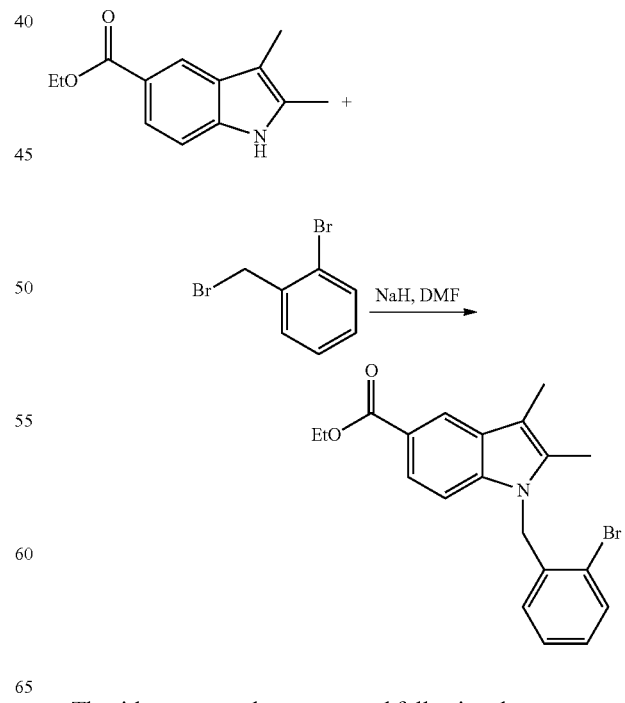

The title compound was prepared following the same protocol as described in Step 6, Example 1, using the 1-bromo- 2-(bromomethyl)benzene instead of the tert-butyl 4'-(bromomethyl)biphenyl-2-carboxylate. ESI-MS (m/z): 386/388 [M+H]+.

Step 2: 1-(2-Bromobenzyl)-2,3-dimethyl-1H-indole-5-carboxylic acid

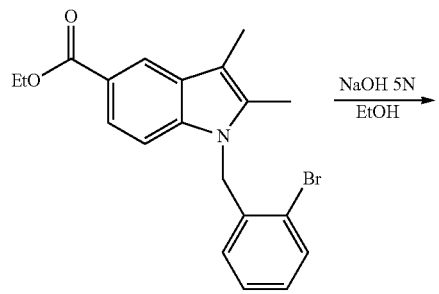

The title compound was prepared following the same protocol as described in Step 7, Example 1, using the ethyl 1-(2-bromobenzyl)-2,3-dimethyl-1H-indole-5-carboxylate instead of the ethyl 1-((2'-(tert-butoxycarbonyl)biphenyl-4-yl)methyl)-2,3-dimethyl-1H-indole-5-carboxylate. ESI-MS (m/z): 358/360 [M+H]+.

Step 3: 1-((3'-(Ethoxycarbonyl)-[1,1'-biphenyl]-2-yl)methyl)-2,3-dimethyl-1H-indole-5-carboxylic acid

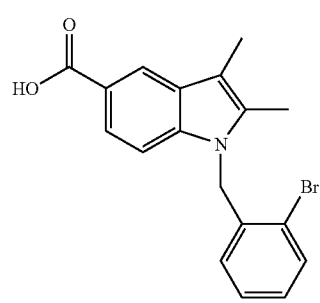

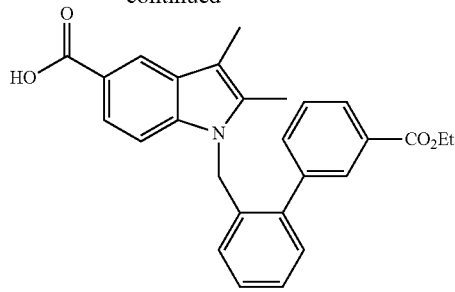

The title compound was prepared following the same protocol as described in Step 5, Example 38, using 1-(2-bromobenzyl)-2,3-dimethyl-1H-indole-5-carboxylic acid instead of the (S)-1-(4-bromobenzyl)-N-(1-(4-nitrophenyl)ethyl)-1H-indole-5-carboxamide and the (3-(ethoxycarbonyl)phenyl)boronic acid instead of the phenylboronic acid. ESI-MS (m/z): 428 [M+H]+.

Step 4: (S)-Ethyl 2'-((5-((1-(4-bromophenyl)ethyl)carbamoyl)-2,3-dimethyl-1H-indol-1-yl)methyl)-[1,1'-biphenyl]-3-carboxylate

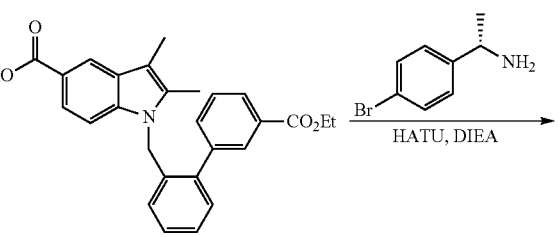

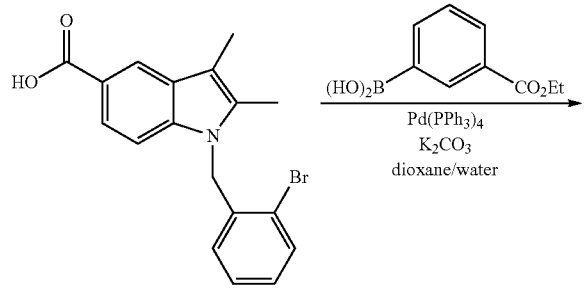

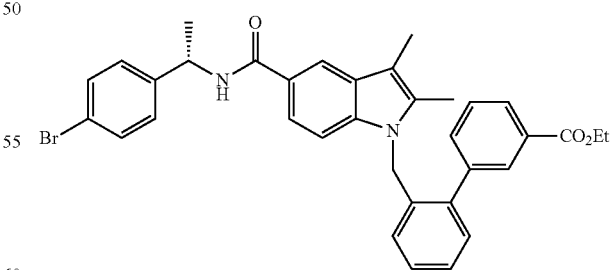

The title compound was prepared following the same protocol as described in Step 8, Example 1, using the 1-((3'-(ethoxycarbonyl)-[1,1'-biphenyl]-2-yl)methyl)-2,3-dimethyl-1H-indole-5-carboxylic acid instead of the 1-((2'-(tert-Butoxycarbonyl)biphenyl-4-yl)methyl)-2,3-dimethyl-1H-indole-5-carboxylic acid.

319

Step 5: (S)-2'-((5-((1-(4-Bromophenyl)ethyl)carbamoyl)-2,3-dimethyl-1H-indol-1-yl)methyl)-[1,1'-biphenyl]-3-carboxylic acid

320

Step 1: (S)-Ethyl 2'-((2,3-dimethyl-5-((1-(4-nitrophenyl)ethyl)carbamoyl)-1H-indol-1-yl)methyl)-[1,1'-biphenyl]-3-carboxylate

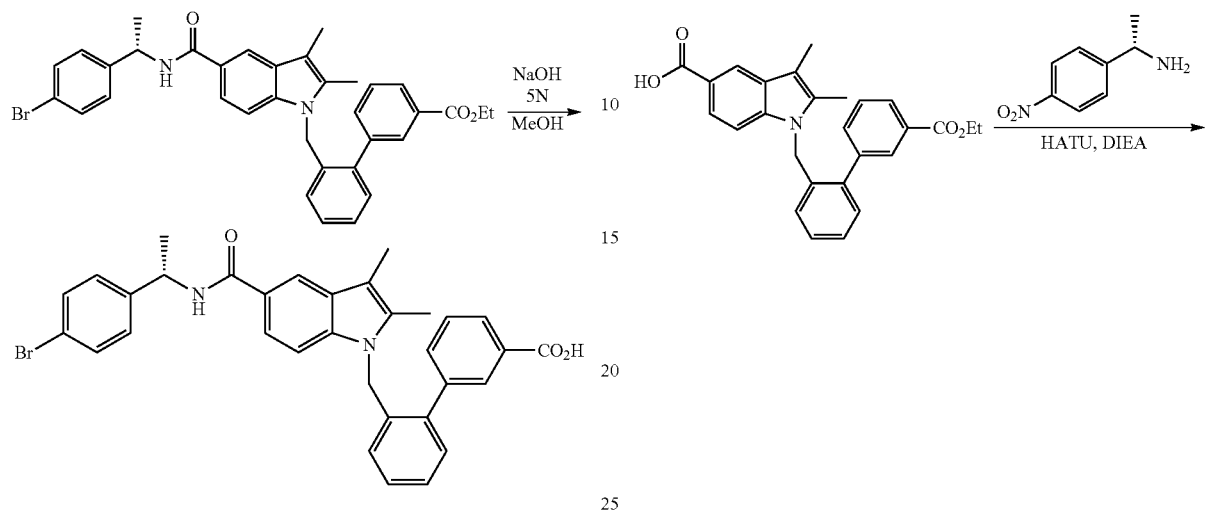

The title compound was prepared following the same protocol as described in Example 59, using (S)-ethyl 2'-((5-((1-(4-bromophenyl)ethyl)carbamoyl)-1H-indol-1-yl)methyl)-[1,1'-biphenyl]-3-carboxylate instead of the (S)-ethyl 4'-((5-((1-(4-nitrophenyl)ethyl)carbamoyl)-1H-indol-1-yl)methyl)-[1,1'-biphenyl]-4-carboxylate. ESI-MS (m/z): 581/583 [M+H]$^+$.

Example 125

(S)-2'-((2,3-Dimethyl-5-((1-(4-nitrophenyl)ethyl)carbamoyl)-1H-indol-1-yl)methyl)-[1,1'-biphenyl]-3-carboxylic acid

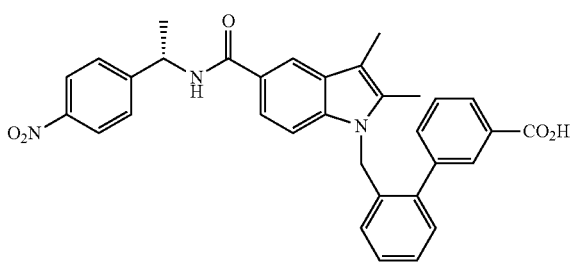 [SMILES: Cc1c(C)n(Cc2ccccc2-c2cccc(C(=O)O)c2)c2ccc(C(=O)N[C@@H](C)c3ccc([N+](=O)[O-])cc3)cc12]

The title compound was prepared following the same protocol as described in Step 8, Example 1, using the 1-((3'-(ethoxycarbonyl)-[1,1'-biphenyl]-2-yl)methyl)-2,3-dimethyl-1H-indole-5-carboxylic acid instead of the 1-((2'-(tert-Butoxycarbonyl)biphenyl-4-yl)methyl)-2,3-dimethyl-1H-indole-5-carboxylic acid and the (S)-1-(4-nitrophenyl)ethanamine instead of the (S)-1-(4-bromophenyl)ethanamine.

Step 2: (S)-2'-((2,3-Dimethyl-5-((1-(4-nitrophenyl)ethyl)carbamoyl)-1H-indol-1-yl)methyl)-[1,1'-biphenyl]-3-carboxylic acid

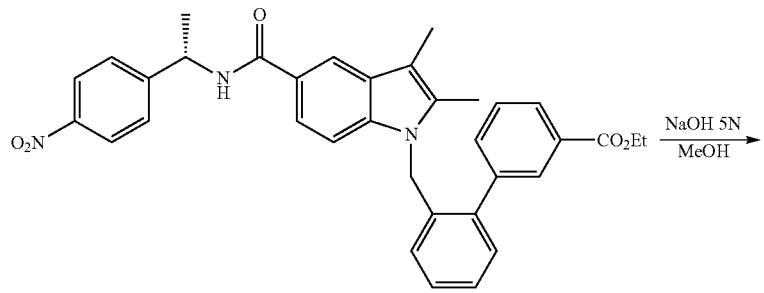

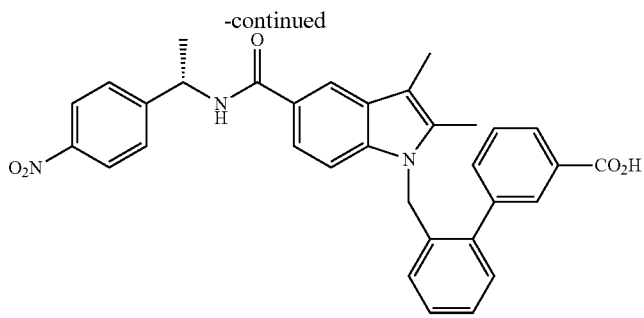

The title compound was prepared following the same protocol as described in Example 59, using (S)-ethyl 2'-((2,3-dimethyl-5-((1-(4-nitrophenyl)ethyl)carbamoyl)-1H-indol-1-yl)methyl)-[1,1'-biphenyl]-3-carboxylate instead of the (S)-ethyl 4'-((5-((1-(4-nitrophenyl)ethyl)carbamoyl)-1H-indol-1-yl)methyl)-[1,1'-biphenyl]-4-carboxylate. ESI-MS (m/z): 548 [M+H]$^+$.

Example 126

2'-((2,3-Dimethyl-5-((1-phenylpropyl)carbamoyl)-1H-indol-1-yl)methyl)-[1,1'-biphenyl]-3-carboxylic acid Step 1: Ethyl 2'-((2,3-dimethyl-5-((1-phenylpropyl)carbamoyl)-1H-indol-1-yl)methyl)-[1,1'-biphenyl]-3-carboxylate

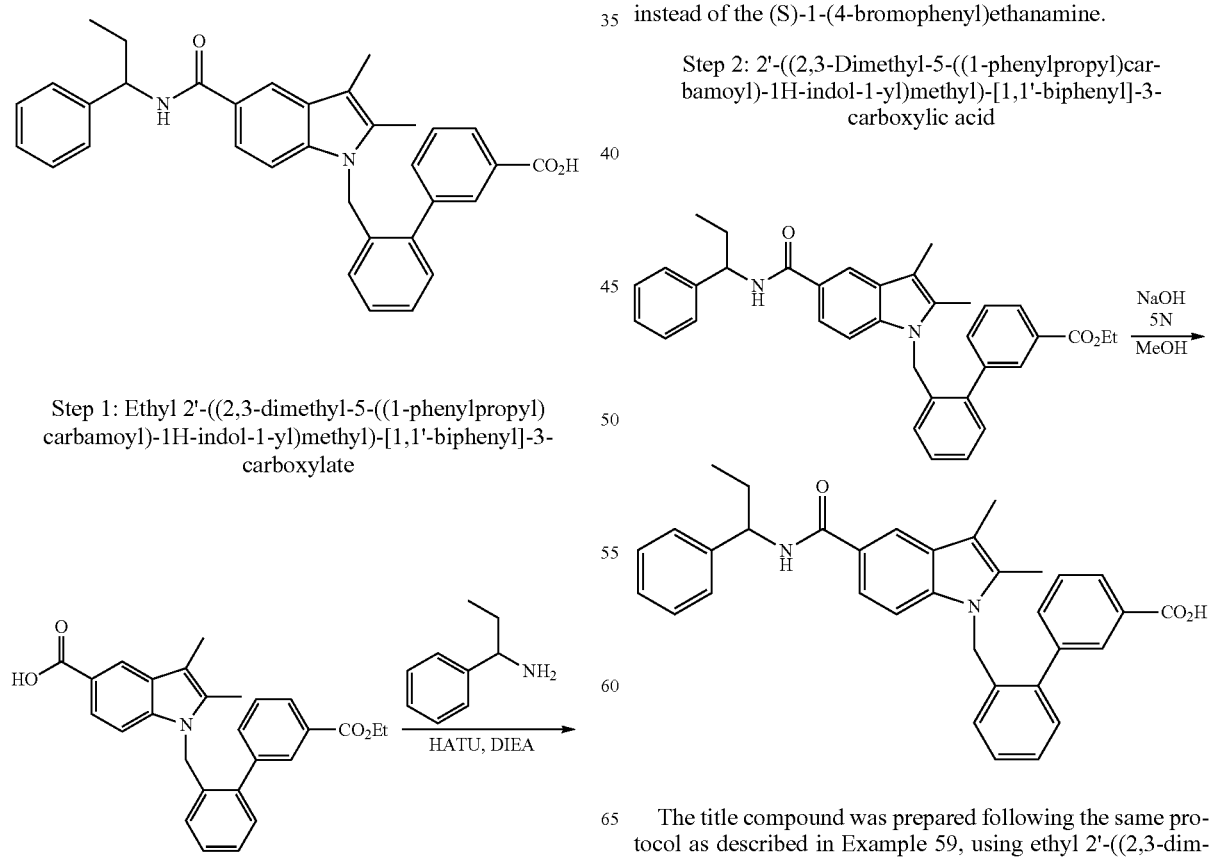

The title compound was prepared following the same protocol as described in Step 8, Example 1, using the 1-((3'-(ethoxycarbonyl)-[1,1'-biphenyl]-2-yl)methyl)-2,3-dimethyl-1H-indole-5-carboxylic acid instead of the 1-((2'-(tert-Butoxycarbonyl)biphenyl-4-yl)methyl)-2,3-dimethyl-1H-indole-5-carboxylic acid and the 1-phenylpropan-1-amine instead of the (S)-1-(4-bromophenyl)ethanamine.

Step 2: 2'-((2,3-Dimethyl-5-((1-phenylpropyl)carbamoyl)-1H-indol-1-yl)methyl)-[1,1'-biphenyl]-3-carboxylic acid The title compound was prepared following the same protocol as described in Example 59, using ethyl 2'-((2,3-dimethyl-5-((1-phenylpropyl)carbamoyl)-1H-indol-1-yl)methyl)-[1,1'-biphenyl]-3-carboxylate instead of the (S)-ethyl 4'-((5-((1-(4-nitrophenyl)ethyl)carbamoyl)-1H-indol-1-yl)methyl)-[1,1'-biphenyl]-4-carboxylate. ESI-MS (m/z): 517 [M+H]+.

Example 127

(S)-2'-((5-((1-(4-bromophenyl)ethyl)carbamoyl)-2,3-dimethyl-1H-indol-1-yl)methyl)-[1,1'-biphenyl]-4-carboxylic acid

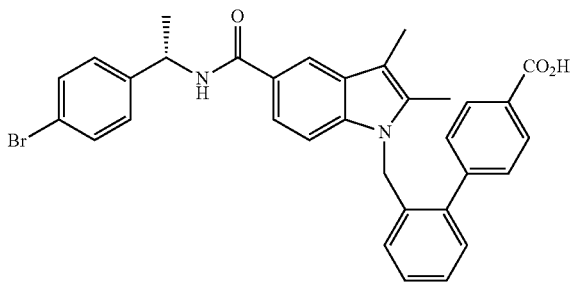 [SMILES: Cc1c(C)n(Cc2ccccc2-c2ccc(C(=O)O)cc2)c2ccc(C(=O)N[C@@H](C)c3ccc(Br)cc3)cc12]

Step 1: 1-((4'-(Ethoxycarbonyl)-[1,1'-biphenyl]-2-yl)methyl)-2,3-dimethyl-1H-indole-5-carboxylic acid

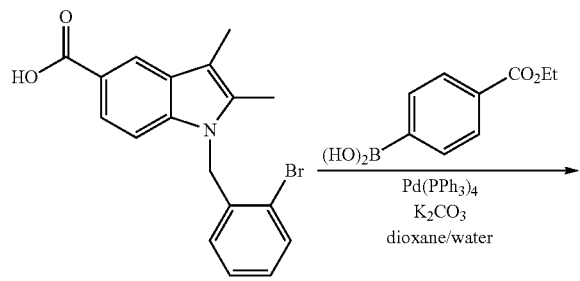

The title compound was prepared following the same protocol as described in Step 5, Example 38, using 1-(2-bromobenzyl)-2,3-dimethyl-1H-indole-5-carboxylic acid instead of the (S)-1-(4-bromobenzyl)-N-(1-(4-nitrophenyl)ethyl)-1H-indole-5-carboxamide and the (4-(ethoxycarbonyl)phenyl)boronic acid instead of the phenylboronic acid. ESI-MS (m/z): 428 [M+H]+.

Step 2: (S)-Ethyl 2'-((5-((1-(4-bromophenyl)ethyl)carbamoyl)-2,3-dimethyl-1H-indol-1-yl)methyl)-[1,1'-biphenyl]-4-carboxylate

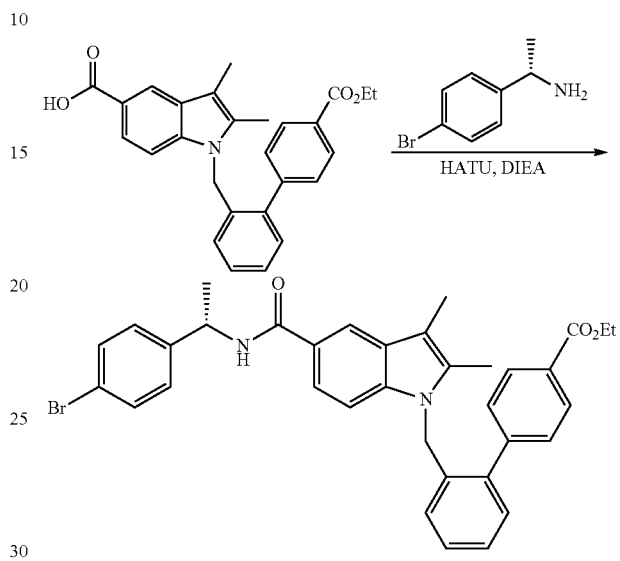

The title compound was prepared following the same protocol as described in Step 8, Example 1, using the 1-((4'-(ethoxycarbonyl)-[1,1'-biphenyl]-2-yl)methyl)-2,3-dimethyl-1H-indole-5-carboxylic acid instead of the 1-((2'-(tert-Butoxycarbonyl)biphenyl-4-yl)methyl)-2,3-dimethyl-1H-indole-5-carboxylic acid.

Step 3: (S)-2'-((5-((1-(4-Bromophenyl)ethyl)carbamoyl)-2,3-dimethyl-1H-indol-1-yl)methyl)-[1,1'-biphenyl]-4-carboxylic acid

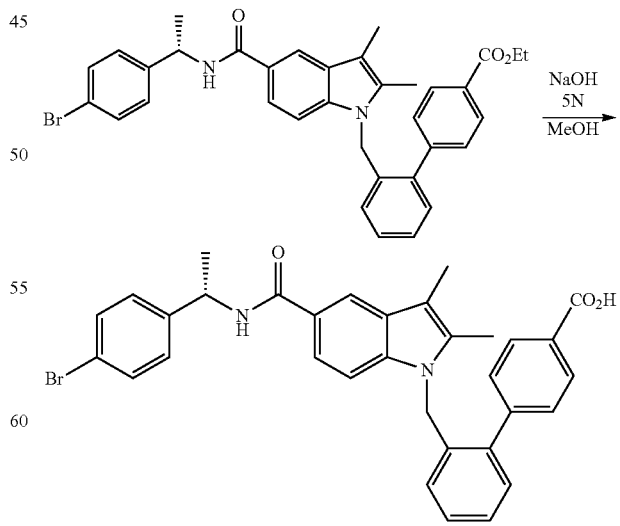

The title compound was prepared following the same protocol as described in Example 59, using (S)-ethyl 2'-((5-((1-

(4-bromophenyl)ethyl)carbamoyl)-1H-indol-1-yl)methyl)-[1,1'-biphenyl]-4-carboxylate instead of the (S)-ethyl 4'-((5-((1-(4-nitrophenyl)ethyl)carbamoyl)-1H-indol-1-yl)methyl)-[1,1'-biphenyl]-4-carboxylate. ESI-MS (m/z): 581/583 [M+H]$^+$.

Example 128

(S)-2'-((2,3-Dimethyl-5-((1-(4-nitrophenyl)ethyl)carbamoyl)-1H-indol-1-yl)methyl)-[1,1'-biphenyl]-4-carboxylic acid

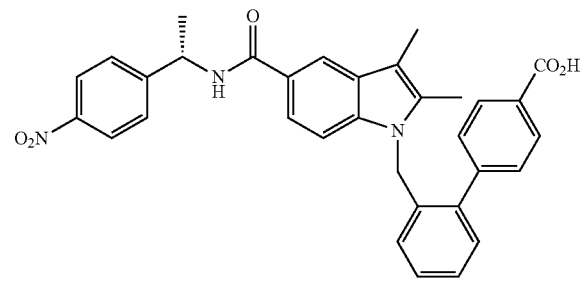 [SMILES: Cc1c(C)n(Cc2ccccc2-c2ccc(C(=O)O)cc2)c2ccc(C(=O)N[C@@H](C)c3ccc([N+](=O)[O-])cc3)cc12]

Step 1: (S)-Ethyl 2'-((2,3-dimethyl-5-((1-(4-nitrophenyl)ethyl)carbamoyl)-1H-indol-1-yl)methyl)-[1,1'-biphenyl]-4-carboxylate

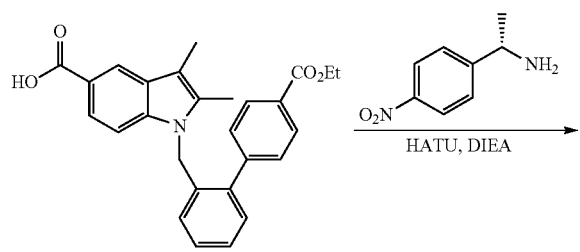

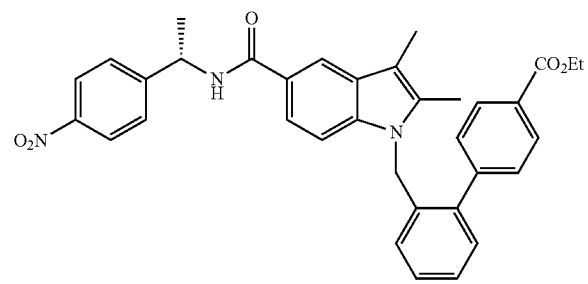

The title compound was prepared following the same protocol as described in Step 8, Example 1, using the 1-((4'-(ethoxycarbonyl)-[1,1'-biphenyl]-2-yl)methyl)-2,3-dimethyl-1H-indole-5-carboxylic acid instead of the 1-((2'-(tert-Butoxycarbonyl)biphenyl-4-yl)methyl)-2,3-dimethyl-1H-indole-5-carboxylic acid and the (S)-1-(4-nitrophenyl)ethanamine instead of the (S)-1-(4-bromophenyl)ethanamine.

Step 2: (S)-2'-((2,3-Dimethyl-5-((1-(4-nitrophenyl)ethyl)carbamoyl)-1H-indol-1-yl)methyl)-[1,1'-biphenyl]-4-carboxylic acid

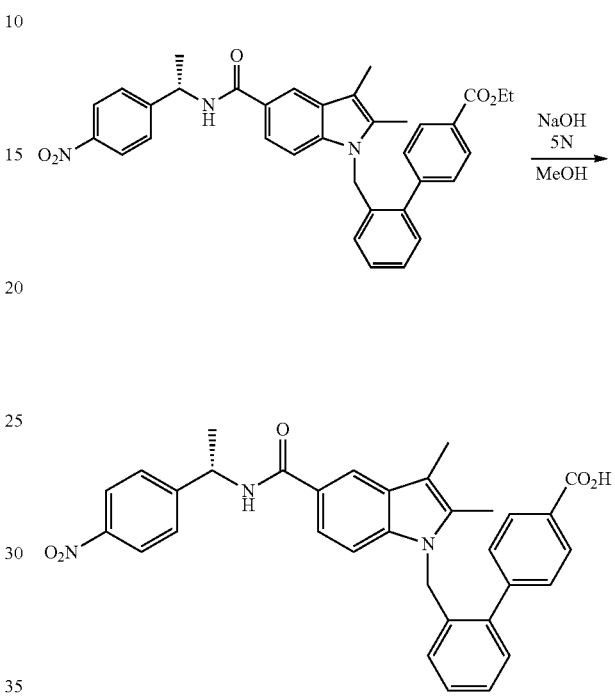

The title compound was prepared following the same protocol as described in Example 59, using (S)-ethyl 2'-((2,3-dimethyl-5-((1-(4-nitrophenyl)ethyl)carbamoyl)-1H-indol-1-yl)methyl)-[1,1'-biphenyl]-4-carboxylate instead of the (S)-ethyl 4'-((5-((1-(4-nitrophenyl)ethyl)carbamoyl)-1H-indol-1-yl)methyl)-[1,1'-biphenyl]-4-carboxylate. ESI-MS (m/z): 548 [M+H]$^+$.

Example 129

2'-((2,3-Dimethyl-5-((1-phenylpropyl)carbamoyl)-1H-indol-1-yl)methyl)-[1,1'-biphenyl]-4-carboxylic acid

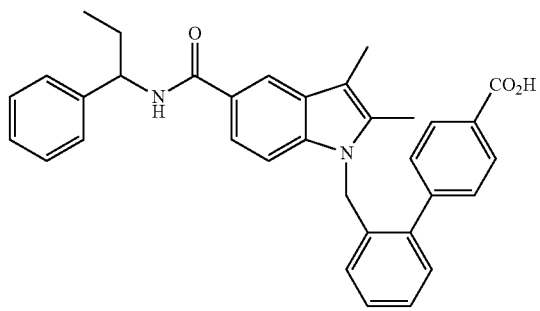

327

Step 1: Ethyl 2'-((2,3-dimethyl-5-((1-phenylpropyl)carbamoyl)-1H-indol-1-yl)methyl)-[1,1'-biphenyl]-4-carboxylate

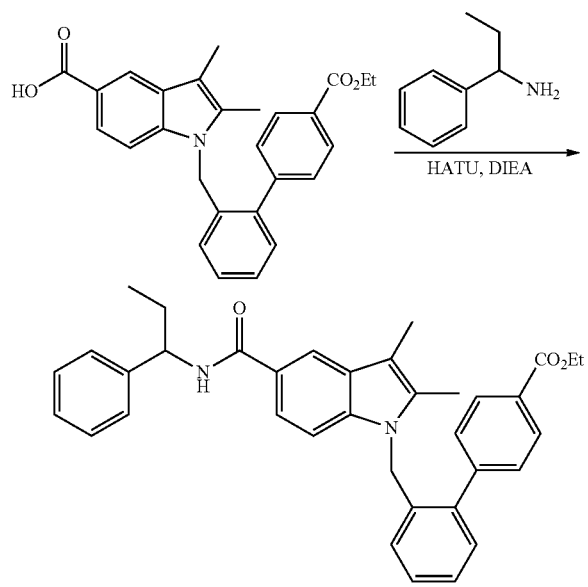

The title compound was prepared following the same protocol as described in Step 8, Example 1, using the 1-((4'-(ethoxycarbonyl)-[1,1'-biphenyl]-2-yl)methyl)-2,3-dimethyl-1H-indole-5-carboxylic acid instead of the 1-((2'-(tert-Butoxycarbonyl)biphenyl-4-yl)methyl)-2,3-dimethyl-1H-indole-5-carboxylic acid and the 1-phenylpropan-1-amine instead of the (S)-1-(4-bromophenyl)ethanamine.

Step 2: 2'-((2,3-Dimethyl-5-((1-phenylpropyl)carbamoyl)-1H-indol-1-yl)methyl)-[1,1'-biphenyl]-4-carboxylic acid

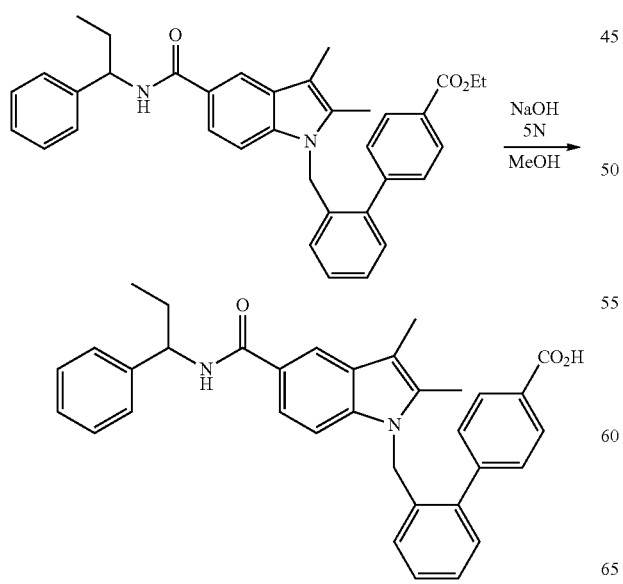

328

The title compound was prepared following the same protocol as described in Example 59, using ethyl 2'-((2,3-dimethyl-5-((1-phenylpropyl)carbamoyl)-1H-indol-1-yl)methyl)-[1,1'-biphenyl]-4-carboxylate instead of the (S)-ethyl 4'-((5-((1-(4-nitrophenyl)ethyl)carbamoyl)-1H-indol-1-yl)methyl)-[1,1'-biphenyl]-4-carboxylate. ESI-MS (m/z): 517 [M+H]$^+$.

Example 130

(S)-4'-((5-((1-(4-Bromophenyl)ethyl)carbamoyl)-1H-indol-1-yl)methyl)-[1,1'-biphenyl]-2-carboxylic acid

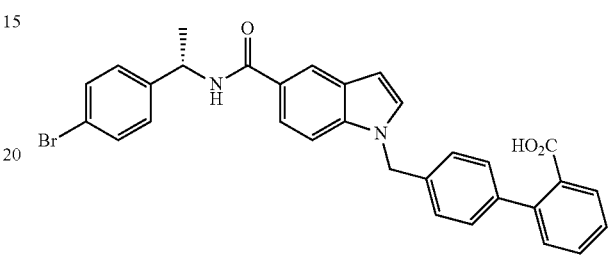

Step 1: 1-((2'-(tert-Butoxycarbonyl)-[1,1'-biphenyl]-4-yl)methyl)-1H-indole-5-carboxylic acid

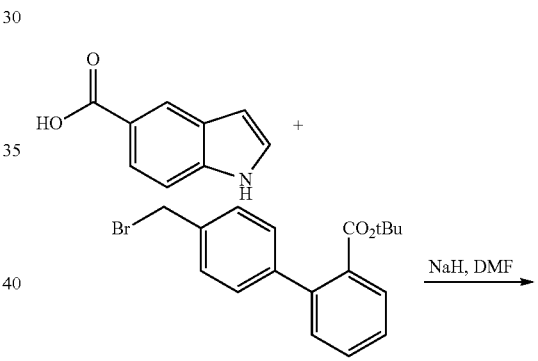

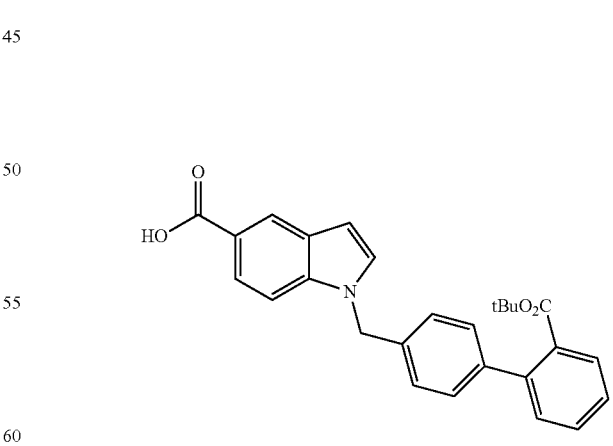

The title compound was prepared following the same protocol as described in Step 2, Example 38, using 1H-indole-5-carboxylic acid instead of the methyl 1H-indole-5-carboxylate, and the tert-butyl 4'-(bromomethyl)biphenyl-2-carboxylate instead of the 1-bromo-4-(bromomethyl)benzene. ESI-MS (m/z): 428 [M+H]$^+$.

Step 2: (S)-tert-Butyl 4'-((5-((1-(4-bromophenyl)ethyl)carbamoyl)-1H-indol-1-yl)methyl)-[1,1'-biphenyl]-2-carboxylate

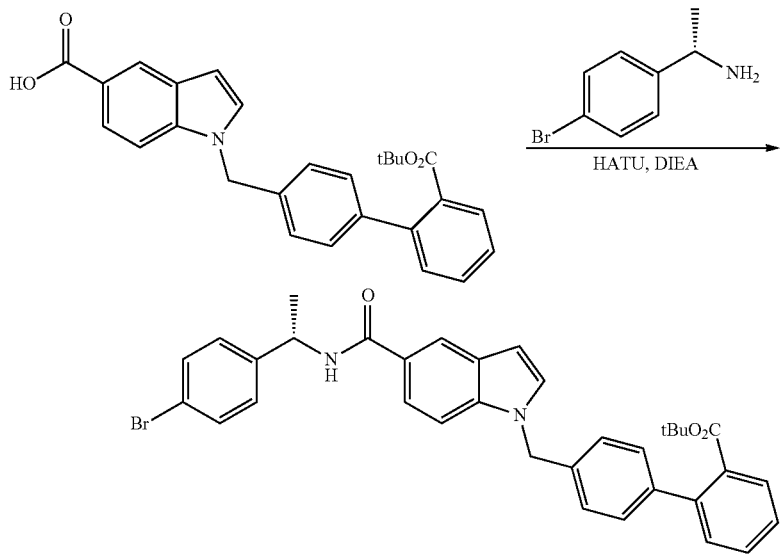

The title compound was prepared following the same protocol as described in Step 8, Example 1, using the 1-((2'-(tert-butoxycarbonyl)-[1,1'-biphenyl]-4-yl)methyl)-1H-indole-5-carboxylic acid instead of the 1-((2'-(tert-Butoxycarbonyl)biphenyl-4-yl)methyl)-2,3-dimethyl-1H-indole-5-carboxylic acid.

Step 3: (S)-4'-((5-((1-(4-Bromophenyl)ethyl)carbamoyl)-1H-indol-1-yl)methyl)-[1,1'-biphenyl]-2-carboxylic acid

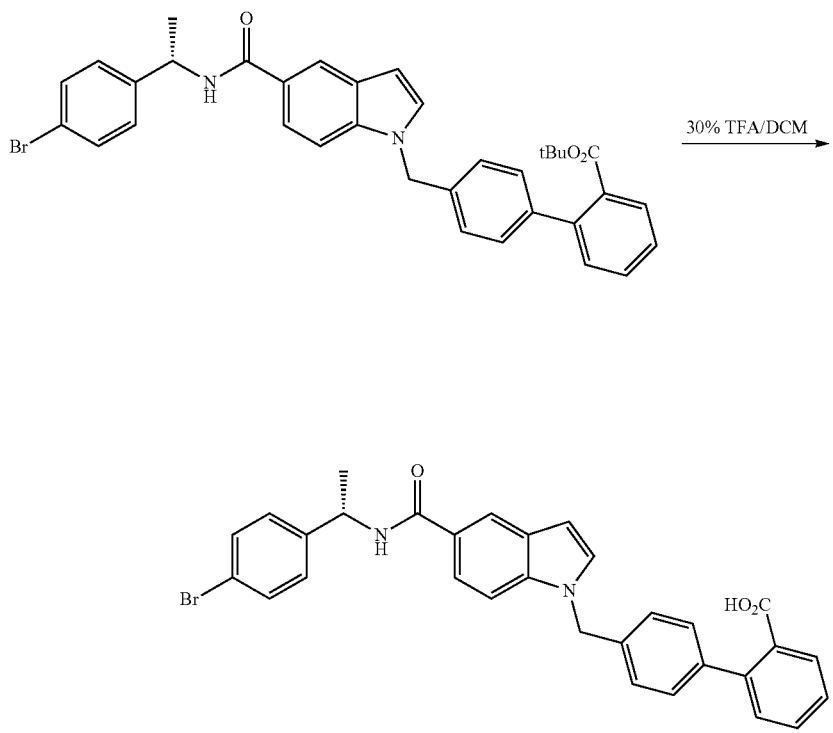

The title compound was prepared following the same protocol as described in Step 9, Example 1, using (S)-tert-Butyl 4'-((5-((1-(4-bromophenyl)ethyl)carbamoyl)-1H-indol-1-yl)methyl)-[1,1'-biphenyl]-2-carboxylate instead of the (S)-tert-Butyl 4'-((5-((1-(4-bromophenyl)ethyl)carbamoyl)-2,3-dimethyl-1H-indol-1-yl)methyl)-[1,1'-biphenyl]-2-carboxylate. ESI-MS (m/z): 553/555 [M+H]⁺.

Example 131

4'-((5-((1-Phenylpropyl)carbamoyl)-1H-indol-1-yl)methyl)-[1,1'-biphenyl]-2-carboxylic acid

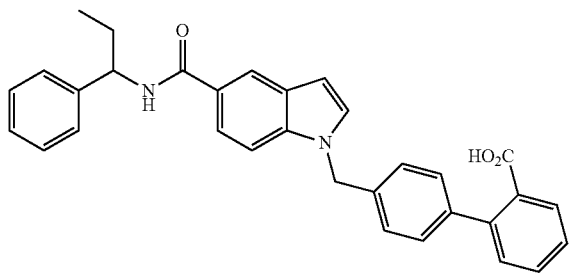 [SMILES: CCC(NC(=O)c1ccc2c(ccn2Cc2ccc(-c3ccccc3C(=O)O)cc2)c1)c1ccccc1]

Step 1: tert-Butyl 4'-((5-((1-phenylpropyl)carbamoyl)-1H-indol-1-yl)methyl)-[1,1'-biphenyl]-2-carboxylate

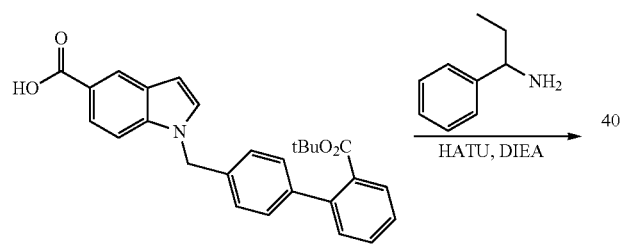

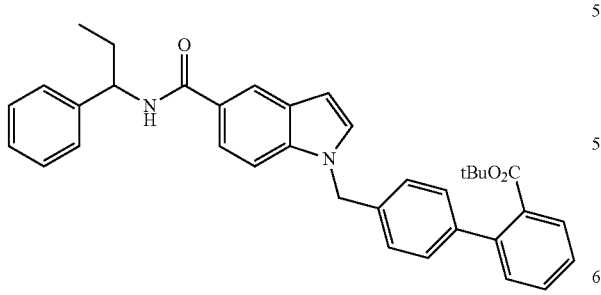

The title compound was prepared following the same protocol as described in Step 8, Example 1, using the 1-((2'-(tert-butoxycarbonyl)-[1,1'-biphenyl]-4-yl)methyl)-1H-indole-5-carboxylic acid instead of the 1-((2'-(tert-Butoxycarbonyl)biphenyl-4-yl)methyl)-2,3-dimethyl-1H-indole-5-carboxylic acid and the 1-phenylpropan-1-amine instead of the (S)-1-(4-bromophenyl)ethanamine.

Step 2: 4'-((5-((1-Phenylpropyl)carbamoyl)-1H-indol-1-yl)methyl)-[1,1'-biphenyl]-2-carboxylic acid

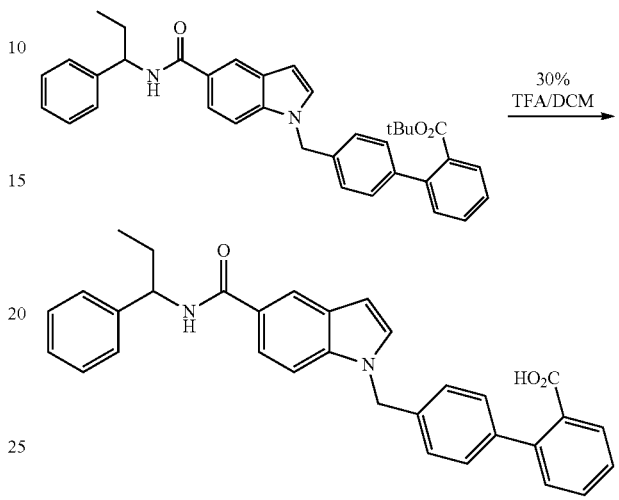

The title compound was prepared following the same protocol as described in Step 9, Example 1, using tert-butyl 4'-((5-((1-phenylpropyl)carbamoyl)-1H-indol-1-yl)methyl)-[1,1'-biphenyl]-2-carboxylate instead of the (S)-tert-butyl 4'-((5-((1-(4-bromophenyl)ethyl)carbamoyl)-2,3-dimethyl-1H-indol-1-yl)methyl)-[1,1'-biphenyl]-2-carboxylate. ESI-MS (m/z): 489 [M+H]⁺.

Example 132

(S)-4'-((5-((1-(4-Bromophenyl)ethyl)carbamoyl)-3-methyl-1H-indol-1-yl)methyl)-[1,1'-biphenyl]-2-carboxylic acid

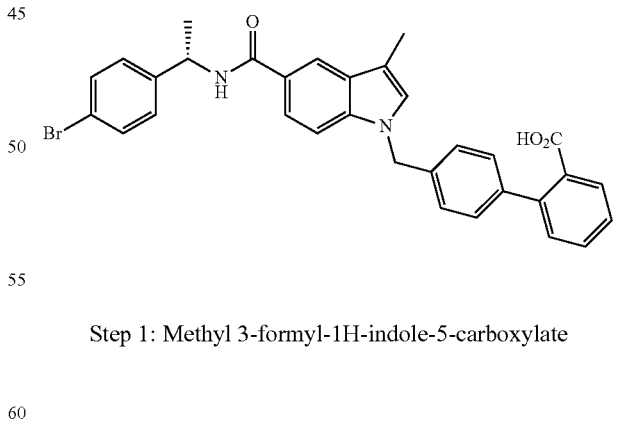

Step 1: Methyl 3-formyl-1H-indole-5-carboxylate

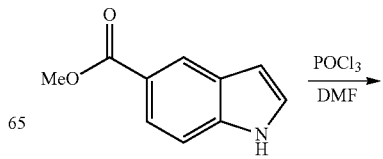

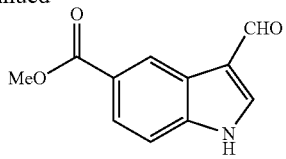

To a solution of anhydrous DMF (12 mL) under argon at 0° C. was added POCl₃ (446 μL, 4.9 mmol). The reaction mixture has been stirred at 0° C. for 5 min. The methyl 1H-indole-5-carboxylate (854 mg, 4.9 mmol) in solution in DMF was added dropwise. The resulting mixture has been heated at 120° C. for 1 h. Then, it is quenched by addition of a saturated solution of NaHCO₃ (2 mL). The mixture is diluted with DCM, washed with brine, dried over MgSO₄ and concentrated. The product is precipitated in hexane/diethyl ether (1/1) to yield a red powder (896 mg, 4.4 mmol, 91%). ESI-MS (m/z): 204 [M+H]⁺.

Step 2: Methyl 3-methyl-1H-indole-5-carboxylate

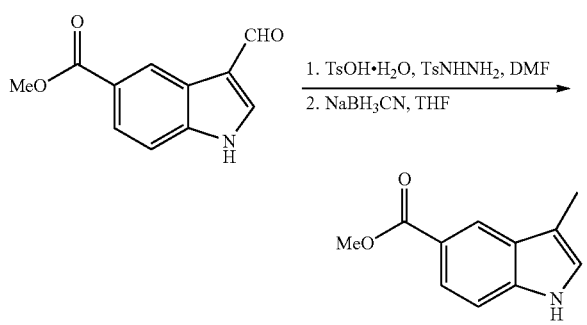

To a solution of the methyl 3-formyl-1H-indole-5-carboxylate (893 mg, 4.4 mmol) in DMF (20 mL) was added the p-toluenesulfonic acid monohydrate (125 mg, 0.7 mmol) and the p-toluenesulfonyl hydrazide (982 mg, 5.3 mmol). The solution has been heated for 20 min at 100° C. The resulting mixture was diluted with ethyl acetate, washed with brine, dried over MgSO₄ and concentrated. The crude product is dissolved in THF (40 mL) and NaBH₃CN (1.1 g, 17.6 mmol) was added. The solution has been heated for 8 h at 75° C. The resulting mixture was diluted with ethyl acetate, washed with a solution of 0.5 N HCl, a saturated solution of NaHCO₃ and brine, dried over MgSO₄ and concentrated. The crude product was purified by flash chromatography (Hexane/AcOEt, from 0 to 30%) to yield a white powder (500 mg, 2.6 mmol, 60%). ESI-MS (m/z): 190 [M+H]⁺.

Step 3: Methyl 1-((2'-(tert-butoxycarbonyl)-[1,1'-biphenyl]-4-yl)methyl)-3-methyl-1H-indole-5-carboxylate

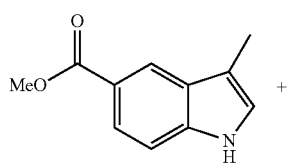

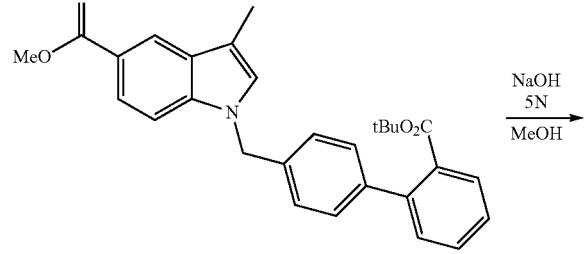

The title compound was prepared following the same protocol as described in Step 2, Example 38, using the methyl 3-methyl-1H-indole-5-carboxylate instead of the methyl 1H-indole-5-carboxylate, and the tert-butyl 4'-(bromomethyl)biphenyl-2-carboxylate instead of the 1-bromo-4-(bromomethyl)benzene. ESI-MS (m/z): 456 [M+H]⁺.

Step 4: 1-((2'-(tert-Butoxycarbonyl)-[1,1'-biphenyl]-4-yl)methyl)-3-methyl-1H-indole-5-carboxylic acid

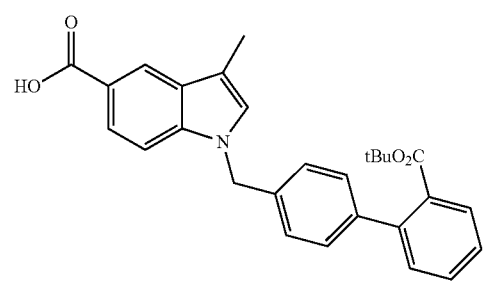

The title compound was prepared following the same protocol as described in Step 3, Example 38, using the methyl 1-((2'-(tert-butoxycarbonyl)-[1,1'-biphenyl]-4-yl)methyl)-3-methyl-1H-indole-5-carboxylate instead of the methyl 1-(4-bromobenzyl)-1H-indole-5-carboxylate. ESI-MS (m/z): 442 [M+H]⁺.

Step 5: (S)-tert-Butyl 4'-((5-((1-(4-bromophenyl)ethyl)carbamoyl)-3-methyl-1H-indol-1-yl)methyl)-[1,1'-biphenyl]-2-carboxylate

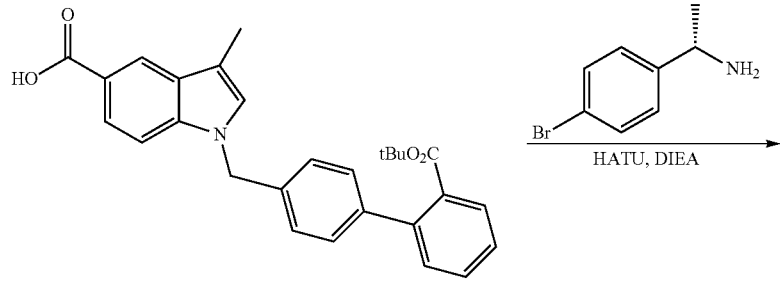

The title compound was prepared following the same protocol as described in Step 8, Example 1, using the 1-((2'-(tert-butoxycarbonyl)-[1,1'-biphenyl]-4-yl)methyl)-3-methyl-1H-indole-5-carboxylic acid instead of the 1-((2'-(tert-Butoxycarbonyl)biphenyl-4-yl)methyl)-2,3-dimethyl-1H-indole-5-carboxylic acid.

Step 6: (S)-4'-((5-((1-(4-Bromophenyl)ethyl)carbamoyl)-3-methyl-1H-indol-1-yl)methyl)-[1,1'-biphenyl]-2-carboxylic acid

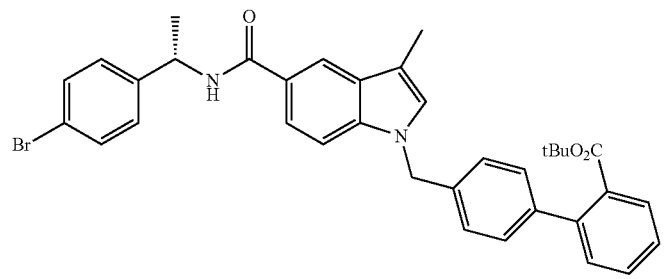 [SMILES: Cc1cc2cc(C(=O)N[C@@H](C)c3ccc(Br)cc3)ccc2n1Cc1ccc(-c2ccccc2C(=O)O)cc1]

The title compound was prepared following the same protocol as described in Step 9, Example 1, using the (S)-tert-Butyl 4'-((5-((1-(4-bromophenyl)ethyl)carbamoyl)-3-methyl-1H-indol-1-yl)methyl)-[1,1'-biphenyl]-2-carboxylate instead of the (S)-tert-Butyl 4'-((5-((1-(4-bromophenyl)ethyl)carbamoyl)-2,3-dimethyl-1H-indol-1-yl)methyl)-[1,1'-biphenyl]-2-carboxylate. ESI-MS (m/z): 566/568 [M+H]⁺.

Example 133

4'-((3-Methyl-5-((1-phenylpropyl)carbamoyl)-1H-indol-1-yl)methyl)-[1,1'-biphenyl]-2-carboxylic acid

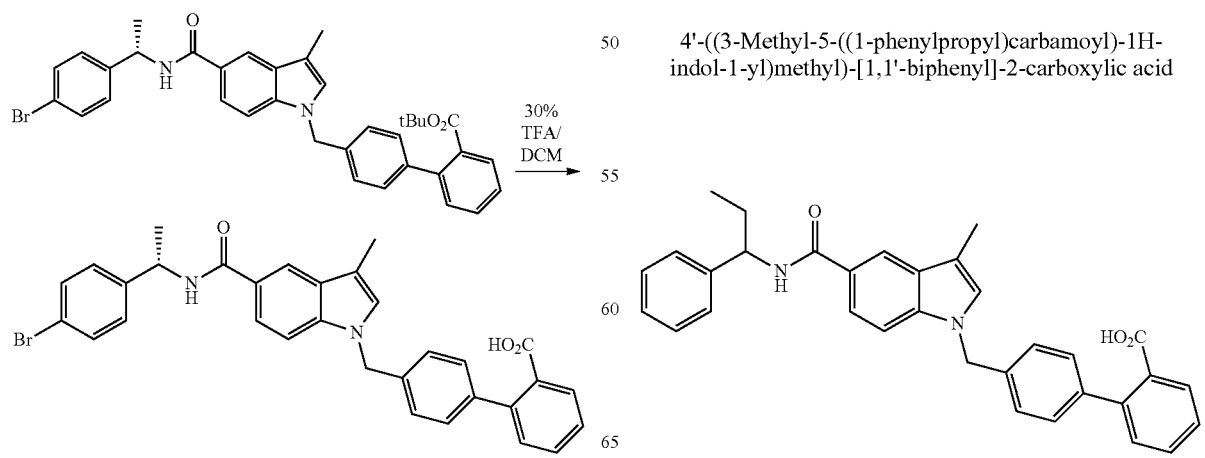

337

Step 1: tert-Butyl 4'-((3-methyl-5-((1-phenylpropyl)carbamoyl)-1H-indol-1-yl)methyl)-[1,1'-biphenyl]-2-carboxylate

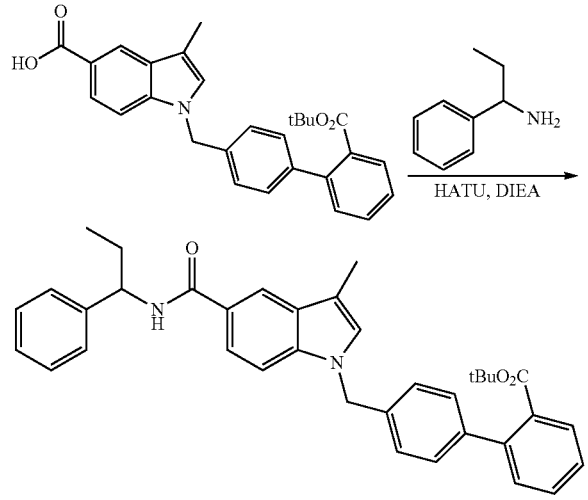

The title compound was prepared following the same protocol as described in Step 8, Example 1, using the 1-((2'-(tert-Butoxycarbonyl)biphenyl-4-yl)methyl)-3-methyl-1H-indole-5-carboxylic acid instead of the 1-((2'-(tert-Butoxycarbonyl)biphenyl-4-yl)methyl)-2,3-dimethyl-1H-indole-5-carboxylic acid and the 1-phenylpropan-1-amine instead of the (S)-1-(4-bromophenyl)ethanamine.

Step 2: 4'-((3-Methyl-5-((1-phenylpropyl)carbamoyl)-1H-indol-1-yl)methyl)-[1,1'-biphenyl]-2-carboxylic acid

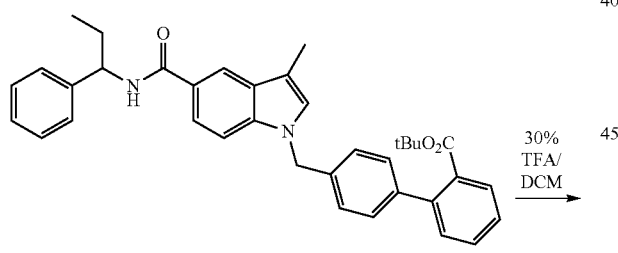

338

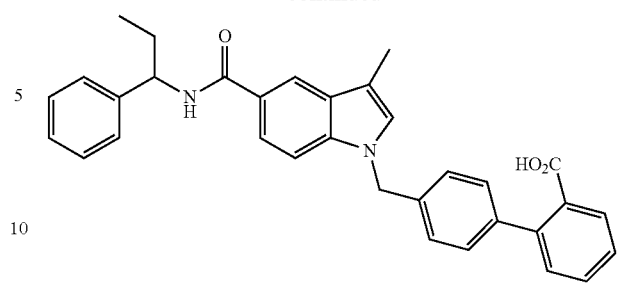

The title compound was prepared following the same protocol as described in Step 9, Example 1, using the tert-Butyl 4'-((3-methyl-5-((1-phenylpropyl)carbamoyl)-1H-indol-1-yl)methyl)-[1,1'-biphenyl]-2-carboxylate instead of the (S)-tert-butyl 4'-((5-((1-(4-bromophenyl)ethyl)carbamoyl)-2,3-dimethyl-1H-indol-1-yl)methyl)-[1,1'-biphenyl]-2-carboxylate. ESI-MS (m/z): 559 [M+H]$^+$.

Example 134

(S)-4'-((3-Methyl-5-((1-(4-nitrophenyl)ethyl)carbamoyl)-1H-indol-1-yl)methyl)-[1,1'-biphenyl]-2-carboxylic acid

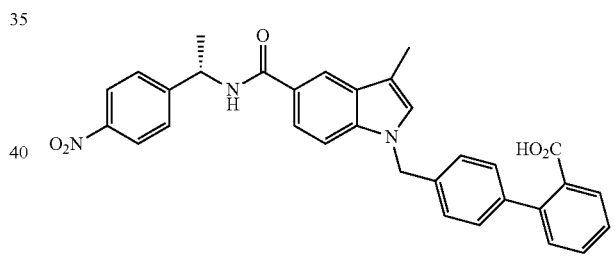

Step 1: (S)-tert-Butyl 4'-((5-((1-(4-nitrophenyl)ethyl)carbamoyl)-3-methyl-1H-indol-1-yl)methyl)-[1,1'-biphenyl]-2-carboxylate

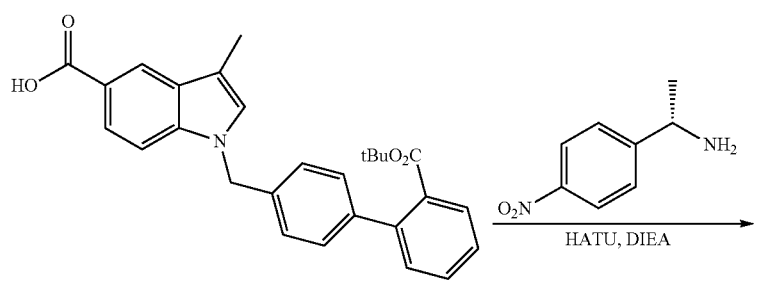

-continued

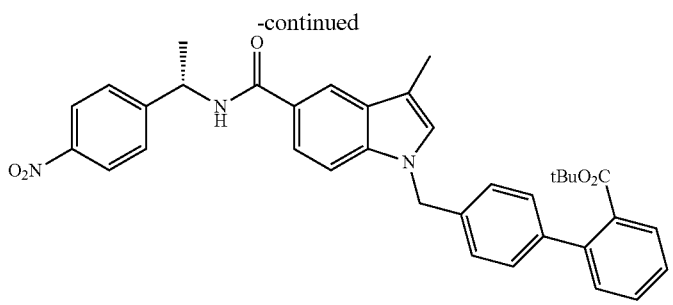

The title compound was prepared following the same protocol as described in Step 8, Example 1, using the 1-((2'-(tert-butoxycarbonyl)-[1,1'-biphenyl]-4-yl)methyl)-3-methyl-1H-indole-5-carboxylic acid instead of the 1-((2'-(tert-Butoxycarbonyl)biphenyl-4-yl)methyl)-2,3-dimethyl-1H-indole-5-carboxylic acid and the (S)-1-(4-nitrophenyl) ethanamine instead of the (S)-1-(4-bromophenyl) ethanamine.

Step 2: (S)-4'-((3-methyl-5-((1-(4-nitrophenyl)ethyl) carbamoyl)-1H-indol-1-yl)methyl)-[1,1'-biphenyl]-2-carboxylic acid

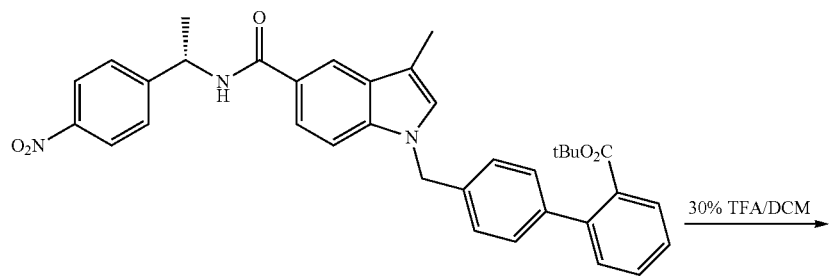

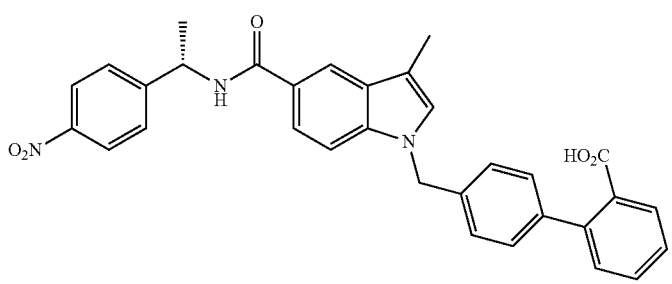

The title compound was prepared following the same protocol as described in Step 9, Example 1, using the (S)-tert-Butyl 4'-((5-(((1-(4-nitrophenyl)ethyl)carbamoyl)-3-methyl-1H-indol-1-yl)methyl)-[1,1'-biphenyl]-2-carboxylate instead of the (S)-tert-Butyl 4'-((5-(((1-(4-bromophenyl) ethyl)carbamoyl)-2,3-dimethyl-1H-indol-1-yl)methyl)-[1,1'-biphenyl]-2-carboxylate. ESI-MS (m/z): 533 [M+H]$^+$.

Example 135

(S)-4'-((5-((1-(4-Bromophenyl)ethyl)carbamoyl)-2-methyl-1H-indol-1-yl)methyl)-[1,1'-biphenyl]-2-carboxylic acid

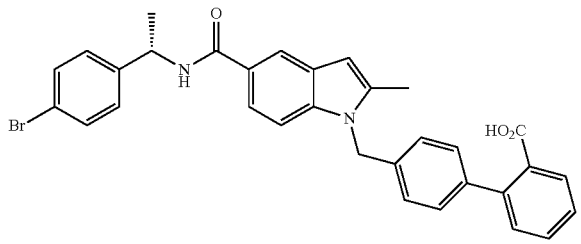

Step 1: Methyl 1-((2'-(tert-butoxycarbonyl)-[1,1'-biphenyl]-4-yl)methyl)-2-methyl-1H-indole-5-carboxylate

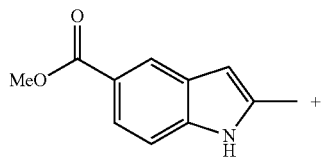

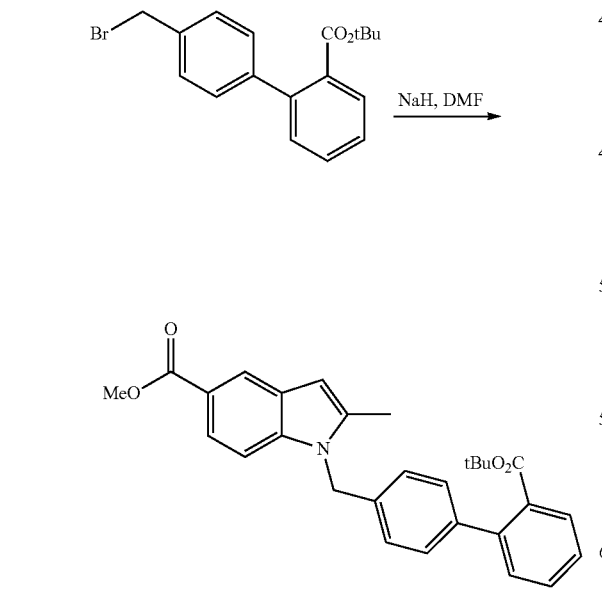

The title compound was prepared following the same protocol as described in Step 2, Example 38, using the methyl 2-methyl-1H-indole-5-carboxylate instead of the methyl 1H-indole-5-carboxylate, and the tert-butyl 4'-(bromomethyl)biphenyl-2-carboxylate instead of the 1-bromo-4-(bromomethyl)benzene. ESI-MS (m/z): 456 [M+H]$^+$.

Step 2: 1-((2'-(tert-Butoxycarbonyl)-[1,1'-biphenyl]-4-yl)methyl)-2-methyl-1H-indole-5-carboxylic acid

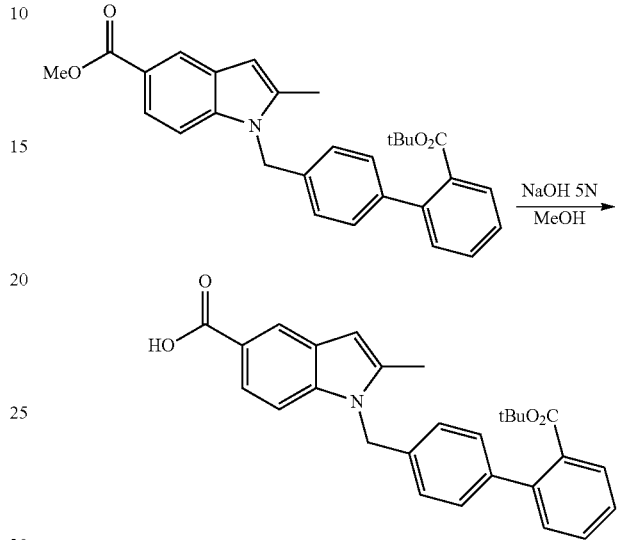

The title compound was prepared following the same protocol as described in Step 3, Example 38, using the methyl 1-((2'-(tert-butoxycarbonyl)-[1,1'-biphenyl]-4-yl)methyl)-2-methyl-1H-indole-5-carboxylate instead of the methyl 1-(4-bromobenzyl)-1H-indole-5-carboxylate. ESI-MS (m/z): 442 [M+H]$^+$.

Step 3: (S)-tert-Butyl 4'-((5-((1-(4-bromophenyl)ethyl)carbamoyl)-2-methyl-1H-indol-1-yl)methyl)-[1,1'-biphenyl]-2-carboxylate The title compound was prepared following the same protocol as described in Step 8, Example 1, using the 1-((2'-(tert-butoxycarbonyl)-[1,1'-biphenyl]-4-yl)methyl)-2-methyl- 1H-indole-5-carboxylic acid instead of the 1-((2'-(tert-Butoxycarbonyl)biphenyl-4-yl)methyl)-2,3-dimethyl-1H-indole-5-carboxylic acid.

Step 4: (S)-4'-((5-((1-(4-Bromophenyl)ethyl)carbamoyl)-2-methyl-1H-indol-1-yl)methyl)-[1,1'-biphenyl]-2-carboxylic acid

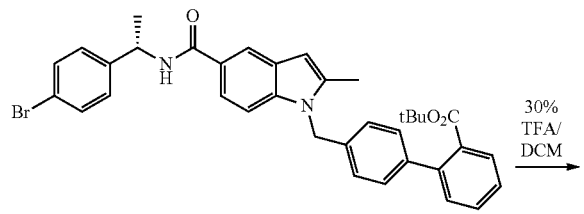

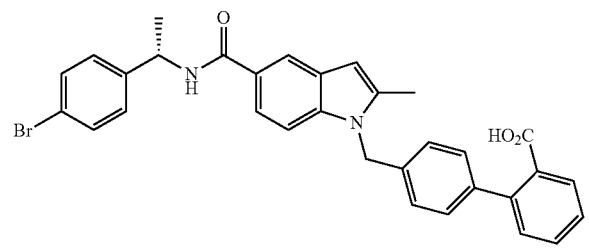

The title compound was prepared following the same protocol as described in Step 9, Example 1, using the (S)-tert-Butyl 4'-((5-(((1-(4-bromophenyl)ethyl)carbamoyl)-2-methyl-1H-indol-1-yl)methyl)-[1,1'-biphenyl]-2-carboxylate instead of the (S)-tert-Butyl 4'-((5-(((1-(4-bromophenyl)ethyl)carbamoyl)-2,3-dimethyl-1H-indol-1-yl)methyl)-[1,1'-biphenyl]-2-carboxylate. ESI-MS (m/z): 566/568 [M+H]$^+$.

Example 136

4'-((2-Methyl-5-((1-phenylpropyl)carbamoyl)-1H-indol-1-yl)methyl)-[1,1'-biphenyl]-2-carboxylic acid

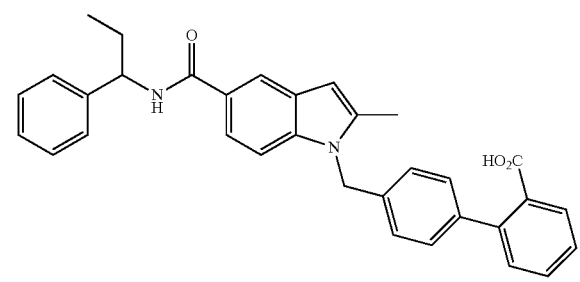 [SMILES: CCC(NC(=O)c1ccc2c(c1)cc(C)n2Cc1ccc(-c2ccccc2C(=O)O)cc1)c1ccccc1]

Step 1: tert-Butyl 4'-((2-methyl-5-((1-phenylpropyl)carbamoyl)-1H-indol-1-yl)methyl)-[1,1'-biphenyl]-2-carboxylate

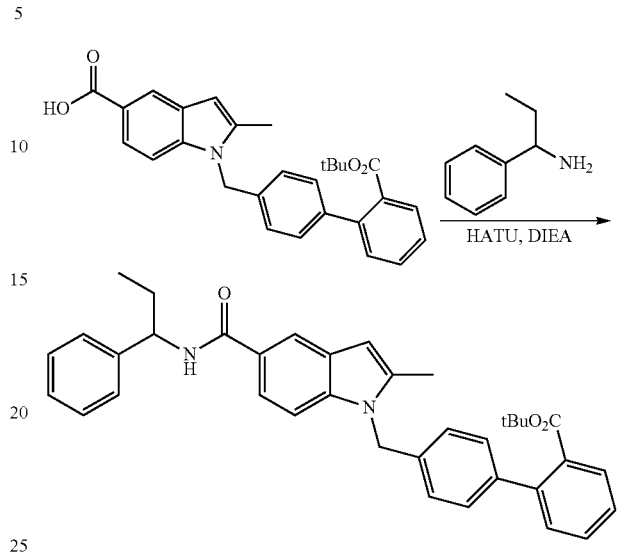

The title compound was prepared following the same protocol as described in Step 8, Example 1, using the 1-((2'-(tert-Butoxycarbonyl)biphenyl-4-yl)methyl)-2-methyl-1H-indole-5-carboxylic acid instead of the 1-((2'-(tert-Butoxycarbonyl)biphenyl-4-yl)methyl)-2,3-dimethyl-1H-indole-5-carboxylic acid and the 1-phenylpropan-1-amine instead of the (S)-1-(4-bromophenyl)ethanamine.

Step 2: 4'-((2-Methyl-5-((1-phenylpropyl)carbamoyl)-1H-indol-1-yl)methyl)-[1,1'-biphenyl]-2-carboxylic acid

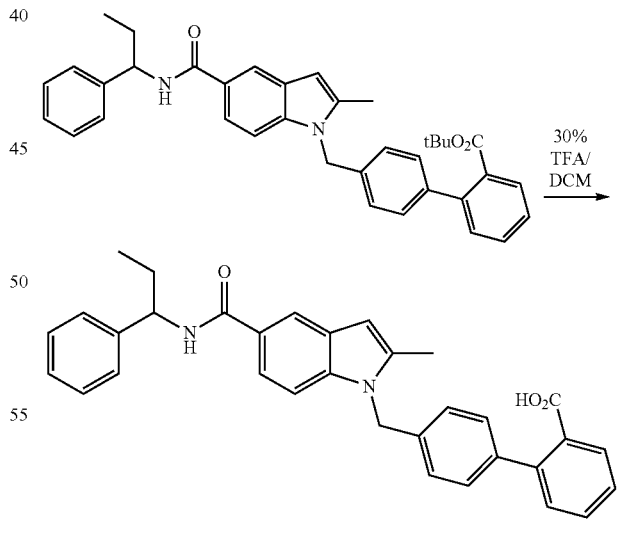

The title compound was prepared following the same protocol as described in Step 9, Example 1, using the tert-Butyl 4'-((2-methyl-5-((1-phenylpropyl)carbamoyl)-1H-indol-1-yl)methyl)-[1,1'-biphenyl]-2-carboxylate instead of the (S)-tert-butyl 4'-((5-(((1-(4-bromophenyl)ethyl)carbamoyl)-2,3-dimethyl-1H-indol-1-yl)methyl)-[1,1'-biphenyl]-2-carboxylate. ESI-MS (m/z): 559 [M+H]$^+$.

Example 137

(S)-4'-((5-((1-(3-isopropylphenyl)ethyl)carbamoyl)-2,3-dimethyl-1H-indol-1-yl)methyl)-[1,1'-biphenyl]-2-carboxylic acid

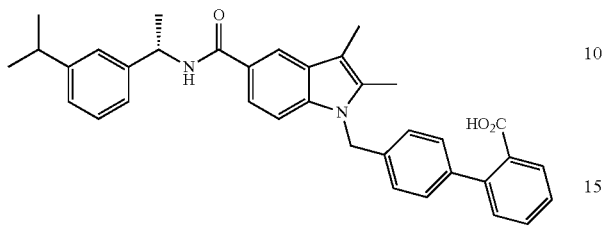

Step 1: (S)-tert-butyl 4'-((2,3-dimethyl-5-((1-(3-(prop-1-en-2-yl)phenyl)ethyl)carbamoyl)-1H-indol-1-yl)methyl)-[1,1'-biphenyl]-2-carboxylate

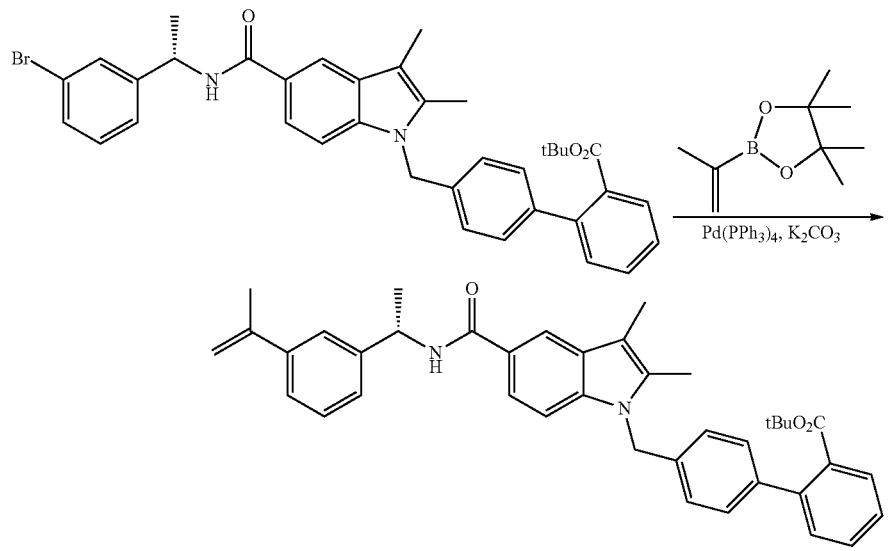

A solution of (S)-tert-butyl 4'-((5-((1-(3-bromophenyl)ethyl)carbamoyl)-2,3-dimethyl-1H-indol-1-yl)methyl)-[1,1'-biphenyl]-2-carboxylate (83 mg, 0.13 mmol, 1 equiv.), K$_2$CO$_3$ (36 mg, 0.26 mmol, 2 equiv.) and Pd(PPh$_3$)$_4$ (15 mg, 0.013 mmol, 0.1 equiv.) in dioxane/water (1.2 mL/0.3 mL) was degassed with argon. The isopropenylboronic acid pinacol ester (49 µL, 0.26 mmol, 2 equiv.) was added and the solution was heated at 100° C. for 1 h under microwave irradiation. The resulting solution was diluted with ethyl acetate, washed with a 0.5 N HCl solution, saturated aqueous NaHCO$_3$ and brine, and then dried over Na$_2$SO$_4$. The obtained oil was used without further purification. ESI-MS (m/z): 599 [M+H]$^+$.

Step 2: (S)-tert-butyl 4'-((5-((1-(3-isopropylphenyl)ethyl)carbamoyl)-2,3-dimethyl-1H-indol-1-yl)methyl)-[1,1'-biphenyl]-2-carboxylate

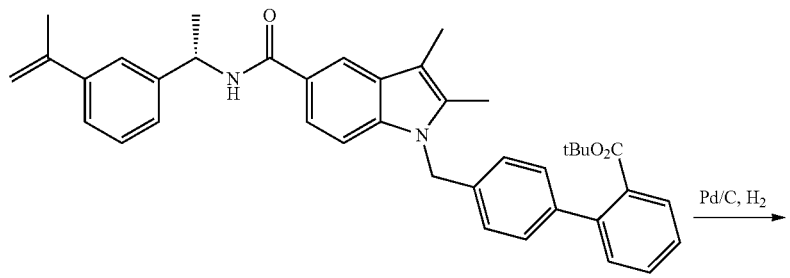

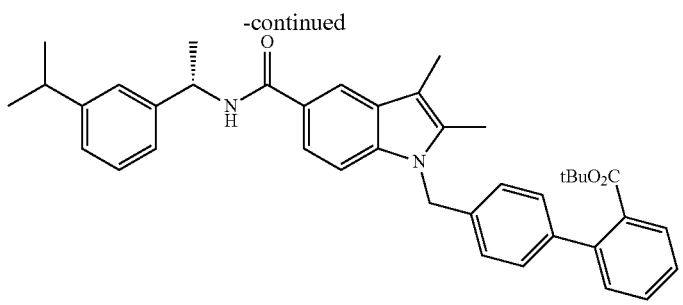

A solution of (S)-tert-butyl 4'-((2,3-dimethyl-5-((1-(3-(prop-1-en-2-yl)phenyl)ethyl)carbamoyl)-1H-indol-1-yl)methyl)-[1,1'-biphenyl]-2-carboxylate (0.13 mmol, 1 equiv.) in ethanol (5 mL) was degassed with argon. A hint of Pd/C 10% was added to the solution. The suspension was stirred at rt for 5 h under $H_2$ bubbling. The resulting mixture was then filtered and concentrated. The obtained oil was used without further purification. ESI-MS (m/z): 601 [M+H]$^+$.

Step 3: (S)-4'-((5-((1-(3-isopropylphenyl)ethyl)carbamoyl)-2,3-dimethyl-1H-indol-1-yl)methyl)-[1,1'-biphenyl]-2-carboxylic acid

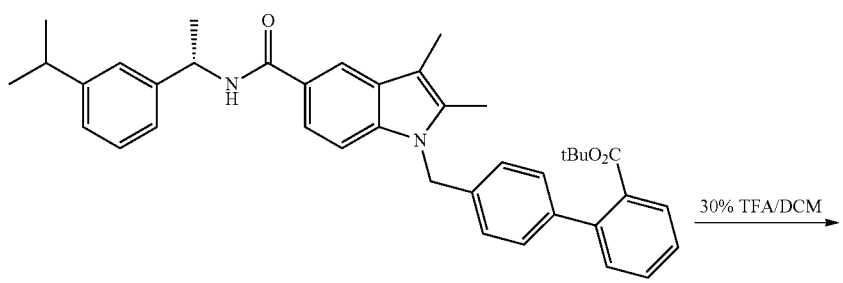

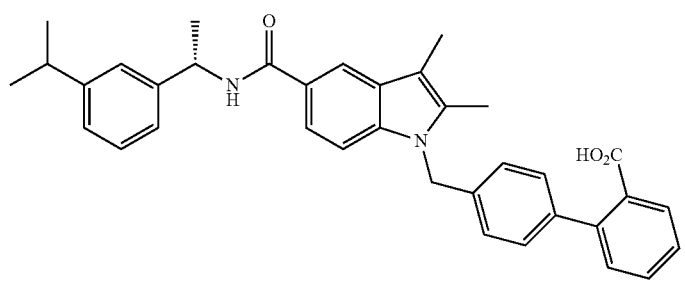 [SMILES: Cc1c(C)n(Cc2ccc(-c3ccccc3C(=O)O)cc2)c2ccc(C(=O)N[C@@H](C)c3cccc(C(C)C)c3)cc12]

The title compound was prepared following the same general protocol as described in Step 9, Example 1. ESI-MS (m/z): 545 [M+H]+.

Example 138

(S)-4'-((5-((1-(3-(tert-butyl)phenyl)ethyl)carbamoyl)-2,3-dimethyl-1H-indol-1-yl)methyl)-[1,1'-biphenyl]-2-carboxylic acid Step 1: (S)-1-(3-(tert-butyl)phenyl)ethanaminium chloride

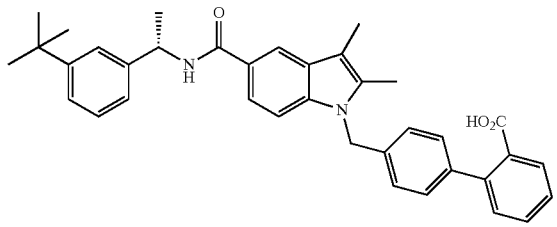 [SMILES: Cc1c(C)n(Cc2ccc(-c3ccccc3C(=O)O)cc2)c2ccc(C(=O)N[C@@H](C)c3cccc(C(C)(C)C)c3)cc12]

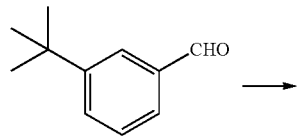

The title compound was prepared following the same general synthetic procedure as described in Steps 1-2, Example 2, using 3-(tert-butyl)benzaldehyde instead of 4-(tert-butyl)benzaldehyde.

Step 2: (S)-4'-((5-((1-(3-(tert-butyl)phenyl)ethyl)carbamoyl)-2,3-dimethyl-1H-indol-1-yl)methyl)-[1,1'-biphenyl]-2-carboxylic acid The title compound was prepared following the same general protocol as described in Step 8-9, Example 1, using (S)-1-(3-(tert-butyl)phenyl)ethanamine and 1-((2'-(tert-butoxycarbonyl)-[1,1'-biphenyl]-4-yl)methyl)-2,3-dimethyl-1H-indole-5-carboxylic acid. ESI-MS (m/z): 559 [M+H]+.

Example 139

(R)-4'-((2,3-dimethyl-5-((2,2,2-trifluoro-1-(3-isopropylphenyl)ethyl)carbamoyl)-1H-indol-1-yl)methyl)-[1,1'-biphenyl]-2-carboxylic acid

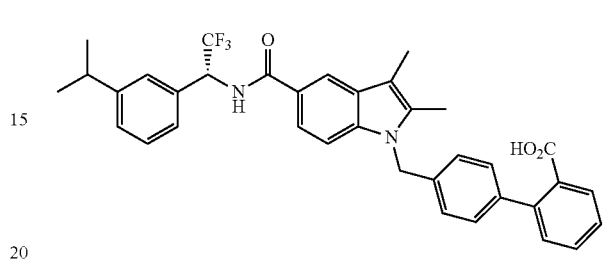

Step 1: (S,E)-N-(3-isopropylbenzylidene)-2-methylpropane-2-sulfinamide

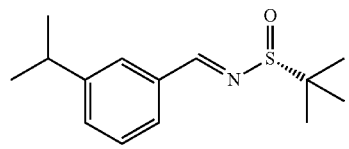 [SMILES: CC(C)c1cccc(/C=N/[S@](=O)C(C)(C)C)c1]

To a solution of 3-isopropylbenzaldehyde (0.711 g, 4.75 mmol) in THF (5 mL) was added (S)-2-methyl-2-propanesulfinamide (0.534 g, 4.32 mmol) and Ti(OiPr)4 (2.75 mL, 8.64 mmol). The resulting mixture was allowed to stir over night at rt where it was then quenched with aqueous NH4Cl (5 mL) and diluted with EtOAc (100 mL). The mixture was then filtered through celite using excess EtOAc to rinse, concentrated to an oil crude and separated by silica gel (EtOAc: Hexanes) to isolate the title compound.

Step 2: (S)-2-methyl-N-((R)-2,2,2-trifluoro-1-(3-isopropylphenyl)ethyl)propane-2-sulfinamide

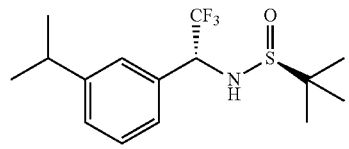 [SMILES: CC(C)c1cccc([C@@H](N[S@@](=O)C(C)(C)C)C(F)(F)F)c1]

Tetra-n-butylammonium difluorotriphenylsilicate (TBAT) (1.19 g, 2.13 mmol) and (trifluoromethyl)trimethylsilane (TMS-CF3) (0.371 mL, 2.33 mmol) was added to a solution of (S,E)-N-(3-isopropylbenzylidene)-2-methylpropane-2-sulfinamide (0.487 g, 1.937 mmol) in anhydrous THF (16 mL) at −20° C. under argon. The reaction was allowed to proceed for ~2 h where the starting material appeared to have been consumed as determined by analytical-HPLC. A saturated solution of NH4Cl (20 mL) was added to quench and the mixture was extracted with EtOAc (100 mL×3) and dried over Na2 SO4. The organic partition was then concentrated to an oil and the title compound was isolated by flash chromatography using silica gel (EtOAc:Hexanes). ESI-MS (m/z): 321 [M+1]+.

Step 3: (R)-2,2,2-trifluoro-1-(3-isopropylphenyl) ethanaminium chloride

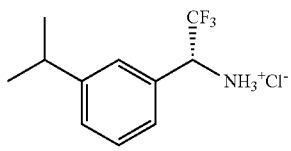

The title compound was prepared following the same general synthetic procedure as described in Step 2, Example 2, using (S)-2-methyl-N-((R)-2,2,2-trifluoro-1-(3-isopropylphenyl)ethyl)propane-2-sulfinamide instead of 4-(tert-butyl)benzaldehyde.

Step 4: (R)-4'-((2,3-dimethyl-5-((2,2,2-trifluoro-1-(3-isopropylphenyl)ethyl)carbamoyl)-1H-indol-1-yl)methyl)-[1,1'-biphenyl]-2-carboxylic acid The title compound was prepared following the same general protocol as described in Step 8-9, Example 1, using (R)-2,2,2-trifluoro-1-(3-isopropylphenyl)ethanamine and 1-((2'-(tert-butoxycarbonyl)-[1,1'-biphenyl]-4-yl)methyl)-2,3-dimethyl-1H-indole-5-carboxylic acid. ESI-MS (m/z): 599 [M+H]+.

Example 140

(S)-4'-((5-((cyclopropyl(3-isopropylphenyl)methyl)carbamoyl)-2,3-dimethyl-1H-indol-1-yl)methyl)-[1,1'-biphenyl]-2-carboxylic acid

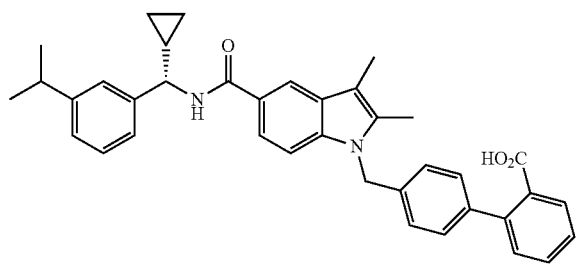 [SMILES: Cc1c(C)n(Cc2ccc(-c3ccccc3C(=O)O)cc2)c2ccc(C(=O)N[C@H](c3cccc(C(C)C)c3)C3CC3)cc12]

Step 1:
(S)-cyclopropyl(3-isopropylphenyl)methanaminium chloride

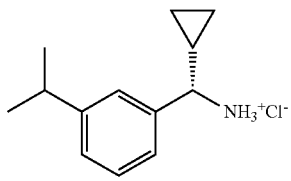

The title compound was prepared following the same general synthetic procedure as described in Steps 1-2, Example 2, using 3-isopropylbenzaldehyde and cyclopropylmagnesium bromide instead of 4-(tert-butyl)benzaldehyde and methylmagnesium bromide.

Step 2: Example: (S)-4'-((5-((cyclopropyl(3-isopropylphenyl)methyl)carbamoyl)-2,3-dimethyl-1H-indol-1-yl)methyl)-[1,1'-biphenyl]-2-carboxylic acid The title compound was prepared following the same general protocol as described in Step 1-2, Example 19, using (S)-cyclopropyl(3-isopropylphenyl)methanamine and 1-((2'-(tert-butoxycarbonyl)-[1,1'-biphenyl]-4-yl)methyl)-2,3-dimethyl-1H-indole-5-carboxylic acid. ESI-MS (m/z): 571 [M+H]+.

Example 141

(R)-4'-((5-((1-(2,6-dichlorophenyl)ethyl)carbamoyl)-2,3-dimethyl-1H-indol-1-yl)methyl)-[1,1'-biphenyl]-2-carboxylic acid

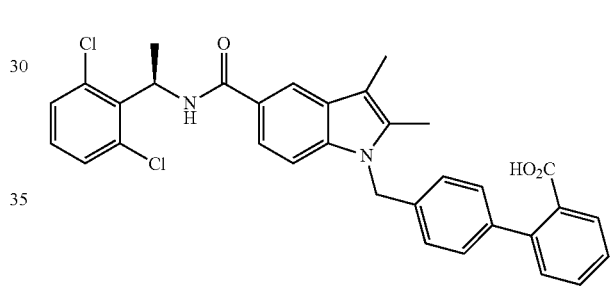

Step 1: (R)-1-(2,6-dichlorophenyl)ethanamine

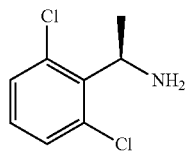

The title compound was prepared following the same general protocol as described in Step 1-2, Example 2, using 2,6-dichlorobenzaldehyde.

Step 2: (R)-4'-((5-((1-(2,6-dichlorophenyl)ethyl)carbamoyl)-2,3-dimethyl-1H-indol-1-yl)methyl)-[1,1'-biphenyl]-2-carboxylic acid The title compound was prepared following the same general protocol as described in Step 8-9, Example 1, using (R)-1-(2,6-dichlorophenyl)ethanamine and 1-((2'-(tert-butoxycarbonyl)-[1,1'-biphenyl]-4-yl)methyl)-2,3-dimethyl-1H-indole-5-carboxylic acid. ESI-MS (m/z): 571 [M+H]+.

Example 142

(S)-4'-((5-((1-(2,6-dichlorophenyl)ethyl)carbamoyl)-2,3-dimethyl-1H-indol-1-yl)methyl)-[1,1'-biphenyl]-2-carboxylic acid

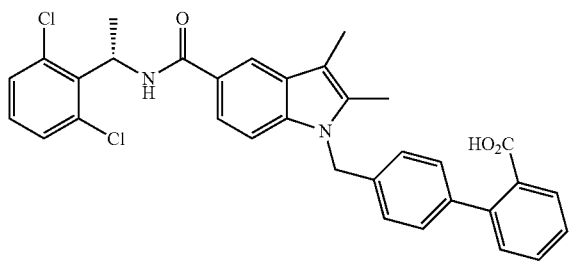 [SMILES: Cc1c(C)n(Cc2ccc(-c3ccccc3C(=O)O)cc2)c2ccc(C(=O)N[C@@H](C)c3c(Cl)cccc3Cl)cc12]

Step 1: (S)-1-(2,6-dichlorophenyl)ethanamine

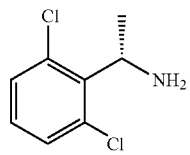

The title compound was prepared following the same general protocol as described in Step 1-2, Example 2, using 2,6-dichlorobenzaldehyde.

Step 2: (S)-4'-((5-((1-(2,6-dichlorophenyl)ethyl)carbamoyl)-2,3-dimethyl-1H-indol-1-yl)methyl)-[1,1'-biphenyl]-2-carboxylic acid The title compound was prepared following the same general protocol as described in Step 8-9, Example 1, using (S)-1-(2,6-dichlorophenyl)ethanamine and 1-((2'-(tert-butoxycarbonyl)-[1,1'-biphenyl]-4-yl)methyl)-2,3-dimethyl-1H-indole-5-carboxylic acid. ESI-MS (m/z): 571 [M+H]+.

Example 143

(S)-4'-((5-((1-(benzo[d][1,3]dioxol-4-yl)ethyl)carbamoyl)-2,3-dimethyl-1H-indol-1-yl)methyl)-[1,1'-biphenyl]-2-carboxylic acid

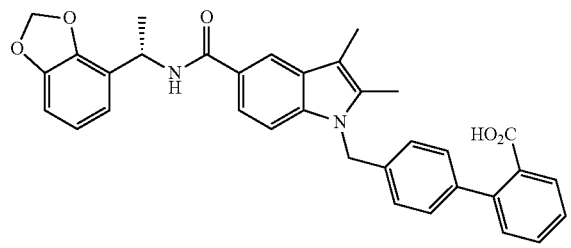 [SMILES: Cc1c(C)n(Cc2ccc(-c3ccccc3C(=O)O)cc2)c2ccc(C(=O)N[C@@H](C)c3cccc4c3OCO4)cc12]

Step 1: (S)-1-(benzo[d][1,3]dioxol-4-yl)ethanamine

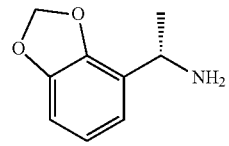

The title compound was prepared following the same general protocol as described in Step 1-2, Example 2, using benzo[d][1,3]dioxole-4-carbaldehyde.

Step 2: (S)-4'-((5-((1-(benzo[d][1,3]dioxol-4-yl)ethyl)carbamoyl)-2,3-dimethyl-1H-indol-1-yl)methyl)-[1,1'-biphenyl]-2-carboxylic acid The title compound was prepared following the same general protocol as described in Step 8-9, Example 1, using (S)-1-(benzo[d][1,3]dioxol-4-yl)ethanamine and 1-((2'-(tert-butoxycarbonyl)-[1,1'-biphenyl]-4-yl)methyl)-2,3-dimethyl-1H-indole-5-carboxylic acid. ESI-MS (m/z): 547 [M+H]+.

Example 144

(S)-4'-((2,3-dimethyl-5-((1-(pyridin-2-yl)ethyl)carbamoyl)-1H-indol-1-yl)methyl)-[1,1'-biphenyl]-2-carboxylic acid

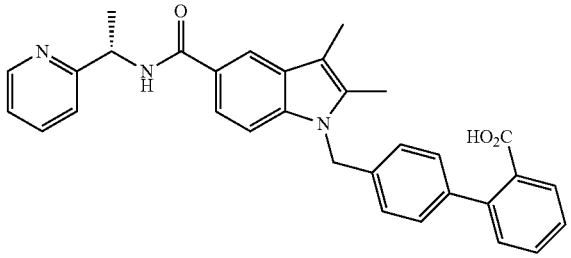 [SMILES: Cc1c(C)n(Cc2ccc(-c3ccccc3C(=O)O)cc2)c2ccc(C(=O)N[C@@H](C)c3ccccn3)cc12]

Step 1: (S)-1-(pyridin-2-yl)ethanamine

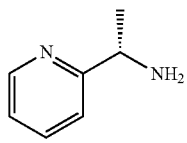

The title compound was prepared following the same general protocol as described in Step 1-2, Example 2, using the picolinaldehyde.

Step 2: (S)-4'-((2,3-dimethyl-5-((1-(pyridin-2-yl)ethyl)carbamoyl)-1H-indol-1-yl)methyl)-[1,1'-biphenyl]-2-carboxylic acid The title compound was prepared following the same general protocol as described in Step 8-9, Example 1, using the (S)-1-(pyridin-2-yl)ethanamine and the 1-((2'-(tert-butoxycarbonyl)-[1,1'-biphenyl]-4-yl)methyl)-2,3-dimethyl-1H-indole-5-carboxylic acid. ESI-MS (m/z): 504 [M+H]$^+$.

Example 145

(S)-4'-((5-((1-(3-fluoro-2-methylphenyl)ethyl)carbamoyl)-2,3-dimethyl-1H-indol-1-yl)methyl)-[1,1'-biphenyl]-2-carboxylic acid

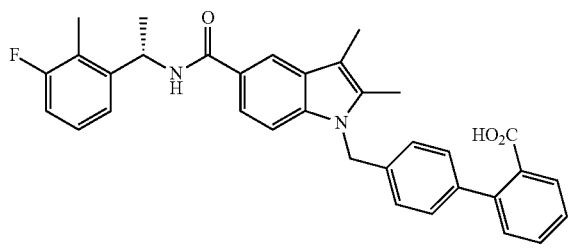

Step 1:
(S)-1-(3-fluoro-2-methylphenyl)ethanaminium chloride

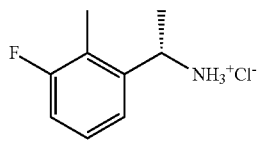

The title compound was prepared following the same general synthetic procedure as described in Steps 1-2, Example 2, using 3-fluoro-2-methylbenzaldehyde instead of 4-(tert-butyl)benzaldehyde.

Step 2: (S)-4'-((5-((1-(3-fluoro-2-methylphenyl)ethyl)carbamoyl)-2,3-dimethyl-1H-indol-1-yl)methyl)-[1,1'-biphenyl]-2-carboxylic acid The title compound was prepared following the same general protocol as described in Step 8-9, Example 1, using the (S)-1-(3-fluoro-2-methylphenyl)ethanamine and the 1-((2'-(tert-butoxycarbonyl)-[1,1'-biphenyl]-4-yl)methyl)-2,3-dimethyl-1H-indole-5-carboxylic acid. ESI-MS (m/z): 535 [M+H]$^+$.

Example 146

(S)-4'-((5-((1-(3-fluoro-5-methoxyphenyl)ethyl)carbamoyl)-2,3-dimethyl-1H-indol-1-yl)methyl)-[1,1'-biphenyl]-2-carboxylic acid

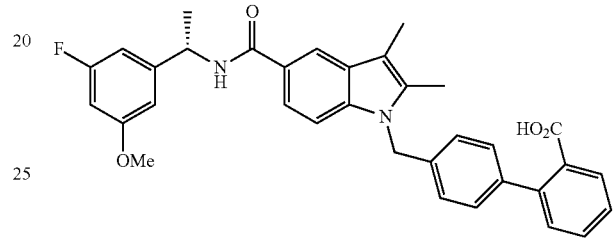

Step 1:
(S)-1-(3-fluoro-5-methoxyphenyl)ethanaminium chloride

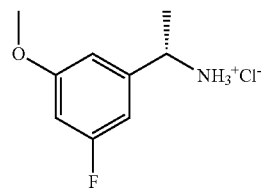

The title compound was prepared following the same general synthetic procedure as described in Steps 1-2, Example 2, using 3-fluoro-5-methoxybenzaldehyde instead of 4-(tert-butyl)benzaldehyde.

Step 2: (S)-4'-((5-((1-(3-fluoro-5-methoxyphenyl)ethyl)carbamoyl)-2,3-dimethyl-1H-indol-1-yl)methyl)-[1,1'-biphenyl]-2-carboxylic acid The title compound was prepared following the same general protocol as described in Step 8-9, Example 1, using the (S)-1-(3-fluoro-5-methoxyphenyl)ethanamine and the 1-((2'-

(tert-butoxycarbonyl)-[1,1'-biphenyl]-4-yl)methyl)-2,3-dimethyl-1H-indole-5-carboxylic acid. ESI-MS (m/z): 551 [M+H]$^+$.

Example 147

(S)-4'-((5-((1-(3,5-dimethoxyphenyl)ethyl)carbamoyl)-2,3-dimethyl-1H-indol-1-yl)methyl)-[1,1'-biphenyl]-2-carboxylic acid

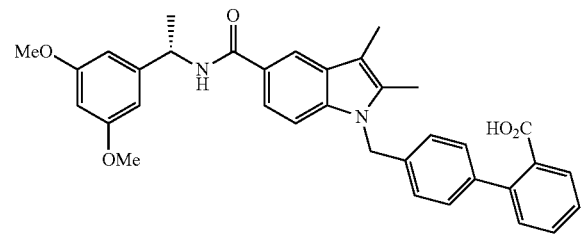 [SMILES: COc1cc(OC)cc([C@H](C)NC(=O)c2ccc3c(c2)c(C)c(C)n3Cc2ccc(-c3ccccc3C(=O)O)cc2)c1]

Step 1: (S)-1-(3,5-dimethoxyphenyl)ethanaminium chloride

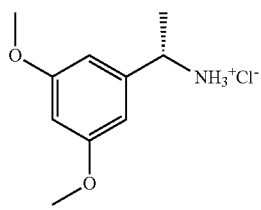

The title compound was prepared following the same general synthetic procedure as described in Steps 1-2, Example 2, using 3,5-dimethoxybenzaldehyde instead of 4-(tert-butyl)benzaldehyde.

Step 2: (S)-4'-((5-((1-(3,5-dimethoxyphenyl)ethyl)carbamoyl)-2,3-dimethyl-1H-indol-1-yl)methyl)-[1,1'-biphenyl]-2-carboxylic acid The title compound was prepared following the same general protocol as described in Step 8-9, Example 1, using the (S)-1-(3,5-dimethoxyphenyl)ethanamine and the 1-((2'-(tert-butoxycarbonyl)-[1,1'-biphenyl]-4-yl)methyl)-2,3-dimethyl-1H-indole-5-carboxylic acid. ESI-MS (m/z): 563 [M+H]$^+$.

Example 148

(S)-4'-((5-((1-(3-chloropyridin-4-yl)ethyl)carbamoyl)-2,3-dimethyl-1H-indol-1-yl)methyl)-[1,1'-biphenyl]-2-carboxylic acid

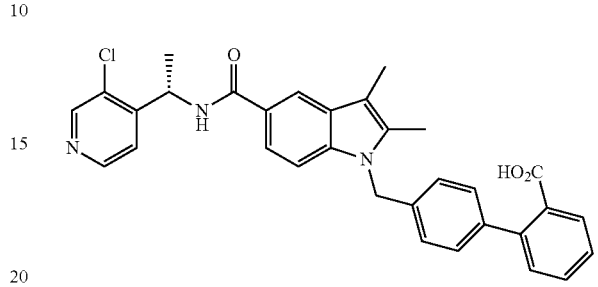

Step 1: (S)-1-(3-chloropyridin-4-yl)ethanamine

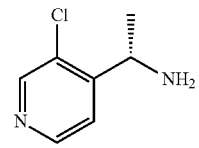

The title compound was prepared following the same general protocol as described in Step 1-2, Example 2, using the 3-chloroisonicotinaldehyde.

Step 2: (S)-4'-((5-((1-(3-chloropyridin-4-yl)ethyl)carbamoyl)-2,3-dimethyl-1H-indol-1-yl)methyl)-[1,1'-biphenyl]-2-carboxylic acid The title compound was prepared following the same general protocol as described in Step 8-9, Example 1, using the (S)-1-(3-chloropyridin-4-yl)ethanamine and the 1-((2'-(tert-butoxycarbonyl)-[1,1'-biphenyl]-4-yl)methyl)-2,3-dimethyl-1H-indole-5-carboxylic acid. ESI-MS (m/z): 538/539/540 [M+H]$^+$.

Example 149

(S)-4'-((2,3-dimethyl-5-((1-(quinolin-4-yl)ethyl)carbamoyl)-1H-indol-1-yl)methyl)-[1,1'-biphenyl]-2-carboxylic acid

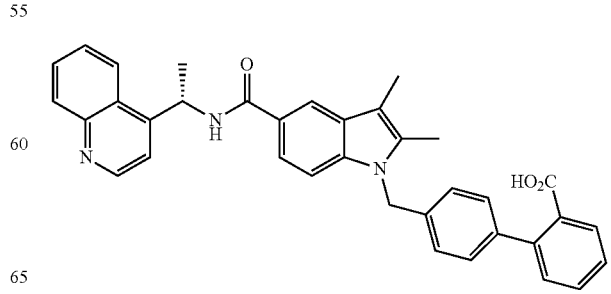

Step 1: (S)-1-(quinolin-4-yl)ethanamine

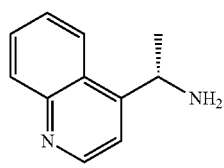

The title compound was prepared following the same general protocol as described in Step 1-2, Example 2, using the quinoline-4-carbaldehyde.

Step 2: (S)-4'-((2,3-dimethyl-5-((1-(quinolin-4-yl)ethyl)carbamoyl)-1H-indol-1-yl)methyl)-[1,1'-biphenyl]-2-carboxylic acid The title compound was prepared following the same general protocol as described in Step 8-9, Example 1, using the (S)-1-(quinolin-4-yl)ethanamine and the 1-((2'-(tert-butoxycarbonyl)-[1,1'-biphenyl]-4-yl)methyl)-2,3-dimethyl-1H-indole-5-carboxylic acid. ESI-MS (m/z): 554 [M+H]$^+$.

Example 150

(S)-4'-((5-((1-(2,4-difluorophenyl)ethyl)carbamoyl)-2,3-dimethyl-1H-indol-1-yl)methyl)-[1,1'-biphenyl]-2-carboxylic acid

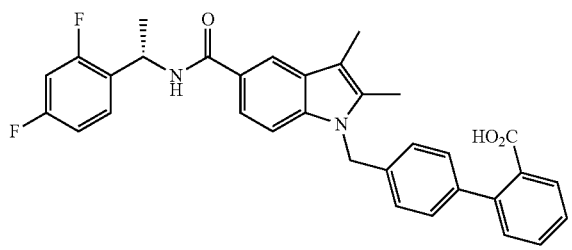

Step 1: (S)-1-(2,4-difluorophenyl)ethanaminium chloride

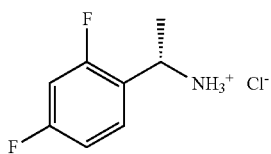

The title compound was prepared following the same general synthetic procedure as described in Steps 1-2, Example 2, using 2,4-difluorobenzaldehyde instead of 4-(tert-butyl)benzaldehyde.

Step 2: (S)-4'-((5-((1-(2,4-difluorophenyl)ethyl)carbamoyl)-2,3-dimethyl-1H-indol-1-yl)methyl)-[1,1'-biphenyl]-2-carboxylic acid The title compound was prepared following the same general protocol as described in Step 8-9, Example 1, using the (S)-1-(2,4-difluorophenyl)ethanamine and the 1-((2'-(tert-butoxycarbonyl)-[1,1'-biphenyl]-4-yl)methyl)-2,3-dimethyl-1H-indole-5-carboxylic acid. ESI-MS (m/z): 539 [M+H]$^+$.

Example 151

(S)-4'-((5-((1-(3-ethoxyphenyl)ethyl)carbamoyl)-2,3-dimethyl-1H-indol-1-yl)methyl)-[1,1'-biphenyl]-2-carboxylic acid

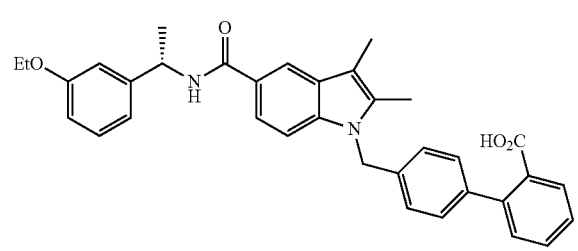 [SMILES: CCOc1cccc([C@H](C)NC(=O)c2ccc3c(c2)c(C)c(C)n3Cc2ccc(-c3ccccc3C(=O)O)cc2)c1]

Step 1: (S)-(3-ethoxyphenyl)ethanamine

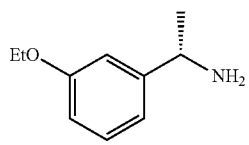

The title compound was prepared following the same general protocol as described in Step 1-2, Example 2, using the 3-ethoxybenzaldehyde.

Step 2: (S)-4'-((5-((1-(3-ethoxyphenyl)ethyl)carbamoyl)-2,3-dimethyl-1H-indol-1-yl)methyl)-[1,1'-biphenyl]-2-carboxylic acid The title compound was prepared following the same general protocol as described in Step 8-9, Example 1, using the (S)-1-(3-ethoxyphenyl)ethanamine and the 1-((2'-(tert-butoxycarbonyl)-[1,1'-biphenyl]-4-yl)methyl)-2,3-dimethyl-1H-indole-5-carboxylic acid. ESI-MS (m/z): 545 [M+H]$^+$.

Example 152

(S)-4'-((2,3-dimethyl-5-((1-(naphthalen-1-yl)ethyl)carbamoyl)-1H-indol-1-yl)methyl)-[1,1'-biphenyl]-2-carboxylic acid

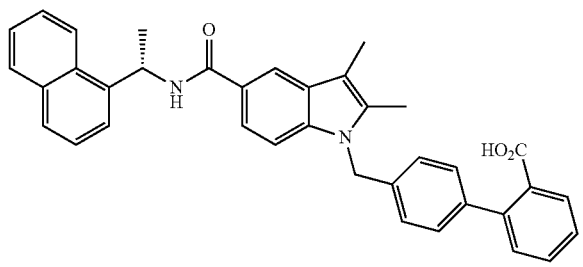

Step 1: (S)-1-(naphthalen-1-yl)ethanamine

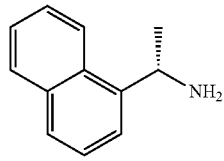

The title compound was prepared following the same general protocol as described in Step 1-2, Example 2, using the 1-naphthaldehyde.

Step 2: (S)-4'-((2,3-dimethyl-5-((1-(naphthalen-1-yl)ethyl)carbamoyl)-1H-indol-1-yl)methyl)-[1,1'-biphenyl]-2-carboxylic acid The title compound was prepared following the same general protocol as described in Step 8-9, Example 1, using the (S)-1-(naphthalen-1-yl)ethanamine and the 1-((2'-(tert-butoxycarbonyl)-[1,1'-biphenyl]-4-yl)methyl)-2,3-dimethyl-1H-indole-5-carboxylic acid. ESI-MS (m/z): 553 [M+H]$^+$.

Example 153

(S)-4'-((2,3-dimethyl-5-((1-(4-(trifluoromethoxy)phenyl)ethyl)carbamoyl)-1H-indol-1-yl)methyl)-[1,1'-biphenyl]-2-carboxylic acid

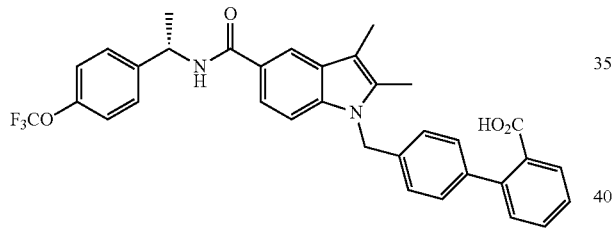

Step 1: (S)-1-(4-(trifluoromethoxy)phenyl)ethanaminium chloride

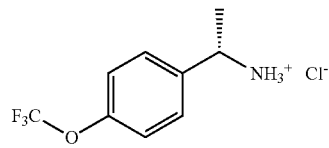

The title compound was prepared following the same general synthetic procedure as described in Steps 1-2, Example 2, using 4-(trifluoromethoxy)benzaldehyde instead of 4-(tert-butyl)benzaldehyde.

Step 2: (S)-4'-((2,3-dimethyl-5-((1-(4-(trifluoromethoxy)phenyl)ethyl)carbamoyl)-1H-indol-1-yl)methyl)-[1,1'-biphenyl]-2-carboxylic acid The title compound was prepared following the same general protocol as described in Step 8-9, Example 1, using the (S)-1-(4-(trifluoromethoxy)phenyl)ethanamine and the 1-((2'-(tert-butoxycarbonyl)-[1,1'-biphenyl]-4-yl)methyl)-2,3-dimethyl-1H-indole-5-carboxylic acid. ESI-MS (m/z): 587 [M+H]$^+$.

Example 154

(S)-4'-((2,3-dimethyl-5-((1-(4-(trifluoromethyl)phenyl)ethyl)carbamoyl)-1H-indol-1-yl)methyl)-[1,1'-biphenyl]-2-carboxylic acid

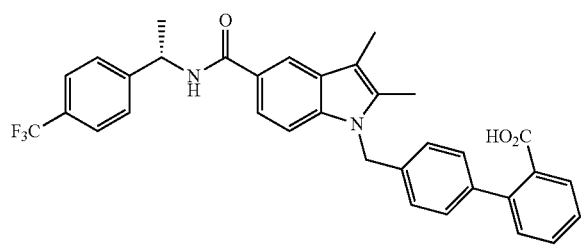 [SMILES: Cc1c(C)n(Cc2ccc(-c3ccccc3C(=O)O)cc2)c2ccc(C(=O)N[C@@H](C)c3ccc(C(F)(F)F)cc3)cc12]

Step 1: (S)-1-(4-(trifluoromethyl)phenyl)ethanamine

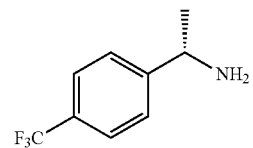

The title compound was prepared following the same general protocol as described in Step 1-2, Example 2, using the 4-trifluoromethylbenzaldehyde.

Step 2: (S)-4'-((2,3-dimethyl-5-((1-(4-(trifluoromethyl)phenyl)ethyl)carbamoyl)-1H-indol-1-yl)methyl)-[1,1'-biphenyl]-2-carboxylic acid The title compound was prepared following the same general protocol as described in Step 8-9, Example 1, using the (S)-1-(4-(trifluoromethyl)phenyl)ethanamine and the 1-((2'-

(tert-butoxycarbonyl)-[1,1'-biphenyl]-4-yl)methyl)-2,3-dimethyl-1H-indole-5-carboxylic acid. ESI-MS (m/z): 571 [M+H]$^+$.

Example 155

(S)-4'-((5-((1-(3-isopropylphenyl)-3-methylbutyl)carbamoyl)-2,3-dimethyl-1H-indol-1-yl)methyl)-[1,1'-biphenyl]-2-carboxylic acid

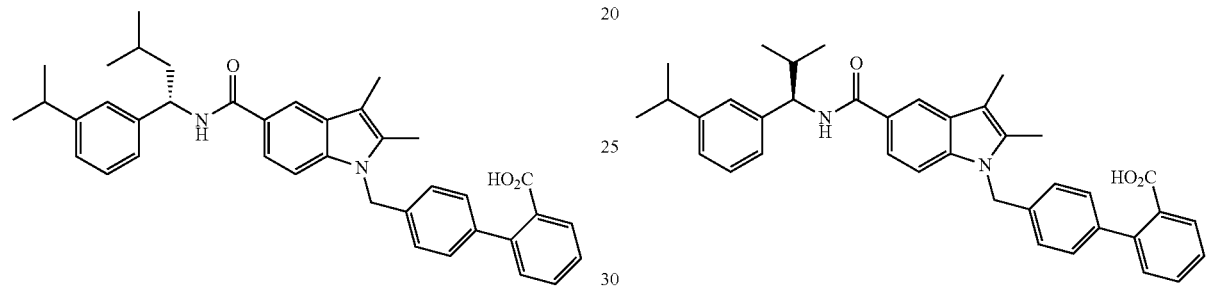

Step 1: (S)-1-(3-isopropylphenyl)-3-methylbutan-1-amine

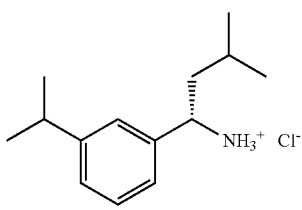

The title compound was prepared following the same general synthetic procedure as described in Steps 1-2, Example 2, using 3-isopropylbenzaldehyde and isobutylmagnesium chloride instead of 4-(tert-butyl)benzaldehyde and methylmagnesium bromide.

Step 2: (S)-4'-((5-((1-(3-isopropylphenyl)-3-methylbutyl)carbamoyl)-2,3-dimethyl-1H-indol-1-yl)methyl)-[1,1'-biphenyl]-2-carboxylic acid The title compound was prepared following the same general protocol as described in Step 8-9, Example 1, using the (S)-1-(3-isopropylphenyl)-3-methylbutan-1-amine and the 1-((2'-(tert-butoxycarbonyl)-[1,1'-biphenyl]-4-yl)methyl)-2,3-dimethyl-1H-indole-5-carboxylic acid. ESI-MS (m/z): 587 [M+H]$^+$.

Example 156

(R)-4'-((5-((1-(3-isopropylphenyl)-2-methylpropyl)carbamoyl)-2,3-dimethyl-1H-indol-1-yl)methyl)-[1,1'-biphenyl]-2-carboxylic acid

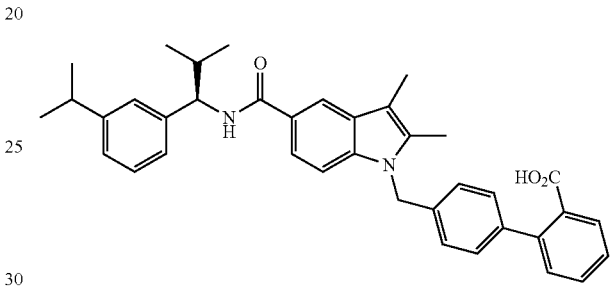

Step 1: (R)-1-(3-isopropylphenyl)-2-methylpropan-1-aminium chloride

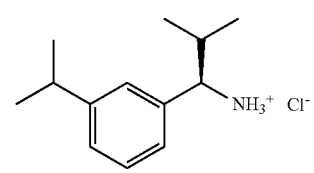

The title compound was prepared following the same general synthetic procedure as described in Steps 1-2, Example 2, using 3-isopropylbenzaldehyde and 2-propyl-magnesium chloride instead of 4-(tert-butyl)benzaldehyde and methylmagnesium bromide.

Step 2: (R)-4'-((5-((1-(3-isopropylphenyl)-2-methylpropyl)carbamoyl)-2,3-dimethyl-1H-indol-1-yl)methyl)-[1,1'-biphenyl]-2-carboxylic acid The title compound was prepared following the same general protocol as described in Step 8-9, Example 1, using the (R)-1-(3-isopropylphenyl)-2-methylpropan-1-amine and the 1-((2'-(tert-butoxycarbonyl)-[1,1'-biphenyl]-4-yl)methyl)-2,3-dimethyl-1H-indole-5-carboxylic acid. ESI-MS (m/z): 573 [M+H]+.

Example 157

(S)-4'-((5-((1-(3-isopropylphenyl)-2-methylpropyl)carbamoyl)-2,3-dimethyl-1H-indol-1-yl)methyl)-[1,1'-biphenyl]-2-carboxylic acid

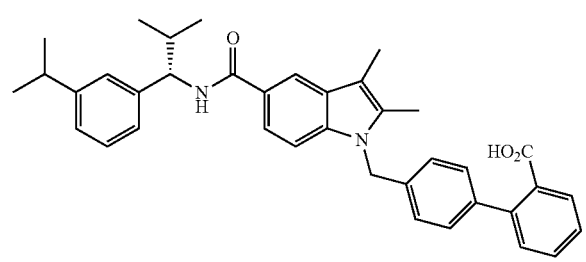 [SMILES: Cc1c(C)n(Cc2ccc(-c3ccccc3C(=O)O)cc2)c2ccc(C(=O)N[C@H](c3cccc(C(C)C)c3)C(C)C)cc12]

Step 1: (R)-1-(3-isopropylphenyl)-2-methylpropan-1-aminium chloride

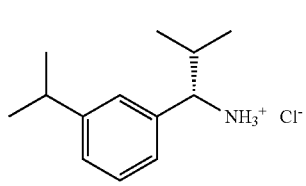

The title compound was prepared following the same general synthetic procedure as described in Steps 1-2, Example 2, using 3-isopropylbenzaldehyde and 2-propyl-magnesium chloride instead of 4-(tert-butyl)benzaldehyde and methylmagnesium bromide.

Step 2: (S)-4'-((5-((1-(3-isopropylphenyl)-2-methylpropyl)carbamoyl)-2,3-dimethyl-1H-indol-1-yl)methyl)-[1,1'-biphenyl]-2-carboxylic acid The title compound was prepared following the same general protocol as described in Step 8-9, Example 1, using the (S)-1-(3-isopropylphenyl)-2-methylpropan-1-amine and the 1-((2'-(tert-butoxycarbonyl)-[1,1'-biphenyl]-4-yl)methyl)-2,3-dimethyl-1H-indole-5-carboxylic acid. ESI-MS (m/z): 573 [M+H]+.

Example 158

(S)-4'-((5-((1-(3-fluorophenyl)ethyl)carbamoyl)-2,3-dimethyl-1H-indol-1-yl)methyl)-[1,1'-biphenyl]-2-carboxylic acid

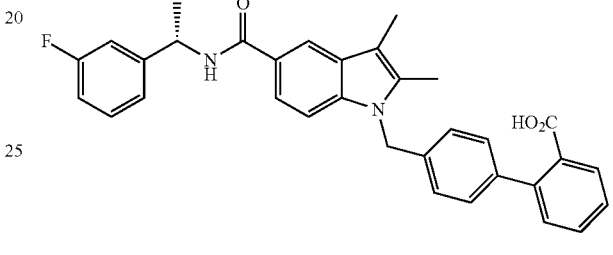

Step 1: (S)-1-(3-fluorophenyl)ethanamine

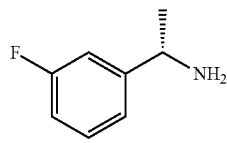

The title compound was prepared following the same general protocol as described in Step 1-2, Example 2, using the 3-fluorobenzaldehyde.

Step 2: (S)-4'-((5-((1-(3-fluorophenyl)ethyl)carbamoyl)-2,3-dimethyl-1H-indol-1-yl)methyl)-[1,1'-biphenyl]-2-carboxylic acid The title compound was prepared following the same general protocol as described in Step 8-9, Example 1, using the (S)-1-(3-fluorophenyl)ethanamine and the 1-((2'-(tert-butoxycarbonyl)-[1,1'-biphenyl]-4-yl)methyl)-2,3-dimethyl-1H-indole-5-carboxylic acid. ESI-MS (m/z): 521 [M+H]$^+$.

Example 159

(S)-4'-((5-((1-(2-chlorophenyl)ethyl)carbamoyl)-2,3-dimethyl-1H-indol-1-yl)methyl)-[1,1'-biphenyl]-2-carboxylic acid

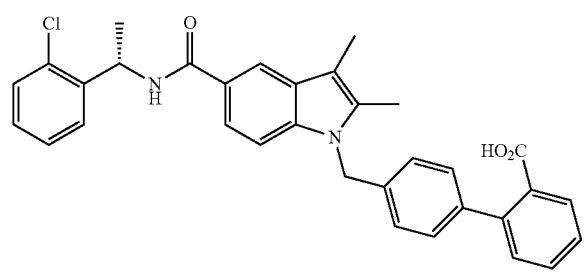

Step 1: (S)-1-(2-chlorophenyl)ethanamine

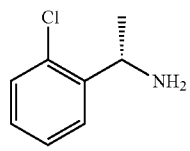

The title compound was prepared following the same general protocol as described in Step 1-2, Example 2, using the 2-chlorobenzaldehyde.

Step 2: (S)-4'-((5-((1-(2-chlorophenyl)ethyl)carbamoyl)-2,3-dimethyl-1H-indol-1-yl)methyl)-[1,1'-biphenyl]-2-carboxylic acid The title compound was prepared following the same general protocol as described in Step 8-9, Example 1, using the (S)-1-(2-chlorophenyl)ethanamine and the 1-((2'-(tert-butoxycarbonyl)-[1,1'-biphenyl]-4-yl)methyl)-2,3-dimethyl-1H-indole-5-carboxylic acid. ESI-MS (m/z): 537/538/539 [M+H]$^+$.

Example 160

(S)-4'-((5-((1-(2-fluorophenyl)ethyl)carbamoyl)-2,3-dimethyl-1H-indol-1-yl)methyl)-[1,1'-biphenyl]-2-carboxylic acid

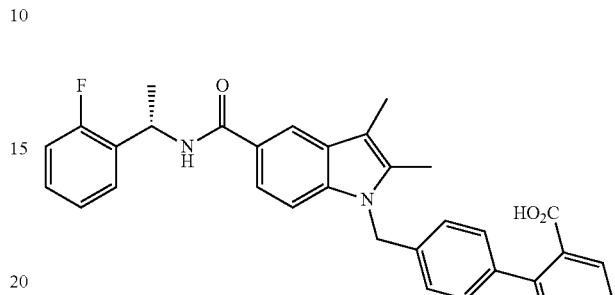

Step 1: (S)-1-(2-fluorophenyl)ethanamine

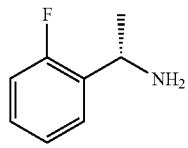

The title compound was prepared following the same general protocol as described in Step 1-2, Example 2, using the 2-fluorobenzaldehyde.

Step 2: (S)-4'-((5-((1-(2-fluorophenyl)ethyl)carbamoyl)-2,3-dimethyl-1H-indol-1-yl)methyl)-[1,1'-biphenyl]-2-carboxylic acid The title compound was prepared following the same general protocol as described in Step 8-9, Example 1, using the (S)-1-(2-fluorophenyl)ethanamine and the 1-((2'-(tert-butoxycarbonyl)-[1,1'-biphenyl]-4-yl)methyl)-2,3-dimethyl-1H-indole-5-carboxylic acid. ESI-MS (m/z): 521 [M+H]$^+$.

Example 161

(R)-4'-((5-((1-(3-methoxyphenyl)ethyl)carbamoyl)-2,3-dimethyl-1H-indol-1-yl)methyl)-[1,1'-biphenyl]-2-carboxylic acid

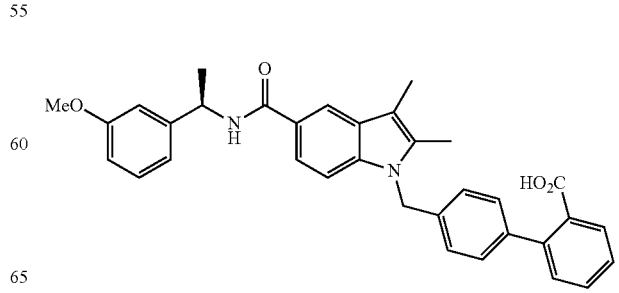

The title compound was prepared following the same general protocol as described in Step 8-9, Example 1, using the (R)-1-(3-methoxyphenyl)ethanamine and the 1-((2'-(tert-butoxycarbonyl)-[1,1'-biphenyl]-4-yl)methyl)-2,3-dimethyl-1H-indole-5-carboxylic acid. ESI-MS (m/z): 533 [M+H]$^+$.

Example 162

(R)-4'-((5-((1-(3-chlorophenyl)ethyl)carbamoyl)-2,3-dimethyl-1H-indol-1-yl)methyl)-[1,1'-biphenyl]-2-carboxylic acid

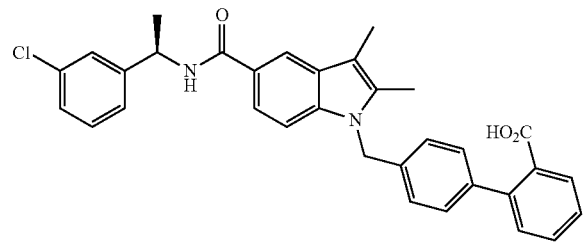 [SMILES: Cc1c(C)n(Cc2ccc(-c3ccccc3C(=O)O)cc2)c2ccc(C(=O)N[C@H](C)c3cccc(Cl)c3)cc12]

The title compound was prepared following the same general protocol as described in Step 8-9, Example 1, using the (R)-1-(3-chlorophenyl)ethanamine and the 1-((2'-(tert-butoxycarbonyl)-[1,1'-biphenyl]-4-yl)methyl)-2,3-dimethyl-1H-indole-5-carboxylic acid. ESI-MS (m/z): 537/538/539 [M+H]$^+$.

Example 163

(S)-4'-((5-((1-(4-isopropylphenyl)ethyl)carbamoyl)-2,3-dimethyl-1H-indol-1-yl)methyl)-[1,1'-biphenyl]-2-carboxylic acid

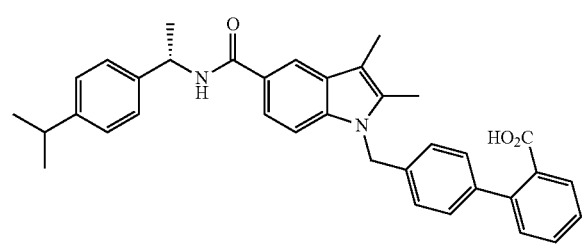 [SMILES: Cc1c(C)n(Cc2ccc(-c3ccccc3C(=O)O)cc2)c2ccc(C(=O)N[C@@H](C)c3ccc(C(C)C)cc3)cc12]

The title compound was prepared following the same general protocol as described in Step 1-2-3, Example 137, using the (S)-tert-butyl 4'-((5-((1-(4-bromophenyl)ethyl)carbamoyl)-2,3-dimethyl-1H-indol-1-yl)methyl)-[1,1'-biphenyl]-2-carboxylate. ESI-MS (m/z): 545 [M+H]$^+$.

Example 164

4'-((5-((2,4-difluorobenzyl)carbamoyl)-2,3-dimethyl-1H-indol-1-yl)methyl)-[1,1'-biphenyl]-2-carboxylic acid The title compound was prepared following the same general protocol as described in Step 8-9, Example 1, using the (2,4-difluorophenyl)methanamine and the 1-((2'-(tert-butoxycarbonyl)-[1,1'-biphenyl]-4-yl)methyl)-2,3-dimethyl-1H-indole-5-carboxylic acid. ESI-MS (m/z): 525 [M+H]$^+$.

Example 165

4'-((5-((4-chloro-2-(trifluoromethyl)benzyl)carbamoyl)-2,3-dimethyl-1H-indol-1-yl)methyl)-[1,1'-biphenyl]-2-carboxylic acid The title compound was prepared following the same general protocol as described in Step 8-9, Example 1, using the (4-chloro-2-(trifluoromethyl)phenyl)methanamine and the 1-((2'-(tert-butoxycarbonyl)-[1,1'-biphenyl]-4-yl)methyl)-2,3-dimethyl-1H-indole-5-carboxylic acid. ESI-MS (m/z): 591 [M+H]$^+$.

Example 166

(R)-4'-((5-((1-(3-isopropylphenyl)ethyl)carbamoyl)-2,3-dimethyl-1H-indol-1-yl)methyl)-[1,1'-biphenyl]-2-carboxylic acid

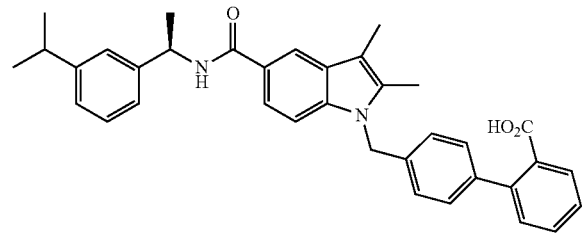 [SMILES: Cc1c(C)n(Cc2ccc(-c3ccccc3C(=O)O)cc2)c2ccc(C(=O)N[C@H](C)c3cccc(C(C)C)c3)cc12]

The title compound was prepared following the same general protocol as described in Step 1-2-3, Example 137, using the (R)-tert-butyl 4'-((5-((1-(3-bromophenyl)ethyl)carbamoyl)-2,3-dimethyl-1H-indol-1-yl)methyl)-[1,1'-biphenyl]-2-carboxylate. ESI-MS (m/z): 545 [M+H]$^+$.

Example 167

4'-((5-((2-fluoro-4-(trifluoromethyl)benzyl)carbamoyl)-2,3-dimethyl-1H-indol-1-yl)methyl)-[1,1'-biphenyl]-2-carboxylic acid

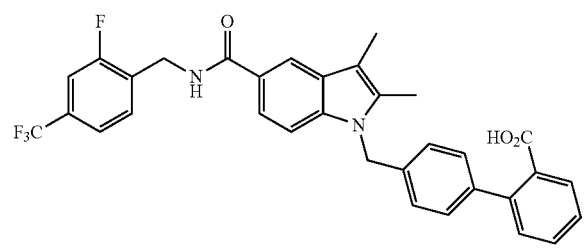 [SMILES: Cc1c(C)n(Cc2ccc(-c3ccccc3C(=O)O)cc2)c2ccc(C(=O)NCc3ccc(C(F)(F)F)cc3F)cc12]

The title compound was prepared following the same general protocol as described in Step 8-9, Example 1, using the (2-fluoro-4-(trifluoromethyl)phenyl)methanamine and the 1-((2'-(tert-butoxycarbonyl)-[1,1'-biphenyl]-4-yl)methyl)-2,3-dimethyl-1H-indole-5-carboxylic acid. ESI-MS (m/z): 575 [M+H]$^+$.

Example 168

4'-((5-((2,4-dichlorobenzyl)carbamoyl)-2,3-dimethyl-1H-indol-1-yl)methyl)-[1,1'-biphenyl]-2-carboxylic acid

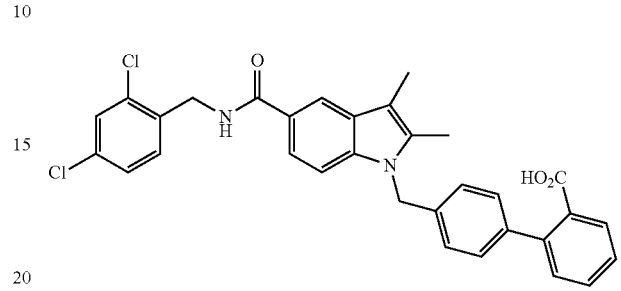

The title compound was prepared following the same general protocol as described in Step 8-9, Example 1, using the (2,4-dichlorophenyl)methanamine and the 1-((2'-(tert-butoxycarbonyl)-[1,1'-biphenyl]-4-yl)methyl)-2,3-dimethyl-1H-indole-5-carboxylic acid. ESI-MS (m/z): 557/559 [M+H]$^+$.

Example 169

(R)-4'-((2,3-dimethyl-5-((1-(pyridin-4-yl)ethyl)carbamoyl)-1H-indol-1-yl)methyl)-[1,1'-biphenyl]-2-carboxylic acid

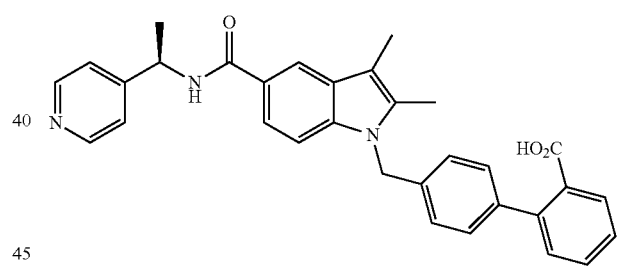

Step 1: (R)-1-(pyridin-4-yl)ethanamine

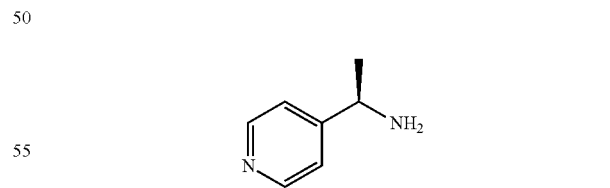

The title compound was prepared following the same general protocol as described in Step 1-2, Example 2, using the isonicotinaldehyde.

Step 2: (R)-4'-((2,3-dimethyl-5-((1-(pyridin-4-yl)ethyl)carbamoyl)-1H-indol-1-yl)methyl)-[1,1'-biphenyl]-2-carboxylic acid The title compound was prepared following the same general protocol as described in Step 8-9, Example 1, using the (R)-1-(pyridin-4-yl)ethanamine and the 1-((2'-(tert-butoxycarbonyl)-[1,1'-biphenyl]-4-yl)methyl)-2,3-dimethyl-1H-indole-5-carboxylic acid. ESI-MS (m/z): 504 [M+H]$^+$.

Example 170

(S)-4'-((5-((1-(2-chloro-3-fluorophenyl)ethyl)carbamoyl)-2,3-dimethyl-1H-indol-1-yl)methyl)-[1,1'-biphenyl]-2-carboxylic acid

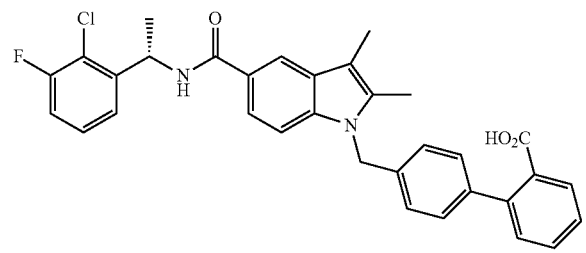

Step 1: (S)-1-(2-chloro-3-fluorophenyl)ethanamine

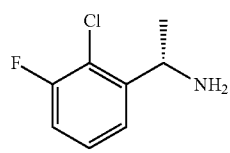

The title compound was prepared following the same general protocol as described in Step 1-2, Example 2, using the 2-chloro-3-fluorobenzaldehyde.

Step 2: (S)-4'-((5-((1-(2-chloro-3-fluorophenyl)ethyl)carbamoyl)-2,3-dimethyl-1H-indol-1-yl)methyl)-[1,1'-biphenyl]-2-carboxylic acid The title compound was prepared following the same general protocol as described in Step 8-9, Example 1, using the (S)-1-(2-chloro-3-fluorophenyl)ethanamine and the 1-((2'-(tert-butoxycarbonyl)-[1,1'-biphenyl]-4-yl)methyl)-2,3-dimethyl-1H-indole-5-carboxylic acid. ESI-MS (m/z): 504 [M+H]$^+$.

Example 171

(R)-4'-((5-((1-(2,3-dichlorophenyl)ethyl)carbamoyl)-2,3-dimethyl-1H-indol-1-yl)methyl)-[1,1'-biphenyl]-2-carboxylic acid

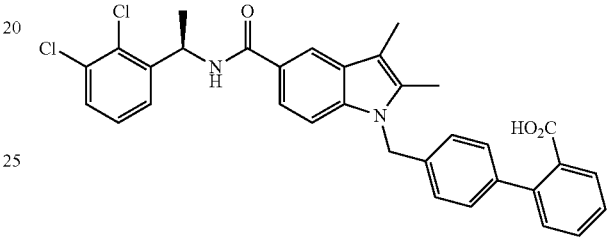

Step 1: (R)-1-(2,3-dichlorophenyl)ethanamine

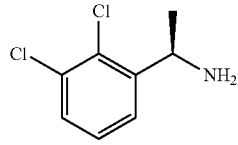

The title compound was prepared following the same general protocol as described in Step 1-2, Example 2, using the 2,3-dichlorobenzaldehyde.

Step 2: (R)-4'-((5-((1-(2,3-dichlorophenyl)ethyl)carbamoyl)-2,3-dimethyl-1H-indol-1-yl)methyl)-[1,1'-biphenyl]-2-carboxylic acid The title compound was prepared following the same general protocol as described in Step 8-9, Example 1, using the (R)-1-(2,3-dichlorophenyl)ethanamine and the 1-((2'-(tert-butoxycarbonyl)-[1,1'-biphenyl]-4-yl)methyl)-2,3-dimethyl-1H-indole-5-carboxylic acid. ESI-MS (m/z): 571 [M+H]⁺.

Example 172

(S)-4'-((5-((1-(2,5-bis(trifluoromethyl)phenyl)ethyl)carbamoyl)-2,3-dimethyl-1H-indol-1-yl)methyl)-[1,1'-biphenyl]-2-carboxylic acid 1-((2'-(tert-butoxycarbonyl)-[1,1'-biphenyl]-4-yl)methyl)-2,3-dimethyl-1H-indole-5-carboxylic acid. ESI-MS (m/z): 639 [M+H]⁺.

Example 173

(R)-4'-((5-((1-(2,5-bis(trifluoromethyl)phenyl)ethyl)carbamoyl)-2,3-dimethyl-1H-indol-1-yl)methyl)-[1,1'-biphenyl]-2-carboxylic acid

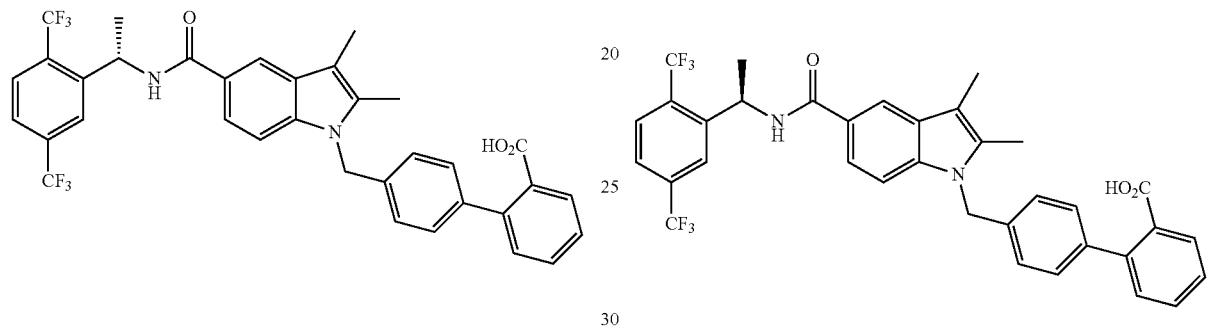

Step 1:
(S)-1-(2,5-bis(trifluoromethyl)phenyl)ethanamine

Step 1:
(R)-1-(2,5-bis(trifluoromethyl)phenyl)ethanamine

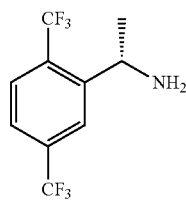 [SMILES: C[C@H](N)c1cc(C(F)(F)F)ccc1C(F)(F)F]

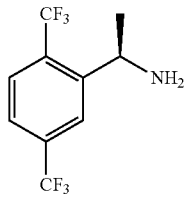

The title compound was prepared following the same general protocol as described in Step 1-2, Example 2, using the 2,5-bis(trifluoromethyl)benzaldehyde.

Step 2: (S)-4'-((5-((1-(2,5-bis(trifluoromethyl)phenyl)ethyl)carbamoyl)-2,3-dimethyl-1H-indol-1-yl)methyl)-[1,1'-biphenyl]-2-carboxylic acid The title compound was prepared following the same general protocol as described in Step 8-9, Example 1, using the (S)-1-(2,5-bis(trifluoromethyl)phenyl)ethanamine and the The title compound was prepared following the same general protocol as described in Step 1-2, Example 2, using the 2,5-bis(trifluoromethyl)benzaldehyde.

Step 2: (R)-4'-((5-((1-(2,5-bis(trifluoromethyl)phenyl)ethyl)carbamoyl)-2,3-dimethyl-1H-indol-1-yl)methyl)-[1,1'-biphenyl]-2-carboxylic acid The title compound was prepared following the same general protocol as described in Step 8-9, Example 1, using the (R)-1-(2,5-bis(trifluoromethyl)phenyl)ethanamine and the 1-((2'-(tert-butoxycarbonyl)-[1,1'-biphenyl]-4-yl)methyl)-2,3-dimethyl-1H-indole-5-carboxylic acid. ESI-MS (m/z): 639 [M+H]⁺.

Example 174

(S)-4'-((5-(((1-(3-chlorophenyl)ethyl)carbamoyl)-2,3-dimethyl-1H-indol-1-yl)methyl)-[1,1'-biphenyl]-2-carboxylic acid

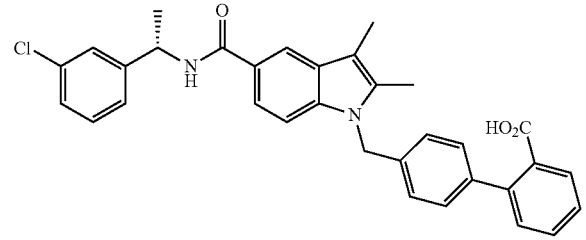 [SMILES: Cc1c(C)n(Cc2ccc(-c3ccccc3C(=O)O)cc2)c2ccc(C(=O)N[C@@H](C)c3cccc(Cl)c3)cc12]

The title compound was prepared following the same general protocol as described in Step 8-9, Example 1, using the (S)-1-(3-chlorophenyl)ethanamine and the 1-((2'-(tert-butoxycarbonyl)-[1,1'-biphenyl]-4-yl)methyl)-2,3-dimethyl-1H-indole-5-carboxylic acid. ESI-MS (m/z): 537/538/539 [M+H]⁺.

Example 175

(S)-4'-((5-(((1-(2-methoxyphenyl)ethyl)carbamoyl)-2,3-dimethyl-1H-indol-1-yl)methyl)-[1,1'-biphenyl]-2-carboxylic acid

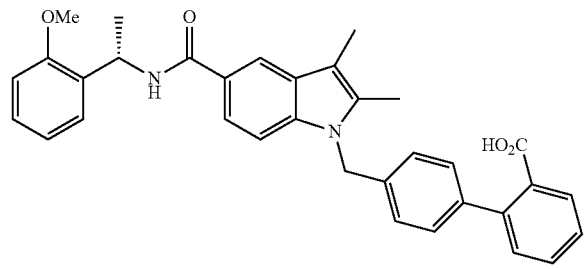

The title compound was prepared following the same general protocol as described in Step 8-9, Example 1, using the (S)-1-(2-methoxyphenyl)ethanamine and the 1-((2'-(tert-butoxycarbonyl)-[1,1'-biphenyl]-4-yl)methyl)-2,3-dimethyl-1H-indole-5-carboxylic acid. ESI-MS (m/z): 533 [M+H]⁺.

Example 176

(S)-4'-((2,3-dimethyl-5-(((1-(3-(trifluoromethyl)phenyl)ethyl)carbamoyl)-1H-indol-1-yl)methyl)-[1,1'-biphenyl]-2-carboxylic acid

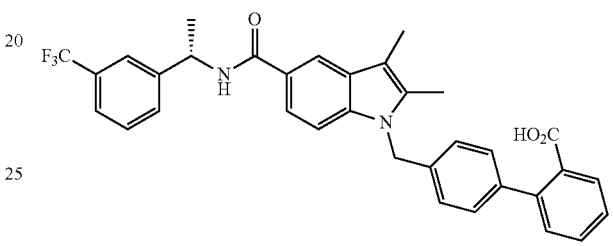

Step 1:
(S)-1-(3-(trifluoromethyl)phenyl)ethanaminium chloride

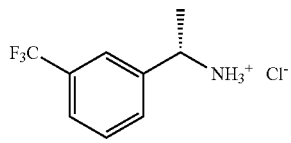

The title compound was prepared following the same general synthetic procedure as described in Steps 1-2, Example 2, using 3-(trifluoromethyl)benzaldehyde instead of 4-(tert-butyl)benzaldehyde.

Step 2: (S)-4'-((2,3-dimethyl-5-((1-(3-(trifluoromethyl)phenyl)ethyl)carbamoyl)-1H-indol-1-yl)methyl)-[1,1'-biphenyl]-2-carboxylic acid The title compound was prepared following the same general protocol as described in Step 8-9, Example 1, using the (S)-1-(3-(trifluoromethyl)phenyl)ethanamine and the 1-((2'-

(tert-butoxycarbonyl)-[1,1'-biphenyl]-4-yl)methyl)-2,3-dimethyl-1H-indole-5-carboxylic acid. ESI-MS (m/z): 571 [M+H]$^+$.

Example 177

(S)-4'-((5-(((1-(3-fluoro-2-methoxyphenyl)ethyl)carbamoyl)-2,3-dimethyl-1H-indol-1-yl)methyl)-[1,1'-biphenyl]-2-carboxylic acid

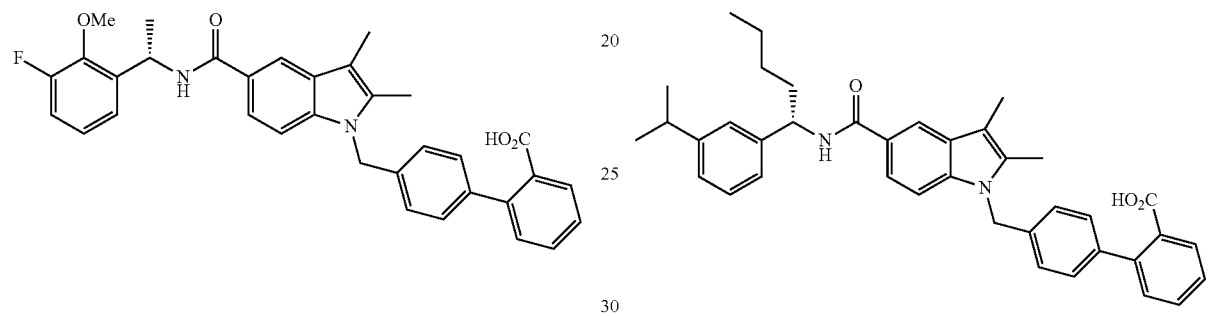

Step 1: (S)-1-(3-fluoro-2-methoxyphenyl)ethanamine

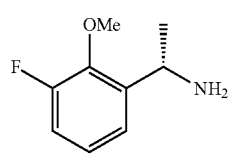

The title compound was prepared following the same general protocol as described in Step 1-2, Example 2, using the 3-fluoro-2-methoxybenzaldehyde.

Step 2: (S)-4'-((5-(((1-(3-fluoro-2-methoxyphenyl)ethyl)carbamoyl)-2,3-dimethyl-1H-indol-1-yl)methyl)-[1,1'-biphenyl]-2-carboxylic acid The title compound was prepared following the same general protocol as described in Step 1-2, Example 2, using the (S)-1-(3-fluoro-2-methoxyphenyl)ethanamine and the 1-((2'-(tert-butoxycarbonyl)-[1,1'-biphenyl]-4-yl)methyl)-2,3-dimethyl-1H-indole-5-carboxylic acid. ESI-MS (m/z): 551 [M+H]$^+$.

Example 178

(S)-4'-((5-(((1-(3-isopropylphenyl)pentyl)carbamoyl)-2,3-dimethyl-1H-indol-1-yl)methyl)-[1,1'-biphenyl]-2-carboxylic acid

Step 1: (S)-1-(3-isopropylphenyl)pentan-1-aminium chloride

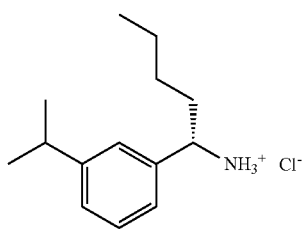

The title compound was prepared following the same general synthetic procedure as described in Steps 1-2, Example 2, using 3-isopropylbenzaldehyde and n-butyl-magnesium bromide instead of 4-(tert-butyl)benzaldehyde and methylmagnesium bromide.

Step 2: (S)-4'-((5-(((1-(3-isopropylphenyl)pentyl)carbamoyl)-2,3-dimethyl-1H-indol-1-yl)methyl)-[1,1'-biphenyl]-2-carboxylic acid The title compound was prepared following the same general protocol as described in Step 8-9, Example 1, using the (S)-1-(3-isopropylphenyl)pentan-1-amine and the 1-((2'-

(tert-butoxycarbonyl)-[1,1'-biphenyl]-4-yl)methyl)-2,3-dimethyl-1H-indole-5-carboxylic acid. ESI-MS (m/z): 587 [M+H]⁺.

Example 179

(S)-4'-((2,3-dimethyl-5-((1-(p-tolyl)ethyl)carbamoyl)-1H-indol-1-yl)methyl)-[1,1'-biphenyl]-2-carboxylic acid

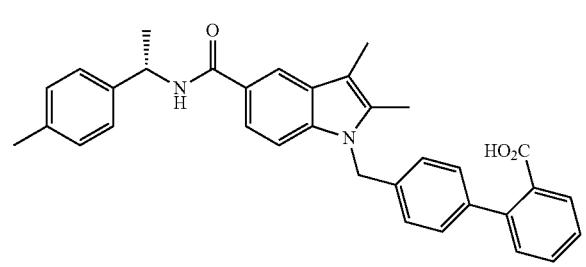 [SMILES: Cc1ccc([C@H](C)NC(=O)c2ccc3c(c2)c(C)c(C)n3Cc2ccc(-c3ccccc3C(=O)O)cc2)cc1]

The title compound was prepared following the same general protocol as described in Step 8-9, Example 1, using the (S)-1-(p-tolyl)ethanamine and the 1-((2'-(tert-butoxycarbonyl)-[1,1'-biphenyl]-4-yl)methyl)-2,3-dimethyl-1H-indole-5-carboxylic acid. ESI-MS (m/z): 517 [M+H]⁺.

Example 180

4'-((5-((2-(4-bromophenyl)propan-2-yl)carbamoyl)-2,3-dimethyl-1H-indol-1-yl)methyl)-[1,1'-biphenyl]-2-carboxylic acid

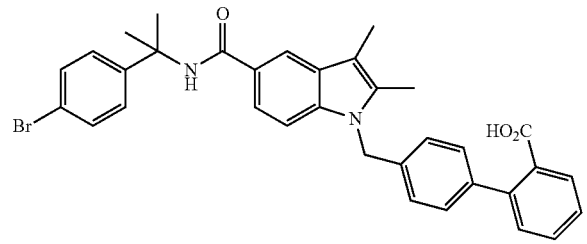 [SMILES: Cc1c(C)n(Cc2ccc(-c3ccccc3C(=O)O)cc2)c2ccc(C(=O)NC(C)(C)c3ccc(Br)cc3)cc12]

The title compound was prepared following the same general protocol as described in Step 8-9, Example 1, using the 2-(4-bromophenyl)propan-2-amine and the 1-((2'-(tert-butoxycarbonyl)-[1,1'-biphenyl]-4-yl)methyl)-2,3-dimethyl-1H-indole-5-carboxylic acid. ESI-MS (m/z): 595/597 [M+H]⁺.

Example 181

(R)-4'-((2,3-dimethyl-5-((1-(quinolin-4-yl)ethyl)carbamoyl)-1H-indol-1-yl)methyl)-[1,1'-biphenyl]-2-carboxylic acid

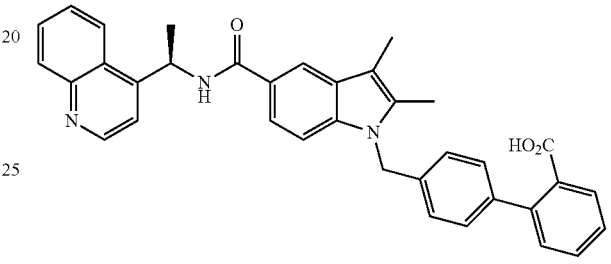

Step 1: (R)-1-(quinolin-4-yl)ethanamine

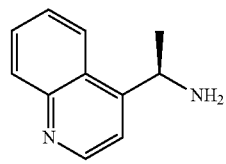

The title compound was prepared following the same general protocol as described in Step 1-2, Example 2, using the quinoline-4-carbaldehyde.

Step 2: (R)-4'-((2,3-dimethyl-5-((1-(quinolin-4-yl)ethyl)carbamoyl)-1H-indol-1-yl)methyl)-[1,1'-biphenyl]-2-carboxylic acid The title compound was prepared following the same general protocol as described in Step 8-9, Example 1, using the (R)-1-(quinolin-4-yl)ethanamine and the 1-((2'-(tert-butoxycarbonyl)-[1,1'-biphenyl]-4-yl)methyl)-2,3-dimethyl-1H-indole-5-carboxylic acid. ESI-MS (m/z): 554 [M+H]⁺.

Example 182

4'-((5-(((3-isopropylbenzyl)carbamoyl)-2,3-dimethyl-1H-indol-1-yl)methyl)-[1,1'-biphenyl]-2-carboxylic acid

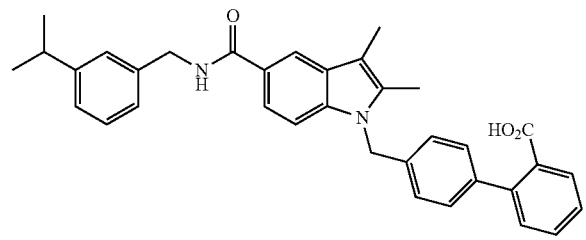 [SMILES: Cc1c(C)n(Cc2ccc(-c3ccccc3C(=O)O)cc2)c2ccc(C(=O)NCc3cccc(C(C)C)c3)cc12]

The title compound was prepared following the same general protocol as described in Step 8-9, Example 1, using the (3-isopropylphenyl)methanamine and the 1-((2'-(tert-butoxycarbonyl)-[1,1'-biphenyl]-4-yl)methyl)-2,3-dimethyl-1H-indole-5-carboxylic acid. ESI-MS (m/z): 531 [M+H]⁺.

Example 183

(S)-4'-((5-(((1-(3-isopropylphenyl)-2-phenylethyl)carbamoyl)-2,3-dimethyl-1H-indol-1-yl)methyl)-[1,1'-biphenyl]-2-carboxylic acid

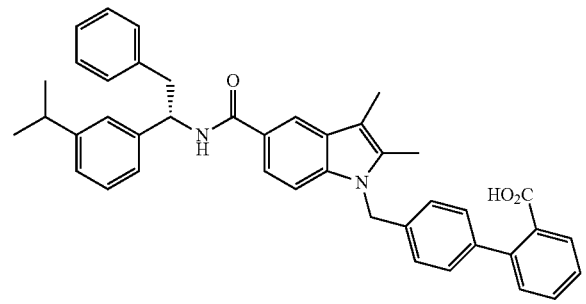 [SMILES: Cc1c(C)n(Cc2ccc(-c3ccccc3C(=O)O)cc2)c2ccc(C(=O)N[C@@H](Cc3ccccc3)c3cccc(C(C)C)c3)cc12]

Step 1:
(S)-1-(3-isopropylphenyl)-2-phenylethanaminium chloride

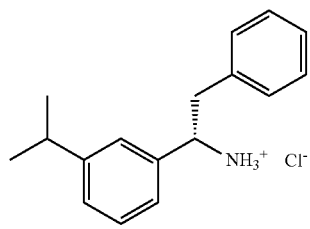 [SMILES: CC(C)c1cccc([C@@H]([NH3+])Cc2ccccc2)c1 ; [Cl-]]

The title compound was prepared following the same general synthetic procedure as described in Steps 1-2, Example 2, using 3-isopropylbenzaldehyde and benzylmagnesium bromide instead of 4-(tert-butyl)benzaldehyde and methylmagnesium bromide.

Step 2: (S)-4'-((5-(((1-(3-isopropylphenyl)-2-phenylethyl)carbamoyl)-2,3-dimethyl-1H-indol-1-yl)methyl)-[1,1'-biphenyl]-2-carboxylic acid The title compound was prepared following the same general protocol as described in Step 8-9, Example 1, using the (S)-1-(3-isopropylphenyl)-2-phenylethanamine and the 1-((2'-(tert-butoxycarbonyl)-[1,1'-biphenyl]-4-yl)methyl)-2,3-dimethyl-1H-indole-5-carboxylic acid. ESI-MS (m/z): 587 [M+H]⁺.

Example 184

(S)—N-(1-(4-(tert-butyl)phenyl)ethyl)-1-((2'-cyano-[1,1'-biphenyl]-4-yl)methyl)-2,3-dimethyl-1H-indole-5-carboxamide

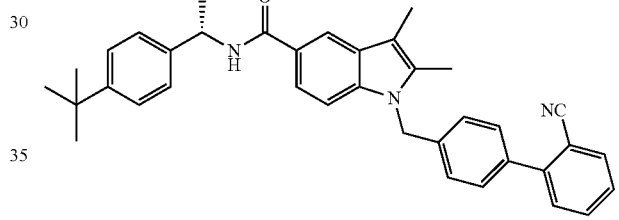

The title compound was prepared following the same general protocol as described in Step 5, Example 34, using the (S)-1-(4-(tert-butyl)phenyl)ethanamine instead of the 1-phenylpropan-1-amine. ESI-MS (m/z): 540 [M+H]⁺.

Example 185

(S)—N-(1-(3-(tert-butyl)phenyl)ethyl)-1-((2'-cyano-[1,1'-biphenyl]-4-yl)methyl)-2,3-dimethyl-1H-indole-5-carboxamide

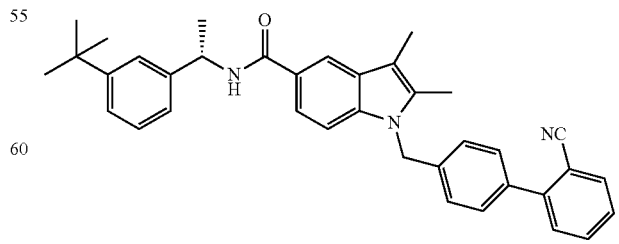

The title compound was prepared following the same general protocol as described in Step 5, Example 34, using the (S)-1-(3-(tert-butyl)phenyl)ethanamine instead of the 1-phenylpropan-1-amine. ESI-MS (m/z): 540 [M+H]+.

Example 186

(S)-1-((2'-cyano-[1,1'-biphenyl]-4-yl)methyl)-N-(1-(4-isopropylphenyl)ethyl)-2,3-dimethyl-1H-indole-5-carboxamide

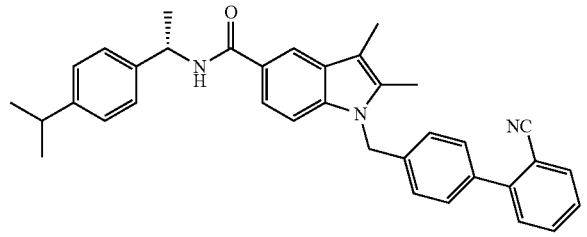 [SMILES: Cc1c(C)n(Cc2ccc(-c3ccccc3C#N)cc2)c2ccc(C(=O)N[C@@H](C)c3ccc(C(C)C)cc3)cc12]

The title compound was prepared following the same general protocol as described in Step 1-2-3, Example 137, using the (S)—N-(1-(4-bromophenyl)ethyl)-1-((2'-cyano-[1,1'-biphenyl]-4-yl)methyl)-2,3-dimethyl-1H-indole-5-carboxamide.
ESI-MS (m/z): 526 [M+H]+.

Example 187

(R)-1-((2'-(1H-tetrazol-5-yl)-[1,1'-biphenyl]-4-yl)methyl)-N-(1-(3-bromophenyl)ethyl)-2,3-dimethyl-1H-indole-5-carboxamide

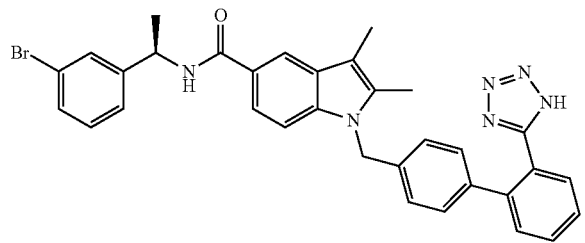 [SMILES: Cc1c(C)n(Cc2ccc(-c3ccccc3-c3nnn[nH]3)cc2)c2ccc(C(=O)N[C@H](C)c3cccc(Br)c3)cc12]

Step 1: (R)—N-(1-(3-bromophenyl)ethyl)-1-((2'-cyano-[1,1'-biphenyl]-4-yl)methyl)-2,3-dimethyl-1H-indole-5-carboxamide

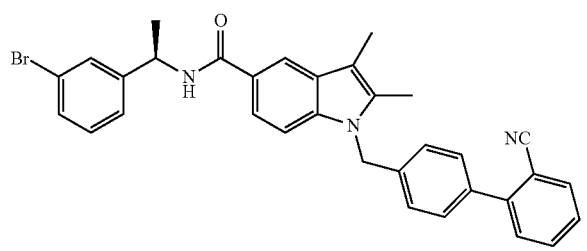

The title compound was prepared following the same general protocol as described in Step 5, Example 34, using the (R)-1-(3-bromophenyl)ethanamine instead of the 1-phenylpropan-1-amine.

Step 2: (R)-1-((2'-(1H-tetrazol-5-yl)-[1,1'-biphenyl]-4-yl)methyl)-N-(1-(3-bromophenyl)ethyl)-2,3-dimethyl-1H-indole-5-carboxamide The title compound was prepared following the same general protocol as described in Example 36, using the (R)—N-(1-(3-bromophenyl)ethyl)-1-((2'-cyano-[1,1'-biphenyl]-4-yl)methyl)-2,3-dimethyl-1H-indole-5-carboxamide. ESI-MS (m/z): 605/607 [M+H]+.

Example 188

(S)-1-((2'-(1H-tetrazol-5-yl)-[1,1'-biphenyl]-4-yl)methyl)-N-(1-(3-cyclopropylphenyl)ethyl)-2,3-dimethyl-1H-indole-5-carboxamide

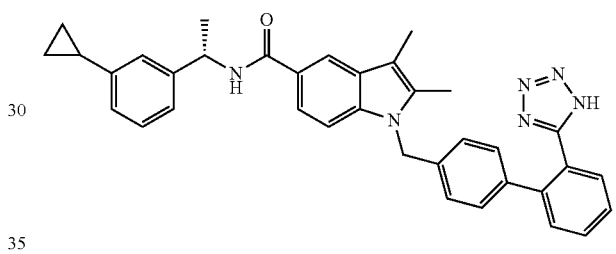

Step 1: (S)-1-((2'-cyano-[1,1'-biphenyl]-4-yl)methyl)-N-(1-(3-cyclopropylphenyl)ethyl)-2,3-dimethyl-1H-indole-5-carboxamide

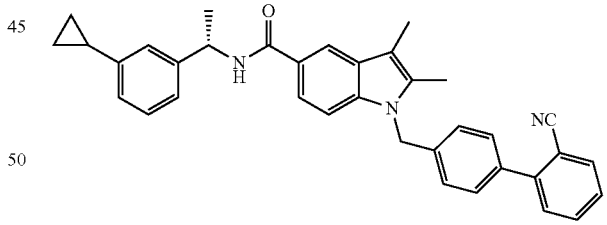

The title compound was prepared following the same general protocol as described in Step 5, Example 34, using the (S)-1-(3-cyclopropylphenyl)ethanamine instead of the 1-phenylpropan-1-amine. ESI-MS (m/z): 524 [M+H]+.

Step 2: (S)-1-((2'-(1H-tetrazol-5-yl)-[1,1'-biphenyl]-4-yl)methyl)-N-(1-(3-cyclopropylphenyl)ethyl)-2,3-dimethyl-1H-indole-5-carboxamide The title compound was prepared following the same general protocol as described in Example 36, using the (S)-1-((2'- cyano-[1,1'-biphenyl]-4-yl)methyl)-N-(1-(3-cyclopropylphenyl)ethyl)-2,3-dimethyl-1H-indole-5-carboxamide. ESI-MS (m/z): 567 [M+H]$^+$.

Example 189

(S)-2'-((5-((1-phenylpropyl)carbamoyl)-1H-indol-1-yl)methyl)-[1,1'-biphenyl]-4-carboxylic acid

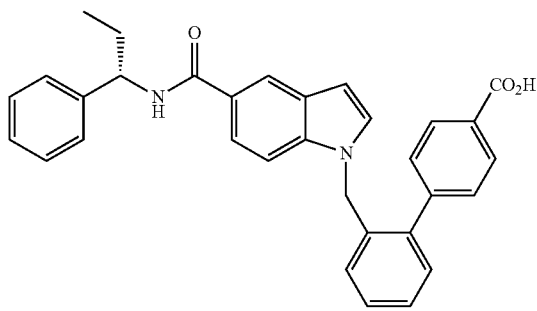 [SMILES: CC[C@H](NC(=O)c1ccc2c(ccn2Cc2ccccc2-c2ccc(C(=O)O)cc2)c1)c1ccccc1]

The title compound was prepared following the same protocol as described in Step 3-4, Example 120 using the (S)-1-phenylpropylamine instead of the (S)-1-(4-bromophenyl)ethanamine. ESI-MS (m/z): 489 [M+H]$^+$.

Example 190

(R)-2'-((5-((1-phenylpropyl)carbamoyl)-1H-indol-1-yl)methyl)-[1,1'-biphenyl]-4-carboxylic acid

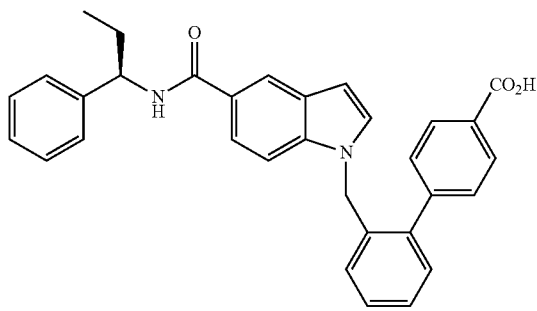 [SMILES: CC[C@@H](NC(=O)c1ccc2c(ccn2Cc2ccccc2-c2ccc(C(=O)O)cc2)c1)c1ccccc1]

The title compound was prepared following the same protocol as described in Step 3-4, Example 120 using the (R)-1-phenylpropylamine instead of the (S)-1-(4-bromophenyl)ethanamine. ESI-MS (m/z): 489 [M+H]$^+$.

Example 191

(S)-2'-((5-((1-phenylpropyl)carbamoyl)-1H-indol-1-yl)methyl)-[1,1'-biphenyl]-3-carboxylic acid

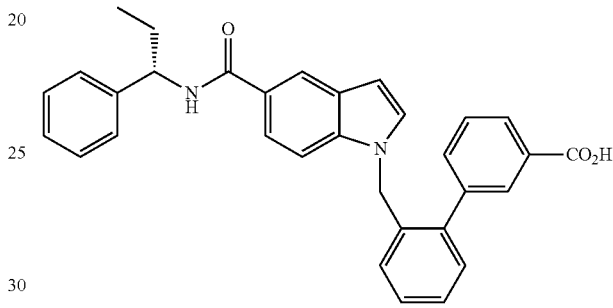

The title compound was prepared following the same protocol as described in Step 3-4, Example 122 using the (S)-1-phenylpropylamine instead of the (S)-1-(4-bromophenyl)ethanamine. ESI-MS (m/z): 489 [M+H]$^+$.

Example 192

(R)-2'-((5-((1-phenylpropyl)carbamoyl)-1H-indol-1-yl)methyl)-[1,1'-biphenyl]-3-carboxylic acid

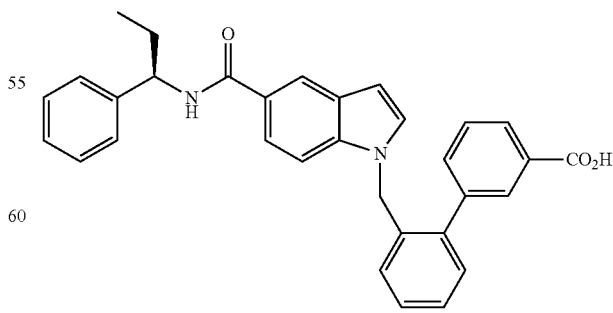

The title compound was prepared following the same protocol as described in Step 2-3, Example 122 using the (R)-1- phenylpropylamine instead of the (S)-1-(4-bromophenyl)ethanamine. ESI-MS (m/z): 489 [M+H]+.

Example 193

(R)-2'-((2,3-dimethyl-5-((1-phenylpropyl)carbamoyl)-1H-indol-1-yl)methyl)-[1,1'-biphenyl]-3-carboxylic acid

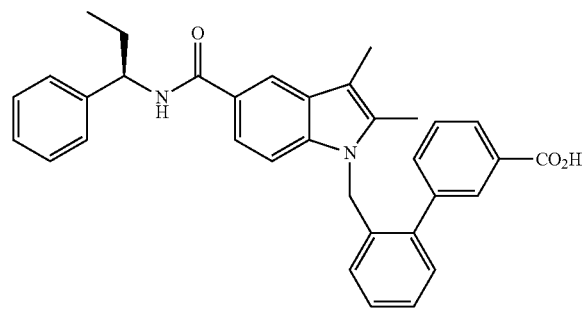 [SMILES: CC[C@@H](NC(=O)c1ccc2c(c1)c(C)c(C)n2Cc1ccccc1-c1cccc(C(=O)O)c1)c1ccccc1]

The title compound was prepared following the same protocol as described in Step 4-5, Example 124 using the (R)-1-phenylpropylamine instead of the (S)-1-(4-bromophenyl)ethanamine. ESI-MS (m/z): 489 [M+H]+.

Example 194

(S)-2'-((2,3-dimethyl-5-((1-phenylpropyl)carbamoyl)-1H-indol-1-yl)methyl)-[1,1'-biphenyl]-3-carboxylic acid

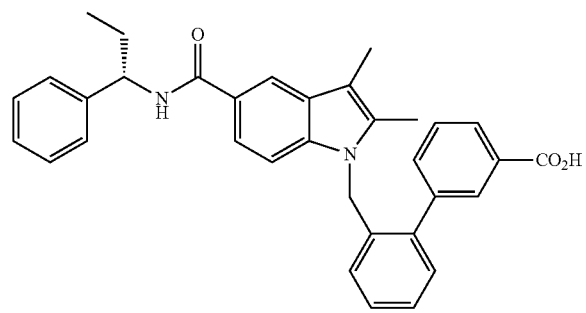

The title compound was prepared following the same protocol as described in Step 4-5, Example 124 using the (S)-1- phenylpropylamine instead of the (S)-1-(4-bromophenyl)ethanamine. ESI-MS (m/z): 489 [M+H]+.

Example 195

(R)-2'-((2,3-dimethyl-5-((1-phenylpropyl)carbamoyl)-1H-indol-1-yl)methyl)-[1,1'-biphenyl]-4-carboxylic acid

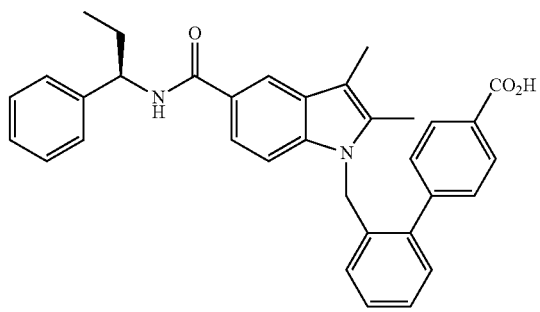 [SMILES: CC[C@@H](NC(=O)c1ccc2c(c1)c(C)c(C)n2Cc1ccccc1-c1ccc(C(=O)O)cc1)c1ccccc1]

The title compound was prepared following the same protocol as described in Step 2-3, Example 127 using the (R)-1-phenylpropylamine instead of the (S)-1-(4-bromophenyl)ethanamine. ESI-MS (m/z): 489 [M+H]+.

Example 196

(S)-2'-((2,3-dimethyl-5-((1-phenylpropyl)carbamoyl)-1H-indol-1-yl)methyl)-[1,1'-biphenyl]-4-carboxylic acid

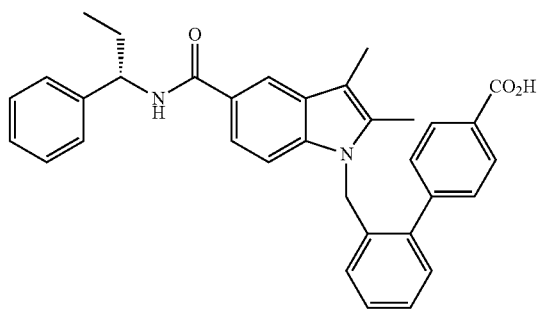 [SMILES: CC[C@H](NC(=O)c1ccc2c(c1)c(C)c(C)n2Cc1ccccc1-c1ccc(C(=O)O)cc1)c1ccccc1]

The title compound was prepared following the same protocol as described in Step 2-3, Example 127 using the (S)-1- phenylpropylamine instead of the (S)-1-(4-bromophenyl)ethanamine. ESI-MS (m/z): 489 [M+H]⁺.

Example 197

(S)-4'-((5-((1-(3-chloro-4-methoxyphenyl)ethyl)carbamoyl)-2,3-dimethyl-1H-indol-1-yl)methyl)-[1,1'-biphenyl]-2-carboxylic acid

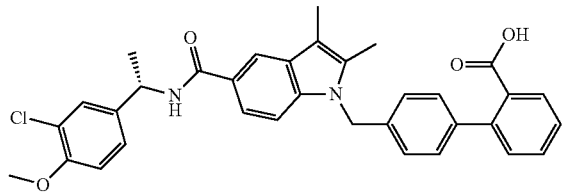 [SMILES: COc1ccc([C@H](C)NC(=O)c2ccc3c(c2)c(C)c(C)n3Cc2ccc(-c3ccccc3C(=O)O)cc2)cc1Cl]

Step 1: (S)-1-(3-chloro-4-methoxyphenyl)ethanaminium chloride

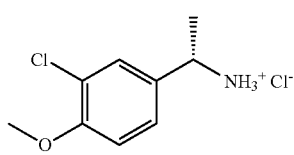

The title compound was prepared following the same general synthetic procedure as described in Steps 1-2, Example 2, using 3-chloro-4-methoxybenzaldehyde instead of 4-(tert-butyl)benzaldehyde.

Step 2: (S)-4'-((5-((1-(3-chloro-4-methoxyphenyl)ethyl)carbamoyl)-2,3-dimethyl-1H-indol-1-yl)methyl)-[1,1'-biphenyl]-2-carboxylic acid

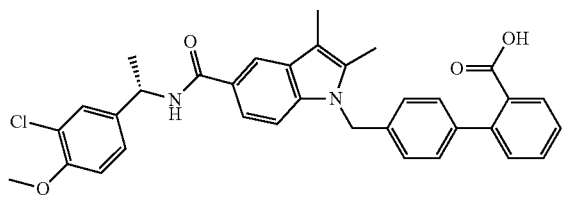 [SMILES: COc1ccc([C@H](C)NC(=O)c2ccc3c(c2)c(C)c(C)n3Cc2ccc(-c3ccccc3C(=O)O)cc2)cc1Cl]

The title compound was prepared following the same general synthetic procedure as described in Steps 3-4, Example 2, starting with (S)-1-(3-chloro-4-methoxyphenyl)ethanaminium chloride and 1-((2'-(tert-butoxycarbonyl)-[1,1'-biphenyl]-4-yl)methyl)-2,3-dimethyl-1H-indole-5-carboxylic acid instead of (S)-1-(4-(tert-butyl)phenyl)ethanaminium chloride and 1-((2'-(tert-butoxycarbonyl)-[1,1'-biphenyl]-4-yl)methyl)-2,3-dimethyl-1H-indole-5-carboxylic acid. ESI-MS (m/z): 567 [M+1]⁺.

Example 198

(S)-4'-((5-((1-(3-isopropylphenyl)propyl)carbamoyl)-2,3-dimethyl-1H-indol-1-yl)methyl)-[1,1'-biphenyl]-2-carboxylic acid

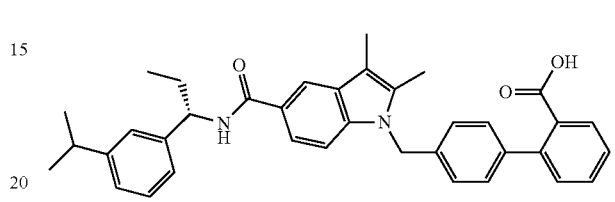

Step 1: (S)-1-(3-isopropylphenyl)propan-1-aminium chloride

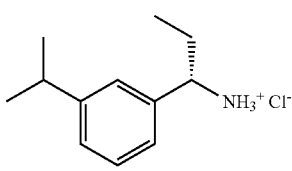

The title compound was prepared following the same general synthetic procedure as described in Steps 1-2, Example 2, using 3-isopropylbenzaldehyde and ethylmagnesium bromide instead of 4-(tert-butyl)benzaldehyde and methylmagnesium bromide.

Step 2: (S)-4'-((5-((1-(3-isopropylphenyl)propyl)carbamoyl)-2,3-dimethyl-1H-indol-1-yl)methyl)-[1,1'-biphenyl]-2-carboxylic acid

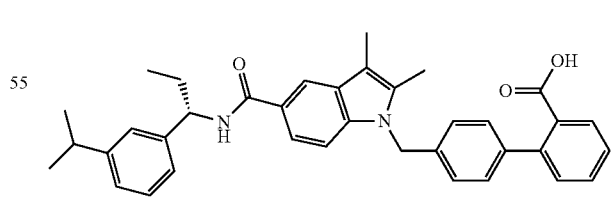

The title compound was prepared following the same general synthetic procedure as described in Steps 3-4, Example 2, starting with (S)-1-(3-isopropylphenyl)propan-1-aminium chloride and 1-((2'-(tert-butoxycarbonyl)-[1,1'-biphenyl]-4-yl)methyl)-2,3-dimethyl-1H-indole-5-carboxylic acid instead of (S)-1-(4-(tert-butyl)phenyl)ethanaminium chloride and 1-((2'-(tert-butoxycarbonyl)-[1,1'-biphenyl]-4-yl)methyl)-2,3-dimethyl-1H-indole-5-carboxylic acid. ESI-MS (m/z): 558 [M+1]$^+$.

Example 199

(S)-4'-((5-((1-(3-isopropoxyphenyl)ethyl)carbamoyl)-2,3-dimethyl-1H-indol-1-yl)methyl)-[1,1'-biphenyl]-2-carboxylic acid

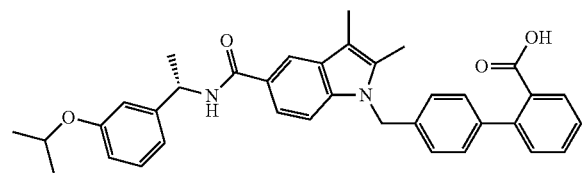 [SMILES: Cc1c(C)n(Cc2ccc(-c3ccccc3C(=O)O)cc2)c2ccc(C(=O)N[C@@H](C)c3cccc(OC(C)C)c3)cc12]

Step 1: (S)-1-(3-isopropoxyphenyl)ethanaminium chloride

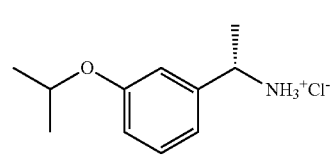

The title compound was prepared following the same general synthetic procedure as described in Steps 1-2, Example 2, using 3-isopropoxybenzaldehyde instead of 4-(tert-butyl)benzaldehyde.

Step 2: (S)-4'-((5-((1-(3-isopropoxyphenyl)ethyl)carbamoyl)-2,3-dimethyl-1H-indol-1-yl)methyl)-[1,1'-biphenyl]-2-carboxylic acid

The title compound was prepared following the same general synthetic procedure as described in Steps 3-4, Example 2, starting with (S)-1-(3-isopropoxyphenyl)ethanaminium chloride and 1-((2'-(tert-butoxycarbonyl)-[1,1'-biphenyl]-4-yl)methyl)-2,3-dimethyl-1H-indole-5-carboxylic acid instead of (S)-1-(4-(tert-butyl)phenyl)ethanaminium chloride and 1-((2'-(tert-butoxycarbonyl)-[1,1'-biphenyl]-4-yl)methyl)-2,3-dimethyl-1H-indole-5-carboxylic acid. ESI-MS (m/z): 560 [M+1]$^+$.

Example 200

(S)-4'-((5-((1-(4-(tert-butoxy)phenyl)ethyl)carbamoyl)-2,3-dimethyl-1H-indol-1-yl)methyl)-[1,1'-biphenyl]-2-carboxylic acid

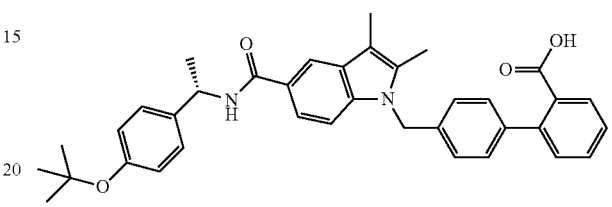

Step 1: (S)-1-(4-(tert-butoxy)phenyl)ethanaminium chloride

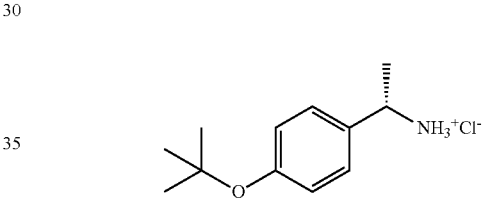

The title compound was prepared following the same general synthetic procedure as described in Steps 1-2, Example 2, using 4-(tert-butoxy)benzaldehyde instead of 4-(tert-butyl)benzaldehyde.

Step 2: (S)-4'-((5-((1-(4-(tert-butoxy)phenyl)ethyl)carbamoyl)-2,3-dimethyl-1H-indol-1-yl)methyl)-[1,1'-biphenyl]-2-carboxylic acid

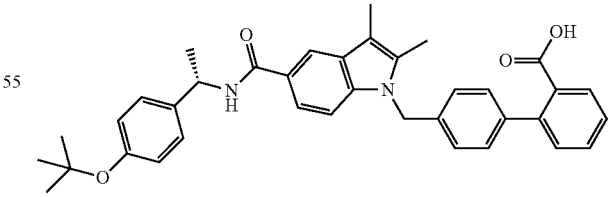

The title compound was prepared following the same general synthetic procedure as described in Steps 3-4, Example 2, starting with (S)-1-(4-(tert-butoxy)phenyl)ethanaminium chloride and 1-((2'-(tert-butoxycarbonyl)-[1,1'-biphenyl]-4-yl)methyl)-2,3-dimethyl-1H-indole-5-carboxylic acid instead of (S)-1-(4-(tert-butyl)phenyl)ethanaminium chloride and 1-((2'-(tert-butoxycarbonyl)-[1,1'-biphenyl]-4-yl)methyl)-2,3-dimethyl-1H-indole-5-carboxylic acid. ESI-MS (m/z): 574 [M+1]⁺.

Example 201

(S)-4'-((5-((1-(4-isopropoxyphenyl)ethyl)carbamoyl)-2,3-dimethyl-1H-indol-1-yl)methyl)-[1,1'-biphenyl]-2-carboxylic acid

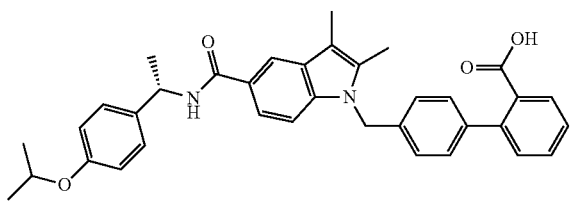 [SMILES: Cc1c(C)n(Cc2ccc(-c3ccccc3C(=O)O)cc2)c2ccc(C(=O)N[C@@H](C)c3ccc(OC(C)C)cc3)cc12]

Step 1: (S)-1-(4-isopropoxyphenyl)ethanaminium chloride

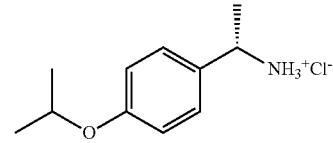

The title compound was prepared following the same general synthetic procedure as described in Steps 1-2, Example 2, using 4-isopropoxybenzaldehyde instead of 4-(tert-butyl)benzaldehyde.

Step 2: (S)-4'-((5-((1-(4-isopropoxyphenyl)ethyl)carbamoyl)-2,3-dimethyl-1H-indol-1-yl)methyl)-[1,1'-biphenyl]-2-carboxylic acid

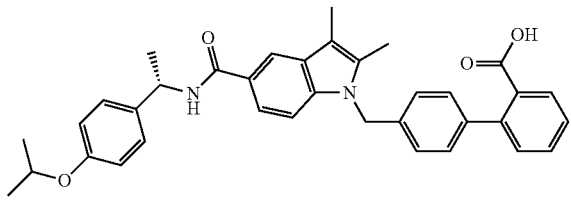 [SMILES: Cc1c(C)n(Cc2ccc(-c3ccccc3C(=O)O)cc2)c2ccc(C(=O)N[C@@H](C)c3ccc(OC(C)C)cc3)cc12]

The title compound was prepared following the same general synthetic procedure as described in Steps 3-4, Example 2, starting with (S)-1-(4-isopropoxyphenyl)ethanaminium chloride and 1-((2'-(tert-butoxycarbonyl)-[1,1'-biphenyl]-4-yl)methyl)-2,3-dimethyl-1H-indole-5-carboxylic acid instead of (S)-1-(4-(tert-butyl)phenyl)ethanaminium chloride and 1-((2'-(tert-butoxycarbonyl)-[1,1'-biphenyl]-4-yl)methyl)-2,3-dimethyl-1H-indole-5-carboxylic acid. ESI-MS (m/z): 560 [M+1]⁺.

Example 202

(S)-4'-((5-((1-(1-((benzyloxy)carbonyl)piperidin-4-yl)ethyl)carbamoyl)-2,3-dimethyl-1H-indol-1-yl)methyl)-[1,1'-biphenyl]-2-carboxylic acid

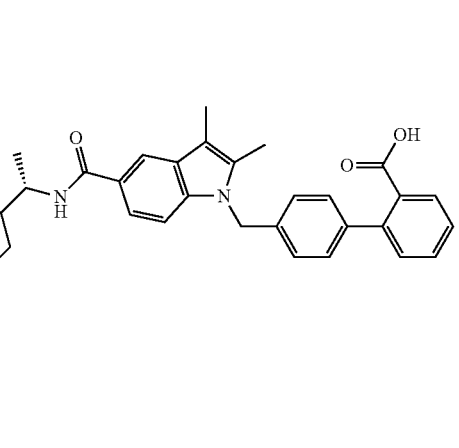

Step 1: (S)-1-(1-((benzyloxy)carbonyl)piperidin-4-yl)ethanaminium chloride

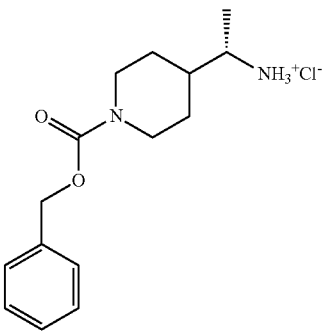

The title compound was prepared following the same general synthetic procedure as described in Steps 1-2, Example 2, using benzyl 4-formylpiperidine-1-carboxylate instead of 4-(tert-butyl)benzaldehyde. ESI-MS (m/z): 263 [M+1]+.

Step 2: (S)-4'-((5-((1-(1-((benzyloxy)carbonyl)piperidin-4-yl)ethyl)carbamoyl)-2,3-dimethyl-1H-indol-1-yl)methyl)-[1,1'-biphenyl]-2-carboxylic acid

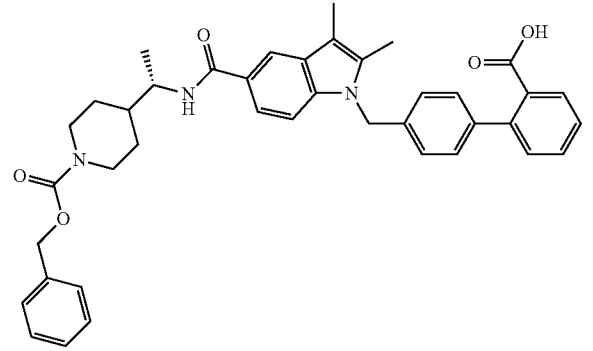

The title compound was prepared following the same general synthetic procedure as described in Steps 3-4, Example 2, starting with ((S)-1-(1-((benzyloxy)carbonyl)piperidin-4-yl)ethanaminium chloride and 1-((2'-(tert-butoxycarbonyl)-[1,1'-biphenyl]-4-yl)methyl)-2,3-dimethyl-1H-indole-5-carboxylic acid instead of (S)-1-(4-(tert-butyl)phenyl)ethanaminium chloride and 1-((2'-(tert-butoxycarbonyl)-[1,1'-biphenyl]-4-yl)methyl)-2,3-dimethyl-H-indole-5-carboxylic acid. ESI-MS (m/z): 643 [M+1]+.

Example 203

(S)-4'-((5-((1-(1-(benzylcarbamoyl)piperidin-4-yl)ethyl)carbamoyl)-2,3-dimethyl-1H-indol-1-yl)methyl)-[1,1'-biphenyl]-2-carboxylic acid 2753

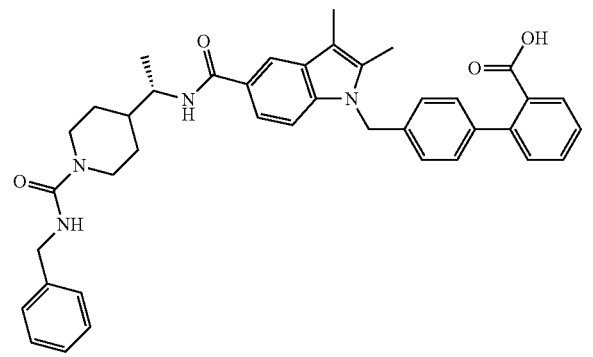

The title compound was prepared from (S)-4'-((5-((1-(1-((benzyloxy)carbonyl)piperidin-4-yl)ethyl)carbamoyl)-2,3-dimethyl-1H-indol-1-yl)methyl)-[1,1'-biphenyl]-2-carboxylic-acid (0.175 g, 0.250 mmol) following palladium catalyzed hydrogenation (18 mg, 10% Pd/c) in AcOH (5 mL) and subsequent coupling of the resulting piperidine ((S)-tert-butyl-4'-((2,3-dimethyl-5-((1-(piperidin-4-yl)ethyl)carbamoyl)-1H-indol-1-yl)methyl)-[1,1'-biphenyl]-2-carboxylate) with benzyl isocyanate (6.8 mg, 0.049 mmol) in dicholoromethane (DCM) (1 mL)/di-isopropylethylamine (9.2 µL, 0.053 mmol) and then removal of t-butyl ester in TFA/DCM (1:1, 2 mL).

Completion at each synthetic step was monitored by analytical HPLC and the title compound was isolated by reverse phase prep-HPLC (MeOH/Acetonitrile/water) ESI-MS (m/z): 642 [M+1]+.

Example 204

(S)-4'-((5-((1-((benzyloxy)carbonyl)pyrrolidin-3-yl)carbamoyl)-2,3-dimethyl-1H-indol-1-yl)methyl)-[1,1'-biphenyl]-2-carboxylic acid

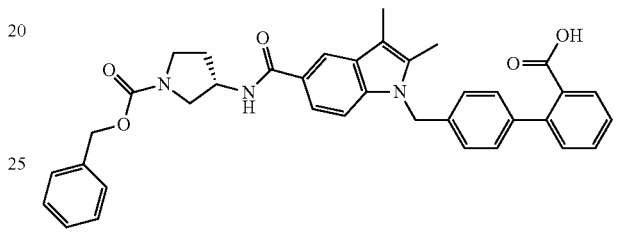

The title compound was prepared following the same general synthetic procedure as described in Steps 3-4, Example 2, starting with (S)-benzyl 3-aminopyrrolidine-1-carboxylate and 1-((2'-(tert-butoxycarbonyl)-[1,1'-biphenyl]-4-yl)methyl)-2,3-dimethyl-1H-indole-5-carboxylic acid instead of (S)-1-(4-(tert-butyl)phenyl)ethanaminium chloride and 1-((2'-(tert-butoxycarbonyl)-[1,1'-biphenyl]-4-yl)methyl)-2,3-dimethyl-1H-indole-5-carboxylic acid. ESI-MS (m/z): 601 [M+1]+.

Example 205

(R)-4'-((5-((1-(5-fluoro-2-methoxyphenyl)ethyl)carbamoyl)-2,3-dimethyl-1H-indol-1-yl)methyl)-[1,1'-biphenyl]-2-carboxylic acid

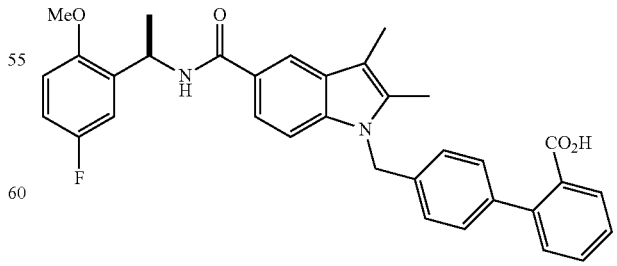

The title compound was prepared following the same general protocol as described in Steps 1-4, Example 1, using 5-fluoro-2-methoxybenzaldehyde and 1-((2'-(tert-butoxycarbonyl)biphenyl-4-yl)methyl)-2,3-dimethyl-1H-indole-5-carboxylic acid. LC-MS 551.2 (M+H).

Example 206

(S)-4'-((5-((1-(5-fluoro-2-methoxyphenyl)ethyl)carbamoyl)-2,3-dimethyl-1H-indol-1-yl)methyl)-[1,1'-biphenyl]-2-carboxylic acid

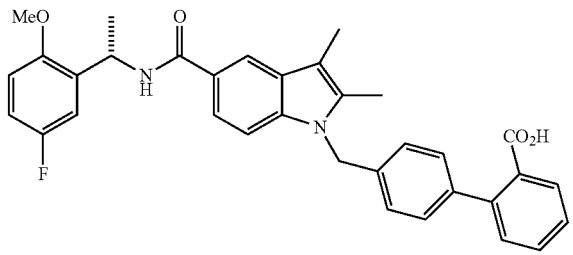 [SMILES: COc1ccc(F)cc1[C@H](C)NC(=O)c1ccc2c(c1)c(C)c(C)n2Cc1ccc(-c2ccccc2C(=O)O)cc1]

The title compound was prepared following the same general protocol as described in Steps 1-4, Example 1, using 5-fluoro-2-methoxybenzaldehyde and 1-((2'-(tert-butoxycarbonyl)biphenyl-4-yl)methyl)-2,3-dimethyl-1H-indole-5-carboxylic acid. LC-MS 551.2 (M+H).

Example 207

(R)-4'-((2,3-dimethyl-5-((1-(2-(trifluoromethyl)phenyl)ethyl)carbamoyl)-1H-indol-1-yl)methyl)-[1,1'-biphenyl]-2-carboxylic acid

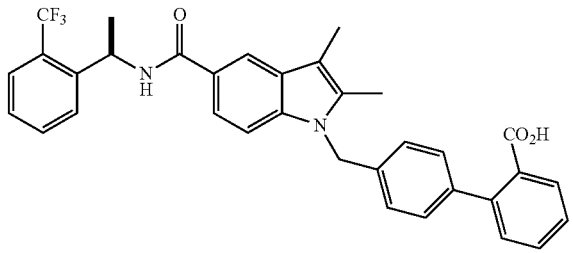 [SMILES: Cc1c(C)n(Cc2ccc(-c3ccccc3C(=O)O)cc2)c2ccc(C(=O)N[C@H](C)c3ccccc3C(F)(F)F)cc12]

The title compound was prepared following the same general protocol as described in Steps 1-4, Example 1, using 2-trifluoromethylbenzaldehyde and 1-((2'-(tert-butoxycarbonyl)biphenyl-4-yl)methyl)-2,3-dimethyl-1H-indole-5-carboxylic acid. LC-MS 571.2 (M+H).

Example 208

(S)-4'-((2,3-dimethyl-5-((1-(2-(trifluoromethyl)phenyl)ethyl)carbamoyl)-1H-indol-1-yl)methyl)-[1,1'-biphenyl]-2-carboxylic acid The title compound was prepared following the same general protocol as described in Steps 1-4, Example 1, using 2-trifluoromethylbenzaldehyde and 1-((2'-(tert-butoxycarbonyl)biphenyl-4-yl)methyl)-2,3-dimethyl-1H-indole-5-carboxylic acid. LC-MS 571.6 (M+H).

Example 209

(R)-4'-((5-((1-(2,4-bis(trifluoromethyl)phenyl)ethyl)carbamoyl)-2,3-dimethyl-1H-indol-1-yl)methyl)-[1,1'-biphenyl]-2-carboxylic acid

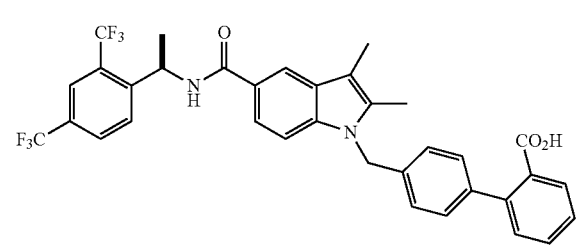 [SMILES: Cc1c(C)n(Cc2ccc(-c3ccccc3C(=O)O)cc2)c2ccc(C(=O)N[C@H](C)c3ccc(C(F)(F)F)cc3C(F)(F)F)cc12]

The title compound was prepared following the same general protocol as described in Steps 1-4, Example 1, using 2,4-bistrifluoromethylbenzaldehyde and 1-((2'-(tert-butoxycarbonyl)biphenyl-4-yl)methyl)-2,3-dimethyl-1H-indole-5-carboxylic acid. LC-MS 639.2 (M+H).

Example 210

(S)-4'-((5-((1-(2,4-bis(trifluoromethyl)phenyl)ethyl)carbamoyl)-2,3-dimethyl-1H-indol-1-yl)methyl)-[1,1'-biphenyl]-2-carboxylic acid

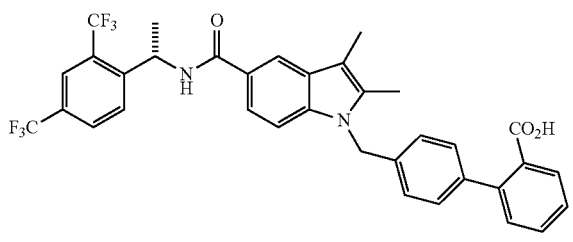 [SMILES: Cc1c(C)n(Cc2ccc(-c3ccccc3C(=O)O)cc2)c2ccc(C(=O)N[C@@H](C)c3ccc(C(F)(F)F)cc3C(F)(F)F)cc12]

The title compound was prepared following the same general protocol as described in Steps 1-4, Example 1, using 2,4-bistrifluoromethylbenzaldehyde and 1-((2'-(tert-butoxycarbonyl)biphenyl-4-yl)methyl)-2,3-dimethyl-1H-indole-5-carboxylic acid. LC-MS 639.2 (M+−H).

Example 211

(S)-4'-((5-((1-(2-fluoro-5-methylphenyl)ethyl)carbamoyl)-2,3-dimethyl-1H-indol-1-yl)methyl)-[1,1'-biphenyl]-2-carboxylic acid

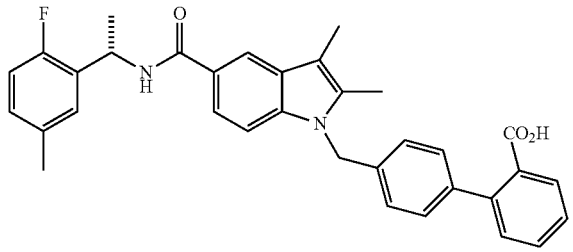 [SMILES: Cc1ccc(F)c([C@H](C)NC(=O)c2ccc3c(c2)c(C)c(C)n3Cc2ccc(-c3ccccc3C(=O)O)cc2)c1]

The title compound was prepared following the same general protocol as described in Steps 1-4, Example 1, using 2-fluoro-5-methylbenzaldehyde and 1-((2'-(tert-butoxycarbonyl)biphenyl-4-yl)methyl)-2,3-dimethyl-1H-indole-5-carboxylic acid. LC-MS 535.2 (M+H).

Example 212

(S)-4'-((5-((1-cyclohexylethyl)carbamoyl)-2,3-dimethyl-1H-indol-1-yl)methyl)-[1,1'-biphenyl]-2-carboxylic acid

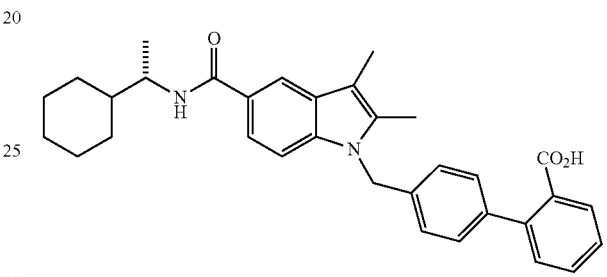

The title compound was prepared following the same general protocol as described in Steps 1-4, Example 1, using cyclohexanecarboxaldehyde and 1-((2'-(tert-butoxycarbonyl)biphenyl-4-yl)methyl)-2,3-dimethyl-1H-indole-5-carboxylic acid. LC-MS 509.2 (M+H).

Example 213

4'-((5-(((1R)-1-(2,3-dihydrobenzo[b][1,4]dioxin-2-yl)ethyl)carbamoyl)-2,3-dimethyl-1H-indol-1-yl)methyl)-[1,1'-biphenyl]-2-carboxylic acid

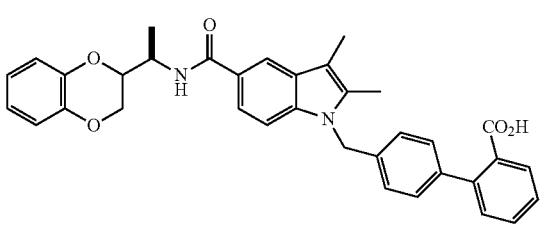 [SMILES: Cc1c(C)n(Cc2ccc(-c3ccccc3C(=O)O)cc2)c2ccc(C(=O)N[C@H](C)C3COc4ccccc4O3)cc12]

The title compound was prepared following the same general protocol as described in Steps 1-4, Example 1, using 2,3-dihydrobenzo[b][1,4]dioxine-2-carbaldehyde and 1-((2'-

(tert-butoxycarbonyl)biphenyl-4-yl)methyl)-2,3-dimethyl-1H-indole-5-carboxylic acid. LC-MS 561.2 (M+H).

Example 214

4'-((5-(((1S)-1-(2,3-dihydrobenzo[b][1,4]dioxin-2-yl)ethyl)carbamoyl)-2,3-dimethyl-1H-indol-1-yl)methyl)-[1,1'-biphenyl]-2-carboxylic acid

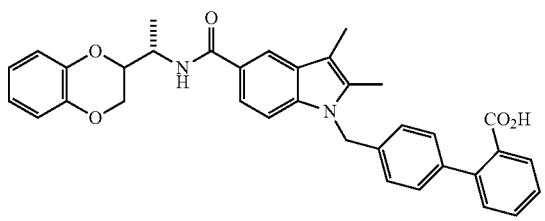 [SMILES: Cc1c(C)n(Cc2ccc(-c3ccccc3C(=O)O)cc2)c2ccc(C(=O)N[C@@H](C)C3COc4ccccc4O3)cc12]

The title compound was prepared following the same general protocol as described in Steps 1-4, Example 1, using 2,3-dihydrobenzo[b][1,4]dioxine-2-carbaldehyde and 1-((2'-(tert-butoxycarbonyl)biphenyl-4-yl)methyl)-2,3-dimethyl-1H-indole-5-carboxylic acid. LC-MS 561.2 (M+H).

Example 215

(R)-4'-((5-((1-(3,5-difluoropyridin-4-yl)ethyl)carbamoyl)-2,3-dimethyl-1H-indol-1-yl)methyl)-[1,1'-biphenyl]-2-carboxylic acid

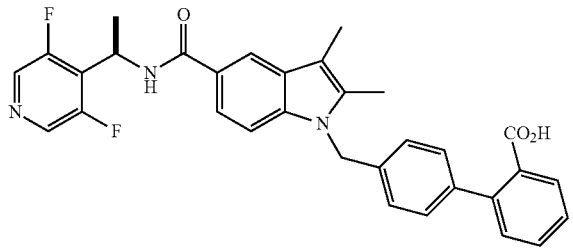 [SMILES: Cc1c(C)n(Cc2ccc(-c3ccccc3C(=O)O)cc2)c2ccc(C(=O)N[C@H](C)c3c(F)cncc3F)cc12]

The title compound was prepared following the same general protocol as described in Steps 1-4, Example 1, using 3,5-difluoroisonicotinaldehyde and 1-((2'-(tert-butoxycarbonyl)biphenyl-4-yl)methyl)-2,3-dimethyl-1H-indole-5-carboxylic acid. LC-MS 540.2 (M+H).

Example 216

(S)-4'-((5-((1-(3,5-difluoropyridin-4-yl)ethyl)carbamoyl)-2,3-dimethyl-1H-indol-1-yl)methyl)-[1,1'-biphenyl]-2-carboxylic acid

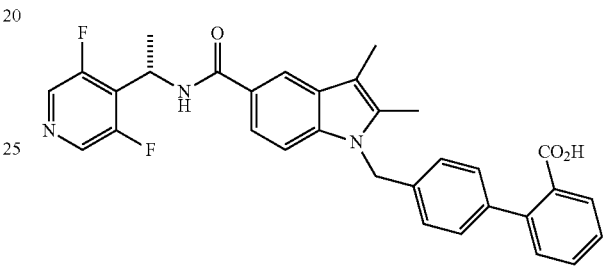

The title compound was prepared following the same general protocol as described in Steps 1-4, Example 1, using 3,5-difluoroisonicotinaldehyde and 1-((2'-(tert-butoxycarbonyl)biphenyl-4-yl)methyl)-2,3-dimethyl-1H-indole-5-carboxylic acid. LC-MS 540.2 (M+H).

Example 217

(S)-4'-((2,3-dimethyl-5-((1-(6-(trifluoromethyl)pyridin-3-yl)ethyl)carbamoyl)-1H-indol-1-yl)methyl)-[1,1'-biphenyl]-2-carboxylic acid

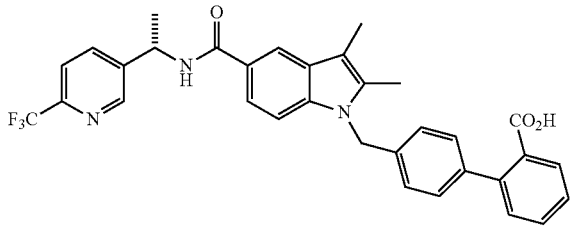 [SMILES: Cc1c(C)n(Cc2ccc(-c3ccccc3C(=O)O)cc2)c2ccc(C(=O)N[C@@H](C)c3ccc(C(F)(F)F)nc3)cc12]

The title compound was prepared following the same general protocol as described in Steps 1-4, Example 1, using 6-(trifluoromethyl)nicotinaldehyde and 1-((2'-(tert-butoxycarbonyl)biphenyl-4-yl)methyl)-2,3-dimethyl-1H-indole-5-carboxylic acid. LC-MS 572.2 (M+H).

Example 218

(S)-4'-((5-((1-(2,3-dihydrobenzofuran-5-yl)ethyl)carbamoyl)-2,3-dimethyl-1H-indol-1-yl)methyl)-[1,1'-biphenyl]-2-carboxylic acid

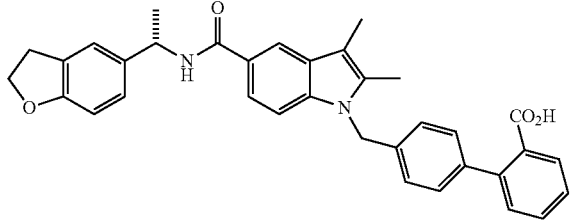 [SMILES: Cc1c(C)n(Cc2ccc(-c3ccccc3C(=O)O)cc2)c2ccc(C(=O)N[C@@H](C)c3ccc4c(c3)CCO4)cc12]

The title compound was prepared following the same general protocol as described in Steps 1-4, Example 1, using 2,3-dihydrobenzofuran-5-carbaldehyde and 1-((2'-(tert-butoxycarbonyl)biphenyl-4-yl)methyl)-2,3-dimethyl-1H-indole-5-carboxylic acid. LC-MS 545.2 (M+H).

Example 219

(S)-4'-((5-((1-(3,5-dichlorophenyl)ethyl)carbamoyl)-2,3-dimethyl-1H-indol-1-yl)methyl)-[1,1'-biphenyl]-2-carboxylic acid

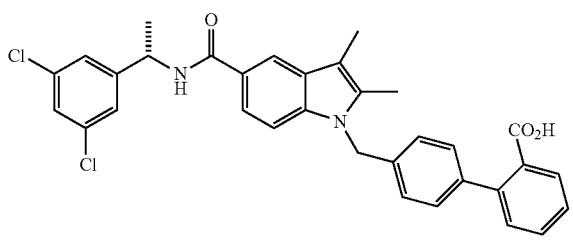 [SMILES: Cc1c(C)n(Cc2ccc(-c3ccccc3C(=O)O)cc2)c2ccc(C(=O)N[C@@H](C)c3cc(Cl)cc(Cl)c3)cc12]

The title compound was prepared following the same general protocol as described in Steps 1-4, Example 1, using 2,4-dichlorobenzaldehyde and 1-((2'-(tert-butoxycarbonyl)biphenyl-4-yl)methyl)-2,3-dimethyl-1H-indole-5-carboxylic acid.
LC-MS 571.1 (M+H).

Example 220

(S)-4'-((5-((1-(3,4-dichlorophenyl)ethyl)carbamoyl)-2,3-dimethyl-1H-indol-1-yl)methyl)-[1,1'-biphenyl]-2-carboxylic acid

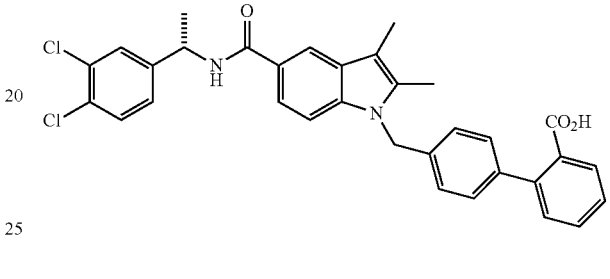

The title compound was prepared following the same general protocol as described in Steps 1-4, Example 1, using 3,4-dichlorobenzaldehyde and 1-((2'-(tert-butoxycarbonyl)biphenyl-4-yl)methyl)-2,3-dimethyl-1H-indole-5-carboxylic acid.
LC-MS 571.1 (M+).

Example 221

(S)-4'-((5-((1-(2-fluoro-5-(trifluoromethyl)phenyl)ethyl)carbamoyl)-2,3-dimethyl-1H-indol-1-yl)methyl)-[1,1'-biphenyl]-2-carboxylic acid

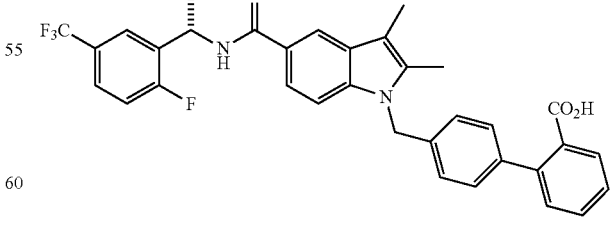

The title compound was prepared following the same general protocol as described in Steps 1-4, Example 1, using 2-fluoro-5-trifluoromethylbenzaldehyde and 1-((2'-(tert-butoxycarbonyl)biphenyl-4-yl)methyl)-2,3-dimethyl-1H-indole-5-carboxylic acid. LC-MS 589.1 (M+H).

Example 222

(S)-4'-((5-((1-(4-chloro-3-(trifluoromethyl)phenyl)ethyl)carbamoyl)-2,3-dimethyl-1H-indol-1-yl)methyl)-[1,1'-biphenyl]-2-carboxylic acid

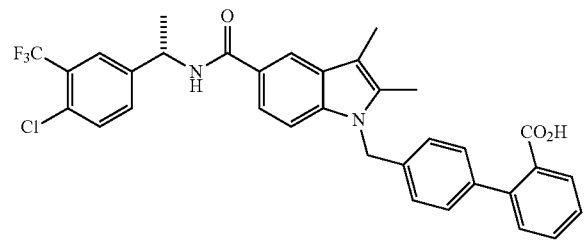

The title compound was prepared following the same general protocol as described in Steps 1-4, Example 1, using 3-trifluoromethyl-4-chlorobenzaldehyde and 1-((2'-(tert-butoxycarbonyl)biphenyl-4-yl)methyl)-2,3-dimethyl-1H-indole-5-carboxylic acid. LC-MS 606.1 (M+H).

Example 223

(S)-4'-((5-((1-(2-methoxy-4-(trifluoromethyl)phenyl)ethyl)carbamoyl)-2,3-dimethyl-1H-indol-1-yl)methyl)-[1,1'-biphenyl]-2-carboxylic acid

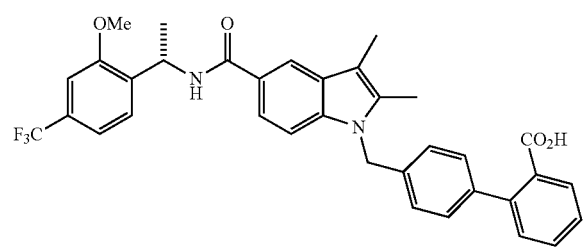

The title compound was prepared following the same general protocol as described in Steps 1-4, Example 1, using 2-methoxy-4-trifluoromethylbenzaldehyde and 1-((2'-(tert-butoxycarbonyl)biphenyl-4-yl)methyl)-2,3-dimethyl-1H-indole-5-carboxylic acid. LC-MS 601.2 (M+H).

Example 224

(R)-4'-((5-((1-(2-methoxy-4-(trifluoromethyl)phenyl)ethyl)carbamoyl)-2,3-dimethyl-1H-indol-1-yl)methyl)-[1,1'-biphenyl]-2-carboxylic acid

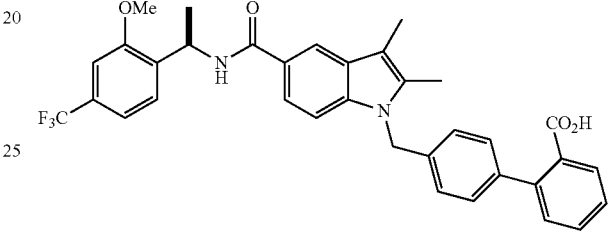

The title compound was prepared following the same general protocol as described in Steps 1-4, Example 1, using 2-methoxy-4-trifluoromethylbenzaldehyde and 1-((2'-(tert-butoxycarbonyl)biphenyl-4-yl)methyl)-2,3-dimethyl-1H-indole-5-carboxylic acid. LC-MS 601.2 (M+H).

Example 225

(S)-4'-((5-((1-(4-ethylphenyl)ethyl)carbamoyl)-2,3-dimethyl-1H-indol-1-yl)methyl)-[1,1'-biphenyl]-2-carboxylic acid

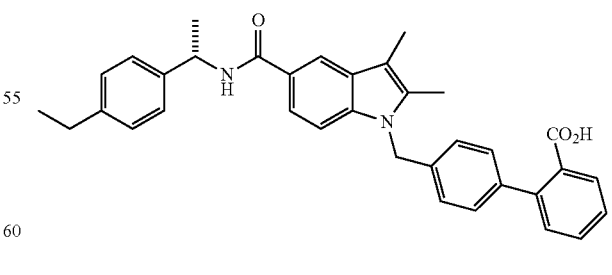

The title compound was prepared following the same general protocol as described in Steps 1-4, Example 1, using 4-ethylbenzaldehyde and 1-((2'-(tert-butoxycarbonyl)biphenyl-4-yl)methyl)-2,3-dimethyl-1H-indole-5-carboxylic acid. LC-MS 531.2 (M+H).

Example 226

(S)-4'-((5-((1-(4-chloro-2-methylphenyl)ethyl)carbamoyl)-2,3-dimethyl-1H-indol-1-yl)methyl)-[1,1'-biphenyl]-2-carboxylic acid

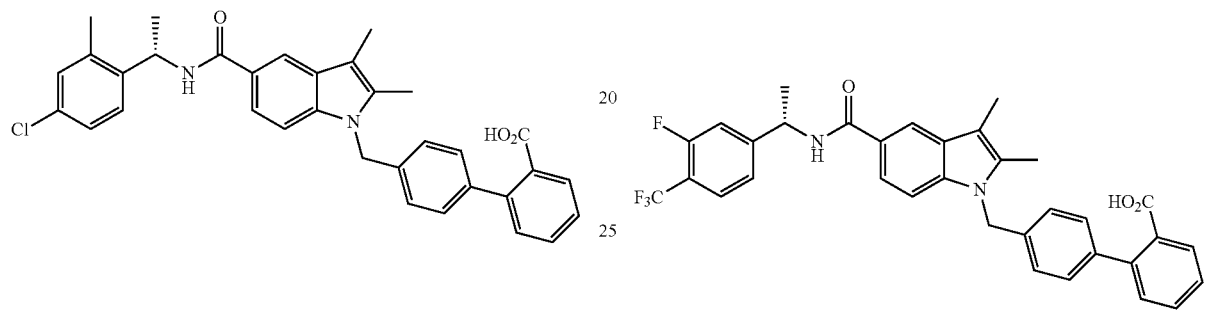

The title compound was prepared following the same general protocol as described in Step 8-9, Example 1, using the (S)-1-(4-chloro-2-methylphenyl)ethanamine hydrochloride and the 1-((2'-(tert-butoxycarbonyl)-[1,1'-biphenyl]-4-yl)methyl)-2,3-dimethyl-1H-indole-5-carboxylic acid. ESI-MS (m/z): 551 [M+H]$^+$.

Example 227

(S)-4'-((5-((1-(4-fluoro-2-(trifluoromethyl)phenyl)ethyl)carbamoyl)-2,3-dimethyl-1H-indol-1-yl)methyl)-[1,1'-biphenyl]-2-carboxylic acid The title compound was prepared following the same general protocol as described in Step 8-9, Example 1, using the (S)-1-(4-fluoro-2-(trifluoromethyl)phenyl)ethanamine hydrochloride and the 1-((2'-(tert-butoxycarbonyl)-[1,1'-biphenyl]-4-yl)methyl)-2,3-dimethyl-1H-indole-5-carboxylic acid. ESI-MS (m/z): 589 [M+H]$^+$.

Example 228

(S)-4'-((5-((1-(3-fluoro-4-(trifluoromethyl)phenyl)ethyl)carbamoyl)-2,3-dimethyl-1H-indol-1-yl)methyl)-[1,1'-biphenyl]-2-carboxylic acid

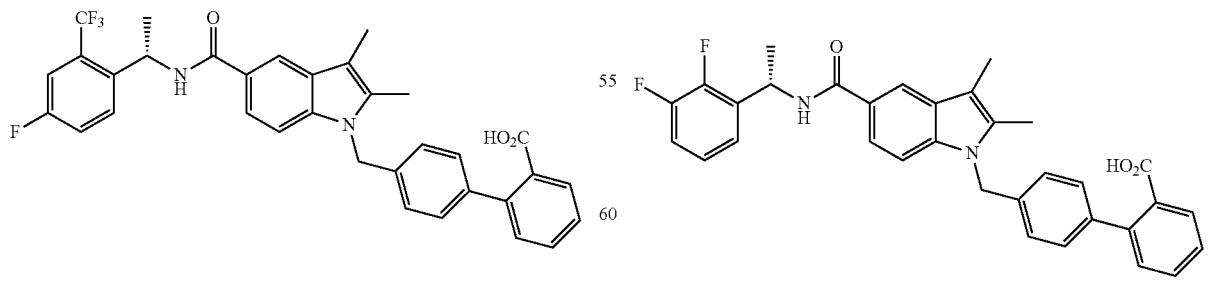

The title compound was prepared following the same general protocol as described in Step 8-9, Example 1, using the (S)-1-(3-fluoro-4-(trifluoromethyl)phenyl)ethanamine hydrochloride and the 1-((2'-(tert-butoxycarbonyl)-[1,1'-biphenyl]-4-yl)methyl)-2,3-dimethyl-1H-indole-5-carboxylic acid. ESI-MS (m/z): 589 [M+H]$^+$.

Example 229

(S)-4'-((5-((1-(2,3-difluorophenyl)ethyl)carbamoyl)-2,3-dimethyl-1H-indol-1-yl)methyl)-[1,1'-biphenyl]-2-carboxylic acid The title compound was prepared following the same general protocol as described in Step 8-9, Example 1, using the (S)-1-(2,3-difluorophenyl)ethanamine hydrochloride and the 1-((2'-(tert-butoxycarbonyl)-[1,1'-biphenyl]-4-yl)methyl)-2,3-dimethyl-1H-indole-5-carboxylic acid. ESI-MS (m/z): 539 [M+H]$^+$.

Example 230

(S)-4'-((5-((1-(2-Chloro-3-(trifluoromethyl)phenyl)ethyl)carbamoyl)-2,3-dimethyl-1H-indol-1-yl)methyl)-[1,1'-biphenyl]-2-carboxylic acid

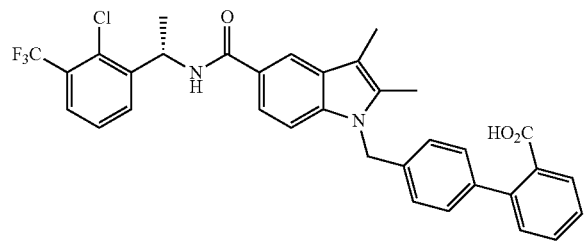 [SMILES: Cc1c(C)n(Cc2ccc(-c3ccccc3C(=O)O)cc2)c2ccc(C(=O)N[C@@H](C)c3cccc(C(F)(F)F)c3Cl)cc12]

The title compound was prepared following the same general protocol as described in Step 8-9, Example 1, using the (S)-1-(2-chloro-3-(trifluoromethyl)phenyl)ethanamine hydrochloride and the 1-((2'-(tert-butoxycarbonyl)-[1,1'-biphenyl]-4-yl)methyl)-2,3-dimethyl-1H-indole-5-carboxylic acid. ESI-MS (m/z): 605 [M+H]$^+$.

Example 231

(R)-4'-((5-((1-(2-chloro-3-(trifluoromethyl)phenyl)ethyl)carbamoyl)-2,3-dimethyl-1H-indol-1-yl)methyl)-[1,1'-biphenyl]-2-carboxylic acid

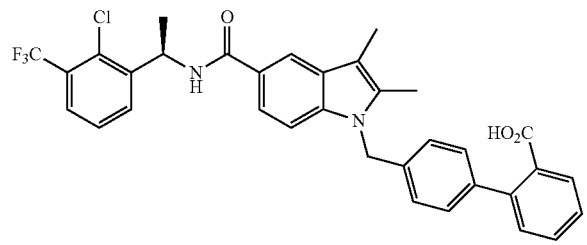 [SMILES: Cc1c(C)n(Cc2ccc(-c3ccccc3C(=O)O)cc2)c2ccc(C(=O)N[C@H](C)c3cccc(C(F)(F)F)c3Cl)cc12]

The title compound was prepared following the same general protocol as described in Step 8-9, Example 1, using the (R)-1-(2-chloro-3-(trifluoromethyl)phenyl)ethanamine hydrochloride and the 1-((2'-(tert-butoxycarbonyl)-[1,1'-biphenyl]-4-yl)methyl)-2,3-dimethyl-1H-indole-5-carboxylic acid. ESI-MS (m/z): 605 [M+H]$^+$.

Example 232

(S)-4'-((5-((1-(3-chloro-2-fluorophenyl)ethyl)carbamoyl)-2,3-dimethyl-1H-indol-1-yl)methyl)-[1,1'-biphenyl]-2-carboxylic acid

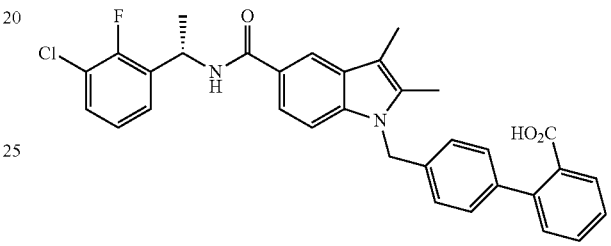

The title compound was prepared following the same general protocol as described in Step 8-9, Example 1, using (S)-1-(3-chloro-2-fluorophenyl)ethanamine hydrochloride and the 1-((2'-(tert-butoxycarbonyl)-[1,1'-biphenyl]-4-yl)methyl)-2,3-dimethyl-1H-indole-5-carboxylic acid. ESI-MS (m/z): 555 [M+H]$^+$.

Example 233

(S)-4'-((5-((1-(3,4-difluorophenyl)ethyl)carbamoyl)-2,3-dimethyl-1H-indol-1-yl)methyl)-[1,1'-biphenyl]-2-carboxylic acid The title compound was prepared following the same general protocol as described in Step 8-9, Example 1, using the (S)-1-(3,4-difluorophenyl)ethanamine hydrochloride and the 1-((2'-(tert-butoxycarbonyl)-[1,1'-biphenyl]-4-yl)methyl)-2,3-dimethyl-1H-indole-5-carboxylic acid. ESI-MS (m/z): 539 [M+H]+.

Example 234

(R)-4'-((5-((1-(3-fluoro-4-(trifluoromethyl)phenyl)ethyl)carbamoyl)-2,3-dimethyl-1H-indol-1-yl)methyl)-[1,1'-biphenyl]-2-carboxylic acid

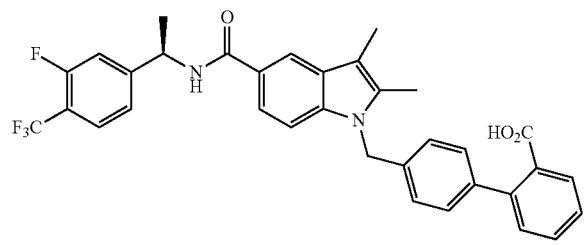 [SMILES: Cc1c(C)n(Cc2ccc(-c3ccccc3C(=O)O)cc2)c2ccc(C(=O)N[C@H](C)c3ccc(C(F)(F)F)c(F)c3)cc12]

The title compound was prepared following the same general protocol as described in Step 8-9, Example 1, using the (R)-1-(3-fluoro-4-(trifluoromethyl)phenyl)ethanamine hydrochloride and the 1-((2'-(tert-butoxycarbonyl)-[1,1'-biphenyl]-4-yl)methyl)-2,3-dimethyl-1H-indole-5-carboxylic acid. ESI-MS (m/z): 589 [M+H]+.

Example 235

(R)-4'-((2,3-dimethyl-5-((1-(2,3,6-trifluorophenyl)ethyl)carbamoyl)-1H-indol-1-yl)methyl)-[1,1'-biphenyl]-2-carboxylic acid

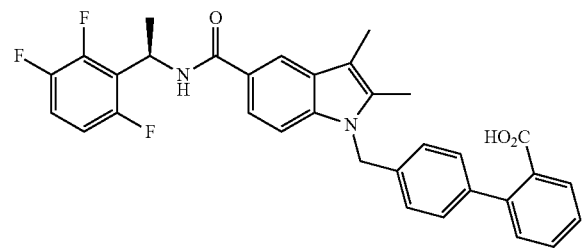 [SMILES: Cc1c(C)n(Cc2ccc(-c3ccccc3C(=O)O)cc2)c2ccc(C(=O)N[C@H](C)c3c(F)ccc(F)c3F)cc12]

The title compound was prepared following the same general protocol as described in Step 8-9, Example 1, using the (R)-1-(2,3,6-trifluorophenyl)ethanamine hydrochloride and the 1-((2'-(tert-butoxycarbonyl)-[1,1'-biphenyl]-4-yl)methyl)-2,3-dimethyl-1H-indole-5-carboxylic acid. ESI-MS (m/z): 557 [M+H]+.

Example 236

(S)-4'-((2,3-dimethyl-5-((1-(2,3,6-trifluorophenyl)ethyl)carbamoyl)-1H-indol-1-yl)methyl)-[1,1'-biphenyl]-2-carboxylic acid

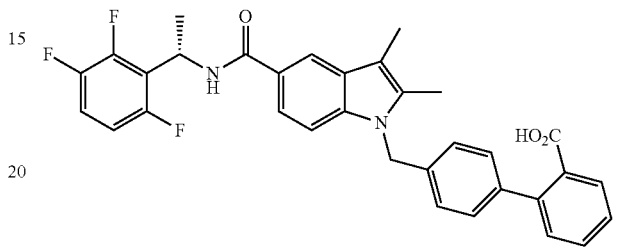

The title compound was prepared following the same general protocol as described in Step 8-9, Example 1, using the (S)-1-(2,3,6-trifluorophenyl)ethanamine hydrochloride and the 1-((2'-(tert-butoxycarbonyl)-[1,1'-biphenyl]-4-yl)methyl)-2,3-dimethyl-1H-indole-5-carboxylic acid. ESI-MS (m/z): 557 [M+H]+.

Example 237

4'-((5-(((S)-1-((S)-1-((benzyloxy)carbonyl)pyrrolidin-2-yl)ethyl)carbamoyl)-2,3-dimethyl-1H-indol-1-yl)methyl)-[1,1'-biphenyl]-2-carboxylic acid

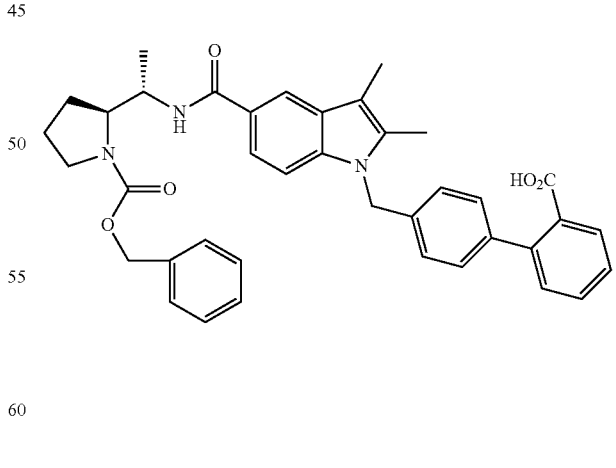

The title compound was prepared following the same general protocol as described in Step 8-9, Example 1, using the (S)-benzyl 2-((S)-1-aminoethyl)pyrrolidine-1-carboxylate hydrochloride and the 1-((2'-(tert-butoxycarbonyl)-[1,1'-biphenyl]-4-yl)methyl)-2,3-dimethyl-1H-indole-5-carboxylic acid. ESI-MS (m/z): 630 [M+H]+.

Example 238

4'-((5-(((S)-1-((R)-1-((benzyloxy)carbonyl)pyrrolidin-2-yl)ethyl)carbamoyl)-2,3-dimethyl-1H-indol-1-yl)methyl)-[1,1'-biphenyl]-2-carboxylic acid

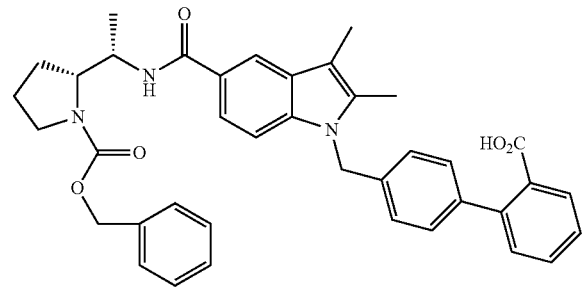 [SMILES: Cc1c(C)n(Cc2ccc(-c3ccccc3C(=O)O)cc2)c2ccc(C(=O)N[C@@H](C)[C@H]3CCCN3C(=O)OCc3ccccc3)cc12]

The title compound was prepared following the same general protocol as described in Step 8-9, Example 1, using the (R)-benzyl 2-((S)-1-aminoethyl)pyrrolidine-1-carboxylate hydrochloride and the 1-((2'-(tert-butoxycarbonyl)-[1,1'-biphenyl]-4-yl)methyl)-2,3-dimethyl-1H-indole-5-carboxylic acid. ESI-MS (m/z): 630 [M+H]+.

Example 239

(R)-4'-((5-(((1-(5-fluoro-2-(trifluoromethyl)phenyl)ethyl)carbamoyl)-2,3-dimethyl-1H-indol-1-yl)methyl)-[1,1'-biphenyl]-2-carboxylic acid

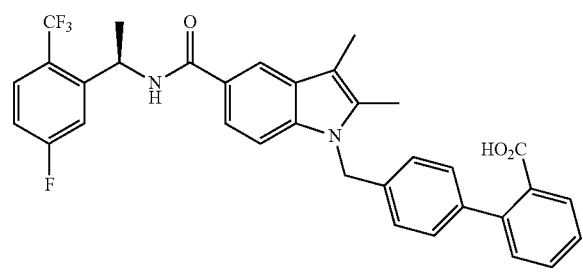 [SMILES: Cc1c(C)n(Cc2ccc(-c3ccccc3C(=O)O)cc2)c2ccc(C(=O)N[C@H](C)c3cc(F)ccc3C(F)(F)F)cc12]

The title compound was prepared following the same general protocol as described in Step 8-9, Example 1, using the (R)-1-(5-fluoro-2-(trifluoromethyl)phenyl)ethanamine hydrochloride and the 1-((2'-(tert-butoxycarbonyl)-[1,1'-biphenyl]-4-yl)methyl)-2,3-dimethyl-1H-indole-5-carboxylic acid. ESI-MS (m/z): 589 [M+H]+.

Example 240

4'-((5-(((S)-1-((R)-1-((benzyloxy)carbonyl)pyrrolidin-3-yl)ethyl)carbamoyl)-2,3-dimethyl-1H-indol-1-yl)methyl)-[1,1'-biphenyl]-2-carboxylic acid

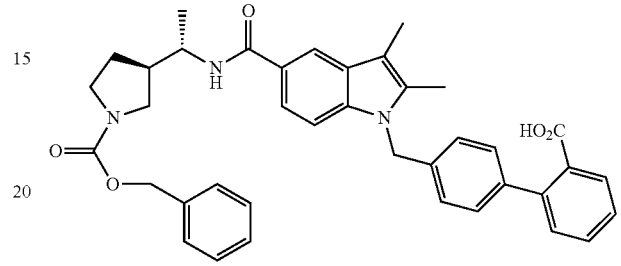

The title compound was prepared following the same general protocol as described in Step 8-9, Example 1, using the (R)-benzyl 3-((S)-1-aminoethyl)pyrrolidine-1-carboxylate hydrochloride and the 1-((2'-(tert-butoxycarbonyl)-[1,1'-biphenyl]-4-yl)methyl)-2,3-dimethyl-1H-indole-5-carboxylic acid. ESI-MS (m/z): 630 [M+H]+.

Example 241

(S)-4'-((5-(((1-(5-fluoro-2-(trifluoromethyl)phenyl)ethyl)carbamoyl)-2,3-dimethyl-1H-indol-1-yl)methyl)-[1,1'-biphenyl]-2-carboxylic acid The title compound was prepared following the same general protocol as described in Step 8-9, Example 1, using the (S)-1-(5-fluoro-2-(trifluoromethyl)phenyl)ethanamine hydrochloride and the 1-((2'-(tert-butoxycarbonyl)-[1,1'-biphenyl]-4-yl)methyl)-2,3-dimethyl-1H-indole-5-carboxylic acid. ESI-MS (m/z): 589 [M+H]⁺.

Example 242

(S)-1-((2'-cyano-[1,1'-biphenyl]-4-yl)methyl)-N-(1-(3-isopropylphenyl)ethyl)-2,3-dimethyl-1H-indole-5-carboxamide

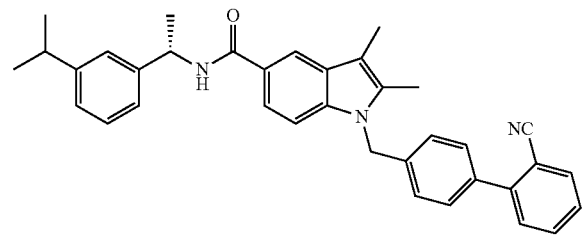 [SMILES: Cc1c(C)n(Cc2ccc(-c3ccccc3C#N)cc2)c2ccc(C(=O)N[C@@H](C)c3cccc(C(C)C)c3)cc12]

The title compound was prepared following the same general protocol as described in Step 8-9, Example 1, using the (S)-1-(5-fluoro-2-(trifluoromethyl)phenyl)ethanamine hydrochloride and the 4'-(bromomethyl)-[1,1'-biphenyl]-2-carbonitrile. ESI-MS (m/z): 526 [M+H]⁺.

Example 243

(S)-1-((2'-(2H-tetrazol-5-yl)-[1,1'-biphenyl]-4-yl)methyl)-N-(1-(3-isopropylphenyl)ethyl)-2,3-dimethyl-1H-indole-5-carboxamide

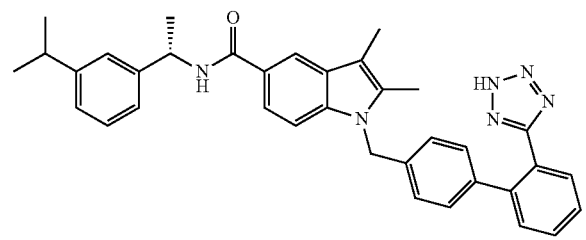 [SMILES: Cc1c(C)n(Cc2ccc(-c3ccccc3-c3nn[nH]n3)cc2)c2ccc(C(=O)N[C@@H](C)c3cccc(C(C)C)c3)cc12]

The mixture of (S)-1-((2'-cyano-[1,1'-biphenyl]-4-yl)methyl)-N-(1-(3-isopropylphenyl)ethyl)-2,3-dimethyl-1H-indole-5-carboxamide (0.1 g, 0.19 mmol), azidotrimethylsilane 90.05 mL, 0.38 mmol) and dibutylstannanone (0.005 g, 0.019 mmol) in toluene (3 mL) was heated at 110° C. oil bath for 16 hr. The solvent was removed and the residue was purified by preparative-HPLC to obtain the title compound. ESI-MS (m/z): 569 [M+H]⁺.

Example 244

(S)—N-(1-(3-isopropylphenyl)ethyl)-2,3-dimethyl-1-((2'-(5-oxo-4,5-dihydro-1,2,4-oxadiazol-3-yl)-[1,1'-biphenyl]-4-yl)methyl)-1H-indole-5-carboxamide

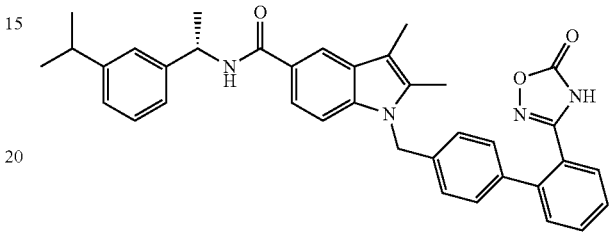

A mixture of hydroxylammoium chloride (0.2 g, 2.88 mmol), sodium hydrogen carbonate (0.3 g, 3.57 mmol) and dimethyl sulfoxide (2 mL) was stirred at 40° C. for 30 min. (S)-1-((2'-cyano-[1,1'-biphenyl]-4-yl)methyl)-N-(1-(3-isopropylphenyl)ethyl)-2,3-dimethyl-1H-indole-5-carboxamide (0.1 g, 0.19 mmol) was added, and the mixture was stirred at 90° C. for 16 hr. The reaction mixture was diluted with ethyl acetate, washed with water and then with brine, and dried over anhydrous sodium sulfate. Thvent was evaporated under reduced pressure, and the residue was dissolved in THF (3 mL), N,N'-carbonyldiimidazole (0.055 g, 0.29 mmol) and then 1,8-diazabicyclo[5,4,0]undec-7-ene (0.05 mL, 0.29 mmol) were added, and the mixture was stirred at room temperature for 2 hr. The reaction mixture was diluted with ethyl acetate, washed with saturated aqueous potassium hydrogensulfate solution and then with brine, and dried over anhydrous sodium sulfate. The solvent was evaporated under reduced pressure, and the residue was purified by preparative-HPLC to obtain the title compound. ESI-MS (m/z): 585 [M+H]⁺.

Example 245

(S)—N-(1-(3-isopropylphenyl)ethyl)-2,3-dimethyl-1-((2'-(5-oxo-4,5-dihydro-1,3,4-oxadiazol-2-yl)-[1,1'-biphenyl]-4-yl)methyl)-1H-indole-5-carboxamide

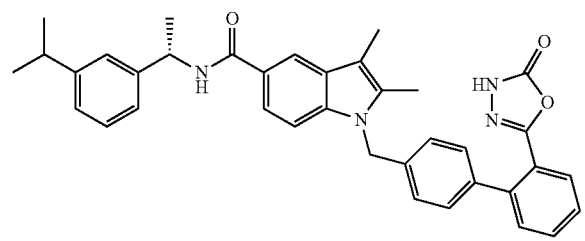 [SMILES: Cc1c(C)n(Cc2ccc(-c3ccccc3-c3n[nH]c(=O)o3)cc2)c2ccc(C(=O)N[C@@H](C)c3cccc(C(C)C)c3)cc12]

Step 1: (S)-1-((2'-(hydrazinocarbonyl)-[1,1'-biphenyl]-4-yl)methyl)-N-(1-(3-isopropylphenyl)ethyl)-2,3-dimethyl-1H-indole-5-carboxamide

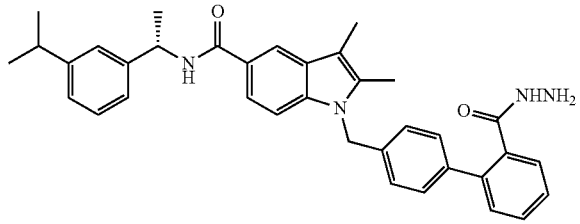 [SMILES: Cc1c(C)n(Cc2ccc(-c3ccccc3C(=O)NN)cc2)c2ccc(C(=O)N[C@@H](C)c3cccc(C(C)C)c3)cc12]

To the mixture of (S)-4'-((5-((1-(3-isopropylphenyl)ethyl)carbamoyl)-2,3-dimethyl-1H-indol-1-yl)methyl)-[1,1'-biphenyl]-2-carboxylic acid (0.11 g, 0.201 mmol), hydrazine hydrochloride (0.028 g, 0.402 mmol) and HATU (0.092 g, 0.24 mmol) in DCM (2 mL) was added DIEA (0.14 mL, 0.8 mmol). The mixture was stirred at room temperature for 16 h. The solvent was removed and the residue was purified by silica gel to obtain the title compound. ESI-MS (m/z): 559 [M+H]$^+$.

Step 2: (S)—N-(1-(3-isopropylphenyl)ethyl)-2,3-dimethyl-1-((2'-(5-oxo-4,5-dihydro-1,3,4-oxadiazol-2-yl)-[1,1'-biphenyl]-4-yl)methyl)-1H-indole-5-carboxamide The mixture of (S)-1-((2'-(hydrazinocarbonyl)-[1,1'-biphenyl]-4-yl)methyl)-N-(1-(3-isopropylphenyl)ethyl)-2,3-dimethyl-1H-indole-5-carboxamide (0.062 g, 0.11 mmol), N,N'-carbonyldiimidazole (0.027 g, 0.16 mmol) and DIEA (0.03 mL, 0.16 mmol) in DMF was stirred at room temperature for 1 h, and then stirred at 50° C. for 1 h. The reaction mixture was poured on to ice-water, and then extracted with ethyl acetate. The combined organic layers were washed with water and brine. The solvent was remove and the residue was purified with preparative-HPLC to obtain the title compound. ESI-MS (m/z): 585 [M+H]$^+$.

Example 246

(S)-1-((2'-(N-(tert-butyl)sulfamoyl)-[1,1'-biphenyl]-4-yl)methyl)-N-(1-(3-isopropylphenyl)ethyl)-2,3-dimethyl-1H-indole-5-carboxamide

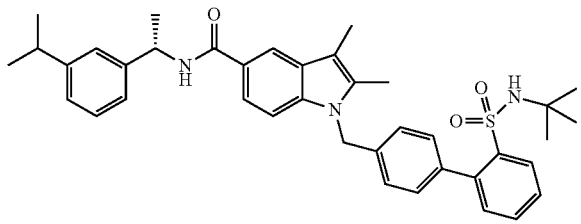 [SMILES: Cc1c(C)n(Cc2ccc(-c3ccccc3S(=O)(=O)NC(C)(C)C)cc2)c2ccc(C(=O)N[C@@H](C)c3cccc(C(C)C)c3)cc12]

Step 1: ethyl 1-((2'-(N-(tert-butyl)sulfamoyl)-[1,1'-biphenyl]-4-yl)methyl)-2,3-dimethyl-1H-indole-5-carboxylate

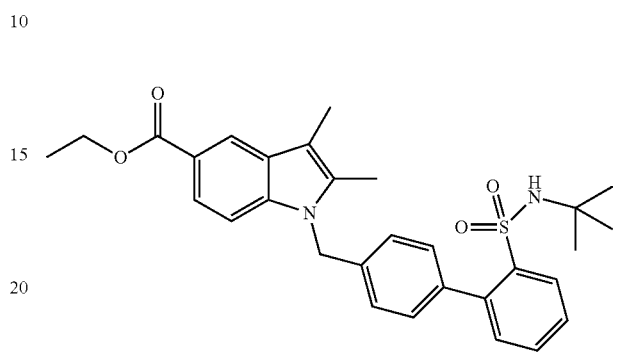

The title compound was prepared following the same general protocol as described in Step 6, Example 1, using the ethyl 2,3-dimethyl-1H-indole-5-carboxylate and 4'-(bromomethyl)-N-(tert-butyl)-[1,1'-biphenyl]-2-sulfonamide.

ESI-MS (m/z): 519 [M+H]$^+$.

Step 2: 1-((2'-(N-(tert-butyl)sulfamoyl)-[1,1'-biphenyl]-4-yl)methyl)-2,3-dimethyl-1H-indole-5-carboxylic acid

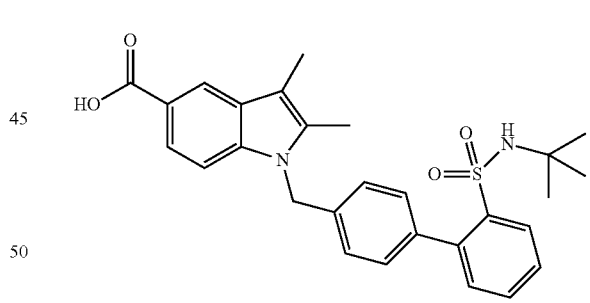

The title compound was prepared following the same general protocol as described in Step 7, Example 1, using the ethyl 1-((2'-(N-(tert-butyl)sulfamoyl)-[1,1'-biphenyl]-4-yl)methyl)-2,3-dimethyl-1H-indole-5-carboxylate. ESI-MS (m/z): 491 [M+H]$^+$.

Step 3: (S)-1-((2'-(N-(tert-butyl)sulfamoyl)-[1,1'-biphenyl]-4-yl)methyl)-N-(1-(3-isopropylphenyl)ethyl)-2,3-dimethyl-1H-indole-5-carboxamide The title compound was prepared following the same general protocol as described in Step 8, Example 1, using the (S)-1-(3-isopropylphenyl)ethanamine hydrochloride and 1-((2'-(N-(tert-butyl)sulfamoyl)-[1,1'-biphenyl]-4-yl)methyl)-2,3-dimethyl-1H-indole-5-carboxylic acid. ESI-MS (m/z): 636 [M+H]$^+$.

Example 247

(S)—N-(1-(3-isopropylphenyl)ethyl)-2,3-dimethyl-1-((2'-sulfamoyl-[1,1'-biphenyl]-4-yl)methyl)-1H-indole-5-carboxamide

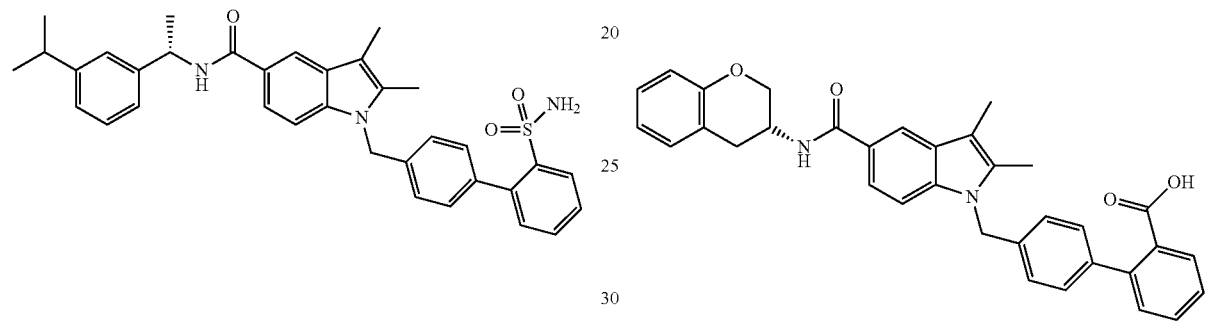

The title compound was prepared following the same general protocol as described in Step 9, Example 1, using the (S)-1-((2'-(N-(tert-butyl)sulfamoyl)-[1,1'-biphenyl]-4-yl)methyl)-N-(1-(3-isopropylphenyl)ethyl)-2,3-dimethyl-1H-indole-5-carboxamide. ESI-MS (m/z): 580 [M+H]$^+$.

Example 248

(S)-1-((2'-(N-acetylsulfamoyl)-[1,1'-biphenyl]-4-yl)methyl)-N-(1-(3-isopropylphenyl)ethyl)-2,3-dimethyl-1H-indole-5-carboxamide

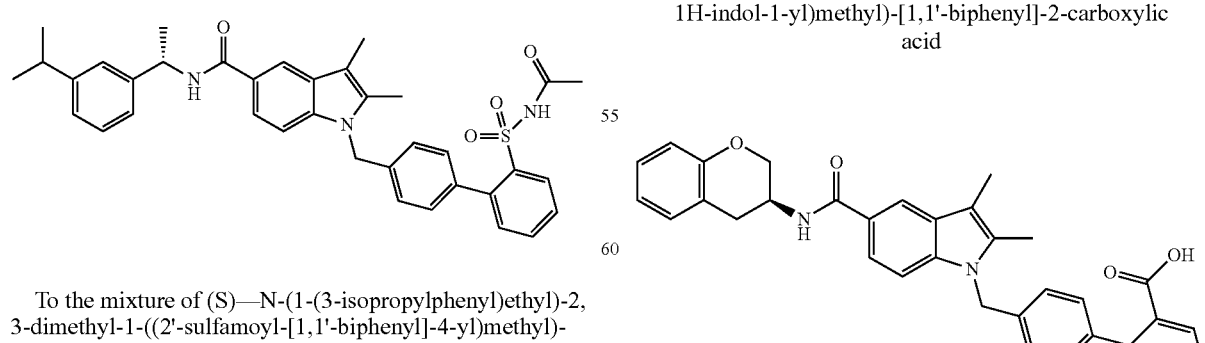

To the mixture of (S)—N-(1-(3-isopropylphenyl)ethyl)-2,3-dimethyl-1-((2'-sulfamoyl-[1,1'-biphenyl]-4-yl)methyl)-1H-indole-5-carboxamide (0.058 g, 0.1 mmol) and TEA (0.03 mL, 0.2 mmol) in DCM (0.5 mL) was slowly added acetyl chloride (0.009 g, 0.11 mmol). The mixture was stirred at room temperature for 1 h.

The solvent was removed and the residue was purified by preparative-HPLC to obtain the title compound ESI-MS (m/z): 622 [M+H]$^+$.

Example 249

(R)-4'-((5-(chroman-3-ylcarbamoyl)-2,3-dimethyl-1H-indol-1-yl)methyl)-[1,1'-biphenyl]-2-carboxylic acid The title compound was prepared following the same protocol as described in Step 8 and 9, Example 1, using (R)-chroman-3-amine instead of the (S)-1-(4-bromophenyl)ethanamine.

Example 250

(S)-4'-((5-(chroman-3-ylcarbamoyl)-2,3-dimethyl-1H-indol-1-yl)methyl)-[1,1'-biphenyl]-2-carboxylic acid The title compound was prepared following the same protocol as described in Step 8 and 9, Example 1, using (S)-chroman-3-amine instead of the (S)-1-(4-bromophenyl)ethanamine.

Example 251

(S)-4'-((2,3-dimethyl-5-(1-(4-propylphenyl)ethylcarbamoyl)-1H-indol-1-yl)methyl)biphenyl-2-carboxylic acid

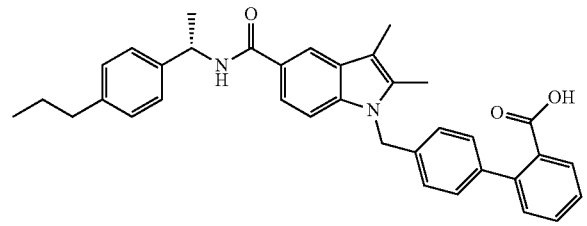 [SMILES: CCCc1ccc([C@H](C)NC(=O)c2ccc3c(c2)c(C)c(C)n3Cc2ccc(-c3ccccc3C(=O)O)cc2)cc1]

The title compound was prepared following the same protocol as described in Step 8 and 9, Example 1, using (S)-1-(4-propylphenyl)ethanaminium chloride instead of the (S)-1-(4-bromophenyl)ethanamine. ESI-MS (m/z): 545 [M+H]⁺.

Example 252

(S)-4'-((2,3-dimethyl-5-(1-o-tolylethylcarbamoyl)-1H-indol-1-yl)methyl)biphenyl-2-carboxylic acid

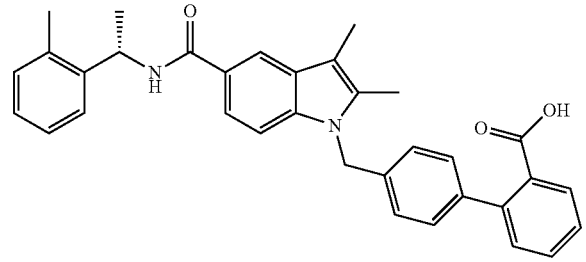 [SMILES: Cc1ccccc1[C@H](C)NC(=O)c1ccc2c(c1)c(C)c(C)n2Cc1ccc(-c2ccccc2C(=O)O)cc1]

The title compound was prepared following the same protocol as described in Step 8 and 9, Example 1, using (S)-1-(o-tolyl)ethanaminium chloride instead of the (S)-1-(4-bromophenyl)ethanamine. ESI-MS (m/z): 517 [M+H]⁺.

Example 253

(S)-4'-((5-(1-(4-ethoxyphenyl)ethylcarbamoyl)-2,3-dimethyl-1H-indol-1-yl)methyl)biphenyl-2-carboxylic acid

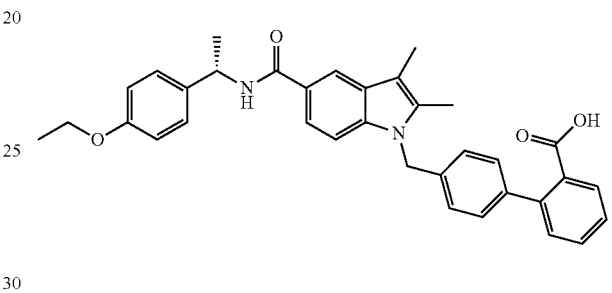

The title compound was prepared following the same protocol as described in Step 8 and 9, Example 1, using (S)-1-(4-ethoxyphenyl)ethanaminium chloride instead of the (S)-1-(4-bromophenyl)ethanamine. ESI-MS (m/z): 547 [M+H]⁺.

Example 254

(S)-4'-((5-(1-(2-bromophenyl)ethylcarbamoyl)-2,3-dimethyl-1H-indol-1-yl)methyl)biphenyl-2-carboxylic acid

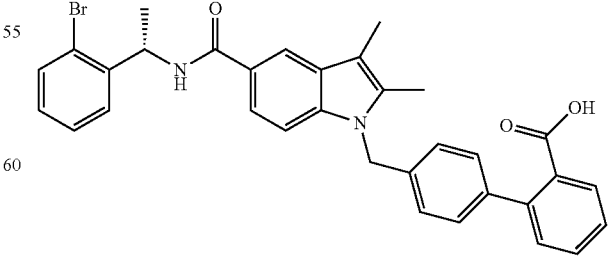

The title compound was prepared following the same protocol as described in Step 8 and 9, Example 1, using (S)-1-

(2-bromophenyl)ethanaminium chloride instead of the (S)-1-(4-bromophenyl)ethanamine. ESI-MS (m/z): 581 [M+H]+.

Example 255

(S)-4'-((5-(1-(2-ethylphenyl)ethylcarbamoyl)-2,3-dimethyl-1H-indol-1-yl)methyl)biphenyl-2-carboxylic acid

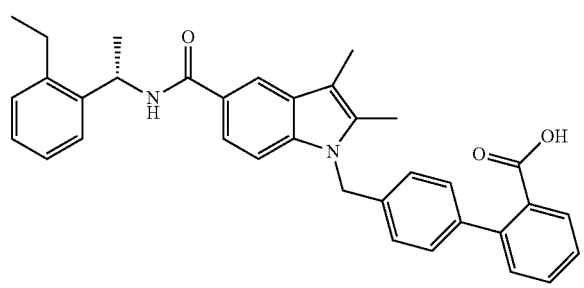

The title compound was prepared following the same protocol as described in Step 8 and 9, Example 1, using (S)-1-(2-ethylphenyl)ethanaminium chloride instead of the (S)-1-(4-bromophenyl)ethanamine. ESI-MS (m/z): 531 [M+H]+.

Example 256

(S)-4'-((2,3-dimethyl-5-(1-(2-(trifluoromethoxy)phenyl)ethylcarbamoyl)-1H-indol-1-yl)methyl)biphenyl-2-carboxylic acid

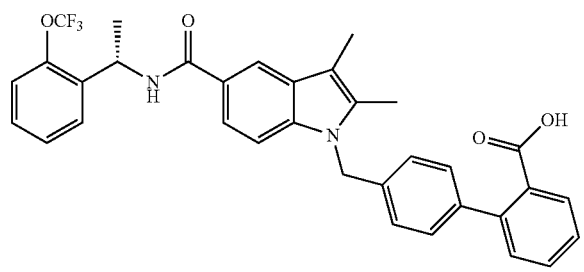 [SMILES: Cc1c(C)n(Cc2ccc(-c3ccccc3C(=O)O)cc2)c2ccc(C(=O)N[C@@H](C)c3ccccc3Br)cc12]

The title compound was prepared following the same protocol as described in Step 8 and 9, Example 1, using (S)-1-(2-(trifluoromethoxy)phenyl)ethanaminium chloride instead of the (S)-1-(4-bromophenyl)ethanamine. ESI-MS (m/z): 587 [M+H]+.

Example 257

(S)-4'-((5-(1-(2-isopropoxyphenyl)ethylcarbamoyl)-2,3-dimethyl-1H-indol-1-yl)methyl)biphenyl-2-carboxylic acid

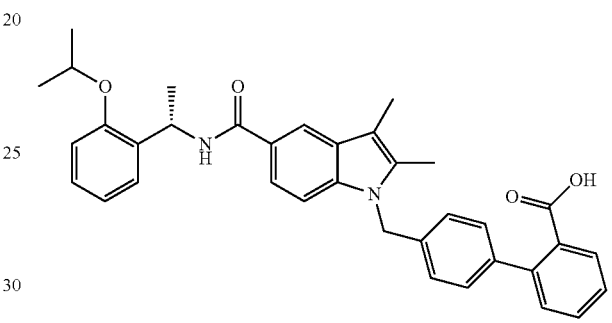

The title compound was prepared following the same protocol as described in Step 8 and 9, Example 1, using (S)-1-(2-isopropoxyphenyl)ethanaminium chloride instead of the (S)-1-(4-bromophenyl)ethanamine. ESI-MS (m/z): 561 [M+H]+.

Example 258

(S)-4'-((2,3-dimethyl-5-(1-(4-(methylsulfonyl)phenyl)ethylcarbamoyl)-1H-indol-1-yl)methyl)biphenyl-2-carboxylic acid

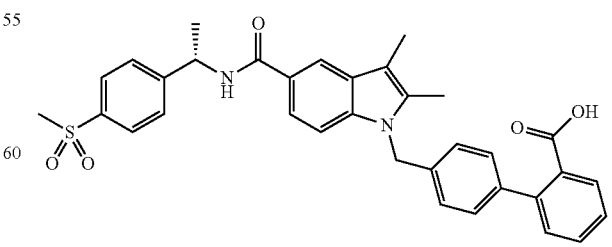

The title compound was prepared following the same protocol as described in Step 8 and 9, Example 1, using (S)-1-

(4-(methylsulfonyl)phenyl)ethanaminium chloride instead of the (S)-1-(4-bromophenyl)ethanamine. ESI-MS (m/z): 581 [M+H]$^+$.

Example 259

4'-((5-(1-(5-cyclopropylpyridin-3-yl)ethylcarbamoyl)-2,3-dimethyl-1H-indol-1-yl)methyl)biphenyl-2-carboxylic acid

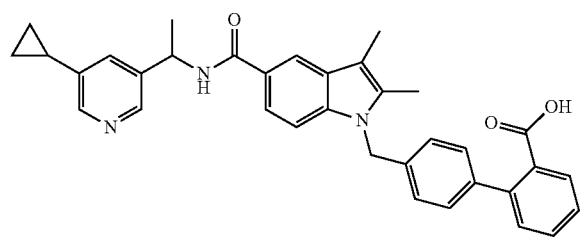 [SMILES: Cc1c(C)n(Cc2ccc(-c3ccccc3C(=O)O)cc2)c2ccc(C(=O)NC(C)c3cncc(C4CC4)c3)cc12]

Step 1: 1-(5-bromopyridin-3-yl)ethanaminium chloride

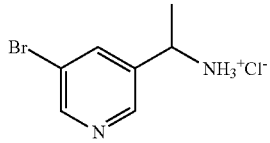

The title compound was prepared following the same general protocol as described in Step 1 and 2, Example 2, using 5-bromonicotinaldehyde instead of 4-t-butylbenzaldehyde.

Step 2: tert-butyl 4'-((5-((1-(5-bromopyridin-3-yl)ethyl)carbamoyl)-2,3-dimethyl-1H-indol-1-yl)methyl)-[1,1'-biphenyl]-2-carboxylate

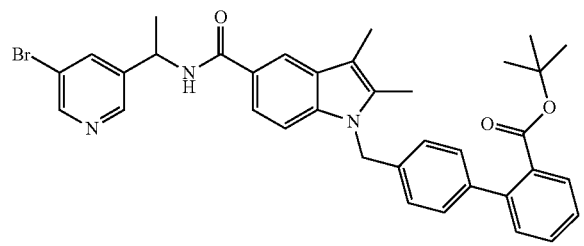 [SMILES: Cc1c(C)n(Cc2ccc(-c3ccccc3C(=O)OC(C)(C)C)cc2)c2ccc(C(=O)NC(C)c3cncc(Br)c3)cc12]

The title compound was prepared following the same general protocol as described in Step 8, Example 1, using 1-(5-bromopyridin-3-yl)ethanaminium chloride instead of (S)-1-(4-bromophenyl)ethanamine.

Step 3: tert-butyl 4'-((5-((1-(5-cyclopropylpyridin-3-yl)ethyl)carbamoyl)-2,3-dimethyl-1H-indol-1-yl)methyl)-[1,1'-biphenyl]-2-carboxylate

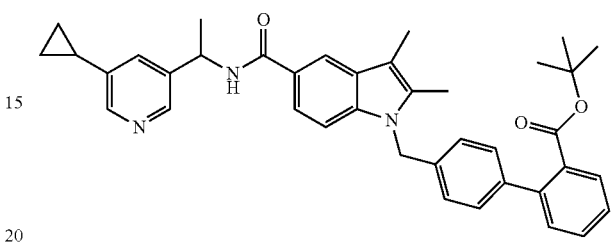

The title compound was prepared following the same general protocol as described in Step 1, Example 261, using tert-butyl 4'-((5-((1-(5-bromopyridin-3-yl)ethyl)carbamoyl)-2,3-dimethyl-1H-indol-1-yl)methyl)-[1,1'-biphenyl]-2-carboxylate instead of (S)-tert-butyl 4'-((5-((1-(5-bromopyridin-2-yl)ethyl)carbamoyl)-2,3-dimethyl-1H-indol-1-yl)methyl)-[1,1'-biphenyl]-2-carboxylate.

Step 4: 4'-((5-((1-(5-cyclopropylpyridin-3-yl)ethyl)carbamoyl)-2,3-dimethyl-1H-indol-1-yl)methyl)-[1,1'-biphenyl]-2-carboxylic acid

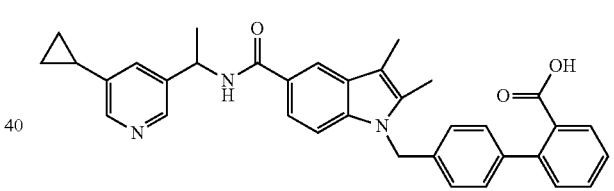

The title compound was prepared following the same general protocol as described in Step 9, Example 1. ESI-MS (m/z): 544 [M+H]$^+$.

Example 260

(S)-4'-((5-((1-(5-bromopyridin-2-yl)ethyl)carbamoyl)-2,3-dimethyl-1H-indol-1-yl)methyl)-[1,1'-biphenyl]-2-carboxylic acid

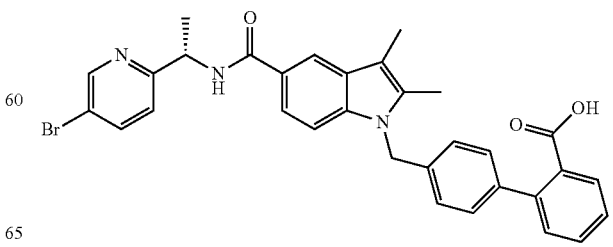

Step 1: (S)-1-(5-bromopyridin-2-yl)ethanaminium chloride

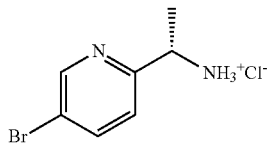

The title compound was prepared following the same general protocol as described in Step 1 and 2, Example 2, using 5-bromopicolinaldehyde instead of 4-t-butylbenzaldehyde.

Step 2: (S)-tert-butyl 4'-((5-((1-(5-bromopyridin-2-yl)ethyl)carbamoyl)-2,3-dimethyl-1H-indol-1-yl)methyl)-[1,1'-biphenyl]-2-carboxylate

The title compound was prepared following the same general protocol as described in Step 8, Example 1, using (S)-1-(5-bromopyridin-2-yl)ethanaminium chloride instead of (S)-1-(4-bromophenyl)ethanamine.

Step 3: (S)-4'-((5-((1-(5-bromopyridin-2-yl)ethyl)carbamoyl)-2,3-dimethyl-1H-indol-1-yl)methyl)-[1,1'-biphenyl]-2-carboxylic acid

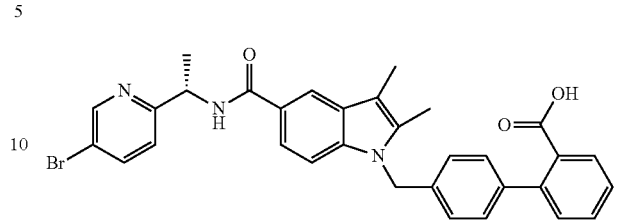

The title compound was prepared following the same general protocol as described in Step 9, Example 1. ESI-MS (m/z): 582 [M+H]$^+$.

Example 261

(S)-4'-((5-((1-(5-cyclopropylpyridin-2-yl)ethyl)carbamoyl)-2,3-dimethyl-1H-indol-1-yl)methyl)-[1,1'-biphenyl]-2-carboxylic acid

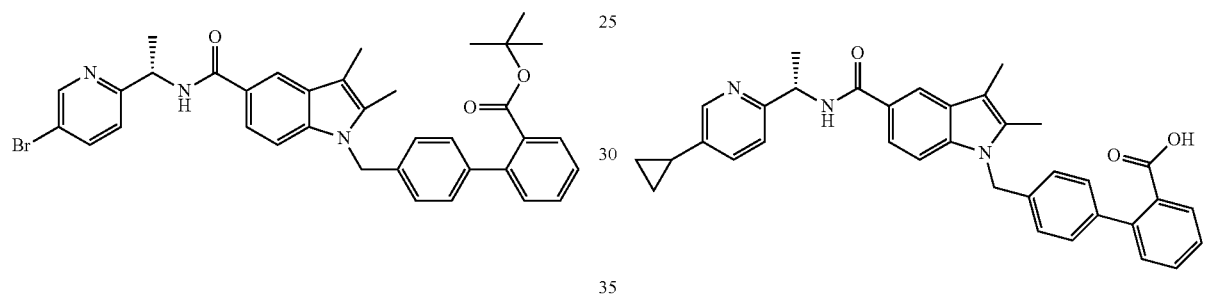

Step 1: (S)-tert-butyl 4'-((5-((1-(5-cyclopropylpyridin-2-yl)ethyl)carbamoyl)-2,3-dimethyl-1H-indol-1-yl)methyl)-[1,1'-biphenyl]-2-carboxylate

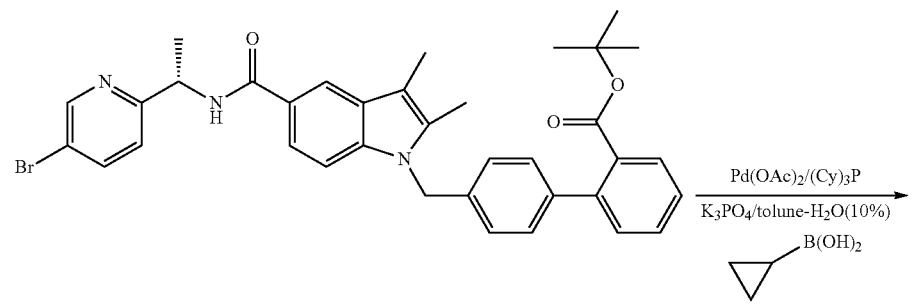

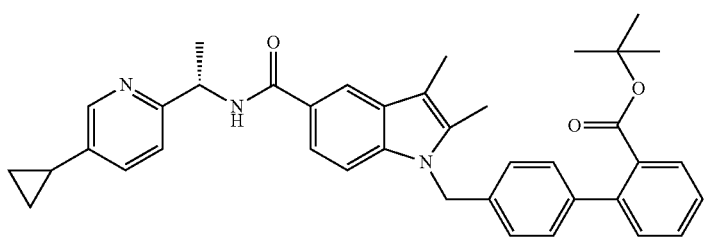

A high-pressure vial was filled with the (S)-tert-butyl 4'-((5-((1-(5-bromopyridin-2-yl)ethyl)carbamoyl)-2,3-dimethyl-1H-indol-1-yl)methyl)-[1,1'-biphenyl]-2-carboxylate (50 mg, 0.078 mmol), cyclopropylboronic acid (8 mg, 0.09 mmol, 1.2 equiv), Pd(OAc)$_2$ (12 mg, 0.055 mmol, 0.7 equiv), (Cy)$_3$P (8.7 mg, 0.031 mmol, 0.4 equiv), K$_3$PO$_4$ (49 mg, 0.23 mmol, 3 equiv), in toluene-water (10%). The reaction mixture was heated at 100° C. for 3 h under microwaves. The mixture was evaporated in vacuo to obtain the crude which was purified by prep. HPLC (MeOH/Acetonitrile/water) to obtain the title compound.

Step 2: (S)-4'-((5-((1-(5-cyclopropylpyridin-2-yl)ethyl)carbamoyl)-2,3-dimethyl-1H-indol-1-yl)methyl)-[1,1'-biphenyl]-2-carboxylic acid

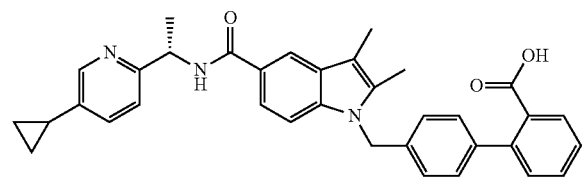 [SMILES: Cc1c(C)n(Cc2ccc(-c3ccccc3C(=O)O)cc2)c2ccc(C(=O)N[C@@H](C)c3ccc(C4CC4)cn3)cc12]

The title compound was prepared following the same general protocol as described in Step 9, Example 1. ESI-MS (m/z): 544 [M+H]$^+$.

Example 262

(S)-4'-((5-((1-(6-chloropyridin-3-yl)ethyl)carbamoyl)-2,3-dimethyl-1H-indol-1-yl)methyl)-[1,1'-biphenyl]-2-carboxylic acid

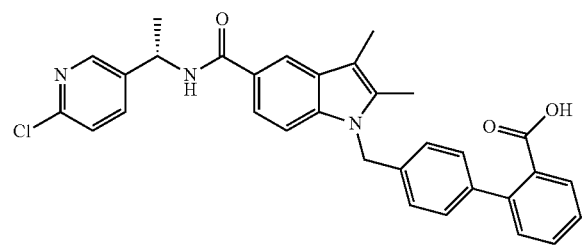 [SMILES: Cc1c(C)n(Cc2ccc(-c3ccccc3C(=O)O)cc2)c2ccc(C(=O)N[C@@H](C)c3ccc(Cl)nc3)cc12]

Step 1: (S)-1-(6-chloropyridin-3-yl)ethanaminium chloride

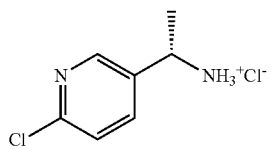

The title compound was prepared following the same general protocol as described in Step 1 and 2, Example 2, using 6-chloronicotinaldehyde instead of 4-t-butylbenzaldehyde.

Step 2: (S)-tert-butyl 4'-((5-((1-(6-chloropyridin-3-yl)ethyl)carbamoyl)-2,3-dimethyl-1H-indol-1-yl)methyl)-[1,1'-biphenyl]-2-carboxylate

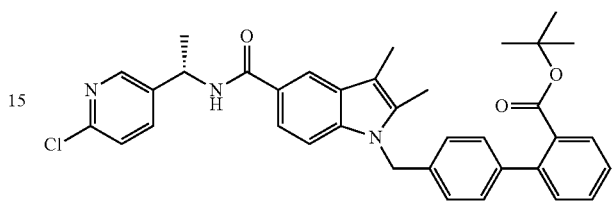

The title compound was prepared following the same general protocol as described in Step 8, Example 1, using (S)-1-(6-chloropyridin-3-yl)ethanaminium chloride instead of (S)-1-(4-bromophenyl)ethanamine.

Step 3: (S)-4'-((5-((1-(6-chloropyridin-3-yl)ethyl)carbamoyl)-2,3-dimethyl-1H-indol-1-yl)methyl)-[1,1'-biphenyl]-2-carboxylic acid

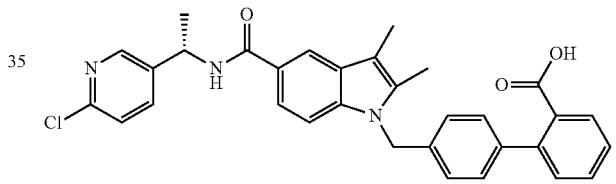

The title compound was prepared following the same general protocol as described in Step 9, Example 1. ESI-MS (m/z): 538 [M+H]$^+$.

Example 263

(S)-4'-((5-((1-(6-cyclopropylpyridin-3-yl)ethyl)carbamoyl)-2,3-dimethyl-1H-indol-1-yl)methyl)-[1,1'-biphenyl]-2-carboxylic acid

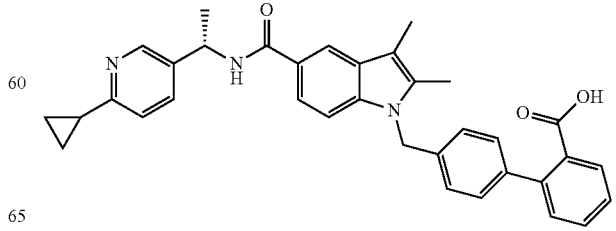

433

Step 1: (S)-tert-butyl 4'-((5-((1-(6-cyclopropylpyridin-3-yl)ethyl)carbamoyl)-2,3-dimethyl-1H-indol-1-yl)methyl)-[1,1'-biphenyl]-2-carboxylate

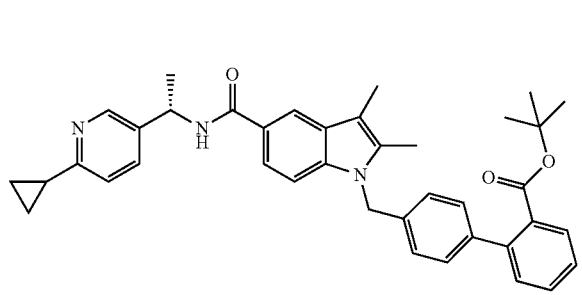 [SMILES: Cc1c(C)n(Cc2ccc(-c3ccccc3C(=O)OC(C)(C)C)cc2)c2ccc(C(=O)N[C@@H](C)c3ccc(C4CC4)nc3)cc12]

The title compound was prepared following the same general protocol as described in Step 1, Example 261, using (S)-tert-butyl 4'-((5-((1-(6-chloropyridin-3-yl)ethyl)carbamoyl)-2,3-dimethyl-1H-indol-1-yl)methyl)-[1,1'-biphenyl]-2-carboxylate instead of (S)-tert-butyl 4'-((5-((1-(5-bromopyridin-2-yl)ethyl)carbamoyl)-2,3-dimethyl-1H-indol-1-yl)methyl)-[1,1'-biphenyl]-2-carboxylate.

Step 2: (S)-4'-((5-((1-(6-cyclopropylpyridin-3-yl)ethyl)carbamoyl)-2,3-dimethyl-1H-indol-1-yl)methyl)-[1,1'-biphenyl]-2-carboxylic acid

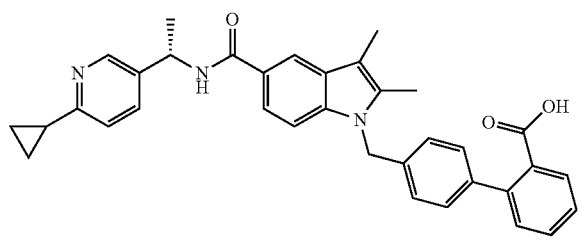 [SMILES: Cc1c(C)n(Cc2ccc(-c3ccccc3C(=O)O)cc2)c2ccc(C(=O)N[C@@H](C)c3ccc(C4CC4)nc3)cc12]

The title compound was prepared following the same general protocol as described in Step 9, Example 1. ESI-MS (m/z): 544 [M+H]+.

Example 264

(R)-4'-((5-((1-(6-cyclopropylpyridin-3-yl)ethyl)carbamoyl)-2,3-dimethyl-1H-indol-1-yl)methyl)-[1,1'-biphenyl]-2-carboxylic acid

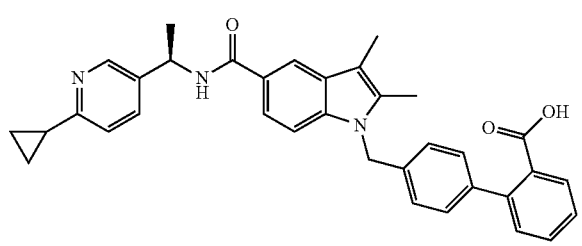 [SMILES: Cc1c(C)n(Cc2ccc(-c3ccccc3C(=O)O)cc2)c2ccc(C(=O)N[C@H](C)c3ccc(C4CC4)nc3)cc12]

434

Step 1: (R)-1-(6-chloropyridin-3-yl)ethanaminium chloride

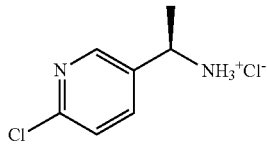

The title compound was prepared following the same general protocol as described in Step 1 and 2, Example 2, using 6-chloronicotinaldehyde instead of 4-t-butylbenzaldehyde.

Step 2: (R)-tert-butyl 4'-((5-((1-(6-chloropyridin-3-yl)ethyl)carbamoyl)-2,3-dimethyl-1H-indol-1-yl)methyl)-[1,1'-biphenyl]-2-carboxylate

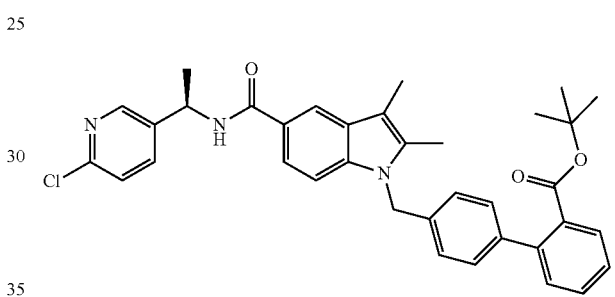

The title compound was prepared following the same general protocol as described in Step 8, Example 1, using (R)-1-(6-chloropyridin-3-yl)ethanaminium chloride instead of (S)-1-(4-bromophenyl)ethanamine.

Step 3: (R)-tert-butyl 4'-((5-((1-(6-cyclopropylpyridin-3-yl)ethyl)carbamoyl)-2,3-dimethyl-1H-indol-1-yl)methyl)-[1,1'-biphenyl]-2-carboxylate

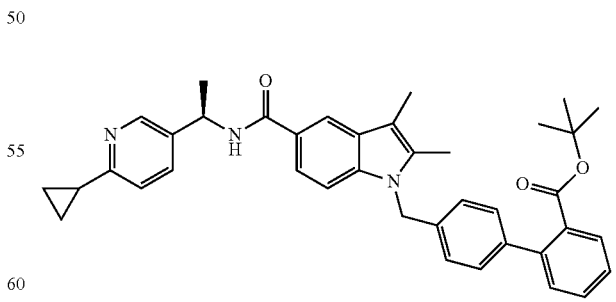

The title compound was prepared following the same general protocol as described in Step 1, Example 261, using (R)-tert-butyl 4'-((5-((1-(6-chloropyridin-3-yl)ethyl)carbamoyl)-2,3-dimethyl-1H-indol-1-yl)methyl)-[1,1'-biphenyl]-2-carboxylate instead of (S)-tert-butyl 4'-((5-((1-(5-bromopyridin-2-yl)ethyl)carbamoyl)-2,3-dimethyl-1H-indol-1-yl)methyl)-[1,1'-biphenyl]-2-carboxylate.

Step 4: (R)-4'-((5-(((1-(6-cyclopropylpyridin-3-yl)ethyl)carbamoyl)-2,3-dimethyl-1H-indol-1-yl)methyl)-[1,1'-biphenyl]-2-carboxylic acid

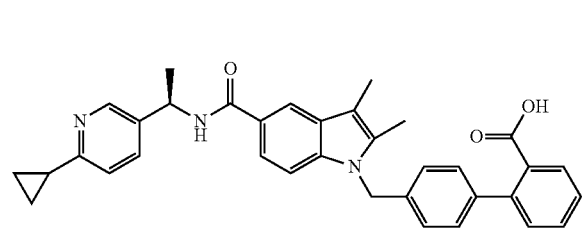 [SMILES: Cc1c(C)n(Cc2ccc(-c3ccccc3C(=O)O)cc2)c2ccc(C(=O)N[C@H](C)c3ccc(C4CC4)nc3)cc12]

The title compound was prepared following the same general protocol as described in Step 9, Example 1. ESI-MS (m/z): 544 [M+H]⁺.

Example 265

(S)-4'-((5-(((1-(4-chloropyridin-2-yl)ethyl)carbamoyl)-2,3-dimethyl-1H-indol-1-yl)methyl)-[1,1'-biphenyl]-2-carboxylic acid

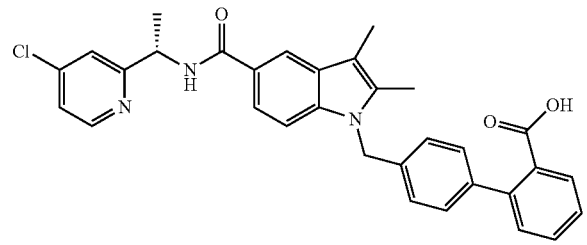 [SMILES: Cc1c(C)n(Cc2ccc(-c3ccccc3C(=O)O)cc2)c2ccc(C(=O)N[C@@H](C)c3cc(Cl)ccn3)cc12]

Step 1: (S)-1-(4-chloropyridin-2-yl)ethanaminium chloride

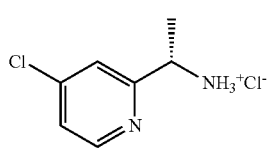

The title compound was prepared following the same general protocol as described in Step 1 and 2, Example 2, using 4-chloropicolinaldehyde instead of 4-t-butylbenzaldehyde.

Step 2: (S)-tert-butyl 4'-((5-(((1-(4-chloropyridin-2-yl)ethyl)carbamoyl)-2,3-dimethyl-1H-indol-1-yl)methyl)-[1,1'-biphenyl]-2-carboxylate

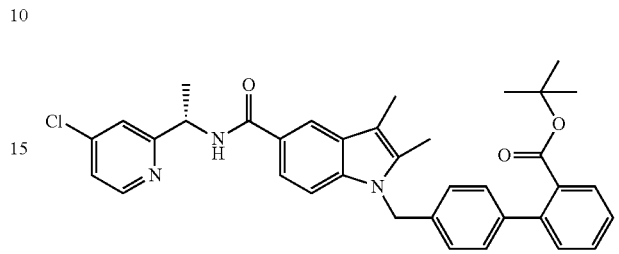

The title compound was prepared following the same general protocol as described in Step 8, Example 1, using (S)-1-(4-chloropyridin-2-yl)ethanaminium chloride instead of (S)-1-(4-bromophenyl)ethanamine.

Step 3: (S)-4'-((5-(((1-(4-chloropyridin-2-yl)ethyl)carbamoyl)-2,3-dimethyl-1H-indol-1-yl)methyl)-[1,1'-biphenyl]-2-carboxylic acid

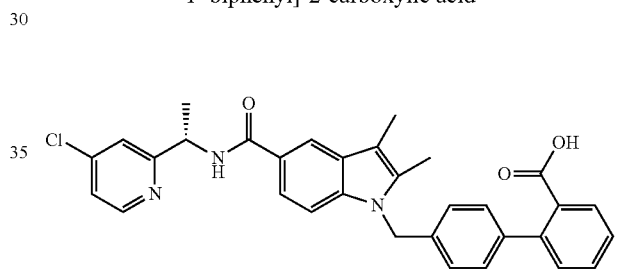

The title compound was prepared following the same general protocol as described in Step 9, Example 1. ESI-MS (m/z): 538 [M+H]⁺.

Example 266

(S)-4'-((5-(((1-(4-cyclopropylpyridin-2-yl)ethyl)carbamoyl)-2,3-dimethyl-1H-indol-1-yl)methyl)-[1,1'-biphenyl]-2-carboxylic acid

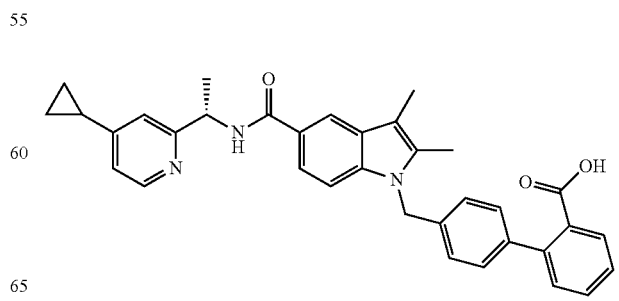

437

Step 1: (S)-tert-butyl 4'-((5-((1-(4-cyclopropylpyridin-2-yl)ethyl)carbamoyl)-2,3-dimethyl-1H-indol-1-yl)methyl)-[1,1'-biphenyl]-2-carboxylate

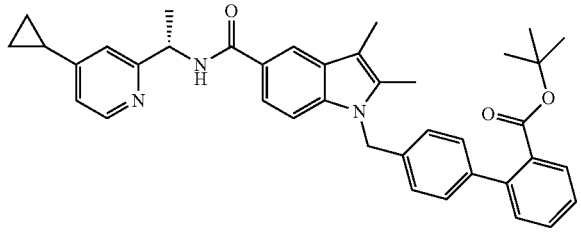 [SMILES: Cc1c(C)n(Cc2ccc(-c3ccccc3C(=O)OC(C)(C)C)cc2)c2ccc(C(=O)N[C@@H](C)c3cc(C4CC4)ccn3)cc12]

The title compound was prepared following the same general protocol as described in Step 1, Example 261, using (S)-tert-butyl 4'-((5-((1-(4-chloropyridin-2-yl)ethyl)carbamoyl)-2,3-dimethyl-1H-indol-1-yl)methyl)-[1,1'-biphenyl]-2-carboxylate instead of (S)-tert-butyl 4'-((5-((1-(5-bromopyridin-2-yl)ethyl)carbamoyl)-2,3-dimethyl-1H-indol-1-yl)methyl)-[1,1'-biphenyl]-2-carboxylate.

Step 2: (S)-4'-((5-((1-(4-cyclopropylpyridin-2-yl)ethyl)carbamoyl)-2,3-dimethyl-1H-indol-1-yl)methyl)-[1,1'-biphenyl]-2-carboxylic acid

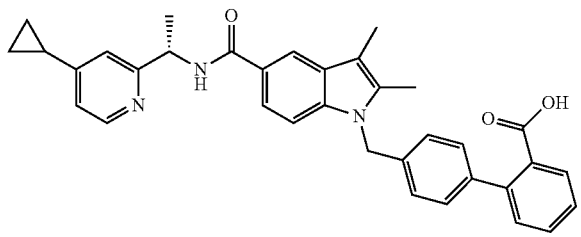

The title compound was prepared following the same general protocol as described in Step 9, Example 1. ESI-MS (m/z): 544 [M+H]+.

Example 267

(S)-4'-((5-(1-(2-bromopyridin-4-yl)ethylcarbamoyl)-2,3-dimethyl-1H-indol-1-yl)methyl)biphenyl-2-carboxylic acid

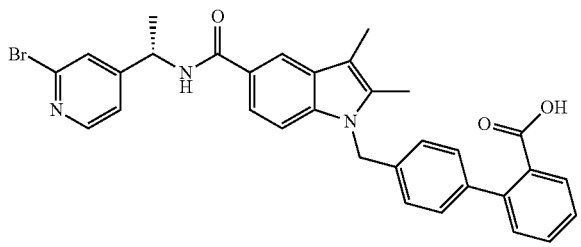

438

Step 1: (S)-1-(2-bromopyridin-4-yl)ethanaminium chloride

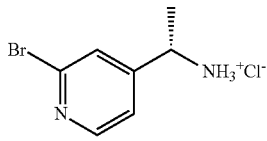

The title compound was prepared following the same general protocol as described in Step 1 and 2, Example 2, using 2-bromoisonicotinaldehyde instead of 4-t-butylbenzaldehyde.

Step 2: (S)-tert-butyl 4'-((5-((1-(2-bromopyridin-4-yl)ethyl)carbamoyl)-2,3-dimethyl-1H-indol-1-yl)methyl)-[1,1'-biphenyl]-2-carboxylate

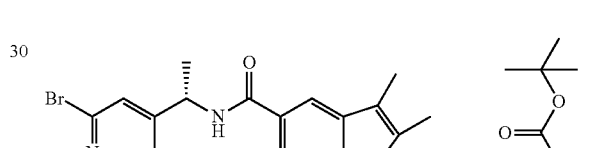
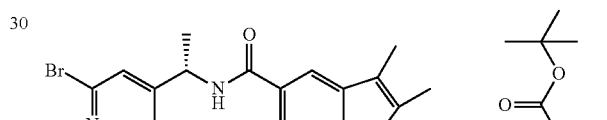
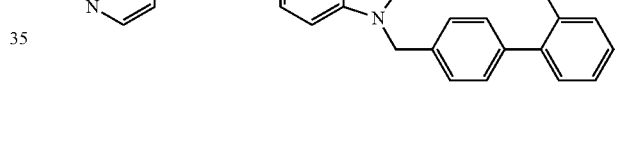

The title compound was prepared following the same general protocol as described in Step 8, Example 1, using (S)-1-(2-bromopyridin-4-yl)ethanaminium chloride instead of (S)-1-(4-bromophenyl)ethanamine.

Step 3: (S)-4'-((5-(1-(2-bromopyridin-4-yl)ethylcarbamoyl)-2,3-dimethyl-1H-indol-1-yl)methyl)biphenyl-2-carboxylic acid

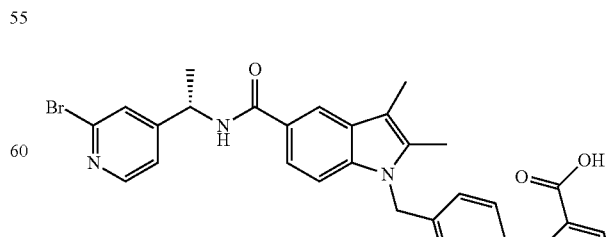

439

The title compound was prepared following the same general protocol as described in Step 9, Example 1. ESI-MS (m/z): 582 [M+H]+.

Example 268

(S)-4'-((5-(1-(2-cyclopropylpyridin-4-yl)ethylcarbamoyl)-2,3-dimethyl-1H-indol-1-yl)methyl)biphenyl-2-carboxylic acid

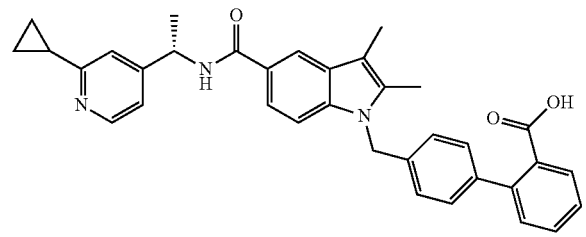 [SMILES: Cc1c(C)n(Cc2ccc(-c3ccccc3C(=O)O)cc2)c2ccc(C(=O)N[C@@H](C)c3ccnc(C4CC4)c3)cc12]

Step 1: (S)-tert-butyl 4'-((5-(((1-(2-cyclopropylpyridin-4-yl)ethyl)carbamoyl)-2,3-dimethyl-1H-indol-1-yl)methyl)-[1,1'-biphenyl]-2-carboxylate

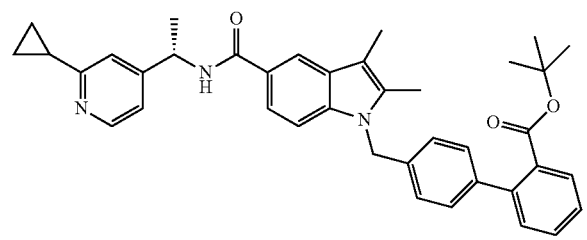 [SMILES: Cc1c(C)n(Cc2ccc(-c3ccccc3C(=O)OC(C)(C)C)cc2)c2ccc(C(=O)N[C@@H](C)c3ccnc(C4CC4)c3)cc12]

The title compound was prepared following the same general protocol as described in Step 1, Example 261, using (S)-tert-butyl 4'-((5-(((1-(2-bromopyridin-4-yl)ethyl)carbamoyl)-2,3-dimethyl-1H-indol-1-yl)methyl)-[1,1'-biphenyl]-2-carboxylate instead of (S)-tert-butyl 4'-((5-((1-(5-bromopyridin-2-yl)ethyl)carbamoyl)-2,3-dimethyl-1H-indol-1-yl)methyl)-[1,1'-biphenyl]-2-carboxylate.

Step 2: (S)-4'-((5-(1-(2-cyclopropylpyridin-4-yl)ethylcarbamoyl)-2,3-dimethyl-1H-indol-1-yl)methyl)biphenyl-2-carboxylic acid

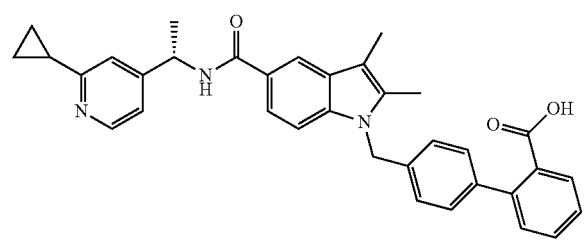 [SMILES: Cc1c(C)n(Cc2ccc(-c3ccccc3C(=O)O)cc2)c2ccc(C(=O)N[C@@H](C)c3ccnc(C4CC4)c3)cc12]

440

The title compound was prepared following the same general protocol as described in Step 9, Example 1. ESI-MS (m/z): 544 [M+H]+.

Example 269

(R)-4'-((5-(1-(2-bromopyridin-4-yl)ethylcarbamoyl)-2,3-dimethyl-1H-indol-1-yl)methyl)biphenyl-2-carboxylic acid

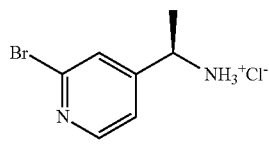

Step 1: (R)-1-(2-bromopyridin-4-yl)ethanaminium chloride

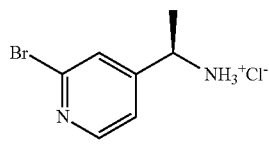

The title compound was prepared following the same general protocol as described in Step 1 and 2, Example 2, using 2-bromoisonicotinaldehyde instead of 4-t-butylbenzaldehyde.

Step 2: (R)-tert-butyl 4'-((5-(((1-(2-bromopyridin-4-yl)ethyl)carbamoyl)-2,3-dimethyl-1H-indol-1-yl)methyl)-[1,1'-biphenyl]-2-carboxylate

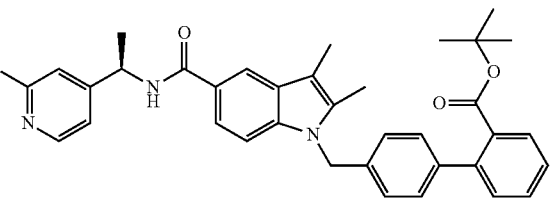

The title compound was prepared following the same general protocol as described in Step 8, Example 1, using (R)-1-

(2-bromopyridin-4-yl)ethanaminium chloride instead of (S)-1-(4-bromophenyl)ethanamine.

Step 3: (R)-4'-((5-(1-(2-bromopyridin-4-yl)ethylcarbamoyl)-2,3-dimethyl-1H-indol-1-yl)methyl)biphenyl-2-carboxylic acid

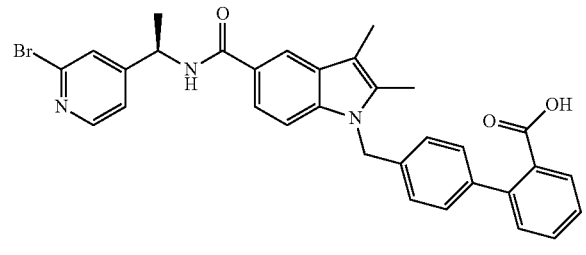 [SMILES: Cc1c(C)n(Cc2ccc(-c3ccccc3C(=O)O)cc2)c2ccc(C(=O)N[C@H](C)c3ccnc(Br)c3)cc12]

The title compound was prepared following the same general protocol as described in Step 9, Example 1. ESI-MS (m/z): 582 [M+H]$^+$.

Example 270

(R)-4'-((5-(1-(2-cyclopropylpyridin-4-yl)ethylcarbamoyl)-2,3-dimethyl-1H-indol-1-yl)methyl)biphenyl-2-carboxylic acid

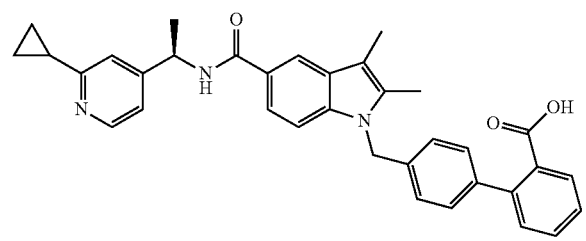 [SMILES: Cc1c(C)n(Cc2ccc(-c3ccccc3C(=O)O)cc2)c2ccc(C(=O)N[C@H](C)c3ccnc(C4CC4)c3)cc12]

Step 1: (R)-tert-butyl 4'-((5-((1-(2-cyclopropylpyridin-4-yl)ethyl)carbamoyl)-2,3-dimethyl-1H-indol-1-yl)methyl)-[1,1'-biphenyl]-2-carboxylate

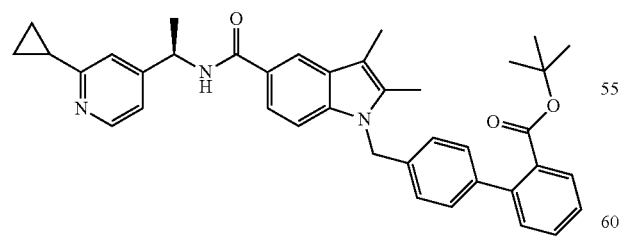

The title compound was prepared following the same general protocol as described in Step 1, Example 261, using (R)-tert-butyl 4'-((5-((1-(2-bromopyridin-4-yl)ethyl)carbamoyl)-2,3-dimethyl-1H-indol-1-yl)methyl)-[1,1'-biphenyl]-2-carboxylate instead of (S)-tert-butyl 4'-((5-((1-(5-bromopyridin-2-yl)ethyl)carbamoyl)-2,3-dimethyl-1H-indol-1-yl)methyl)-[1,1'-biphenyl]-2-carboxylate.

Step 2: (R)-4'-((5-(1-(2-cyclopropylpyridin-4-yl)ethylcarbamoyl)-2,3-dimethyl-1H-indol-1-yl)methyl)biphenyl-2-carboxylic acid

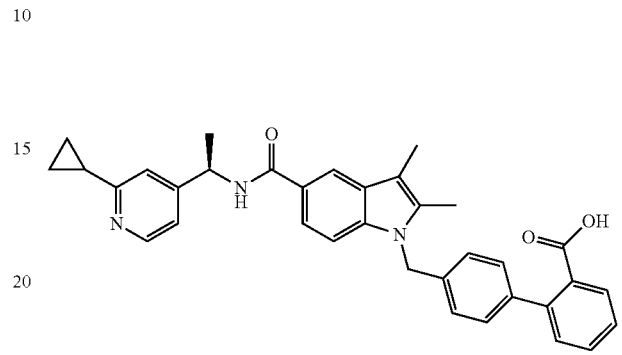

The title compound was prepared following the same general protocol as described in Step 9, Example 1. ESI-MS (m/z): 544 [M+H]$^+$.

Example 271

(R)-4'-((5-(1-(6-bromopyridin-2-yl)ethylcarbamoyl)-2,3-dimethyl-1H-indol-1-yl)methyl)biphenyl-2-carboxylic acid

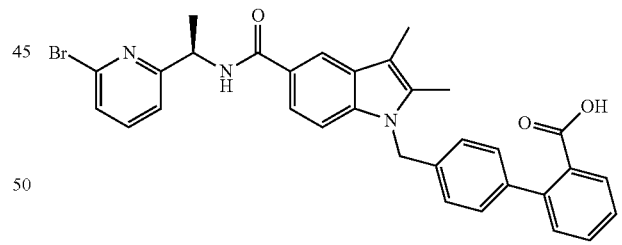

Step 1: (R)-1-(6-bromopyridin-2-yl)ethanaminium chloride

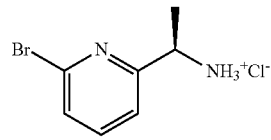

443

The title compound was prepared following the same general protocol as described in Step 1 and 2, Example 2, using 6-bromopicolinaldehyde instead of 4-t-butylbenzaldehyde.

Step 2: (R)-tert-butyl 4'-((5-((1-(6-bromopyridin-2-yl)ethyl)carbamoyl)-2,3-dimethyl-1H-indol-1-yl)methyl)-[1,1'-biphenyl]-2-carboxylate

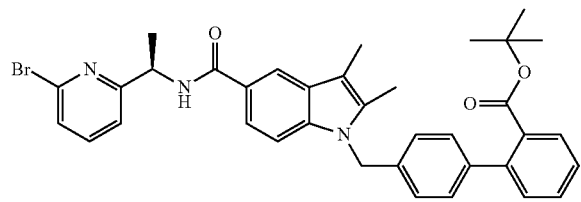 [SMILES: Cc1c(C)n(Cc2ccc(-c3ccccc3C(=O)OC(C)(C)C)cc2)c2ccc(C(=O)N[C@H](C)c3cccc(Br)n3)cc12]

The title compound was prepared following the same general protocol as described in Step 8, Example 1, using (R)-1-(6-bromopyridin-2-yl)ethanaminium chloride instead of (S)-1-(4-bromophenyl)ethanamine.

Step 3: (R)-4'-((5-(1-(6-bromopyridin-2-yl)ethylcarbamoyl)-2,3-dimethyl-1H-indol-1-yl)methyl)biphenyl-2-carboxylic acid

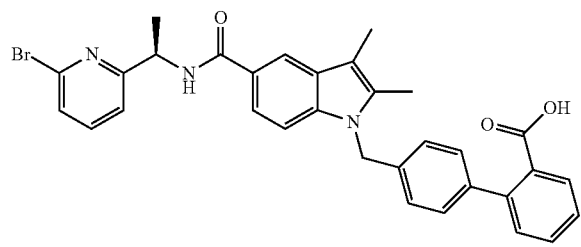

The title compound was prepared following the same general protocol as described in Step 9, Example 1. ESI-MS (m/z): 582 [M+H]+.

Example 272

4'-((5-(1-(6-cyclopropylpyridin-2-yl)ethylcarbamoyl)-2,3-dimethyl-1H-indol-1-yl)methyl)biphenyl-2-carboxylic acid

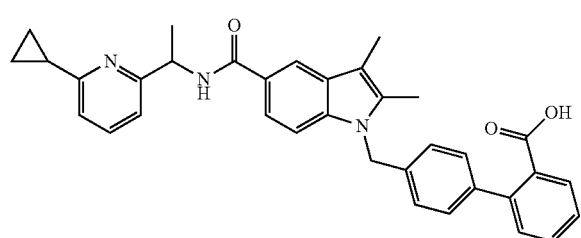

444

Step 1: 1-(6-bromopyridin-2-yl)ethanaminium chloride

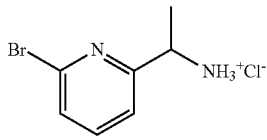

The title compound was prepared following the same general protocol as described in Step 1 and 2, Example 2, using 6-bromopicolinaldehyde instead of 4-t-butylbenzaldehyde.

Step 2: tert-butyl 4'-((5-((1-(6-bromopyridin-2-yl)ethyl)carbamoyl)-2,3-dimethyl-1H-indol-1-yl)methyl)-[1,1'-biphenyl]-2-carboxylate

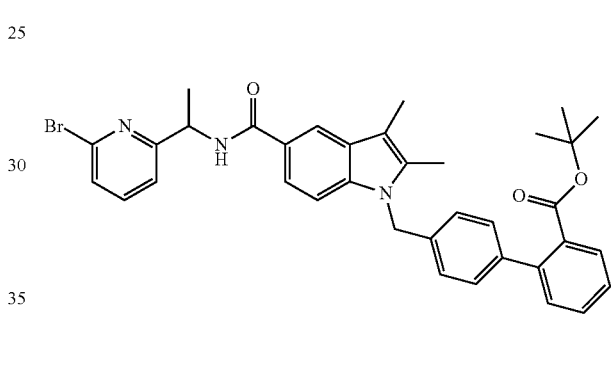

The title compound was prepared following the same general protocol as described in Step 8, Example 1, using (R)-1-(6-chloropyridin-3-yl)ethanaminium chloride instead of (S)-1-(4-bromophenyl)ethanamine.

Step 3: tert-butyl 4'-((5-((1-(6-cyclopropylpyridin-2-yl)ethyl)carbamoyl)-2,3-dimethyl-1H-indol-1-yl)methyl)-[1,1'-biphenyl]-2-carboxylate

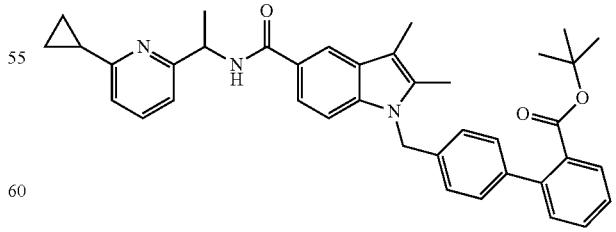

The title compound was prepared following the same general protocol as described in Step 1, Example 261, using tert-butyl 4'-((5-((1-(6-bromopyridin-2-yl)ethyl)carbamoyl)-2,3-dimethyl-1H-indol-1-yl)methyl)-[1,1'-biphenyl]-2-carboxylate instead of (S)-tert-butyl 4'-((5-((1-(5-bromopyridin-2-yl)ethyl)carbamoyl)-2,3-dimethyl-1H-indol-1-yl)methyl)-[1,1'-biphenyl]-2-carboxylate.

Step 4: 4'-((5-((1-(6-cyclopropylpyridin-2-yl)ethyl)carbamoyl)-2,3-dimethyl-1H-indol-1-yl)methyl)-[1,1'-biphenyl]-2-carboxylic acid

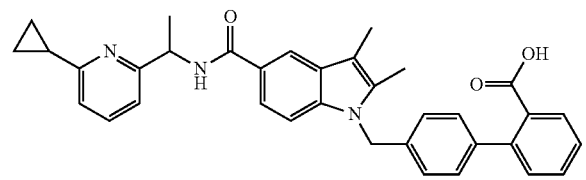 [SMILES: Cc1c(C)n(Cc2ccc(-c3ccccc3C(=O)O)cc2)c2ccc(C(=O)NC(C)c3cccc(C4CC4)n3)cc12]

The title compound was prepared following the same general protocol as described in Step 9, Example 1. ESI-MS (m/z): 544 [M+H]$^+$.

Example 273

(S)-4'-((5-(1-(6-bromopyridin-2-yl)ethylcarbamoyl)-2,3-dimethyl-1H-indol-1-yl)methyl)biphenyl-2-carboxylic acid

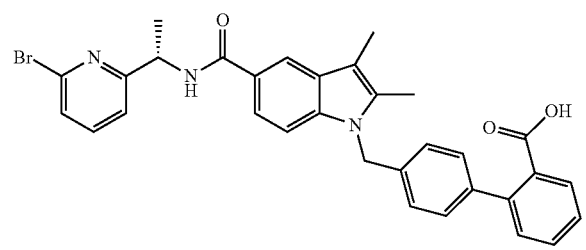

Step 1: (S)-1-(6-bromopyridin-2-yl)ethanaminium chloride

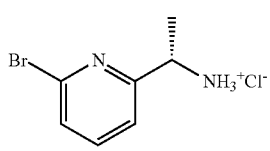

The title compound was prepared following the same general protocol as described in Step 1 and 2, Example 2, using 6-bromopicolinaldehyde instead of 4-t-butylbenzaldehyde.

Step 2: (S)-tert-butyl 4'-((5-((1-(6-bromopyridin-2-yl)ethyl)carbamoyl)-2,3-dimethyl-1H-indol-1-yl)methyl)-[1,1'-biphenyl]-2-carboxylate

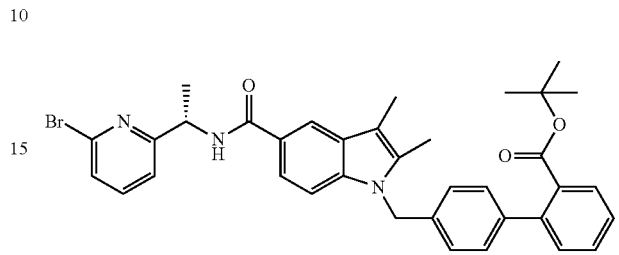

The title compound was prepared following the same general protocol as described in Step 8, Example 1, using (S)-1-(6-bromopyridin-2-yl)ethanaminium chloride instead of (S)-1-(4-bromophenyl)ethanamine.

Step 3: (S)-4'-((5-(1-(6-bromopyridin-2-yl)ethylcarbamoyl)-2,3-dimethyl-1H-indol-1-yl)methyl)biphenyl-2-carboxylic acid

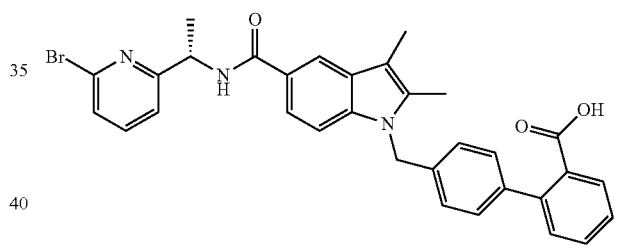

The title compound was prepared following the same general protocol as described in Step 9, Example 1. ESI-MS (m/z): 582 [M+H]$^+$.

Example 274

(S)-4'-((5-(1-(6-cyclopropylpyridin-2-yl)ethylcarbamoyl)-2,3-dimethyl-1H-indol-1-yl)methyl)biphenyl-2-carboxylic acid

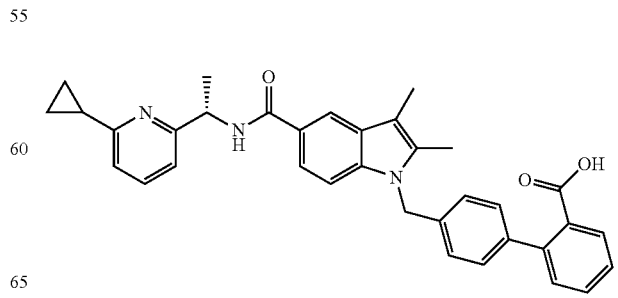

447

Step 1: (S)-tert-butyl 4'-((5-((1-(6-cyclopropylpyridin-2-yl)ethyl)carbamoyl)-2,3-dimethyl-1H-indol-1-yl)methyl)-[1,1'-biphenyl]-2-carboxylate

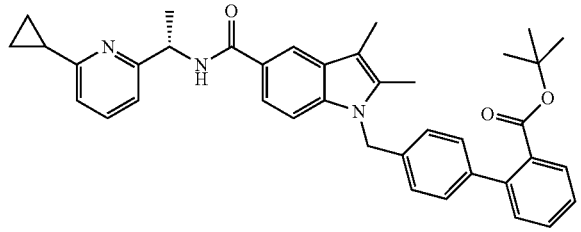 [SMILES: Cc1c(C)n(Cc2ccc(-c3ccccc3C(=O)OC(C)(C)C)cc2)c2ccc(C(=O)N[C@@H](C)c3cccc(C4CC4)n3)cc12]

The title compound was prepared following the same general protocol as described in Step 1, Example 261, using (S)-tert-butyl 4'-((5-((1-(6-bromopyridin-2-yl)ethyl)carbamoyl)-2,3-dimethyl-1H-indol-1-yl)methyl)-[1,1'-biphenyl]-2-carboxylate instead of (S)-tert-butyl 4'-((5-((1-(5-bromopyridin-2-yl)ethyl)carbamoyl)-2,3-dimethyl-1H-indol-1-yl)methyl)-[1,1'-biphenyl]-2-carboxylate.

Step 2: (S)-4'-((5-(1-(6-cyclopropylpyridin-2-yl)ethylcarbamoyl)-2,3-dimethyl-1H-indol-1-yl)methyl)biphenyl-2-carboxylic acid

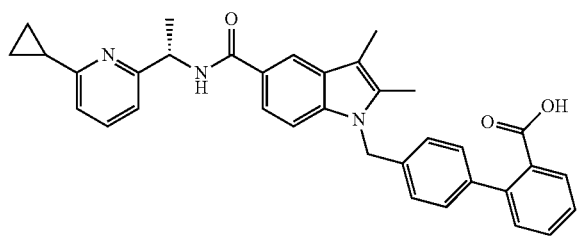

The title compound was prepared following the same general protocol as described in Step 9, Example 1. ESI-MS (m/z): 544 [M+H]$^+$.

Example 275

4'-((5-(1-(5-bromopyridin-3-yl)ethylcarbamoyl)-2,3-dimethyl-1H-indol-1-yl)methyl)biphenyl-2-carboxylic acid

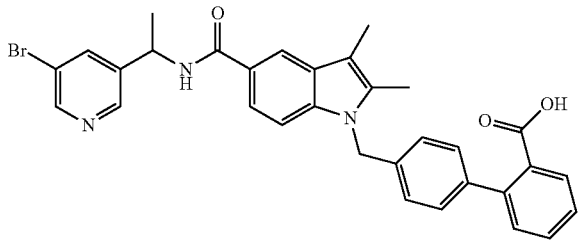 [SMILES: Cc1c(C)n(Cc2ccc(-c3ccccc3C(=O)O)cc2)c2ccc(C(=O)NC(C)c3cncc(Br)c3)cc12]

448

Step 1: 1-(5-bromopyridin-3-yl)ethanaminium chloride

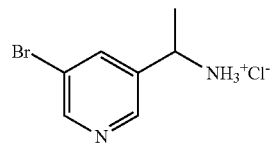

The title compound was prepared following the same general protocol as described in Step 1 and 2, Example 2, using 5-bromonicotinaldehyde instead of 4-t-butylbenzaldehyde.

Step 2: tert-butyl 4'-((5-((1-(5-bromopyridin-3-yl)ethyl)carbamoyl)-2,3-dimethyl-1H-indol-1-yl)methyl)-[1,1'-biphenyl]-2-carboxylate

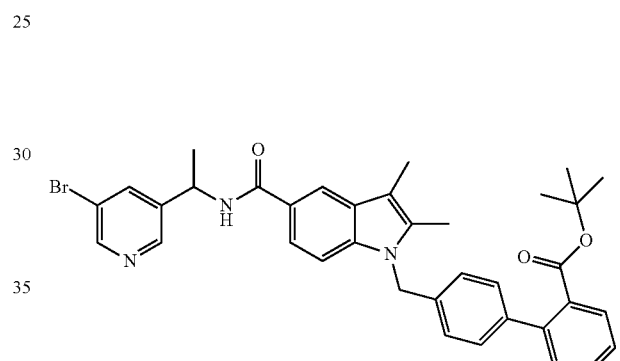

The title compound was prepared following the same general protocol as described in Step 8, Example 1, using 1-(5-bromopyridin-3-yl)ethanaminium chloride instead of (S)-1-(4-bromophenyl)ethanamine.

Step 3: 4'-((5-(1-(5-bromopyridin-3-yl)ethylcarbamoyl)-2,3-dimethyl-1H-indol-1-yl)methyl)biphenyl-2-carboxylic acid

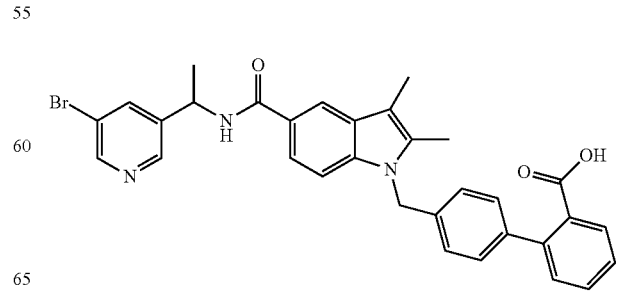

The title compound was prepared following the same general protocol as described in Step 9, Example 1. ESI-MS (m/z): 582 [M+H]⁺.

Example 276

(R)-4'-((2,3-dimethyl-5-(1-(4-(methylsulfonyl)phenyl)ethylcarbamoyl)-1H-indol-1-yl)methyl)biphenyl-2-carboxylic acid

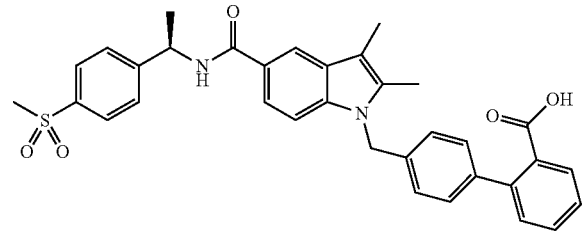 [SMILES: Cc1c(C)n(Cc2ccc(-c3ccccc3C(=O)O)cc2)c2ccc(C(=O)N[C@H](C)c3ccc(S(C)(=O)=O)cc3)cc12]

Step 1:
(R)-1-(4-(methylsulfonyl)phenyl)ethanaminium chloride

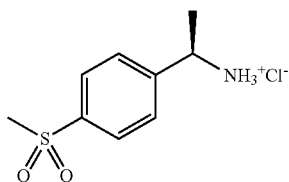

The title compound was prepared following the same general protocol as described in Step 1 and 2, Example 2, using 4-(methylsulfonyl)benzaldehyde instead of 4-t-butylbenzaldehyde.

Step 2: (R)-tert-butyl 4'-((2,3-dimethyl-5-((1-(4-(methylsulfonyl)phenyl)ethyl)carbamoyl)-1H-indol-1-yl)methyl)-[1,1'-biphenyl]-2-carboxylate

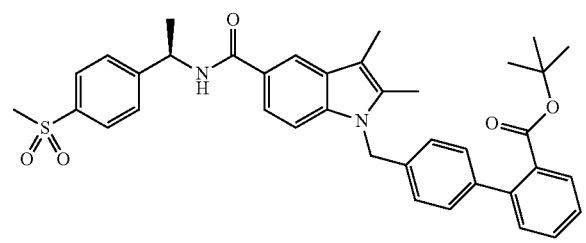 [SMILES: Cc1c(C)n(Cc2ccc(-c3ccccc3C(=O)OC(C)(C)C)cc2)c2ccc(C(=O)N[C@H](C)c3ccc(S(C)(=O)=O)cc3)cc12]

The title compound was prepared following the same general protocol as described in Step 8, Example 1, using (R)-1-(4-(methylsulfonyl)phenyl)ethanaminium chloride instead of (S)-1-(4-bromophenyl)ethanamine.

Step 3: (R)-4'-((2,3-dimethyl-5-(1-(4-(methylsulfonyl)phenyl)ethylcarbamoyl)-1H-indol-1-yl)methyl)biphenyl-2-carboxylic acid

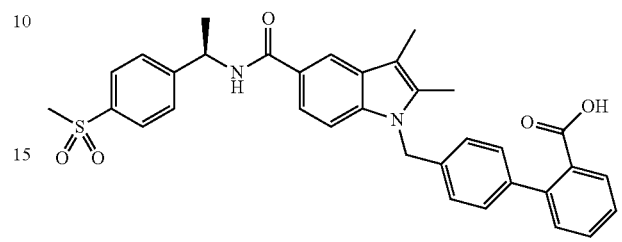

The title compound was prepared following the same general protocol as described in Step 9, Example 1. ESI-MS (m/z): 581 [M+H]⁺.

Example 277

(S)-1-((2'-cyano-[1,1'-biphenyl]-4-yl)methyl)-2,3-dimethyl-N-(1-(4-(trifluoromethyl)phenyl)ethyl)-1H-indole-5-carboxamide

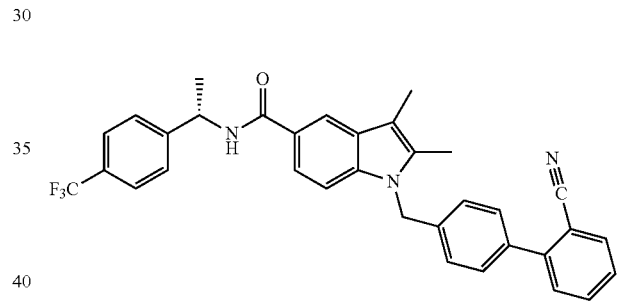

The title compound was prepared following the same protocol as described in Step 5, Example 34, using (S)-1-(4-(trifluoromethyl)phenyl)ethanamine instead of the 1-phenyl propan-1-amine. ESI-MS (m/z): 552 [M+H]⁺.

Example 278

(S)-1-((2'-cyano-[1,1'-biphenyl]-4-yl)methyl)-N-(1-(4-isopropoxyphenyl)ethyl)-2,3-dimethyl-1H-indole-5-carboxamide

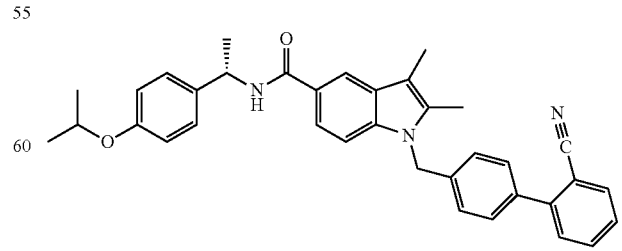

The title compound was prepared following the same protocol as described in Step 5, Example 34, using (S)-1-(4- isopropoxyphenyl)ethanamine instead of the 1-phenyl propan-1-amine. ESI-MS (m/z): 542 [M+H]⁺.

Example 279

(S)-1-((2'-cyano-[1,1'-biphenyl]-4-yl)methyl)-2,3-dimethyl-N-(1-(4-(trifluoromethoxy)phenyl)ethyl)-1H-indole-5-carboxamide

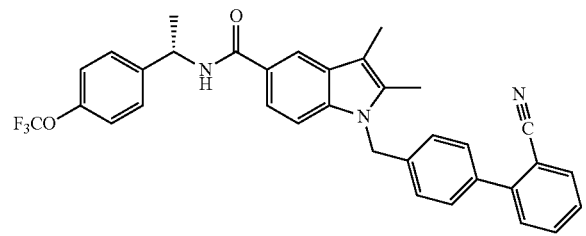 [SMILES: Cc1c(C)n(Cc2ccc(-c3ccccc3C#N)cc2)c2ccc(C(=O)N[C@@H](C)c3ccc(OC(F)(F)F)cc3)cc12]

The title compound was prepared following the same protocol as described in Step 5, Example 34, using (S)-1-(4-(trifluoromethoxy)phenyl)ethanamine instead of the 1-phenyl propan-1-amine. ESI-MS (m/z): 568 [M+H]⁺.

Example 280

(S)-1-((2'-cyano-[1,1'-biphenyl]-4-yl)methyl)-N-(1-(3-ethoxyphenyl)ethyl)-2,3-dimethyl-1H-indole-5-carboxamide

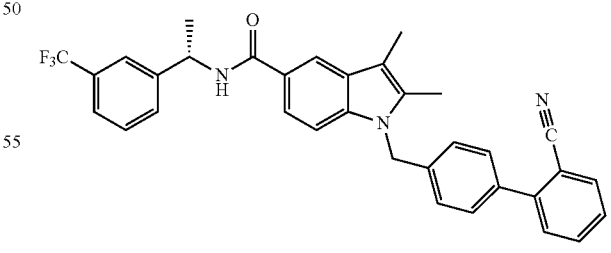

The title compound was prepared following the same protocol as described in Step 5, Example 34, using (S)-1-(3- ethoxyphenyl)ethanamine instead of the 1-phenyl propan-1-amine. ESI-MS (m/z): 528 [M+H]⁺.

Example 281

(S)—N-(1-(3-chlorophenyl)ethyl)-1-((2'-cyano-[1,1'-biphenyl]-4-yl)methyl)-2,3-dimethyl-1H-indole-5-carboxamide

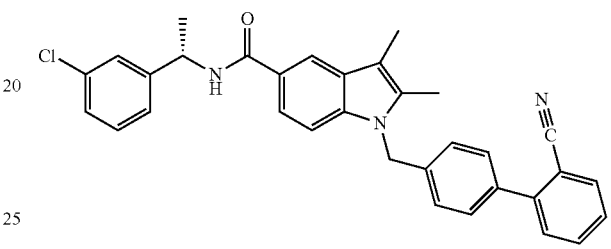

The title compound was prepared following the same protocol as described in Step 5, Example 34, using (S)-1-(3-chlorophenyl)ethanamine instead of the 1-phenyl propan-1-amine. ESI-MS (m/z): 518 [M+H]⁺.

Example 282

(S)-1-((2'-cyano-[1,1'-biphenyl]-4-yl)methyl)-2,3-dimethyl-N-(1-(3-(trifluoromethyl)phenyl)ethyl)-1H-indole-5-carboxamide The title compound was prepared following the same protocol as described in Step 5, Example 34, using (S)-1-(3-

(trifluoromethyl)phenyl)ethanamine instead of the 1-phenyl propan-1-amine. ESI-MS (m/z): 552 [M+H]⁺.

Example 283

(S)—N-(1-(4-chlorophenyl)ethyl)-1-((2'-cyano-[1,1'-biphenyl]-4-yl)methyl)-2,3-dimethyl-1H-indole-5-carboxamide

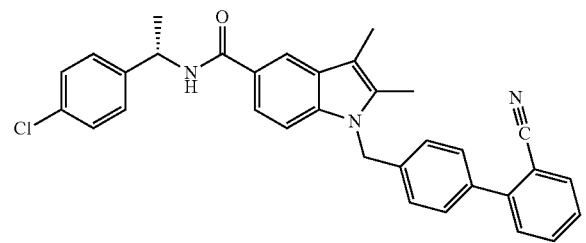

The title compound was prepared following the same protocol as described in Step 5, Example 34, using (S)-1-(4-chlorophenyl)ethanamine instead of the 1-phenyl propan-1-amine. ESI-MS (m/z): 518 [M+H]⁺.

Example 284

(S)—N-(1-(3-bromophenyl)ethyl)-1-((2'-cyano-[1,1'-biphenyl]-4-yl)methyl)-2,3-dimethyl-1H-indole-5-carboxamide

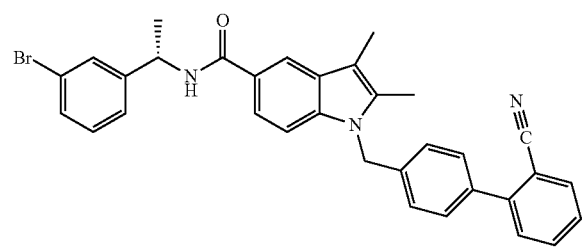 [SMILES: Cc1c(C)n(Cc2ccc(-c3ccccc3C#N)cc2)c2ccc(C(=O)N[C@@H](C)c3cccc(Cl)c3)cc12]

The title compound was prepared following the same protocol as described in Step 5, Example 34, using (S)-1-(3-bromophenyl)ethanamine instead of the 1-phenyl propan-1-amine. ESI-MS (m/z): 562 [M+H]⁺.

Example 285

(S)-1-((2'-cyano-[1,1'-biphenyl]-4-yl)methyl)-N-(1-(4-methoxyphenyl)ethyl)-2,3-dimethyl-1H-indole-5-carboxamide

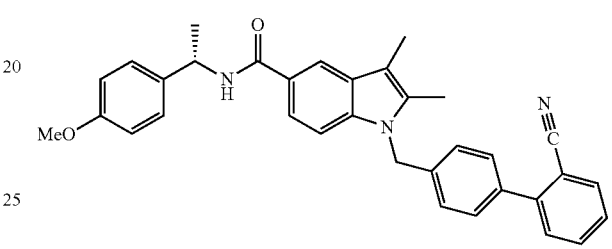

The title compound was prepared following the same protocol as described in Step 5, Example 34, using (S)-1-(4-methoxyphenyl)ethanamine instead of the 1-phenyl propan-1-amine. ESI-MS (m/z): 514 [M+H]⁺.

Example 286

(S)-1-((2'-cyano-[1,1'-biphenyl]-4-yl)methyl)-N-(1-(2,4-difluorophenyl)ethyl)-2,3-dimethyl-1H-indole-5-carboxamide

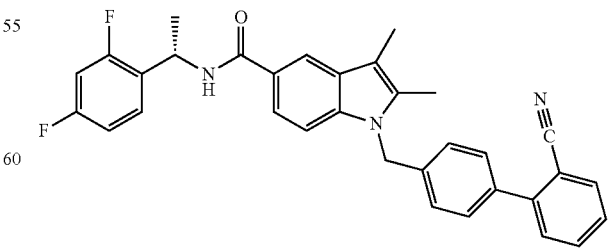

The title compound was prepared following the same protocol as described in Step 5, Example 34, using (S)-1-(2,4- difluorophenyl)ethanamine instead of the 1-phenyl propan-1-amine. ESI-MS (m/z): 520 [M+H]+.

Example 287

(S)—N-(1-(2-chlorophenyl)ethyl)-1-((2'-cyano-[1,1'-biphenyl]-4-yl)methyl)-2,3-dimethyl-1H-indole-5-carboxamide

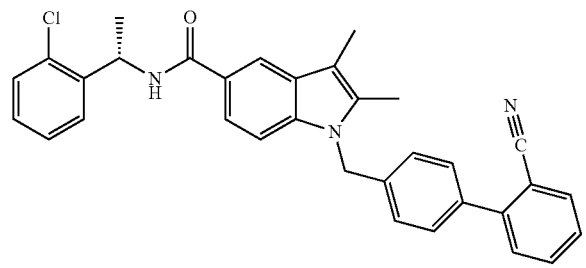 [SMILES: Cc1c(C)n(Cc2ccc(-c3ccccc3C#N)cc2)c2ccc(C(=O)N[C@@H](C)c3ccccc3Cl)cc12]

The title compound was prepared following the same protocol as described in Step 5, Example 34, using (S)-1-(2-chlorophenyl)ethanamine instead of the 1-phenyl propan-1-amine. ESI-MS (m/z): 518 [M+H]+.

Example 288

(S)-1-((2'-cyano-[1,1'-biphenyl]-4-yl)methyl)-2,3-dimethyl-N-(1-(p-tolyl)ethyl)-1H-indole-5-carboxamide

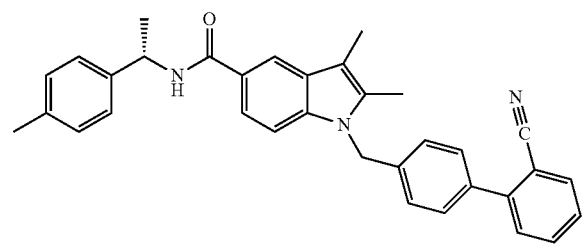 [SMILES: Cc1ccc([C@H](C)NC(=O)c2ccc3c(c2)c(C)c(C)n3Cc2ccc(-c3ccccc3C#N)cc2)cc1]

The title compound was prepared following the same protocol as described in Step 5, Example 34, using (S)-1-(4-methylphenyl)ethanamine instead of the 1-phenyl propan-1-amine. ESI-MS (m/z): 498 [M+H]+.

Example 289

(S)-1-((2'-cyano-[1,1'-biphenyl]-4-yl)methyl)-N-(1-(4-ethylphenyl)ethyl)-2,3-dimethyl-1H-indole-5-carboxamide

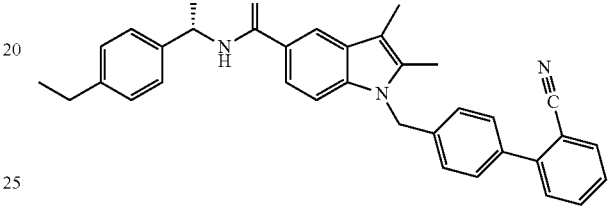

The title compound was prepared following the same protocol as described in Step 5, Example 34, using (S)-1-(4-ethylphenyl)ethanamine instead of the 1-phenyl propan-1-amine. ESI-MS (m/z): 512 [M+H]+.

Example 290

(S)-1-((2'-cyano-[1,1'-biphenyl]-4-yl)methyl)-N-(1-(3,4-dichlorophenyl)ethyl)-2,3-dimethyl-1H-indole-5-carboxamide

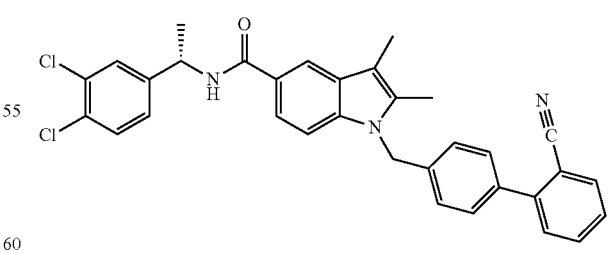

The title compound was prepared following the same protocol as described in Step 5, Example 34, using (S)-1-(3,4- dichlorophenyl)ethanamine instead of the 1-phenyl propan-1-amine. ESI-MS (m/z): 552 [M+H]+.

Example 291

(S)-1-((2'-cyano-[1,1'-biphenyl]-4-yl)methyl)-2,3-dimethyl-N-(1-phenylethyl)-1H-indole-5-carboxamide

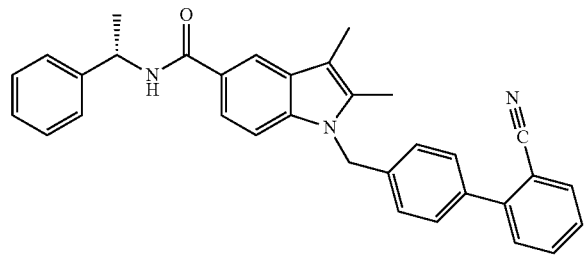 [SMILES: Cc1c(C)n(Cc2ccc(-c3ccccc3C#N)cc2)c2ccc(C(=O)N[C@@H](C)c3ccccc3)cc12]

The title compound was prepared following the same protocol as described in Step 5, Example 34, using (S)-1-phenylethanamine instead of the 1-phenyl propan-1-amine. ESI-MS (m/z): 484 [M+H]+.

Example 292

(S)-1-((2'-cyano-[1,1'-biphenyl]-4-yl)methyl)-N-(1-(2-methoxyphenyl)ethyl)-2,3-dimethyl-1H-indole-5-carboxamide

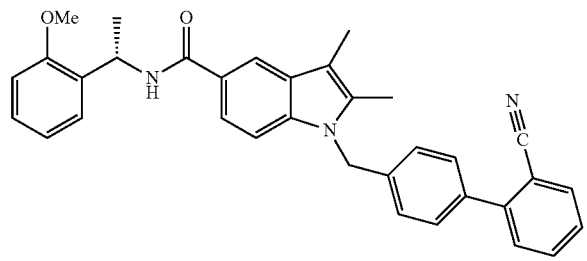 [SMILES: COc1ccccc1[C@H](C)NC(=O)c1ccc2c(c1)c(C)c(C)n2Cc1ccc(-c2ccccc2C#N)cc1]

The title compound was prepared following the same protocol as described in Step 5, Example 34, using (S)-1-(2-methoxyphenyl)ethanamine instead of the 1-phenyl propan-1-amine. ESI-MS (m/z): 514 [M+H]+.

Example 293

(S)-1-((2'-cyano-[1,1'-biphenyl]-4-yl)methyl)-N-(1-(3-fluorophenyl)ethyl)-2,3-dimethyl-1H-indole-5-carboxamide

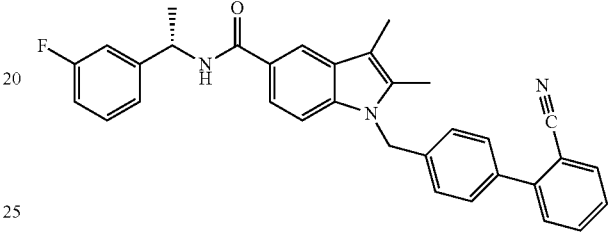

The title compound was prepared following the same protocol as described in Step 5, Example 34, using (S)-1-(3-fluorophenyl)ethanamine instead of the 1-phenyl propan-1-amine. ESI-MS (m/z): 502 [M+H]+.

Example 294

4'-((2,3-Dimethyl-5-(((1R,2S)-2-phenylcyclopropyl)carbamoyl)-1H-indol-1-yl)methyl)-[1,1'-biphenyl]-2-carboxylic acid

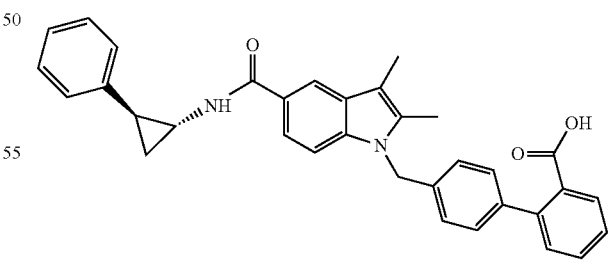

The title compound was prepared following the same general protocol as described in Step 8-9, Example 1, using (1R,2S)-2-phenylcyclopropanamine hydrochloride and 1-((2'-(tert-butoxycarbonyl)-[1,1'-biphenyl]-4-yl)methyl)-2,3-dimethyl-1H-indole-5-carboxylic acid. ESI-MS (m/z): 515 [M+H]$^+$.

Example 295

(S)-4'-((2,3-Dimethyl-5-((1-(m-tolyl)ethyl)carbamoyl)-1H-indol-1-yl)methyl)-[1,1'-biphenyl]-2-carboxylic acid

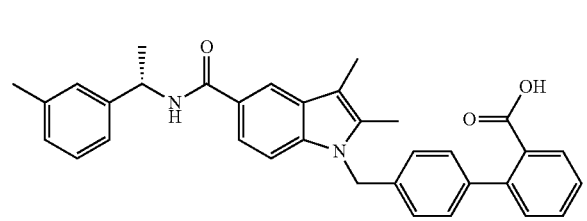 [SMILES: Cc1cccc([C@H](C)NC(=O)c2ccc3c(c2)c(C)c(C)n3Cc2ccc(-c3ccccc3C(=O)O)cc2)c1]

Step 1: (S)-tert-Butyl 4'-((2,3-dimethyl-5-((1-(m-tolyl)ethyl)carbamoyl)-1H-indol-1-yl)methyl)-[1,1'-biphenyl]-2-carboxylate

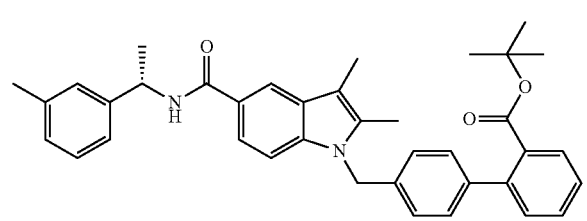 [SMILES: Cc1cccc([C@H](C)NC(=O)c2ccc3c(c2)c(C)c(C)n3Cc2ccc(-c3ccccc3C(=O)OC(C)(C)C)cc2)c1]

A mixture of (S)-tert-butyl 4'-((5-((1-(3-bromophenyl)ethyl)carbamoyl)-2,3-dimethyl-1H-indol-1-yl)methyl)-[1,1'-biphenyl]-2-carboxylate (24 mg, 0.038 mmol), trimethylboroxine (10 μL, 0.072 mmol), Pd(PPh$_3$)$_4$ (11 mg, 0.0095 mmol) and K$_2$CO$_3$ (15 mg, 0.11 mmol) in Dioxane (0.7 ml) were heated in a Biotage Microwave reactor at 100° C. for 2 h. The solvent was removed and the residue was purified by reverse phase prep-HPLC (MeOH/Acetonitrile/water) to obtain the title compound.

Step 2: (S)-4'-((2,3-Dimethyl-5-((1-(m-tolyl)ethyl)carbamoyl)-1H-indol-1-yl)methyl)-[1,1'-biphenyl]-2-carboxylic acid

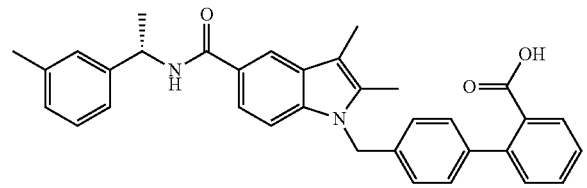 [SMILES: Cc1cccc([C@H](C)NC(=O)c2ccc3c(c2)c(C)c(C)n3Cc2ccc(-c3ccccc3C(=O)O)cc2)c1]

The title compound was prepared following the same general protocol as described in Step 9, Example 1. ESI-MS (m/z): 517 [M+H]$^+$.

Example 296

(R)-4'-((5-((1-(3-Bromophenyl)ethyl)carbamoyl)-2,3-dimethyl-1H-indol-1-yl)methyl)-[1,1'-biphenyl]-2-carboxylic acid

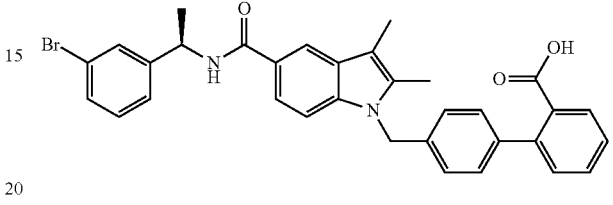

Step 1: (R)-tert-Butyl 4'-((5-((1-(3-bromophenyl)ethyl)carbamoyl)-2,3-dimethyl-1H-indol-1-yl)methyl)-[1,1'-biphenyl]-2-carboxylate

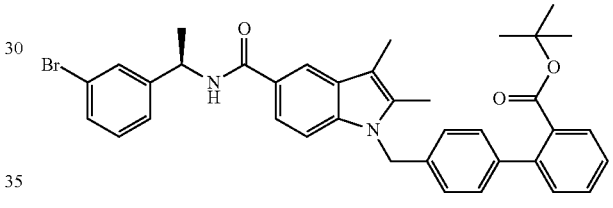

The title compound was prepared following the same general protocol as described in Step 8, Example 1, using (R)-1-(3-bromophenyl)ethanamine instead of (S)-1-(4-bromophenyl)ethanamine.

Step 2: (R)-4'-((5-((1-(3-Bromophenyl)ethyl)carbamoyl)-2,3-dimethyl-1H-indol-1-yl)methyl)-[1,1'-biphenyl]-2-carboxylic acid The title compound was prepared following the same general protocol as described in Step 9, Example 1. ESI-MS (m/z): 581/583 [M+H]$^+$.

Example 297

(S)-4'-((5-((1-(3-Cyclopropylphenyl)ethyl)carbamoyl)-2,3-dimethyl-1H-indol-1-yl)methyl)-[1,1'-biphenyl]-2-carboxylic acid

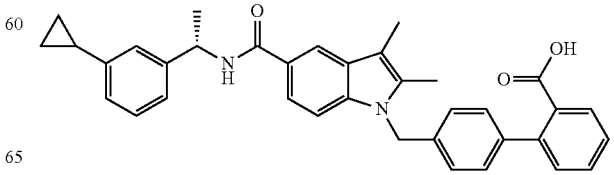

461

Step 1: (S)-tert-Butyl 4'-((5-((1-(3-cyclopropylphenyl)ethyl)carbamoyl)-2,3-dimethyl-1H-indol-1-yl)methyl)-[1,1'-biphenyl]-2-carboxylate

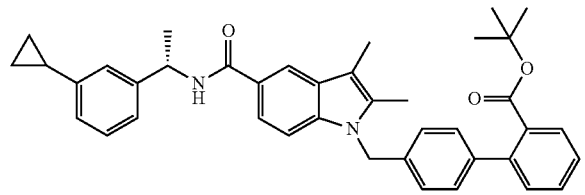 [SMILES: Cc1c(C)n(Cc2ccc(-c3ccccc3C(=O)OC(C)(C)C)cc2)c2ccc(C(=O)N[C@@H](C)c3cccc(C4CC4)c3)cc12]

A mixture of (S)-tert-butyl 4'-((5-((1-(3-bromophenyl)ethyl)carbamoyl)-2,3-dimethyl-1H-indol-1-yl)methyl)-[1,1'-biphenyl]-2-carboxylate (24 mg, 0.038 mmol), cyclopropylboronic acid (7 mg, 0.081 mmol), Palladium(II) acetate (3.5 mg, 0.016 mmol) tricyclohexylphosphine (9 mg, 0.032 mmol) and potassium phosphate, tribasic, (23 mg, 0.11 mmol) in toluene (0.7 mL) and water (0.07 mL) was heated at 100° C. for 1 h in a Biotage Microwave reactor. The solvent was removed; the residue was filtered and purified by preparative HPLC to yield the title compound as a white solid.

Step 2: (S)-4'-((5-((1-(3-Cyclopropylphenyl)ethyl)carbamoyl)-2,3-dimethyl-1H-indol-1-yl)methyl)-[1,1'-biphenyl]-2-carboxylic acid

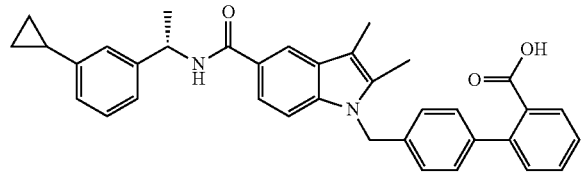 [SMILES: Cc1c(C)n(Cc2ccc(-c3ccccc3C(=O)O)cc2)c2ccc(C(=O)N[C@@H](C)c3cccc(C4CC4)c3)cc12]

The title compound was prepared following the same general protocol as described in Step 9, Example 1. ESI-MS (m/z): 543 [M+H]$^+$.

Example 298

(S)-4'-((5-((1-(2-Fluoro-4-(trifluoromethyl)phenyl)ethyl)carbamoyl)-2,3-dimethyl-1H-indol-1-yl)methyl)-[1,1'-biphenyl]-2-carboxylic acid

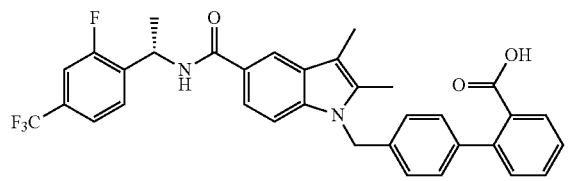 [SMILES: Cc1c(C)n(Cc2ccc(-c3ccccc3C(=O)O)cc2)c2ccc(C(=O)N[C@@H](C)c3ccc(C(F)(F)F)cc3F)cc12]

462

Step 1: (S)-tert-Butyl 4'-((5-((1-(2-fluoro-4-(trifluoromethyl)phenyl)ethyl)carbamoyl)-2,3-dimethyl-1H-indol-1-yl)methyl)-[1,1'-biphenyl]-2-carboxylate

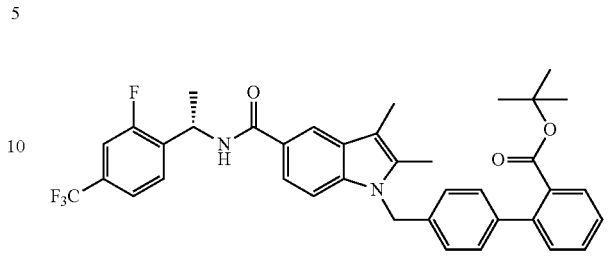

The title compound was prepared following the same general protocol as described in Step 8, Example 1, using (S)-1-(2-fluoro-4-(trifluoromethyl)phenyl)ethanamine instead of (S)-1-(4-bromophenyl)ethanamine Step 2: (S)-4'-((5-((1-(2-Fluoro-4-(trifluoromethyl)phenyl)ethyl)carbamoyl)-2,3-dimethyl-1H-indol-1-yl)methyl)-[1,1'-biphenyl]-2-carboxylic acid

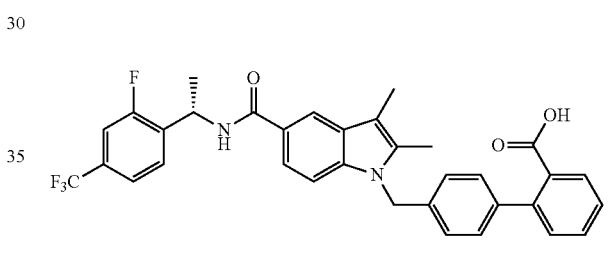

The title compound was prepared following the same general protocol as described in Step 9, Example 1. ESI-MS (m/z): 589 [M+H]$^+$.

Example 299

(S)-4'-((5-((1-(2-Fluoro-3-(trifluoromethyl)phenyl)ethyl)carbamoyl)-2,3-dimethyl-1H-indol-1-yl)methyl)-[1,1'-biphenyl]-2-carboxylic acid

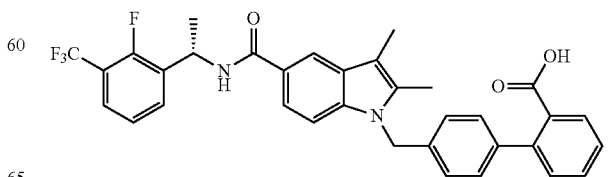

463

Step 1: (S)-tert-Butyl 4'-((5-((1-(2-fluoro-3-(trifluoromethyl)phenyl)ethyl)carbamoyl)-2,3-dimethyl-1H-indol-1-yl)methyl)-[1,1'-biphenyl]-2-carboxylate

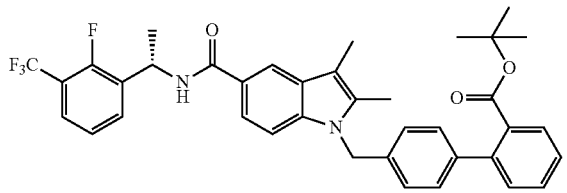 [SMILES: Cc1c(C)n(Cc2ccc(-c3ccccc3C(=O)OC(C)(C)C)cc2)c2ccc(C(=O)N[C@@H](C)c3cccc(C(F)(F)F)c3F)cc12]

The title compound was prepared following the same general protocol as described in Step 8, Example 1, using (S)-1-(2-fluoro-3-(trifluoromethyl)phenyl)ethanamine instead of (S)-1-(4-bromophenyl)ethanamine.

Step 2: (S)-4'-((5-((1-(2-Fluoro-3-(trifluoromethyl)phenyl)ethyl)carbamoyl)-2,3-dimethyl-1H-indol-1-yl)methyl)-[1,1'-biphenyl]-2-carboxylic acid

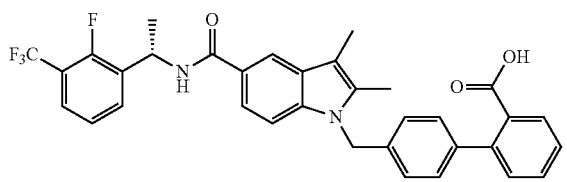 [SMILES: Cc1c(C)n(Cc2ccc(-c3ccccc3C(=O)O)cc2)c2ccc(C(=O)N[C@@H](C)c3cccc(C(F)(F)F)c3F)cc12]

The title compound was prepared following the same general protocol as described in Step 9, Example 1. ESI-MS (m/z): 589 [M+H]$^+$.

Example 300

(S)-4'-((5-((1-(2-Fluoro-6-(trifluoromethyl)phenyl)ethyl)carbamoyl)-2,3-dimethyl-1H-indol-1-yl)methyl)-[1,1'-biphenyl]-2-carboxylic acid

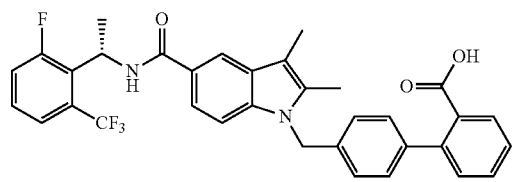 [SMILES: Cc1c(C)n(Cc2ccc(-c3ccccc3C(=O)O)cc2)c2ccc(C(=O)N[C@@H](C)c3c(F)cccc3C(F)(F)F)cc12]

464

Step 1: (S)-tert-Butyl 4'-((5-((1-(2-fluoro-6-(trifluoromethyl)phenyl)ethyl)carbamoyl)-2,3-dimethyl-1H-indol-1-yl)methyl)-[1,1'-biphenyl]-2-carboxylate

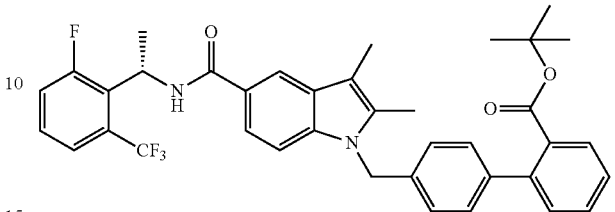

The title compound was prepared following the same general protocol as described in Step 8, Example 1, using (S)-1-(2-fluoro-6-(trifluoromethyl)phenyl)ethanamine instead of (S)-1-(4-bromophenyl)ethanamine.

Step 2: (S)-4'-((5-((1-(2-Fluoro-6-(trifluoromethyl)phenyl)ethyl)carbamoyl)-2,3-dimethyl-1H-indol-1-yl)methyl)-[1,1'-biphenyl]-2-carboxylic acid

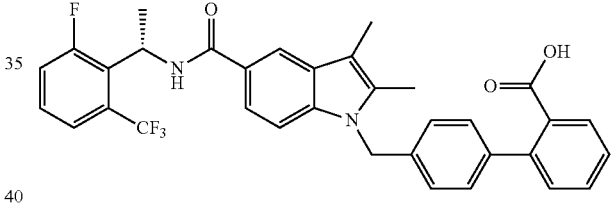

The title compound was prepared following the same general protocol as described in Step 9, Example 1. ESI-MS (m/z): 589 [M+H]$^+$.

Example 301

(S)-4'-((2,3-Dimethyl-5-((1-(2,4,5-trifluorophenyl)ethyl)carbamoyl)-1H-indol-1-yl)methyl)-[1,1'-biphenyl]-2-carboxylic acid

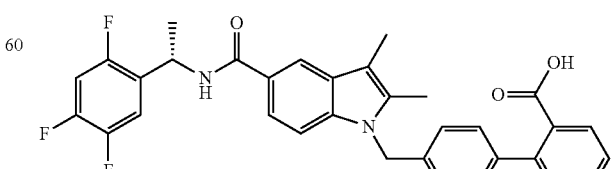

465

Step 1: (S)-tert-Butyl 4'-((2,3-dimethyl-5-((1-(2,4,5-trifluorophenyl)ethyl)carbamoyl)-1H-indol-1-yl)methyl)-[1,1'-biphenyl]-2-carboxylate

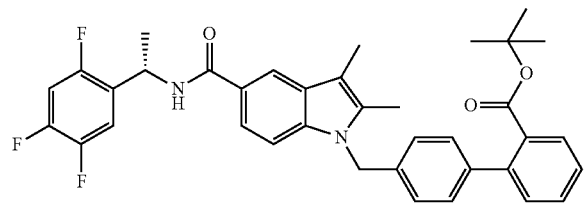 [SMILES: Cc1c(C)n(Cc2ccc(-c3ccccc3C(=O)OC(C)(C)C)cc2)c2ccc(C(=O)N[C@@H](C)c3cc(F)c(F)cc3F)cc12]

The title compound was prepared following the same general protocol as described in Step 8, Example 1, using (S)-1-(2,4,5-trifluorophenyl)ethanamine instead of (S)-1-(4-bromophenyl)ethanamine.

Step 2: (S)-4'-((2,3-Dimethyl-5-((1-(2,4,5-trifluorophenyl)ethyl)carbamoyl)-1H-indol-1-yl)methyl)-[1,1'-biphenyl]-2-carboxylic acid

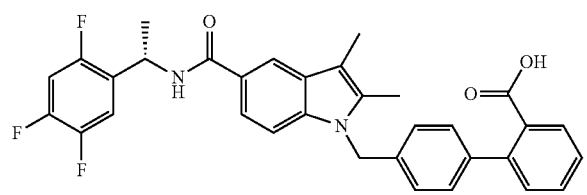 [SMILES: Cc1c(C)n(Cc2ccc(-c3ccccc3C(=O)O)cc2)c2ccc(C(=O)N[C@@H](C)c3cc(F)c(F)cc3F)cc12]

The title compound was prepared following the same general protocol as described in Step 9, Example 1. ESI-MS (m/z): 557 [M+H]$^+$.

Example 302

(S)-4'-((5-((1-(2-Chloro-5-(trifluoromethyl)phenyl)ethyl)carbamoyl)-2,3-dimethyl-1H-indol-1-yl)methyl)-[1,1'-biphenyl]-2-carboxylic acid

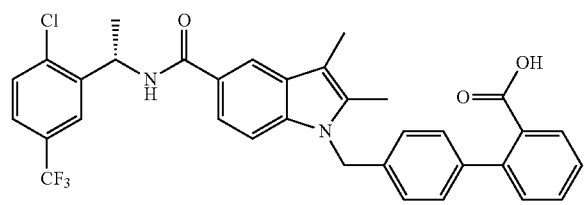 [SMILES: Cc1c(C)n(Cc2ccc(-c3ccccc3C(=O)O)cc2)c2ccc(C(=O)N[C@@H](C)c3cc(C(F)(F)F)ccc3Cl)cc12]

466

Step 1: (S)-tert-butyl 4'-((5-((1-(2-chloro-5-(trifluoromethyl)phenyl)ethyl)carbamoyl)-2,3-dimethyl-1H-indol-1-yl)methyl)-[1,1'-biphenyl]-2-carboxylate

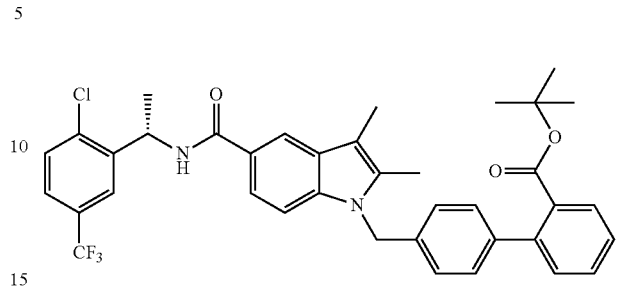

The title compound was prepared following the same general protocol as described in Step 8, Example 1, using (S)-1-(2-chloro-5-(trifluoromethyl)phenyl)ethanamine instead of (S)-1-(4-bromophenyl)ethanamine.

Step 2: (S)-4'-((5-((1-(2-Chloro-5-(trifluoromethyl)phenyl)ethyl)carbamoyl)-2,3-dimethyl-1H-indol-1-yl)methyl)-[1,1'-biphenyl]-2-carboxylic acid The title compound was prepared following the same general protocol as described in Step 9, Example 1. ESI-MS (m/z): 605 [M+H]$^+$.

Example 303

(S)-4'-((5-((1-(2,4-Dichlorophenyl)ethyl)carbamoyl)-2,3-dimethyl-1H-indol-1-yl)methyl)-[1,1'-biphenyl]-2-carboxylic acid

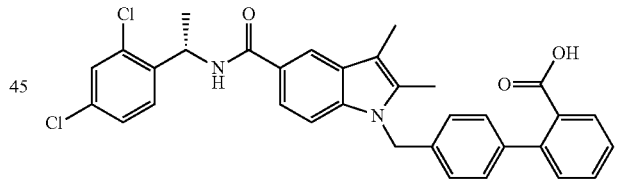

Step 1: (S)-tert-Butyl 4'-((5-((1-(2,4-dichlorophenyl)ethyl)carbamoyl)-2,3-dimethyl-1H-indol-1-yl)methyl)-[1,1'-biphenyl]-2-carboxylate

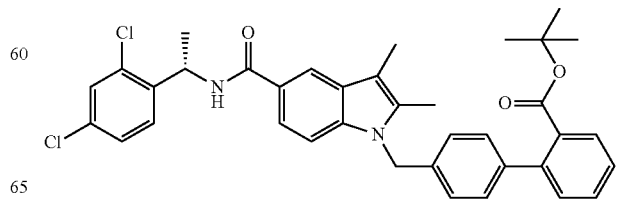

The title compound was prepared following the same general protocol as described in Step 8, Example 1, using (S)-1-(2,4-dichlorophenyl)ethanamine instead of (S)-1-(4-bromophenyl)ethanamine.

Step 2: (S)-4'-((5-((1-(2,4-Dichlorophenyl)ethyl)carbamoyl)-2,3-dimethyl-1H-indol-1-yl)methyl)-[1,1'-biphenyl]-2-carboxylic acid

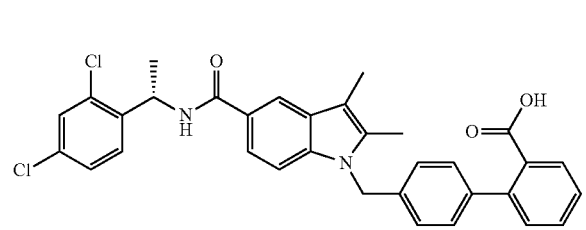 [SMILES: Cc1c(C)n(Cc2ccc(-c3ccccc3C(=O)O)cc2)c2ccc(C(=O)N[C@@H](C)c3ccc(Cl)cc3Cl)cc12]

The title compound was prepared following the same general protocol as described in Step 9, Example 1. ESI-MS (m/z): 571 [M+H]⁺.

Example 304

(S)-4'-((5-((1-(4-Cyclopropylphenyl)ethyl)carbamoyl)-2,3-dimethyl-1H-indol-1-yl)methyl)-[1,1'-biphenyl]-2-carboxylic acid

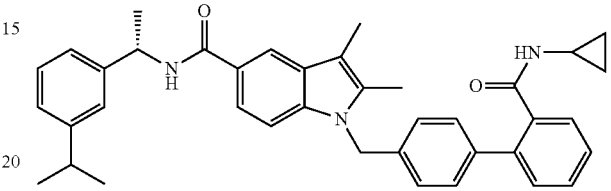

A mixture of (S)-4'-((5-((1-(4-bromophenyl)ethyl)carbamoyl)-2,3-dimethyl-1H-indol-1-yl)methyl)-[1,1'-biphenyl]-2-carboxylic acid (28 mg, 0.048 mmol), cyclopropylboronic acid (9 mg, 0.10 mmol), Palladium(II) acetate (3.9 mg, 0.017 mmol) tricyclohexylphosphine (10 mg, 0.036 mmol) and potassium phosphate, tribasic, (22 mg, 0.10 mmol) in toluene (2.5 mL) and water (0.3 mL) was heated at 100° C. for 1 h in a Biotage Microwave reactor. The solvent was removed; the residue was filtered and purified by preparative HPLC to yield the title compound as a white solid. ESI-MS (m/z): 543 [M+H]⁺.

Example 305

(S)-1-((2'-(Cyclopropylcarbamoyl)-[1,1'-biphenyl]-4-yl)methyl)-N-(1-(3-isopropylphenyl)ethyl)-2,3-dimethyl-1H-indole-5-carboxamide

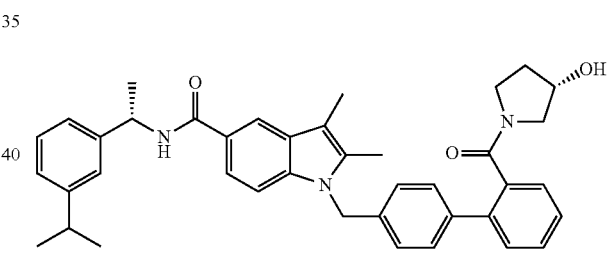

The title compound was prepared using the same general protocol as described in Step 8, Example 1. ESI-MS (m/z): 584 [M+H]⁺.

Example 306

1-((2'-((S)-3-Hydroxypyrrolidine-1-carbonyl)-[1,1'-biphenyl]-4-yl)methyl)-N-((S)-1-(3-isopropylphenyl)ethyl)-2,3-dimethyl-1H-indole-5-carboxamide

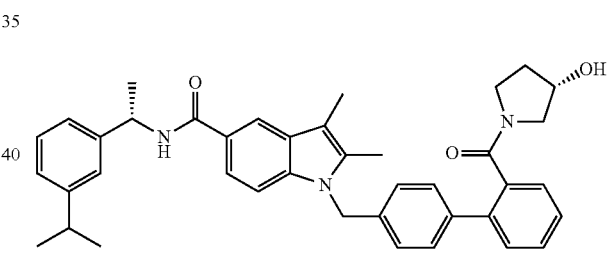

The title compound was prepared using the same general protocol as described in Step 8, Example 1. ESI-MS (m/z): 614 [M+H]⁺.

Example 307

(S)-1-((2'-((2-Hydroxyethyl)carbamoyl)-[1,1'-biphenyl]-4-yl)methyl)-N-(1-(3-isopropylphenyl)ethyl)-2,3-dimethyl-1H-indole-5-carboxamide

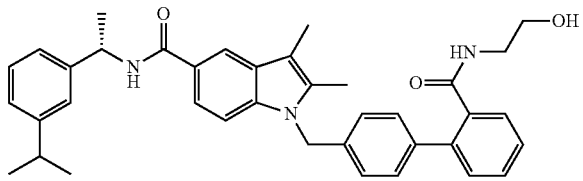 [SMILES: Cc1c(C)n(Cc2ccc(-c3ccccc3C(=O)NCCO)cc2)c2ccc(C(=O)N[C@@H](C)c3cccc(C(C)C)c3)cc12]

The title compound was prepared using the same general protocol as described in Step 8, Example 1. ESI-MS (m/z): 588 [M+H]⁺.

Example 308

(S)-1-((2'-(Cyclohexylcarbamoyl)-[1,1'-biphenyl]-4-yl)methyl)-N-(1-(3-isopropylphenyl)ethyl)-2,3-dimethyl-1H-indole-5-carboxamide

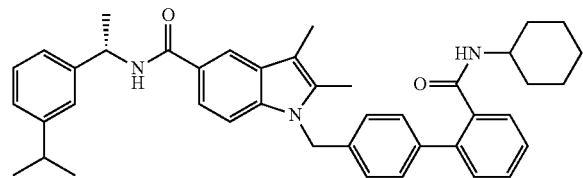 [SMILES: Cc1c(C)n(Cc2ccc(-c3ccccc3C(=O)NC3CCCCC3)cc2)c2ccc(C(=O)N[C@@H](C)c3cccc(C(C)C)c3)cc12]

The title compound was prepared using the same general protocol as described in Step 8, Example 1. ESI-MS (m/z): 626 [M+H]⁺.

Example 309

1-((2'-(((R)-3-(Dimethylamino)-2-hydroxy-3-oxopropyl)carbamoyl)-[1,1'-biphenyl]-4-yl)methyl)-N-((S)-1-(3-isopropylphenyl)ethyl)-2,3-dimethyl-1H-indole-5-carboxamide

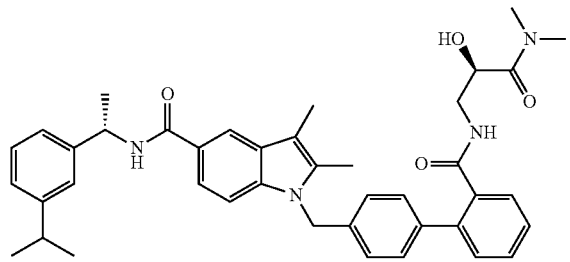 [SMILES: Cc1c(C)n(Cc2ccc(-c3ccccc3C(=O)NC[C@@H](O)C(=O)N(C)C)cc2)c2ccc(C(=O)N[C@@H](C)c3cccc(C(C)C)c3)cc12]

The title compound was prepared using the same general protocol as described in Step 8, Example 1. ESI-MS (m/z): 659 [M+H]⁺.

Example 310

(S)-1-((2'-((2-(Dimethylamino)ethyl)carbamoyl)-[1,1'-biphenyl]-4-yl)methyl)-N-(1-(3-isopropylphenyl)ethyl)-2,3-dimethyl-1H-indole-5-carboxamide

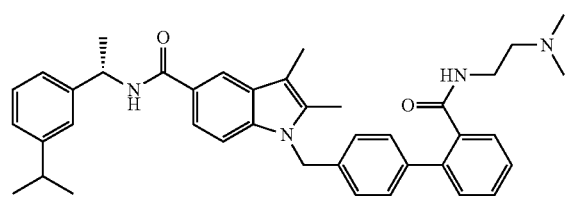 [SMILES: Cc1c(C)n(Cc2ccc(-c3ccccc3C(=O)NCCN(C)C)cc2)c2ccc(C(=O)N[C@@H](C)c3cccc(C(C)C)c3)cc12]

The title compound was prepared using the same general protocol as described in Step 8, Example 1. The TFA salt of the title compound was obtained.
ESI-MS (m/z): 615 [M+H]⁺.

Example 311

(S)—N-(1-(3-Isopropylphenyl)ethyl)-2,3-dimethyl-1-((2'-(methylcarbamoyl)-[1,1'-biphenyl]-4-yl)methyl)-1H-indole-5-carboxamide

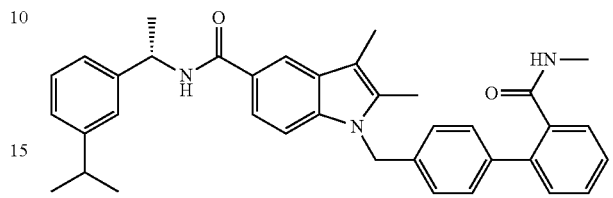

The title compound was prepared using the same general protocol as described in Step 8, Example 1. ESI-MS (m/z): 558 [M+H]⁺.

Example 312

(S)-1-((2'-(Dimethylcarbamoyl)-[1,1'-biphenyl]-4-yl)methyl)-N-(1-(3-isopropylphenyl)ethyl)-2,3-dimethyl-1H-indole-5-carboxamide

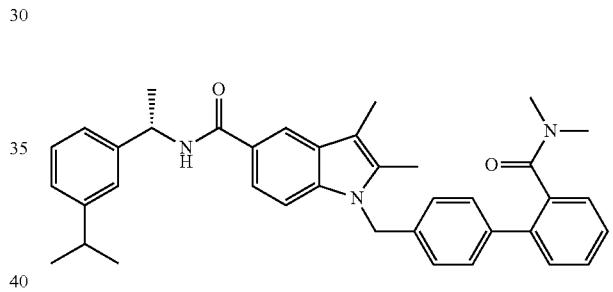

The title compound was prepared using the same general protocol as described in Step 8, Example 1. ESI-MS (m/z): 572 [M+H]⁺.

Example 313

((S)-1-((2'-(Hydroxycarbamoyl)-[1,1'-biphenyl]-4-yl)methyl)-N-(1-(3-isopropylphenyl)ethyl)-2,3-dimethyl-1H-indole-5-carboxamide

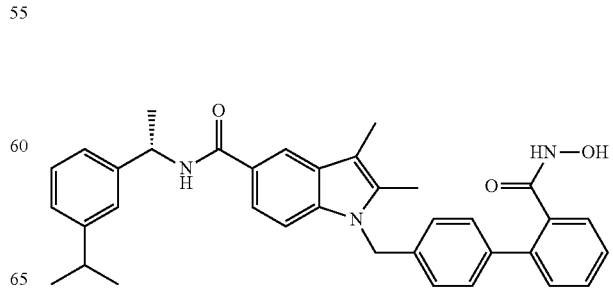

Step 1: (S)-1-((2'-(((tert-Butyldimethylsilyl)oxy)carbamoyl)-[1,1'-biphenyl]-4-yl)methyl)-N-(1-(3-isopropylphenyl)ethyl)-2,3-dimethyl-1H-indole-5-carboxamide

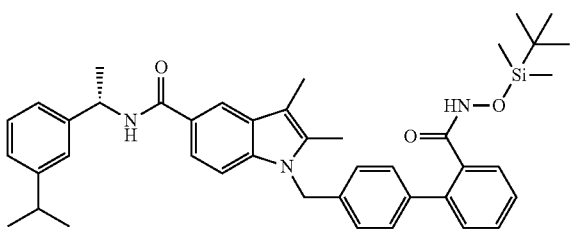 [SMILES: Cc1c(C)n(Cc2ccc(-c3ccccc3C(=O)NO[Si](C)(C)C(C)(C)C)cc2)c2ccc(C(=O)N[C@@H](C)c3cccc(C(C)C)c3)cc12]

The title compound was prepared using the same general protocol as described in Step 8, Example 1.

Step 2: ((S)-1-((2'-(Hydroxycarbamoyl)-[1,1'-biphenyl]-4-yl)methyl)-N-(1-(3-isopropylphenyl)ethyl)-2,3-dimethyl-1H-indole-5-carboxamide

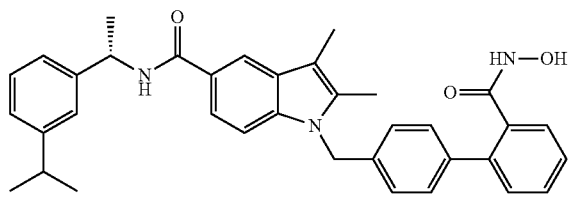 [SMILES: Cc1c(C)n(Cc2ccc(-c3ccccc3C(=O)NO)cc2)c2ccc(C(=O)N[C@@H](C)c3cccc(C(C)C)c3)cc12]

The solution of (S)-1-((2'-(((tert-Butyldimethylsilyl)oxy)carbamoyl)-[1,1'-biphenyl]-4-yl)methyl)-N-(1-(3-isopropylphenyl)ethyl)-2,3-dimethyl-1H-indole-5-carboxamide in DCM (3 mL) and TFA (0.5 mL) was stirred for 1 h at rt. The solvent was removed and the residue was purified by reverse phase prep-HPLC (MeOH/Acetonitrile/water) to obtain the title compound. ESI-MS (m/z): 560 [M+H]$^+$.

Example 314

(S)—N-(1-(3-Isopropylphenyl)ethyl)-2,3-dimethyl-1-((2'-((methylsulfonyl)carbamoyl)-[1,1'-biphenyl]-4-yl)methyl)-1H-indole-5-carboxamide

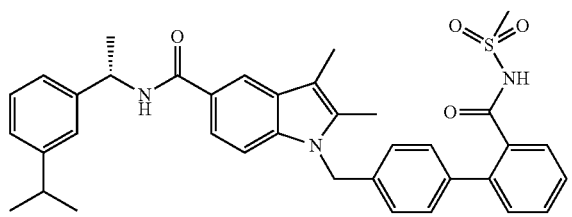 [SMILES: Cc1c(C)n(Cc2ccc(-c3ccccc3C(=O)NS(C)(=O)=O)cc2)c2ccc(C(=O)N[C@@H](C)c3cccc(C(C)C)c3)cc12]

The mixture of (S)-4'-((5-((1-(3-isopropylphenyl)ethyl)carbamoyl)-2,3-dimethyl-1H-indol-1-yl)methyl)-[1,1'-biphenyl]-2-carboxylic acid (30 mg, 0.055 mmol), methanesulfonamide (15 mg, 0.16 mmol), EDAC (25 mg, 0.13 mmol) and DMAP (26 mg, 0.21 mmol) in DMF (3 mL) was stirred at rt for 15 h. The solvent was removed and the residue was purified by reverse phase prep-HPLC (MeOH/Acetonitrile/water) to obtain the title compound. ESI-MS (m/z): 622 [M+H]$^+$.

Example 315

(S)-1-((2'-Carbamoyl-[1,1'-biphenyl]-4-yl)methyl)-N-(1-(3-isopropylphenyl)ethyl)-2,3-dimethyl-1H-indole-5-carboxamide

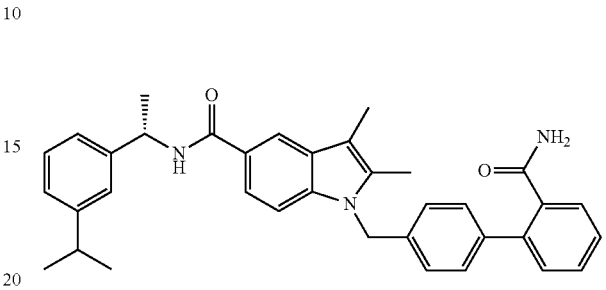

The title compound was prepared using the same general protocol as described in Step 8, Example 1. ESI-MS (m/z): 544 [M+H]$^+$.

Bioassay Procedures

Lanthascreen PPARG Competitive Binding Assay (Invitrogen)

The assay was performed according to manufacturer protocol. A mixture of nM GST-PPARG-LBD, 5 nM Tb-GST-antibody, 5 nM Fluormone Pan-PPAR Green, and serial dilutions of the experimental compound, beginning at 10 μM downwards, was added to wells of black 384-well low-volume plates (Greiner) to a total volume of 18 μL. All dilutions were made in TR-FRET assay buffer C. DMSO at 2% final concentration was used as a no-ligand control. Experiment was performed in triplicate, and incubated for 2 hours in the dark prior to assay read in Perkin Elmer ViewLux ultra HTS microplate reader. FRET signal was measured by excitation at 340 nm and emission at 520 nm for fluorescein and 490 nm for terbium. Fold change over DMSO was calculated using GraphPad Prism Software (La Jolla, Calif.) by calculating 520 nm/490 nm ratio. Graphs were plotted as fold change of FRET signal for compound treatment over DMSO-only control.

Cell-Based Transactivation Assay:

PPRE is a DNA that contains a binding site for PPARG; thus PPRE is a PPAR response element, used herein as a promoter reporter. The binding site is a DR1 response element with the sequence AGGTCA repeated 3 times in tandem and then fused to a construct for luciferase.

Thus, PPRE is the basis of the cell based transactivation assay described below. The plasmid DNA is co-transfected along with a plasmid for PPARG into COS-1 cells. After an overnight incubation, cells are treated with DMSO or compounds. In this assay rosiglitazone activates the reporter about 5 fold. Partial agonists such as MRL24 transactivate the reporter about 25% of rosiglitazone response. Compounds of the invention which are non-activators afford no transactivation of the reporter.

Confluent COS-1 cells were transfected with 4.5 μg murine PPARg2-pSV Sport or full-length human PPAR9-pSport6, 4.5 μg 3×PPRE-luciferase reporter and 27 μL X-treme Gene 9 transfection reagent in serum-free opti-mem media (Gibco), followed by overnight incubation at 37° C., 5% CO$_2$. Transfected cells were plated in white Perkin Elmer 384-well plates and incubated 4 hours. Cells were treated with DMSO vehicle only or experimental compounds in increasing doses from 2 μM-220 μM for mouse receptor and 10 μM-111 fM for human. After 18 hour incubation, treated cells were developed with Brite Lite Plus (Perkin Elmer) and read in 384-well Luminescence Perkin Elmer EnVision Multilabel plate reader. Graphs were plotted in triplicate in GraphPad Prism Software as fold change of treated cells over DMSO control cells.

The human PPAR nuclear receptor ligand binding domain (LBD) is fused to the DNA-Binding Domain of the yeast GAL4 transcription factor. The hybrid fusion-protein nuclear receptor can activate the luciferase reporter under the control of the GAL4 Upstream Activator Sequence (UAS).

The plasmid Gal-4-PPAR DNA is co-transfected along with a plasmid for UAS-luc into HEK 293T cells. After an overnight incubation, cells are treated with DMSO or compounds. In this assay rosiglitazone activates the reporter about 100-fold. Partial agonists transactivate the reporter about 30-40% of rosiglitazone response. Compounds of the invention which are non-activators exhibit <5% transactivation of the receptor at 1 μM.

HEK 293T cells were transfected with 4.5 μg of Gal-4-PPAR9, 4.5 μg UAS-luciferase reporter and 27 μL X-treme Gene 9 transfection reagent in serum-free opti-mem media (Gibco), followed by overnight incubation at 37° C., 5% $CO_2$. Transfected cells were replated in white Perkin Elmer 384-well plates and incubated 4 hours. Cells were treated with DMSO vehicle only or experimental compounds in doses from 10 μM-111 fM. After 18 hour incubation, treated cells were developed with Brite Lite Plus (Perkin Elmer) and read in 384-well Luminescence Perkin Elmer EnVision Multilabel plate reader. Graphs were plotted in triplicate in GraphPad Prism Software as fold change of treated cells over DMSO control cells.

Biodata Tables 1-5, below, provides biological data for the specifically claimed compounds as shown in Table 1, above, listing compound examples of the invention covering almost all of compound examples 1-320. Each line of Biodata Tables 1-5 represents biodata for the corresponding single compound of the set listed in Table 1, with respect to $IC_{50}$ as determined by the Lanthascreen procedure, and EC50 as determined by the cell-based transactivation assay. A compound with a relatively low IC50 concentration is indicated to have potent PPARG binding activity, whereas a compound with a relatively high EC50 value in the cell-based transactivation assay is indicated to possess non-agonistic properties. In various embodiments, the invention provides compounds combining these two properties, non-agonistic and PPARG binding.

Evaluations

It is within ordinary skill to evaluate any compound disclosed and claimed herein for effectiveness in non-agonistic binding to PPARG and in the various cellular assays using the procedures described above or found in the scientific literature. Accordingly, the person of ordinary skill can prepare and evaluate any of the claimed compounds without undue experimentation.

Any compound found to be an effective non-agonist PPARG binding molecular entity can likewise be tested in animal models and in human clinical studies using the skill and experience of the investigator to guide the selection of dosages and treatment regimens.

| Biodata Table 1 | | |
|---|---|---|
| Ex. | $IC_{50}$ (nM) Lantha | $EC_{50}$ (nM) PPRE |
| 1 | 28 | NA (0%) |
| 2 | 5 | *499 (2%) |
| 3 | 206 | NT |
| 4 | 230 | NA (0%) |
| 5 | 157 | NA (0%) |
| 6 | 0.7 | 0.8 (17%) |
| 7 | 4 | 19 (23%) |
| 8 | 34 | 9000 (12%) |
| 9 | 23 | 7 (18%) |
| 10 | 553 | NA (0%) |
| 11 | 13 | 154 (29%) |
| 12 | 14 | 28 (24%) |
| 13 | 667 | 22 (17%) |
| 14 | 4 | 70 (21%) |
| 15 | NT | 83 (20%) |
| 16 | 2 | 59 (23%) |
| 17 | 300 | NA (0%) |
| 19 | 0.9 | 10 (15%) |
| 20 | 16 | NA (0%) |
| 21 | 13 | 46 (12%) |
| 22 | 10 | NT |
| 23 | 0.5 | 1 (19%) |
| 24 | 125 | NA (0%) |
| 25 | 0.5 | 2.5 (15%) |
| 26 | >1000 | NT |
| 27 | 53 | 33 (6%) |
| 30 | 58 | 20 (18%) |
| 31 | 244 | NT |
| 34 | 0.54 | 0.5 (23%) |
| 35 | 40 | 380 (9%) |
| 36 | 6 | 2 (23%) |
| 37 | >1000 | 1000 (19%) |
| 38 | >1000 | NT |
| 39 | NA | NT |
| 40 | >1000 | NT |
| 41 | NA | NT |
| 47 | 300 | NA (0%) |
| 48 | NA | NT |
| 49 | NA | NT |
| 50 | >1000 | NT |
| 51 | >1000 | NT |
| 52 | >1000 | NT |
| 53 | >1000 | NT |
| 54 | >1000 | NT |
| 55 | >1000 | NT |
| 56 | NA | NT |
| 57 | >1000 | NT |
| 58 | >1000 | NT |
| 59 | >1000 | NT |
| 60 | >1000 | NT |
| 61 | 646 | NT |
| 62 | 150 | NT |
| 65 | 6 | 116 (18%) |
| 66 | NT | NT |
| 67 | 2 | 2 (8%) |
| 68 | >1000 | NT |
| 69 | 4 | NA (0%) |
| 70 | 10 | NA (0%) |
| 72 | 2 | 20 (23%) |
| 73 | 80 | NA (0%) |
| 74 | 76 | 300 (26%) |
| 75 | 26 | 1 (15%) |
| 76 | 5 | 23 (15%) |
| 77 | 31 | 95 (20%) |
| 78 | 33 | 1000 (30%) |
| 79 | 37 | 297 (25%) | rosiglitazone: Lantha $IC_{50}$ 18 nM;
PPRE $EC_{50}$ 7 nM (100%);
NA = not active;
NT = not tested
*GAL4 transactivation data

| Biodata Table 2 | | |
|---|---|---|
| Ex. | IC$_{50}$ (nM) Lantha | EC$_{50}$ (nM) PPRE |
| 80 | 13 | 2700 (20%) |
| 81 | 78 | 6 (12%) |
| 82 | >1000 | NT |
| 83 | 1 | 8 (15%) |
| 84 | 12 | 40 (17%) |
| 85 | >1000 | NA (0%) |
| 86 | 10 | NA (0%) |
| 87 | 17 | 200 (18%) |
| 88 | 11 | 170 (17%) |
| 89 | 32 | 250 (17%) |
| 90 | 25 | >1000 (18%) |
| 91 | NA | NT |
| 92 | 17 | >1000 (9%) |
| 93 | 1 | 6 (8%) |
| 94 | 32 | 300 (30%) |
| 95 | 4 | NA (0%) |
| 96 | 38 | 2000 (35%) |
| 97 | 0.1 | (0.3 (9%) |
| 98 | 3 | 10 (18%) |
| 99 | 240 | NT |
| 100 | 191 | 281 (21%) |
| 101 | 208 | NT |
| 102 | 247 | 1.2 (29%) |
| 103 | 4 | 3.2 (15%) |
| 104 | 7 | NT |
| 105 | 5 | 7.7 (17%) |
| 106 | 4 | 9 (30%) |
| 107 | 6 | 4 (9%) |
| 108 | 6 | 535 (15%) |
| 109 | 2 | 12 (21%) |
| 110 | 20 | 43 (18%) |
| 111 | 13 | NT |
| 112 | 21 | 65 (15%) |
| 113 | 0.8 | 6 (9%) |
| 114 | 0.8 | 8 (14%) |
| 115 | 64 | NT |
| 116 | 2 | 5 (16%) |
| 117 | 3 | 3 (17%) |
| 118 | 17 | 86 (8%) |
| 119 | 24 | 688 (18%) |
| 120 | NA | NT |
| 121 | NA | NT |
| 122 | NA | NT |
| 123 | NA | NT |
| 124 | NA | NT |
| 125 | NA | NT |
| 126 | 99 | NT |
| 127 | NA | NT |
| 128 | NA | NT |
| 129 | NA | NT |
| 130 | 163 | NA (0%) |
| 131 | 6 | 6 (20%) |
| 132 | 24 | NT |
| 133 | 2 | NT |
| 134 | 126 | NT |
| 135 | 80 | NA (0%) |
| 136 | 2 | NT |
| 137 | 30 | NA (0%) | rosiglitazone: Lantha IC$_{50}$ 18 nM;
PPRE EC$_{50}$ 7 nM (100%);
NA = not active;
NT = not tested

| Biodata Table 3 | | |
|---|---|---|
| Ex. | IC$_{50}$ (nM) Lantha | [1]EC$_{50}$ (nM) GAL4 |
| 138 | 65 | 487 (8%) |
| 139 | 17 | 100 (10%) |
| 140 | 8 | 60 (18%) |
| 141 | 30 | 529 (20%) |
| 142 | 51 | 6055 (15%) |
| 143 | 10 | 189 (45%) |
| 144 | 2 | 13 (25%) |
| 145 | <1 | 70 (35%) |
| 146 | 12 | 455 (30%) |
| 147 | 20 | 9285 (20%) |
| 148 | 41 | 7539 (35%) |
| 149 | 6 | 1677 (15%) |
| 150 | 5 | 180 (30%) |
| 151 | 21 | 618 (25%) |
| 152 | 256 | 766 (17%) |
| 153 | 28 | 4165 (25%) |
| 154 | 61 | 522 (5%) |
| 155 | 1222 | 226 (18%) |
| 156 | <1 | 32 (30%) |
| 157 | 80 | 133 (10%) |
| 158 | 8 | 259 (40%) |
| 159 | <1 | 152 (30%) |
| 160 | 7 | 383 (35%) |
| 161 | 2 | 55 (30%) |
| 162 | <1 | 31 (30%) |
| 163 | 8 | 1141 (10%) |
| 164 | 19 | 987 (30%) |
| 165 | 2 | 507 (15%) |
| 166 | <1 | 21 (35%) |
| 167 | NT | 596 (10%) |
| 168 | NT | 931 (18%) |
| 169 | 11 | 608 (20%) |
| 170 | 4 | 114 (50%) |
| 171 | 5 | 388 (10%) |

| | | EC$_{50}$ (nM) GAL4 |
|---|---|---|
| 172 | 9 | 106 (8%) |
| 173 | 4 | 161 (1%) |
| 174 | 3 | 116 (35%) |
| 175 | 16 | 360 (20%) |
| 176 | 39 | 185 (20%) |
| 177 | 21 | NT |
| 178 | 81 | 116 (15%) |
| 179 | 13 | 344 (30%) |
| 180 | 1 | 119 (60%) |
| 181 | 512 | 5240 (40%) |
| 182 | 5 | 133 (30%) |
| 183 | 97 | 150 (20%) |
| 184 | [2]inc | NT |
| 185 | inc | NT |
| 186 | inc | NT |
| 187 | <1 | 5 (20%) |
| 188 | 10 | 3149 (20%) |
| 189 | 100 | NT |
| 190 | 5 | 51 (45%) |
| 191 | 80 | 1000 (20%) |
| 192 | 4 | 27 (40%) |
| 193 | 20 | 191 (40%) |
| 194 | 80 | 793 (18%) |
| 195 | 80 | 169 (35%) |
| 196 | >1000 | NT |
| 197 | 17 | 1635 (20%) |
| 198 | 9 | 100 (15%) |
| 199 | 19 | 2751 (10%) |
| 200 | 449 | NT |
| 201 | 34 | 941 (10%) |
| 202 | 35 | 1754 (40%) |
| 203 | 805 | NT |
| 204 | 536 | NA (0%) |
| 205 | 5 | 637 (20%) |

[1]% transactivation at 10 μM;
[2]inc = incomplete curve;
rosiglitazone: Lantha IC$_{50}$ 18 nM;
PPRE EC$_{50}$ 7 nM (100%);
NA = not active;
NT = not tested

| Biodata Table 4 | | |
|---|---|---|
| Ex. | IC$_{50}$ (nM) Lantha | $^1$EC$_{50}$ (nM) GAL4 |
| 206 | 26 | 405 (20%) |
| 207 | 1 | 629 (20%) |
| 208 | 22 | 369 (20%) |
| 209 | 11 | 211 (10%) |
| 210 | 241 | 1289 (20%) |
| 211 | 6 | 251 (20%) |
| 212 | 4 | 209 (20%) |
| 213 | 3 | 672 (40%) |
| 214 | 25 | 2348 (20%) |
| 215 | 309 | NT |
| 216 | 33 | 884 (30%) |
| 217 | 230 | 2803 (15%) |
| 218 | 223 | 2551 (45%) |
| 219 | 15 | 155 (30%) |
| 220 | 10 | 142 (30%) |
| 221 | 11 | 156 (20%) |
| 222 | 15 | 193 (5%) |
| 223 | 73 | 676 (10%) |
| 224 | 2 | 86 (20%) |
| 225 | 43 | 1128 (20%) |
| 226 | 11 | 172 (20%) |
| 227 | 36 | 173 (20%) |
| 228 | 53 | 1062 (15%) |
| 229 | 9 | 354 (30%) |
| 230 | 103 | 709 (20%) |
| 231 | 2 | 131 (10%) |
| 232 | 18 | 297 (30%) |
| 233 | 9 | 166 (40%) |
| 234 | <1 | 40 (50%) |
| 235 | 3 | 37 (30%) |
| 236 | 17 | 293 (20%) |
| 237 | 118 | 417 (30%) |
| 238 | 20 | 193 (55%) |
| 239 | 17 | 169 (15%) |
| | | EC$_{50}$ (nM) GAL4 |
| 240 | 58 | 1304 (25%) |
| 241 | 57 | 453 (20%) |
| 242 | inc | NT |
| 243 | 22 | 1603 (10%) |
| 244 | 40 | 921 (8%) |
| 245 | 7 | 454 (10%) |
| 246 | >1000 | NT |
| 247 | >1000 | NT |
| 248 | >1000 | NT |
| 249 | 22 | *80 (1%) |
| 250 | 88 | *NA (0%) |
| 251 | 40 | 1609 (30%) |
| 252 | 3 | 147 (25%) |
| 253 | 5 | 86 (45%) |
| 254 | 1 | 147 (25%) |
| 255 | 6 | 334 (20%) |
| 256 | 38 | NT |
| 257 | 1046 | 4907 (20%) |
| 258 | 636 | NT |
| 259 | 19 | 1480 (15%) |
| 260 | 2 | 42 (25%) |
| 261 | 4 | 50 (30%) |
| 262 | 144 | 3997 (35%) |
| 263 | 59 | 3758 (20%) |
| 264 | 32 | 1991 (35%) |
| 265 | 4 | NT |
| 266 | 8 | 588 (25%) |
| 267 | 98 | 2487 (40%) |
| 268 | 352 | 8973 (20%) |
| 269 | 8 | 907 (40%) |
| 270 | 15 | 686 (40%) |
| 271 | 2 | 52 (20%) |
| 272 | <1 | 2 (20%) |

$^1$% transactivation at 10 μM;
$^2$inc = incomplete curve;
rosiglitazone: Lantha IC$_{50}$ 18 nM;
PPRE EC$_{50}$ 7 nM (100%);
NA = not active;
NT = not tested;
*PPRE transactivation data

| Biodata Table 5 | | |
|---|---|---|
| Ex. | IC$_{50}$ (nM) Lantha | $^1$EC$_{50}$ (nM) GAL4 |
| 273 | 15 | 294 (30%) |
| 274 | 19 | 159 (30%) |
| 275 | 8 | 572 (35%) |
| 276 | 11 | NT |
| 277 | inc | NT |
| 278 | 808 | NT |
| 279 | inc | NT |
| 280 | inc | NT |
| 281 | inc | NT |
| 282 | inc | NT |
| 283 | inc | NT |
| 284 | inc | NT |
| 285 | inc | NT |
| 286 | inc | NT |
| 287 | inc | NT |
| 288 | inc | NT |
| 289 | inc | NT |
| 290 | inc | NT |
| 291 | inc | NT |
| 292 | inc | NT |
| 293 | inc | NT |
| 294 | 22 | *517 (28%) |
| | | EC$_{50}$ (nM) GAL4 |
| 295 | 11 | 60 (10%) |
| 296 | <1 | 69 (35%) |
| 297 | 10 | 4333 (15%) |
| 298 | 11 | 448 (10%) |
| 299 | 27 | 346 (15%) |
| 300 | 9 | 167 (15%) |
| 301 | 8 | 198 (40%) |
| 302 | 3 | 48 (20%) |
| 303 | 4 | 219 (25%) |
| 304 | 50 | 2425 (15%) |
| 305 | 94 | NT |
| 306 | >500 | NT |
| 307 | 600 | NT |
| 308 | NA | NT |
| 309 | >1000 | NT |
| 310 | >1000 | NT |
| 311 | 76 | 441 (10%) |
| 312 | 148 | 914 (10%) |
| 313 | 77 | 242 (4%) |
| 314 | 285 | 1654 (5%) |
| 315 | 62 | 137 (2%) |

$^1$% transactivation at 10 μM;
$^2$inc = incomplete curve;
rosiglitazone: Lantha IC$_{50}$ 18 nM;
PPRE EC$_{50}$ 7 nM (100%);
NA = not active;
NT = not tested;
*PPRE transactivation data

STATEMENTS OF THE INVENTION

1. A non-agonist PPARG modulatory compound of formula (I), or a pharmaceutically acceptable salt thereof:

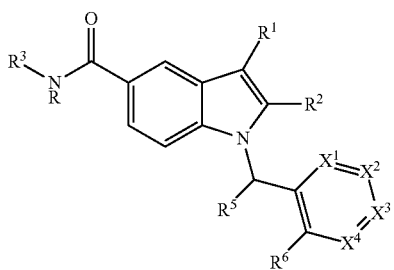

wherein:

R is H or $(C_1-C_4)$alkyl;

$R^1$ and $R^2$ are independently H, $(C_1-C_6)$alkyl, $(C_3-C_9)$cycloalkyl, or $(C_1-C_6)$haloalkyl; or $R^1$ and $R^2$ together with the atoms to which they are bonded form a 5- to 9-membered ring, comprising 0-3 heteroatoms selected from the group consisting of O, NR, and $SO_q$ wherein q is 0, 1, or 2, and optionally mono- or pluri-substituted with independently selected $(C_1-C_6)$alkyl, $(C_2-C_6)$alkenyl, $(C_2-C_6)$alkynyl, $(C_6-C_{10})$aryl, $(C_3-C_9)$cycloalkyl, halo, $(C_1-C_6)$haloalkyl, nitro, cyano-$(C_0-C_6)$alkyl, $R'O_2C$—$(C_0-C_6)$alkyl, methylenedioxy, $R'O$—$(C_0-C_6)$alkyl, $(R')_2N$—$(C_0-C_6)$alkyl, $(R')_2NC(=O)$—$(C_0-C_6)$alkyl, $(C_1-C_6)$alkyl-$S(O)_q(C_0-C_6)$alkyl, aryl, aroyl, or $SO_2NR'_2$; $R^3$ is optionally mono- or multi-substituted $(C_1-C_6)$alkyl, $(C_1-C_6)$alkenyl, $(C_1-C_6)$alkynyl, aryl, arylalkyl, heteroaryl, heteroarylalkyl, cycloalkyl, heterocyclyl, cycloalkylalkyl, or heterocyclylalkyl; wherein if present each substituent on $R^3$ is independently selected from the group consisting of $(C_1-C_6)$alkyl, $(C_2-C_6)$alkenyl, $(C_2-C_6)$alkynyl, $(C_6-C_{10})$aryl, $(C_3-C_9)$cycloalkyl, 3-9 membered mono- and bicyclic heterocyclyl, 3-9 membered mono- and bicyclic heteroaryl, halo, haloalkyl, haloalkoxy, nitro, cyano, $CO_2R'$, methylenedioxy, OR', $N(R')_2$, $C(O)N(R')_2$, $(C_1-C_4)$alkyl-$S(O)_q$, $SO_2NR'_2$, and $(C_1-C_6)$alkoxy, wherein R' is independently H, $(C_1-C_6)$ alkyl, $(C_1-C_6)$ haloalkyl, or $(C_3-C_9)$cycloalkyl, or wherein two R' bonded to an atom together with the atom form a 3-8 membered ring optionally further comprising a heteroatom selected from the group consisting of O, NR', and $S(O)_q$, and wherein alkyl, alkenyl, alkynyl, aryl, arylalkyl, or cycloalkyl is optionally mono- or independently multi-substituted with $(C_1-C_6)$alkyl, $(C_1-C_6)$haloalkyl, $(C_1-C_6)$alkoxy, $(C_1-C_6)$haloalkoxy, halo, OR', $N(R')_2$, aryl, or aroyl; and wherein an alkyl or an alkyl group of a cycloalkylalkyl, heterocyclylalkyl, arylalkyl or heteroarylalkyl can be substituted with oxo;

each of $X^1-X^4$ is independently N or is C substituted with an independently selected $R^7$ or with Z, provided that no more than one of $X^1-X^4$ is N, and provided that there is one and only one Z group, present in the ring comprising $X^1$, Z is a group of formula

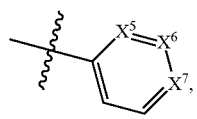

wherein a wavy line indicates a point of attachment, each $X^5-X^7$ is independently N or is C substituted with an independently selected H or $R^4$ provided that no more than one of $X^5-X^7$ is N;

each $R^4$ is independently halo, nitro, $(C_1-C_6)$fluoroalkyl, R"—$(C_1-C_6)$alkyl, $R"O_2C$—$(C_0-C_6)$alkyl, NC—$(C_0-C_6)$alkyl, R"O—$(C_0-C_6)$alkyl, $(R")_2N$—$(C_0-C_6)$alkyl, $(R')_2NC(=O)$—$(C_0-C_6)$alkyl, C-bonded tetrazolyl, 3-hydroxypyrrolidin-1-carbonyl, 2-hydroxyethylaminocarbonyl, cyclohexylaminocarbonyl, 2-(N,N-dimethylaminocarbonyl)-2-hydroxyethylaminocarbonyl, N,N-dimethylaminoethylcarbonyl, N-methylaminocarbonyl, N-hydroxylaminocarbonyl, (1,3,4-oxadiazol-2(3H)-on)-yl, (1,2,4-oxadiazol-5(4H)-on)-3-yl, $(C_1-C_6)$alkyl-$S(O)_q(C_0-C_6)$alkyl, $R'S(O)_2NHC(O)$, $R'C(O)NHS(O)_2$, an unsubstituted or substituted aryl, an unsubstituted or substituted heteroaryl, $(C_1-C_6)$alkyl or $(C_3-C_9)$cycloalkyl-$(C_0-C_6)$alkyl, wherein any alkyl or cycloalkyl is optionally mono- or independently multi-substituted with R", OR", $N(R")_2$, C-bonded tetrazolyl, $(C_1-C_6)$alkyl-$S(O)_q(C_0-C_6)$alkyl, an unsubstituted or substituted aryl, or an unsubstituted or substituted heteroaryl; or $R^4$ is —$(C(R")_2)_mCO_2R"$, —$(C(R")_2)_mCON(R")_2$, or —$(C(R")_2)_mCN$, —$O(C(R")_2)_mCO_2R"$, —$O(C(R")_2)_mCON(R")_2$, or —$O(C(R")_2)_mCN$, wherein m is 1, 2, or 3;

R" is H, or $(C_1-C_6)$ alkyl, or two R" together with an atom to which they are bonded form a $(C_3-C_9)$cycloalkyl;

q is 0, 1 or 2;

$R^5$ is H or $(C_1-C_4)$alkyl; $R^6$ is $R^7$; or $R^5$ and $R^6$ taken together form a —$CH_2CH_2$— group; and, $R^7$ is H, halo, $CO_2R'$, CN, OR', $N(R')_2$, $C(O)N(R')_2$, $(C_1-C_4)$alkyl or $(C_1-C_4)$fluoroalkyl optionally substituted with OR' or $N(R')_2$, C-bonded tetrazolyl, or $(C_1-C_4)$alkyl-$S(O)_q$; or $R^7$ is —$(C(R')_2)_mCO_2R'$ wherein m is 1, 2, or 3.

2. The compound of statement 1 wherein $R^1$ and $R^2$ are each independently H or methyl.

3. The compound of statement 1 or 2 wherein $R^3$ is unsubstituted or substituted arylalkyl.

4. The compound of statement 1 or 2 wherein $R^3$ is unsubstituted or substituted benzyl or α-phenethyl.

5. The compound of statement 1 or 2 wherein $R^3$ is unsubstituted or substituted cycloalkyl.

6. The compound of statement 1 or 2 wherein $R^3$ is any one of:

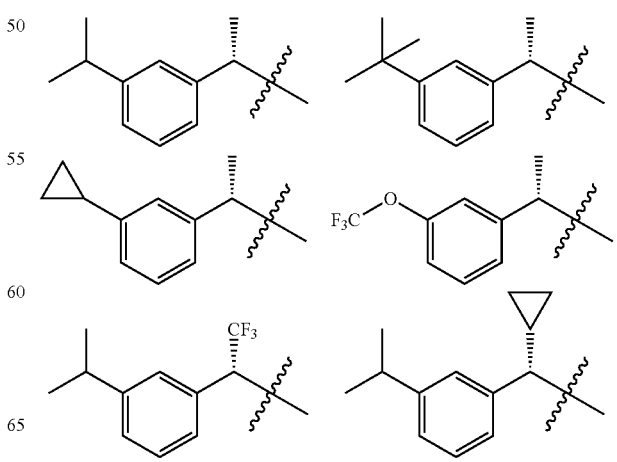

481
-continued

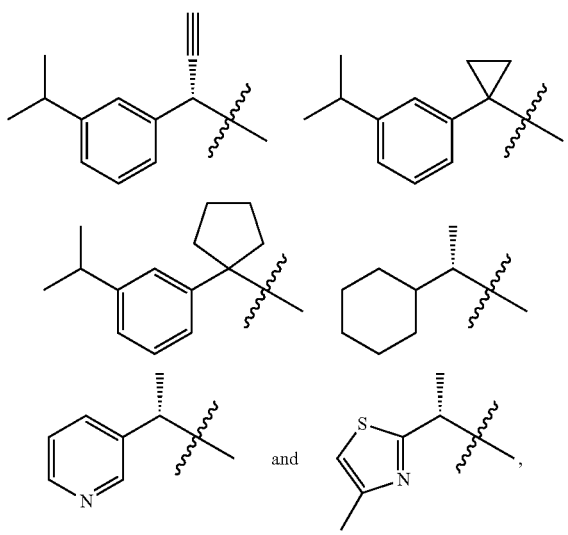

wherein a wavy line indicates a point of attachment.

7. The compound of any one of statements 1-6 wherein $X^5$, $X^6$, and $X^7$ all represent carbon.

8. The compound of any one of statements 1-7 wherein $R^4$ is —CH$_2$CO$_2$H.

9. The compound of any one of statements 1-8 wherein $X^3$ is C substituted with Z.

10. The compound of any one of statements 1-9 wherein $R^4$ is disposed on $X^5$.

11. The compound of any one of statements 1-7 wherein $R^4$ is CO$_2$H, CN, 2-hydroxyethylaminocarbonyl, cyclohexylaminocarbonyl, 2-(N,N-dimethylaminocarbonyl)-2-hydroxyethylaminocarbonyl, N,N-dimethylaminoethylcarbonyl, N-methylaminocarbonyl, N-hydroxylaminocarbonyl, 3-hydroxypyrrolidin-1-carbonyl, or C-bonded tetrazolyl.

12. The compound of any one of statements 1-11 wherein $R^5$ and $R^6$ are H.

13. The compound of statement 1 wherein the compound is any one of:

1

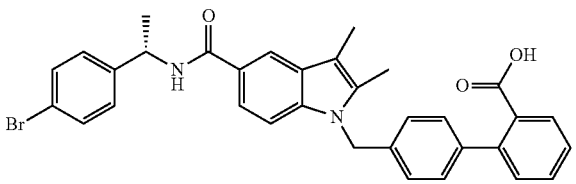

2

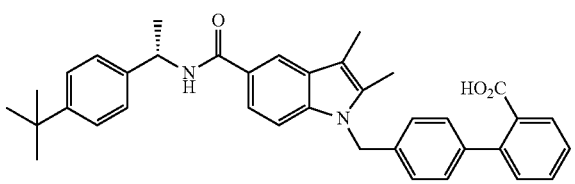

482
-continued

3

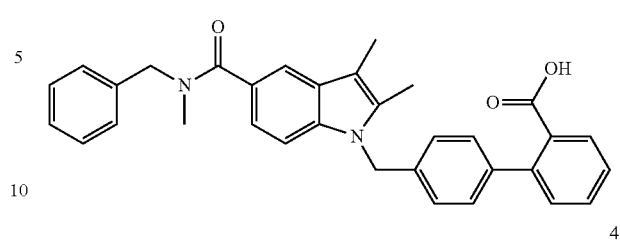

4

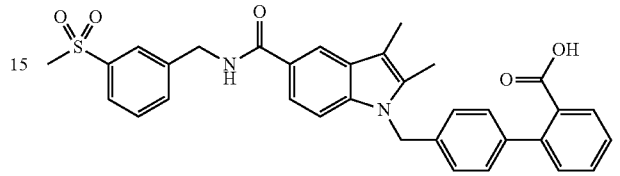

5

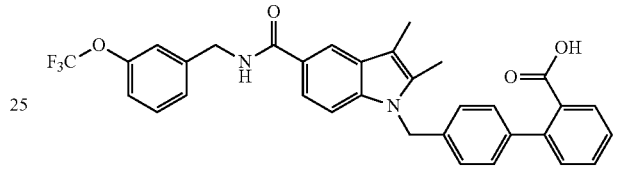

6

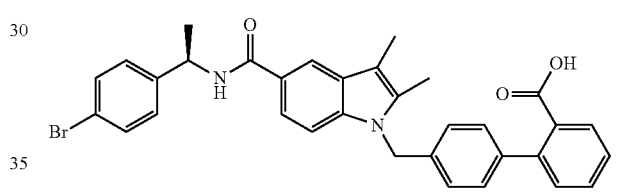

7

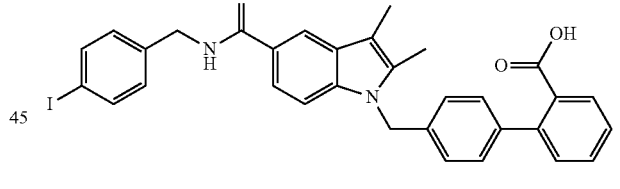

8

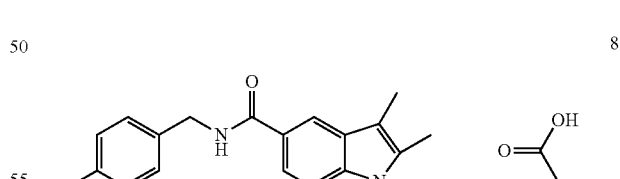

9

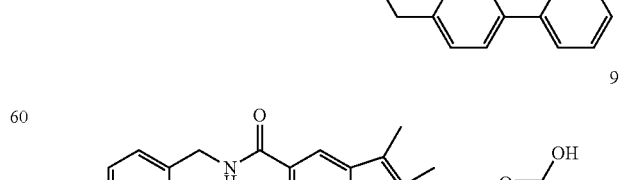

485
-continued
25
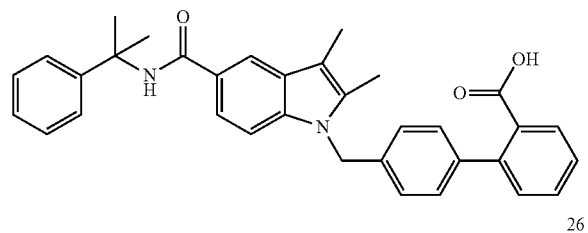
26
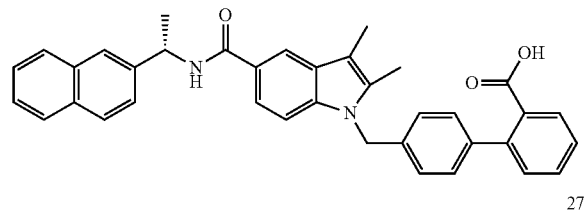
27
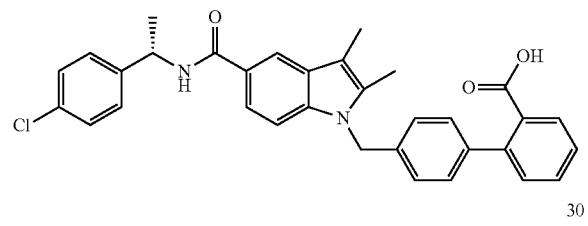
31
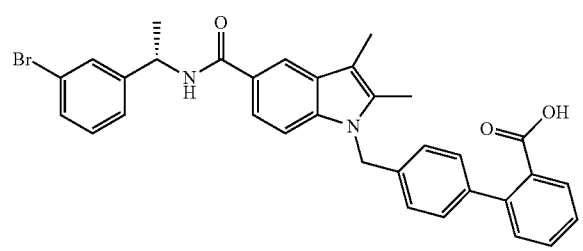
33
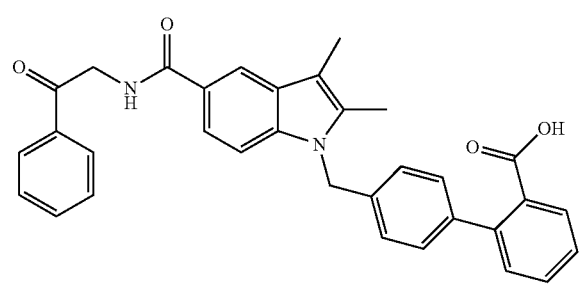
34
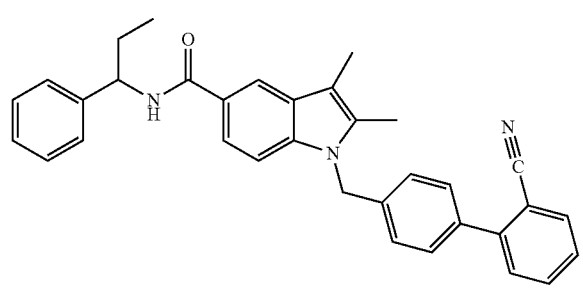
486
-continued
35
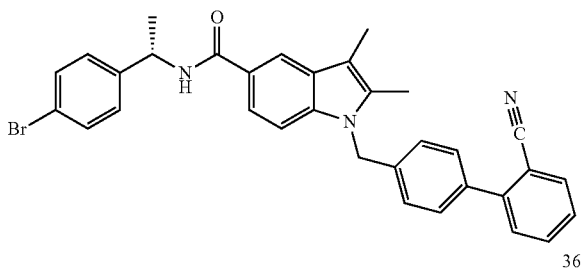
36
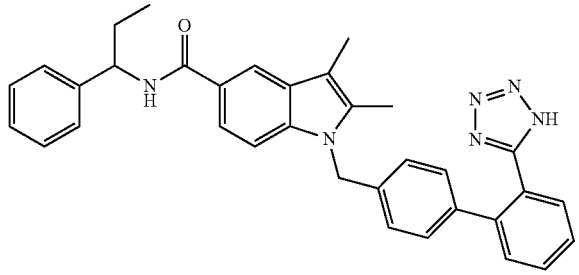
37
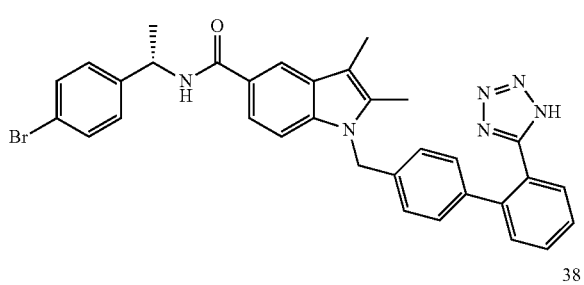
38
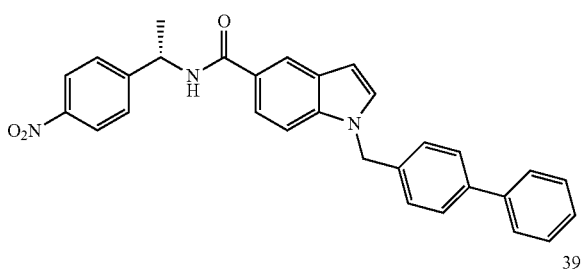
39
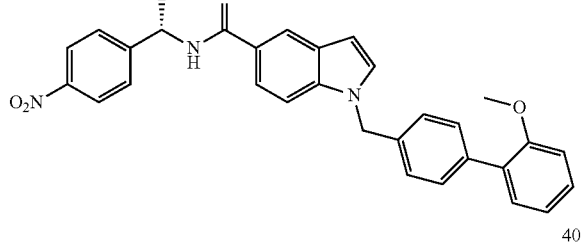
40
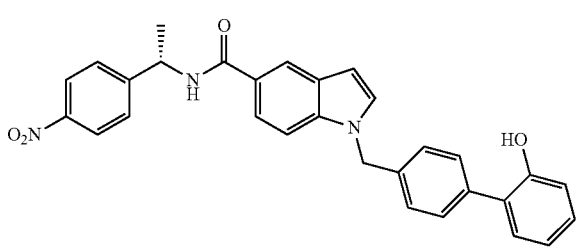

487
-continued
41
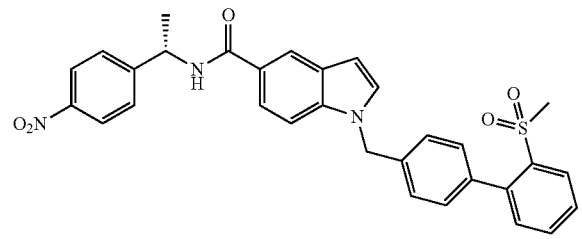
42
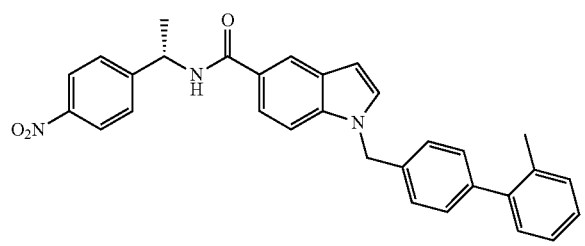
43
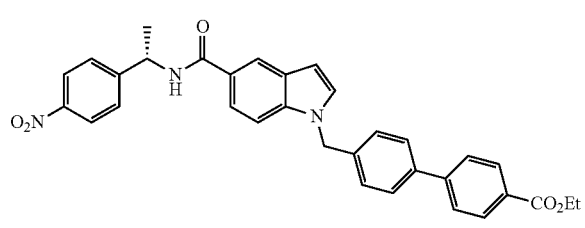
44
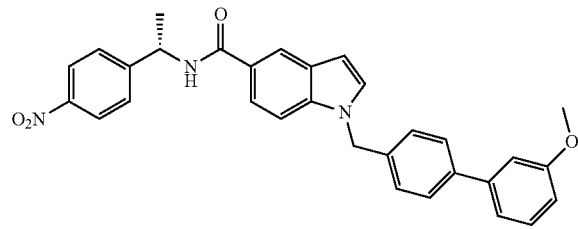
45
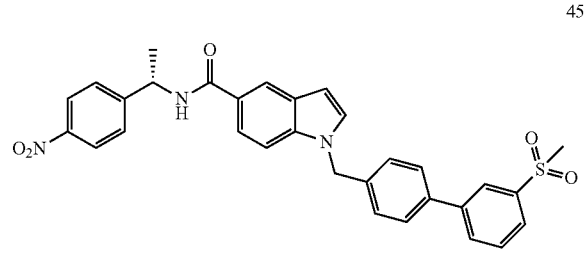
46
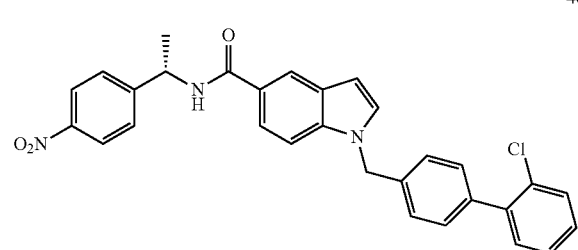
488
-continued
47
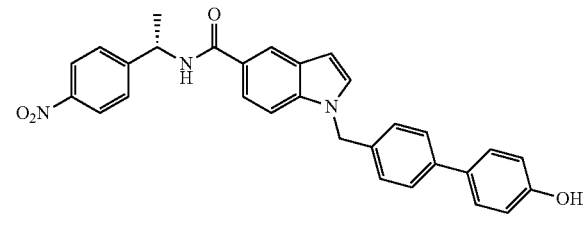
48
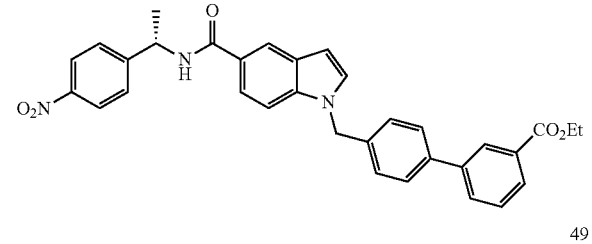
49
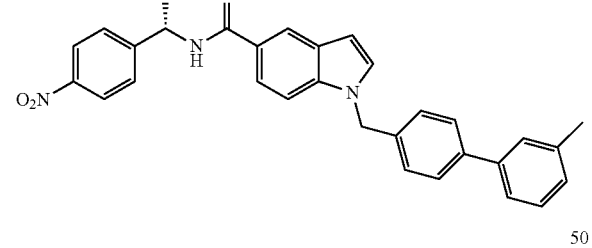
50
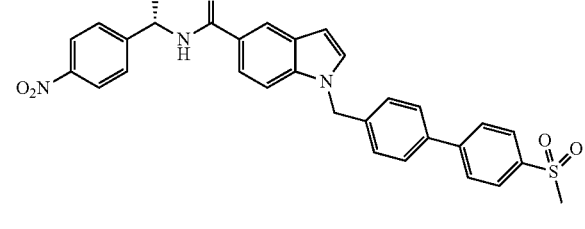
51
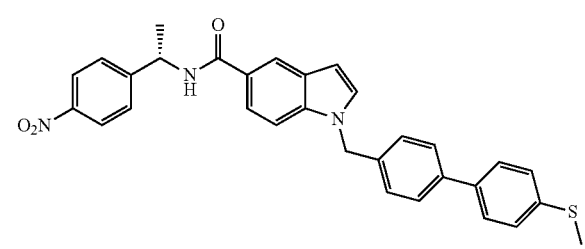
52
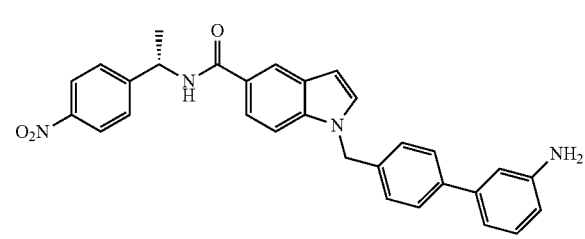

53
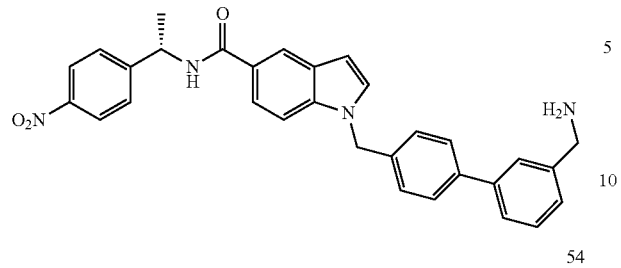
54
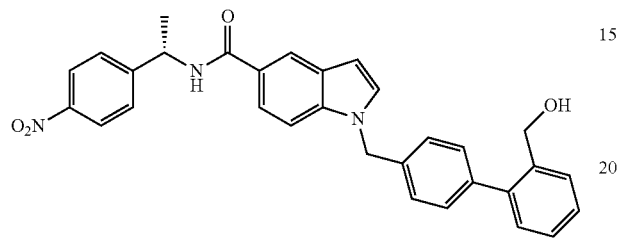
55
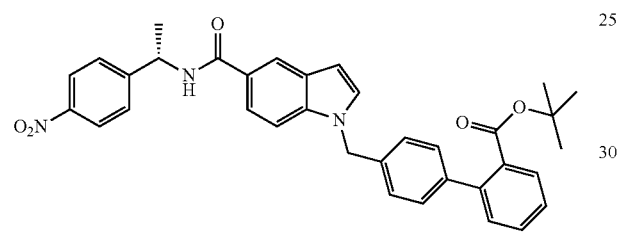
56
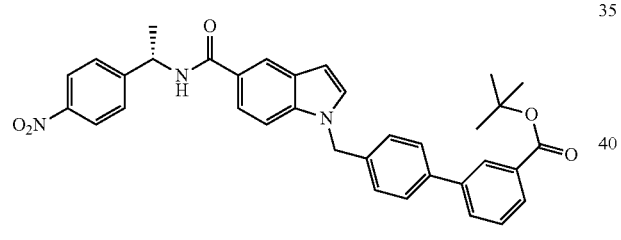
57
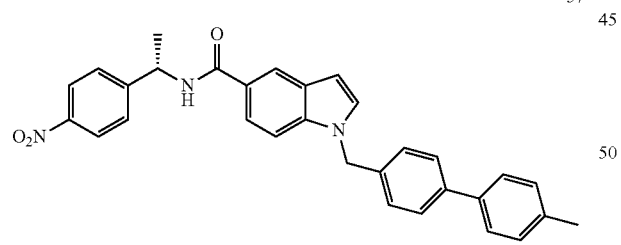
58
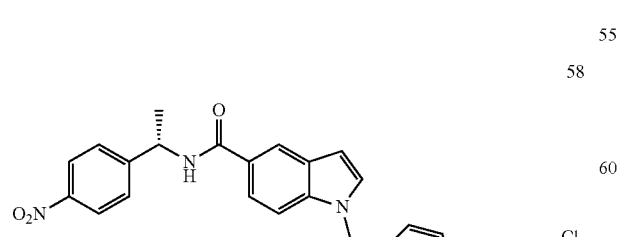
59
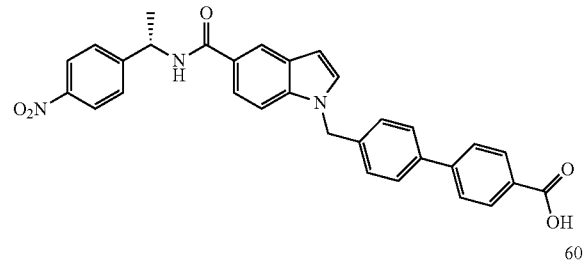
60
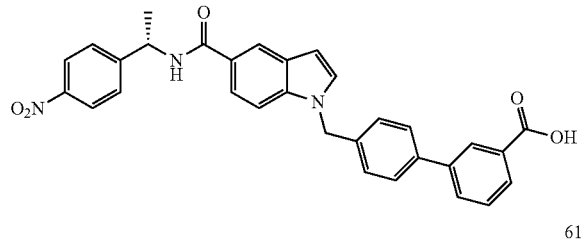
61
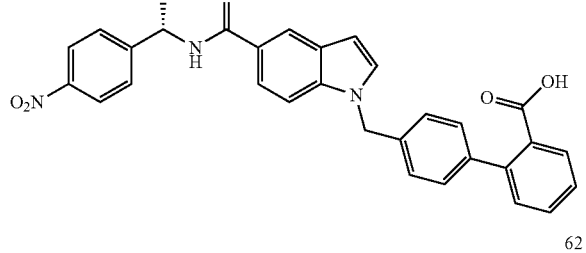
62
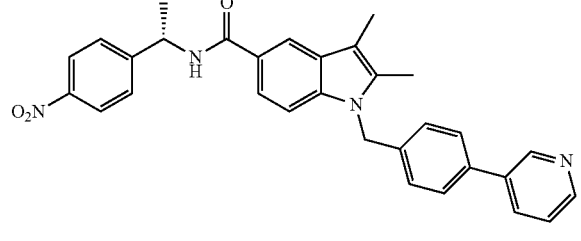
63
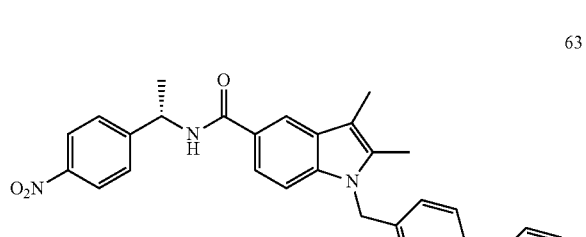
64
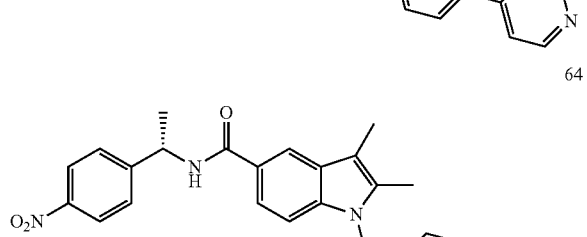

491
-continued
65
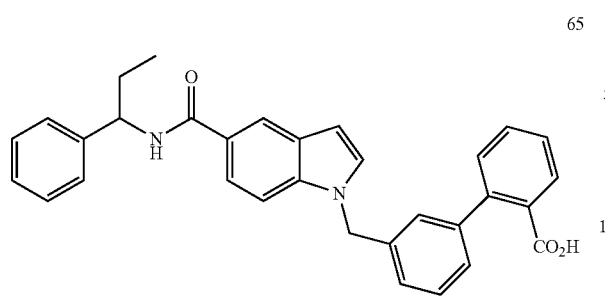
66
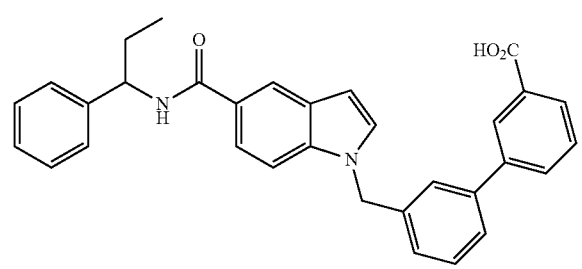
67
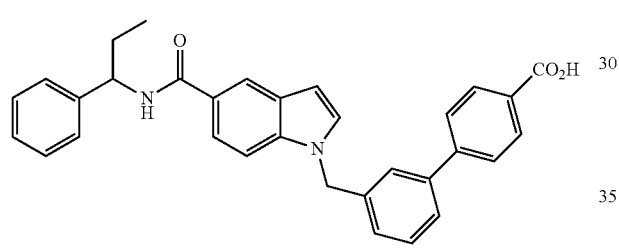
68
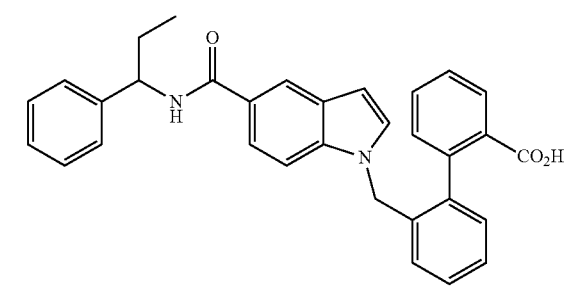
69
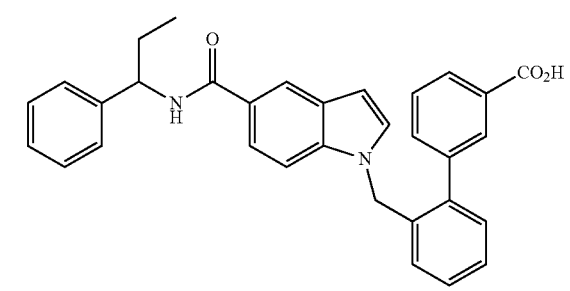
492
-continued
70
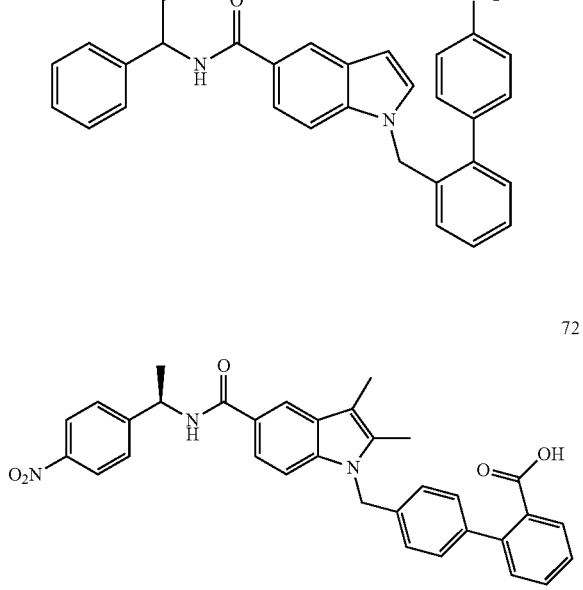
72
73
74
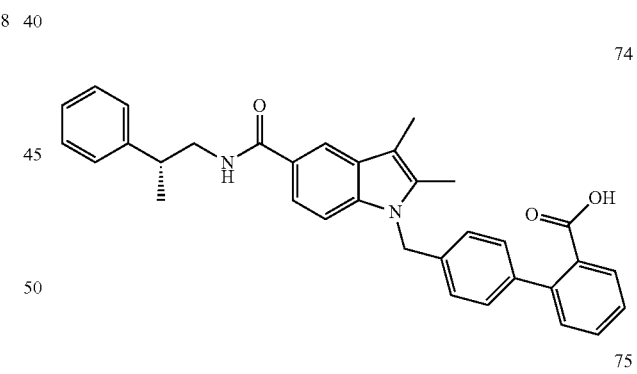
75
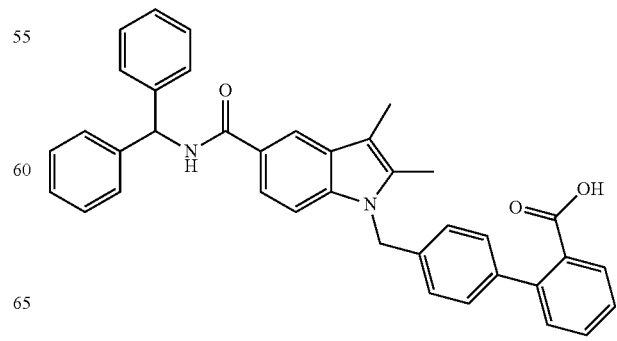

76
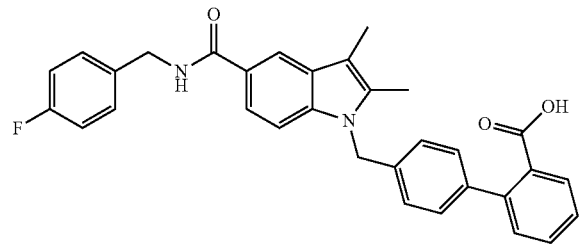
77
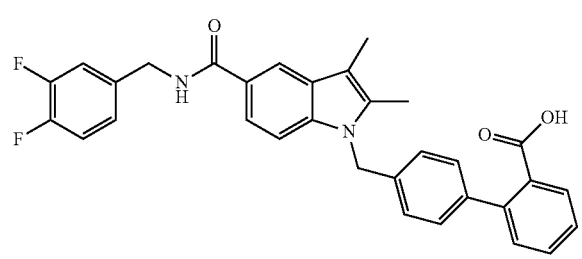
78
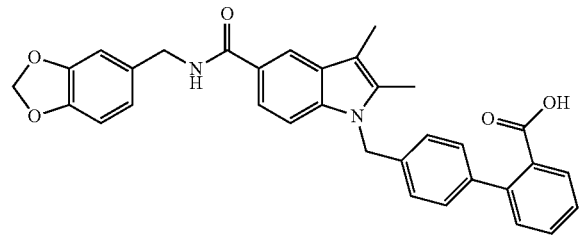
79
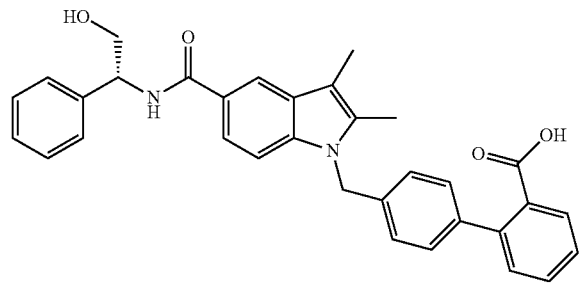
80
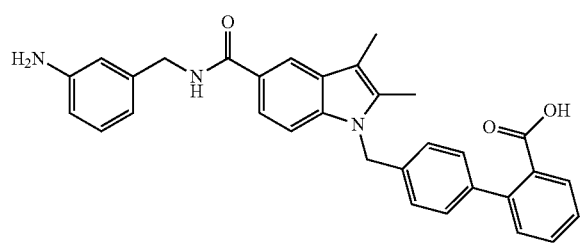
81
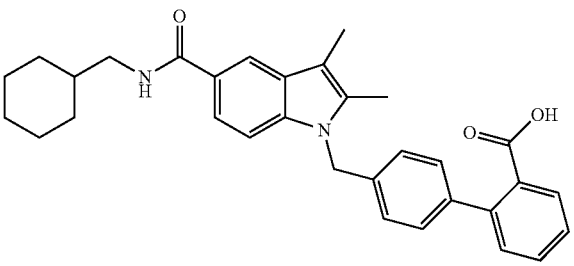
82
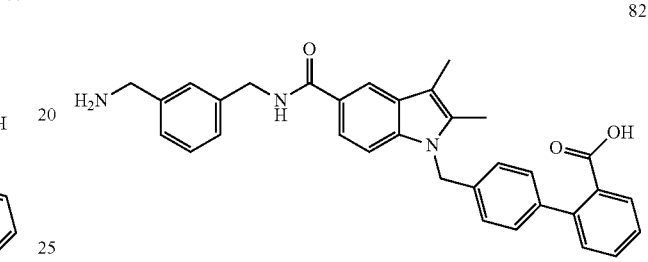
83
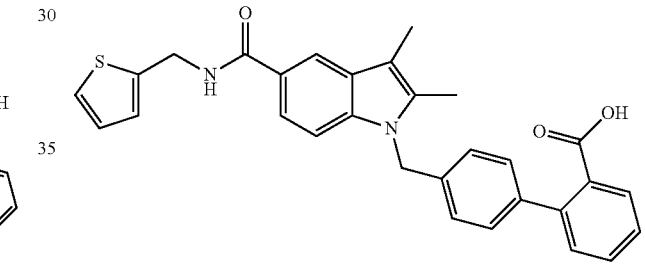
84
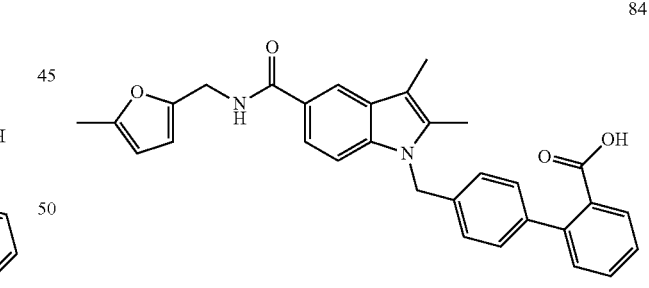
85
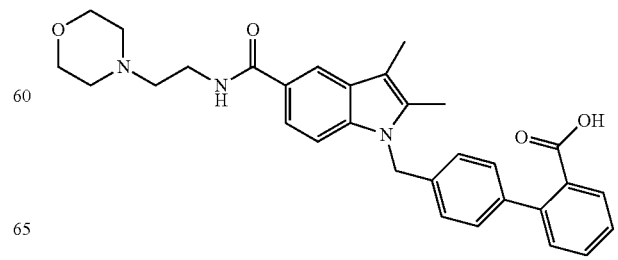

-continued
86
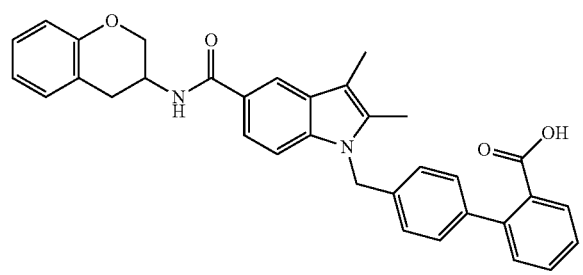
87
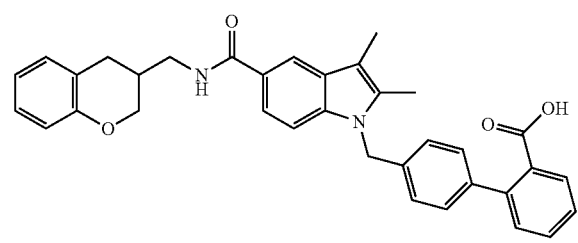
88
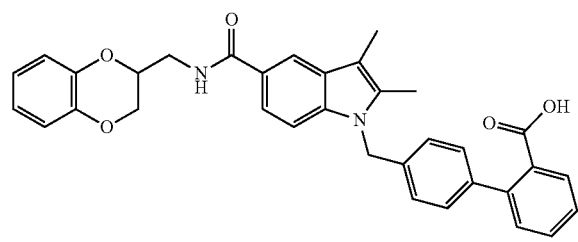
89
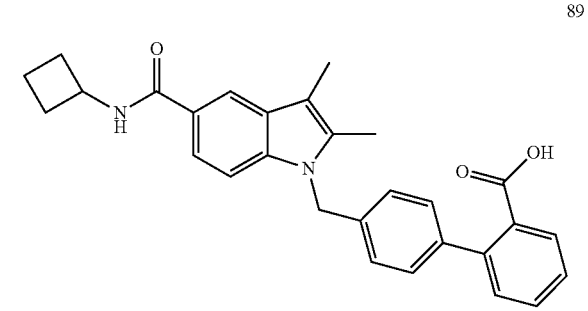
90
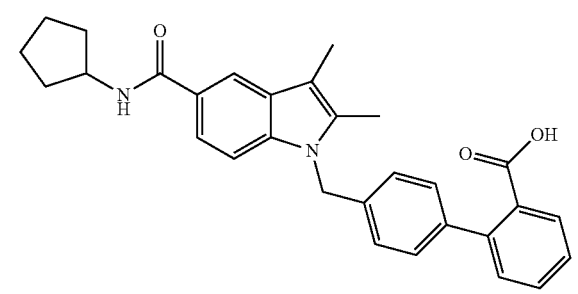
-continued
91
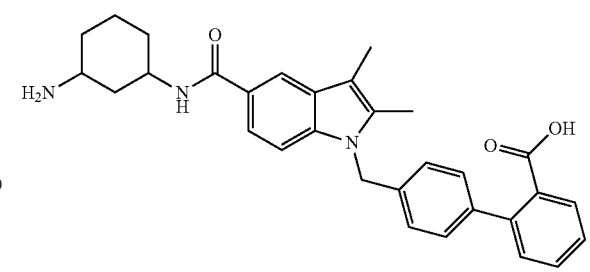
92
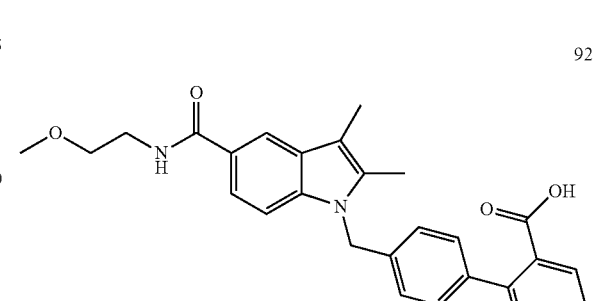
93
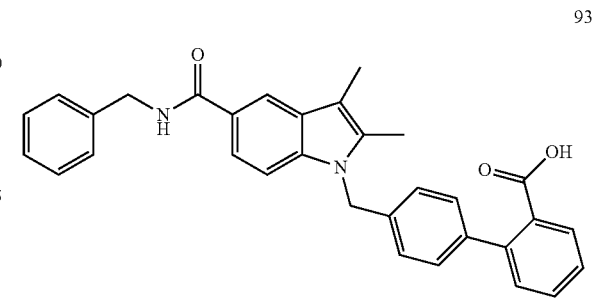
94
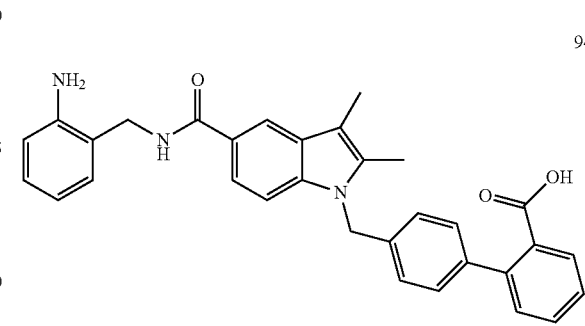
95
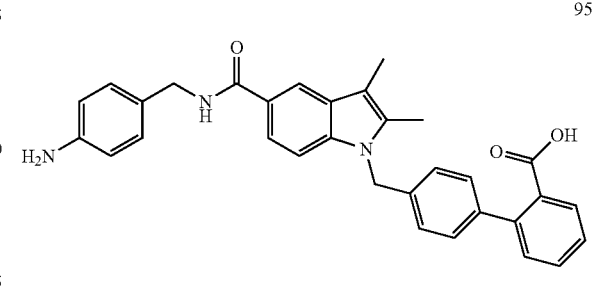

497
-continued
96
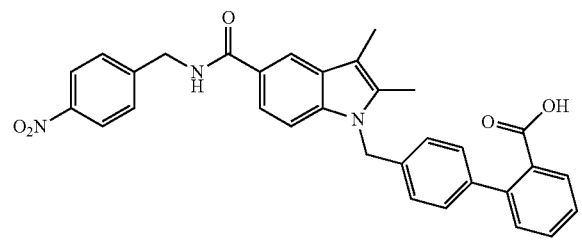
97
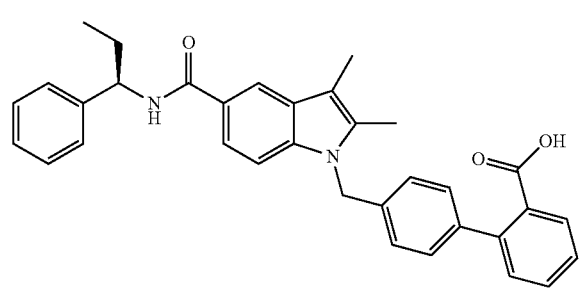
98
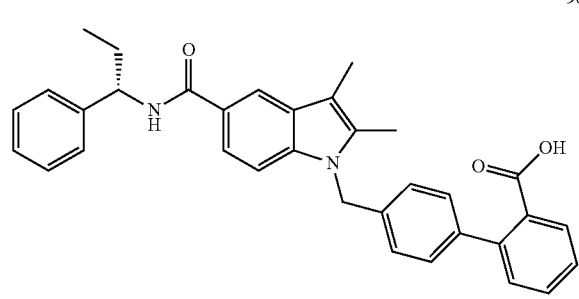
99
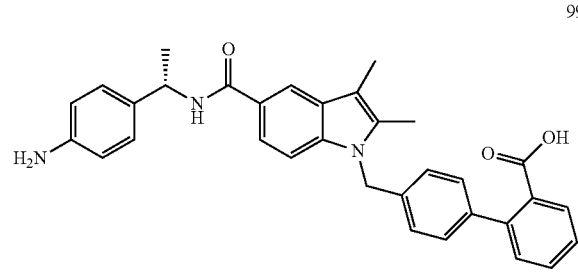
100
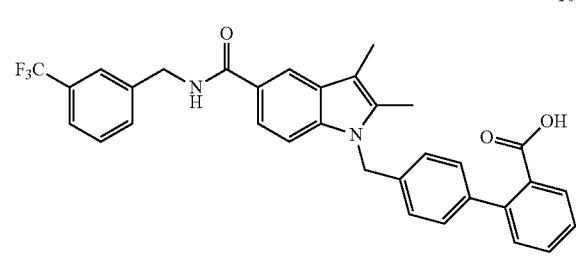
498
-continued
101
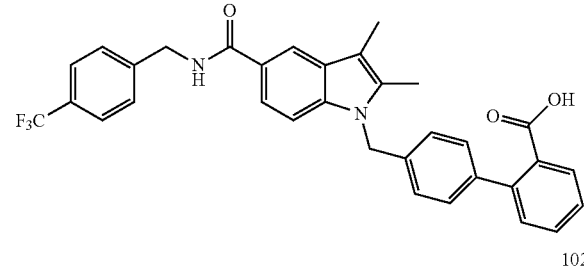
102
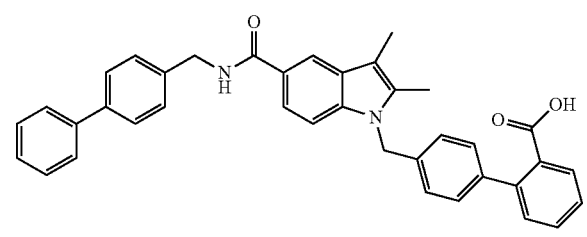
103
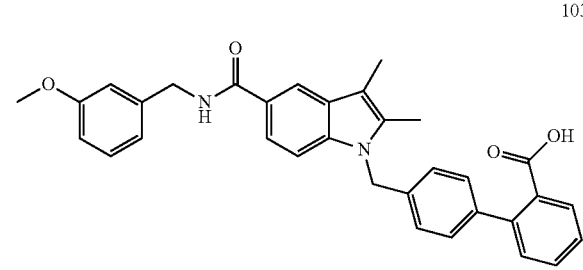
104
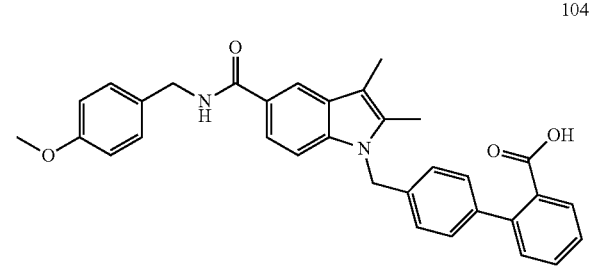
105
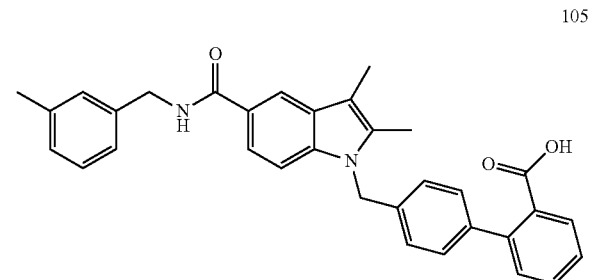
106
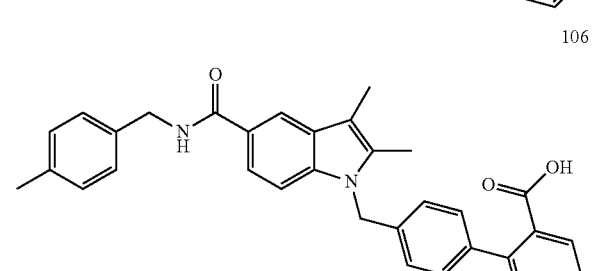

107
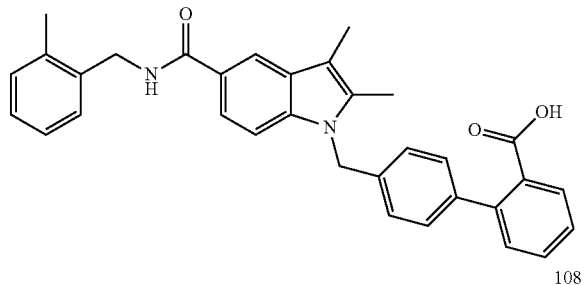
108
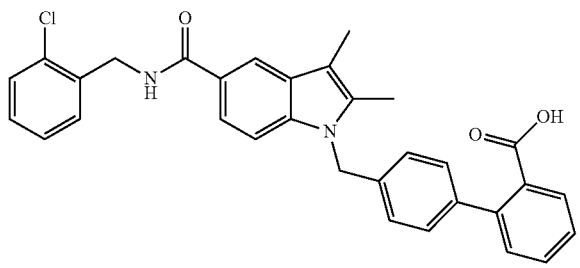
109
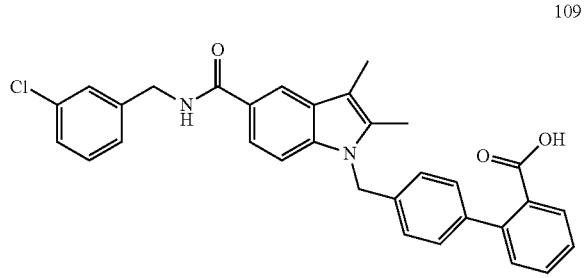
110
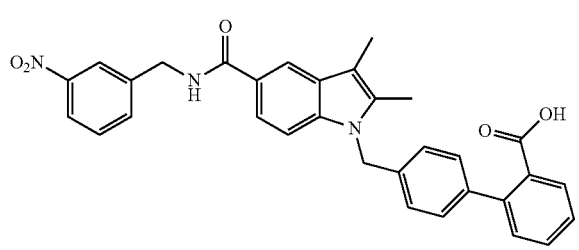
111
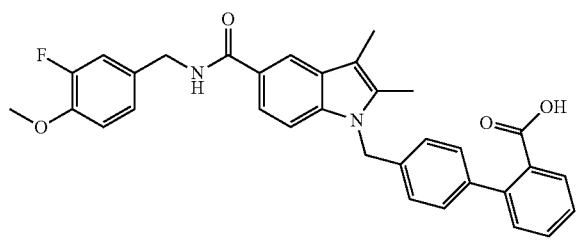
112
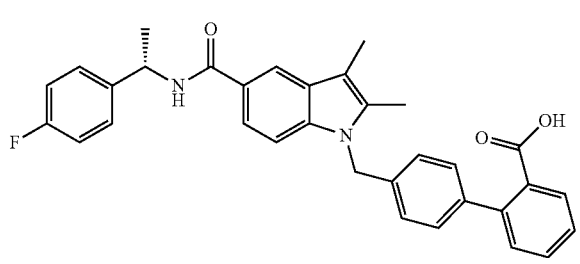
113
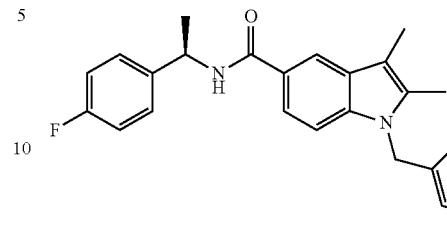
114
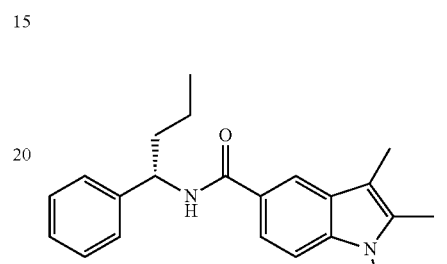
115
116
117

118
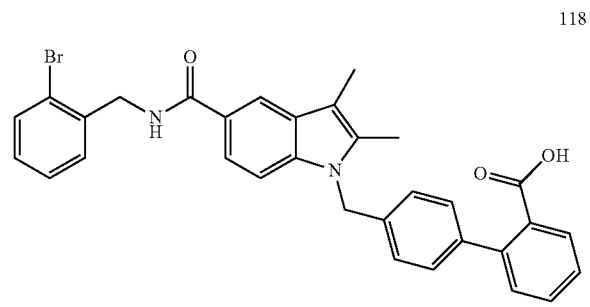
119
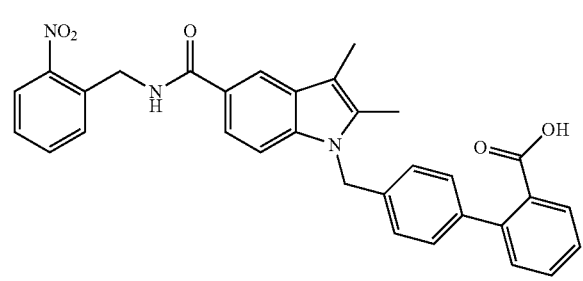
120
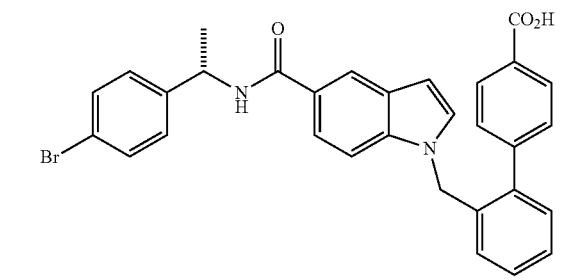
121
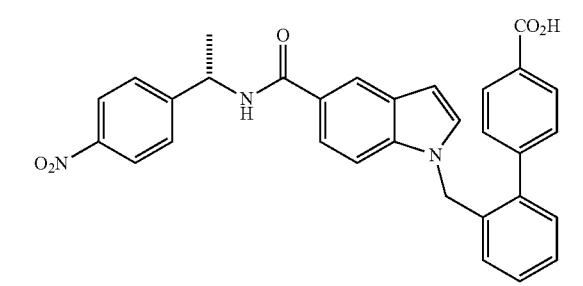
122
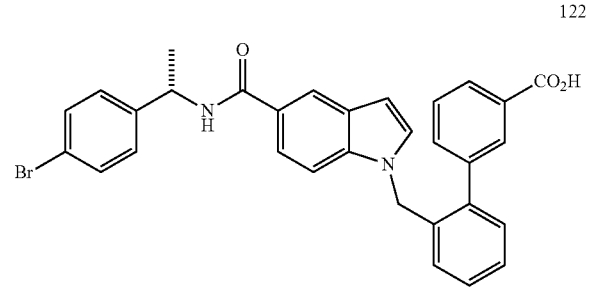
123
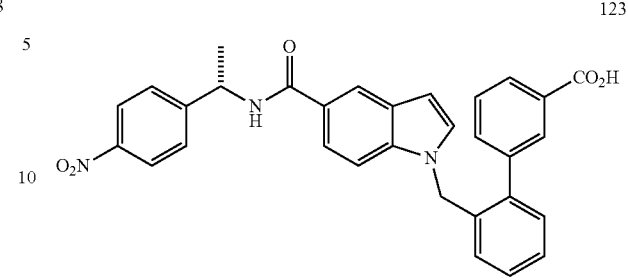
124
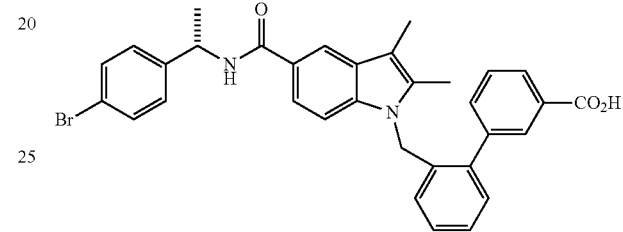
125
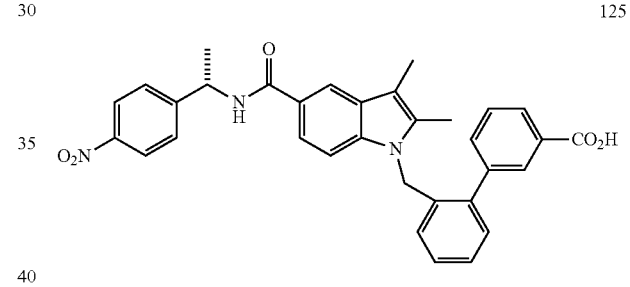
126
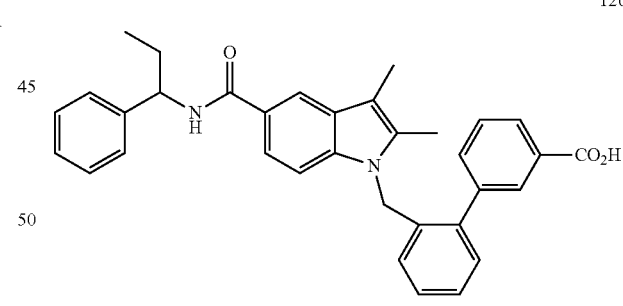
127
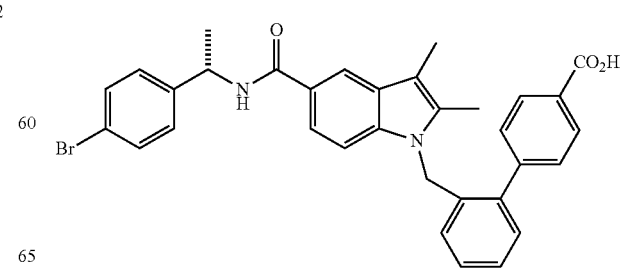

128
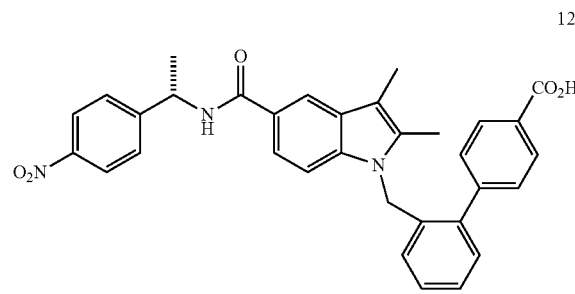
129
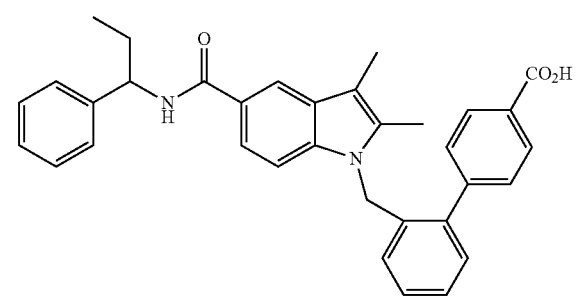
130
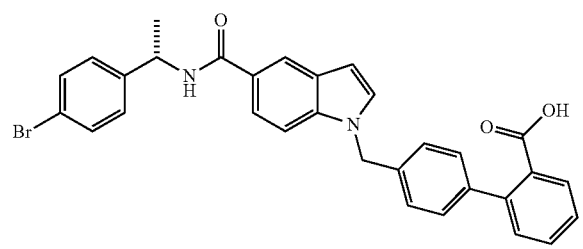
131
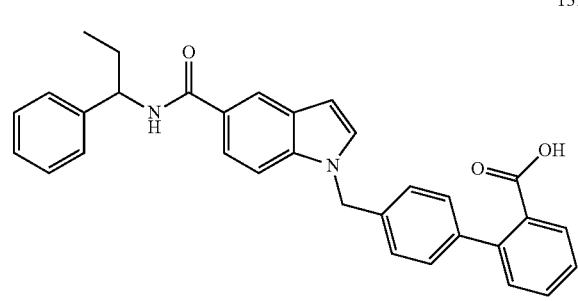
132
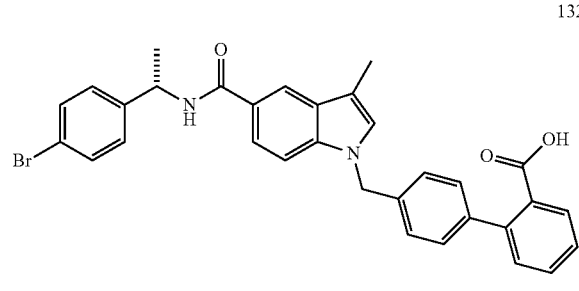
133
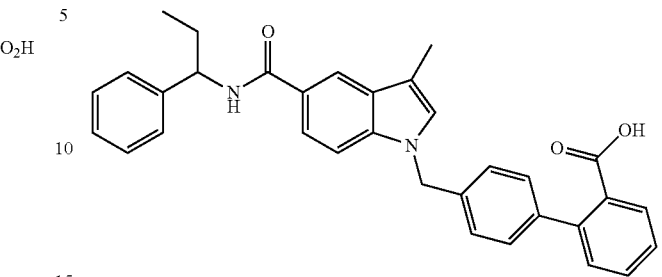
134
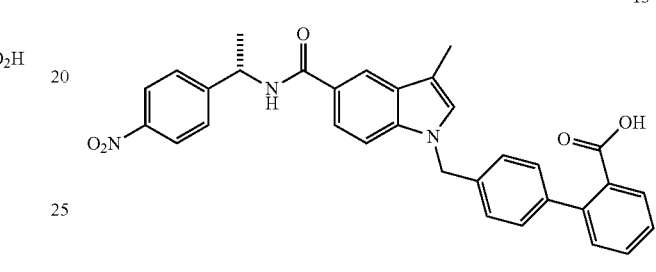
135
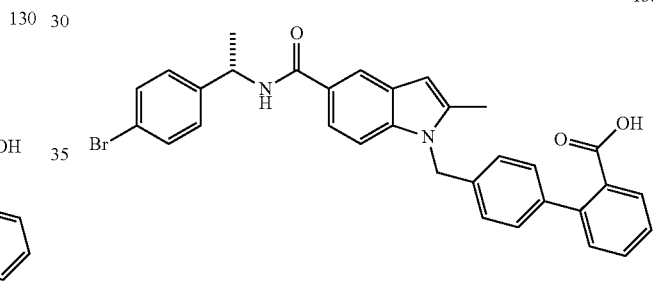
136
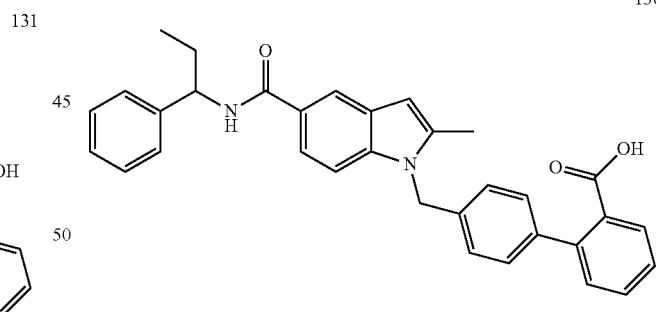
137
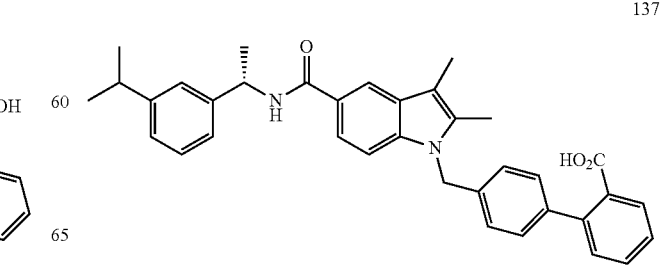

505
-continued
138
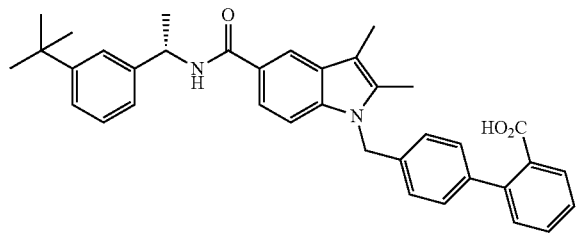
139
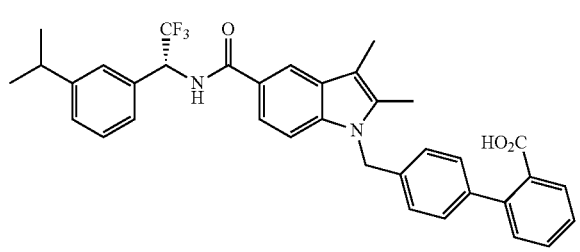
140
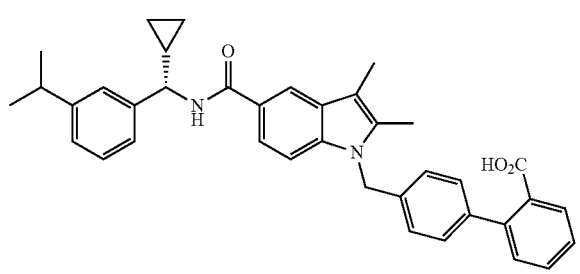
141
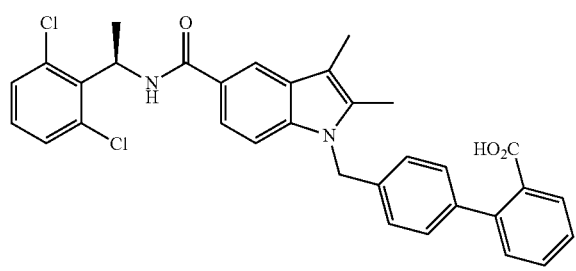
142
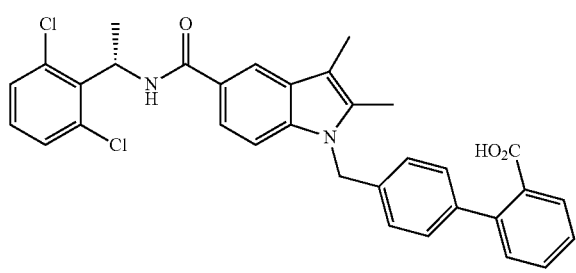
506
-continued
143
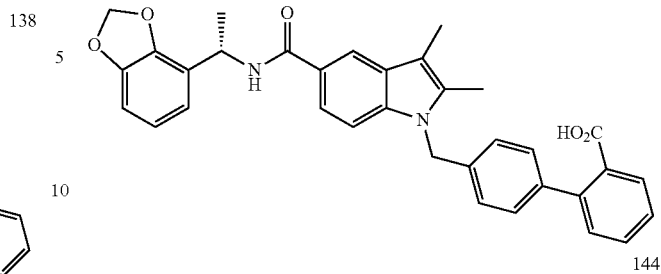
144
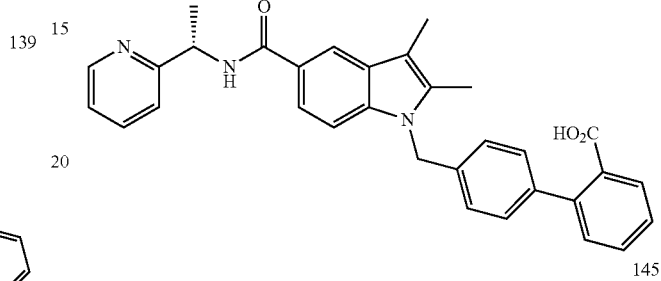
145
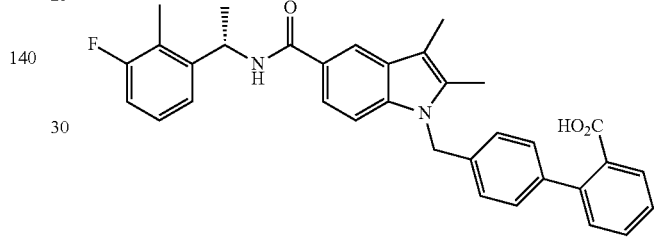
146
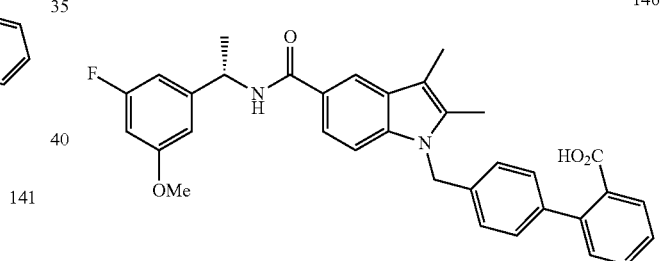
147
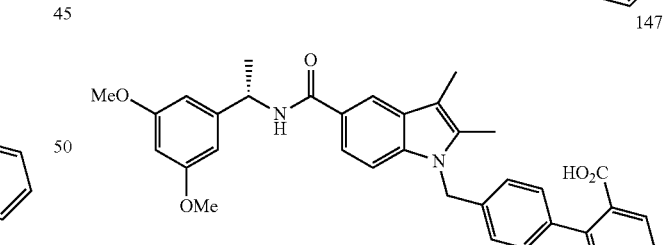
148
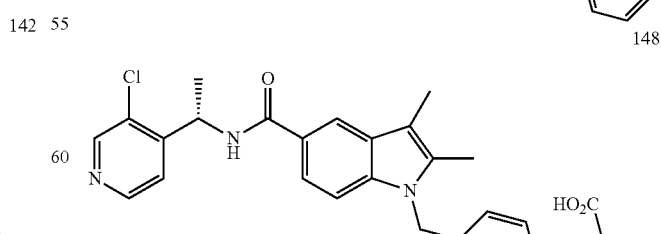

507 -continued
149
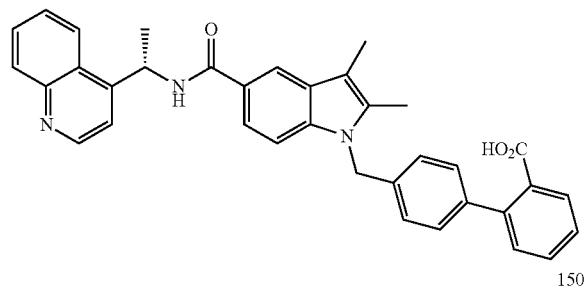
150
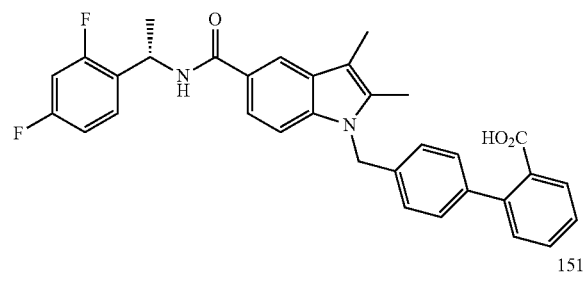
151
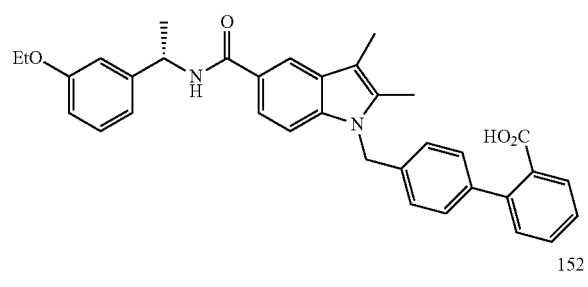
152
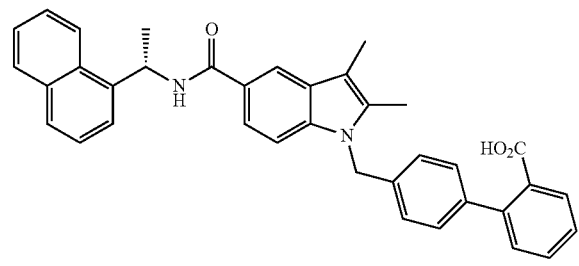
153
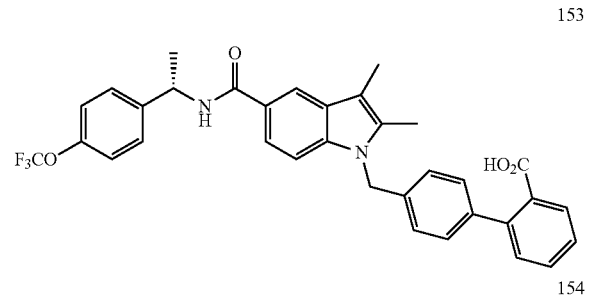
154
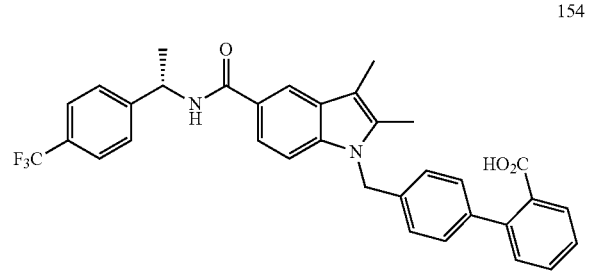
508 -continued
155
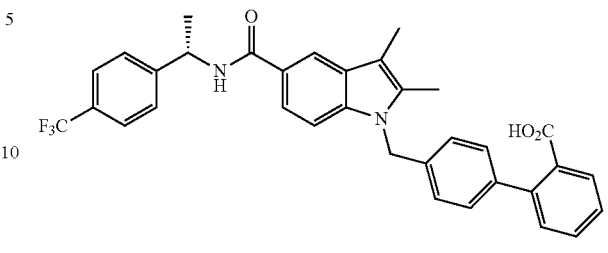
156
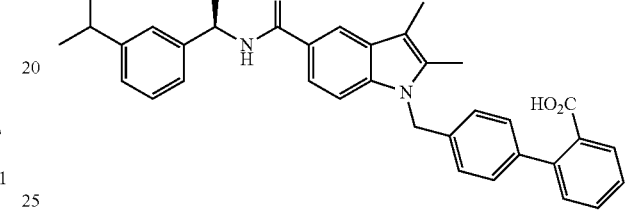
157
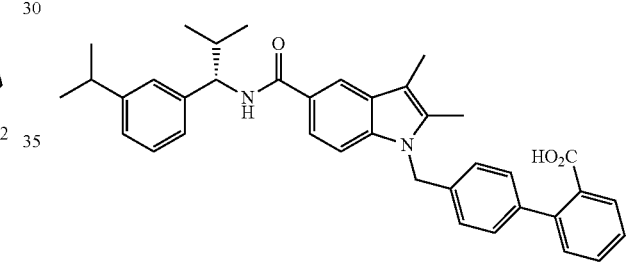
158
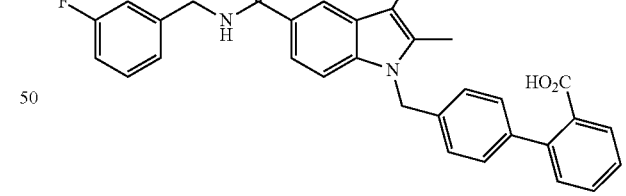
159
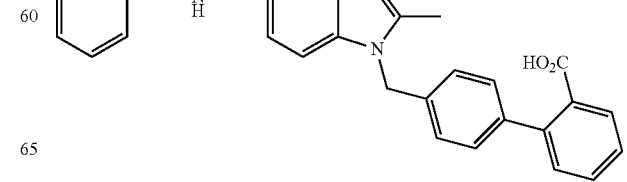

160
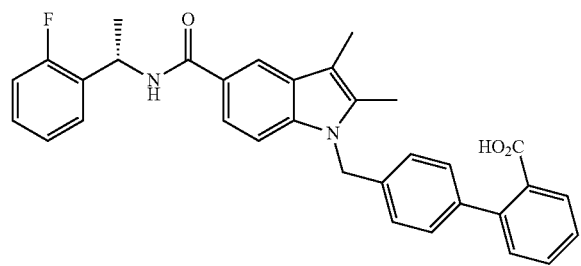
161
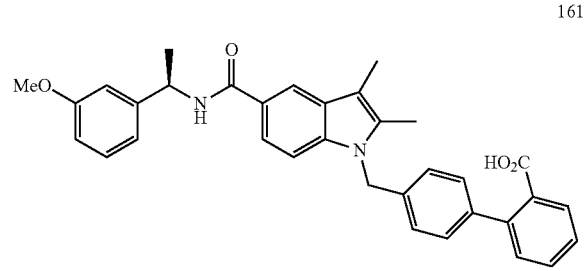
162
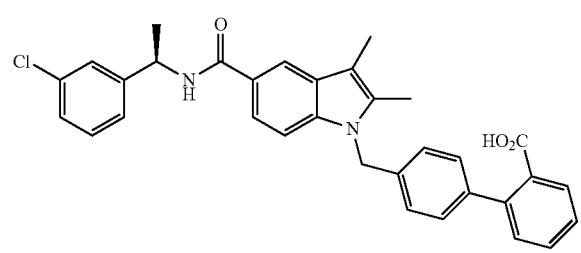
163
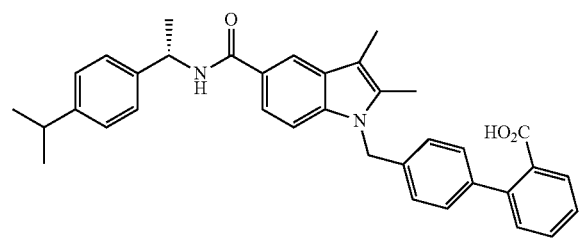
164
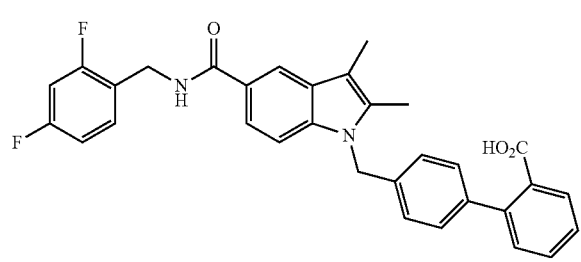
165
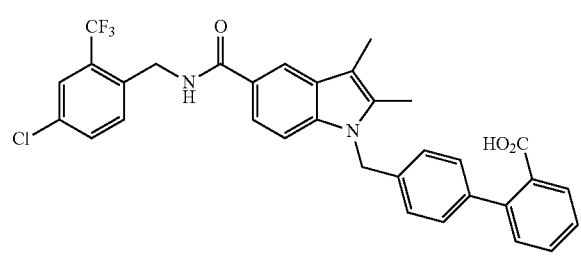
166
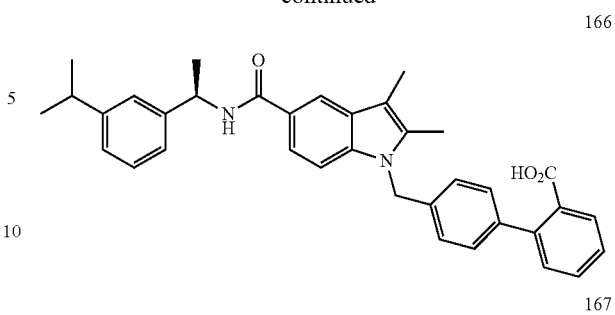
167
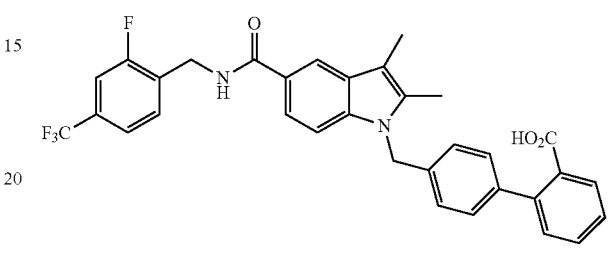
168
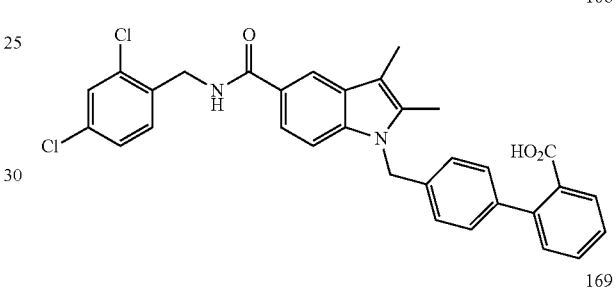
169
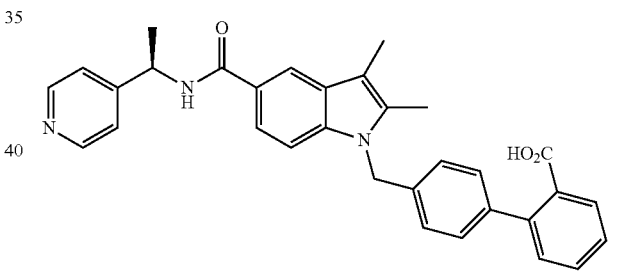
170
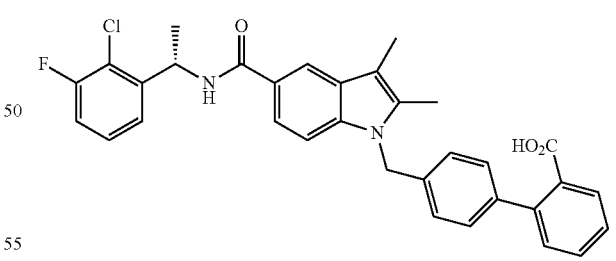
171
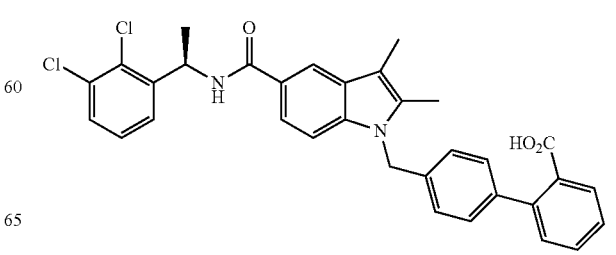

511
-continued
172
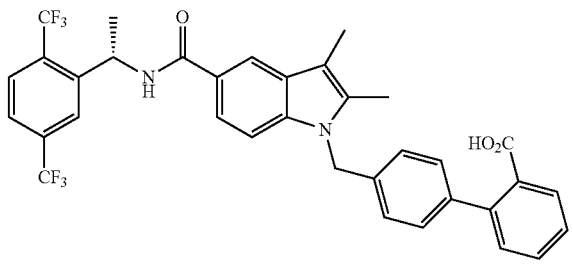
173
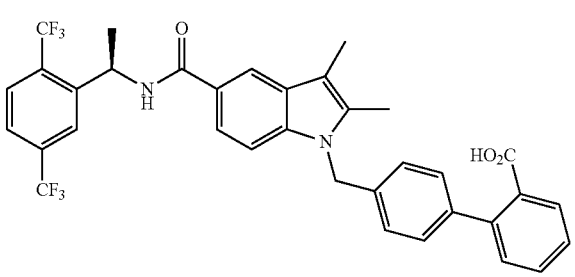
174
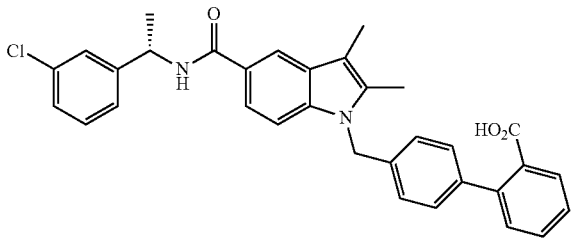
175
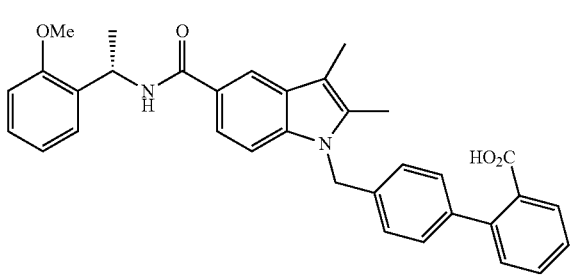
176
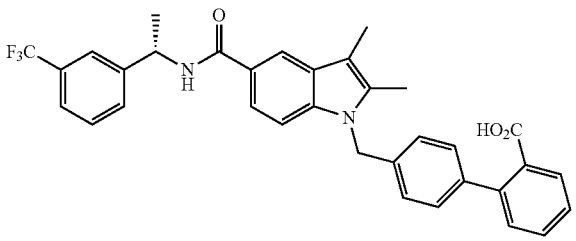
512
-continued
177
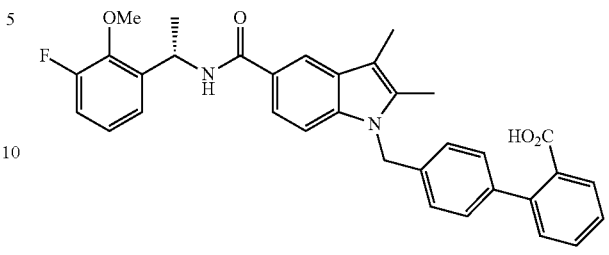
178
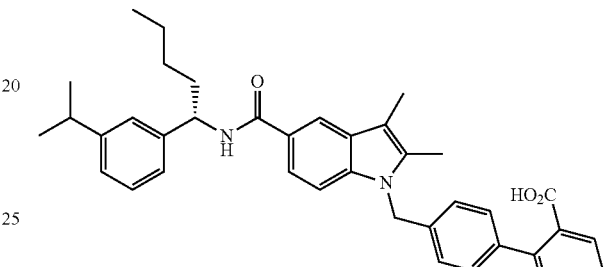
179
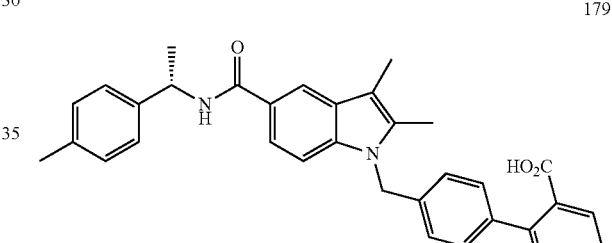
180
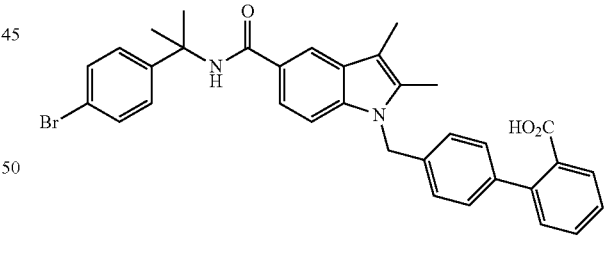
181
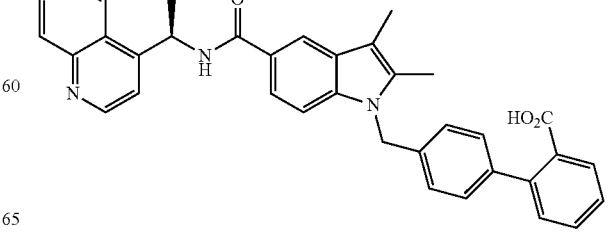

513
-continued
182
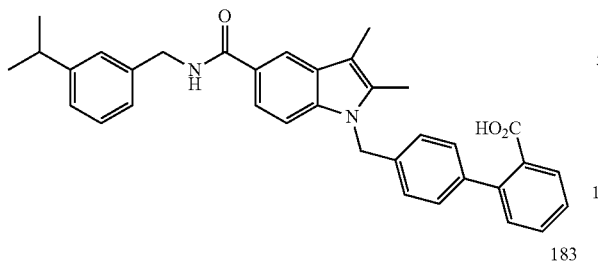
183
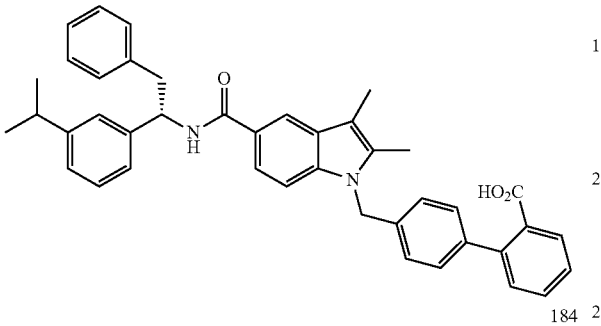
184
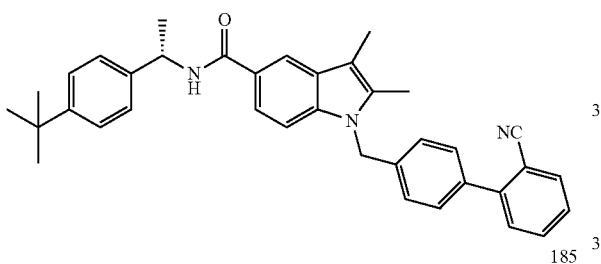
185
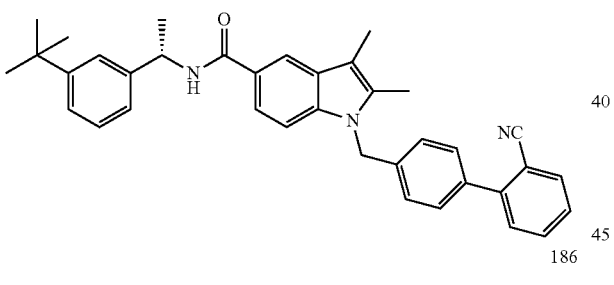
186
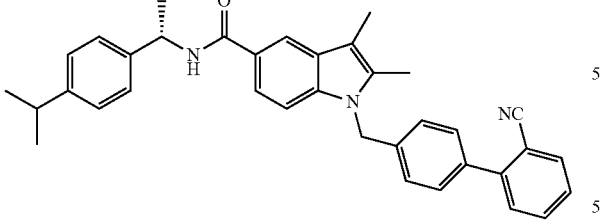
187
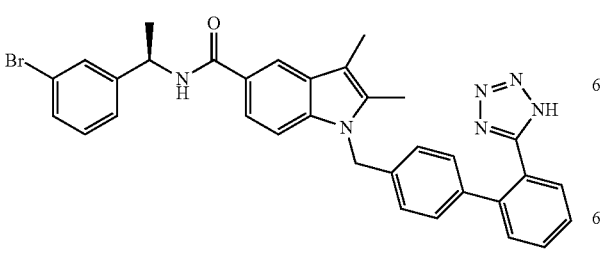
514
-continued
188
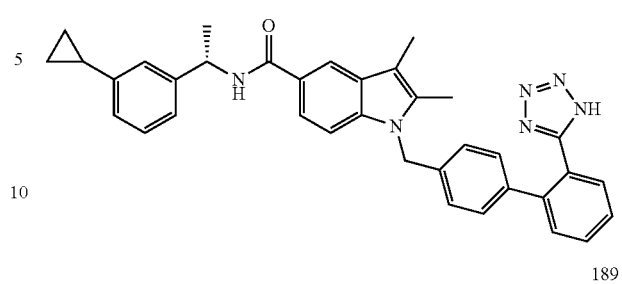
189
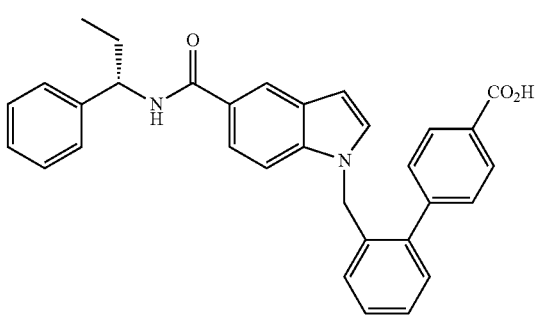
190
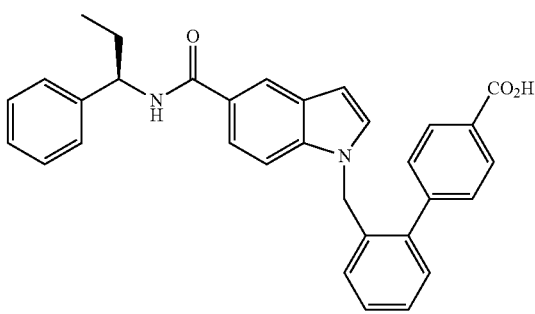
191
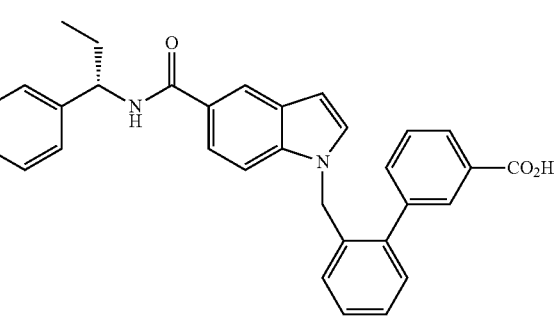
192
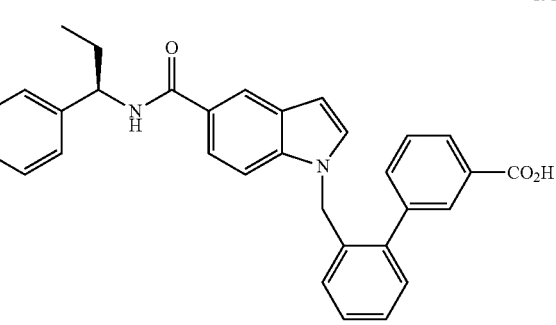

515
-continued
193
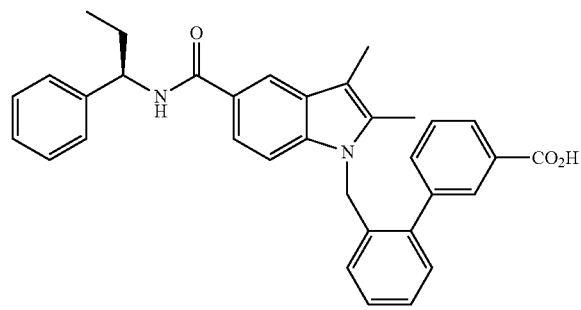
194
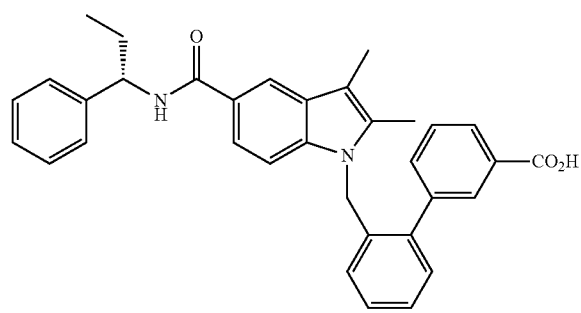
195
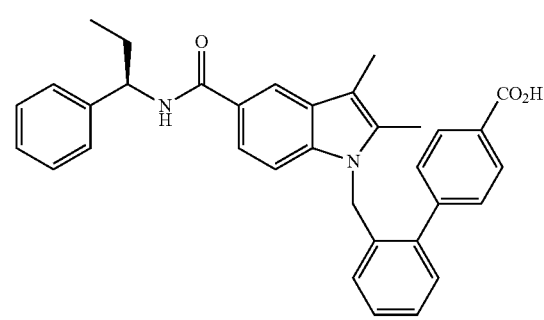
196
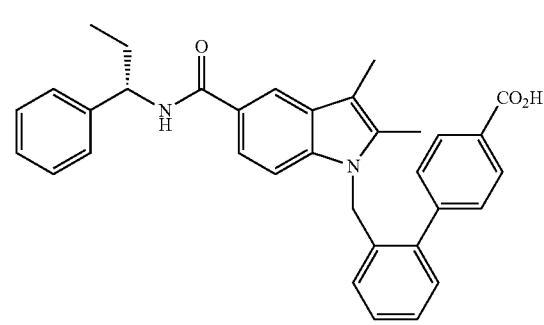
197
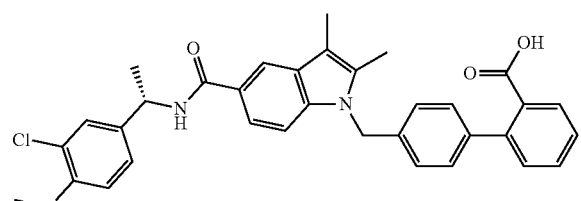
516
-continued
198
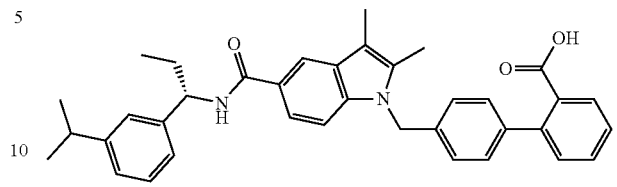
199
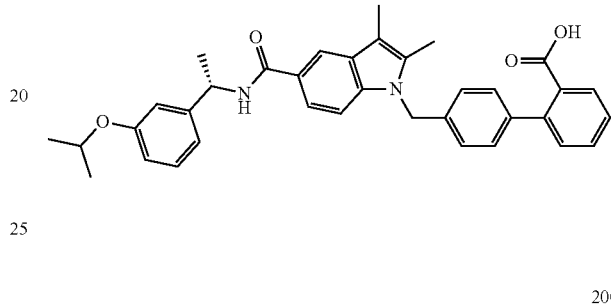
200
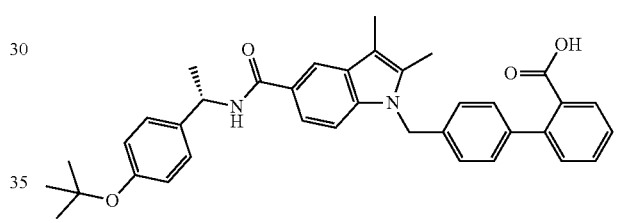
201
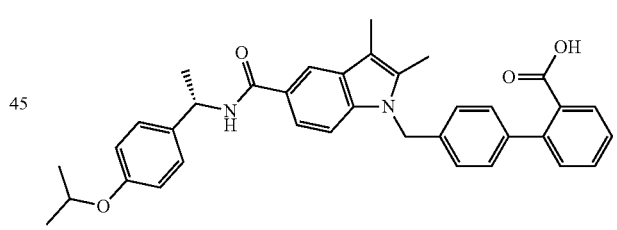
202
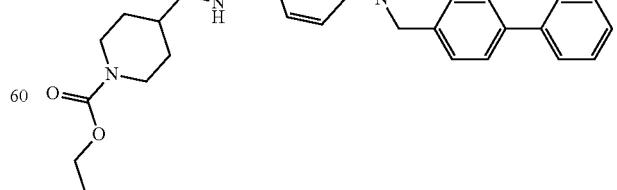

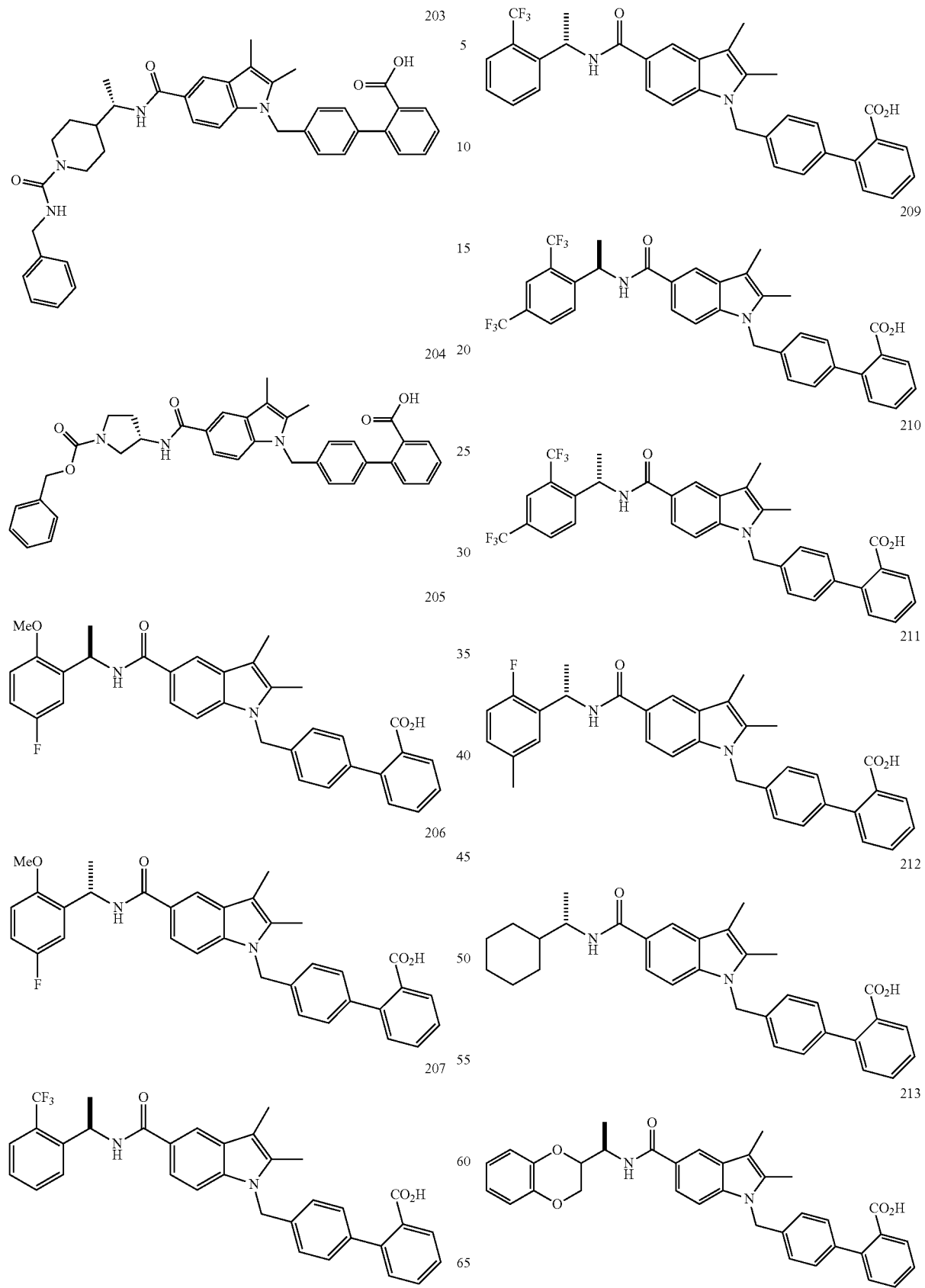

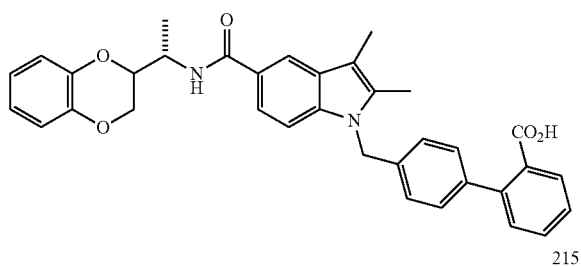
214
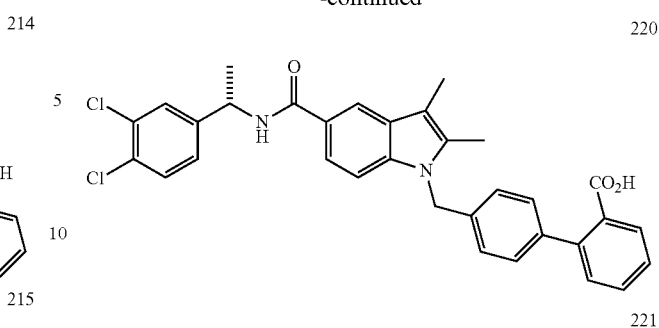
220
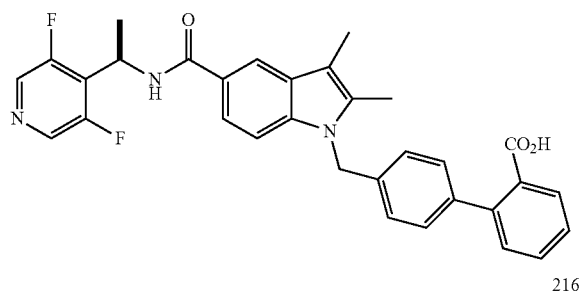
215
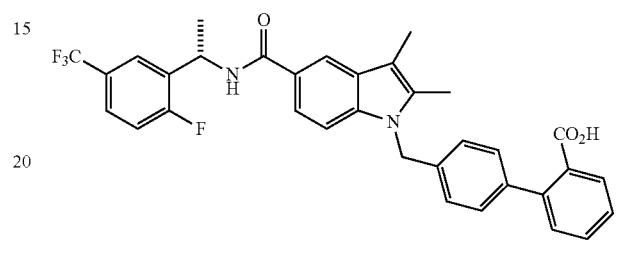
221
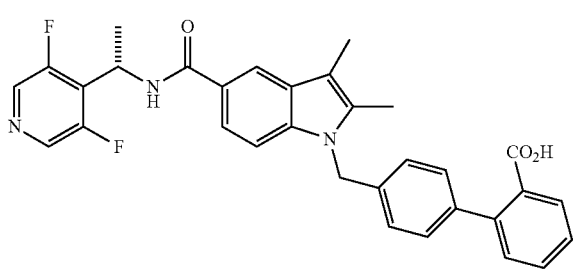
216
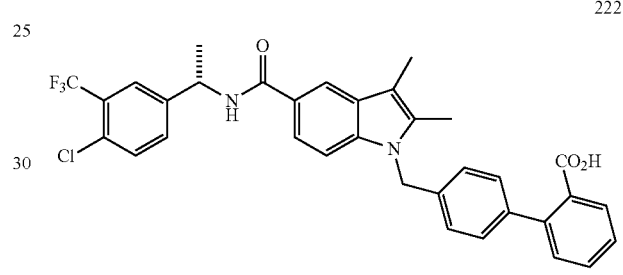
222
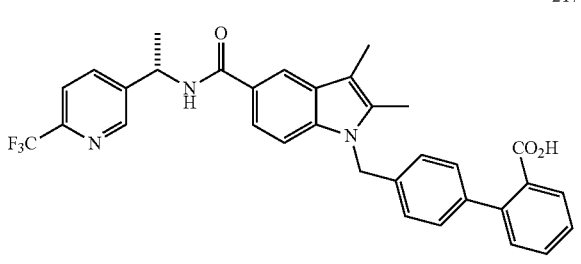
217
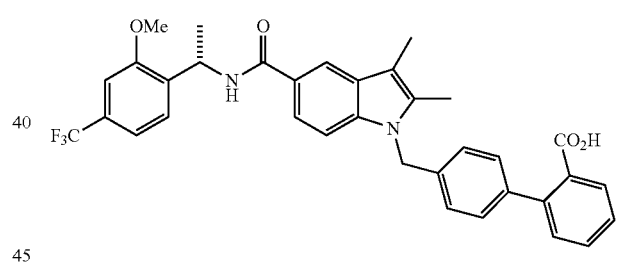
223
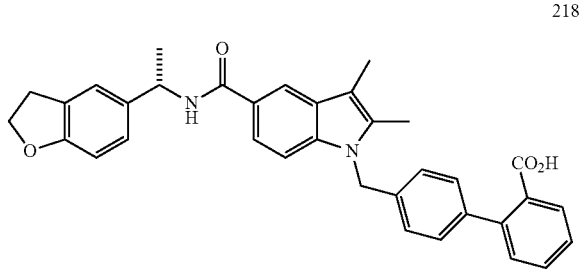
218
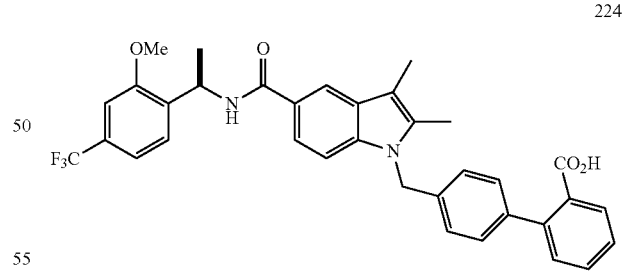
224
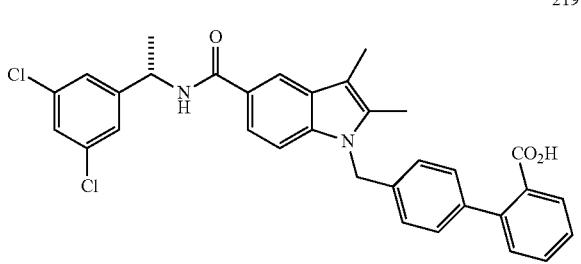
219
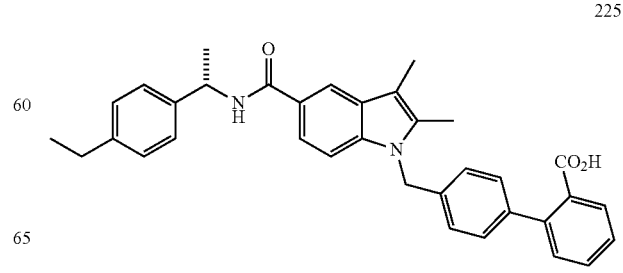
225

226
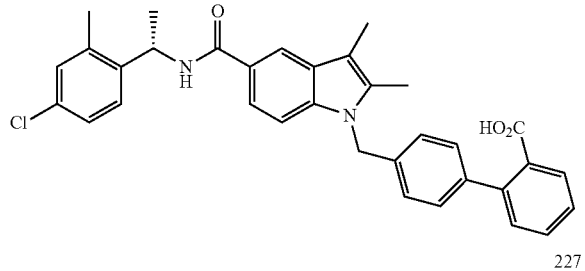
227
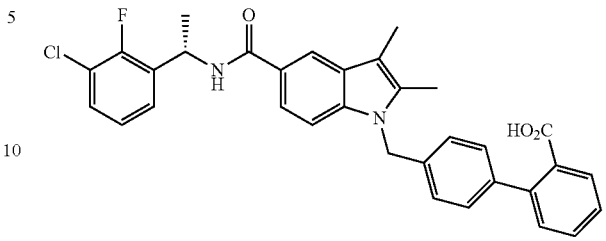
228
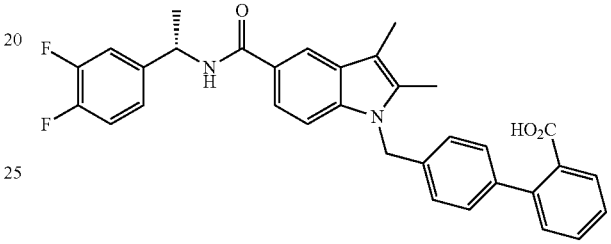
229
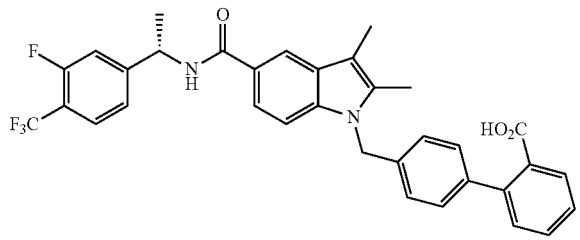
230
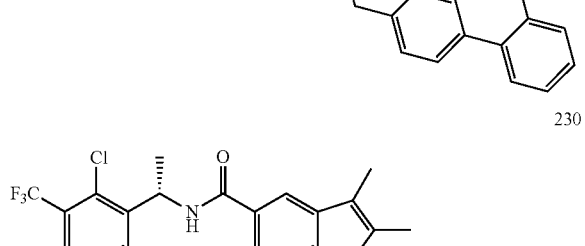
231
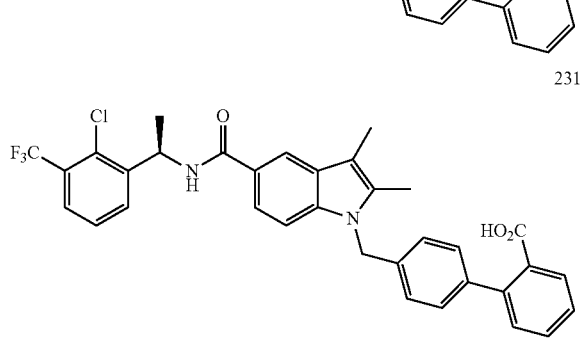
232
233
234
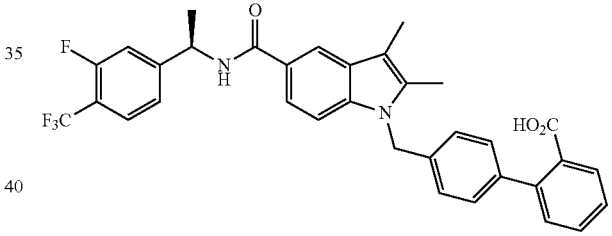
235
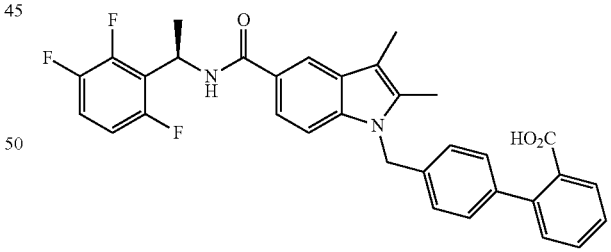
236
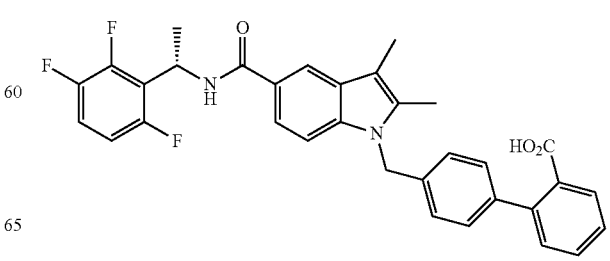

237
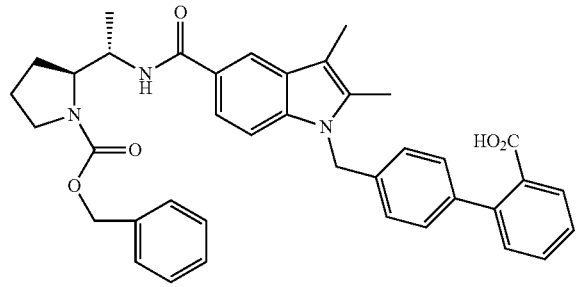
242
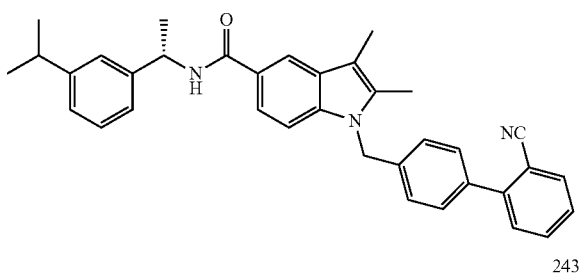
238
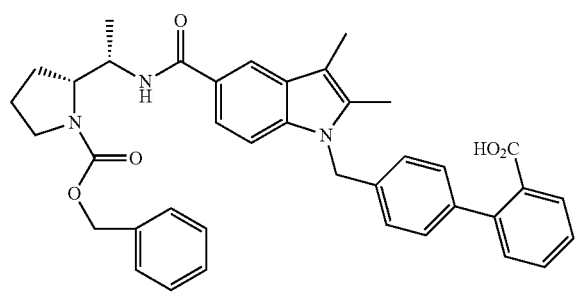
243
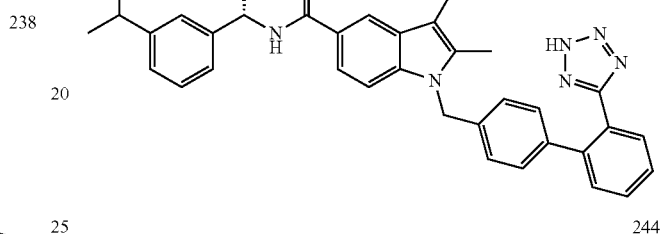
244
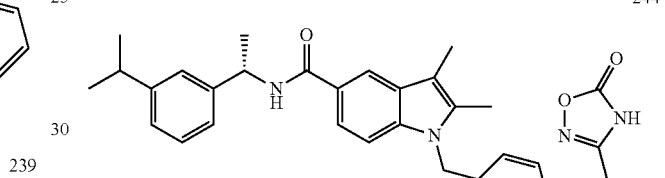
239
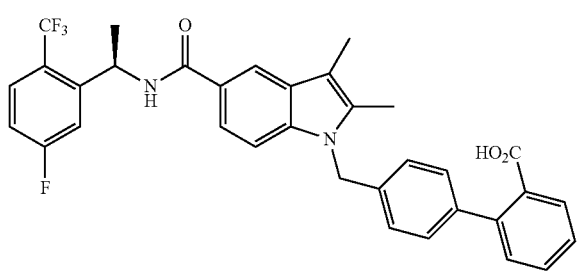
245
240
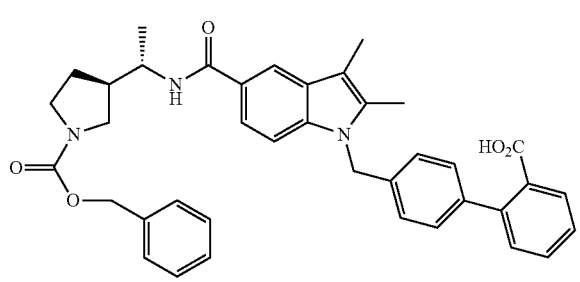
246
241
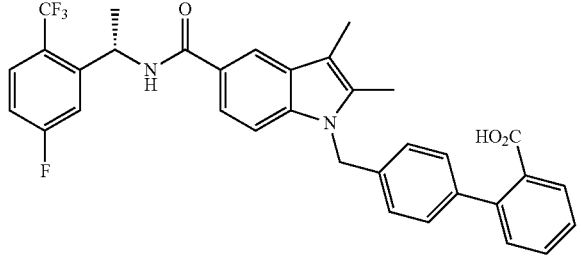
247
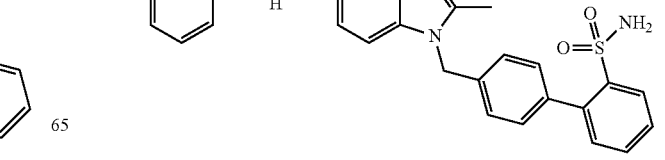

248
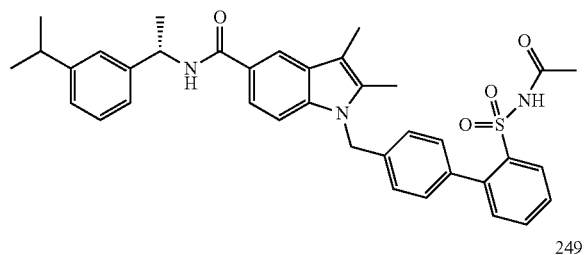
249
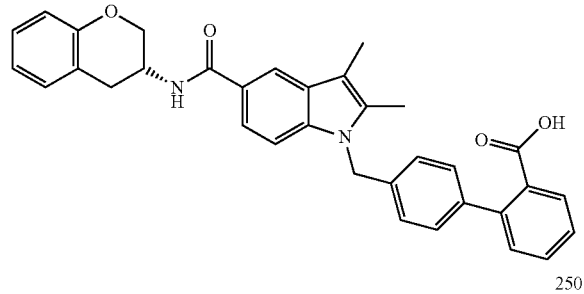
250
251
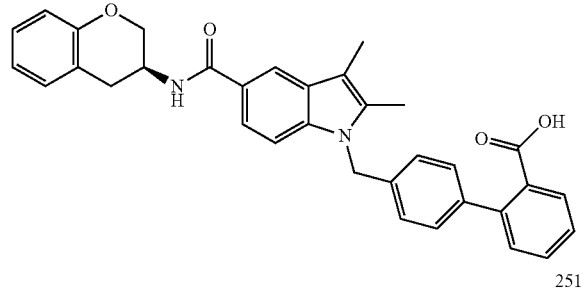
252
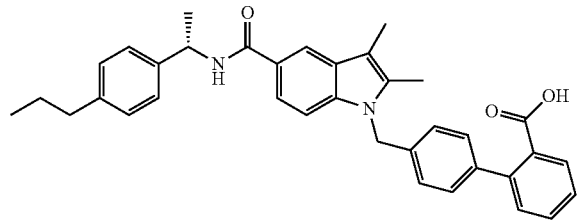
253
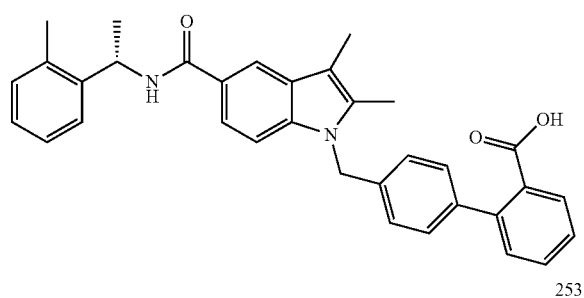
254
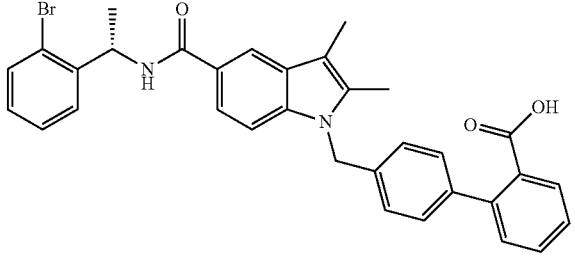
255
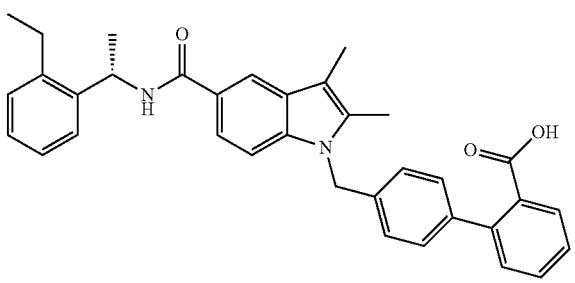
256
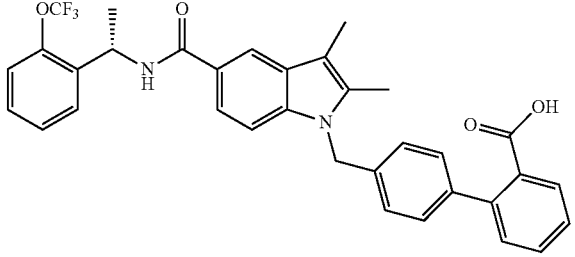
257
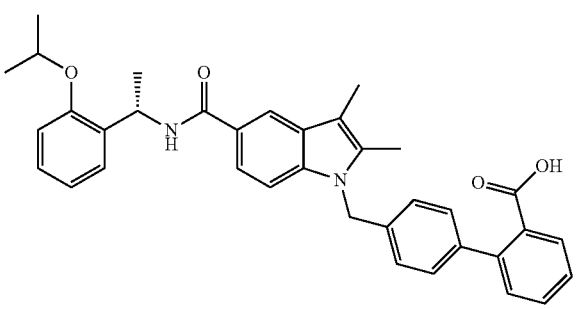
258
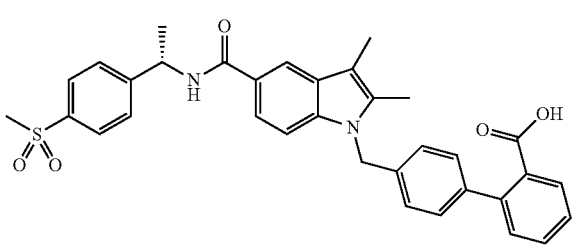

259
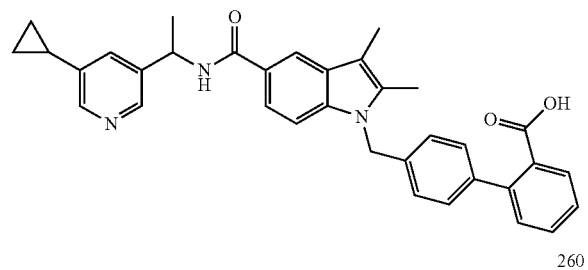
260
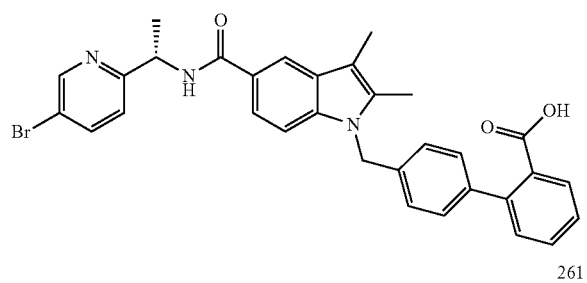
261
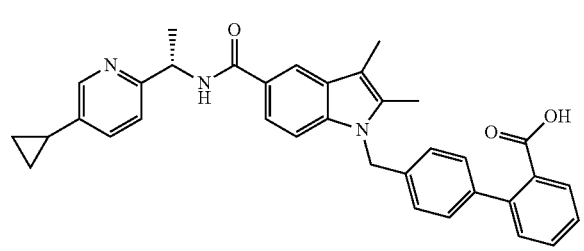
262
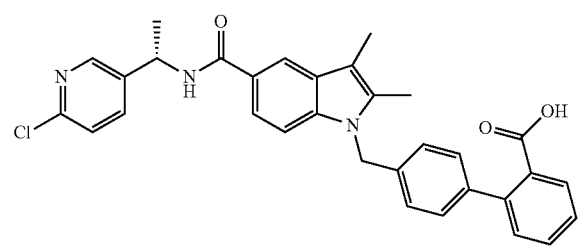
263
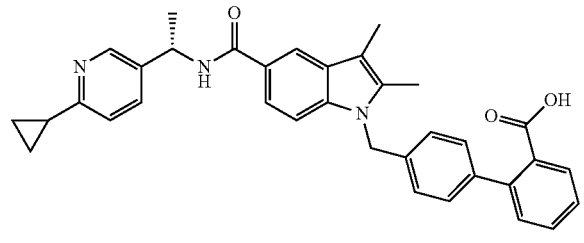
264
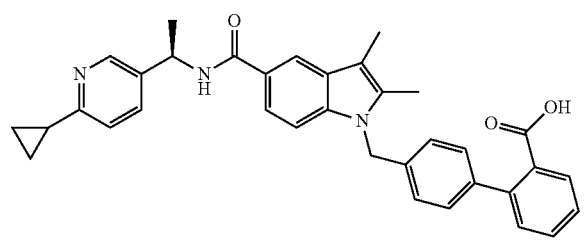
265
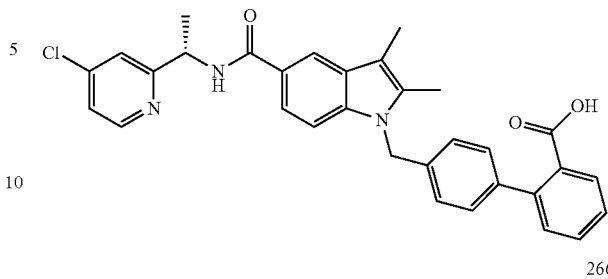
266
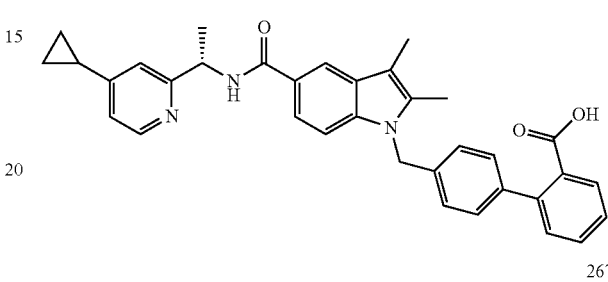
267
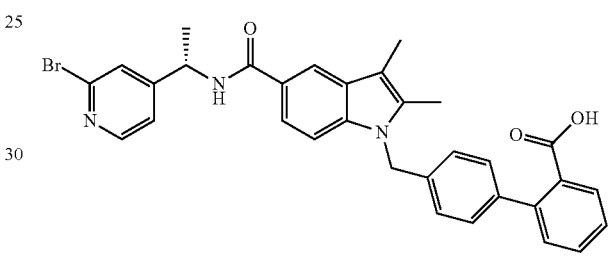
268
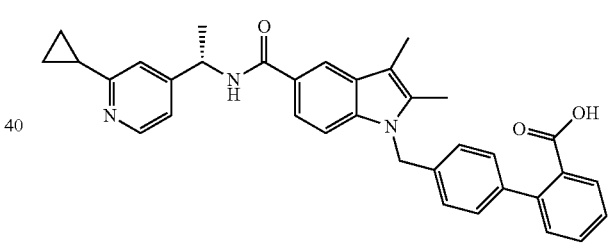
269
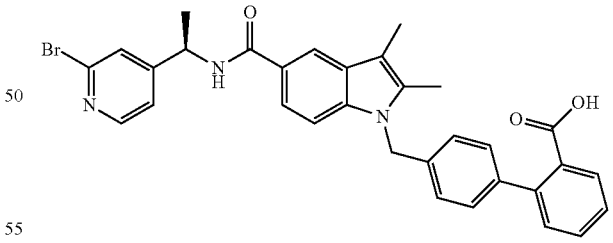
270
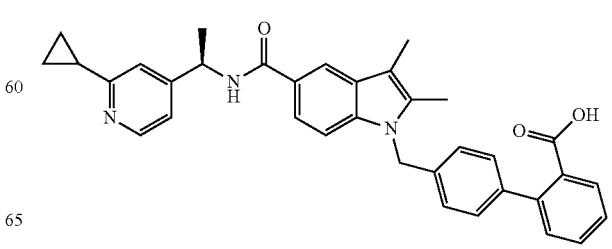

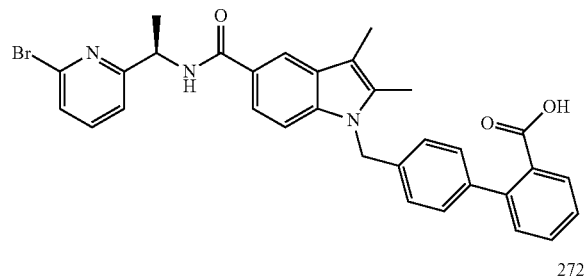
271
272
273
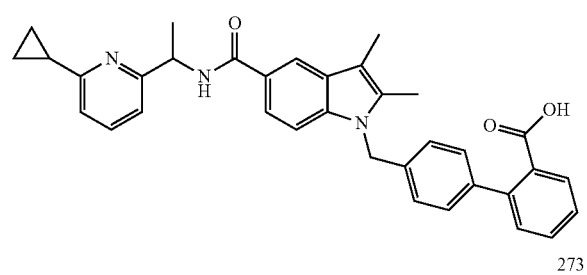
274
275
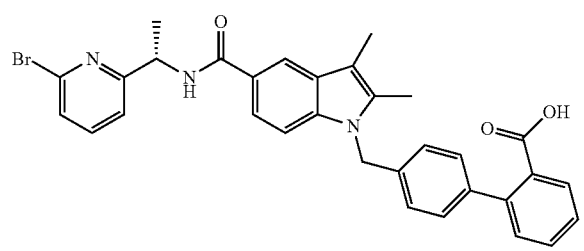
276
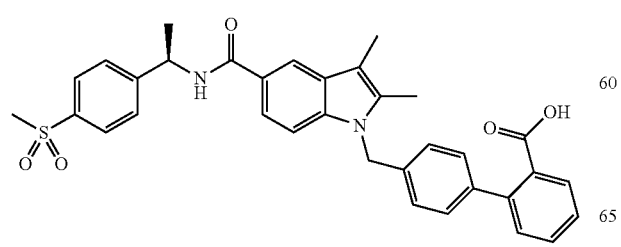
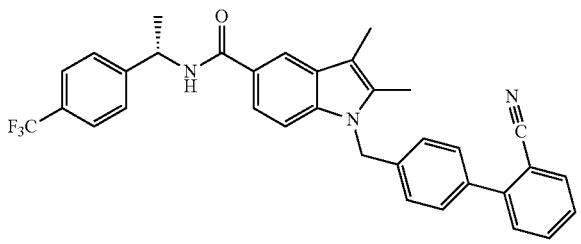
277
278
279
280
281
282
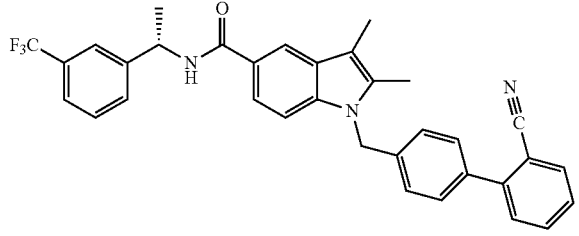

531
283
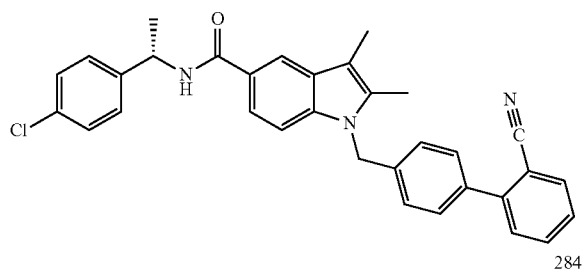
284
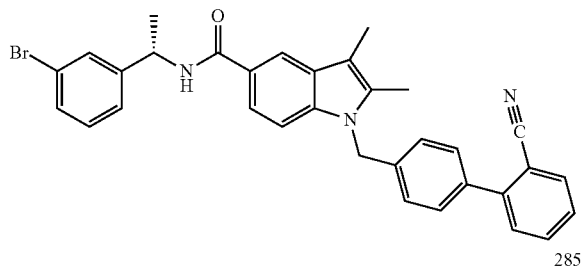
285
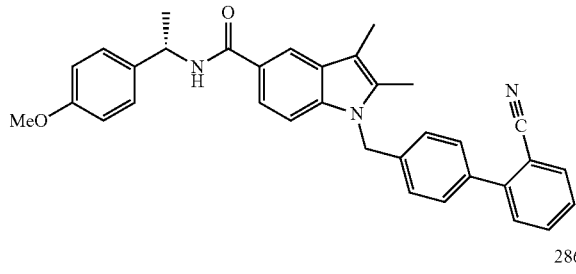
286
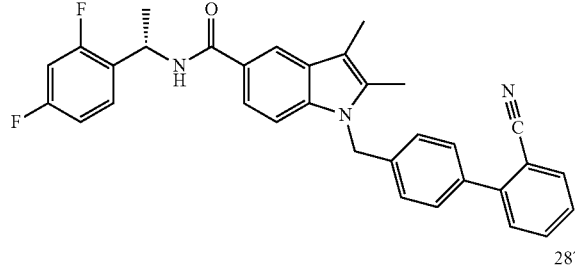
287
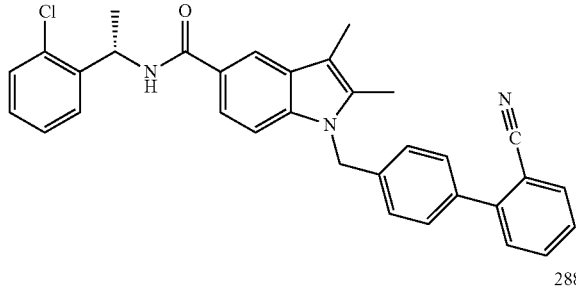
288
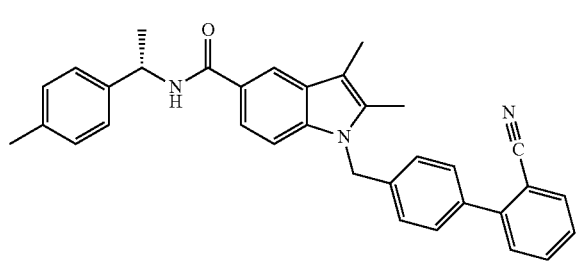
532
289
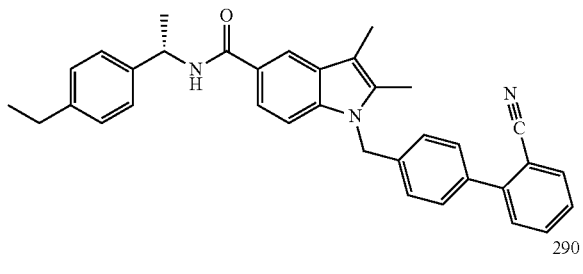
290
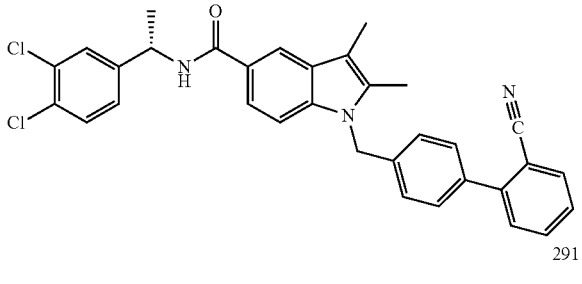
291
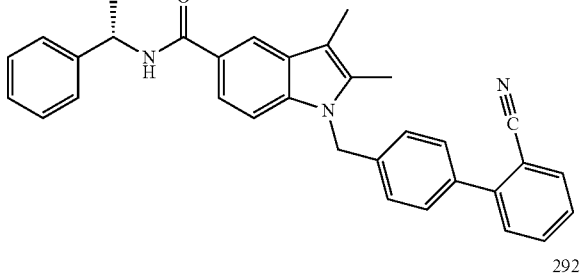
292
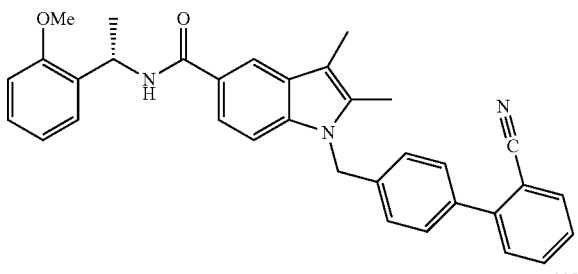
293
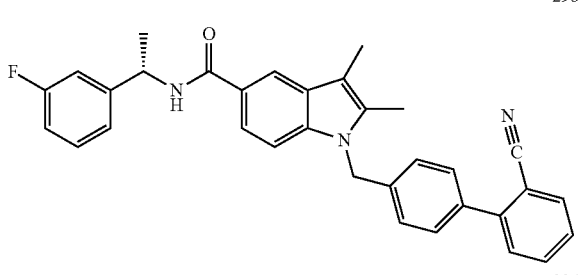
294
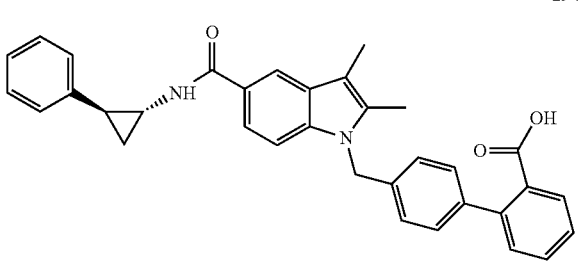

533
-continued
295
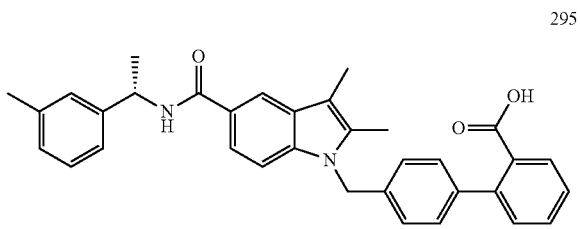
296
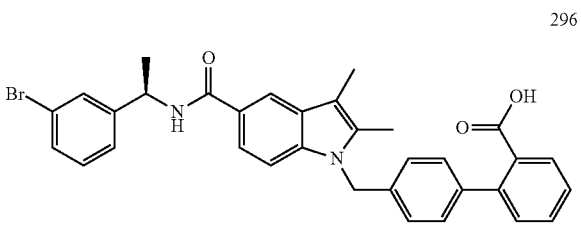
297
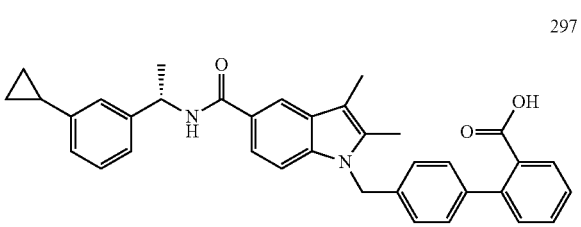
298
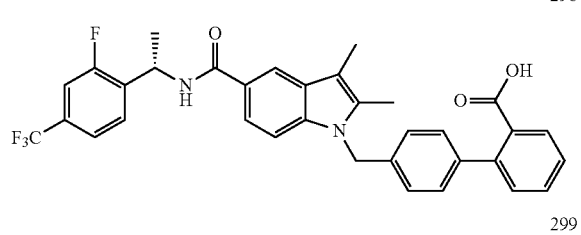
299
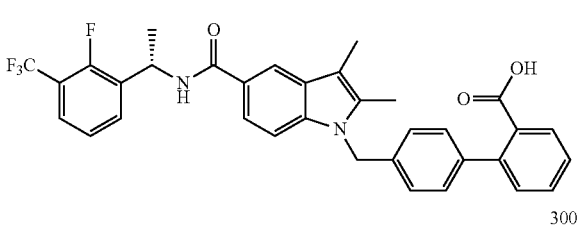
300
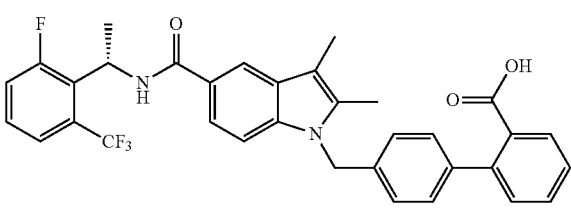
301
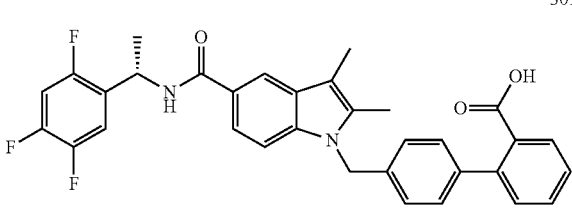
534
-continued
302
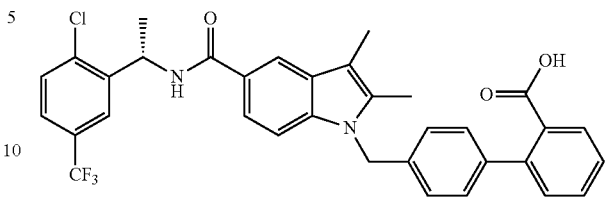
303
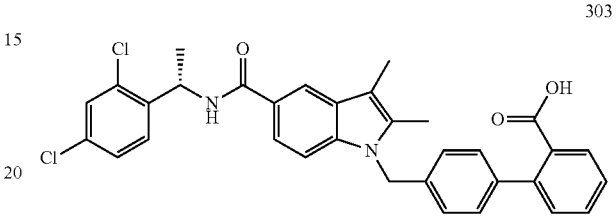
304
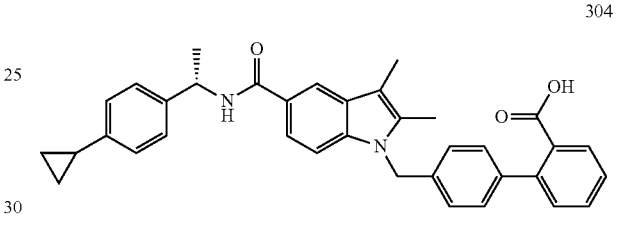
305
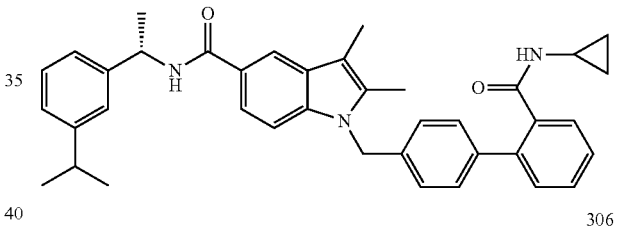
306
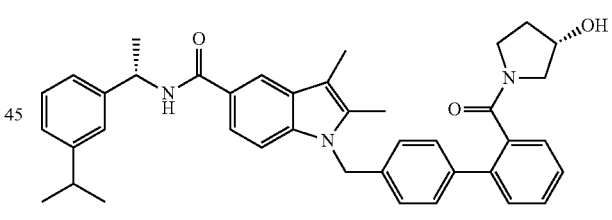
307
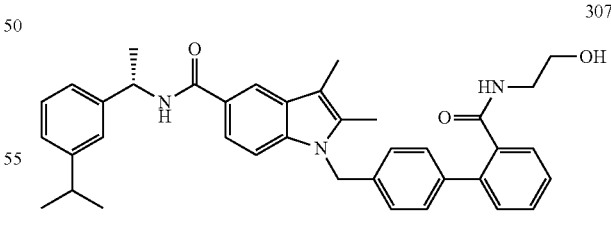
308
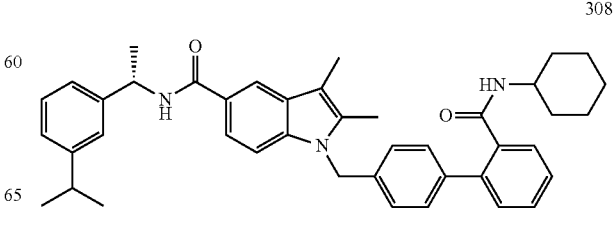

535
-continued
309
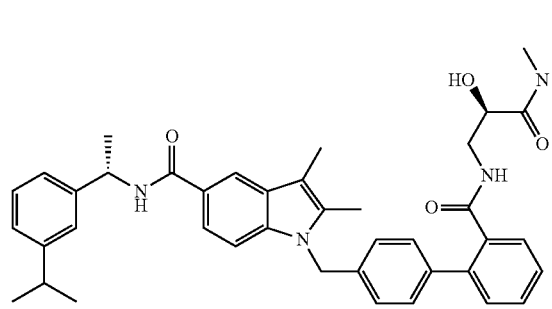
310
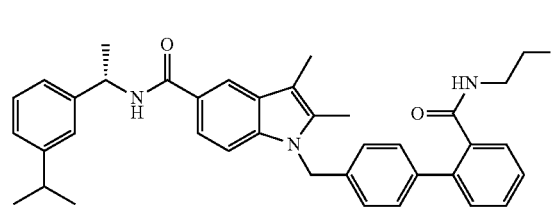
311
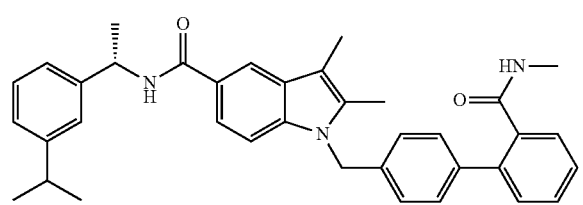
312
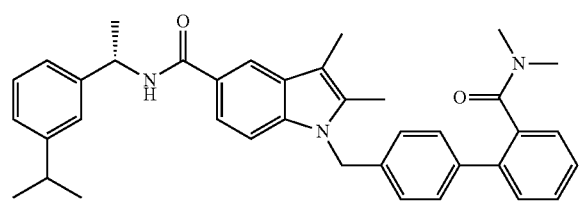
313
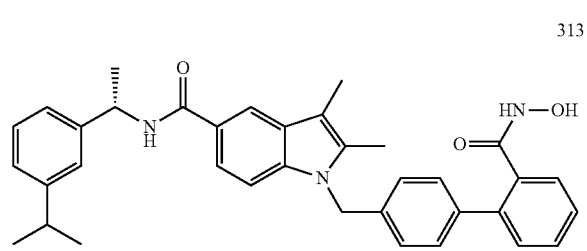
314
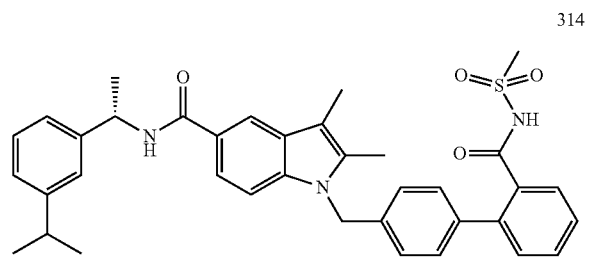
536
-continued
315
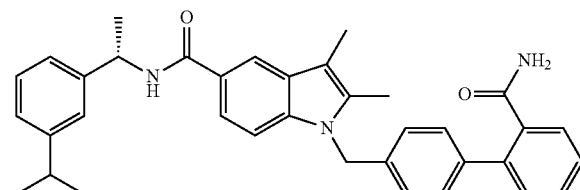
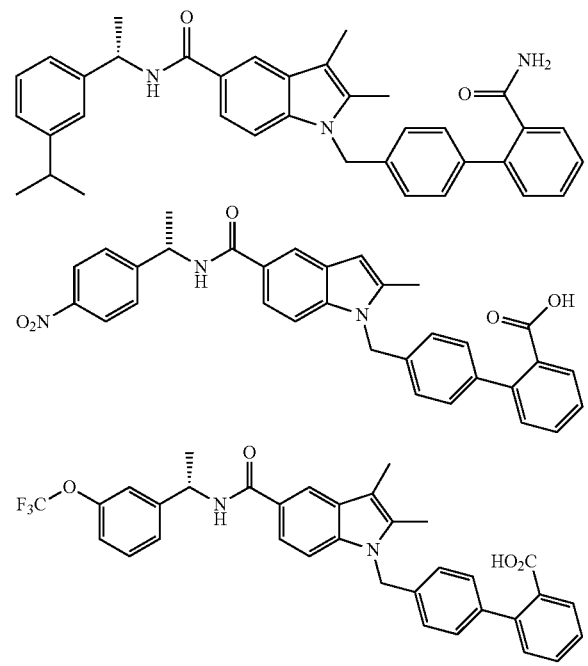
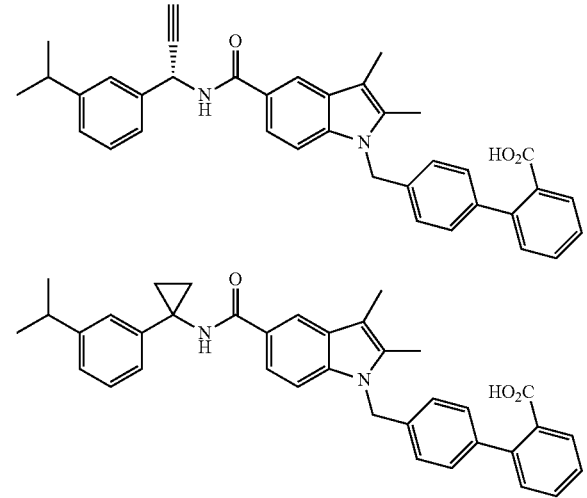
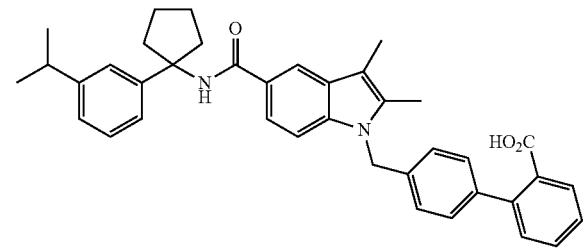
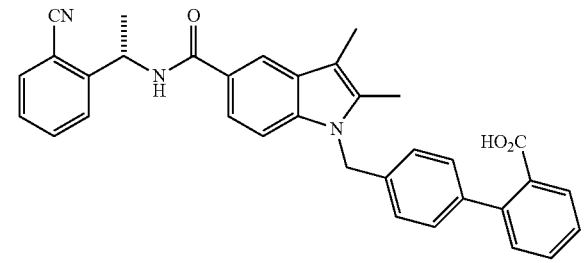

537
-continued
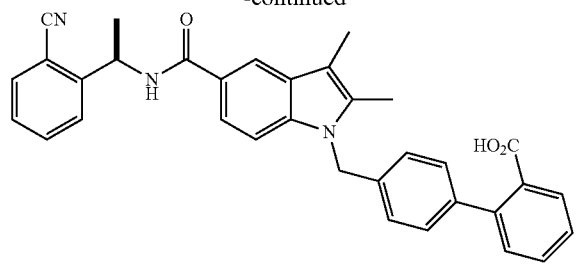
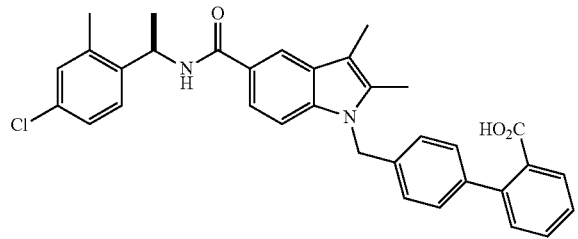
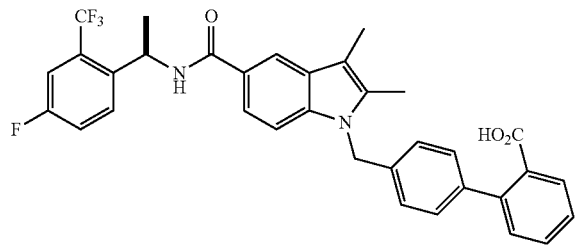
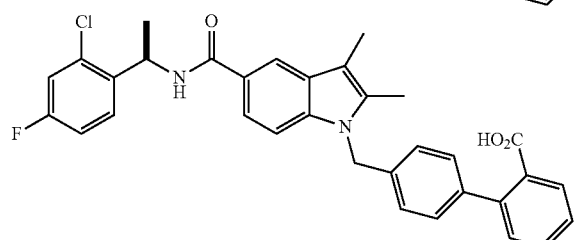
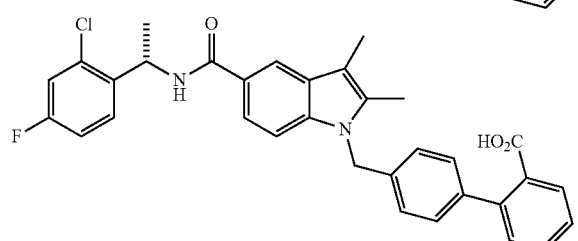
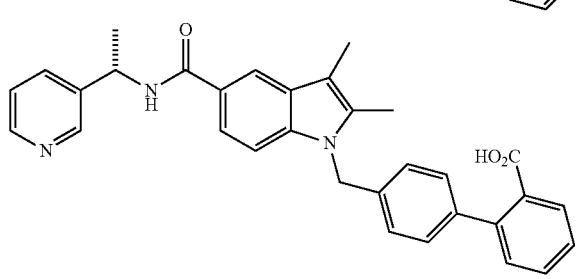
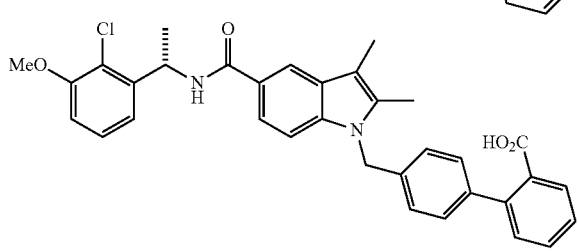
538
-continued
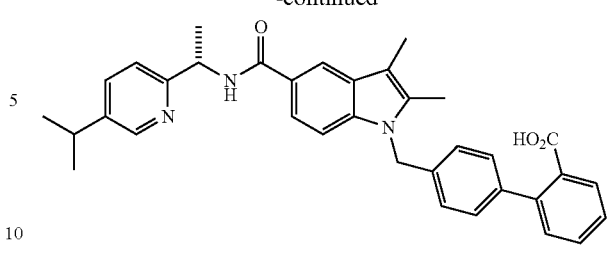
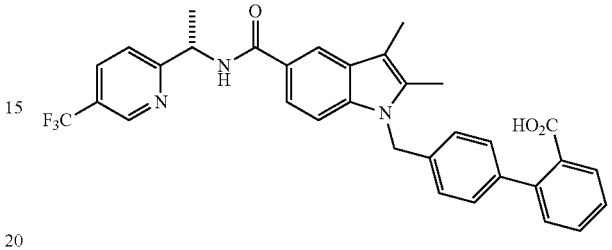
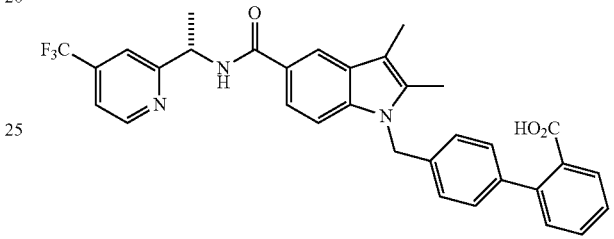
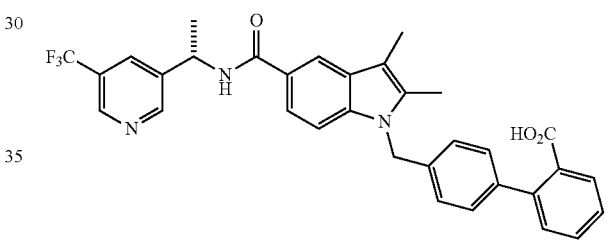
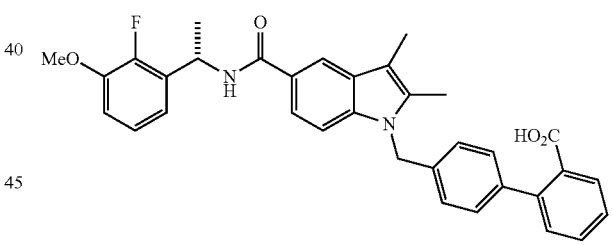
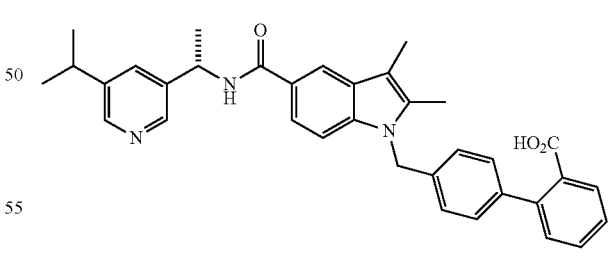
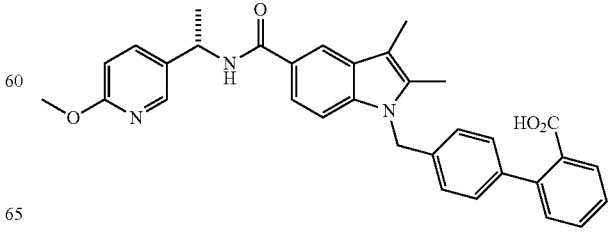

539
-continued
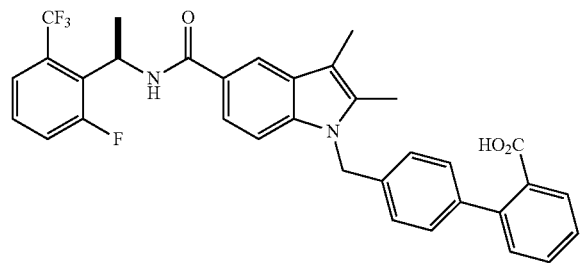
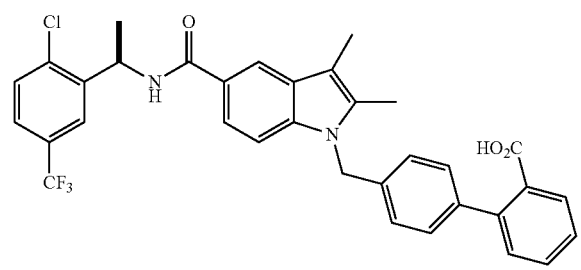
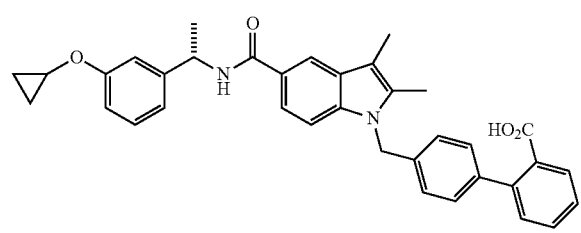
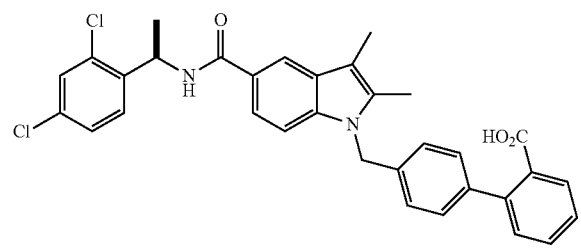
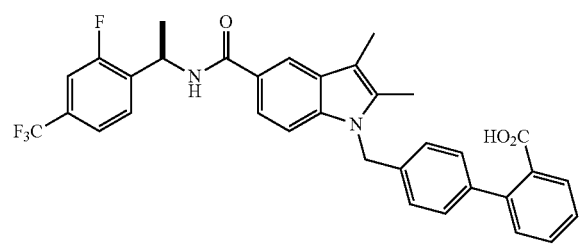
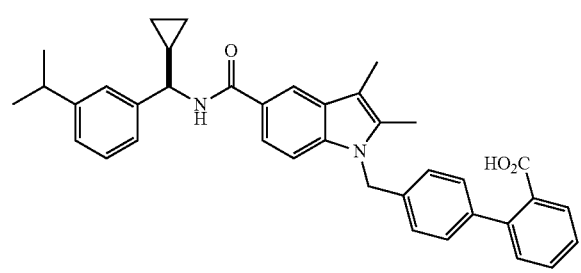
540
-continued
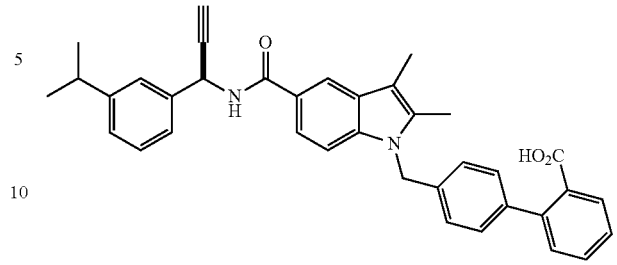
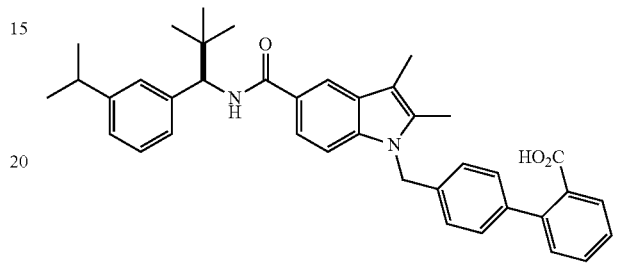
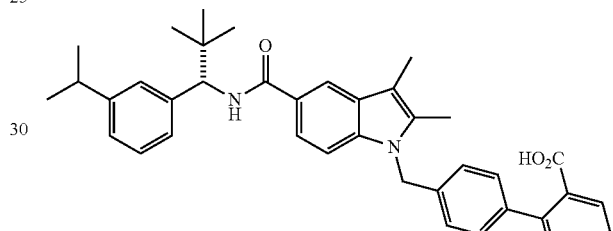
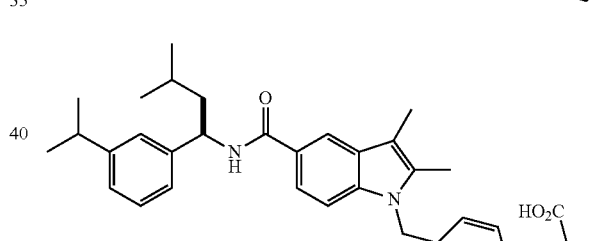
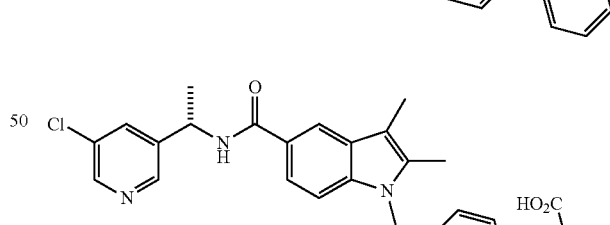
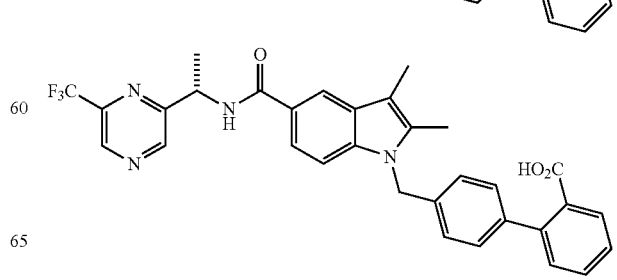

541
-continued
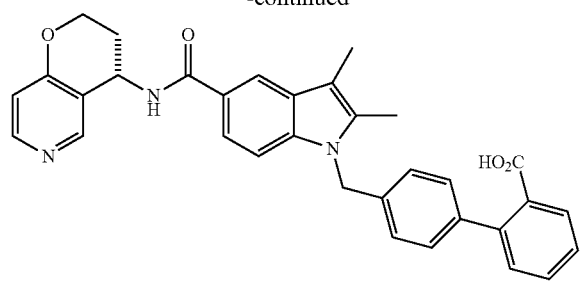
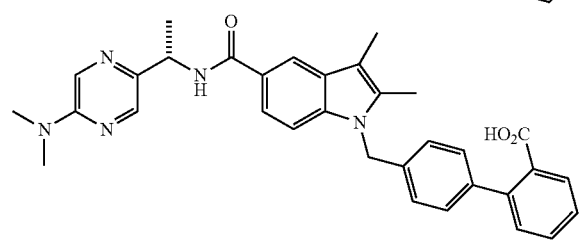
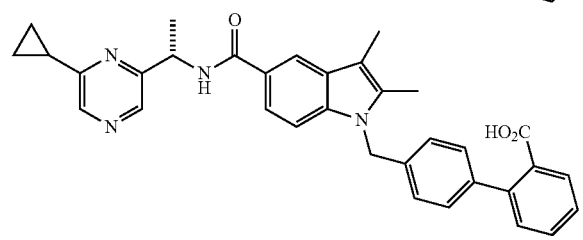
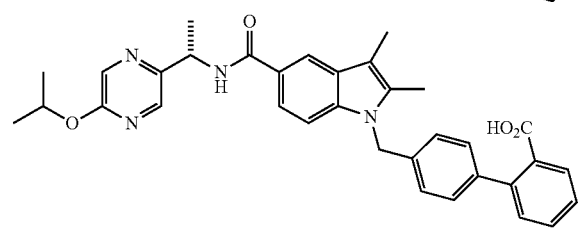
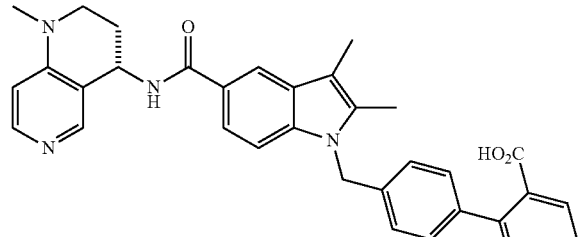
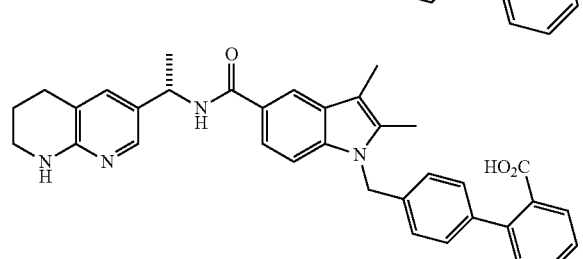
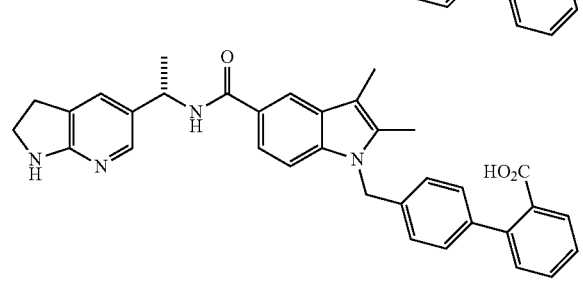
542
-continued
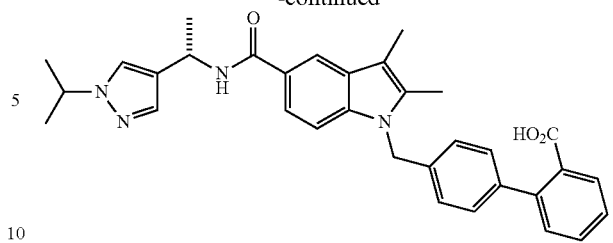
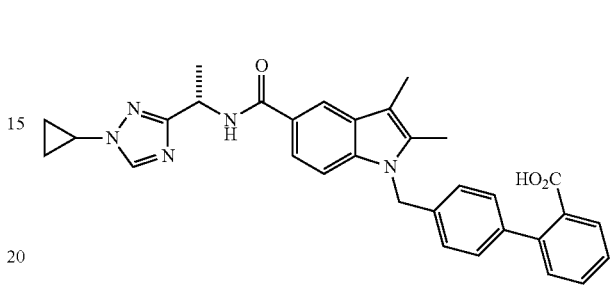
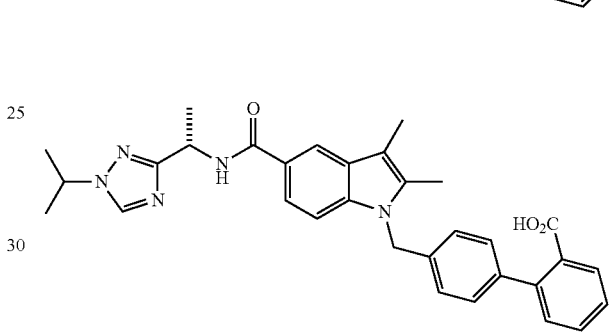
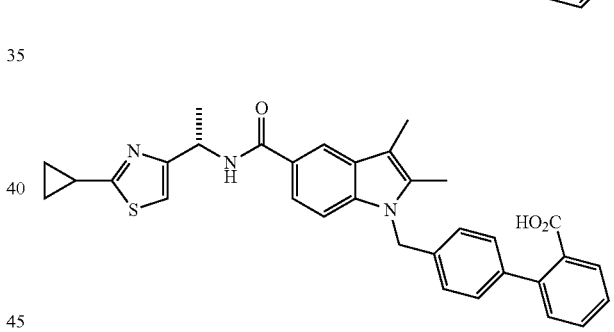
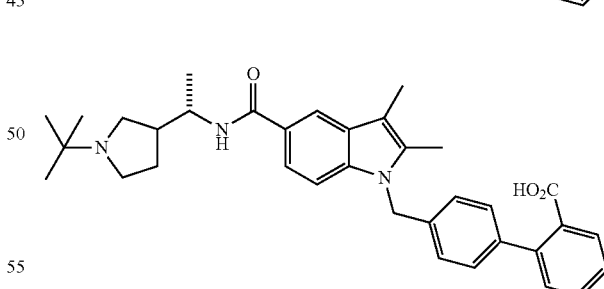
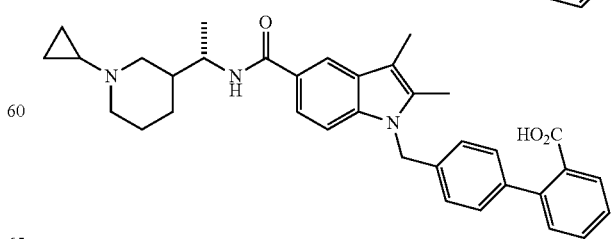

14. The compound of statement 1 wherein the compound is

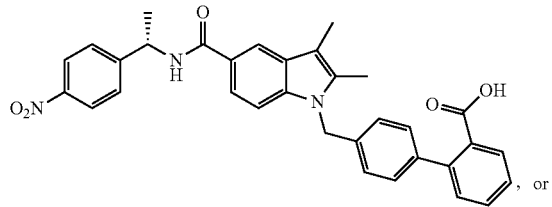, or

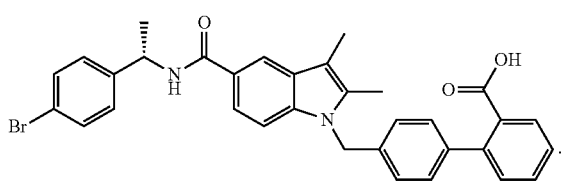.

15. A pharmaceutical composition, comprising a compound of any one of statements 1-14; and a pharmaceutically acceptable excipient.
16. A method of inhibiting kinase-mediated phosphorylation of PPARG in a mammal, comprising administering to the mammal an effective amount of a compound of any one of statements 1-14.
17. The method of statement 16 wherein the kinase-mediated phosphorylation of PPARG is cdk5-mediated.
18. The method of statement 16 wherein the effective amount of the compound for inhibiting cdk5-mediated phosphorylation of PPARG does not produce an agonistic effect on PPARG.
19. A method of treating a condition in a mammal, wherein binding of a ligand to PPARG or inhibition of cdk5-mediated phosphorylation of PPARG, or both, is medically indicated, comprising administering to the mammal an effective amount of a compound of any one of statements 1-14 at a frequency of dosing and for a duration of dosing effective to provide a beneficial effect to the mammal.
20. The method of statement 19 wherein the kinase-mediated phosphorylation of PPARG is cdk5-mediated.
21. The method of statement 19, wherein the mammal is a human.
22. The method of statement 19, wherein the effective amount, frequency of dosing, and duration of dosing of the compound do not produce an agonistic effect on PPARG.
23. The method of statement 19, wherein the condition is diabetes, insulin resistance, impaired glucose tolerance, pre-diabetes, hyperglycemia, hyperinsulinemia, obesity, or inflammation.
24. The method of statement 23, wherein the effective amount, frequency of dosing, and duration of dosing of the compound does not produce side effects of significant weight gain, edema, impairment of bone growth or formation, or cardiac hypertrophy, or any combination thereof, in the mammal receiving the compound.
25. A method of treating a condition comprising diabetes, insulin resistance, impaired glucose tolerance, pre-diabetes, hyperglycemia, hyperinsulinemia, obesity, or inflammation in a human, comprising administering to the human regularly over a duration of time an effective amount of a compound of any one of statements 1-14, optionally in conjunction with a second medicament effective for the treatment of the condition.

All patents and publications referred to herein are incorporated by reference herein to the same extent as if each individual publication was specifically and individually indicated to be incorporated by reference in its entirety.

The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:
1. A method of inhibiting kinase-mediated phosphorylation of PPARG in a mammal, comprising administering to the mammal an effective amount of a compound of formula (I), or a pharmaceutically acceptable salt thereof:

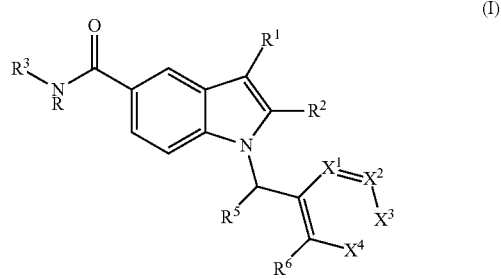

wherein:
R is H or $(C_1-C_4)$alkyl;
$R^1$ and $R^2$ are independently H, or $(C_1-C_6)$alkyl;
$R^3$ is mono- or multi-substituted arylalkyl, wherein each substituent on $R^3$ is independently selected from the group consisting of $(C_1-C_6)$alkyl, $(C_2-C_6)$alkenyl, $(C_2-C_6)$alkynyl, $(C_6-C_{10})$aryl, $(C_3-C_9)$cycloalkyl, 3-9 membered mono- and bicyclic heterocyclyl, 3-9 membered mono- and bicyclic heteroaryl, halo, haloalkyl, haloalkoxy, nitro, cyano, $CO_2R'$, methylenedioxy, OR', $N(R')_2$, $C(O)N(R')_2$, $(C_1-C_4)$alkyl-S$(O)_q$, $SO_2NR'_2$, and $(C_1-C_6)$alkoxyl,
wherein R' is independently H, $(C_1-C_6)$ alkyl, $(C_1-C_6)$ haloalkyl, or $(C_3-C_9)$cycloalkyl, or wherein two R' bonded to an atom together with the atom form a 3-8 membered ring optionally further comprising a heteroatom selected from the group consisting of O, NR', and $S(O)_q$, and wherein alkyl, alkenyl, alkynyl, aryl, arylalkyl, or cycloalkyl is optionally mono- or independently multi-substituted with $(C_1-C_6)$alkyl, $(C_1-C_6)$haloalkyl, $(C_1-C_6)$alkoxy, $(C_1-C_6)$haloalkoxy, halo, OR', $N(R')_2$, aryl, or aroyl; and wherein an alkyl or an alkyl group of a cycloalkylalkyl, heterocyclylalkyl, arylalkyl or heteroarylalkyl can be substituted with oxo;
each of $X^1$-$X^4$ is independently N or is C substituted with an independently selected $R^7$ or with Z, provided that no more than one of $X^1$-$X^4$ is N, and provided that there is one and only one Z group, present in the ring comprising $X^1$, Z is a group of formula

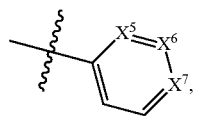

wherein a wavy line indicates a point of attachment, each $X^5$-$X^7$ is independently N or is C substituted with an independently selected H or $R^4$; provided that no more than one of $X^5$-$X^7$ is N;

each $R^4$ is independently halo, nitro, $(C_1$-$C_6)$fluoroalkyl, R"—$(C_1$-$C_6)$alkyl, R"$O_2$C—$(C_0$-$C_6)$alkyl, NC—$(C_0$-$C_6)$alkyl, R"O—$(C_0$-$C_6)$alkyl, $(R")_2$N—$(C_0$-$C_6)$alkyl, $(R')_2$NC(=O)—$(C_0$-$C_6)$alkyl, C-bonded tetrazolyl, 3-hydroxypyrrolidin-1-carbonyl, 2-hydroxyethylaminocarbonyl, cyclohexylaminocarbonyl, 2-(N,N-dimethylaminocarbonyl)-2-hydroxyethylaminocarbonyl, N,N-dimethylaminoethylcarbonyl, N-methylaminocarbonyl, N-hydroxylaminocarbonyl, (1,3,4-oxadiazol-2(3H)-on)-yl, (1,2,4-oxadiazol-5(4H)-on)-3-yl, $(C_1$-$C_6)$alkyl-S(O)$_q$$(C_0$-$C_6)$alkyl, R'S(O)$_2$NHC(O), or R'C(O)NHS(O)$_2$, or $R^4$ is —$(C(R")_2)_m$CO$_2$R", —$(C(R")_2)_m$CON(R")$_2$, or —$(C(R")_2)_m$CN, —O$(C(R")_2)_m$CO$_2$R", —O$(C(R")_2)_m$CON(R")$_2$, or —O$(C(R")_2)_m$CN, wherein m is 1, 2, or 3;

R" is H, or $(C_1$-$C_6)$ alkyl, or two R" together with an atom to which they are bonded form a (C3-C9)cycloalkyl;

q is 0, 1 or 2;

$R^5$ is H or $(C_1$-$C_4)$alkyl; $R^6$ is $R^7$; or $R^5$ and $R^6$ taken together form a —CH$_2$CH$_2$— group; and, $R^7$ is H, halo, CO$_2$R', CN, OR', N(R')$_2$, C(O)N(R')$_2$, $(C_1$-$C_4)$alkyl or $(C_1$-$C_4)$fluoroalkyl optionally substituted with OR' or N(R')$_2$, C-bonded tetrazolyl, or $(C_1$-$C_4)$ alkyl-S(O)$_q$; or $R^7$ is —$(C(R')_2)_m$CO$_2$R' wherein m is 1, 2, or 3.

2. The method of inhibiting kinase-mediated phosphorylation of PPARG in a mammal of claim 1, comprising administering to the mammal an effective amount of a compound selected from the group consisting of:

1

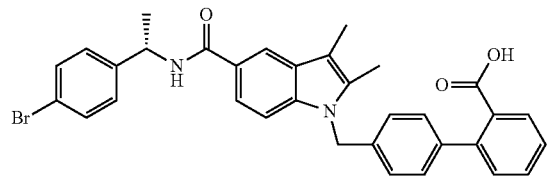

2

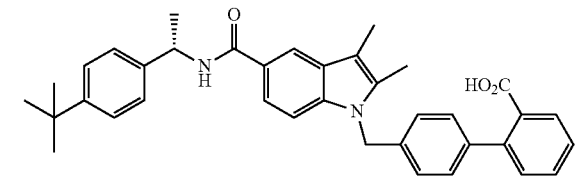

3

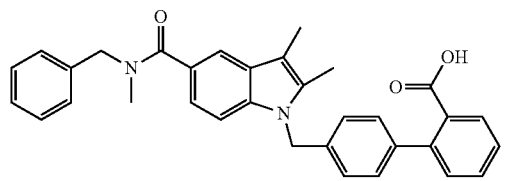

4

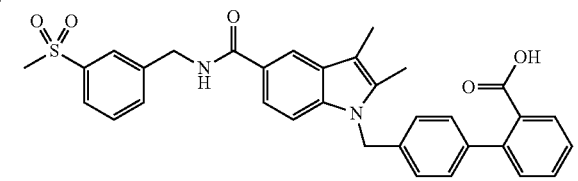

5

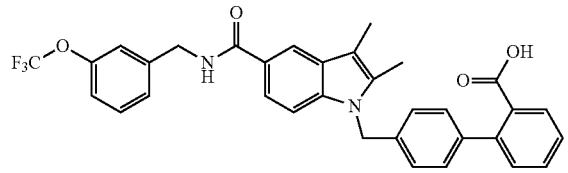

6

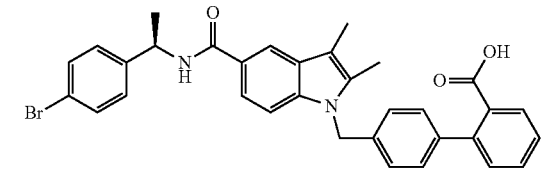

7

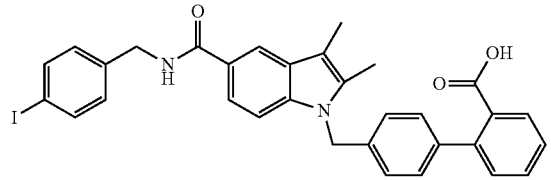

8

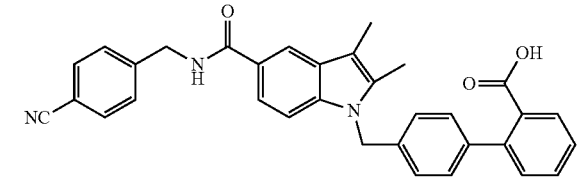

9

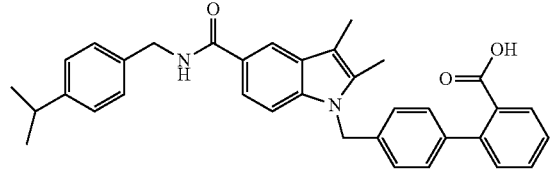

10

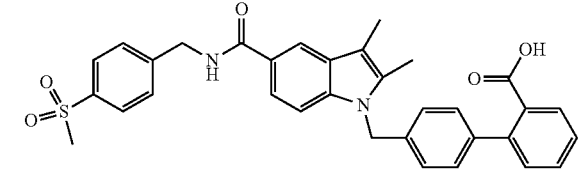

-continued
11
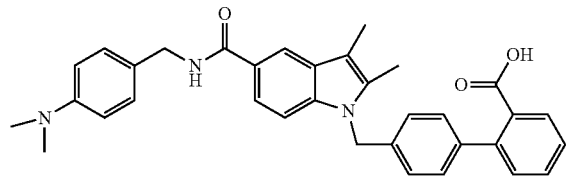
12
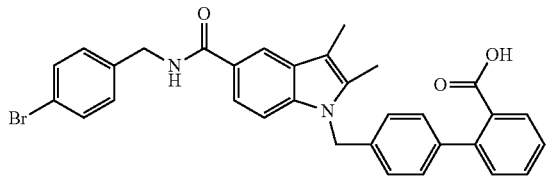
13
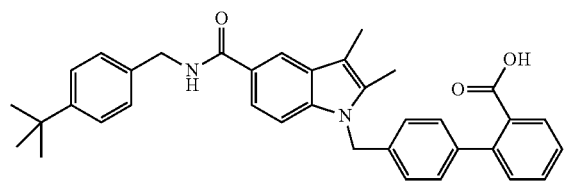
14
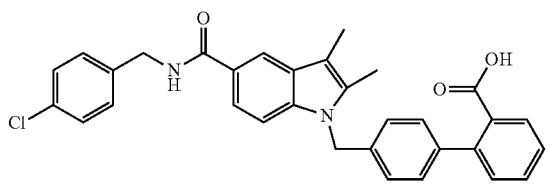
15
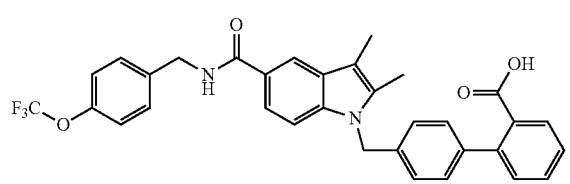
16
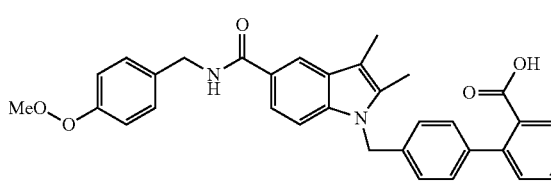
17
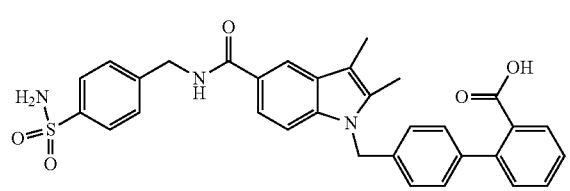
18
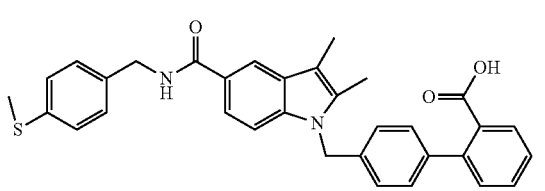
19
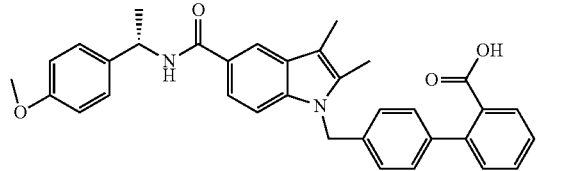
20
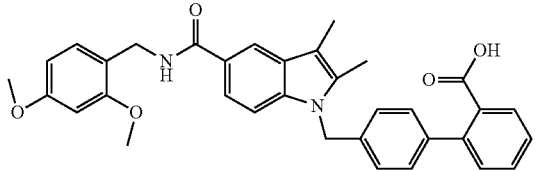
21
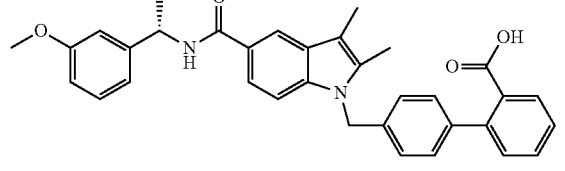
22
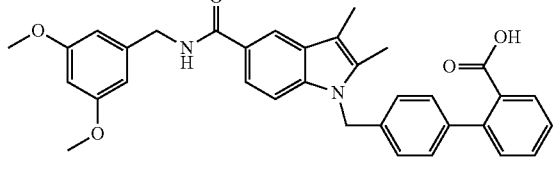
23
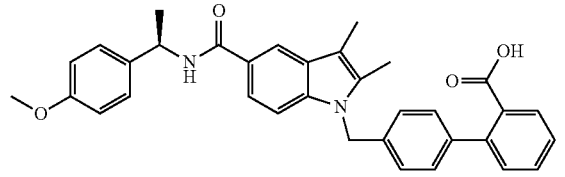
24
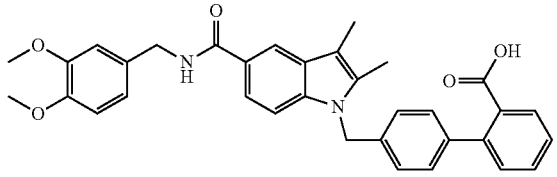
25
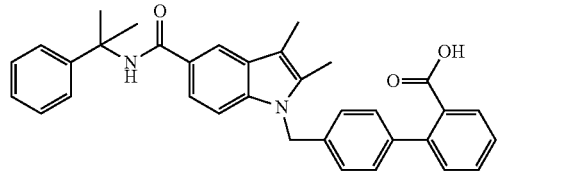
26
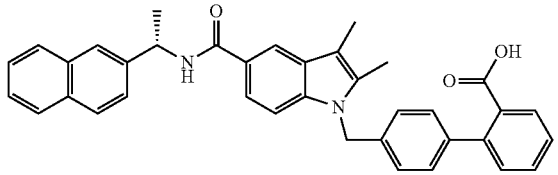

-continued
27 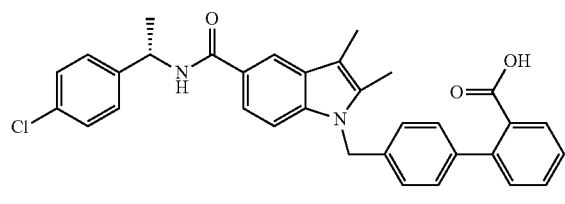
30 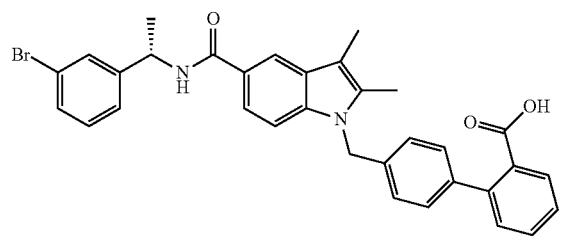
31 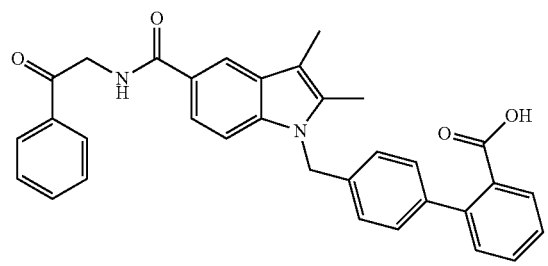
34 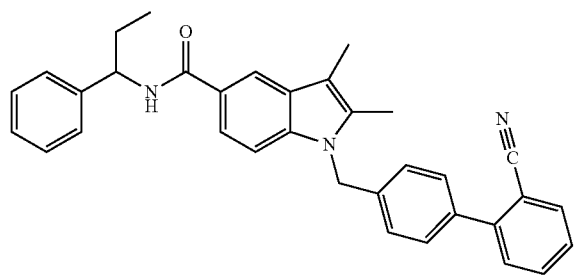
35 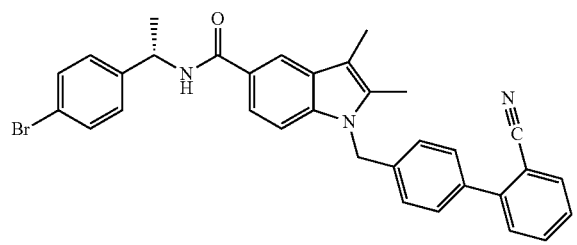
36 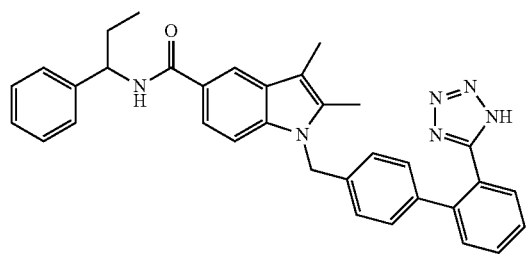
37 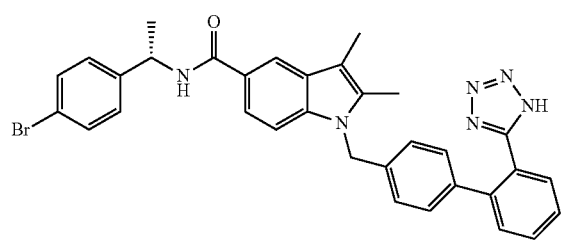
38 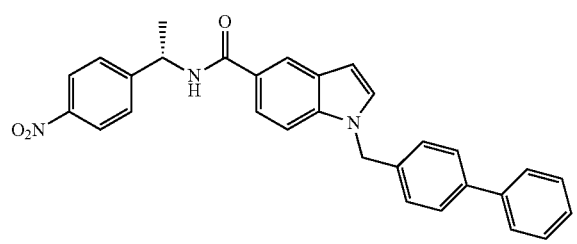
39 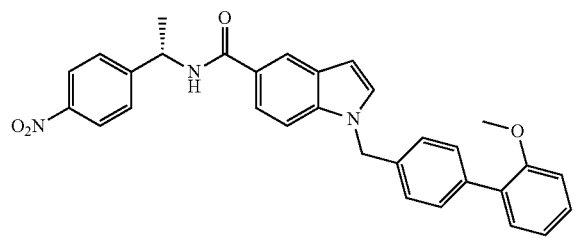
40 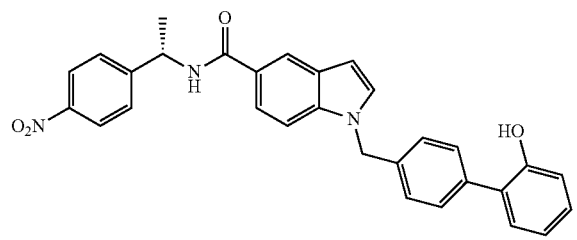
41 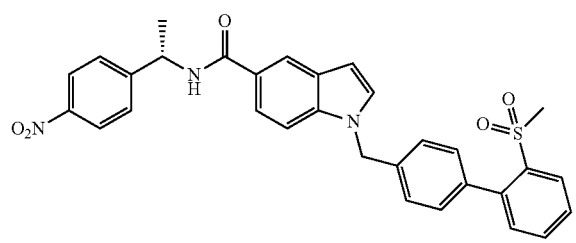
42 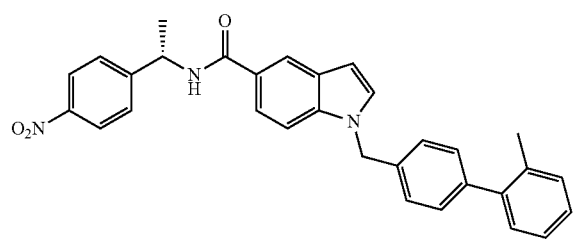

43
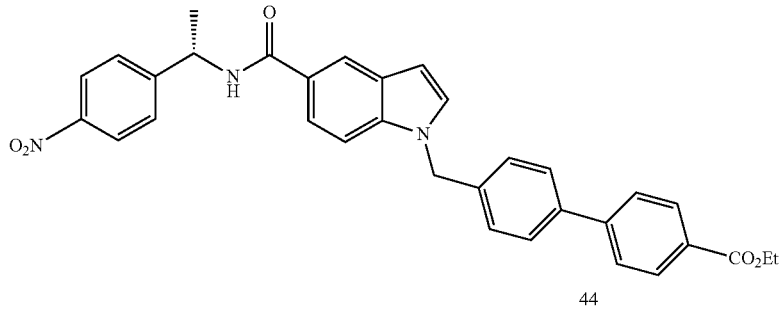
| 44 | 45 |
|---|---|
| 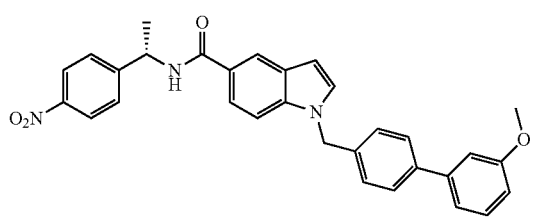 | 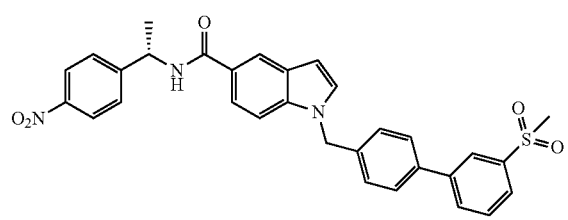 |
| 46 | 47 |
| 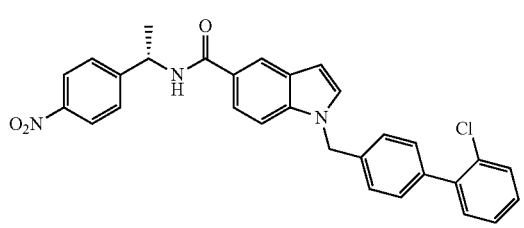 | 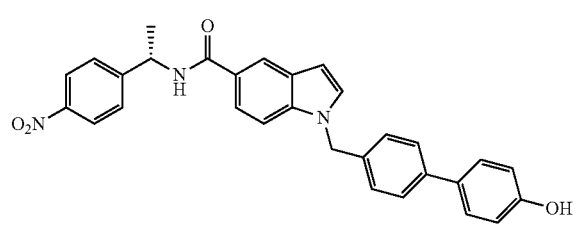 |
| 48 | 49 |
| 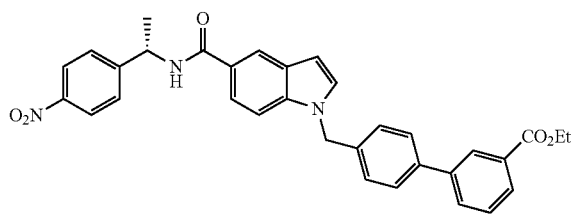 | 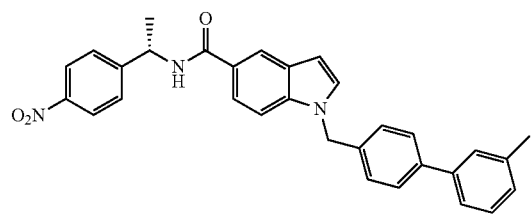 |
| 50 | 51 |
| 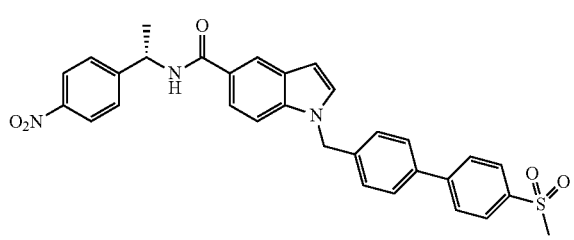 | 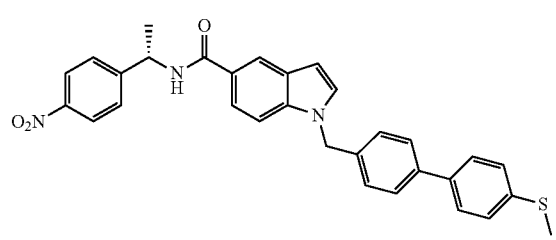 |
| 52 | 53 |
| 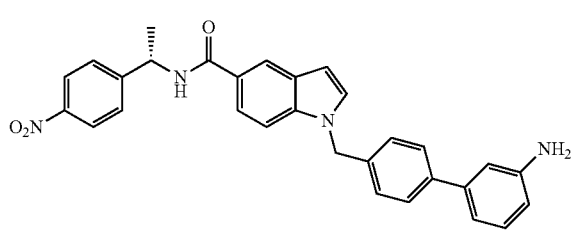 | 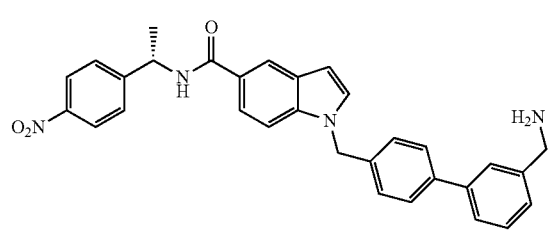 |

-continued
54
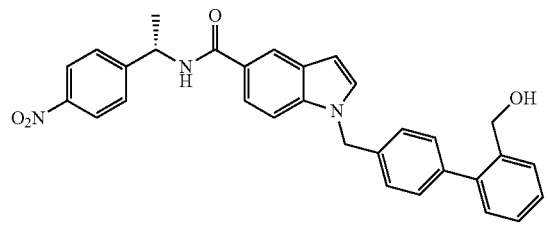
55
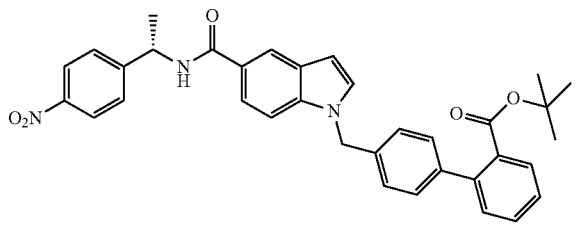
56
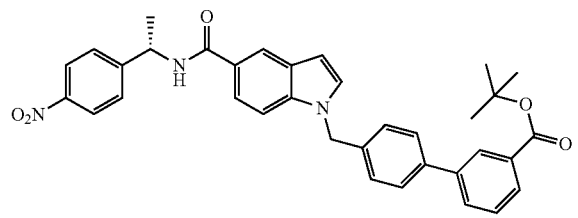
57
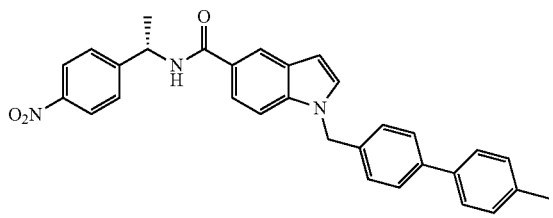
58
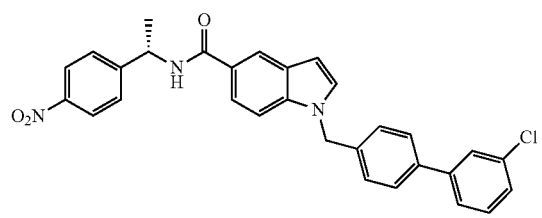
59
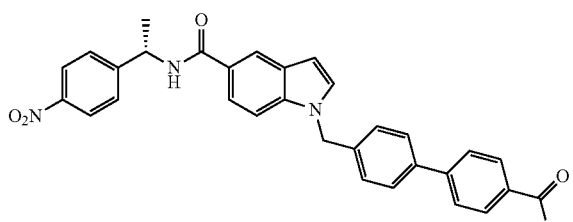
60
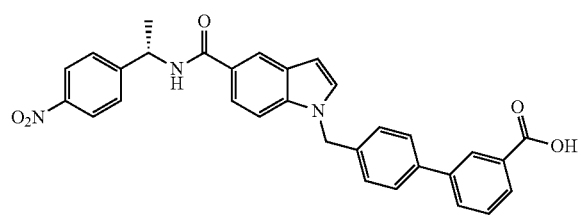
61
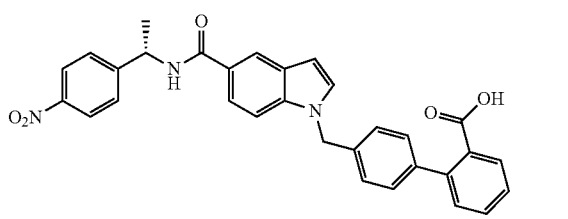
62
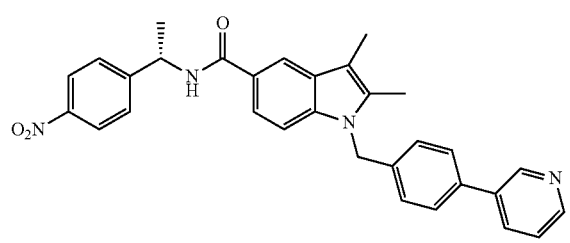
63
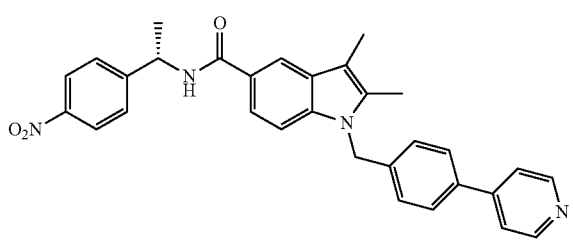
64
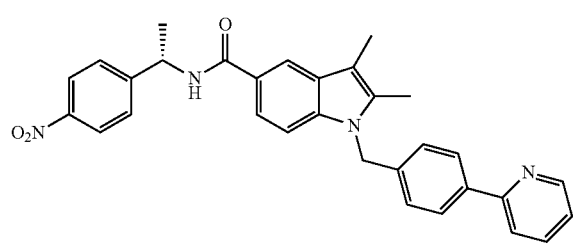
72
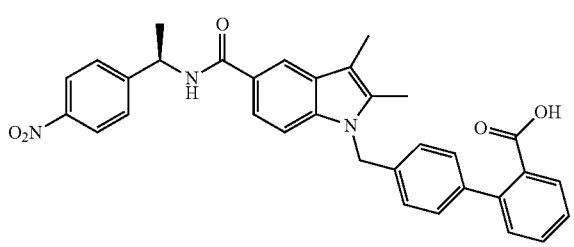

-continued
| 73 | 76 |
|---|---|
| 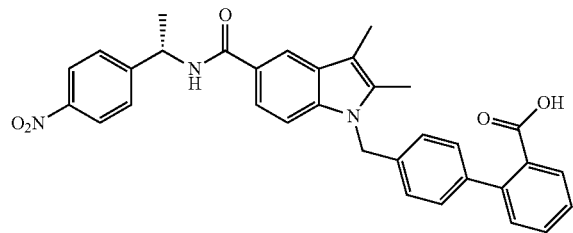 | 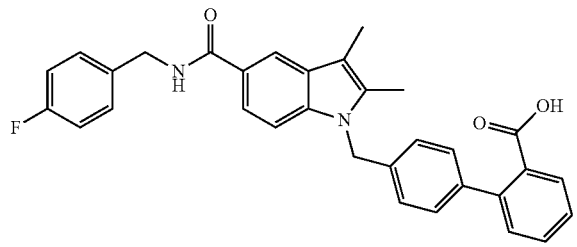 |
| 77 | 78 |
|---|---|
| 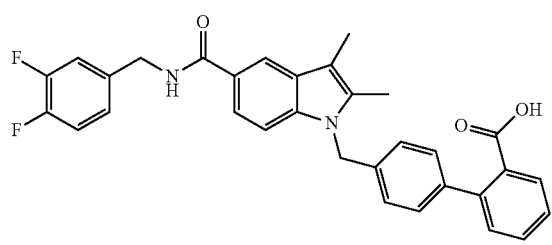 | 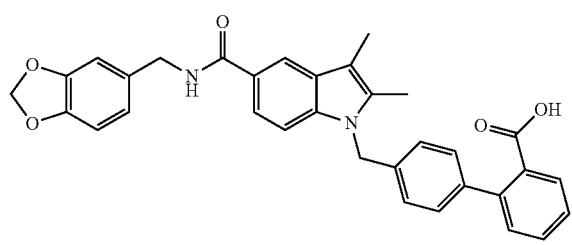 |
| 79 | 80 |
|---|---|
| 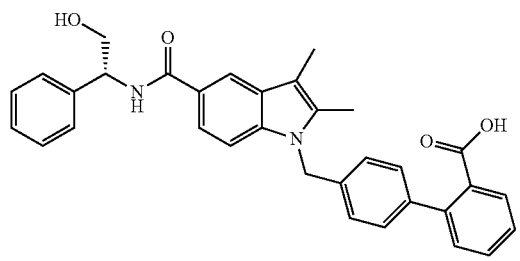 | 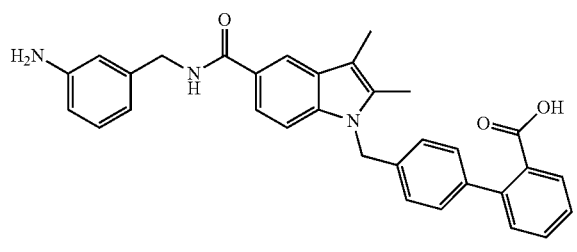 |
| 81 | 82 |
|---|---|
| 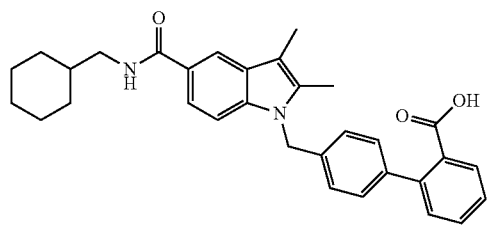 | 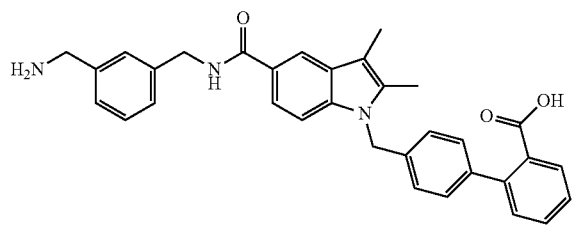 |
| 81 | 82 |
|---|---|
| 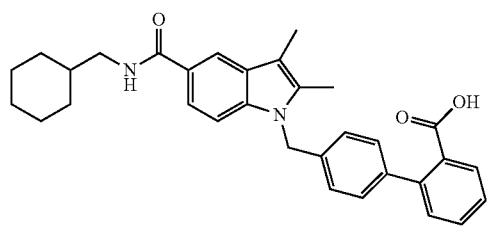 | 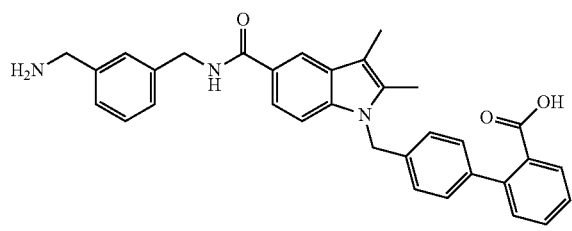 |
| 94 | 95 |
|---|---|
| 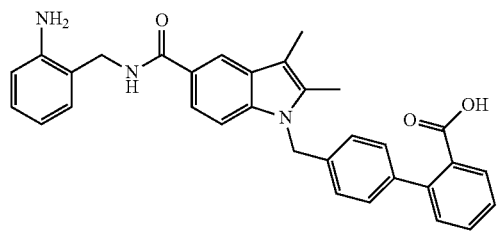 | |

-continued
96
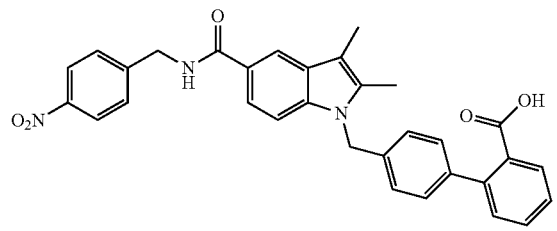
99
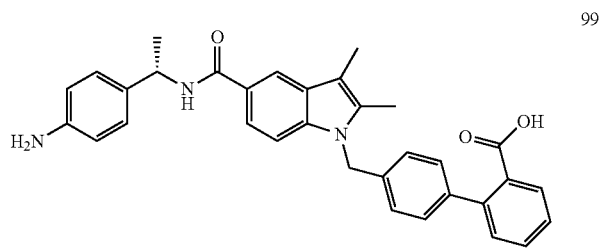
100
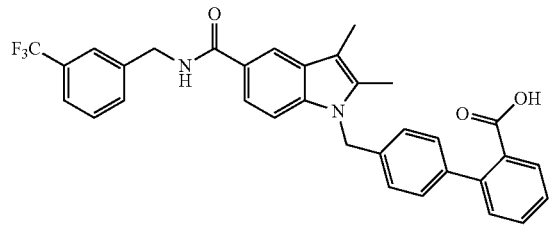
101
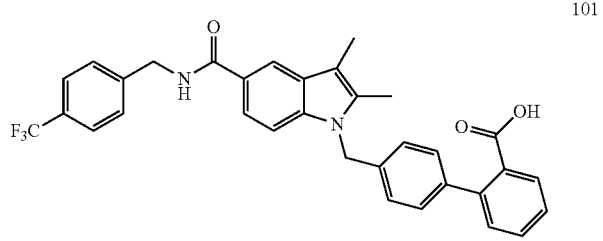
103
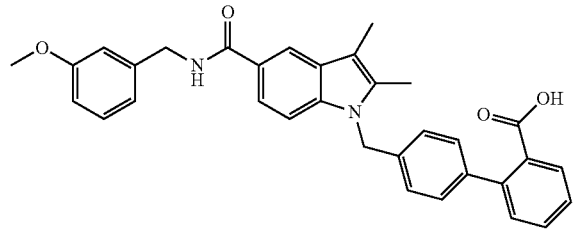
104
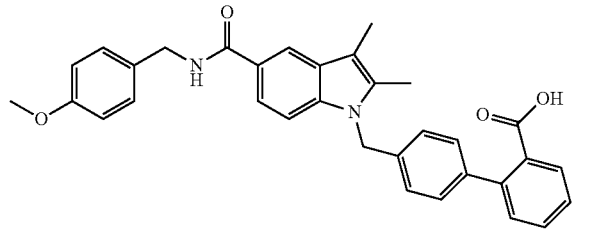
108
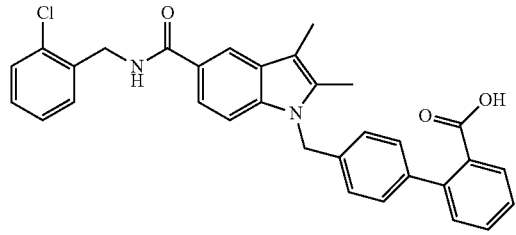
109
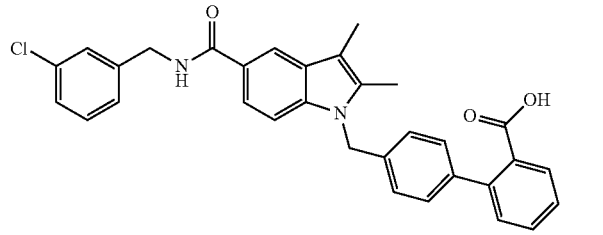
110
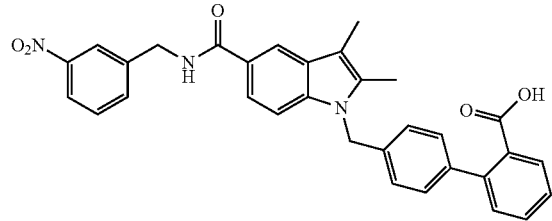
111
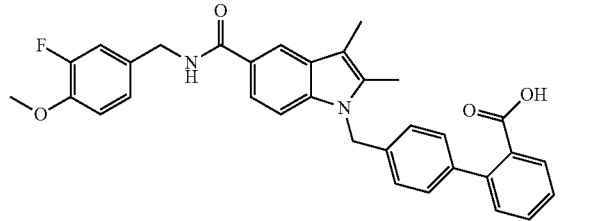
112
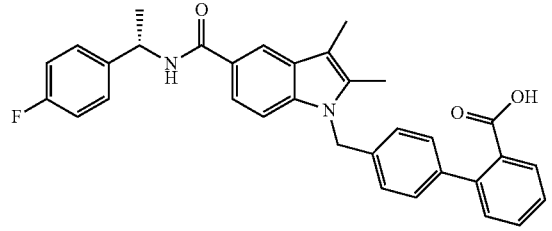
113
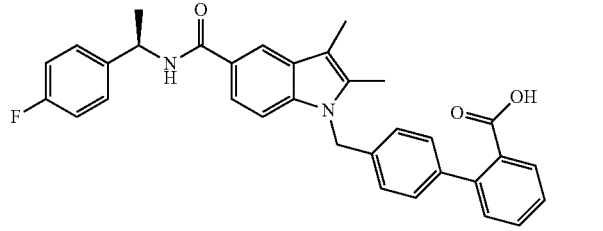

115 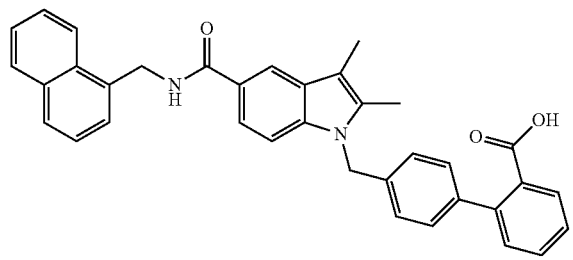
116 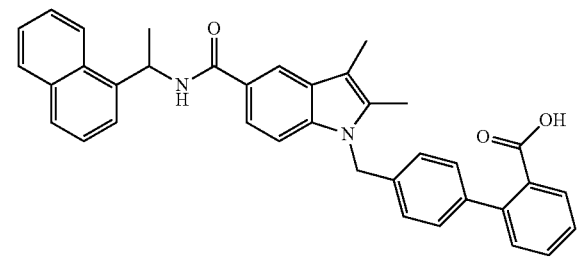
118 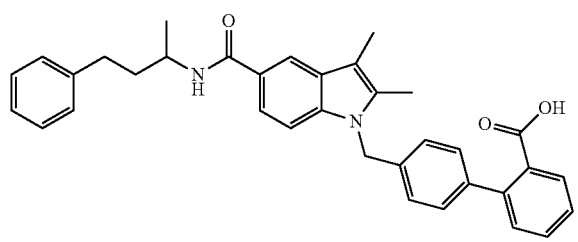
119 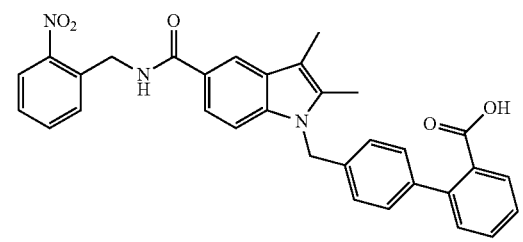
120 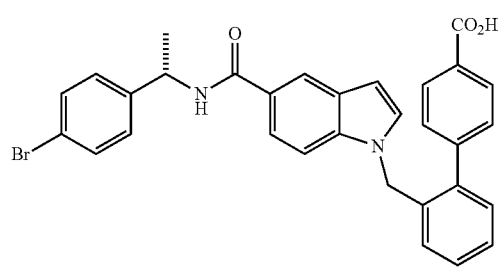
121 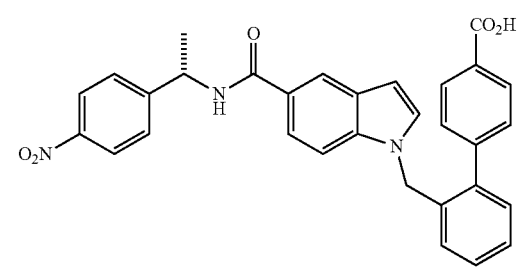
122 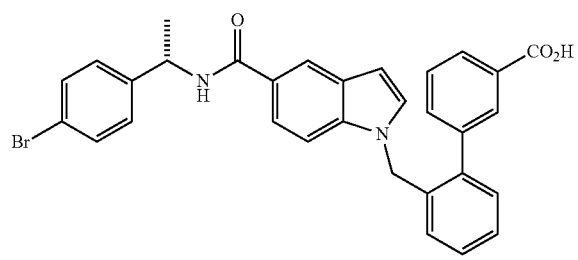
123 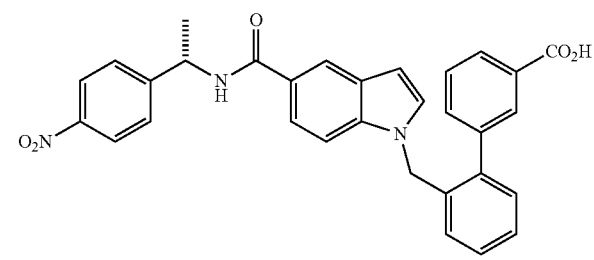
124 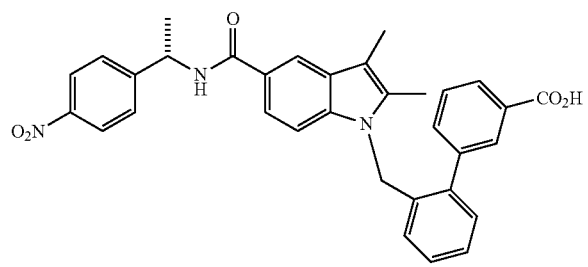
125 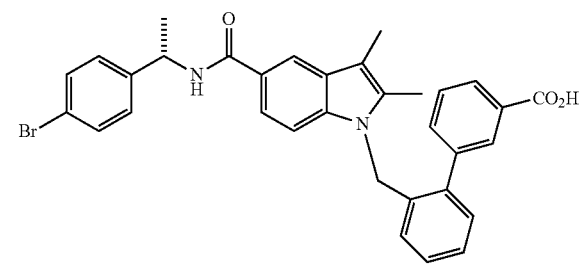

-continued
127
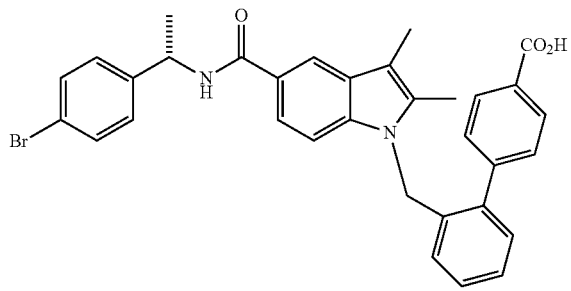
128
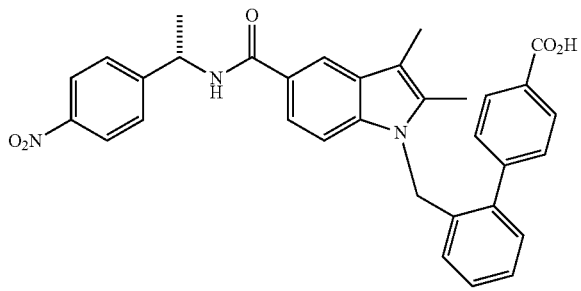
130
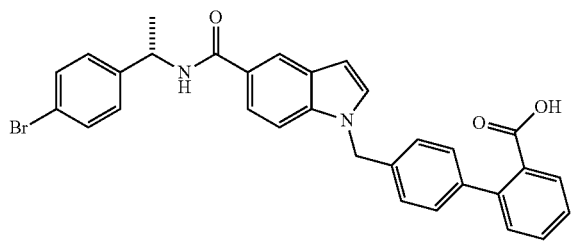
132
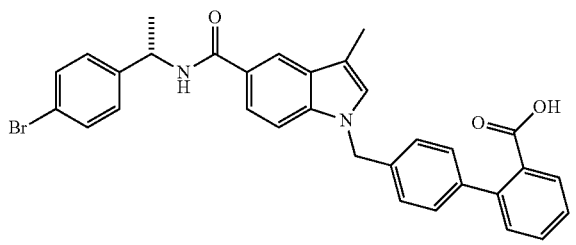
134
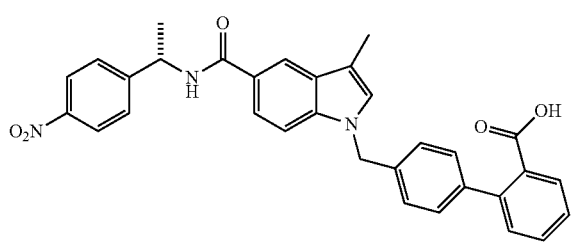
135
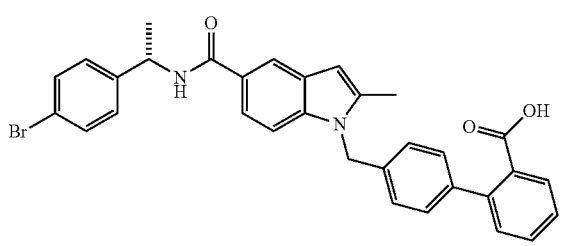
137
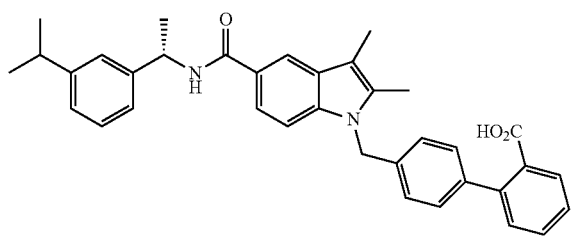
138
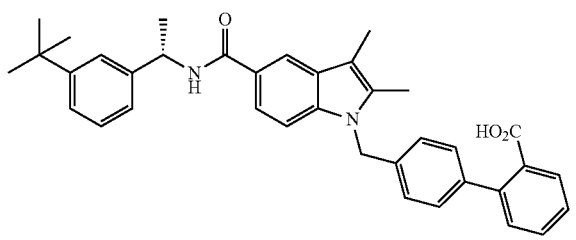
139
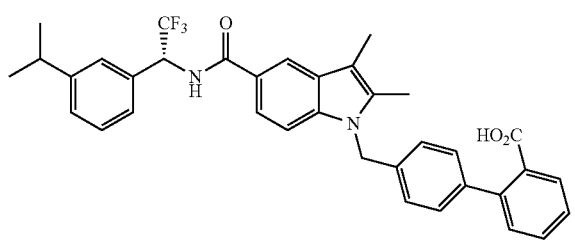
141
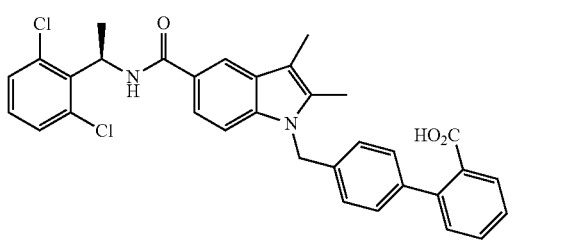
142
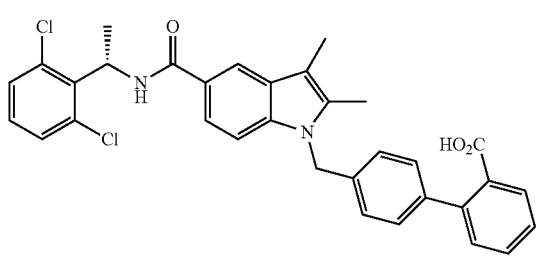
143
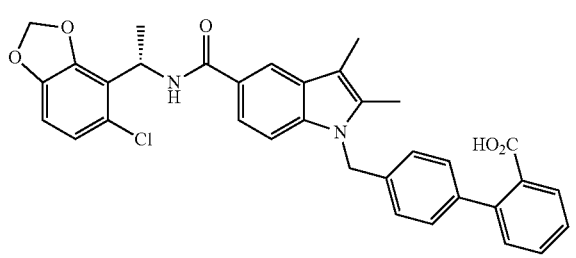

-continued
145
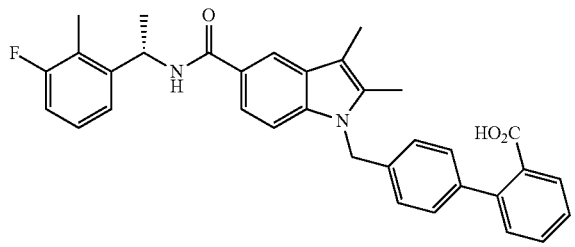
146
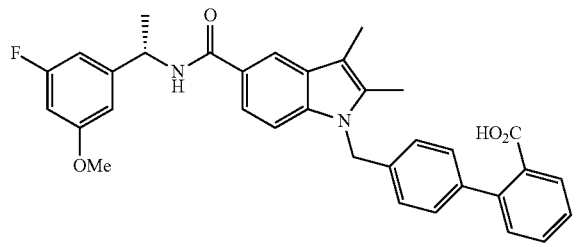
147
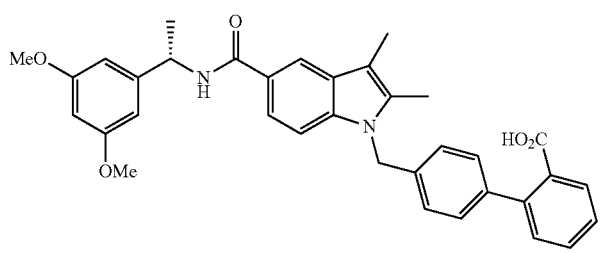
150
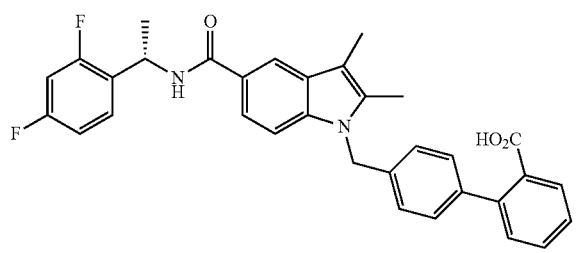
151
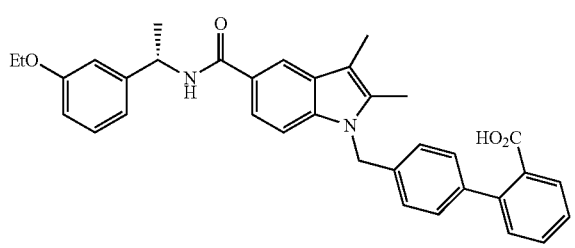
152
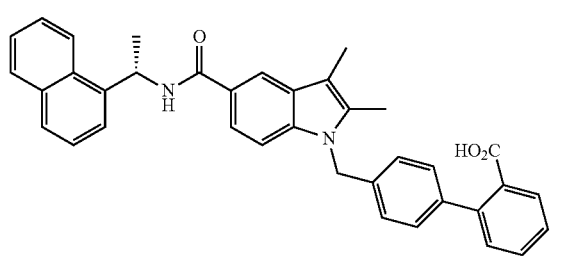
153
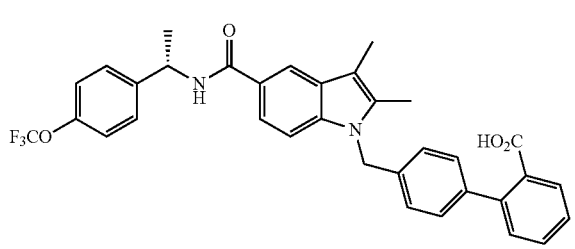
154
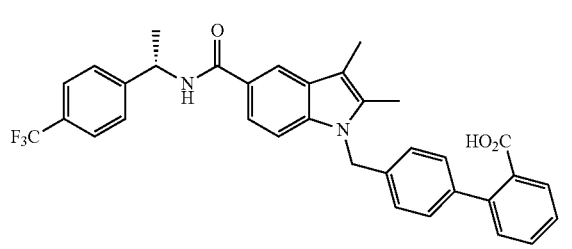
155
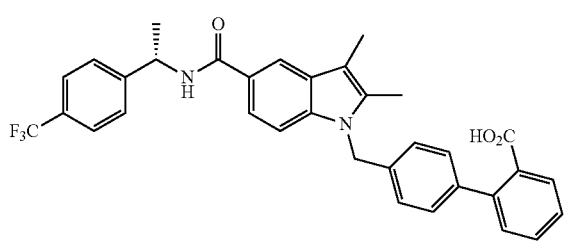
156
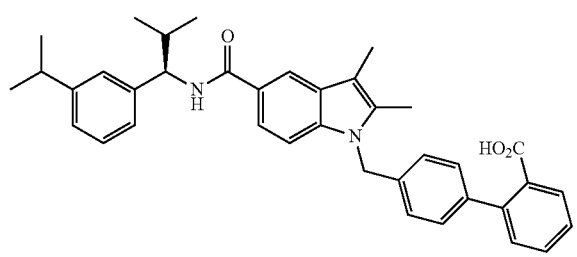
157
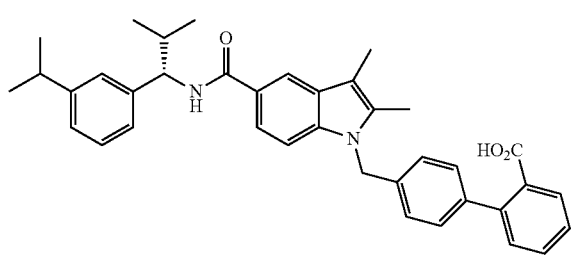
158
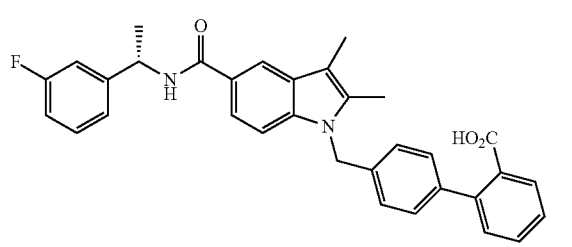

-continued
159
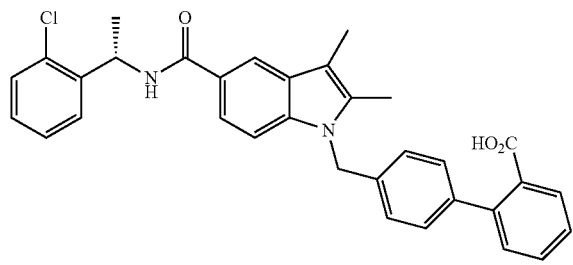
160
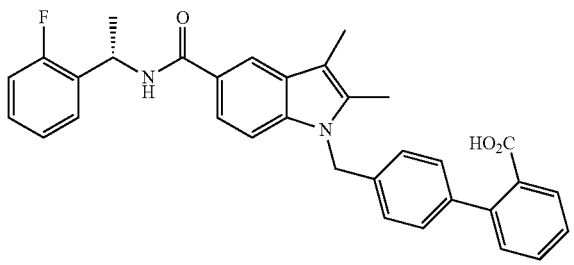
161
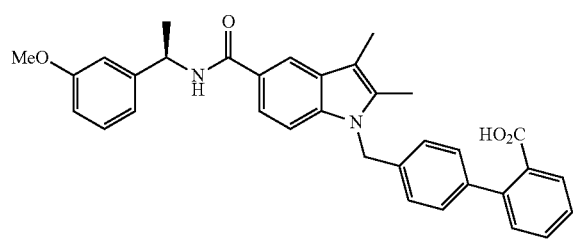
162
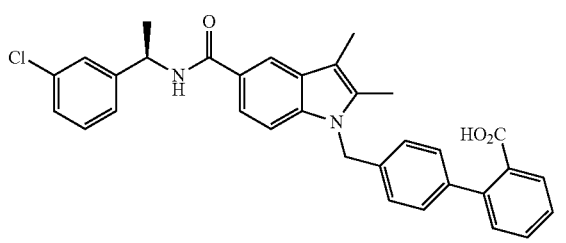
163
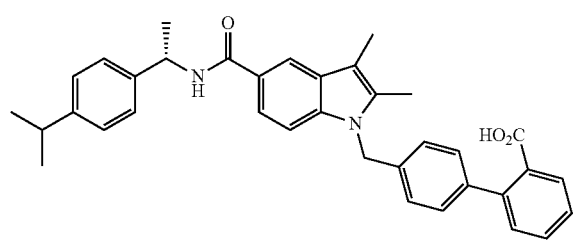
164
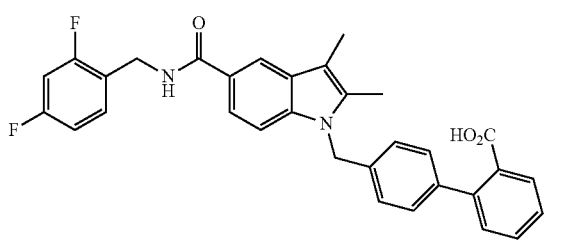
165
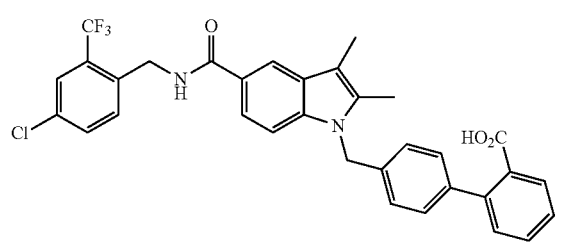
166
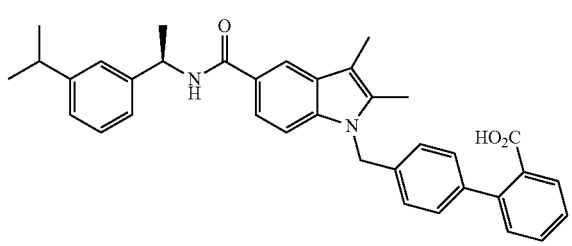
167
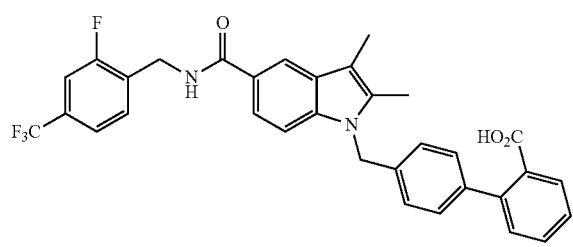
168
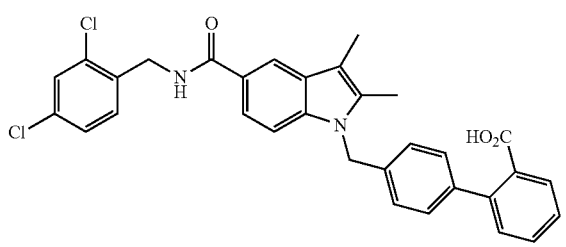
170
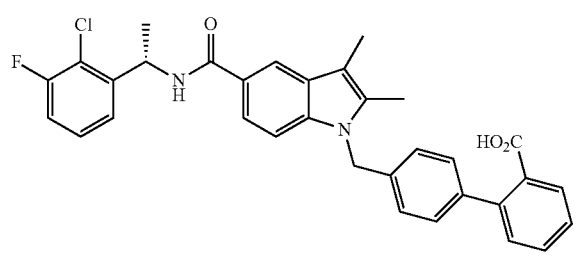

171 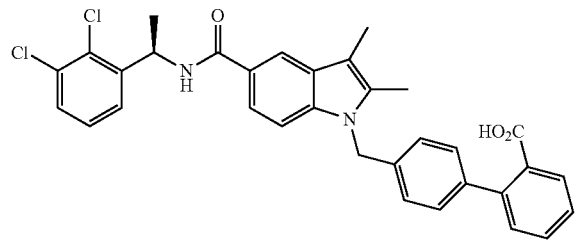 172 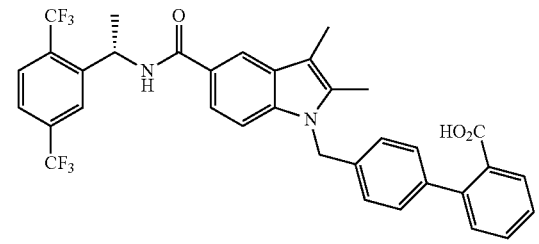
173 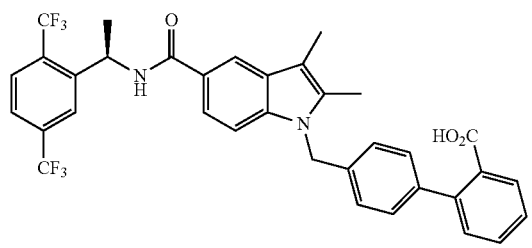 174 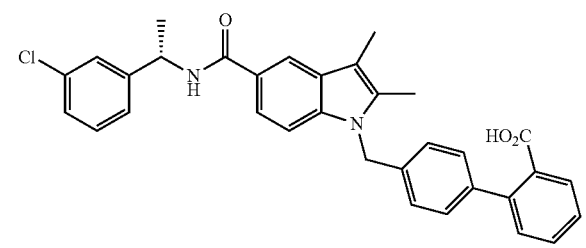
175 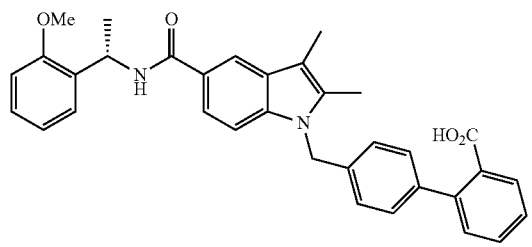 176 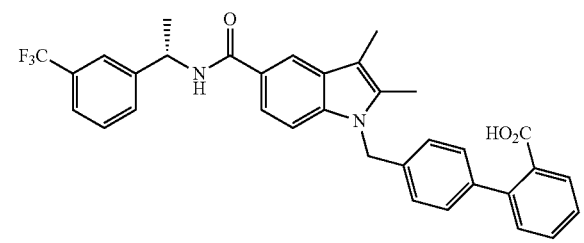
177 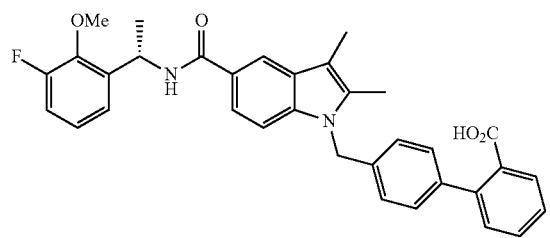 178 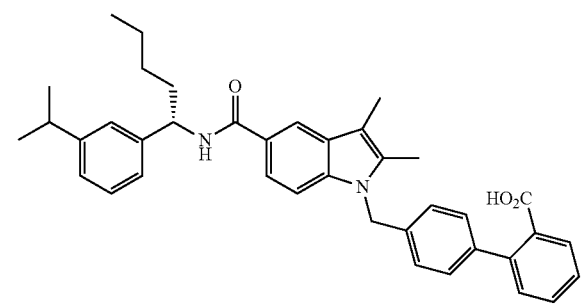
180 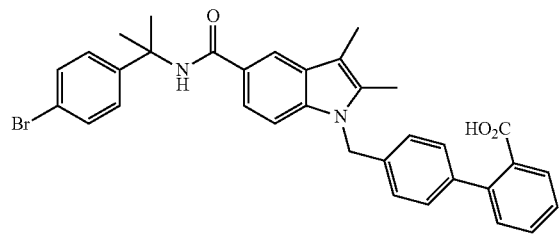 181 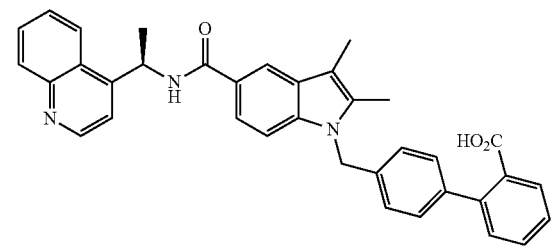

-continued
182
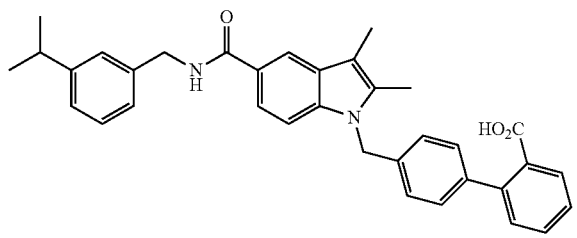
184
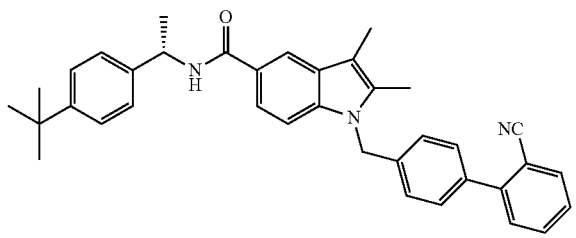
185
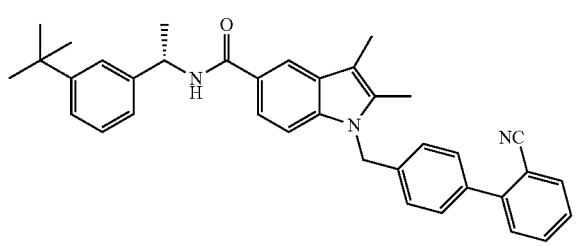
186
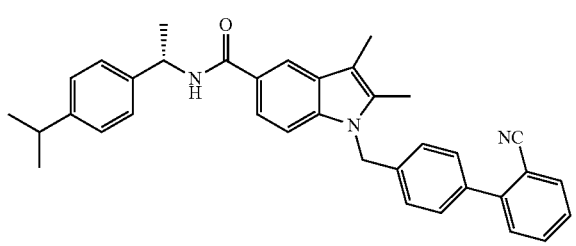
187
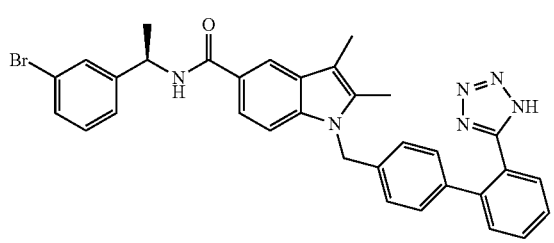
188
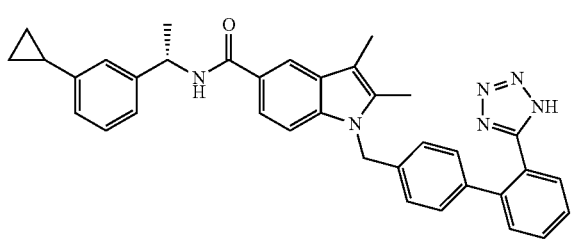
197
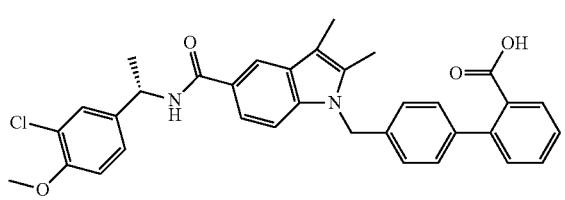
198
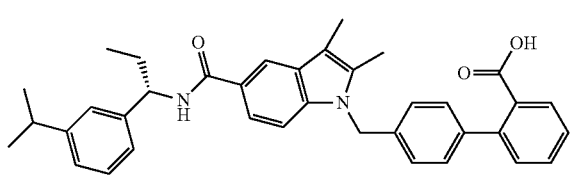
199
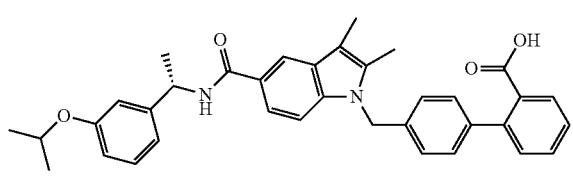
200
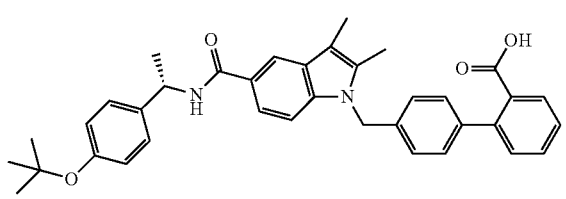
201
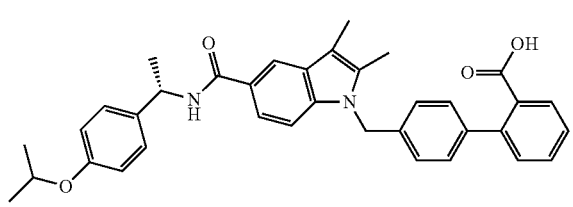

-continued
205
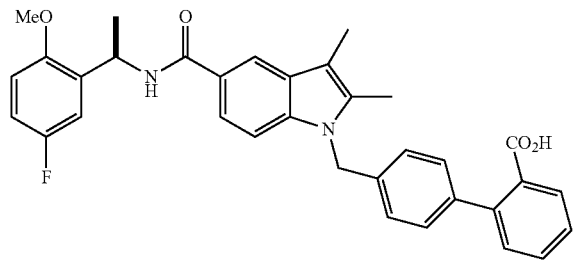
206
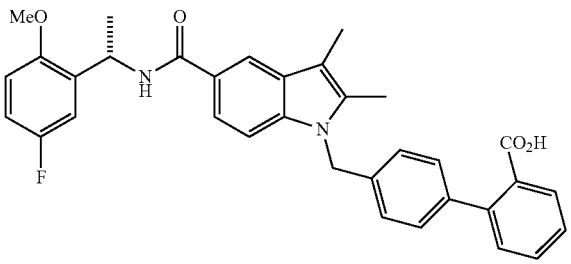
207
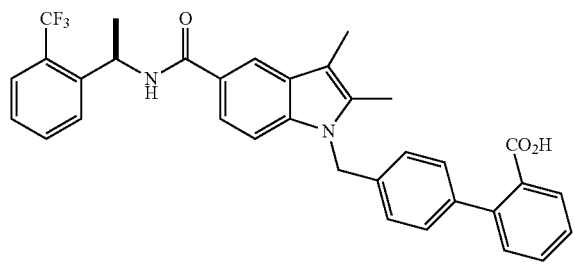
208
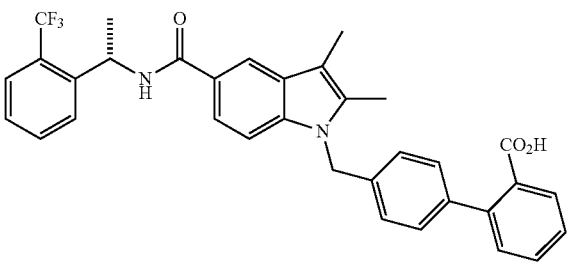
209
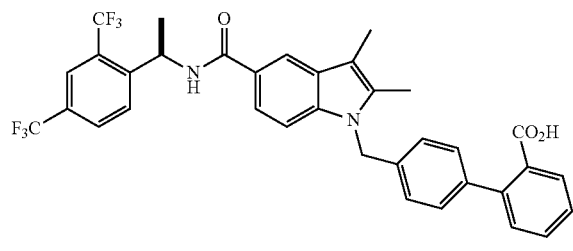
210
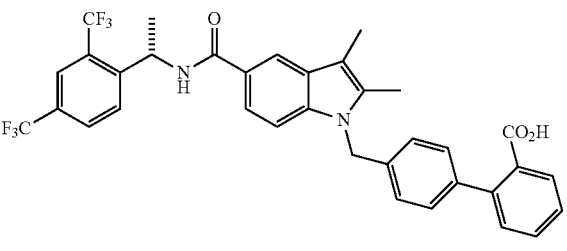
211
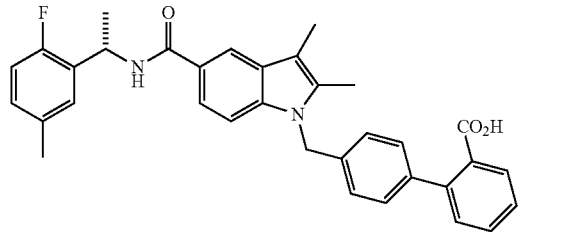
218
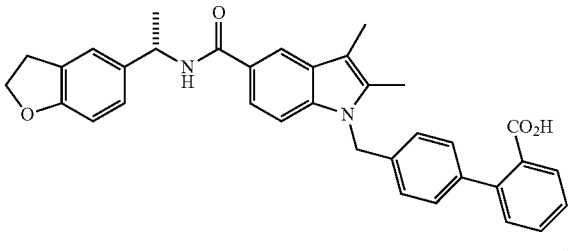
219
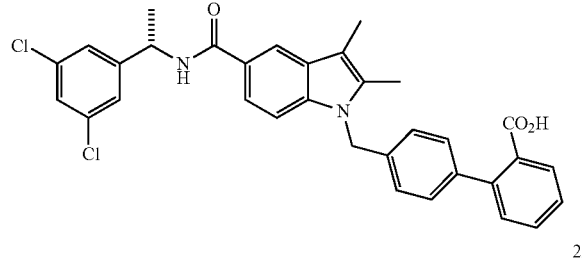
220
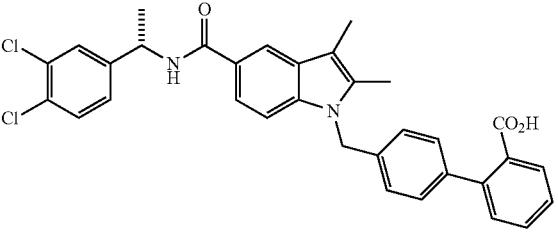
221
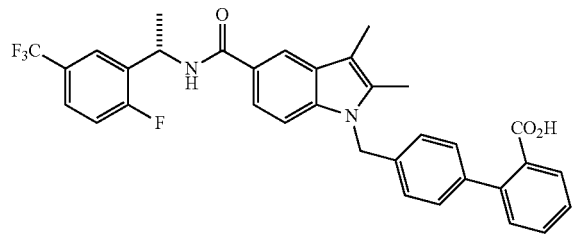
222
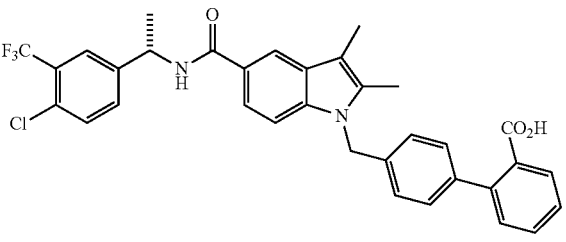

-continued
223
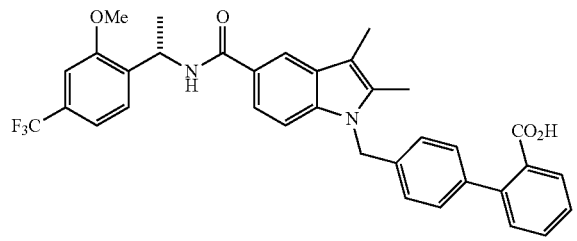
224
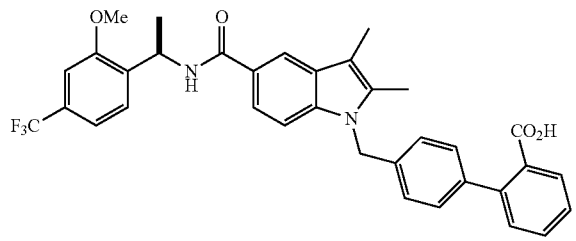
225
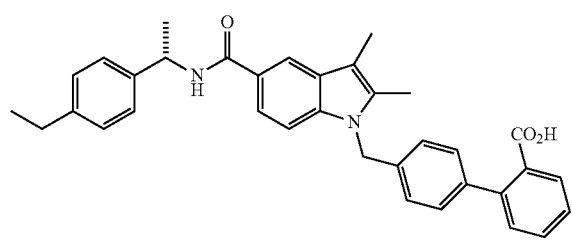
226
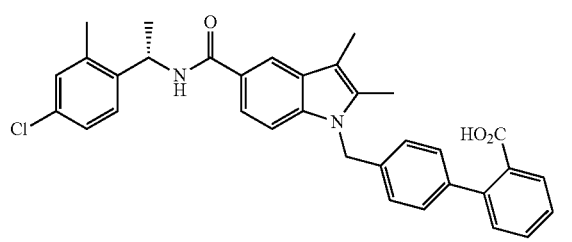
227
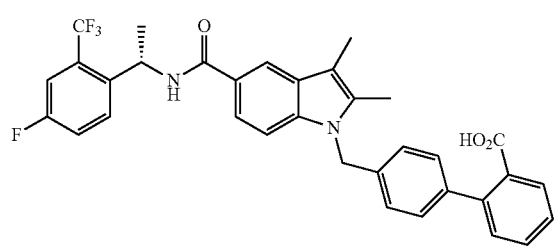
228
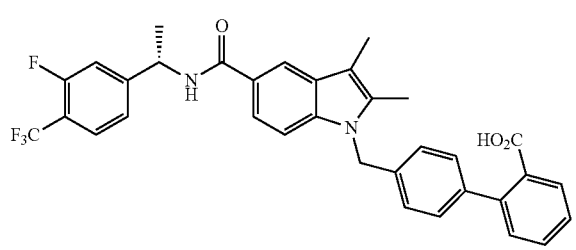
229
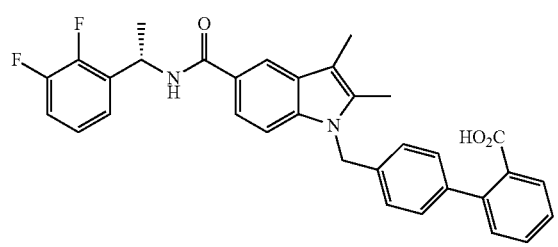
230
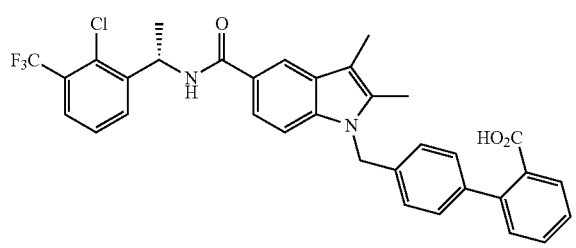
231
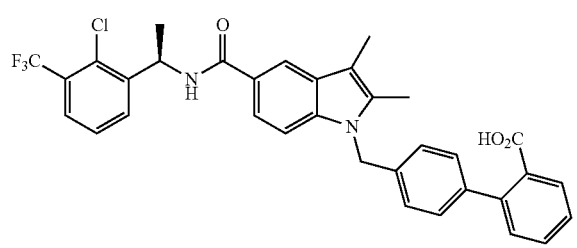
232
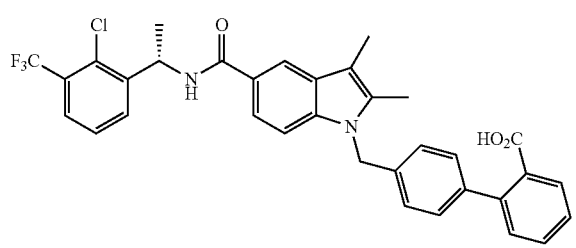
233
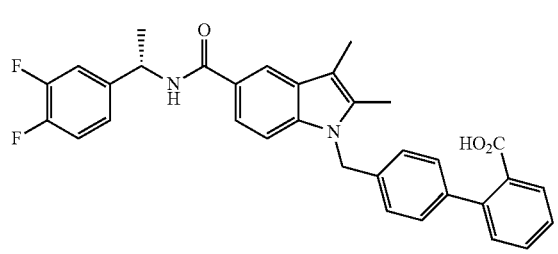
234
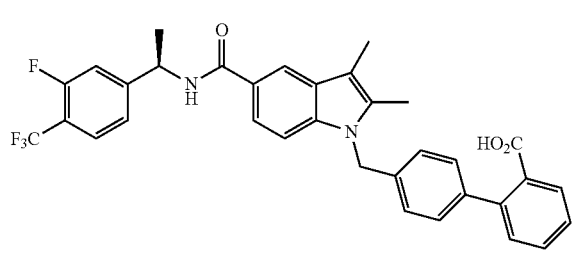

235 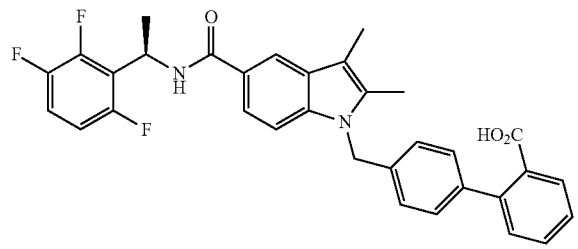
236 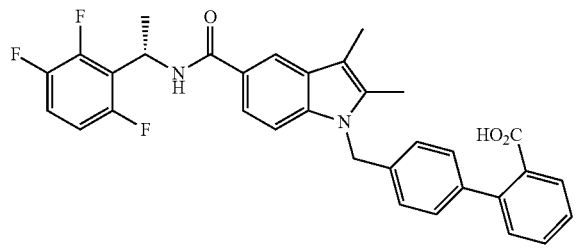
239 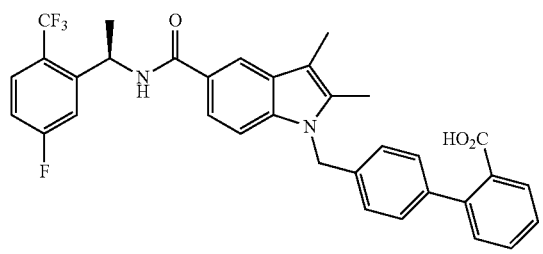
241 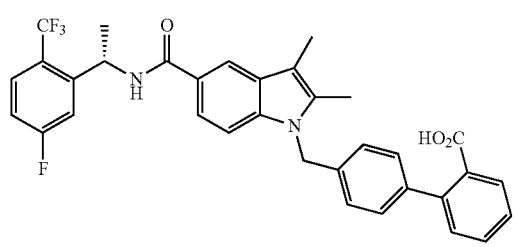
242 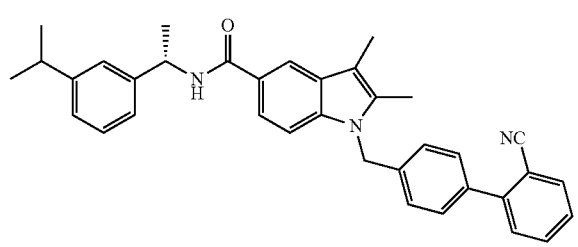
243 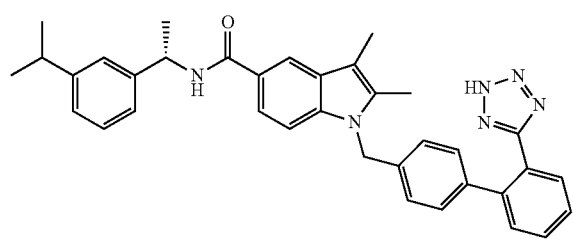
244 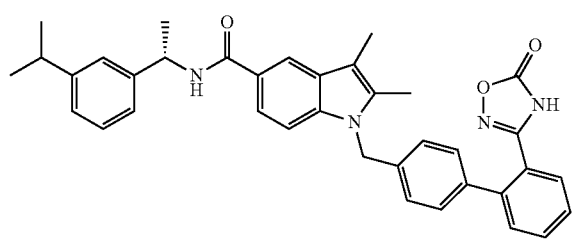
245 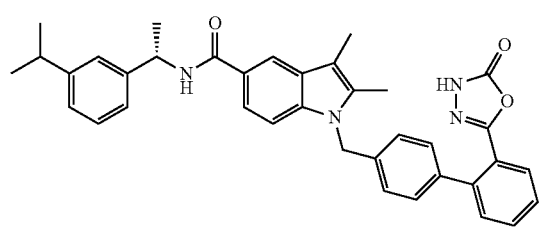
246 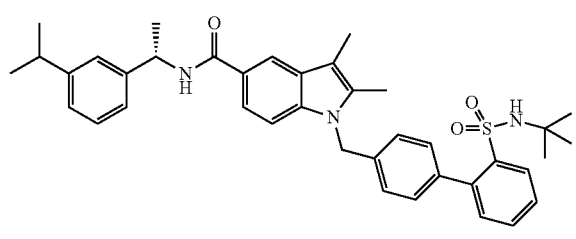
247 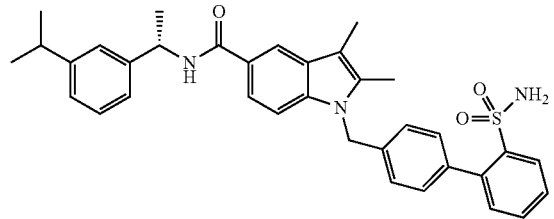
248 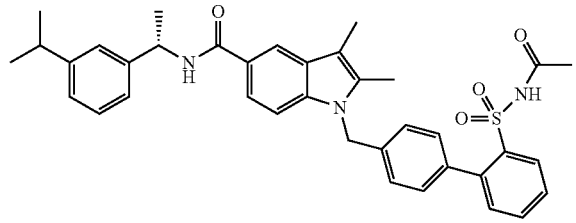

251 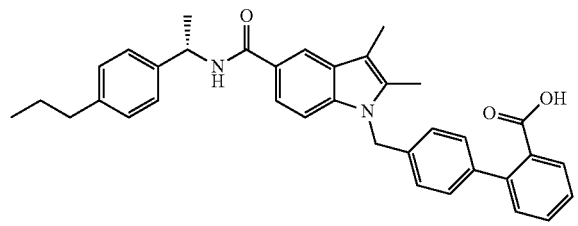
252 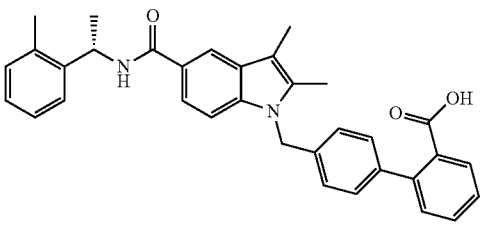
253 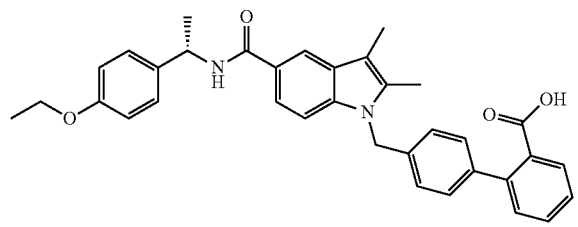
254 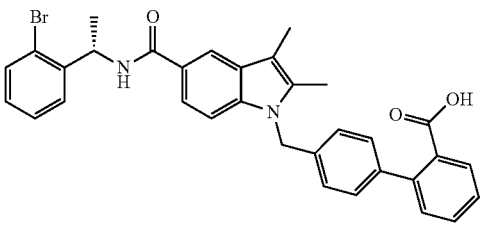
255 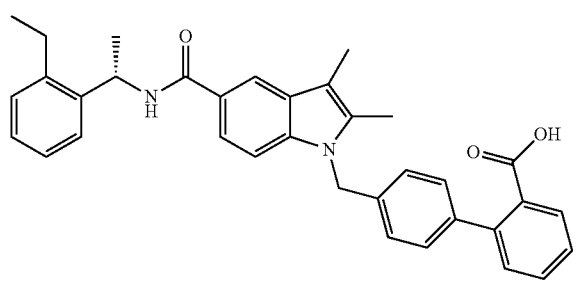
256 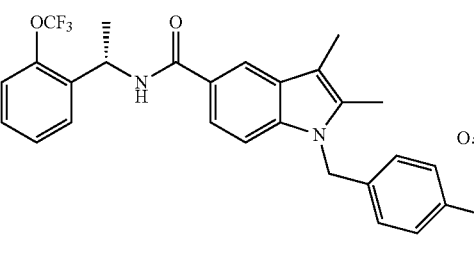
257 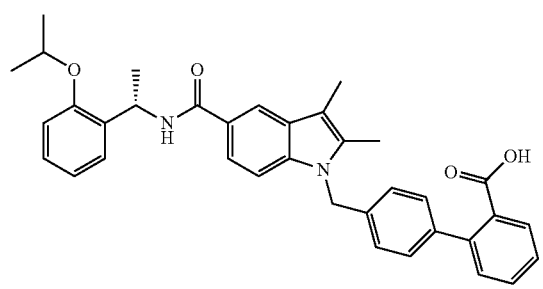
258 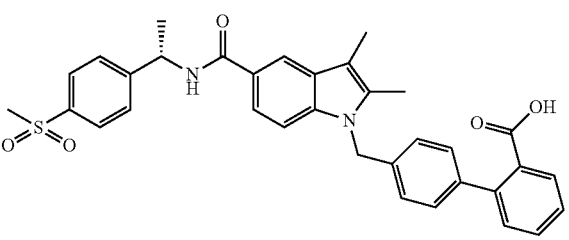
276 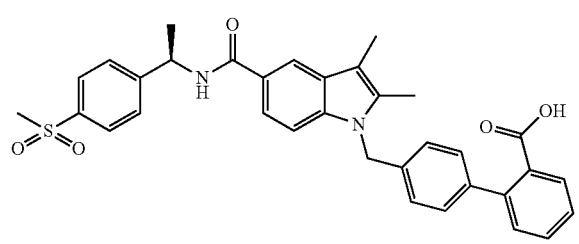
277 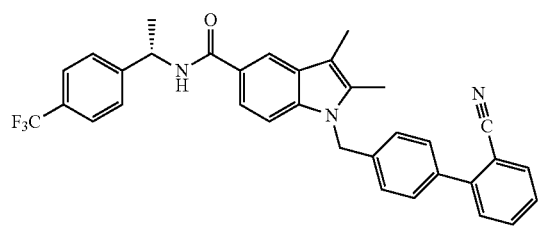
278 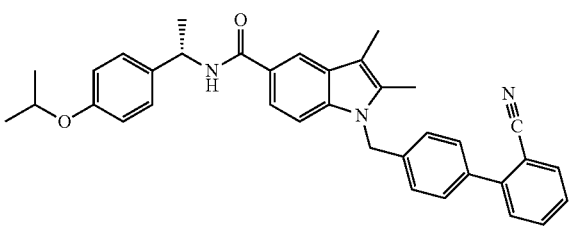

-continued
279
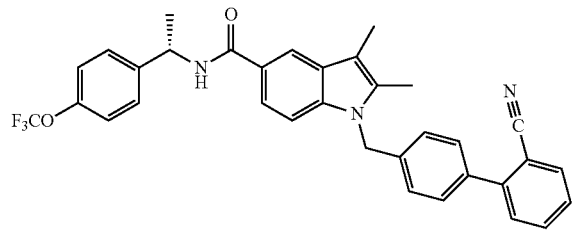
280
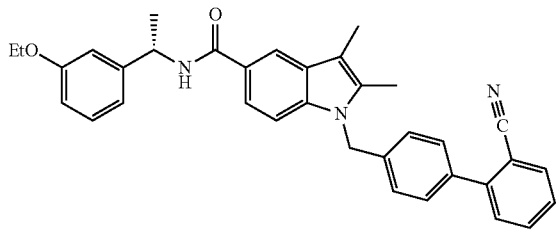
281
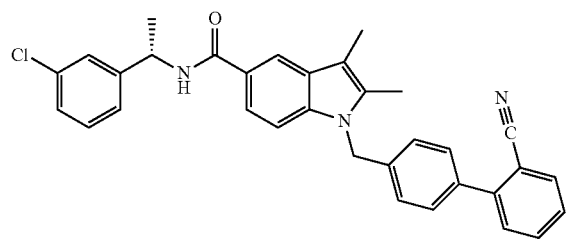
282
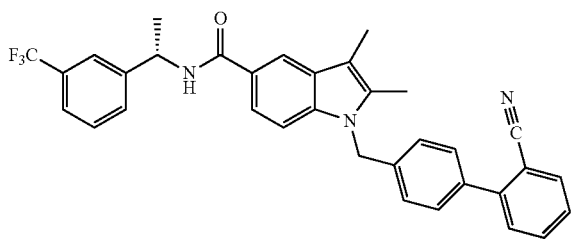
283
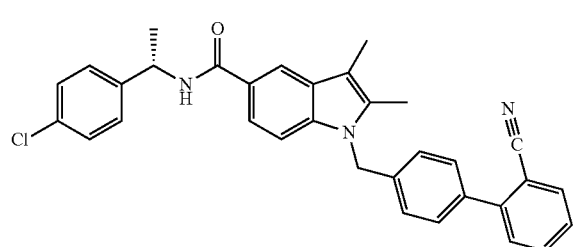
284
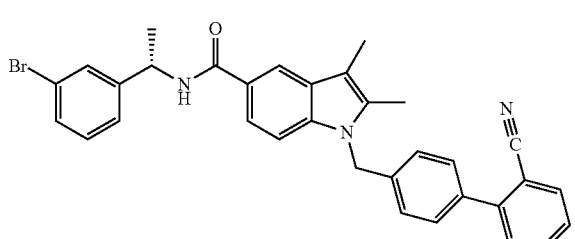
285
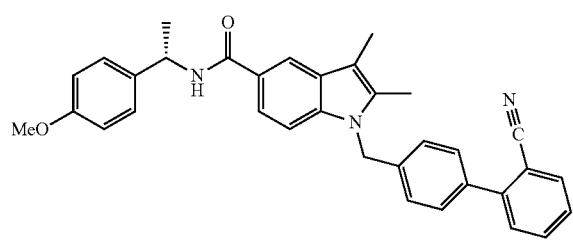
286
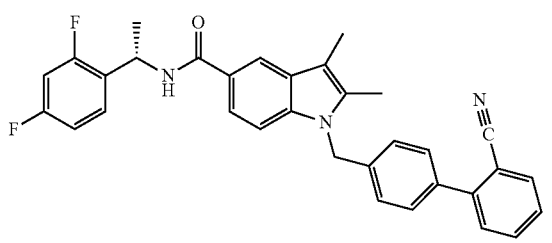
287
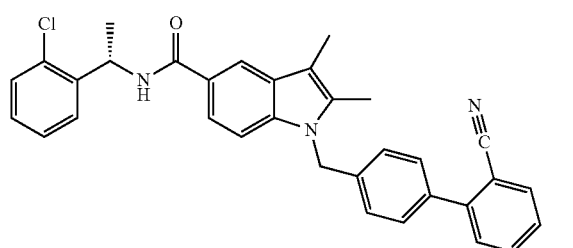
288
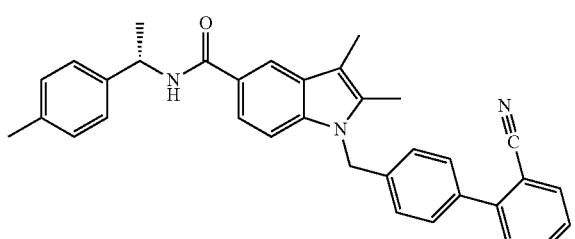
289
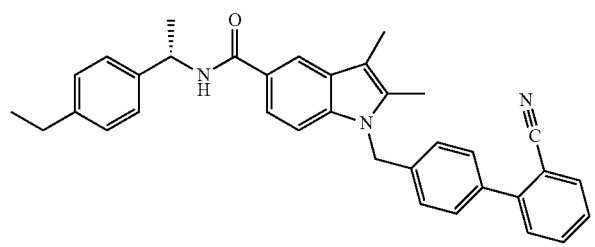
290
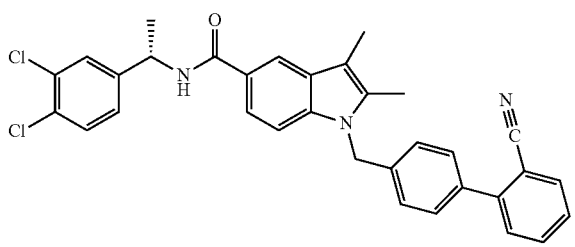

-continued
291
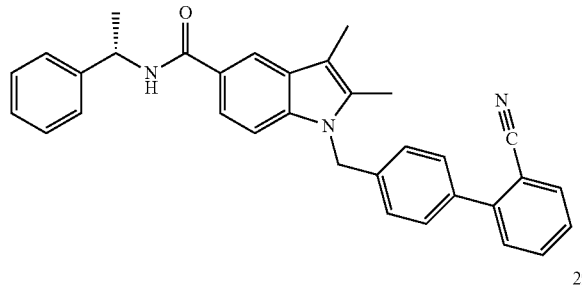
292
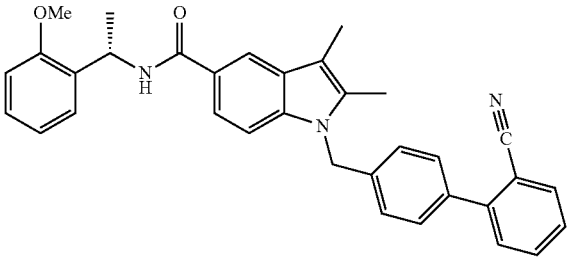
293
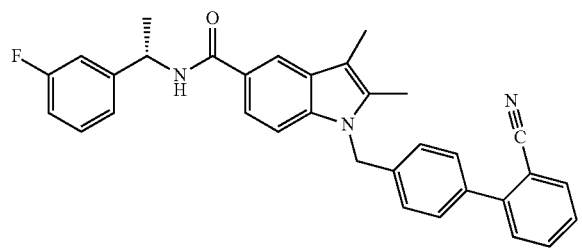
295
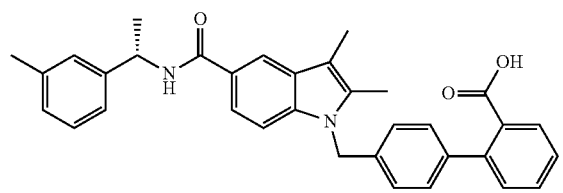
296
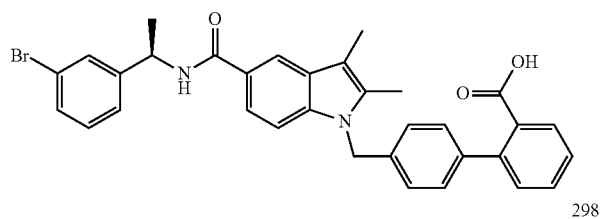
297
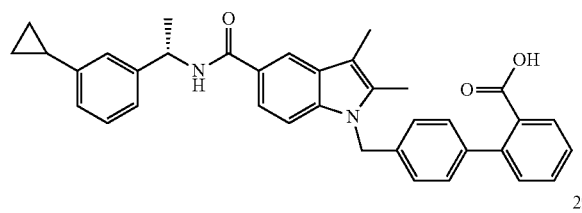
298
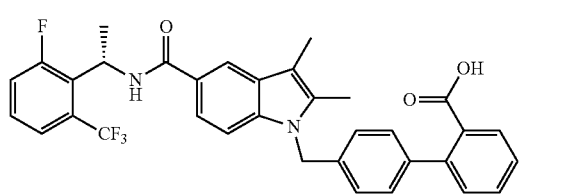
299
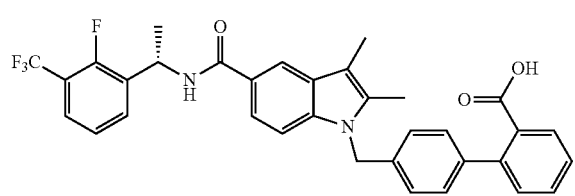
300
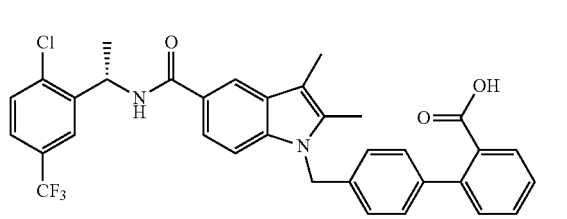
301
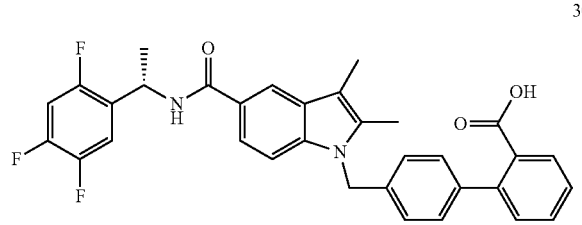
302
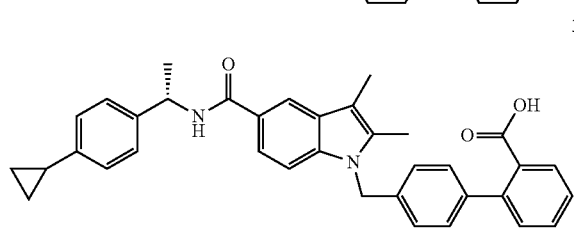
303
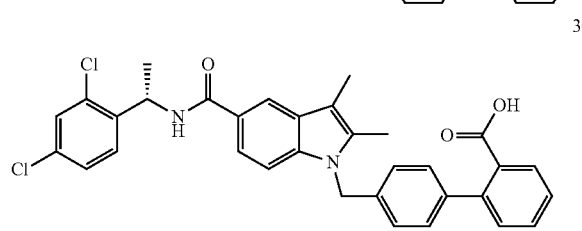
304

305
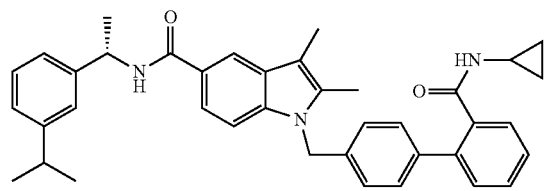
306
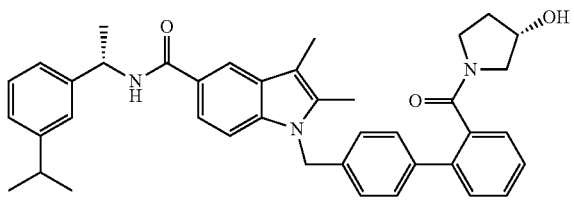
307
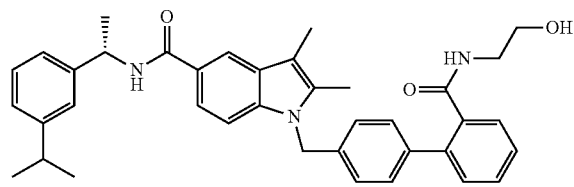
308
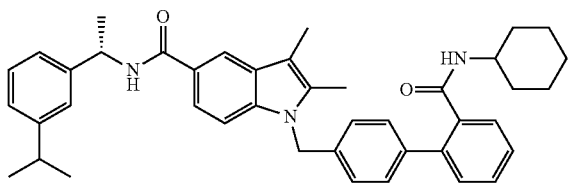
309
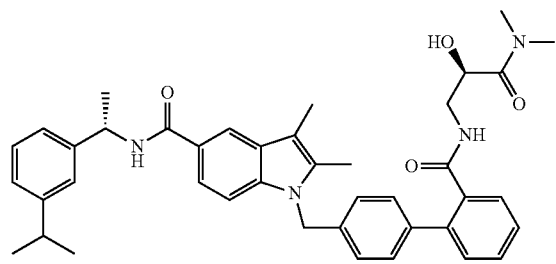
310
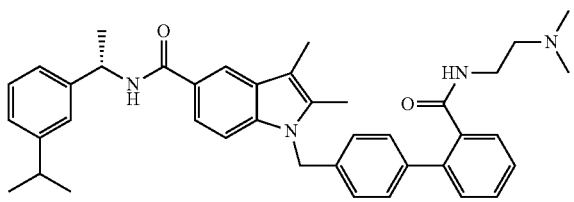
311
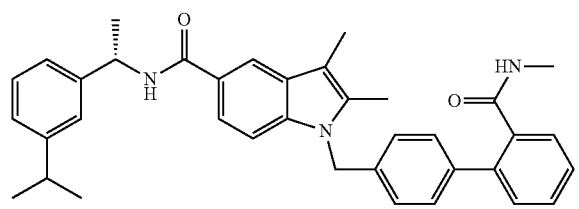
312
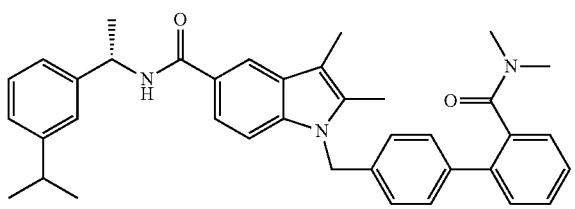
313
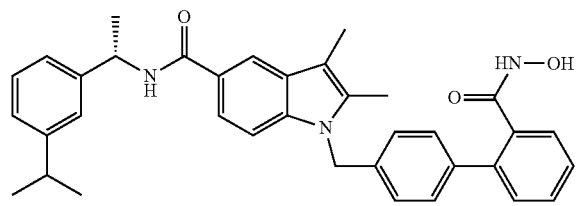
314
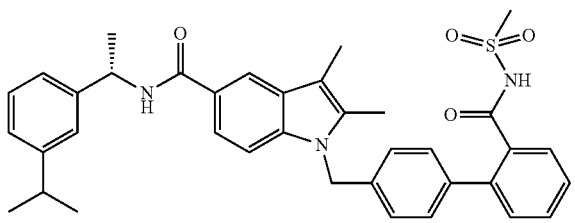
315
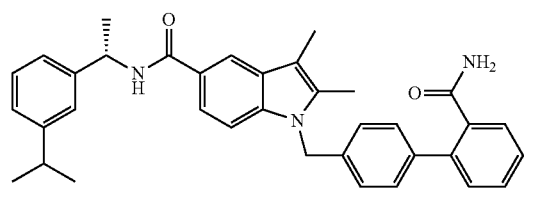
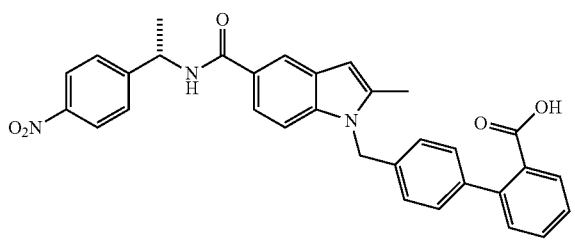

585
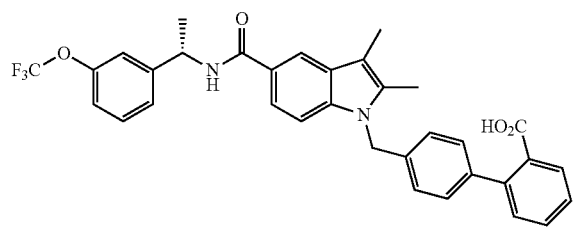
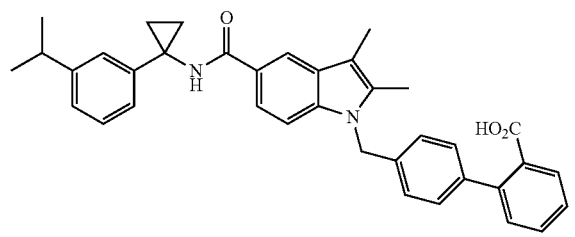
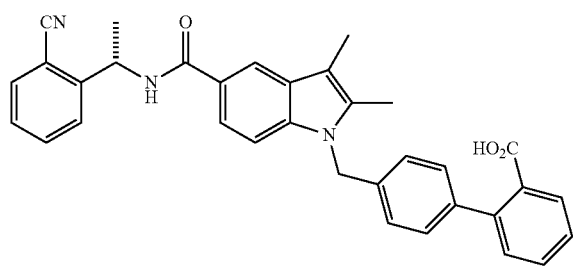
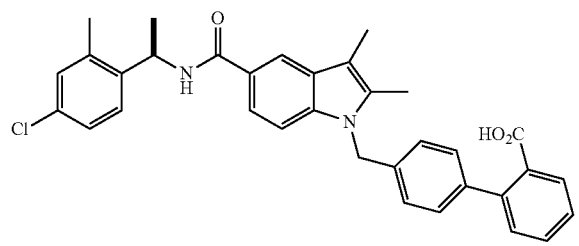
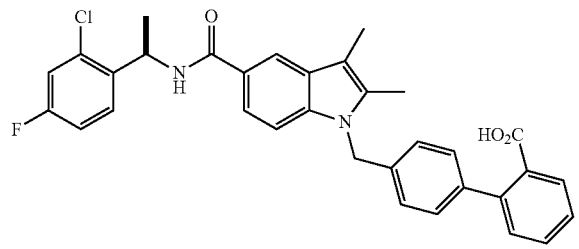
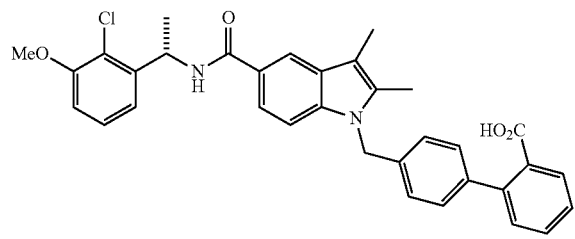
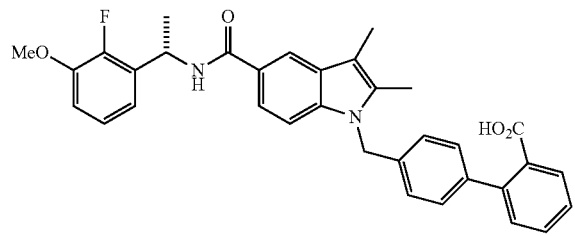
586
-continued
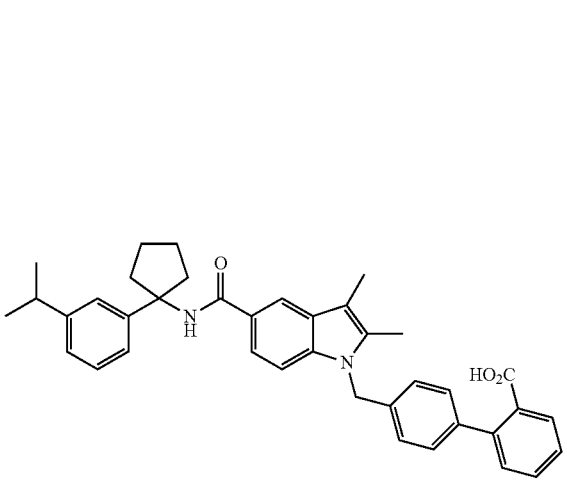
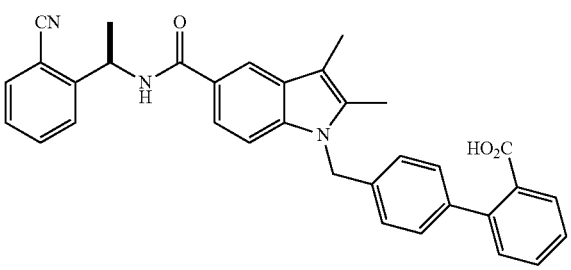
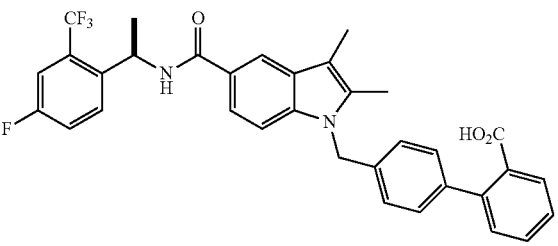
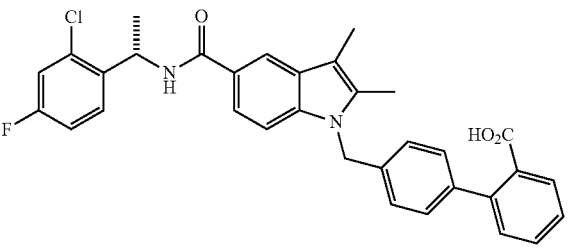
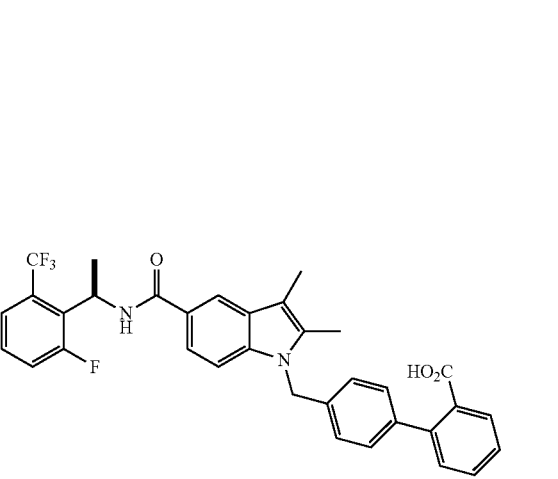

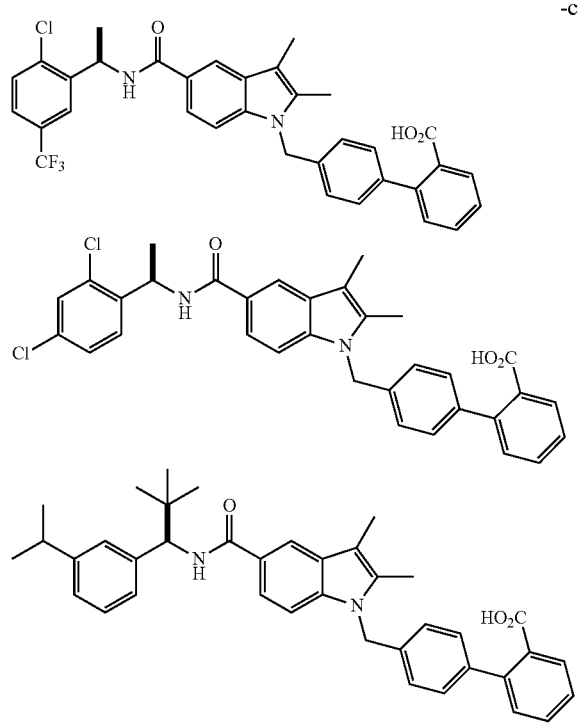

and

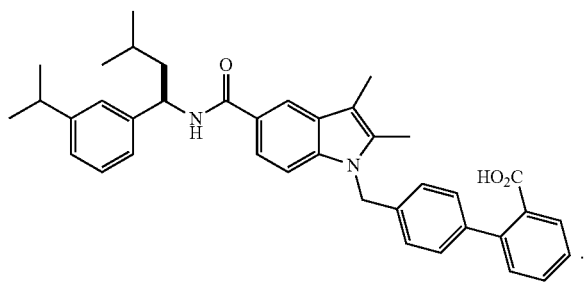 [SMILES: Cc1c(C)n(Cc2ccc(-c3ccccc3C(=O)O)cc2)c2ccc(C(=O)N[C@H](CC(C)C)c3cccc(C(C)C)c3)cc12]

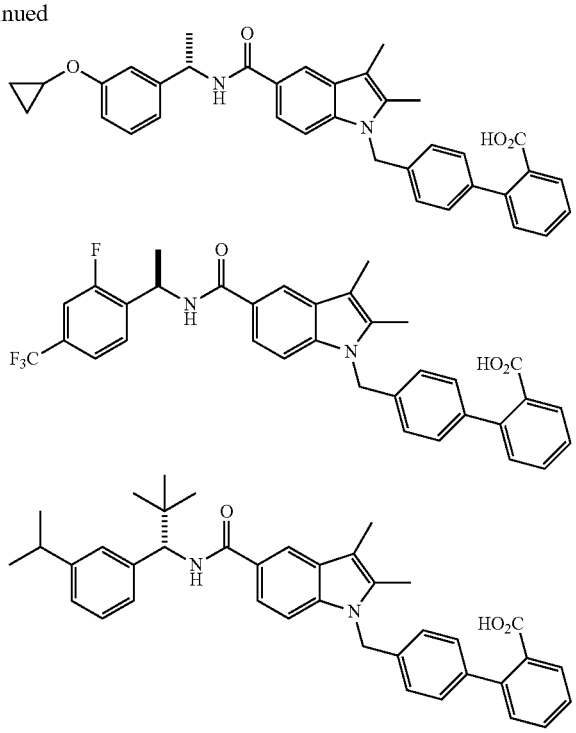

3. The method of inhibiting kinase-mediated phosphorylation of PPARG in a mammal of claim 1, comprising administering to the mammal an effective amount of a compound selected from the group consisting of

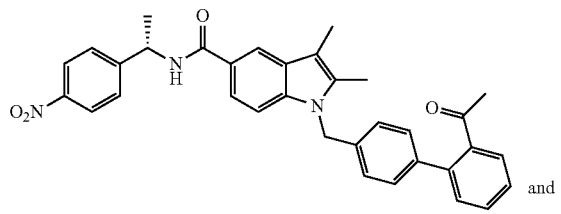

and

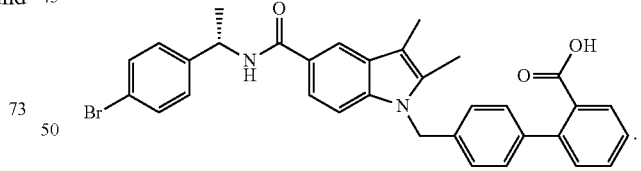

4. The method of claim 1 wherein the kinase-mediated phosphorylation of PPARG is cdk5-mediated.

5. The method of claim 4 wherein the effective amount of the compound for inhibiting cdk5-mediated phosphorylation of PPARG does not produce an agonistic effect on PPARG.

* * * * *